United States Patent
Moebius et al.

(10) Patent No.: US 11,040,981 B2
(45) Date of Patent: Jun. 22, 2021

(54) PYRROLOTRIAZINE COMPOUNDS AND METHODS OF INHIBITING TAM KINASES

(71) Applicant: Syros Pharmaceuticals, Inc., Cambridge, MA (US)

(72) Inventors: David Moebius, Westwood, MA (US); Jason J. Marineau, Franklin, MA (US); Yi Zhang, Belmont, MA (US); Claudio Edmundo Chuaqui, Arlington, MA (US); Goran Malojcic, Boston, MA (US); William Sinko, Roslindale, MA (US); Huiping Amy Guan, Acton, MA (US); Stephane Ciblat, Montreal (CA); Clint James, Laval (CA); Amandine Xolin, Montreal (CA); Sylvain Bernard, Longueuil (CA); Malay Doshi, Pointe-Claire (CA)

(73) Assignee: Syros Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 16/755,051

(22) PCT Filed: Oct. 9, 2018

(86) PCT No.: PCT/US2018/055070
§ 371 (c)(1),
(2) Date: Apr. 9, 2020

(87) PCT Pub. No.: WO2019/074962
PCT Pub. Date: Apr. 18, 2019

(65) Prior Publication Data
US 2020/0317676 A1    Oct. 8, 2020

Related U.S. Application Data

(60) Provisional application No. 62/570,381, filed on Oct. 10, 2017.

(51) Int. Cl.
| | |
|---|---|
| *C07D 487/04* | (2006.01) |
| *C07D 519/00* | (2006.01) |
| *A61K 31/53* | (2006.01) |
| *A61P 35/00* | (2006.01) |
| *C07D 401/04* | (2006.01) |

(52) U.S. Cl.
CPC ............ *C07D 487/04* (2013.01); *A61K 31/53* (2013.01); *A61P 35/00* (2018.01); *C07D 401/04* (2013.01); *C07D 519/00* (2013.01)

(58) Field of Classification Search
CPC .. C07D 487/04; C07D 401/04; C07D 403/04; A61K 31/53; A61P 35/00
USPC .......................................... 544/183; 514/243
See application file for complete search history.

(56) References Cited

U.S. PATENT DOCUMENTS 9,708,333 B2 * 7/2017 Li ..................... A61K 31/53
2017/0044164 A1 * 2/2017 Li ..................... A61P 35/00

FOREIGN PATENT DOCUMENTS

WO     2017027717 A1    2/2017

OTHER PUBLICATIONS

International Search Report for PCT/US2018/055070 dated Dec. 5, 2018.

* cited by examiner

*Primary Examiner* — Venkataraman Balasubramanian
(74) *Attorney, Agent, or Firm* — Goodwin Procter LLP

(57) ABSTRACT

Described herein are compounds, methods of making such compounds, pharmaceutical compositions, and medicaments comprising such compounds, and methods of using such compounds to treat cancer.

28 Claims, 128 Drawing Sheets

FIG. 1

| No. | Structure |
|---|---|
| 110 | 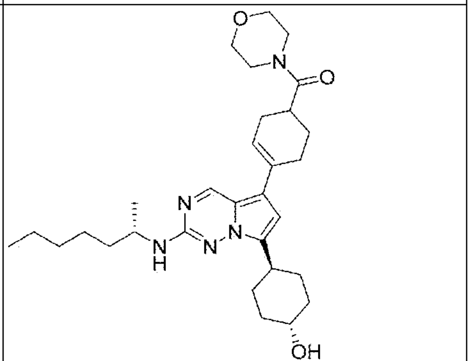 |
| 111 | 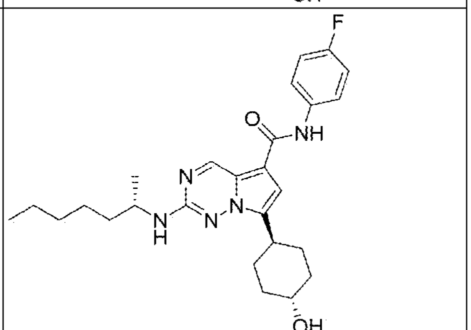 |
| 112 | 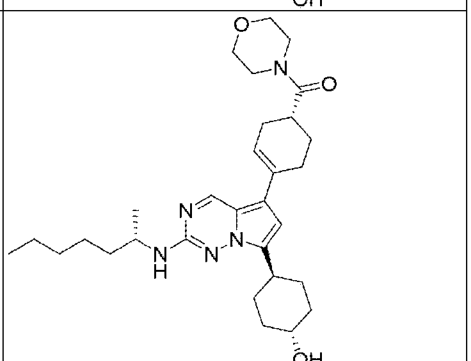 |
| 113 | 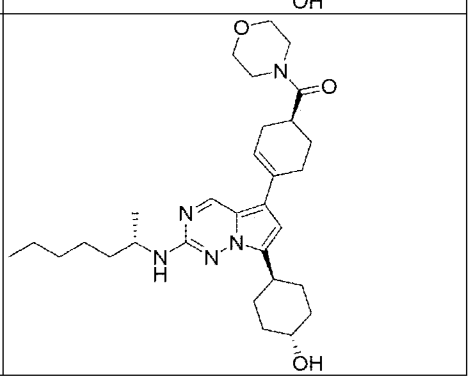 |

| No. | Structure |
|---|---|
| 114 | 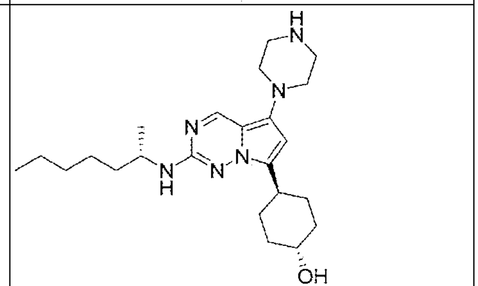 |
| 115 | 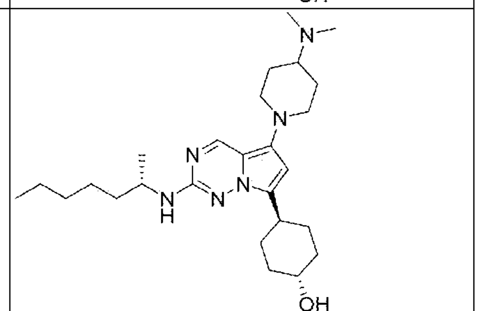 |
| 116 | 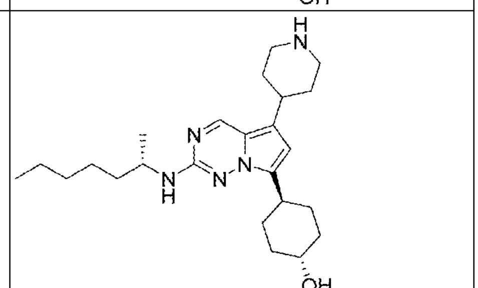 |
| 117 | 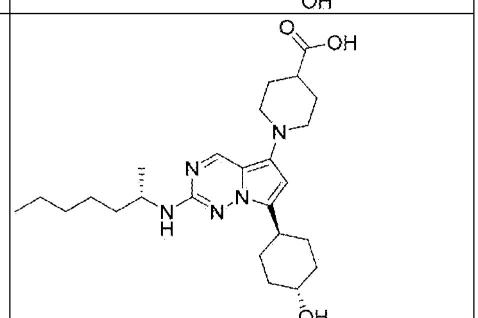 |
| 118 | 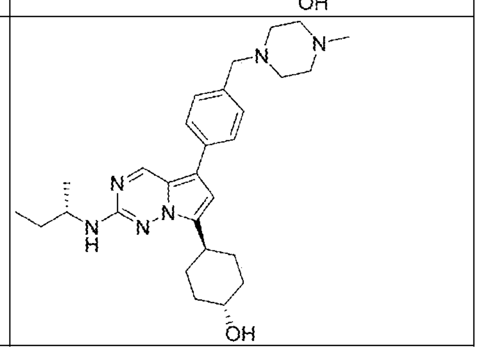 |

| No. | Structure |
|-----|-----------|
| 176 | 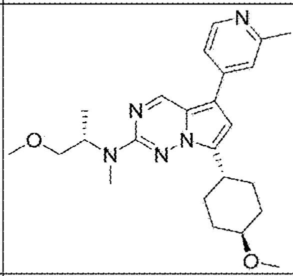 |
| 177 | 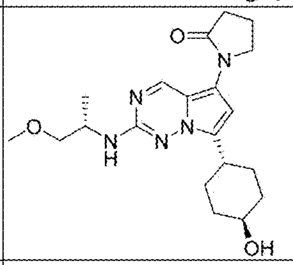 |
| 178 | 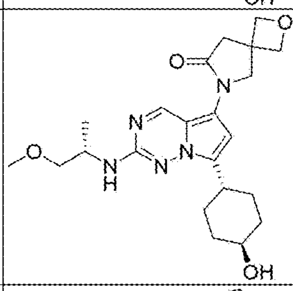 |
| 179 | 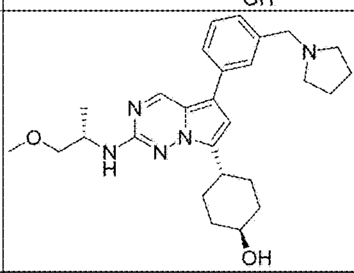 |
| 180 | 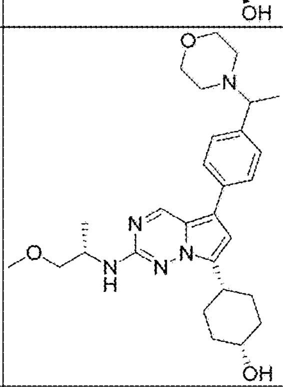 |

| No. | Structure |
|-----|-----------|
| 181 | 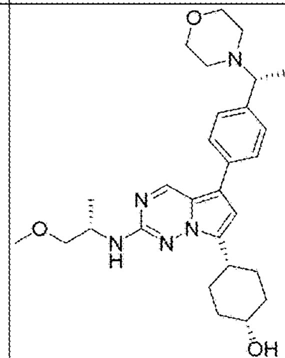 |
| 182 | 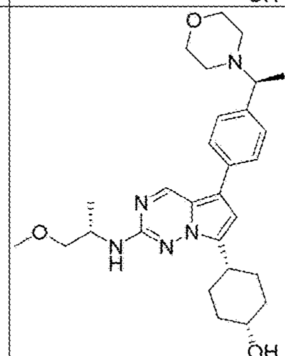 |
| 183 | 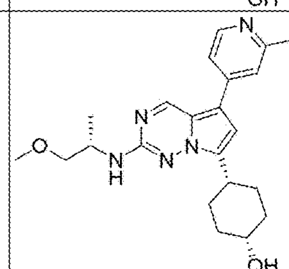 |
| 184 | 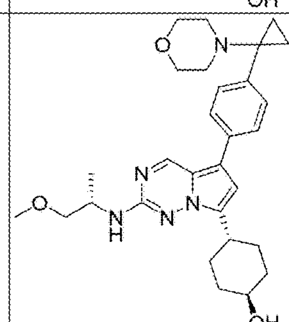 |
| 185 | 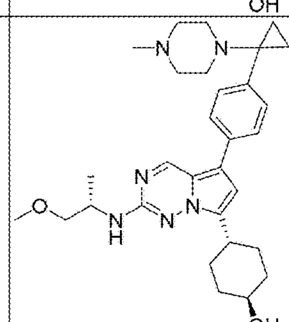 |

| No. | Structure |
|---|---|
| 186 | 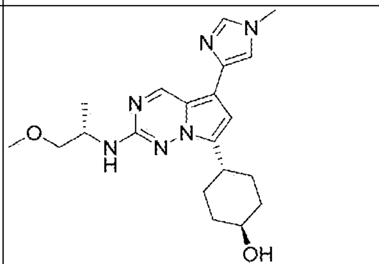 |
| 187 | 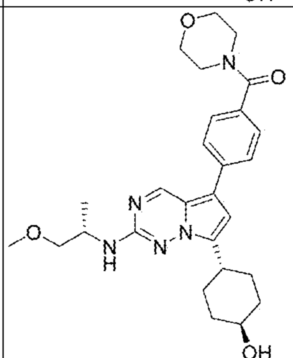 |
| 188 | 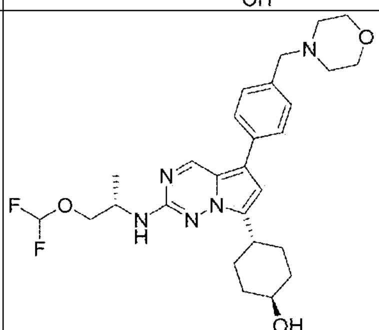 |
| 189 | 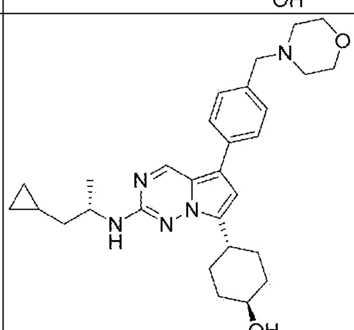 |
| 190 | 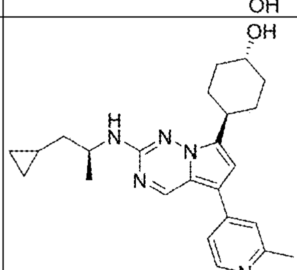 |

| No. | Structure |
|---|---|
| 191 | 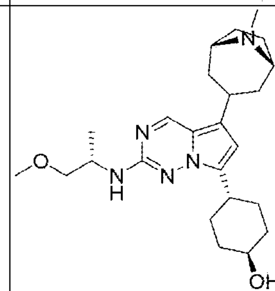 |
| 192 | 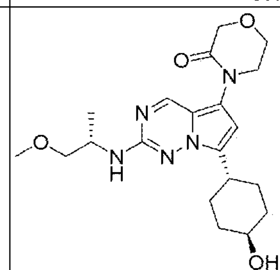 |
| 193 | 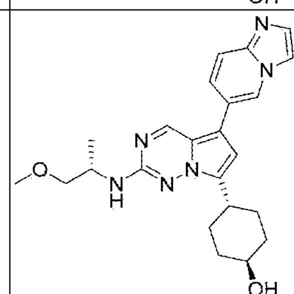 |
| 194 | 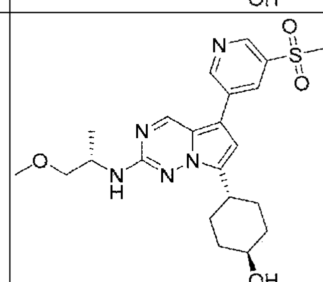 |
| 195 | 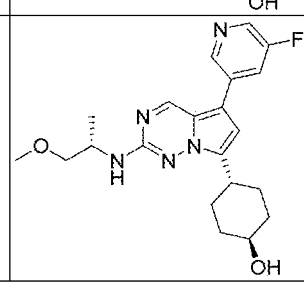 |

| No. | Structure |
|---|---|
| 205 | 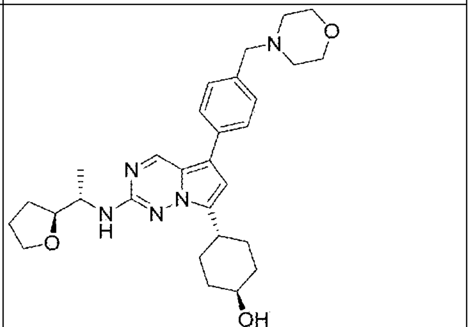 |
| 206 | 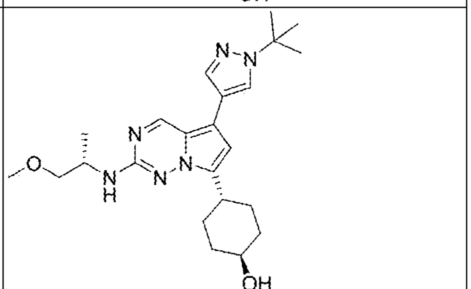 |
| 207 | 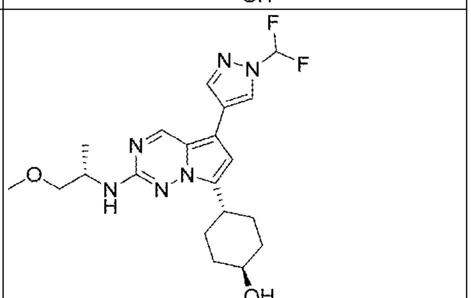 |
| 208 | 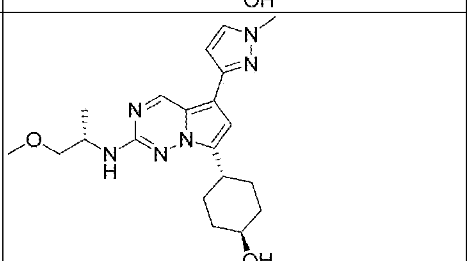 |
| 209 | 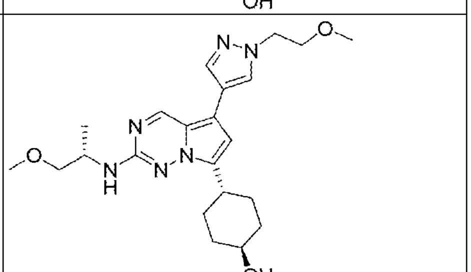 |

| No. | Structure |
|---|---|
| 210 | 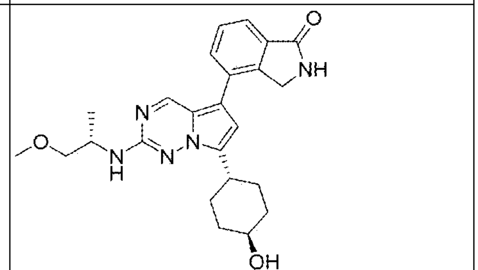 |
| 211 | 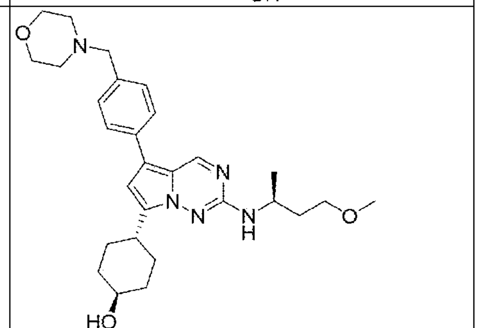 |
| 212 | 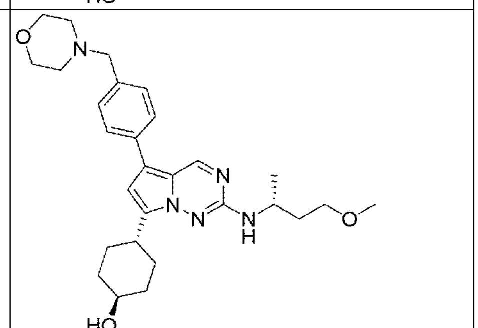 |
| 213 | 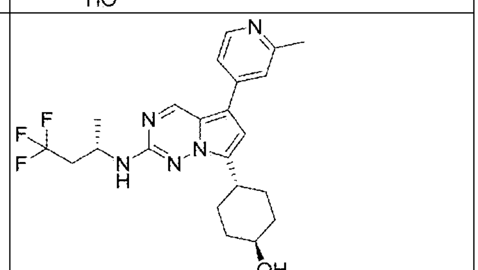 |
| 214 | 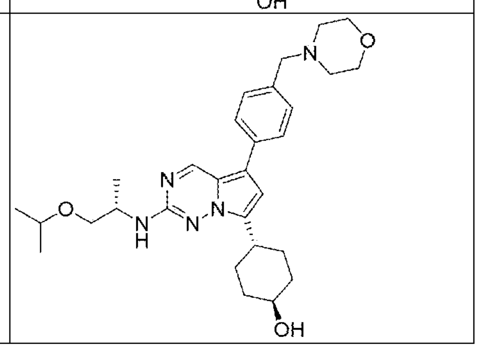 |

| No. | Structure |
|---|---|
| 288 | 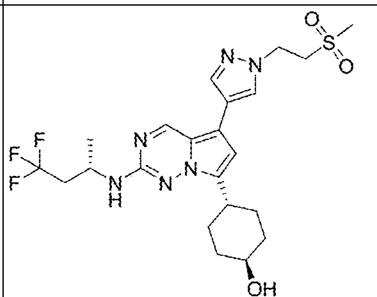 |
| 289 | 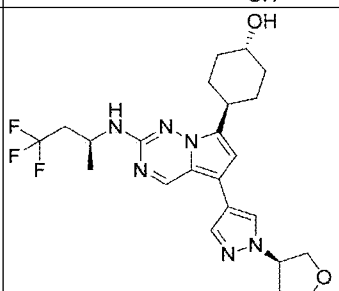 |
| 290 | 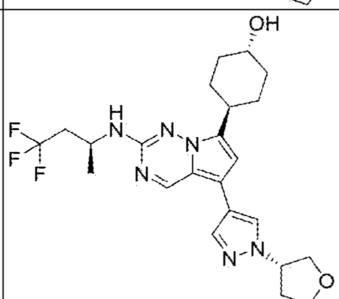 |
| 291 | 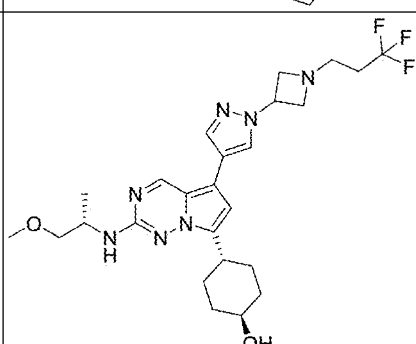 |
| 292 | 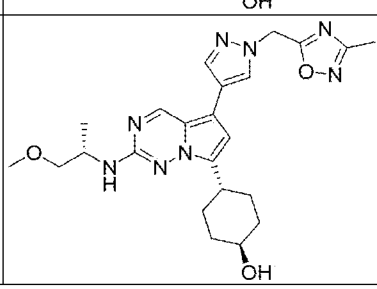 |

| No. | Structure |
|---|---|
| 293 | 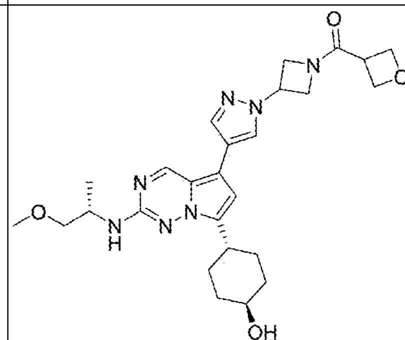 |
| 294 | 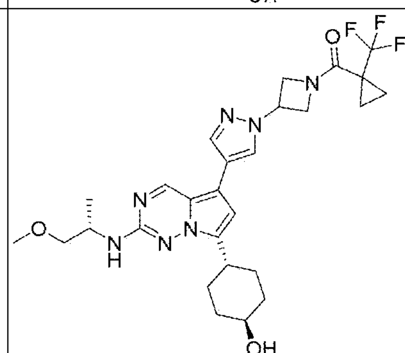 |
| 295 | 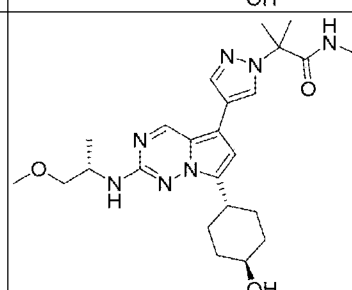 |
| 296 | 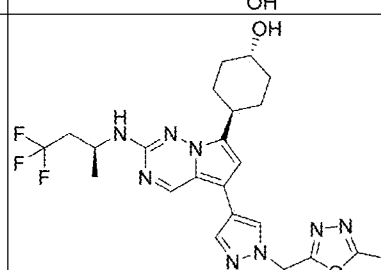 |
| 297 | 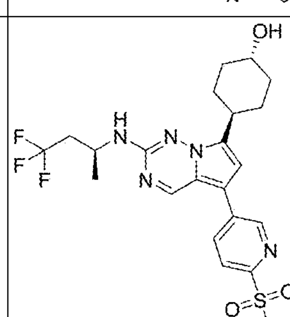 |

| No. | Structure |
|---|---|
| 350 | 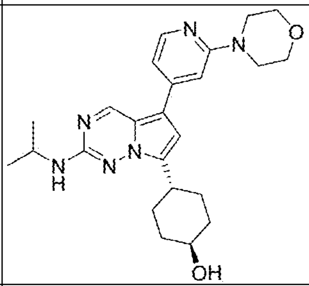 |
| 351 | 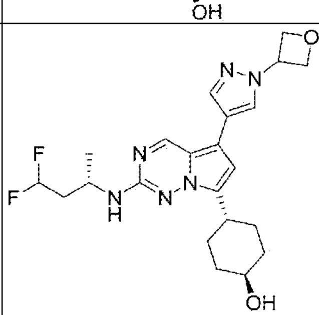 |
| 352 | 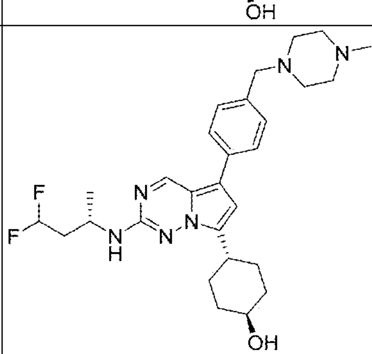 |
| 353 | 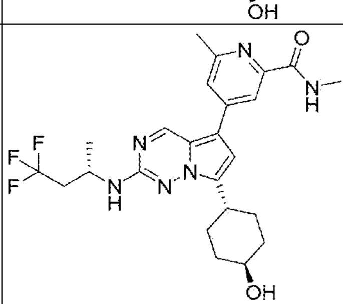 |
| 354 | 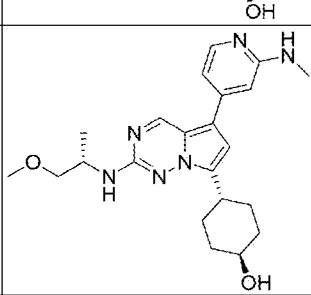 |

| No. | Structure |
|---|---|
| 355 | 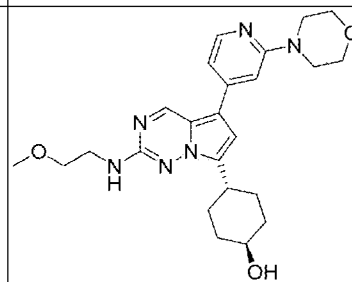 |
| 356 | 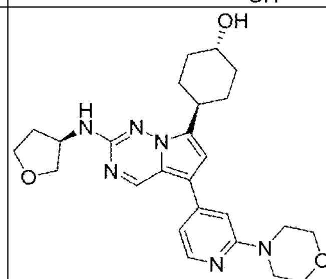 |
| 357 | 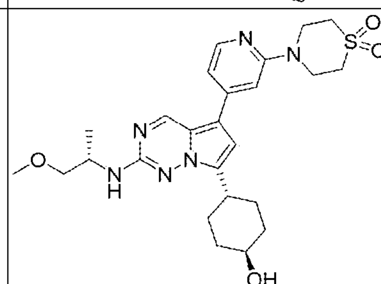 |
| 358 | 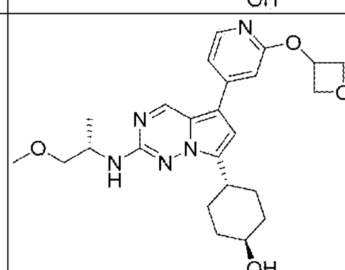 |
| 359 | 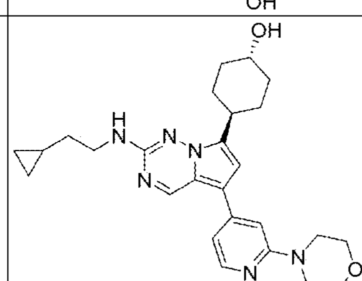 |

| No. | Structure |
|-----|-----------|
| 424 |  |
| 425 |  |
| 426 |  |
| 427 |  |
| 428 |  |

| No. | Structure |
|-----|-----------|
| 429 | 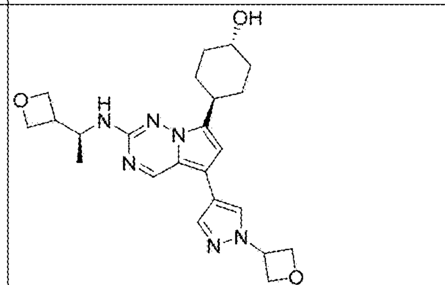 |
| 430 | 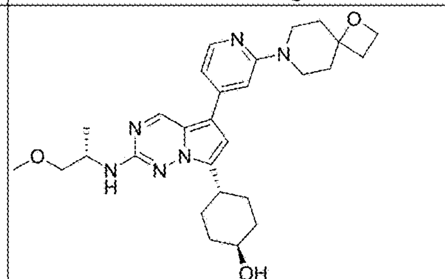 |
| 431 | 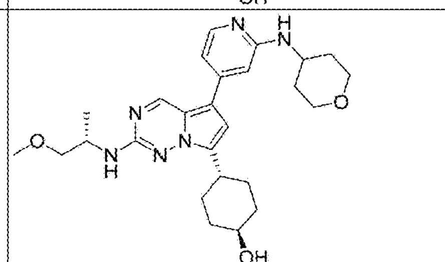 |
| 432 | 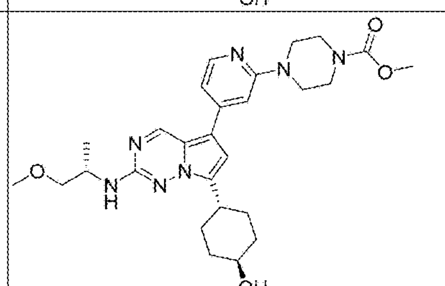 |
| 433 | 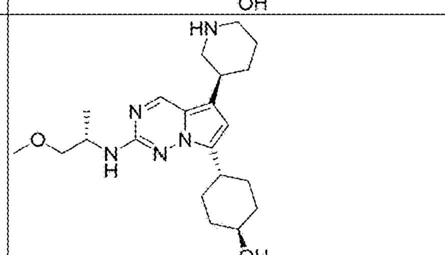 |
| 434 | 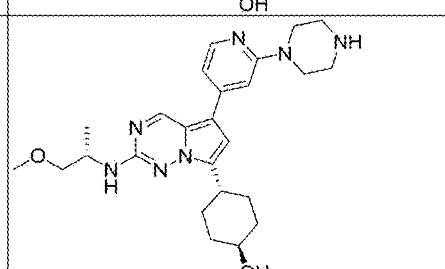 |

| No. | Structure |
|---|---|
| 445 | 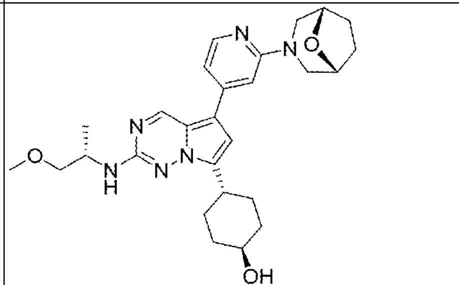 |
| 446 | 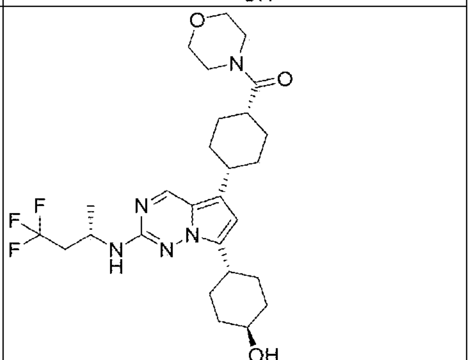 |
| 447 | 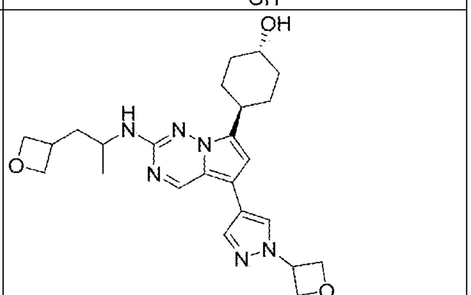 |
| 448 | 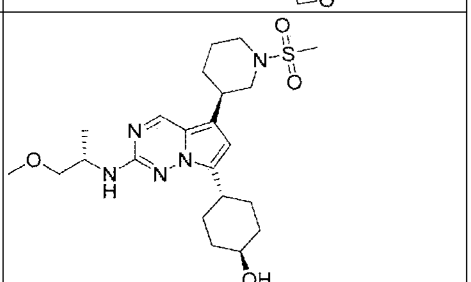 |
| 449 | 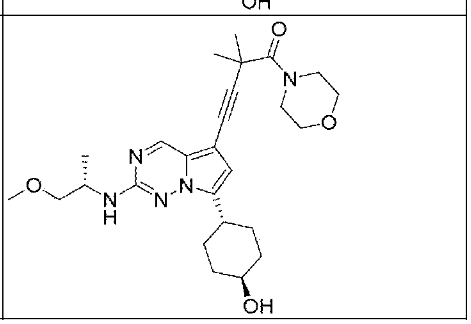 |

| No. | Structure |
|---|---|
| 450 | 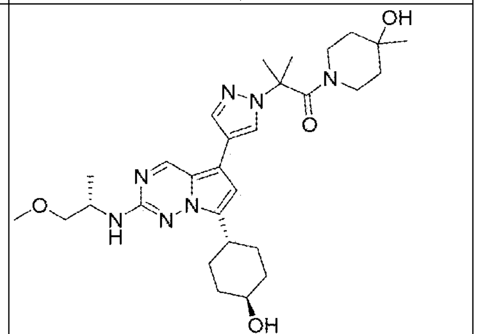 |
| 451 | 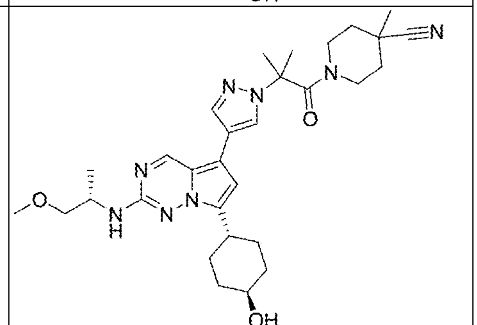 |
| 452 | 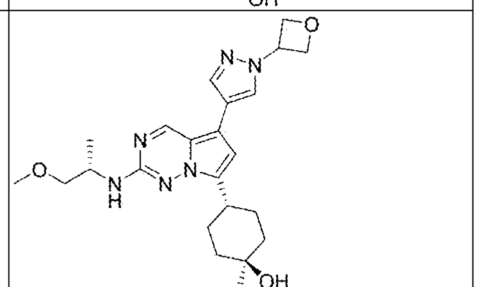 |
| 453 | 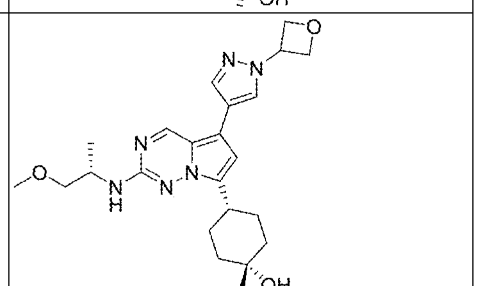 |
| 454 | 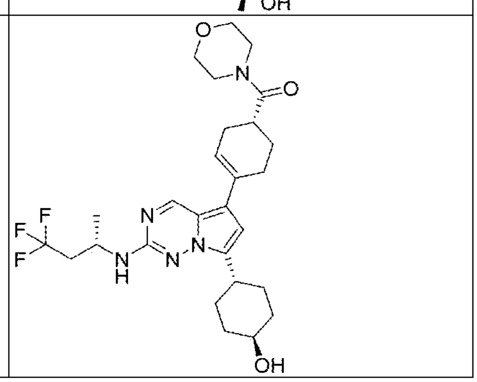 |

| No. | Structure |
|-----|-----------|
| 476 | 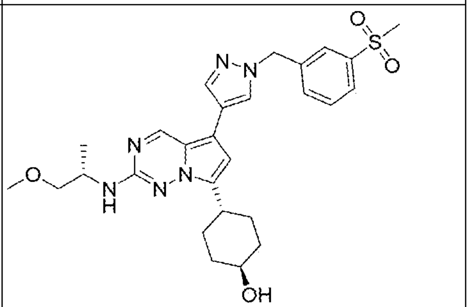 |
| 477 | 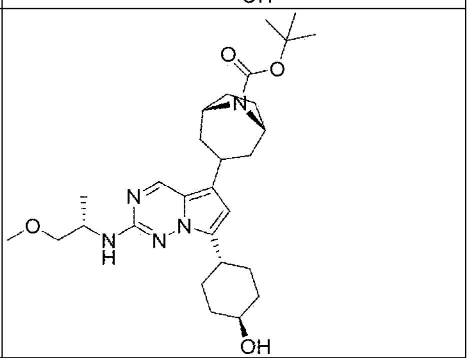 |
| 478 | 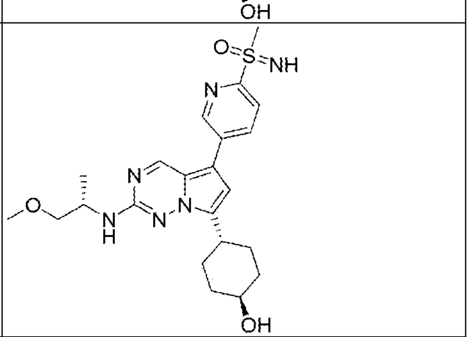 |
| 479 | 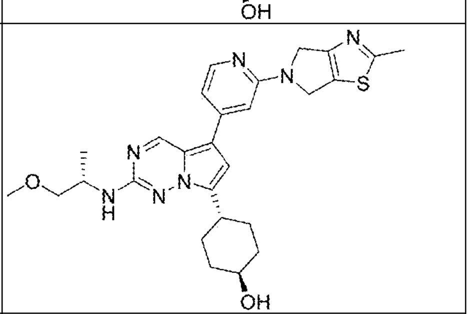 |
| 480 | 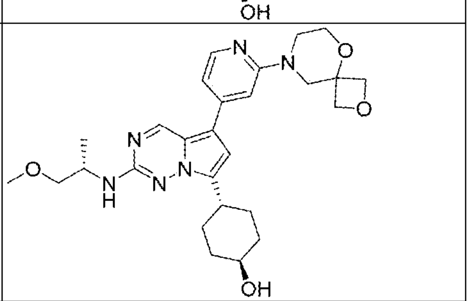 |

| No. | Structure |
|-----|-----------|
| 481 | 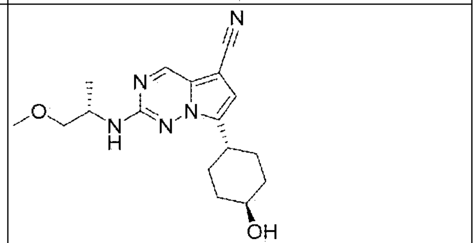 |
| 482 | 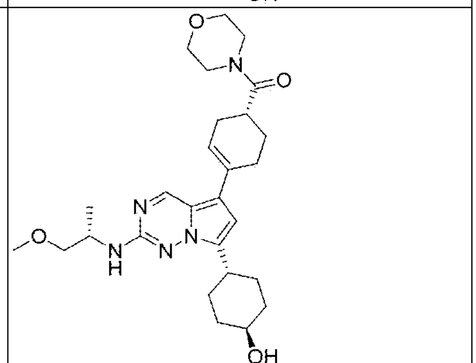 |
| 483 | 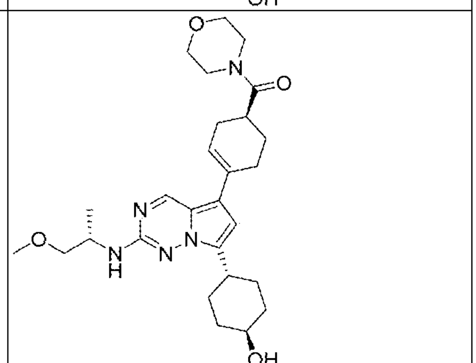 |
| 484 | 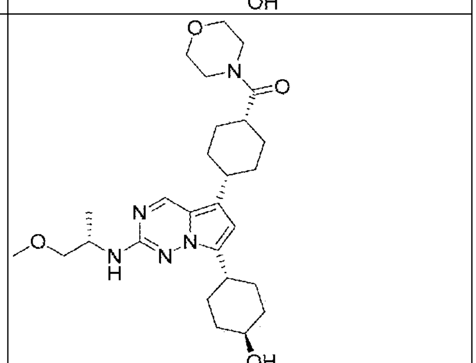 |
| 485 | 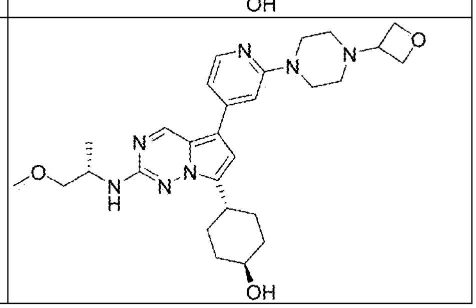 |

| No. | Structure |
|---|---|
| 542 | 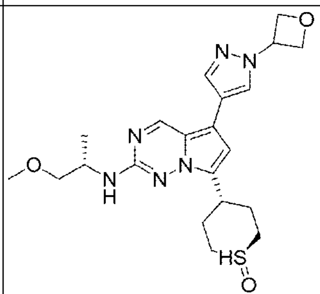 |
| 543 | 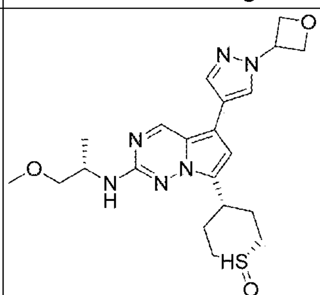 |
| 544 | 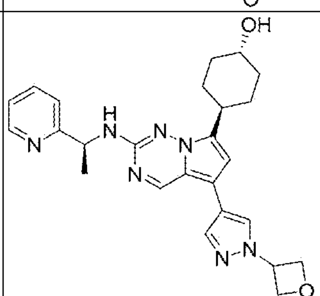 |
| 545 | 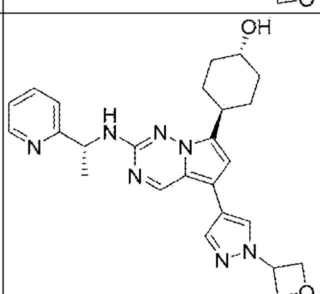 |
| 546 | 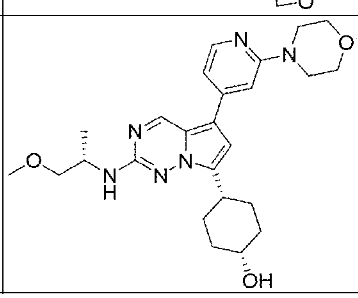 |

| No. | Structure |
|---|---|
| 547 | 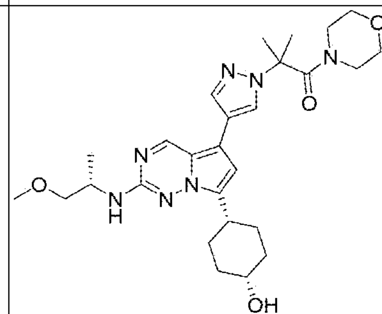 |
| 548 | 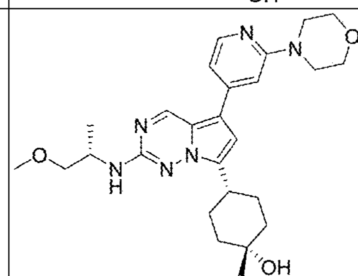 |
| 549 | 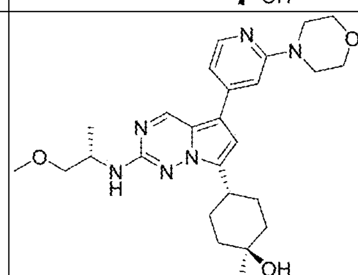 |
| 550 | 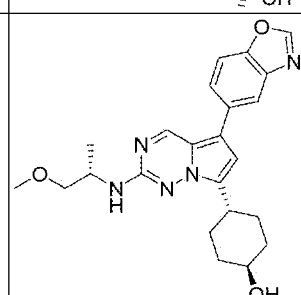 |
| 551 | 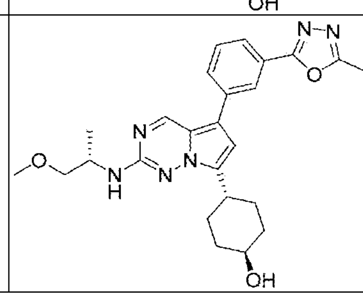 |

| No. | Structure |
|---|---|
| 552 | 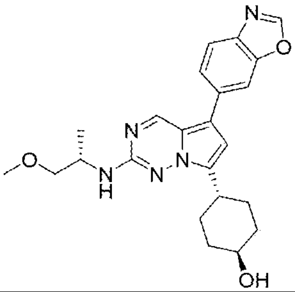 |
| 553 | 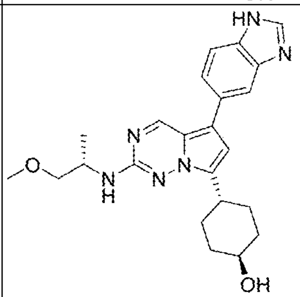 |
| 554 | 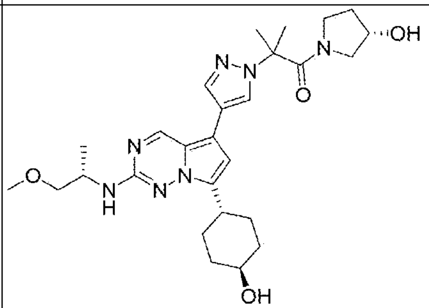 |
| 555 | 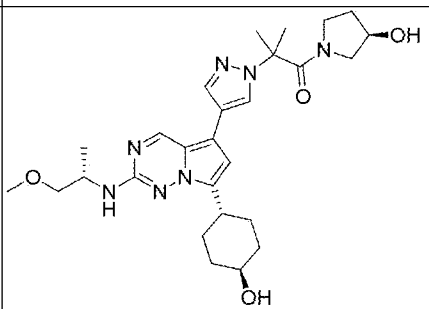 |
| 556 | 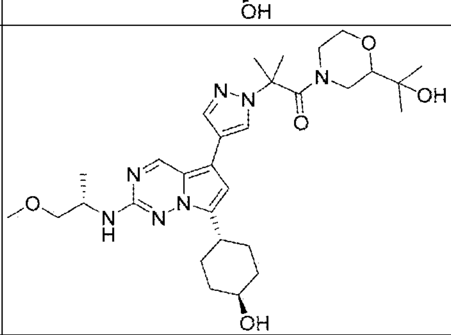 |

| No. | Structure |
|---|---|
| 557 | 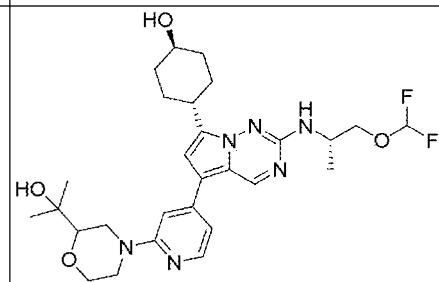 |
| 558 | 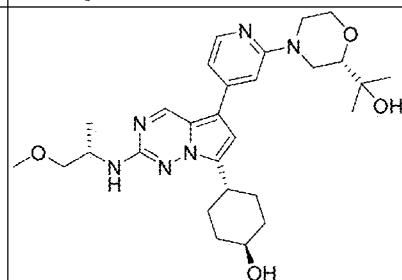 |
| 559 | 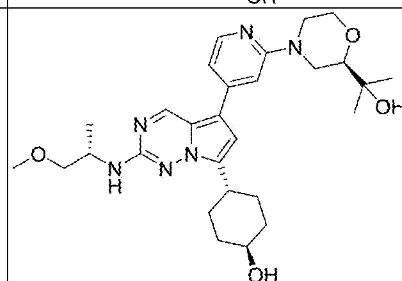 |
| 560 | 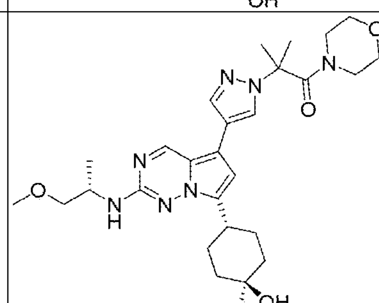 |
| 561 | 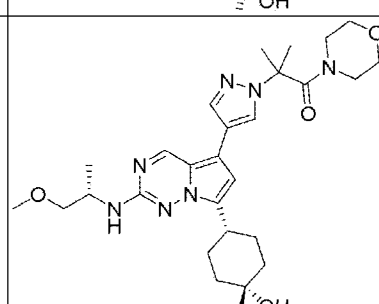 |

| No. | Structure |
|-----|-----------|
| 631 | 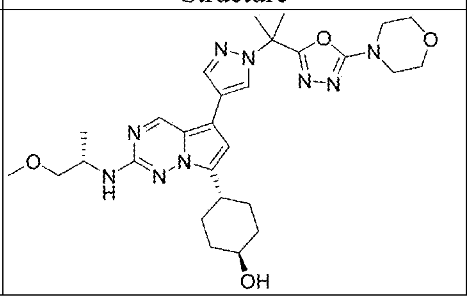 |

| No. | Structure |
|-----|-----------|
| 632 | 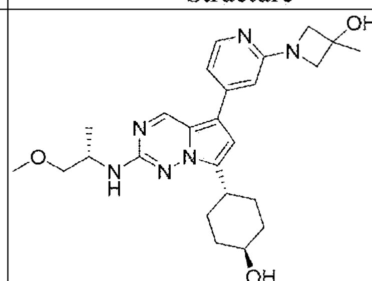 |
| 633 | 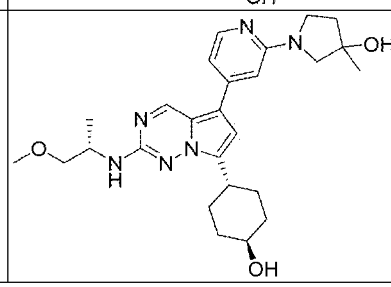 |

FIG. 2

| No. | General Scheme | NMR | MS |
|---|---|---|---|
| 101 | 1 | $^1$H NMR (400 MHz, CDCl$_3$) δ 8.80 (s, 1H), 7.81 (d, J=8.4 Hz, 2H), 7.70 (d, J=8.0 Hz, 2H), 6.66 (s, 1H), 4.75 (t, J=6.0 Hz, 1H), 3.80 - 3.78 (m, 5H), 3.41 (q, J=6.8 Hz, 2H), 3.20 - 3.14 (m, 1H), 3.09 - 3.07 (m, 4H), 2.28 - 2.25 (m, 2H), 2.20 - 2.16 (m, 2H), 1.71 - 1.61 (m, 4H), 1.51 - 1.46 (m, 4H), 1.02 (t, J=7.2 Hz, 3H). | 514.2 |
| 102 | 1 | $^1$H NMR (400 MHz, CDCl$_3$) δ 8.65 (br s, 1H), 7.88 (br d, J=7.2 Hz, 2H), 7.68 (br d, J=7.6 Hz, 2H), 6.97 (s, 1H), 3.94 - 3.89 (m, 1H), 3.80 - 3.76 (m, 5H), 3.21 (br t, J=12.0 Hz, 1H), 3.08 (br s, 4H), 2.23 (br s, 4H), 1.79 - 1.72 (m, 1H), 1.70 - 1.42 (m, 7H), 1.36 - 1.34 (m, 7H), 0.92 (t, J=6.4 Hz, 3H). | 556.3 |
| 103 | 1 | $^1$H NMR (400 MHz, CDCl$_3$) δ 8.65 (br s, 1H), 7.86 (br d, J=8.0 Hz, 2H), 7.69 (br d, J=8.0 Hz, 2H), 6.94 (s, 1H), 4.22 (br s, 1H), 3.94 - 3.91 (m, 1H), 3.81 - 3.79 (m, 4H), 3.30 - 3.28 (m, 1H), 3.08 (br s, 4H), 2.07 - 1.95 (m, 6H), 1.83 - 1.72 (m, 3H), 1.59 - 1.52 (m, 1H), 1.44 (br s, 2H), 1.36 - 1.32 (m, 7H), 0.92 (br t, J=6.8 Hz, 3H). | 556.3 |
| 104 | 1 | $^1$H NMR (400 MHz, CD$_3$OD) δ 8.95 (s, 1H), 7.85 - 7.78 (m, 4H), 7.35 (s, 1H), 4.52 (s, 2H), 4.03 - 3.96 (m, 1H), 3.73 - 3.50 (m, 9H), 3.04 (s, 3H), 2.18 (br t, J=14.8 Hz, 4H), 1.82 - 1.45 (m, 8H), 1.41 - 1.38 (m, 4H), 1.35 (d, J=6.8 Hz, 3H), 0.96 (t, J=7.2 Hz, 3H) | 519.4 |
| 105 | 1 | $^1$H NMR (400 MHz, CD$_3$OD) δ 8.95 (s, 1H), 7.85 - 7.78 (m, 4H), 7.34 (s, 1H), 4.49 (s, 2H), 4.12 (br s, 1H), 4.03 - 3.96 (m, 1H), 3.87 - 3.46 (m, 8H), 3.03 (s, 3H), 2.15 - 1.56 (m, 10H), 1.48 (br s, 2H), 1.43 - 1.37 (m, 4H), 1.34 (d, J=6.4 Hz, 3H), 0.94 (t, J=7.2 Hz, 3H). | 519.4 |
| 106 | 1 | $^1$H NMR (400 MHz, CD$_3$OD) δ 8.51 (s, 1H), 7.31 - 7.21 (m, 2H), 7.16 - 7.11 (m, 2H), 6.36 (s, 1H), 3.90 - 3.83 (m, 1H), 3.67 - 3.61 (m, 1H), 3.15 - 2.99 (m, 1H), 2.18 - 2.01 (m, 4H), 1.76 - 1.51 (m, 4H), 1.50 - 1.34 (m, 8H), 1.29 (d, J=6.4 Hz, 3H), 0.95 (t, J=7.2 Hz, 3H). | 440.3 |
| 107 | 1 | $^1$H NMR (400 MHz, CD$_3$OD) δ 8.41 (s, 1H), 5.98 (s, 1H), 3.90 - 3.80 (m, 1H), 3.70 - 3.60 (m, 3H), 3.50 - 3.40 (m, 1H), 3.25 - 3.00 (m, 2H), 3.00-2.80 (m, 2H), 3.45 - 3.27 (m, 2H), 3.94-2.92(m, 2H), 2.43 - 2.05 (m, 5H), 1.90 -1.70 (m, 2H), 1.70 - 1.35 (m, 12H), 1.26 (d, J=6.4 Hz, 3H), 0.94 (t, J=7.2 Hz, 3H). | 443.2 |
| 108 | 1 | $^1$H NMR (400 MHz, CD$_3$OD) δ 8.80 (s, 1H), 6.96 (s, 1H), 3.97 - 3.89 (m, 1H), 3.68 - 3.65 (m, 5H), 3.62 - 3.60 (m, 4H), 3.20 - 3.14 (m, 2H), 3.00 (br t, J=4.8 Hz, 1H), 2.13 - 2.03 (m, 6H), 1.96 - 1.88 (m, 4H), 1.80 - 1.70 (m, 4H), 1.67 - 1.53 (m, 2H), 1.50 - 1.45 (m, 4H), 1.41 - 1.37 (m, 4H), 1.32 (d, J=6.8 Hz, 3H), 0.94 (t, J=6.8 Hz, 3H) | 526.4 |
| 109 | 1 | $^1$H NMR (400 MHz, CD$_3$OD) δ 8.80 (s, 1H), 6.99(s, 1H), 4.09 (br s, 1H), 3.97 - 3.90 (m, 1H), 3.69 (br s, 4H), 3.62 - 3.60(m, 4H), 3.30 - 3.22 (m, 1H), 3.16 - 3.14 (m, 1H), 3.02 - 2.99 (m, 1H), 2.13 - 2.00 (m, 4H), 1.97 - 1.91 (m, 6H), 1.82 - 1.55 (m, 8H), 1.47 - 1.42 (m, 2H), 1.38 - 1.36 (m, 4H), 1.31 (d, J=6.8 Hz, 3H), 0.94 (t, J=6.8 Hz, 3H). | 526.4 |

FIG. 2 (Cont'd)

| No. | General Scheme | NMR | MS |
|---|---|---|---|
| 110 | 1 | $^1$H NMR (400 MHz, CD$_3$OD) δ 8.77 (s, 1H), 7.00 (s, 1H), 6.33 (br s, 1H), 3.98 - 3.90 (m, 1H), 3.72 - 3.65 (m, 9H), 3.20 - 3.13 (m, 1H), 3.06 - 3.01 (m, 1H), 2.59 (br s, 2H), 2.53 - 2.48 (m, 1H), 2.44 - 2.39 (m, 1H), 2.13 (br d, J=11.2 Hz, 4H), 2.06 - 2.02 (m, 1H), 1.91 - 1.81 (m, 1H), 1.79 - 1.66 (m, 3H), 1.63 - 1.54 (m, 1H), 1.50 - 1.45 (m, 4H), 1.40 - 1.38 (m, 4H), 1.32 (d, J=6.4 Hz, 3H), 0.95 (t, J=6.8 Hz, 3H). | 524.4 |
| 111 | 2 | $^1$H NMR (400 MHz, CD$_3$OD) δ 9.23 (s, 1 H), 7.72-7.67 (m, 2 H), 7.17 (s, 1 H), 7.11 (t, J =8.8 Hz, 2 H), 4.76 (s, 1 H), 3.94-3.86 (m, 1 H), 3.71-3.63 (m, 1 H), 3.18-3.04 (m, 1 H), 2.25 (d, J =12.4 Hz, 2 H), 2.12 (d, J =12.4, 2 H), 1.77-1.53 (m, 4 H), 1.52-1.43 (m, 4 H), 1.40-1.34 (m, 4 H), 1.28 (d, J =6.4 Hz, 3 H), 0.94 (t, J =6.8 Hz, 3 H). | 468.2 |
| 112 | 1 | $^1$H NMR (400 MHz, CD$_3$OD) δ 8.55 (s, 1H), 6.41 (s, 1H), 5.98 (br s, 1H), 3.79 - 3.74 (m, 1H), 3.60 - 3.53 (m, 9H), 2.98 - 2.85 (m, 2H), 2.45 - 2.22 (m, 4H), 2.04 - 1.87 (m, 5H),, 1.78 - 1.68 (m, 1H), 1.65 - 1.58 (m, 1H), 1.56 - 1.46 (m, 2H), 1.42- 1.31 (m, 5H), 1.26 - 1.24 (m, 4H), 1.15 (d, J=6.4 Hz, 3H), 0.81 (t, J=7.2 Hz, 3H). | 524.4 |
| 113 | 1 | $^1$H NMR (400 MHz, CD$_3$OD) δ 8.64 (s, 1H), 6.46 (s, 1H), 6.06 (br s, 1H), 3.88 - 3.82 (m, 1H), 3.69 - 3.60 (m, 9H), 3.07 - 2.95 (m, 2H), 2.55 - 2.31 (m, 4H), 2.15 - 1.97 (m, 5H), 1.88 - 1.78 (m, 1H), 1.74 - 1.55 (m, 3H), 1.51 - 1.47 (m, 1H), 1.45 - 1.39 (m, 4H), 1.36 - 1.34 (m, 4H), 1.24 (d, J=6.4 Hz, 3H), 0.91 (t, J=7.2 Hz, 3H). | 524.4 |
| 114 | 1 | $^1$H NMR (400 MHz, CD$_3$OD) δ 8.75 (s, 1H), 6.34 (s, 1H), 3.89 - 3.81 (m, 1H), 3.66 - 3.55 (m, 5H), 3.45 - 3.38 (m, 4H), 3.11 - 3.02 (m, 1H), 2.13 - 2.02 (m, 4H), 1.74 - 1.48 (m, 4H), 1.47 - 1.31 (m, 8H), 1.27 (d, J=6.4 Hz, 3H), 0.91 (t, J=7.2 Hz, 3H). | 415.2 |
| 115 | 1 | $^1$H NMR (400 MHz, CD$_3$OD) δ 8.64 (s, 1H), 6.22 (s, 1H), 4.01 - 3.82 (m, 2H), 3.74 - 3.57 (m, 2H), 3.55 - 3.40 (m, 2H), 3.15 - 3.04 (m, 2H), 2.96 - 2.89 (m, 6H), 2.23 (d, J=13.6 Hz, 2H), 2.16 - 2.00 (m, 4H), 1.99 - 1.86 (m, 2H), 1.77 - 1.33 (m, 12H), 1.29 (d, J=6.4 Hz, 3H), 0.94 (t, J=7.2 Hz, 3H) | 457.3 |
| 116 | 1 | $^1$H NMR (400 MHz, CD$_3$OD) δ 8.98 (s, 1H), 6.93 (s, 1H), 3.94 (q, J=6.4 Hz, 1H), 3.69-3.64 (m, 1H), 3.55-3.52 (m, 2H), 3.40 - 3.36 (m, 1H), 3.24 - 3.14 (m, 3H), 2.21 - 2.11 (m, 6H), 2.07 - 1.97 (m, 2H), 1.79 - 1.65 (m, 3H), 1.62 - 1.53 (m, 1H), 1.50 - 1.43 (m, 4H), 1.39 - 1.37 (m, 4H), 1.32 (d, J=6.4 Hz, 3H), 0.94 (t, J=7.2 Hz, 3H). | 414.3 |
| 117 | 1 | $^1$H NMR (400 MHz, CD$_3$OD) δ 8.53 (s, 1H), 6.12 (s, 1H), 3.89 - 3.81 (m, 1H), 3.76 (br d, J=12.8 Hz, 2H), 3.69 - 3.60 (m, 1H), 3.21 - 3.12 (m, 2H), 3.04 (br t, J=12.0 Hz, 1H), 2.66 - 2.56 (m, 1H), 2.08 (br d, J=12.4 Hz, 6H), 1.93 - 1.80 (m, 2H), 1.76 - 1.50 (m, 4H), 1.49 - 1.33 (m, 8H), 1.28 (d, J=6.4 Hz, 3H), 0.94 (t, J=7.2 Hz, 3H). | 458.4 |

FIG. 2 (Cont'd)

| No. | General Scheme | NMR | MS |
|---|---|---|---|
| 118 | 4 | ¹H NMR (500 MHz, CDCl₃) δ 8.64 (s, 1H), 8.26 (s, 1H), 7.40 (d, J = 8.2 Hz, 2H), 7.28 (d, J = 8.2 Hz, 2H), 6.47 (s, 1H), 4.47 (d, J = 7.7 Hz, 1H), 3.79 – 3.71 (m, 1H), 3.69-3.62 (m, 1H), 3.52 (s, 2H), 3.02 (tt, J = 12.4, 3.7, 1H), 2.84-2.58 (m, 6H), 2.44 (s, 3H), 2.14 (d, J = 10.7 Hz, 2H), 2.05 (d, J = 11.8 Hz, 2H), 1.65 – 1.57 (m, 2H), 1.56 – 1.37 (m, 6H), 1.18 (d, J = 6.5 Hz, 3H), 0.91 (t, J = 7.5 Hz, 3H). | 477.6 |
| 119 | 4 | ¹H NMR (500 MHz, CDCl₃) δ 8.97 (d, J = 23.0 Hz, 2H), 8.71 (s, 1H), 8.24 (t, J = 1.9 Hz, 1H), 6.60 (s, 1H), 4.58 (d, J = 7.7 Hz, 1H), 3.76 (dq, J = 12.9, 6.4 Hz, 1H), 3.72 – 3.64 (m, 1H), 3.09 (s, 3H), 3.05 (tt, J = 11.9, 7.7 Hz, 1H), 2.19-2.12 (m, 2H), 2.12 – 2.05 (m, 2H), 1.68 – 1.59 (m, 1H), 1.56-1.39 (m, 7H), 1.21 (d, J = 6.5 Hz, 3H), 0.93 (t, J = 7.5 Hz, 3H). | 444.2 |
| 120 | 4 | ¹H NMR (500 MHz, CDCl₃) δ 8.96 (dd, J = 27.5, 1.7 Hz, 2H), 8.69 (s, 1H), 8.24 (t, J = 2.0 Hz, 1H), 6.67 (s, 1H), 4.56 (d, J = 7.7 Hz, 1H), 4.10-4.06 (m, 1H), 3.77 (dt, J = 13.4, 6.5 Hz, 1H), 3.14 (td, J = 10.5, 5.1 Hz, 1H), 3.09 (s, 3H), 1.88 (td, J = 23.8, 14.0 Hz, 2H), 1.70 (t, J = 12.7 Hz, 2H), 1.65 – 1.56 (m, 1H), 1.55 – 1.45 (m, 7H), 1.19 (d, J = 6.5 Hz, 3H), 0.92 (t, J = 7.4 Hz, 3H). | 444.2 |
| 121 | 3 | ¹H NMR (500 MHz, CD₃OD) δ 8.73 (s, 1H), 7.56 (d, J = 8.0 Hz, 2H), 7.40 (d, J = 8.0 Hz, 2H), 6.68 (s, 1H), 4.06 (t, J = 8.9 Hz, 1H), 3.69-3.64 (m, 1H), 3.60 (s, 2H), 3.17-3.12 (m, 1H), 2.65 (br s, 8H), 2.40 (s, 3H), 2.31-2.23 (m, 2H), 2.15-2.07 (m, 3H), 1.99-1.93 (m, 1H), 1.67-1.56 (m, 4H), 1.51-1.39 (m, 2H), 1.34 (s, 3H), 1.09 (s, 3H). | 503.5 |
| 122 | 1 | ¹H NMR (500 MHz, CD₃OD) δ 8.63 (s, 1H), 6.44 (s, 1H), 6.04 (s, 1H), 3.89-3.81 (m, 1H), 3.68-3.59 (m, 1H), 3.20-3.12 (m, 3H), 3.08-2.99 (m, 1H), 2.60-2.38 (m, 4H), 2.19-2.02 (m, 4H), 1.88-1.52 (m, 3H), 1.51-1.39 (m, 4H), 1.38-1.27 (m, 5H), 1.24 (d, J = 6.5 Hz, 3H), 0.91 (t, J = 6.3 Hz, 3H). | 455.5 |
| 123 | 4 | ¹H NMR (400 MHz, CDCl₃) δ 8.43 (s, 1H), 6.19 (s, 1H), 4.43 (d, J = 7.1 Hz, 1H), 3.84 – 3.64 (m, 2H), 3.08 – 2.97 (m, 1H), 2.32 (s, 3H), 2.20-2.05 (m, 4H), 1.71 – 1.66 (m, 1H), 1.60-1.40 (m, 5H), 1.25 (brs, 1H), 1.23 (d, J = 6.4 Hz, 3H), 0.97 (t, J = 7.4 Hz, 3H). | 303.4 |
| 124 | 3 (See Example 7) | ¹H NMR (500 MHz, CD₃OD) δ 8.75 (s, 1H), 7.58 (d, J = 8.0 Hz, 2H), 7.42 (d, J = 8.0 Hz, 2H), 6.70 (s, 1H), 4.14-4.07 (m, 1H), 3.66 (s, 2H), 3.61-3.58 (m, 1H), 3.46- 3.44 (m, 1H), 3.42 (s, 3H), 3.17-3.10 (m, 2H), 2.94 (br s, 4H), 2.70 (br s, 4H), 2.62 (s, 3H), 2.21-2.10 (m, 4H), 1.72-1.61 (m, 2H), 1.50-1.42 (m, 2H), 1.30 (d, J = 6.7 Hz, 3H). | 493.4 |
| 125 | 1 | ¹H NMR (500 MHz, CD₃OD) δ 8.53 (s, 1H), 6.30 (s, 1H), 3.89-3.81 (m, 1H), 3.67- 3.56 (m, 1H), 3.05-3.01 (m, 1H), 2.94-2.91 (m, 1H), 2.69 (br s, 1H), 2.22-2.20 (m, 2H), 2.13-2.04 (m, 4H), 1.85-1.65 (m, 7H), 1.61-1.50 (m, 2H), 1.50-1.23 (m, 9H), 1.24 (d, J = 6.5 Hz, 3H), 0.91 (t, J = 6.6 Hz, 3H). | 457.5 |

FIG. 2 (Cont'd)

| No. | General Scheme | NMR | MS |
|---|---|---|---|
| 126 | 3 | $^1$H NMR (500 MHz, CD$_3$OD) δ 8.76 (s, 1H), 7.59 (d, J = 8.2 Hz, 2H), 7.43 (d, J = 8.1 Hz, 2H), 6.69 (s, 1H), 3.71-3.65 (m, 1H), 3.67 (s, 2H), 3.10-3.05 (m, 1H), 3.02-2.65 (m, 8H), 2.61 (s, 3H), 2.45-2.39 (m, 2H), 2.22-2.09 (m, 7H), 2.01-1.87 (m, 2H), 1.71-.64 (m, 2H), 1.50-1.39 (m, 3H), 0.92 (t, J = 7.4 Hz, 3H). | 503.7 |
| 127 | 4 (see Example 10) | $^1$H NMR (500 MHz, CD$_3$OD) δ 8.55 (s, 1H), 6.41 (s, 1H), 3.87-3.83 (m, 1H), 3.65-3.61 (m, 5H), 3.11-2.99 (m, 2H), 2.94-2.92 (m, 1H), 2.47-2.42 (m, 4H), 2.32 (s, 3H), 2.15-1.99 (m, 6H), 1.94-1.88 (m, 2H), 1.86-1.79 (m, 2H), 1.73-1.68 (m, 3H), 1.64-1.52 (m, 2H), 1.50-1.40 (m, 5H), 1.36-1.33 (m, 4H), 1.23 (d, J = 6.5 Hz, 3H), 0.91 (t, J = 7.0 Hz, 3H). | 539.5 |
| 128 | 4 | $^1$H NMR (500 MHz, MeOD) δ 8.71 (s, 1H), 6.51 (s, 1H), 6.12 – 6.03 (m, 1H), 4.32 (q, J = 2.8 Hz, 2H), 3.94 (t, J = 5.5 Hz, 2H), 3.80 (dd, J = 13.0, 6.4 Hz, 1H), 3.71 – 3.58 (m, 1H), 3.12 – 3.00 (m, 1H), 2.60 – 2.51 (m, 2H), 2.13 (dd, J = 29.8, 12.8 Hz, 4H), 1.76 – 1.68 (m, 1H), 1.67 – 1.52 (m, 3H), 1.45 (dd, J = 22.9, 10.1 Hz, 2H), 1.26 (d, J = 6.5 Hz, 3H), 1.01 (t, J = 7.5 Hz, 3H). | 371.4 |
| 129 | 5 | $^1$H NMR (500 MHz, MeOD) δ 8.49 (s, 1H), 6.26 (s, 1H), 3.95 – 3.88 (m, 2H), 3.67 (h, J = 6.5 Hz, 1H), 3.56 – 3.46 (m, 3H), 3.06 – 2.99 (m, 1H), 2.94 (tt, J = 12.2, 3.5 Hz, 1H), 2.00 (dd, J = 23.0, 11.9 Hz, 4H), 1.73 (ddd, J = 12.4, 11.0, 3.7 Hz, 4H), 1.65 – 1.55 (m, 1H), 1.55 – 1.41 (m, 3H), 1.33 (td, J = 13.4, 3.1 Hz, 2H), 1.14 (t, J = 5.1 Hz, 3H), 0.89 (t, J = 7.5 Hz, 3H). | 373.3 |
| 130 | 5 | $^1$H NMR (500 MHz, MeOD) δ 8.58 (d, J = 51.5 Hz, 1H), 8.44 (s, 1H), 6.46 (s, 1H), 5.95 (s, 1H), 3.75 (s, 2H), 3.72 – 3.64 (m, 1H), 3.54 – 3.50 (m, 1H), 3.36 (t, J = 6.1 Hz, 2H), 2.95 (tt, J = 12.0, 3.4 Hz, 1H), 2.72 (s, 2H), 2.01 (dd, J = 29.3, 11.9 Hz, 4H), 1.65 – 1.56 (m, 1H), 1.55 – 1.41 (m, 3H), 1.34 (td, J = 13.4, 3.0 Hz, 2H), 1.15 (d, J = 6.5 Hz, 3H), 0.89 (t, J = 7.4 Hz, 3H). | 370.4 |
| 131 | 1 | $^1$H NMR (500 MHz, MeOD) δ 8.74 (s, 1H), 7.56 (d, J = 8.2 Hz, 2H), 7.40 (d, J = 8.2 Hz, 2H), 6.71 (s, 1H), 3.82 (dd, J = 13.0, 6.5 Hz, 1H), 3.58 (s, 2H), 3.18-3.07 (m, 1H), 2.56 (brs, 8H), 2.32 (s, 3H), 2.12-2.09 (m, 2H), 1.83-1.79 (m, 4H), 1.75-1.64 (m, 3H), 1.61-1.57 (m, 1H), 1.34 (s, 3H), 1.26 (d, J = 6.5 Hz, 3H), 1.00 (t, J = 7.5 Hz, 3H). | 491.4 |
| 132 | 1 | $^1$H NMR (500 MHz, MeOD) δ 8.63 (s, 1H), 7.46 (d, J = 8.2 Hz, 2H), 7.30 (d, J = 8.2 Hz, 2H), 6.60 (s, 1H), 3.72 (dd, J = 13.0, 6.5 Hz, 1H), 3.48 (s, 2H), 3.07-2.98 (m, 1H), 2.45 (brs, 8H), 2.21 (s, 3H), 1.91-1.76 (m, 4H), 1.72-1.69 (m, 3H), 1.67-1.54 (m, 1H), 1.54-1.39 (m, 3H), 1.17 (s, 3H), 1.16 (d, J = 6.5 Hz, 3H), 0.90 (t, J = 7.4 Hz, 3H). | 491.4 |
| 133 | 3 | $^1$H NMR (500 MHz, MeOD) δ 8.74 (s, 1H), 7.55 – 7.51 (m, 2H), 7.35 (d, J = 8.3 Hz, 2H), 6.69 (s, 1H), 4.17 – 4.00 (m, 1H), 3.69 – 3.64 (m, 1H), 3.63 (s, 2H), 3.59 (dd, J = 9.4, 5.2 Hz, 1H), 3.46 – 3.42 (m, 1H), 3.42 (s, 3H), 3.11 (tt, J = 12.1, 3.4 Hz, 1H), 2.23 – 2.14 (m, 2H), 2.10 (dd, J = 7.1, 5.5 Hz, 2H), 1.72 – 1.57 (m, 2H), 1.45 (q, J = 11.1 Hz, 2H), 1.30 (d, J = 6.6 Hz, 3H). | 439.3 |

FIG. 2 (Cont'd)

| No. | General Scheme | NMR | MS |
|---|---|---|---|
| 134 | 3 | ¹H NMR (500 MHz, MeOD) δ 8.87 (s, 1H), 8.13 – 8.00 (m, 2H), 7.87 – 7.71 (m, 2H), 6.83 (s, 1H), 4.18 – 3.99 (m, 1H), 3.66 (tt, J = 10.7, 4.2 Hz, 1H), 3.59 (dd, J = 9.4, 5.2 Hz, 1H), 3.47 – 3.43 (m, 1H), 3.42 (s, 3H), 3.13 (tt, J = 12.0, 3.4 Hz, 1H), 2.27 – 2.16 (m, 2H), 2.11 (ddd, J = 9.8, 5.6, 3.8 Hz, 2H), 1.74 – 1.60 (m, 2H), 1.52 – 1.41 (m, 2H), 1.31 (d, J = 6.6 Hz, 3H). | 449.2 |
| 135 | 5 | ¹H NMR (500 MHz, MeOD) δ 8.59 (s, 1H), 6.35 (s, 1H), 3.77 (dd, J = 12.8, 6.4 Hz, 1H), 3.62 (t, J = 11.0 Hz, 1H), 3.16 (d, J = 11.8 Hz, 2H), 3.04 (s, 2H), 2.80 (t, J = 12.4 Hz, 2H), 2.10 (dd, J = 25.0, 11.1 Hz, 4H), 1.89 (d, J = 13.6 Hz, 2H), 1.71 (dt, J = 13.8, 9.6 Hz, 3H), 1.56 (dt, J = 13.9, 10.4 Hz, 3H), 1.43 (dd, J = 23.3, 10.4 Hz, 2H), 1.24 (d, J = 6.5 Hz, 3H), 0.99 (t, J = 7.4 Hz, 3H). | 373.1 |
| 136 | 5 | ¹H NMR (500 MHz, MeOD) δ 8.59 (s, 1H), 8.12 (d, J = 5.0 Hz, 1H), 6.44 (d, J = 5.1 Hz, 1H), 6.30 (s, 1H), 4.86 (s, 1H), 3.75 (h, J = 6.4 Hz, 1H), 3.63 – 3.55 (m, 1H), 3.19 – 3.11 (m, 1H), 3.03 – 2.96 (m, 3H), 2.30 (s, 3H), 2.06 (dd, J = 22.9, 11.8 Hz, 4H), 1.91 (d, J = 11.0 Hz, 2H), 1.73 – 1.60 (m, 3H), 1.58 – 1.48 (m, 3H), 1.44 – 1.33 (m, 3H), 1.22 (d, J = 6.5 Hz, 3H), 0.96 (t, J = 7.5 Hz, 3H). | 464.4 |
| 137 | 1 (see Example 11) | ¹H NMR (500 MHz, MeOD) δ 8.56 (s, 1H), 6.40 (s, 1H), 4.05 (brs, 4H), 3.85 (dd, J = 12.9, 6.4 Hz, 1H), 3.66-3.60 (m, 1H), 3.23-3.10 (m, 4H), 3.10-2.96 (m, 3H), 2.17-1.99 (m, 6H), 1.98-1.79 (m, 4H), 1.79-1.52 (m, 5H), 1.52-1.31 (m, 9H), 1.24 (d, J = 6.5 Hz, 3H), 0.91 (t, J = 7.1 Hz, 3H). | 574.4 |
| 138 | 4 | ¹H NMR (500 MHz, MeOD) δ 8.74 (s, 1H), 7.55 (d, J = 8.2 Hz, 2H), 7.39 (d, J = 8.1 Hz, 2H), 6.69 (s, 1H), 4.08 (dd, J = 11.9, 6.3 Hz, 1H), 3.69-3.54 (m, 6H), 3.47-3.44 (m, 1H), 3.14-3.08 (m, 1H), 2.54 (brs, 8H), 2.29 (s, 3H), 2.20-2.08 (m, 4H), 1.68-1.61 (m, 2H), 1.49-1.41 (m, 2H), 1.30 (d, J = 6.6 Hz, 3H), 1.22 (t, J = 7.0 Hz, 3H). | 507.6 |
| 139 | 4 | ¹H NMR (500 MHz, MeOD) δ 8.85 (s, 1H), 8.07 (d, J = 8.6 Hz, 2H), 7.69 (d, J = 8.5 Hz, 2H), 6.80 (s, 1H), 4.16 – 4.06 (m, 1H), 3.71 – 3.62 (m, 1H), 3.59 (dd, J = 9.4, 5.2 Hz, 1H), 3.47 – 3.43 (m, 1H), 3.42 (s, 3H), 3.19 – 3.07 (m, 1H), 2.25 – 2.15 (m, 2H), 2.16 – 2.02 (m, 2H), 1.75 – 1.56 (m, 2H), 1.53 – 1.41 (m, 2H), 1.30 (d, J = 6.6 Hz, 3H) | 425.3 |
| 140 | 4 | ¹H NMR (500 MHz, MeOD) δ 8.74 (s, 1H), 7.55 (d, J = 8.2 Hz, 2H), 7.40 (d, J = 8.2 Hz, 2H), 6.69 (s, 1H), 4.13 – 4.06 (m, 1H), 3.74 – 3.68 (m, 4H), 3.68 – 3.63 (m, 1H), 3.59 (dd, J = 9.4, 5.2 Hz, 1H), 3.55 (s, 2H), 3.46 – 3.43 (m, 1H), 3.42 (s, 3H), 3.16 – 3.02 (m, 1H), 2.54 – 2.42 (m, 4H), 2.23 – 2.16 (m, 2H), 2.14 – 2.01 (m, 2H), 1.72 – 1.56 (m, 2H), 1.53 – 1.36 (m, 2H), 1.30 (d, J = 6.6 Hz, 3H). | 480.4 |

FIG. 2 (Cont'd)

| No. | General Scheme | NMR | MS |
|---|---|---|---|
| 141 | 4 | ¹H NMR (500 MHz, MeOD) δ 8.70 (s, 1H), 6.51 (s, 1H), 6.18 – 5.93 (m, 1H), 4.34 – 4.24 (m, 2H), 4.12 – 3.99 (m, 1H), 3.92 (t, J = 5.5 Hz, 2H), 3.69 – 3.59 (m, 1H), 3.57 (dd, J = 9.4, 5.2 Hz, 1H), 3.44 – 3.41 (m, 1H), 3.41 (d, J = 4.3 Hz, 3H), 3.09 – 3.00 (m, 1H), 2.54 (dt, J = 7.1, 2.7 Hz, 2H), 2.19 – 1.96 (m, 4H), 1.67 – 1.51 (m, 2H), 1.49 – 1.36 (m, 2H), 1.28 (d, J = 6.6 Hz, 3H). | 387.3 |
| 142 | 4 | ¹H NMR (500 MHz, MeOD) δ 8.65 (s, 1H), 7.46 (d, J = 8.3 Hz, 2H), 7.31 (d, J = 8.3 Hz, 2H), 6.60 (s, 1H), 4.00 (dd, J = 11.9, 6.0 Hz, 1H), 3.58 (s, 2H), 3.55 (dd, J = 9.7, 5.6 Hz, 1H), 3.49 (dd, J = 9.4, 5.2 Hz, 1H), 3.33 (dd, J = 7.8, 4.4 Hz, 1H), 3.32 (s, 3H), 3.05 – 2.96 (m, 1H), 2.50 (s, 4H), 2.05 (dd, J = 45.8, 10.3 Hz, 4H), 1.77 – 1.68 (m, 4H), 1.54 (dd, J = 21.7, 11.0 Hz, 2H), 1.35 (dd, J = 24.3, 11.1 Hz, 2H), 1.20 (d, J = 6.6 Hz, 3H). | 464.4 |
| 143 | 4 | ¹H NMR (500 MHz, MeOD) δ 8.74 (s, 1H), 7.55 (d, J = 8.3 Hz, 2H), 7.39 (d, J = 8.2 Hz, 2H), 6.69 (s, 1H), 4.09 (dd, J = 11.8, 6.1 Hz, 1H), 3.68 (t, J = 4.7 Hz, 4H), 3.64 (dd, J = 9.5, 5.4 Hz, 1H), 3.58 (dd, J = 9.4, 5.2 Hz, 1H), 3.46 – 3.42 (m, 1H), 3.41 (s, 3H), 3.39 (d, J = 6.9 Hz, 1H), 3.11 (dd, J = 14.1, 10.2 Hz, 1H), 2.54 (s, 2H), 2.45 – 2.38 (m, 2H), 2.14 (dd, J = 44.3, 11.7 Hz, 4H), 1.72 – 1.59 (m, 2H), 1.50 – 1.43 (m, 2H), 1.41 (d, J = 6.7 Hz, 3H), 1.29 (d, J = 6.6 Hz, 3H). | 494.4 |
| 144 | 4 | ¹H NMR (500 MHz, MeOD) δ 8.72 (s, 1H), 7.64 – 7.57 (m, 2H), 7.43 – 7.36 (m, 2H), 6.67 (s, 1H), 4.05 – 3.94 (m, 1H), 3.80 – 3.41 (m, 6H), 3.38 – 3.30 (m, 4H), 3.07 – 2.99 (m, 1H), 2.50-2.30 (m, 4H), 2.24 (s, 3H), 2.05 (dd, J = 47.7, 10.3 Hz, 4H), 1.64 – 1.50 (m, 2H), 1.36 (dd, J = 23.9, 11.2 Hz, 2H), 1.20 (d, J = 6.6 Hz, 3H). | 507.3 |
| 145 | 4 | (formate salt) ¹H NMR (500 MHz, MeOD) δ 8.79 (s, 1H), 8.50 (brs, 1H), 7.58 (d, J = 8.2 Hz, 2H), 7.42 (d, J = 8.2 Hz, 2H), 6.73 (s, 1H), 4.24-4.15 (m, 1H), 3.71-3.62 (m, 1H), 3.66 (s, 2H), 3.18-3.09 (m, 1H), 3.08-2.64(m, 10H), 2.62 (s, 3H), 2.22-2.18 (m, 2H), 2.12-2.09 (m, 2H), 1.73-1.60 (m, 2H), 1.54-1.47 (m, 2H), 1.46 (d, J = 6.7 Hz, 3H). | 488.5 |
| 146 | 4 | ¹H NMR (500 MHz, MeOD) δ 8.96 (s, 1H), 8.37 (d, J = 5.4 Hz, 1H), 7.54 (s, 1H), 7.47 (dd, J = 5.4, 1.4 Hz, 1H), 6.90 (s, 1H), 4.17 – 4.02 (m, 1H), 3.71 – 3.62 (m, 1H), 3.59 (dd, J = 9.4, 5.3 Hz, 1H), 3.44 (dd, J = 9.5, 6.0 Hz, 1H), 3.42 (s, 3H), 3.18 – 3.01 (m, 1H), 2.57 (s, 3H), 2.26 – 2.15 (m, 2H), 2.16 – 2.01 (m, 2H), 1.74 – 1.59 (m, 2H), 1.53 – 1.37 (m, 2H), 1.30 (d, J = 6.6 Hz, 3H). | 396.2 |
| 147 | 4 | ¹H NMR (500 MHz, MeOD) δ 8.88 (s, 1H), 8.87 (dd, J = 2.2, 0.8 Hz, 1H), 8.15 (dd, J = 8.2, 2.2 Hz, 1H), 8.11 (dd, J = 8.2, 0.8 Hz, 1H), 6.87 (s, 1H), 4.16 – 4.02 (m, 1H), 3.70 – 3.62 (m, 1H), 3.59 (dd, J = 9.5, 5.2 Hz, 1H), 3.48 – 3.43 (m, 1H), 3.42 (s, 3H), 3.18 – 3.08 (m, 1H), 2.99 (s, 3H), 2.26 – 2.16 (m, 2H), 2.16 – 2.05 (m, 2H), 1.80 – 1.60 (m, 2H), 1.54 – 1.38 (m, 2H), 1.30 (d, J = 6.7 Hz, 3H). | 439.3 |

FIG. 2 (Cont'd)

| No. | General Scheme | NMR | MS |
|---|---|---|---|
| 148 | 4 | $^1$H NMR (500 MHz, MeOD) δ 8.79 (s, 1H), 7.58 (d, J = 8.2 Hz, 2H), 7.42 (d, J = 8.2 Hz, 2H), 6.73 (s, 1H), 6.18-5.85 (m, 1H), 4.38-4.22 (m, 1H), 3.71-3.64 (m, 1H), 3.62 (s, 2H), 3.15-3.05 (m, 1H), 3.05-2.50 (m, 8H), 2.47 (s, 3H), 2.20-2.10 (m, 4H), 1.71-1.57 (m, 2H), 1.51-1.46 (m, 2H), 1.34 (d, J = 6.9 Hz, 3H). | 499.4 |
| 149 | 4 | (formate salt) $^1$H NMR (500 MHz, MeOD) δ 8.75 (s, 1H), 8.50 (brs, 1H), 7.58 (d, J = 7.8 Hz, 2H), 7.41 (d, J = 8.0 Hz, 2H), 6.71 (s, 1H), 3.67 (s, 5H), 3.40 (s, 3H), 3.13-3.08 (m, 1H), 3.05-2.63 (m, 13H), 2.16 (dd, J = 52.6, 11.0 Hz, 4H), 1.75-1.68 (m, 2H), 1.49-1.42 (m, 2H), 0.88 (d, J = 7.0 Hz, 4H). | 505.4 |
| 150 | See Example 21 | $^1$H NMR (500 MHz, MeOD) δ 8.65 (s, 1H), 7.51 – 7.41 (m, 2H), 7.31 (d, J = 8.2 Hz, 2H), 6.60 (s, 1H), 4.05 – 3.93 (m, 1H), 3.55 (tt, J = 11.0, 4.3 Hz, 1H), 3.52 – 3.43 (m, 7H), 3.37 – 3.29 (m, 4H), 3.01 (ddd, J = 12.0, 7.7, 3.4 Hz, 1H), 2.43 – 2.34 (m, 4H), 2.13 – 1.99 (m, 3H), 1.99 (s, 4H), 1.63 – 1.48 (m, 2H), 1.41 – 1.30 (m, 2H), 1.20 (d, J = 6.6 Hz, 3H). | 521.4 |
| 150-1 | See Example 20 | $^1$H NMR (500 MHz, MeOD) δ 8.77 (s, 1H), 7.58 (d, J = 8.2 Hz, 2H), 7.42 (d, J = 8.1 Hz, 2H), 6.72 (s, 1H), 4.12 (dd, J = 12.1, 6.1 Hz, 1H), 3.72 – 3.64 (m, 2H), 3.63 – 3.57 (m, 3H), 3.48 – 3.41 (m, 4H), 2.91 (t, J = 4.9 Hz, 3H), 2.53 (s, 3H), 2.17 (dd, J = 47.6, 11.9 Hz, 4H), 1.68 (dd, J = 16.3, 6.5 Hz, 2H), 1.48 (q, J = 11.1 Hz, 2H), 1.32 (d, J = 6.6 Hz, 3H). | 479.3 |
| 151 | 4 | $^1$H NMR (500 MHz, MeOD) δ 8.74 (s, 1H), 8.03 (s, 1H), 7.79 (s, 1H), 6.62 (s, 1H), 4.51 – 4.35 (m, 1H), 4.15 – 4.00 (m, 3H), 3.68 – 3.62 (m, 1H), 3.62 – 3.58 (m, 2H), 3.58 – 3.55 (m, 1H), 3.45 – 3.42 (m, 1H), 3.41 (s, 3H), 3.12 – 3.04 (m, 1H), 2.20 – 2.04 (m, 8H), 1.69 – 1.57 (m, 2H), 1.50 – 1.39 (m, 2H), 1.29 (d, J = 6.6 Hz, 3H) | 455.9 |
| 152 | 4 | $^1$H NMR (500 MHz, MeOD) δ 8.72 (s, 1H), 7.92 (s, 1H), 7.75 (s, J = 0.7 Hz, 1H), 6.60 (s, 1H), 4.14 – 4.02 (m, 1H), 3.93 (s, 3H), 3.69 – 3.60 (m, 1H), 3.58 (dd, J = 9.4, 5.2 Hz, 1H), 3.46 – 3.42 (m, 1H), 3.41 (s, 3H), 3.12 – 3.03 (m, 1H), 2.22 – 2.13 (m, 2H), 2.13 – 2.02 (m, 2H), 1.71 – 1.54 (m, 2H), 1.51 – 1.37 (m, 2H), 1.29 (d, J = 6.6 Hz, 3H). | 385.2 |
| 153 | 4 | $^1$H NMR (500 MHz, MeOD) δ 8.72 (s, 1H), 8.01 (s, 1H), 7.78 (s, 1H), 6.61 (s, 1H), 4.32 (t, J = 6.5 Hz, 2H), 4.12-4.04 (m, 1H), 3.70-3.66 (m, 4H), 3.66-3.60 (m, 1H), 3.58 (dd, J = 9.4, 5.2 Hz, 1H), 3.45-3.41 (m, 1H), 3.41 (s, 3H), 3.08 (tt, J = 12.1, 3.5 Hz, 1H), 2.84 (t, J = 6.6 Hz, 2H), 2.57-2.43 (m, 4H), 2.18-2.08 (m, 4H), 1.70-1.56 (m, 2H), 1.49-1.38 (m, 2H), 1.29 (d, J = 6.6 Hz, 3H). | 484.3 |

FIG. 2 (Cont'd)

| No. | General Scheme | NMR | MS |
|---|---|---|---|
| 154 | 5 (See Example 22) | $^1$H NMR (500 MHz, MeOD) δ 8.76 (s, 1H), 8.49 (s, 1H), 8.15 (d, J = 5.0 Hz, 1H), 7.59 (d, J = 8.0 Hz, 2H), 7.45 (d, J = 7.9 Hz, 2H), 6.71 (s, 1H), 6.50 (d, J = 5.0 Hz, 1H), 4.10 (dd, J = 12.1, 6.0 Hz, 1H), 3.85 (s, 4H), 3.71 (s, 2H), 3.69 – 3.62 (m, 1H), 3.58 (dt, J = 14.4, 7.2 Hz, 1H), 3.44 (dd, J = 8.0, 4.5 Hz, 1H), 3.42 (s, 3H), 3.11 (dd, J = 13.6, 10.4 Hz, 1H), 2.68 – 2.63 (m, 4H), 2.31 (s, 3H), 2.23 – 2.05 (m, 4H), 1.71 – 1.57 (m, 2H), 1.45 (dd, J = 23.9, 11.2 Hz, 2H), 1.30 (d, J = 6.6 Hz, 3H). | 571.6 |
| 155 | 4 | $^1$H NMR (500 MHz, MeOD) δ 8.75 (s, 1H), 7.57 (d, J = 8.2 Hz, 2H), 7.40 (d, J = 8.2 Hz, 2H), 6.74 (s, 1H), 4.15 – 4.07 (m, 1H), 4.05 (s, 1H), 3.61 – 3.55 (m, 3H), 3.47 – 3.42 (m, 1H), 3.41 (s, 3H), 3.23 (ddd, J = 11.3, 7.7, 3.5 Hz, 1H), 2.53 (s, 7H), 2.30 (s, 3H), 2.01 (dd, J = 19.1, 8.6 Hz, 2H), 1.93 – 1.87 (m, 4H), 1.75 (dd, J = 17.2, 7.6 Hz, 2H), 1.29 (d, J = 6.6 Hz, 3H). | 493.4 |
| 156 | 4 (See Example 15) | $^1$H NMR (400 MHz, MeOD) δ 8.75 (s, 1H), 7.56 (d, J = 7.9 Hz, 2H), 7.40 (d, J = 8.1 Hz, 2H), 6.70 (s, 1H), 4.10 (dd, J = 12.4, 6.0 Hz, 1H), 3.69 (t, J = 4.6 Hz, 4H), 3.67-3.61 (m, 1H), 3.59 (dd, J = 9.4, 5.2 Hz, 1H), 3.47-3.42 (m, 1H), 3.42 (s, 3H), 3.38 (q, J = 6.6 Hz, 1H), 3.16-3.06 (m, 1H), 2.59-2.50 (m, 2H), 2.46-2.37 (m, 2H), 2.15 (dd, J = 37.3, 11.5 Hz, 4H), 1.73-1.59 (m, 2H), 1.51-1.44 (m, 2H), 1.41 (d, J = 6.7 Hz, 3H), 1.30 (d, J = 6.6 Hz, 3H). | 494.4 |
| 157 | 4 (See Example 15) | $^1$H NMR (400 MHz, MeOD) δ 8.75 (s, 1H), 7.56 (d, J = 8.0 Hz, 2H), 7.40 (d, J = 8.2 Hz, 2H), 6.70 (s, 1H), 4.10 (dd, J = 12.2, 5.9 Hz, 1H), 3.69 (t, J = 4.7 Hz, 4H), 3.67-3.62 (m, 1H), 3.59 (dd, J = 9.4, 5.2 Hz, 1H), 3.47-3.43 (m, 1H), 3.42 (s, 3H), 3.38 (q, J = 6.0 Hz, 1H), 3.18-3.10 (m, 1H), 2.61-2.50 (m, 2H), 2.47-2.37 (m, 2H), 2.20 (d, J = 11.7 Hz, 2H), 2.11 (d, J = 9.3 Hz, 2H), 1.73-1.59 (m, 2H), 1.52-1.43 (m, 2H), 1.41 (d, J = 6.7 Hz, 3H), 1.30 (d, J = 6.6 Hz, 3H). | 494.5 |
| 158 | 4 | $^1$H NMR (500 MHz, MeOD) δ 8.69 (s, 1H), 7.50 (t, J = 1.7 Hz, 1H), 7.41 – 7.37 (m, 1H), 7.28 (t, J = 7.7 Hz, 1H), 7.16 (dd, J = 7.6, 1.3 Hz, 1H), 6.62 (s, 1H), 4.06 – 3.94 (m, 1H), 3.56 (tt, J = 10.8, 4.2 Hz, 1H), 3.49 (dd, J = 9.4, 5.2 Hz, 1H), 3.36 – 3.33 (m, 1H), 3.32 (s, 3H), 3.24 (dd, J = 11.0, 4.7 Hz, 1H), 3.02 (tt, J = 12.1, 3.5 Hz, 1H), 2.64 – 2.53 (m, 2H), 2.40 – 2.30 (m, 2H), 2.10 (dd, J = 13.0, 3.2 Hz, 2H), 2.00 (dd, J = 12.5, 3.5 Hz, 2H), 1.77 – 1.68 (m, 4H), 1.62 – 1.50 (m, 2H), 1.38 (d, J = 6.6 Hz, 4H), 1.35 – 1.30 (m, 1H), 1.20 (d, J = 6.6 Hz, 3H). | 478.4 |
| 159 | 4 | (formate salt) $^1$H NMR (500 MHz, MeOD) δ 8.73 (s, 1H), 8.55 (brs, 1H), 8.01 (s, 1H), 7.83 (s, 1H), 6.64 (s, 1H), 5.04 (s, 2H), 4.25 (q, J = 7.1 Hz, 2H), 4.09 (dd, J = 12.0, 5.9 Hz, 1H), 3.69-3.61 (m, 1H), 3.58 (dd, J = 9.4, 5.2 Hz, 1H), 3.45-3.42 (m, 1H), 3.42 (s, 3H), 3.09 (tt, J = 12.1, 3.5 Hz, 1H), 2.21-2.06 (m, 4H), 1.70-1.58 (m, 2H), 1.50-1.40 (m, 2H), 1.30 (t, J = 7.1 Hz, 3H), 1.29 (d, J = 6.6 Hz, 3H). | 457.1 |

FIG. 2 (Cont'd)

| No. | General Scheme | NMR | MS |
|---|---|---|---|
| 160 | 5 | $^1$H NMR (400 MHz, MeOD) δ 8.72 (s, 1H), 7.91 (s, 1H), 7.70 (s, 1H), 6.58 (s, 1H), 4.76 (s, 2H), 4.09-4.00 (m, 1H), 3.65-3.57 (m, 1H), 3.55 (dd, J = 9.4, 5.1 Hz, 1H), 3.42-3.30 (m, 4H), 3.08-3.00 (m, 1H), 2.17-2.00 (m, 4H), 1.67-1.52 (m, 2H), 1.40 (q, J = 11.5 Hz, 2H), 1.25 (d, J = 6.6 Hz, 3H). | 429.2 |
| 161 | 4 | $^1$H NMR (500 MHz, MeOD) δ 8.74 (s, 1H), 7.56 (d, J = 8.1 Hz, 2H), 7.42 (d, J = 8.0 Hz, 2H), 6.69 (s, 1H), 4.08-4.01 (m, 1H), 3.72 (s, 2H), 3.65 (tt, J = 10.8, 4.2 Hz, 1H), 3.60-3.51 (m, 2H), 3.35 (s, 3H), 3.11 (tt, J = 11.7, 3.4 Hz, 1H), 2.65 (brs, 4H), 2.22-2.16 (m, 2H), 2.13-2.06 (m, 2H), 1.99-1.89 (m, 1H), 1.88-1.77 (m, 5H), 1.65 (q, J = 12.9 Hz, 2H), 1.53-1.40 (m, 2H), 1.30 (d, J = 6.5 Hz, 3H). | 478.4 |
| 162 | 5 | $^1$H NMR (400 MHz, MeOD) δ 8.73 (s, 1H), 7.94 (s, 1H), 7.81 (s, 1H), 6.62 (s, 1H), 5.18 (s, 2H), 4.13-4.01 (m, 1H), 3.76-3.54 (m, 10H), 3.48-3.36 (m, 4H), 3.08 (tt, J = 12.3, 3.3 Hz, 1H), 2.22-2.03 (m, 4H), 1.71-1.55 (m, 2H), 1.44 (q, J = 10.8 Hz, 2H), 1.29 (d, J = 6.6 Hz, 3H). | 498.4 |
| 163 | 5 (See Example 23) | $^1$H NMR (500 MHz, CDCl$_3$) δ 8.66 (s, 1H), 7.41 (d, J = 8.1 Hz, 2H), 7.30 (d, J = 8.1 Hz, 2H), 6.48 (s, 1H), 4.40 (d, J = 7.7 Hz, 1H), 3.79 – 3.71 (m, 1H), 3.69-3.62 (m, 1H), 3.49 (s, 2H), 3.03 (tt, J = 11.7, 3.3 Hz, 1H), 2.51 (m, 8H), 2.27 (s, 3H), 2.11 (dd, J = 40.6, 10.1 Hz, 4H), 1.65 – 1.35 (m, 8H), 1.19 (d, J = 6.5 Hz, 3H), 0.92 (t, J = 7.4 Hz, 3H). | 480.2 |
| 164 | 4 | $^1$H NMR (500 MHz, MeOD) δ 8.65 (s, 1H), 7.46 (d, J = 8.3 Hz, 2H), 7.32 (d, J = 8.2 Hz, 2H), 6.60 (s, 1H), 4.06 – 3.93 (m, 1H), 3.55 (tt, J = 10.8, 4.2 Hz, 1H), 3.49 (dd, J = 9.4, 5.2 Hz, 1H), 3.36 – 3.33 (m, 1H), 3.32 (s, 3H), 3.01 (tt, J = 12.1, 3.5 Hz, 1H), 2.59 (s, 2H), 2.39 (s, 2H), 2.05 (dd, J = 43.7, 12.7 Hz, 4H), 1.73 (d, J = 6.1 Hz, 4H), 1.62 – 1.50 (m, 2H), 1.40 – 1.31 (m, 5H), 1.20 (d, J = 6.6 Hz, 3H). | 478.5 |
| 165 | Diastereomers of Compund 164 separated by chiral column | $^1$H NMR (500 MHz, MeOD) δ 8.65 (s, 1H), 7.47 – 7.42 (m, 2H), 7.32 (d, J = 8.2 Hz, 2H), 6.60 (s, 1H), 4.07 – 3.93 (m, 1H), 3.55 (tt, J = 10.9, 4.3 Hz, 1H), 3.49 (dd, J = 9.4, 5.2 Hz, 1H), 3.36 – 3.33 (m, 1H), 3.32 (s, 3H), 3.01 (ddd, J = 12.1, 7.7, 3.4 Hz, 1H), 2.57 (s, 2H), 2.37 (s, 2H), 2.05 (dd, J = 44.5, 12.2 Hz, 4H), 1.75 – 1.66 (m, 4H), 1.55 (tdd, J = 13.3, 10.3, 6.6 Hz, 2H), 1.42 – 1.30 (m, 5H), 1.20 (d, J = 6.6 Hz, 3H). | 478.3 |
| 166 | Diastereomers of Compound 164 separated by chiral column | $^1$H NMR (500 MHz, MeOD) δ 8.65 (s, 1H), 7.45 (d, J = 8.3 Hz, 2H), 7.31 (d, J = 8.2 Hz, 2H), 6.60 (s, 1H), 3.99 (dt, J = 12.7, 6.3 Hz, 1H), 3.64 – 3.51 (m, 1H), 3.48 (dt, J = 14.5, 7.3 Hz, 1H), 3.39 – 3.32 (m, 2H), 3.32 (s, 3H), 3.01 (ddd, J = 12.0, 8.7, 3.5 Hz, 1H), 2.57 (d, J = 9.1 Hz, 2H), 2.35 (d, J = 8.8 Hz, 2H), 2.13 – 1.97 (m, 4H), 1.75 – 1.68 (m, 4H), 1.55 (ddd, J = 22.6, 10.4, 6.9 Hz, 2H), 1.41 – 1.30 (m, 5H), 1.20 (d, J = 6.6 Hz, 4H). | 478.2 |

FIG. 2 (Cont'd)

| No. | General Scheme | NMR | MS |
|---|---|---|---|
| 167 | 4 | ¹H NMR (500 MHz, MeOD) δ 8.72 (s, 1H), 7.95 (s, J = 0.7 Hz, 1H), 7.78 (s, 1H), 6.61 (s, 1H), 4.12 – 4.04 (m, 1H), 3.98 (d, J = 7.3 Hz, 2H), 3.69 – 3.60 (m, 1H), 3.58 (dd, J = 9.4, 5.2 Hz, 1H), 3.45 – 3.42 (m, 1H), 3.41 (s, 3H), 3.12 – 3.03 (m, 1H), 2.28 – 2.19 (m, 1H), 2.19 – 2.13 (m, 2H), 2.13 – 2.02 (m, 2H), 1.69 – 1.54 (m, 2H), 1.51 – 1.37 (m, 2H), 1.29 (d, J = 6.6 Hz, 3H), 0.94 (d, J = 6.7 Hz, 6H). | 427.1 |
| 168 | 4 | ¹H NMR (500 MHz, MeOD) δ 8.40 (s, 2H), 8.36 (d, J = 5.1 Hz, 1H), 7.39 (d, J = 5.2 Hz, 1H), 6.60 (s, 1H), 4.15 – 4.07 (m, 1H), 3.69 – 3.61 (m, 1H), 3.59 (dd, J = 9.4, 5.2 Hz, 1H), 3.47 – 3.42 (m, 1H), 3.42 (s, 3H), 3.19 – 3.09 (m, 1H), 2.38 (s, 3H), 2.25 – 2.17 (m, 2H), 2.15 – 2.05 (m, 2H), 1.73 – 1.59 (m, 2H), 1.53 – 1.40 (m, 2H), 1.30 (d, J = 6.6 Hz, 3H). | 396.1 |
| 169 | 4 | ¹H NMR (500 MHz, CDCl₃) δ 8.90 (s, 1H), 7.78 – 7.69 (m, 1H), 7.63 – 7.53 (m, 2H), 6.86 (s, 1H), 4.14 – 4.06 (m, 1H), 3.69 – 3.60 (m, 1H), 3.58 (dd, J = 9.4, 5.3 Hz, 1H), 3.46 – 3.42 (m, 1H), 3.41 (s, 3H), 3.15 – 3.05 (m, 1H), 2.23 – 2.14 (m, 2H), 2.13 – 2.05 (m, 2H), 1.71 – 1.57 (m, 2H), 1.51 – 1.39 (m, 2H), 1.30 (d, J = 6.6 Hz, 3H). | 424.1 |
| 170 | 5 | ¹H NMR (500 MHz, MeOD) δ 8.72 (s, J = 20.6 Hz, 1H), 6.51 (s, 1H), 6.30 (d, J = 5.8 Hz, 1H), 4.11 – 3.99 (m, 3H), 3.66 – 3.59 (m, 1H), 3.56 (dd, J = 9.1, 4.9 Hz, 1H), 3.42 (dd, J = 8.5, 5.0 Hz, 1H), 3.40 (s, 3H), 3.10 – 2.96 (m, 2H), 2.51 (d, J = 17.6 Hz, 1H), 2.21 (dt, J = 12.4, 11.5 Hz, 2H), 2.16 – 2.03 (m, 5H), 1.93 – 1.82 (m, 1H), 1.58 (dt, J = 12.7, 11.3 Hz, 2H), 1.42 (dd, J = 23.5, 12.1 Hz, 2H), 1.28 (d, J = 6.6 Hz, 3H). | 412.1 |
| 171 | 5 | ¹H NMR (500 MHz, MeOD) δ 8.78 (s, 1H), 7.58 (d, J = 8.4 Hz, 2H), 7.28 (d, J = 8.4 Hz, 2H), 6.79 (s, 1H), 4.16 – 4.05 (m, 1H), 3.73 (dt, J = 13.3, 6.6 Hz, 1H), 3.68 – 3.62 (m, 3H), 3.58 (dd, J = 9.5, 5.3 Hz, 3H), 3.45 (dd, J = 9.4, 5.8 Hz, 2H), 3.42 (s, 3H), 3.23 (q, J = 7.6 Hz, 1H), 3.13 (ddd, J = 12.1, 7.7, 3.4 Hz, 1H), 2.23 – 2.15 (m, 2H), 2.15 – 2.07 (m, 2H), 1.72 – 1.60 (m, 2H), 1.48 (d, J = 11.2 Hz, 1H), 1.42 (dd, J = 7.0, 4.7 Hz, 2H), 1.37 (dd, J = 6.6, 4.3 Hz, 4H), 1.32 – 1.29 (m, 3H), 1.29 – 1.27 (m, 2H). | 534.2 |
| 172 | 5 | ¹H NMR (400 MHz, dmso) δ 8.89 (s, 1H), 7.59 (d, J = 8.2 Hz, 2H), 7.21 (d, J = 8.3 Hz, 2H), 6.73 (s, 1H), 6.63 (d, J = 7.6 Hz, 1H), 4.59 (d, J = 4.5 Hz, 1H), 3.99 (dd, J = 13.0, 6.4 Hz, 1H), 3.95 – 3.74 (m, 4H), 3.60 – 3.40 (m, 2H), 3.30 (s, 3H), 3.26 (dd, J = 11.9, 5.0 Hz, 1H), 3.20 – 2.79 (m, 5H), 2.05 (dd, J = 7.0, 5.2 Hz, 2H), 2.00 – 1.90 (m, 2H), 1.70 – 1.49 (m, 2H), 1.44 (q, J = 4.7 Hz, 2H), 1.38 – 1.25 (m, 2H), 1.23 (dd, J = 10.2, 4.5 Hz, 2H), 1.19 (d, J = 6.6 Hz, 3H). | 582.4 |

FIG. 2 (Cont'd)

| No. | General Scheme | NMR | MS |
|---|---|---|---|
| 173 | 5 | $^1$H NMR (400 MHz, dmso) δ 8.89 (s, 1H), 7.54 (d, J = 7.3 Hz, 2H), 7.35 (d, J = 7.4 Hz, 2H), 6.72 (s, 1H), 6.62 (d, J = 7.3 Hz, 1H), 4.59 (d, J = 3.9 Hz, 1H), 4.07 – 3.88 (m, 1H), 3.57 (s, 1H), 3.50 (d, J = 5.9 Hz, 2H), 2.96 (ddd, J = 12.6, 8.9, 4.2 Hz, 1H), 2.11 – 2.01 (m, 2H), 1.94 (s, 2H), 1.63 – 1.48 (m, 2H), 1.47 – 1.41 (m, 2H), 1.29 (qdd, J = 5.7, 4.6, 1.8 Hz, 2H), 1.19 (d, J = 6.9 Hz, 3H), 1.14 (dd, J = 6.5, 2.7 Hz, 2H). | 465.2 |
| 174 | 5 | $^1$H NMR (500 MHz, MeOD) δ 8.75 (s, 1H), 7.97 (s, 1H), 7.77 (s, 1H), 6.62 (s, 1H), 4.87 (s, 2H), 4.12-4.04 (m, 1H), 3.64 (tt, J = 10.7, 4.1 Hz, 1H), 3.58 (dd, J = 9.4, 5.1 Hz, 1H), 3.45-3.42 (m, 1H), 3.41 (s, 3H), 3.08 (s, 3H), 3.11-3.04 (m, 1H), 2.22-2.13 (m, 2H), 2.12-2.05 (m, 2H), 1.70-1.56 (m, 2H), 1.50-1.40 (m, 2H), 1.29 (d, J = 6.6 Hz, 3H). | 506.3 |
| 175 | See Example 24 | $^1$H NMR (500 MHz, DMSO) δ 9.19 (s, 1H), 8.40 (d, J = 5.3 Hz, 1H), 7.56 (s, 1H), 7.47 (dd, J = 5.2, 1.4 Hz, 1H), 7.01 (s, 1H), 4.99 (dd, J = 13.4, 6.9 Hz, 1H), 4.62 (d, J = 4.5 Hz, 1H), 3.54 (dd, J = 10.2, 8.1 Hz, 1H), 3.51-3.45 (m, 1H), 3.39 (dd, J = 10.2, 5.7 Hz, 1H), 3.26 (s, 3H), 3.01 (tt, J = 12.1, 3.3 Hz, 1H), 2.95 (s, 3H), 2.12-2.04 (m, 2H), 2.01-1.92 (m, 2H), 1.62-1.51 (m, 2H), 1.39-1.28 (m, 2H), 1.15 (d, J = 6.9 Hz, 3H) | 410.3 |
| 176 | See Example 24 | H NMR (500 MHz, DMSO) δ 9.20 (s, 1H), 8.41 (d, J = 5.3 Hz, 1H), 7.57 (s, 1H), 7.48 (dd, J = 5.2, 1.4 Hz, 1H), 7.02 (s, 1H), 5.00 (dd, J = 12.5, 6.5 Hz, 1H), 3.54 (dd, J = 10.2, 8.1 Hz, 1H), 3.39 (dd, J = 10.2, 5.6 Hz, 1H), 3.29 (s, 3H), 3.26 (s, 3H), 3.24-3.18 (m, 1H), 3.06 (tt, J = 11.9, 3.0 Hz, 1H), 2.95 (s, 3H), 2.20-2.06 (m, 4H), 1.63-1.49 (m, 2H), 1.37-1.20 (m, 2H), 1.16 (d, J = 6.9 Hz, 3H) | 424.3 |
| 177 | 4 (see Example 30) | $^1$H NMR (400 MHz, CD$_3$OD) δ 8.99 (s, J = 16.6 Hz, 1H), 6.46 (s, 1H), 4.11 – 4.01 (m, 1H), 3.94 (t, J = 7.1 Hz, 2H), 3.67 – 3.59 (m, 1H), 3.56 (dd, J = 9.5, 5.2 Hz, 1H), 3.45 – 3.41 (m, 1H), 3.40 (s, 3H), 3.14 – 3.03 (m, 1H), 2.60 (t, J = 8.1 Hz, 2H), 2.30 – 2.20 (m, 2H), 2.18 – 2.01 (m, 4H), 1.67 – 1.51 (m, 2H), 1.50 – 1.36 (m, 2H), 1.28 (d, J = 6.6 Hz, 3H). | 388.8 |
| 178 | 4 (see Example 31) | $^1$H NMR (500 MHz, MeOD) δ 8.94 (s, 1H), 6.45 (s, 1H), 4.78 – 4.72 (m, 3H), 4.70 – 4.61 (m, 1H), 4.23 (s, 2H), 4.10 – 4.00 (m, 1H), 3.66 – 3.58 (m, 1H), 3.56 (dd, J = 9.4, 5.2 Hz, 1H), 3.44 – 3.40 (m, 1H), 3.40 (s, 3H), 3.08 (ddt, J = 14.5, 11.0, 5.5 Hz, 1H), 2.98 (s, 2H), 2.17 – 2.11 (m, 2H), 2.11 – 2.01 (m, 2H), 1.66 – 1.52 (m, 2H), 1.48 – 1.38 (m, 2H), 1.27 (d, J = 6.6 Hz, 3H) | 430.9 |
| 179 | 4 | $^1$H NMR (500 MHz, MeOD) δ 8.82 (s, 1H), 7.60 (s, 1H), 7.52 (d, J = 7.9 Hz, 1H), 7.40 (t, J = 7.6 Hz, 1H), 7.27 (d, J = 7.6 Hz, 1H), 6.72 (s, 1H), 4.15 – 4.06 (m, 1H), 3.76 (s, 2H), 3.69 – 3.62 (m, 1H), 3.59 (dd, J = 9.4, 5.2 Hz, 1H), 3.46 – 3.43 (m, 1H), 3.42 (s, 3H), 3.15 – 3.08 (m, 1H), 2.72 – 2.59 (m, 4H), 2.23 – 2.16 (m, 2H), 2.15 – 2.04 (m, 2H), 1.89 – 1.81 (m, 4H), 1.73 – 1.57 (m, 2H), 1.54 – 1.38 (m, 2H), 1.30 (d, J = 6.6 Hz, 3H). | 465 |

FIG. 2 (Cont'd)

| No. | General Scheme | NMR | MS |
|---|---|---|---|
| 180 | 4 | ¹H NMR (500 MHz, MeOD) δ 8.65 (s, 1H), 7.51 – 7.42 (m, 2H), 7.30 (d, J = 8.2 Hz, 2H), 6.62 (d, J = 17.5 Hz, 1H), 4.05 – 3.91 (m, 2H), 3.59 (t, J = 4.7 Hz, 4H), 3.47 (dt, J = 11.3, 5.7 Hz, 1H), 3.36 – 3.33 (m, 1H), 3.30 (d, J = 2.7 Hz, 3H), 3.13 (ddd, J = 14.5, 7.3, 3.5 Hz, 1H), 2.45 (s, 2H), 2.37 – 2.29 (m, 2H), 1.98 – 1.86 (m, 2H), 1.80 (d, J = 10.0 Hz, 4H), 1.65 (ddd, J = 15.0, 8.8, 2.5 Hz, 2H), 1.32 (d, J = 6.7 Hz, 3H), 1.19 (d, J = 6.6 Hz, 3H). | 495 |
| 181 | 4 | ¹H NMR (500 MHz, MeOD) δ 8.65 (s, 1H), 7.50 – 7.40 (m, 2H), 7.29 (d, J = 8.2 Hz, 2H), 6.64 (s, 1H), 4.04 – 3.97 (m, 1H), 3.95 (s, 1H), 3.58 (t, J = 4.7 Hz, 4H), 3.47 (dd, J = 9.4, 5.2 Hz, 1H), 3.36 – 3.31 (m, 1H), 3.31 (s, 3H), 3.27 (q, J = 6.7 Hz, 1H), 3.16 – 3.07 (m, 1H), 2.43 (s, 2H), 2.35 – 2.26 (m, 2H), 1.97 – 1.86 (m, 2H), 1.80 (d, J = 10.1 Hz, 4H), 1.68 – 1.60 (m, 2H), 1.31 (d, J = 6.7 Hz, 3H), 1.19 (d, J = 6.6 Hz, 3H). | 495 |
| 182 | 4 | ¹H NMR (500 MHz, MeOD) δ 8.65 (s, 1H), 7.50 – 7.41 (m, 2H), 7.29 (d, J = 8.2 Hz, 2H), 6.64 (s, 1H), 4.05 – 3.97 (m, 1H), 3.95 (s, 1H), 3.58 (t, J = 4.7 Hz, 4H), 3.47 (dd, J = 9.4, 5.2 Hz, 1H), 3.36 – 3.31 (m, 1H), 3.31 (s, 3H), 3.27 (q, J = 6.7 Hz, 1H), 3.12 (ddd, J = 11.0, 7.6, 3.2 Hz, 1H), 2.44 (s, 2H), 2.36 – 2.24 (m, 2H), 1.98 – 1.85 (m, 2H), 1.80 (d, J = 10.0 Hz, 4H), 1.70 – 1.57 (m, 2H), 1.31 (d, J = 6.7 Hz, 3H), 1.19 (d, J = 6.6 Hz, 3H). | 495 |
| 183 | 4 | ¹H NMR (500 MHz, MeOD) δ 8.86 (s, 1H), 8.27 (d, J = 5.4 Hz, 1H), 7.46 (s, 1H), 7.42 – 7.36 (m, 1H), 6.84 (s, 1H), 4.02 (dt, J = 12.2, 6.1 Hz, 1H), 3.96 (s, 1H), 3.47 (dt, J = 11.3, 5.7 Hz, 1H), 3.36 – 3.32 (m, 1H), 3.31 (s, 3H), 3.15 – 3.07 (m, 1H), 2.48 (s, 3H), 1.99 – 1.85 (m, 2H), 1.80 (d, J = 10.3 Hz, 4H), 1.69 – 1.59 (m, 2H), 1.19 (d, J = 6.6 Hz, 3H). | 396.3 |
| 184 | 4 | ¹H NMR (500 MHz, MeOD) δ 8.78 (s, 1H), 7.57 (d, J = 8.1 Hz, 2H), 7.39 (d, J = 8.1 Hz, 2H), 6.72 (s, 1H), 4.17 – 4.06 (m, 1H), 3.72 – 3.57 (m, 6H), 3.49 – 3.45 (m, 1H), 3.44 (s, 3H), 3.17 – 3.08 (m, 1H), 2.65-2.55 (m, 4H), 2.17 (dd, J = 45.6, 11.6 Hz, 4H), 1.74 – 1.60 (m, 2H), 1.47 (q, J = 11.4 Hz, 2H), 1.32 (d, J = 6.6 Hz, 3H), 1.00 (q, J = 4.1 Hz, 2H), 0.86 (q, J = 4.2 Hz, 2H). | 507 |
| 185 | 4 | ¹H NMR (500 MHz, MeOD) δ 8.75 (s, 1H), 7.59 – 7.52 (m, 2H), 7.43 – 7.37 (m, 2H), 6.70 (s, 1H), 4.16 – 4.06 (m, 1H), 3.71 – 3.63 (m, 1H), 3.61 (dd, J = 9.4, 5.2 Hz, 1H), 3.46 (dd, J = 6.3, 3.1 Hz, 1H), 3.44 (s, 3H), 3.13 (ddd, J = 12.0, 8.5, 3.5 Hz, 1H), 2.90-2.25 (m, 8H), 2.22 (d, J = 7.2 Hz, 5H), 2.12 (d, J = 11.9 Hz, 2H), 1.68 (tt, J = 13.3, 10.1 Hz, 2H), 1.47 (dd, J = 24.6, 11.7 Hz, 2H), 1.32 (d, J = 6.6 Hz, 3H), 1.02 – 0.95 (m, 2H), 0.87 (q, J = 4.3 Hz, 2H). | 520.1 |
| 186 | 4 | ¹H NMR (500 MHz, DMSO) δ 9.14 (s, 1H), 7.60 (d, J = 0.8 Hz, 1H), 7.46 (d, J = 1.2 Hz, 1H), 6.60 (s, 1H), 6.50 (d, J = 7.7 Hz, 1H), 4.59 (d, J = 4.5 Hz, 1H), 3.97 (dt, J = 13.3, 6.7 Hz, 1H), 3.66 (s, 3H), 3.48 (ddd, J = 23.5, 10.1, 4.9 Hz, 2H), 3.30 (s, 3H), 3.26 (dd, J = 9.4, 7.0 Hz, 1H), 2.93 (tt, J = 11.7, 3.4 Hz, 1H), 2.08 – 1.98 (m, 2H), 1.94 (d, J = 12.5 Hz, 2H), 1.60 – 1.43 (m, 2H), 1.28 (td, J = 13.1, 3.9 Hz, 2H), 1.18 (d, J = 6.6 Hz, 3H). | 385.3 |

FIG. 2 (Cont'd)

| No. | General Scheme | NMR | MS |
|---|---|---|---|
| 187 | 5 (See Example 25) | ¹H NMR (500 MHz, DMSO) δ 8.12 (s, 1H), 6.87 (d, J = 8.1 Hz, 2H), 6.62 (d, J = 8.1 Hz, 2H), 5.96 (s, 1H), 5.83 (d, J = 7.6 Hz, 1H), 3.78 (d, J = 3.4 Hz, 1H), 3.24 – 3.12 (m, 1H), 2.86 – 2.61 (m, 9H), 2.48 (s, 3H), 2.47 – 2.44 (m, 1H), 2.20 – 2.09 (m, 1H), 1.67 (s, 1H), 1.28 – 1.10 (m, 4H), 0.81 – 0.66 (m, 2H), 0.48 (td, J = 12.8, 3.6 Hz, 2H), 0.37 (d, J = 6.6 Hz, 3H). | 495 |
| 188 | 4 | ¹H NMR (500 MHz, MeOD) δ 8.78 (s, 1H), 7.62 (d, J = 7.9 Hz, 2H), 7.46 (d, J = 8.0 Hz, 2H), 6.73 (s, 1H), 6.44 (t, J = 75.4 Hz, 1H), 4.19- 4.10 (m, 2H), 3.85 (dd, J = 9.5, 6.3 Hz, 1H), 3.76 (brs, 4H), 3.65 (dt, J = 6.4, 4.2 Hz, 1H), 3.13 (ddd, J = 12.1, 8.6, 3.4 Hz, 1H), 2.71 (brs, 4H), 2.23-2.17 (m, 2H), 2.13-2.07 (m, 2H), 1.71-1.60 (m, 2H), 1.52-1.44 (m, 2H), 1.36 (d, J = 6.6 Hz, 3H). | 516.4 |
| 189 | 4 | ¹H NMR (500 MHz, MeOD) δ 8.74 (s, 1H), 7.56 (d, J = 8.1 Hz, 2H), 7.41 (d, J = 8.1 Hz, 2H), 6.68 (s, 1H), 3.99 (dd, J = 13.0, 6.7 Hz, 1H), 3.74-3.69 (m, 4H), 3.69-3.62 (m, 1H), 3.58 (s, 2H), 3.11 (tt, J = 12.0, 3.2 Hz, 1H), 2.52 (brs, 4H), 2.24-2.16 (m, 2H), 2.15-2.07 (m, 2H), 1.72-1.57 (m, 3H), 1.56-1.39 (m, 3H), 1.33 (d, J = 6.6 Hz, 3H), 0.91-0.70 (m, 1H), 0.53-0.46 (m, 2H), 0.22-0.08 (m, 2H). | 491 |
| 190 | 4 | ¹H NMR (500 MHz, MeOD) δ 8.95 (s, 1H), 8.38 (d, J = 5.1 Hz, 1H), 7.55 (s, 1H), 7.49 (d, J = 5.2 Hz, 1H), 6.90 (s, 1H), 4.00 (dd, J = 13.0, 6.8 Hz, 1H), 3.71-3.63 (m, 1H), 3.13 (tt, J = 12.5, 3.7 Hz, 1H), 2.58 (s, 3H), 2.25-2.16 (m, 2H), 2.16-2.05 (m, 2H), 1.72-1.57 (m, 3H), 1.55-1.41 (m, 3H), 1.34 (d, J = 6.6 Hz, 3H), 0.88-0.79 (m, 1H), 0.54-0.44 (m, 2H), 0.22-0.09 (m, 2H). | 406.9 |
| 191 | 5 | ¹H NMR [10:3] diastereoisomer ratio major product described: (500 MHz, MeOD) δ 8.56 (s, 2H), 6.51 (s, 1H), 4.09 – 4.01 (m, 1H), 3.67 – 3.59 (m, 1H), 3.56 (dd, J = 9.4, 5.2 Hz, 1H), 3.43 – 3.41 (m, 1H), 3.40 (s, J = 2.3 Hz, 3H), 3.10 – 3.01 (m, 1H), 2.53 – 2.44 (m, 2H), 2.44 – 2.37 (m, 1H), 2.35 (s, 3H), 2.16 – 1.97 (m, 10H), 1.70 – 1.64 (m, 2H), 1.64 – 1.54 (m, 2H), 1.48 – 1.38 (m, 2H), 1.27 (d, J = 6.6 Hz, 2H). | 429 |
| 192 | 4 (see Example 29) | ¹H NMR (500 MHz, MeOD) δ 8.60 (s, 1H), 6.47 (s, 1H), 4.32 (s, 2H), 4.11 – 4.03 (m, 3H), 3.83 (dd, J = 5.8, 4.3 Hz, 2H), 3.66 – 3.59 (m, 1H), 3.57 (dd, J = 9.4, 5.2 Hz, 1H), 3.44 – 3.41 (m, 1H), 3.40 (s, 3H), 3.14 – 3.06 (m, 1H), 2.20 – 2.03 (m, 4H), 1.65 – 1.54 (m, 2H), 1.49 – 1.37 (m, 2H), 1.28 (d, J = 6.6 Hz, 3H). | 404.9 |
| 193 | 4 | ¹H NMR (500 MHz, MeOD) δ 8.84 (s, 1H), 8.70 (s, 1H), 7.88 (s, 1H), 7.64 – 7.54 (m, 3H), 6.77 (s, 1H), 4.15 – 4.07 (m, 1H), 3.70 – 3.62 (m, 1H), 3.59 (dd, J = 9.4, 5.2 Hz, 1H), 3.44 (dd, J = 9.4, 6.0 Hz, 1H), 3.42 (s, 3H), 3.17 – 3.06 (m, 1H), 2.23 – 2.17 (m, 2H), 2.14 – 2.07 (m, 2H), 1.73 – 1.59 (m, 2H), 1.52 – 1.40 (m, 2H), 1.30 (d, J = 6.6 Hz, 3H) | 421.9 |

FIG. 2 (Cont'd)

| No. | General Scheme | NMR | MS |
|---|---|---|---|
| 194 | 4 | $^1$H NMR (500 MHz, MeOD) δ 9.11 (d, J = 2.1 Hz, 1H), 8.95 (d, J = 2.2 Hz, 1H), 8.90 (s, 1H), 8.48 (t, J = 2.1 Hz, 1H), 6.93 (s, 1H), 4.15 – 4.09 (m, 1H), 3.70 – 3.62 (m, 1H), 3.59 (dd, J = 9.5, 5.3 Hz, 1H), 3.44 (dd, J = 9.5, 6.0 Hz, 1H), 3.42 (s, 3H), 3.29 (s, J = 6.1 Hz, 3H), 3.18 – 3.08 (m, 1H), 2.25 – 2.17 (m, 2H), 2.14 – 2.06 (m, 3H), 1.74 – 1.61 (m, 2H), 1.46 (dd, J = 24.1, 11.5 Hz, 3H), 1.31 (d, J = 6.7 Hz, 4H) | 460.8 |
| 195 | 4 | $^1$H NMR (500 MHz, MeOD) δ 8.85 (s, 1H), 8.69 – 8.59 (m, 1H), 8.35 (d, J = 2.7 Hz, 1H), 7.87 (ddd, J = 9.9, 2.7, 1.8 Hz, 1H), 6.84 (s, 1H), 4.15 – 4.06 (m, 1H), 3.70 – 3.61 (m, 1H), 3.59 (dd, J = 9.4, 5.3 Hz, 1H), 3.46 – 3.42 (m, 1H), 3.42 (s, 3H), 3.15 – 3.07 (m, 1H), 2.24 – 2.15 (m, 2H), 2.14 – 2.05 (m, 2H), 1.73 – 1.58 (m, 2H), 1.53 – 1.40 (m, 2H), 1.30 (d, J = 6.7 Hz, 3H). | 400.3 |
| 196 | 4 | $^1$H NMR (500 MHz, DMSO) δ 8.98 (s, 1H), 7.74 – 7.66 (m, 2H), 7.62 – 7.52 (m, 2H), 6.83 (s, 1H), 6.70 (d, J = 7.7 Hz, 1H), 4.61 (s, 1H), 4.01 (dt, J = 13.1, 6.7 Hz, 1H), 3.56 – 3.44 (m, 6H), 3.32 (s, 4H), 3.31 – 3.27 (m, 1H), 2.99 (tt, J = 12.0, 3.5 Hz, 1H), 2.11 – 2.04 (m, 3H), 1.97 (dd, J = 8.9, 3.6 Hz, 2H), 1.93 – 1.78 (m, 4H), 1.65 – 1.49 (m, 2H), 1.36 – 1.26 (m, 2H), 1.20 (d, J = 6.6 Hz, 3H). | 478.9 |
| 197 | 5 | $^1$H NMR (500 MHz, DMSO) δ 8.99 (s, 1H), 7.76 – 7.70 (m, 2H), 7.58 – 7.50 (m, 2H), 6.84 (s, 1H), 6.71 (d, J = 7.7 Hz, 1H), 4.61 (d, J = 4.5 Hz, 1H), 4.07 – 3.74 (m, 5H), 3.56 – 3.43 (m, 2H), 3.32 (s, 3H), 3.28 (dd, J = 15.7, 8.8 Hz, 4H), 2.99 (ddd, J = 11.9, 8.6, 3.5 Hz, 1H), 2.03 (ddd, J = 51.0, 9.8, 6.2 Hz, 4H), 1.66 – 1.49 (m, 2H), 1.37 – 1.26 (m, 2H), 1.20 (d, J = 6.6 Hz, 3H). | 542.9 |
| 198 | 4 | $^1$H NMR (500 MHz, MeOD) δ 8.85 (s, 1H), 8.06 – 8.01 (m, 2H), 7.80 – 7.74 (m, 2H), 6.80 (s, 1H), 4.16 – 4.05 (m, 1H), 3.65 (tt, J = 10.9, 4.2 Hz, 1H), 3.59 (dd, J = 9.4, 5.2 Hz, 1H), 3.46 – 3.43 (m, 1H), 3.42 (s, 3H), 3.10 (tt, J = 12.1, 3.5 Hz, 1H), 2.63 (s, 3H), 2.15 (dd, J = 46.8, 11.8 Hz, 4H), 1.70 – 1.56 (m, 2H), 1.45 (dd, J = 24.0, 11.4 Hz, 2H), 1.30 (d, J = 6.6 Hz, 3H). | 463.9 |
| 199 | 4 | $^1$H NMR (500 MHz, MeOD) δ 8.67 (s, 1H), 6.47 (s, 1H), 6.34 (d, J = 5.4 Hz, 1H), 4.47 (s, 1H), 4.42 (s, 1H), 4.10 – 3.96 (m, 1H), 3.67 – 3.59 (m, 1H), 3.56 (dd, J = 9.4, 5.2 Hz, 1H), 3.44 – 3.41 (m, 1H), 3.40 (s, 3H), 3.09 – 2.99 (m, 2H), 2.40 – 2.28 (m, 1H), 2.28 – 2.18 (m, 1H), 2.16 – 2.09 (m, 2H), 2.07 (d, J = 12.3 Hz, 2H), 2.04 – 1.96 (m, 2H), 1.84 – 1.74 (m, 1H), 1.65 – 1.52 (m, 2H), 1.46 (s, 9H), 1.44 – 1.37 (m, 2H), 1.27 (d, J = 6.6 Hz, 3H). | 513 |
| 200 | 4 | $^1$H NMR (500 MHz, MeOD) δ 8.67 (s, 1H), 6.47 (s, 1H), 6.34 (d, J = 5.5 Hz, 1H), 4.51 – 4.45 (m, 1H), 4.45 – 4.37 (m, 1H), 4.10 – 4.00 (m, 1H), 3.67 – 3.58 (m, 1H), 3.56 (dd, J = 9.4, 5.2 Hz, 1H), 3.43 – 3.40 (m, 1H), 3.40 (d, J = 2.5 Hz, 3H), 3.09 – 2.99 (m, 1H), 2.39 – 2.29 (m, 1H), 2.29 – 2.18 (m, 1H), 2.16 – 2.09 (m, 2H), 2.09 – 2.04 (m, 2H), 2.04 – 1.96 (m, 2H), 1.84 – 1.69 (m, 1H), 1.66 – 1.51 (m, 2H), 1.46 (s, 9H), 1.44 – 1.36 (m, 2H), 1.27 (d, J = 6.6 Hz, 3H). | 513 |

FIG. 2 (Cont'd)

| No. | General Scheme | NMR | MS |
|---|---|---|---|
| 201 | 4 | ¹H NMR (500 MHz, MeOD) δ 9.06 (d, J = 2.1 Hz, 1H), 8.90 (s, 1H), 8.77 (d, J = 1.8 Hz, 1H), 8.41 (t, J = 2.1 Hz, 1H), 6.89 (s, 1H), 4.16 – 4.06 (m, 1H), 3.70 – 3.61 (m, 1H), 3.59 (dd, J = 9.4, 5.3 Hz, 1H), 3.44 (dd, J = 9.5, 6.0 Hz, 1H), 3.42 (s, 3H), 3.16 – 3.08 (m, 1H), 2.24 – 2.17 (m, 2H), 2.14 – 2.06 (m, 2H), 1.72 – 1.60 (m, 2H), 1.51 – 1.40 (m, 2H), 1.30 (d, J = 6.7 Hz, 3H) | 407.8 |
| 202 | 4 | ¹H NMR (500 MHz, MeOD) δ 8.81 (s, 1H), 7.58 (d, J = 8.2 Hz, 2H), 7.42 (d, J = 8.1 Hz, 2H), 6.74 (s, 1H), 4.78 (dd, J = 14.4, 7.2 Hz, 1H), 3.74-3.70 (m, 4H), 3.65 (tt, J = 10.9, 4.3 Hz, 1H), 3.60 (s, 2H), 3.11 (tt, J = 11.8, 3.1 Hz, 1H), 2.53 (brs, 4H), 2.23-2.07 (m, 4H), 1.73-1.55 (m, 2H), 1.52-1.45 (m, 2H), 1.44 (d, J = 7.1 Hz, 3H). | 504.2 |
| 203 | 4 | ¹H NMR (400 MHz, CD₃OD) δ 8.76 (s, 1H), 7.56 (d, J = 8.2 Hz, 2H), 7.41 (d, J = 8.2 Hz, 2H), 6.70 (s, 1H), 4.30-4.20 (m, 1H), 3.75-3.68 (m, 4H), 3.69-3.61 (m, 1H), 3.57 (s, 2H), 3.12 (tt, J = 12.0, 3.3 Hz, 1H), 2.89-2.72 (m, 1H), 2.58-2.41 (m, 4H), 2.39-2.23 (m, 1H), 2.25-2.04 (m, 4H), 1.74-1.53 (m, 2H), 1.52-1.42 (m, 2H), 1.41 (d, J = 6.7 Hz, 3H). | 518.2 |
| 204 | 4 (see Example 13) | ¹H NMR (400 MHz, MeOD) δ 8.76 (s, 1H), 7.57 (d, J = 8.3 Hz, 2H), 7.42 (d, J = 8.2 Hz, 2H), 6.70 (s, 1H), 4.10-3.97 (m, 2H), 3.97-3.89 (m, 1H), 3.83-3.75 (m, 1H), 3.74-3.68 (m, 4H), 3.68-3.61 (m, 1H), 3.56 (s, 2H), 3.12 (tt, J = 11.9, 3.4 Hz, 1H), 2.53-2.46 (m, 4H), 2.24-2.06 (m, 4H), 2.06-1.88 (m, 3H), 1.85-1.74 (m, 1H), 1.72-1.59 (m, 2H), 1.53-1.41 (m, 2H), 1.31 (d, J = 6.5 Hz, 3H). | 506.4 |
| 205 | 4 (see Example 13) | ¹H NMR (400 MHz, MeOD) δ 8.74 (s, 1H), 7.55 (d, J = 8.2 Hz, 2H), 7.40 (d, J = 8.2 Hz, 2H), 6.69 (s, 1H), 4.03-3.95 (m, 2H), 3.94-3.88 (m, 1H), 3.82-3.75 (m, 1H), 3.73-3.68 (m, 4H), 3.67-3.60 (m, 1H), 3.55 (s, 2H), 3.15-3.04 (m, 1H), 2.53-2.44 (m, 4H), 2.24-2.06 (m, 4H), 2.06-1.84 (m, 4H), 1.74-1.55 (m, 2H), 1.53-1.39 (m, 2H), 1.28 (d, J = 6.3 Hz, 3H). | 506.4 |
| 206 | 4 | ¹H NMR (500 MHz, MeOD) δ 8.75 (s, 1H), 8.05 (d, J = 0.8 Hz, 1H), 7.80 (d, J = 0.7 Hz, 1H), 6.64 (s, 1H), 4.10 (dd, J = 11.9, 6.0 Hz, 1H), 3.66 (td, J = 10.7, 5.3 Hz, 1H), 3.61 – 3.57 (m, 1H), 3.47 – 3.44 (m, 1H), 3.43 (s, 3H), 3.14 – 3.07 (m, 1H), 2.15 (dd, J = 38.4, 12.9 Hz, 4H), 1.65 (s, 11H), 1.46 (dd, J = 24.1, 11.2 Hz, 2H), 1.31 (d, J = 6.6 Hz, 3H). | 427.2 |
| 207 | 4 | ¹H NMR (500 MHz, MeOD) δ 8.80 (s, 1H), 8.37 (s, 1H), 8.05 (s, 1H), 7.49 (t, J = 59.8 Hz, 1H), 6.71 (s, 1H), 4.14 – 4.05 (m, 1H), 3.69 – 3.61 (m, 1H), 3.58 (dd, J = 9.4, 5.2 Hz, 1H), 3.44 (dd, J = 9.0, 3.0 Hz, 1H), 3.41 (s, 3H), 3.09 (tt, J = 12.0, 3.5 Hz, 1H), 2.13 (dd, J = 38.4, 12.7 Hz, 4H), 1.70 – 1.58 (m, 2H), 1.45 (dd, J = 24.3, 11.2 Hz, 2H), 1.29 (d, J = 6.6 Hz, 3H). | 421.2 |

FIG. 2 (Cont'd)

| No. | General Scheme | NMR | MS |
|---|---|---|---|
| 208 | 4 | ¹H NMR (500 MHz, MeOD) δ 8.99 (s, 1H), 7.57 (d, J = 2.3 Hz, 1H), 6.73 (s, 1H), 6.52 (d, J = 2.3 Hz, 1H), 4.13 – 4.04 (m, 1H), 3.93 (s, J = 6.7 Hz, 3H), 3.69 – 3.61 (m, 1H), 3.58 (dd, J = 9.4, 5.2 Hz, 1H), 3.47 – 3.42 (m, 1H), 3.41 (s, 3H), 3.13 – 3.04 (m, 1H), 2.22 – 2.15 (m, 2H), 2.12 – 2.03 (m, 2H), 1.67 – 1.56 (m, 2H), 1.50 – 1.39 (m, 2H), 1.29 (d, J = 6.6 Hz, 3H) | 385.2 |
| 209 | 4 | ¹H NMR (500 MHz, MeOD) δ 8.71 (s, 1H), 7.95 (s, J = 0.5 Hz, 1H), 7.78 (s, J = 15.7 Hz, 1H), 6.60 (s, J = 3.5 Hz, 1H), 4.33 (t, J = 5.3 Hz, 2H), 4.11 – 4.04 (m, 1H), 3.77 (t, J = 5.3 Hz, 2H), 3.68 – 3.60 (m, 1H), 3.58 (dd, J = 9.4, 5.2 Hz, 1H), 3.45 – 3.42 (m, 1H), 3.41 (s, 3H), 3.34 (d, J = 2.4 Hz, 3H), 3.12 – 3.01 (m, 1H), 2.20 – 2.13 (m, 2H), 2.11 – 2.03 (m, 2H), 1.68 – 1.56 (m, 2H), 1.44 (q, J = 11.1 Hz, 2H), 1.29 (d, J = 6.6 Hz, 3H) | 429.3 |
| 210 | 4 | ¹H NMR (500 MHz, MeOD) δ 8.64 (s, 1H), 7.80 – 7.70 (m, 2H), 7.61 (t, J = 7.6 Hz, 1H), 6.74 (s, 1H), 4.57 (s, 2H), 4.15 – 4.07 (m, 1H), 3.69 – 3.62 (m, 1H), 3.59 (dd, J = 9.4, 5.3 Hz, 1H), 3.44 (dd, J = 9.5, 6.0 Hz, 1H), 3.42 (s, 3H), 3.19 – 3.10 (m, 1H), 2.24 – 2.16 (m, 2H), 2.15 – 2.07 (m, 2H), 1.74 – 1.62 (m, 2H), 1.52 – 1.41 (m, 2H), 1.30 (d, J = 6.6 Hz, 3H) | 436.3 |
| 211 | 4 (See Example 14) | ¹H NMR (500 MHz, MeOD) δ 8.74 (s, 1H), 7.56 (d, J = 8.1 Hz, 2H), 7.41 (d, J = 8.1 Hz, 2H), 6.69 (s, 1H), 4.09-4.01 (m, 1H), 3.74-3.69 (m, 4H), 3.69-3.62 (m, 1H), 3.61-3.51 (m, 4H), 3.35 (s, 3H), 3.12 (ddd, J = 12.2, 7.9, 3.5 Hz, 1H), 2.50 (brs, 4H), 2.23-2.07 (m, 4H), 1.95 (td, J = 13.5, 6.0 Hz, 1H), 1.82 (td, J = 13.3, 6.2 Hz, 1H), 1.71-1.61 (m, 2H), 1.52-1.42 (m, 2H), 1.30 (d, J = 6.5 Hz, 3H). | 494.2 |
| 212 | 4 (See Example 14) | ¹H NMR (500 MHz, MeOD) δ 8.74 (s, 1H), 7.56 (d, J = 8.2 Hz, 2H), 7.41 (d, J = 8.2 Hz, 2H), 6.69 (s, 1H), 4.09-4.01 (m, 1H), 3.73-3.69 (m, 4H), 3.70-3.63 (m, 1H), 3.61-3.52 (m, 4H), 3.36 (s, 3H), 3.12 (tt, J = 12.2, 3.5 Hz, 1H), 2.50 (brs, 4H), 2.23-2.08 (m, 4H), 1.99-1.91 (m, 1H), 1.87-1.79 (m, 1H), 1.71-1.61 (m, 2H), 1.52-1.42 (m, 2H), 1.31 (d, J = 6.5 Hz, 3H). | 494.2 |
| 213 | 4 | ¹H NMR (400 MHz, CD₃OD) δ 8.98 (s, 1H), 8.38 (d, J = 5.3 Hz, 1H), 7.55 (s, 1H), 7.48 (d, J = 5.3 Hz, 1H), 6.91 (s, 1H), 4.33-4.21 (m, 1H), 3.66 (tt, J = 7.5, 4.1 Hz, 1H), 3.13 (tt, J = 11.7, 3.4 Hz, 1H), 2.87-2.70 (m, 1H), 2.57 (s, 3H), 2.41-2.24 (m, 1H), 2.24-2.05 (m, 4H), 1.73-1.54 (m, 2H), 1.54-1.44 (m, 2H), 1.42 (d, J = 6.7 Hz, 3H). | 434.1 |
| 214 | 4 | ¹H NMR (400 MHz, MeOD) δ 8.75 (s, 1H), 7.56 (d, J = 8.1 Hz, 2H), 7.41 (d, J = 8.1 Hz, 2H), 6.70 (s, 1H), 4.10-3.99 (m, 1H), 3.74-3.70 (m, 4H), 3.69-3.61 (m, 3H), 3.59 (s, 2H), 3.45 (dd, J = 9.3, 6.3 Hz, 1H), 3.12 (tt, J = 11.5, 3.3 Hz, 1H), 2.54 (brs, 4H), 2.23-2.06 (m, 4H), 1.73-1.59 (m, 2H), 1.53-1.39 (m, 2H), 1.31 (d, J = 6.6 Hz, 3H), 1.20 (dd, J = 7.8, 6.2 Hz, 6H). | 508.5 |

FIG. 2 (Cont'd)

| No. | General Scheme | NMR | MS |
|---|---|---|---|
| 215 | 4 | ¹H NMR (400 MHz, MeOD) δ 8.95 (s, 1H), 8.37 (d, J = 5.4 Hz, 1H), 7.54 (s, 1H), 7.47 (d, J = 5.3 Hz, 1H), 6.90 (s, 1H), 4.09-3.99 (m, 1H), 3.73-3.61 (m, 3H), 3.44 (dd, J = 9.4, 6.4 Hz, 1H), 3.18-3.06 (m, 1H), 2.57 (s, 3H), 2.24-2.05 (m, 4H), 1.73-1.57 (m, 2H), 1.53-1.39 (m, 2H), 1.31 (d, J = 6.6 Hz, 3H), 1.19 (dd, J = 7.7, 6.2 Hz, 6H). | 424.4 |
| 216 | 4 | ¹H NMR (400 MHz, MeOD) δ 8.73 (s, 1H), 7.56 (d, J = 8.2 Hz, 2H), 7.40 (d, J = 8.2 Hz, 2H), 6.68 (s, 1H), 4.04-3.94 (m, 1H), 3.67 (tt, J = 10.6, 4.3 Hz, 1H), 3.59 (s, 2H), 3.12 (tt, J = 12.0, 3.3 Hz, 1H), 2.57 (brs, 8H), 2.34 (s, 3H), 2.25-2.16 (m, 2H), 2.15-2.06 (m, 2H), 1.72-1.57 (m, 3H), 1.54-1.40 (m, 3H), 1.34 (d, J = 6.6 Hz, 3H), 0.82 (d, J = 7.9 Hz, 1H), 0.50 (dd, J = 8.1, 1.5 Hz, 2H), 0.15 (td, J = 10.5, 5.5 Hz, 2H). | 503.4 |
| 217 | 4 | ¹H NMR (500 MHz, MeOD) δ 8.77 (s, 1H), 7.57 (s, J = 14.6 Hz, 1H), 7.49 (d, J = 7.8 Hz, 1H), 7.38 (t, J = 7.6 Hz, 1H), 7.25 (d, J = 7.6 Hz, 1H), 6.70 (s, 1H), 4.13 – 4.06 (m, 1H), 3.73 – 3.68 (m, 4H), 3.68 – 3.61 (m, 1H), 3.62 – 3.58 (m, 1H), 3.57 (s, J = 7.6 Hz, 2H), 3.47 – 3.42 (m, 1H), 3.41 (s, 3H), 3.14 – 3.05 (m, 1H), 2.55 – 2.45 (m, 4H), 2.23 – 2.15 (m, 2H), 2.14 – 1.98 (m, 2H), 1.72 – 1.58 (m, 2H), 1.52 – 1.37 (m, 2H), 1.30 (d, J = 6.6 Hz, 3H) | 480.2 |
| 218 | 4 | ¹H NMR (500 MHz, MeOD) δ 8.77 (s, 1H), 7.56 (s, 1H), 7.49 (d, J = 7.9 Hz, 1H), 7.38 (t, J = 7.6 Hz, 1H), 7.24 (d, J = 7.6 Hz, 1H), 6.70 (s, 1H), 4.14 – 4.05 (m, 1H), 3.70 – 3.62 (m, 1H), 3.61 – 3.55 (m, 3H), 3.47 – 3.43 (m, 1H), 3.42 (s, 3H), 3.16 – 3.01 (m, 1H), 2.70 – 2.37 (m, 8H), 2.31 – 2.26 (m, 3H), 2.24 – 2.16 (m, 2H), 2.14 – 2.01 (m, 2H), 1.71 – 1.59 (m, 2H), 1.53 – 1.39 (m, 2H), 1.30 (d, J = 6.6 Hz, 3H) | 493.3 |
| 219 | 5 | ¹H NMR (500 MHz, MeOD) δ 8.83 (s, 1H), 8.69 (s, 1H), 8.40 (s, 1H), 8.04 (t, J = 2.0 Hz, 1H), 6.81 (s, 1H), 4.15 – 4.07 (m, 1H), 3.74 – 3.69 (m, 4H), 3.69 – 3.64 (m, 1H), 3.64 (d, J = 5.5 Hz, 2H), 3.59 (dd, J = 9.4, 5.2 Hz, 1H), 3.47 – 3.42 (m, 1H), 3.42 (s, 3H), 3.17 – 3.06 (m, 1H), 2.57 – 2.47 (m, 4H), 2.25 – 2.15 (m, 2H), 2.14 – 2.04 (m, 2H), 1.72 – 1.59 (m, 2H), 1.52 – 1.39 (m, 2H), 1.30 (d, J = 6.6 Hz, 3H). | 481.3 |
| 220 | 5 | ¹H NMR (500 MHz, MeOD) δ 8.73 (s, 1H), 8.51 (d, J = 1.8 Hz, 1H), 8.49 (dd, J = 4.9, 1.5 Hz, 1H), 8.12 (s, 1H), 7.84 (s, 1H), 7.79 – 7.70 (m, 1H), 7.43 (dd, J = 7.9, 4.9 Hz, 1H), 6.62 (s, 1H), 5.45 (s, 2H), 4.12 – 4.02 (m, 1H), 3.68 – 3.60 (m, 1H), 3.57 (dd, J = 9.4, 5.2 Hz, 1H), 3.46 – 3.41 (m, 1H), 3.41 (s, 3H), 3.13 – 3.00 (m, 1H), 2.20 – 2.12 (m, 2H), 2.12 – 2.02 (m, 2H), 1.69 – 1.54 (m, 2H), 1.49 – 1.36 (m, 2H), 1.28 (d, J = 6.6 Hz, 3H). | 462.3 |
| 221 | 4 | ¹H NMR (500 MHz, MeOD) δ 8.75 (s, 1H), 8.11 (s, 1H), 7.90 (s, 1H), 6.63 (s, 1H), 5.63 – 5.56 (m, 1H), 5.11 – 5.04 (m, 4H), 4.12 – 4.05 (m, 1H), 3.68 – 3.60 (m, 1H), 3.58 (dd, J = 9.4, 5.2 Hz, 1H), 3.45 – 3.42 (m, 1H), 3.41 (s, 3H), 3.13 – 3.03 (m, 1H), 2.21 – 2.13 (m, 2H), 2.13 – 2.04 (m, 2H), 1.69 – 1.57 (m, 2H), 1.51 – 1.38 (m, 2H), 1.29 (d, J = 6.6 Hz, 3H) | 427.2 |

FIG. 2 (Cont'd)

| No. | General Scheme | NMR | MS |
|---|---|---|---|
| 222 | 4 | ¹H NMR (500 MHz, MeOD) δ 8.73 (s, 1H), 8.05 (s, 1H), 7.85 (s, 1H), 6.63 (s, 1H), 4.47 (t, J = 6.5 Hz, 2H), 4.12 – 4.02 (m, 1H), 3.68 – 3.61 (m, 1H), 3.58 (dd, J = 9.4, 5.2 Hz, 1H), 3.46 – 3.42 (m, 1H), 3.41 (s, 3H), 3.12 – 3.03 (m, 1H), 3.06 (t, J = 6.5 Hz, 2H), 2.21 – 2.13 (m, 2H), 2.13 – 2.04 (m, 2H), 1.70 – 1.56 (m, 2H), 1.51 – 1.39 (m, 2H), 1.29 (d, J = 6.6 Hz, 3H). | 424.3 |
| 223 | 5 (See Example 17) | ¹H NMR (500 MHz, MeOD) δ 8.77 (s, 1H), 7.56 (s, 1H), 7.50 (dd, J = 5.3, 3.9 Hz, 1H), 7.39 (t, J = 7.6 Hz, 1H), 7.26 (d, J = 7.6 Hz, 1H), 6.71 (s, 1H), 4.14 – 4.04 (m, 1H), 3.70 (s, 2H), 3.69 – 3.62 (m, 1H), 3.59 (dd, J = 9.4, 5.2 Hz, 1H), 3.47 – 3.42 (m, 1H), 3.42 (s, 3H), 3.15 – 3.04 (m, 1H), 2.92 (t, J = 13.2 Hz, 2H), 2.80 (t, J = 7.0 Hz, 2H), 2.35 – 2.23 (m, 2H), 2.23 – 2.16 (m, 2H), 2.13 – 2.05 (m, 2H), 1.72 – 1.60 (m, 2H), 1.51 – 1.39 (m, 2H), 1.30 (d, J = 6.6 Hz, 3H). | 500.3 |
| 224 | 5 | ¹H NMR (500 MHz, MeOD) δ 8.80 (s, 1H), 7.61 (d, J = 1.5 Hz, 1H), 7.55 – 7.49 (m, 1H), 7.40 (t, J = 7.6 Hz, 1H), 7.30 (d, J = 7.7 Hz, 1H), 6.71 (s, 1H), 5.30 – 5.13 (m, 1H), 4.15 – 4.04 (m, 1H), 3.80 (dd, J = 34.0, 12.7 Hz, 2H), 3.69 – 3.61 (m, 1H), 3.59 (dd, J = 9.4, 5.2 Hz, 1H), 3.46 – 3.42 (m, 1H), 3.41 (s, 3H), 3.15 – 3.06 (m, 1H), 3.06 – 2.94 (m, 2H), 2.81 (ddd, J = 31.1, 12.0, 5.0 Hz, 1H), 2.65 – 2.53 (m, 1H), 2.31 – 2.22 (m, 1H), 2.22 – 2.15 (m, 2H), 2.13 – 2.06 (m, 2H), 2.06 – 1.99 (m, 1H), 1.72 – 1.57 (m, 2H), 1.52 – 1.37 (m, 2H), 1.30 (d, J = 6.6 Hz, 3H). | 482.4 |
| 225 | 5 | ¹H NMR (500 MHz, MeOD) δ 8.81 (s, 1H), 7.60 (s, 1H), 7.51 (d, J = 7.8 Hz, 1H), 7.39 (t, J = 7.6 Hz, 1H), 7.27 (d, J = 7.6 Hz, 1H), 6.72 (s, 1H), 5.19 (ddd, J = 55.6, 6.6, 5.2 Hz, 1H), 4.14 – 4.05 (m, 1H), 3.73 (dd, J = 36.3, 12.7 Hz, 2H), 3.68 – 3.61 (m, 1H), 3.59 (dd, J = 9.4, 5.2 Hz, 1H), 3.47 – 3.43 (m, 1H), 3.42 (s, 3H), 3.15 – 3.07 (m, 1H), 2.98 – 2.87 (m, 2H), 2.72 (ddd, J = 30.8, 11.9, 5.0 Hz, 1H), 2.50 (dd, J = 15.2, 8.6 Hz, 1H), 2.29 – 2.22 (m, 1H), 2.22 – 2.15 (m, 2H), 2.09 (t, J = 9.4 Hz, 2H), 2.07 – 1.92 (m, 1H), 1.72 – 1.58 (m, 2H), 1.52 – 1.40 (m, 2H), 1.30 (d, J = 6.6 Hz, 3H) | 482.4 |
| 226 | 5 | ¹H NMR (400 MHz, CD₃OD) δ 8.88 (d, J = 1.7 Hz, 1H), 8.84 (d, J = 1.3 Hz, 1H), 8.16 (dd, J = 8.2, 2.2 Hz, 1H), 7.67 (d, J = 8.2 Hz, 1H), 6.86 (s, 1H), 4.17 – 4.06 (m, 1H), 3.91 – 3.75 (m, 2H), 3.73 – 3.55 (m, 4H), 3.48 – 3.43 (m, 1H), 3.43 (s, 3H), 3.13 (tt, J = 12.9, 3.8 Hz, 1H), 2.65 – 2.54 (m, 2H), 2.53 – 2.44 (m, 2H), 2.34 (s, 3H), 2.25 – 2.16 (m, 2H), 2.16 – 2.04 (m, 2H), 1.77 – 1.59 (m, 2H), 1.46 (q, J = 11.2 Hz, 2H), 1.30 (dd, J = 6.6, 1.6 Hz, 3H). | 508.5 |

FIG. 2 (Cont'd)

| No. | General Scheme | NMR | MS |
|---|---|---|---|
| 227 | 5 | $^1$H NMR (400 MHz, CD$_3$OD) δ 8.88 (s, 1H), 8.84 (dd, J = 2.2, 0.8 Hz, 1H), 8.16 (dd, J = 8.1, 2.3 Hz, 1H), 7.70 (dd, J = 8.1, 0.8 Hz, 1H), 6.86 (s, 1H), 4.18 – 4.04 (m, 1H), 3.80 (s, 4H), 3.68 (dd, J = 6.4, 3.9 Hz, 3H), 3.64 (dd, J = 4.3, 3.3 Hz, 2H), 3.59 (dd, J = 9.4, 5.3 Hz, 1H), 3.47 – 3.43 (m, 1H), 3.42 (s, 3H), 3.13 (tt, J = 12.0, 3.3 Hz, 1H), 2.24 – 2.15 (m, 2H), 2.11 (ddt, J = 11.0, 7.2, 2.5 Hz, 2H), 1.75 – 1.57 (m, 2H), 1.54 – 1.38 (m, 2H), 1.30 (d, J = 6.6 Hz, 3H). | 495.4 |
| 228 | 5 (See Example 16) | $^1$H NMR (400 MHz, CD$_3$OD) δ 8.89 (s, 1H), 8.87 (dd, J = 2.2, 0.8 Hz, 1H), 8.16 (dd, J = 8.2, 2.2 Hz, 1H), 8.11 (dd, J = 8.2, 0.9 Hz, 1H), 6.87 (s, 1H), 4.23 (dt, J = 7.9, 6.6 Hz, 1H), 4.16 – 4.07 (m, 1H), 3.71 – 3.62 (m, 1H), 3.62 – 3.55 (m, 1H), 3.47 – 3.43 (m, 1H), 3.43 – 3.41 (m, 3H), 3.18 – 3.08 (m, 1H), 2.25 – 2.16 (m, 2H), 2.16 – 2.06 (m, 2H), 1.75 – 1.58 (m, 2H), 1.53 – 1.40 (m, 2H), 1.30 (dd, J = 6.6, 2.1 Hz, 9H). | 467.4 |
| 229 | 7 | $^1$H NMR (400 MHz, dmso) δ 8.90 (s, 1H), 7.59 (d, J = 8.2 Hz, 2H), 7.34 (d, J = 8.2 Hz, 2H), 6.73 (s, 1H), 6.60 (d, J = 7.8 Hz, 1H), 3.99 (dt, J = 13.3, 6.7 Hz, 1H), 3.62 – 3.55 (m, 4H), 3.51 (dd, J = 9.4, 5.4 Hz, 1H), 3.47 (s, 2H), 3.03 – 2.90 (m, 1H), 2.64 – 2.56 (m, 1H), 2.41 – 2.34 (m, 4H), 2.07 – 1.99 (m, 2H), 1.89 (dd, J = 9.8, 8.1 Hz, 2H), 1.63 – 1.44 (m, 2H), 1.25 – 1.10 (m, 5H). Note that some signals were obscured by H2O. | 479.4 |
| 230 | 4 | $^1$H NMR (500 MHz, MeOD) δ 8.80 (s, 1H), 8.72 (dd, J = 2.3, 0.7 Hz, 1H), 8.04 (dd, J = 8.1, 2.3 Hz, 1H), 7.60 (d, J = 7.8 Hz, 1H), 6.79 (s, 1H), 4.14 – 4.06 (m, 1H), 3.74 – 3.70 (m, 4H), 3.68 (s, 2H), 3.65 (ddd, J = 10.9, 7.6, 3.2 Hz, 1H), 3.59 (dd, J = 9.4, 5.2 Hz, 1H), 3.46 – 3.43 (m, 1H), 3.42 (s, 3H), 3.12 (tt, J = 12.1, 3.5 Hz, 1H), 2.57 – 2.50 (m, 4H), 2.27 – 2.04 (m, 4H), 1.73 – 1.60 (m, 2H), 1.51 – 1.39 (m, 2H), 1.30 (d, J = 6.6 Hz, 3H). | 481.3 |
| 231 | 4 | $^1$H NMR (500 MHz, MeOD) δ 8.82 (s, 1H), 8.59 (d, J = 1.7 Hz, 1H), 8.30 (s, 1H), 7.91 (s, 1H), 6.80 (s, 1H), 4.12 (dd, J = 12.1, 6.0 Hz, 1H), 3.71 – 3.64 (m, 1H), 3.61 (dd, J = 9.4, 5.2 Hz, 1H), 3.48 – 3.45 (m, 1H), 3.44 (s, 3H), 3.14 (dd, J = 13.8, 10.4 Hz, 1H), 2.45 (s, 3H), 2.17 (dd, J = 45.6, 12.1 Hz, 4H), 1.67 (dd, J = 22.1, 11.3 Hz, 2H), 1.48 (dd, J = 23.9, 11.0 Hz, 2H), 1.32 (d, J = 6.6 Hz, 3H). | 396.2 |
| 232 | 5 | $^1$H NMR (500 MHz, MeOD) δ 8.90 – 8.85 (m, 1H), 8.60 (s, 1H), 8.17 (s, 1H), 6.86 (s, 1H), 4.11 (dd, J = 11.9, 5.9 Hz, 1H), 3.69 – 3.62 (m, 2H), 3.61 – 3.54 (m, 2H), 3.49 – 3.43 (m, 2H), 3.42 (s, 3H), 3.14 (t, J = 13.8 Hz, 1H), 2.15 (dd, J = 48.7, 12.2 Hz, 4H), 2.06 – 2.00 (m, 2H), 1.99 – 1.93 (m, 2H), 1.73 – 1.61 (m, 2H), 1.46 (q, J = 11.9 Hz, 2H), 1.30 (d, J = 6.5 Hz, 3H). | 479.4 |
| 233 | 5 | $^1$H NMR (500 MHz, MeOD) δ 8.92 – 8.82 (m, 2H), 8.51 (s, 1H), 8.10 (s, 1H), 6.86 (s, 1H), 4.11 (h, J = 6.1 Hz, 1H), 3.91 – 3.63 (m, 7H), 3.62 – 3.50 (m, 3H), 3.44 (dd, J = 8.1, 4.9 Hz, 1H), 3.42 (s, 3H), 3.14 (dd, J = 20.1, 7.9 Hz, 1H), 2.16 (dd, J = 48.0, 12.2 Hz, 4H), 1.76 – 1.59 (m, 2H), 1.46 (q, J = 11.8 Hz, 2H), 1.31 (d, J = 6.6 Hz, 3H). | 495.4 |

FIG. 2 (Cont'd)

| No. | General Scheme | NMR | MS |
|---|---|---|---|
| 234 | 5 | ¹H NMR (500 MHz, MeOD) δ 8.89 (d, J = 2.2 Hz, 1H), 8.86 (s, 1H), 8.49 (d, J = 2.0 Hz, 1H), 8.08 (t, J = 2.1 Hz, 1H), 6.86 (s, 1H), 4.15 – 4.07 (m, 1H), 3.83 (s, 2H), 3.66 (tt, J = 10.8, 4.2 Hz, 1H), 3.61 – 3.51 (m, 3H), 3.44 (dd, J = 6.2, 3.3 Hz, 1H), 3.42 (s, 3H), 3.18 – 3.09 (m, 1H), 2.64 – 2.41 (m, 4H), 2.34 (s, 3H), 2.15 (dd, J = 47.8, 10.4 Hz, 4H), 1.72 – 1.61 (m, 2H), 1.46 (q, J = 11.2 Hz, 2H), 1.30 (d, J = 6.6 Hz, 3H). | 508.4 |
| 235 | 5 | ¹H NMR (400 MHz, MeOD) δ 8.75 (s, 1H), 7.99 (s, 1H), 7.82 (s, 1H), 6.63 (s, 1H), 4.84 (s, 2H), 4.13-4.05 (m, 1H), 4.05-3.94 (m, 1H), 3.65 (ddd, J = 10.8, 7.9, 4.4 Hz, 1H), 3.58 (dd, J = 9.4, 5.2 Hz, 1H), 3.47-3.41 (m, 1H), 3.41 (s, 3H), 3.09 (tt, J = 11.8, 3.3 Hz, 1H), 2.20-2.05 (m, 4H), 1.72-1.54 (m, 2H), 1.51-1.38 (m, 2H), 1.29 (d, J = 6.6 Hz, 3H), 1.17 (d, J = 6.6 Hz, 6H). | 470.4 |
| 236 | 5 | ¹H NMR (400 MHz, MeOD) δ 8.71 (s, 1H), 7.95 (s, 1H), 7.79 (s, 1H), 6.59 (s, 1H), 4.85 (s, 2H), 4.41-4.34 (m, 1H), 4.10-3.99 (m, 1H), 3.89 (dd, J = 15.9, 7.3 Hz, 1H), 3.85-3.72 (m, 2H), 3.66-3.57 (m, 2H), 3.55 (dd, J = 9.4, 5.2 Hz, 1H), 3.42-3.38 (m, 1H), 3.38 (s, 3H), 3.05 (tt, J = 12.4, 3.6 Hz, 1H), 2.27-2.17 (m, 1H), 2.17-2.01 (m, 4H), 1.89-1.80 (m, 1H), 1.68-1.53 (m, 2H), 1.47-1.35 (m, 2H), 1.26 (d, J = 6.6 Hz, 3H). | 498.4 |
| 237 | 5 | ¹H NMR (400 MHz, MeOD) δ 8.75 (s, 1H), 8.00 (s, 1H), 7.83 (s, 1H), 6.63 (s, 1H), 4.89 (s, 2H), 4.47-4.37 (m, 1H), 4.15-4.04 (m, 1H), 3.94 (dd, J = 15.8, 7.4 Hz, 1H), 3.89-3.76 (m, 2H), 3.70-3.62 (m, 2H), 3.59 (dd, J = 9.4, 5.2 Hz, 1H), 3.47-3.42 (m, 1H), 3.42 (s, 3H), 3.14-3.04 (m, 1H), 2.32-2.21 (m, 1H), 2.21-2.04 (m, 4H), 1.96-1.83 (m, 1H), 1.73-1.56 (m, 2H), 1.53-1.38 (m, 2H), 1.30 (d, J = 6.6 Hz, 3H). | 498.4 |
| 238 | 5 | ¹H NMR (500 MHz, MeOD) δ 8.74 (s, 1H), 8.49 (brs, 1H), 7.94 (d, J = 0.7 Hz, 1H), 7.81 (d, J = 0.7 Hz, 1H), 6.63 (s, 1H), 5.17 (s, 2H), 4.12-4.05 (m, 1H), 3.65 (tt, J = 10.9, 4.2 Hz, 1H), 3.58 (dd, J = 9.4, 5.2 Hz, 1H), 3.46-3.42 (m, 1H), 3.42 (s, 3H), 3.15 (s, 3H), 3.09 (tt, J = 11.8, 3.4 Hz, 1H), 3.00 (s, 3H), 2.20-2.06 (m, 4H), 1.69-1.57 (m, 2H), 1.50-1.40 (m, 2H), 1.29 (d, J = 6.6 Hz, 3H). | 456.4 |
| 239 | 5 | ¹H NMR (500 MHz, MeOD) δ 8.75 (s, 1H), 7.97 (s, 1H), 7.82 (s, 1H), 6.63 (s, 1H), 5.08 (s, 2H), 4.12-4.05 (m, 1H), 3.68-3.62 (m, 1H), 3.62-3.56 (m, 3H), 3.48 (t, J = 6.9 Hz, 2H), 3.46-3.42 (m, 1H), 3.42 (s, 3H), 3.09 (tt, J = 12.3, 3.7 Hz, 1H), 2.22-2.02 (m, 6H), 1.96-1.89 (m, 2H), 1.70-1.57 (m, 2H), 1.50-1.40 (m, 2H), 1.29 (d, J = 6.6 Hz, 3H). | 482.3 |
| 240 | 5 | (formate salt) ¹H NMR (500 MHz, MeOD) δ 8.74 (s, 1H), 8.32 (brs, 1H), 7.95 (s, 1H), 7.82 (s, 1H), 6.63 (s, 1H), 5.19 (s, 2H), 4.12-4.05 (m, 1H), 3.71-3.61 (m, 5H), 3.58 (dd, J = 9.4, 5.2 Hz, 1H), 3.46-3.43 (m, 1H), 3.42 (s, 3H), 3.09 (tt, J = 12.2, 3.5 Hz, 1H), 2.66-2.50 (m, 4H), 2.41 (s, 3H), 2.22-2.03 (m, 4H), 1.70-1.56 (m, 2H), 1.49-1.40 (m, 2H), 1.29 (d, J = 6.6 Hz, 3H). | 511.2 |

FIG. 2 (Cont'd)

| No. | General Scheme | NMR | MS |
|---|---|---|---|
| 241 | 5 | ¹H NMR (500 MHz, MeOD) δ 8.75 (s, 1H), 8.01 (s, 1H), 7.84 (s, 1H), 6.63 (s, 1H), 4.88 (s, 2H), 4.13-4.03 (m, 1H), 3.65 (tt, J = 10.8, 4.2 Hz, 1H), 3.58 (dd, J = 9.4, 5.2 Hz, 1H), 3.47-3.43 (m, 1H), 3.42 (s, 3H), 3.09 (tt, J = 12.2, 3.5 Hz, 1H), 2.78 (s, 3H), 2.21-2.04 (m, 4H), 1.70-1.56 (m, 2H), 1.50-1.39 (m, 2H), 1.29 (d, J = 6.6 Hz, 3H). | 442.3 |
| 242 | 4 (diastereomers separated by chiral column) | ¹H NMR (400 MHz, CD₃OD) δ 8.73 (s, 1H), 8.00 (s, 1H), 7.79 (s, 1H), 6.61 (s, 1H), 5.10 – 5.03 (m, 1H), 4.19 – 4.10 (m, 1H), 4.10 – 4.03 (m, 3H), 3.97 – 3.87 (m, 1H), 3.69 – 3.60 (m, 1H), 3.58 (dd, J = 9.4, 5.1 Hz, 1H), 3.46 – 3.42 (m, 1H), 3.41 (s, 3H), 3.12 – 3.01 (m, 1H), 2.57 – 2.45 (m, 1H), 2.43 – 2.33 (m, 1H), 2.22 – 2.13 (m, 2H), 2.13 – 2.01 (m, 2H), 1.71 – 1.55 (m, 2H), 1.52 – 1.37 (m, 2H), 1.29 (d, J = 6.6 Hz, 3H) | 441.1 |
| 243 | 4 (diastereomers separated by chiral column) | ¹H NMR (400 MHz, CD₃OD) δ 8.73 (s, 1H), 7.99 (s, 1H), 7.79 (s, 1H), 6.61 (s, 1H), 5.10 – 5.02 (m, 1H), 4.19 – 4.10 (m, 1H), 4.11 – 4.03 (m, 3H), 3.93 (td, J = 8.4, 5.8 Hz, 1H), 3.69 – 3.61 (m, 1H), 3.58 (dd, J = 9.4, 5.2 Hz, 1H), 3.46 – 3.41 (m, 1H), 3.41 (s, 3H), 3.13 – 3.02 (m, 1H), 2.58 – 2.45 (m, 1H), 2.43 – 2.31 (m, 1H), 2.21 – 2.13 (m, 2H), 2.13 – 2.04 (m, 2H), 1.71 – 1.55 (m, 2H), 1.51 – 1.38 (m, 2H), 1.29 (d, J = 6.6 Hz, 3H). | 441.1 |
| 244 | 4 | ¹H NMR (400 MHz, CD₃OD) δ 8.71 (s, 1H), 7.56 – 7.47 (m, 2H), 7.38 (d, J = 8.1 Hz, 2H), 6.65 (s, 1H), 4.68 – 4.55 (m, 1H), 4.54 – 4.41 (m, 1H), 4.12 – 4.01 (m, 1H), 3.70 – 3.65 (m, 4H), 3.64 – 3.58 (m, 1H), 3.55 (s, 2H), 3.07 (tt, J = 11.8, 3.3 Hz, 1H), 2.54 – 2.43 (m, 4H), 2.21 – 2.12 (m, 2H), 2.09 – 1.83 (m, 4H), 1.69 – 1.53 (m, 2H), 1.49 – 1.37 (m, 2H), 1.29 (d, J = 6.6 Hz, 3H). | 482.2 |
| 245 | 4 | ¹H NMR (400 MHz, MeOD) δ 8.91 (d, J = 3.4 Hz, 2H), 8.84 (s, 1H), 8.47 (s, 1H), 8.39 (t, J = 2.1 Hz, 1H), 6.86 (s, 1H), 4.11 (dd, J = 12.1, 5.9 Hz, 1H), 3.65 (td, J = 10.8, 5.4 Hz, 1H), 3.59 (dd, J = 9.4, 5.2 Hz, 1H), 3.47 – 3.43 (m, 1H), 3.42 (s, 3H), 3.13 (dd, J = 13.7, 10.5 Hz, 1H), 2.97 (s, 3H), 2.16 (dd, J = 39.6, 10.4 Hz, 4H), 1.76 – 1.57 (m, 2H), 1.46 (q, J = 10.7 Hz, 2H), 1.30 (d, J = 6.6 Hz, 3H). | 439.2 |
| 246 | 4 | ¹H NMR (400 MHz, MeOD) δ 8.77 (s, 1H), 8.63 (d, J = 2.1 Hz, 1H), 7.95 (dd, J = 8.1, 2.3 Hz, 1H), 7.36 (d, J = 8.1 Hz, 1H), 6.76 (s, 1H), 4.10 (dd, J = 12.1, 6.0 Hz, 1H), 3.70 – 3.62 (m, 1H), 3.59 (dd, J = 9.4, 5.2 Hz, 1H), 3.46 – 3.42 (m, 1H), 3.42 (s, 3H), 3.17 – 3.07 (m, 1H), 2.56 (s, 3H), 2.15 (dd, J = 37.1, 10.1 Hz, 4H), 1.74 – 1.58 (m, 2H), 1.46 (q, J = 11.0 Hz, 2H), 1.30 (d, J = 6.6 Hz, 3H). | 396.2 |
| 247 | 5 | ¹H NMR (500 MHz, MeOD) δ 8.93 (d, J = 2.0 Hz, 1H), 8.90 (s, 2H), 8.45 (t, J = 2.1 Hz, 1H), 6.86 (d, J = 10.8 Hz, 1H), 4.15 – 4.06 (m, 1H), 3.71 – 3.62 (m, 1H), 3.59 (dd, J = 9.5, 5.3 Hz, 1H), 3.44 (dd, J = 9.5, 6.0 Hz, 1H), 3.42 (s, 3H), 3.17 – 3.09 (m, 1H), 2.26 – 2.06 (m, 4H), 1.74 – 1.60 (m, 2H), 1.52 – 1.40 (m, 2H), 1.30 (d, J = 6.6 Hz, 3H). | 425.2 |

FIG. 2 (Cont'd)

| No. | General Scheme | NMR | MS |
|---|---|---|---|
| 248 | See Example 28 | ¹H NMR (500 MHz, MeOD) δ 9.04 (s, 1H), 8.09 (s, 1H), 6.79 (s, 1H), 4.14 – 4.06 (m, 1H), 4.05 (s, 2H), 3.68 – 3.61 (m, 1H), 3.59 (dd, J = 9.4, 5.2 Hz, 1H), 3.46 – 3.42 (m, 1H), 3.41 (s, 3H), 3.14 – 3.06 (m, 1H), 2.25 – 2.14 (m, 2H), 2.13 – 2.04 (m, 2H), 1.70 – 1.56 (m, 2H), 1.51 – 1.39 (m, 2H), 1.30 (d, J = 6.6 Hz, 3H), 0.17 (s, J = 3.4 Hz, 9H). | 458.1 |
| 249 | 4 | ¹H NMR (500 MHz, MeOD) δ 8.73 (s, 1H), 7.29 (d, J = 7.6 Hz, 1H), 7.21 (dd, J = 7.7, 1.5 Hz, 1H), 7.08 (d, J = 1.4 Hz, 1H), 6.67 (s, 1H), 4.14 – 4.04 (m, 1H), 3.69 – 3.61 (m, 1H), 3.59 (dd, J = 9.4, 5.2 Hz, 1H), 3.55 (s, 1H), 3.53 (s, 1H), 3.46 – 3.42 (m, 1H), 3.42 (s, J = 3.4 Hz, 3H), 3.15 – 3.03 (m, 1H), 2.23 – 2.15 (m, 2H), 2.14 – 2.03 (m, 2H), 1.71 – 1.58 (m, 2H), 1.51 – 1.39 (m, 2H), 1.30 (d, J = 6.6 Hz, 3H). | 436.1 |
| 250 | See Example 28 | ¹H NMR (500 MHz, MeOD) δ 9.04 (s, 1H), 8.19 (s, 1H), 6.79 (s, 1H), 4.15 (s, 3H), 4.13 – 4.05 (m, 1H), 3.69 – 3.60 (m, 1H), 3.59 (dd, J = 9.5, 5.2 Hz, 1H), 3.46 – 3.43 (m, 1H), 3.42 (s, 3H), 3.15 – 3.06 (m, 1H), 2.24 – 2.14 (m, 2H), 2.14 – 2.03 (m, 2H), 1.70 – 1.57 (m, 2H), 1.50 – 1.40 (m, 2H), 1.30 (d, J = 6.6 Hz, 3H). | 386.1 |
| 251 | 4 | ¹H NMR (500 MHz, MeOD) δ 8.97 (s, 1H), 7.93 – 7.87 (m, 2H), 7.81 (dd, J = 7.9, 1.4 Hz, 1H), 7.34 (s, 1H), 4.55 (s, 2H), 4.22 – 4.12 (m, 1H), 3.73 – 3.63 (m, 1H), 3.59 – 3.51 (m, 2H), 3.43 (s, 3H), 3.28 – 3.19 (m, 1H), 2.23 – 2.11 (m, 4H), 1.79 – 1.68 (m, 2H), 1.53 – 1.42 (m, 2H), 1.35 (d, J = 6.7 Hz, 3H) | 436 |
| 252 | 4 | ¹H NMR (500 MHz, MeOD) δ 8.82 (s, 1H), 7.58 – 7.49 (m, 2H), 7.14 (s, 1H), 7.02 (d, J = 8.1 Hz, 1H), 4.19 – 4.11 (m, 1H), 3.71 – 3.64 (m, 1H), 3.62 – 3.58 (m, 2H), 3.58 – 3.49 (m, 2H), 3.43 (s, 3H), 3.24 – 3.15 (m, 1H), 2.21 – 2.08 (m, 4H), 1.77 – 1.65 (m, 2H), 1.53 – 1.41 (m, 2H), 1.34 (d, J = 6.7 Hz, 3H | 436 |
| 253 | 4 | ¹H NMR (500 MHz, MeOD) δ 9.44 (s, 1H), 7.65 (t, J = 7.8 Hz, 1H), 7.51 (d, J = 7.8 Hz, 1H), 7.06 (d, J = 7.4 Hz, 1H), 6.95 (s, 1H), 4.14 – 4.06 (m, 1H), 3.70 – 3.62 (m, 1H), 3.59 (dd, J = 9.4, 5.2 Hz, 1H), 3.46 – 3.42 (m, 1H), 3.42 (s, 3H), 3.16 – 3.05 (m, 1H), 2.56 (s, 3H), 2.24 – 2.04 (m, 4H), 1.72 – 1.58 (m, 2H), 1.52 – 1.39 (m, 2H), 1.30 (d, J = 6.6 Hz, 3H). | 396.3 |
| 254 | 4 | ¹H NMR (500 MHz, MeOD) δ 8.68 (s, 1H), 8.35 (d, J = 2.4 Hz, 1H), 7.81 (dd, J = 8.8, 2.5 Hz, 1H), 6.90 (d, J = 8.8 Hz, 1H), 6.64 (s, 1H), 4.14 – 4.04 (m, 1H), 3.85 – 3.79 (m, 4H), 3.71 – 3.62 (m, 1H), 3.58 (dd, J = 9.4, 5.2 Hz, 1H), 3.54 – 3.49 (m, 4H), 3.46 – 3.42 (m, 1H), 3.42 (s, 3H), 3.11 (tt, J = 12.2, 3.5 Hz, 1H), 2.23 – 2.06 (m, 4H), 1.72 – 1.56 (m, 2H), 1.50 – 1.38 (m, 2H), 1.30 (d, J = 6.6 Hz, 3H). | 467.2 |
| 255 | 4 | ¹H NMR (500 MHz, MeOD) δ 8.76 (s, 1H), 7.59 (d, J = 8.2 Hz, 2H), 7.44 (d, J = 8.1 Hz, 2H), 6.70 (s, 1H), 6.35 (t, J = 75.7 Hz, 1H), 4.14-4.06 (m, 1H), 4.05-3.94 (m, 2H), 3.77-3.72 (m, 4H), 3.70 (s, 2H), 3.65 (tt, J = 10.9, 4.2 Hz, 1H), 3.12 (tt, J = 12.3, 3.6 Hz, 1H), 2.64 (brs, 4H), 2.23-2.07 (m, 4H), 2.06-2.00 (m, 1H), 1.93-1.84 (m, 1H), 1.71-1.59 (m, 2H), 1.52-1.42 (m, 2H), 1.32 (d, J = 6.6 Hz, 3H). | 530.2 |

FIG. 2 (Cont'd)

| No. | General Scheme | NMR | MS |
|---|---|---|---|
| 256 | 4 | ¹H NMR (400 MHz, MeOD) δ 8.87 (s, 1H), 8.11 (d, J = 5.3 Hz, 1H), 6.99 – 6.92 (m, 2H), 6.85 (s, 1H), 4.16 – 4.06 (m, 1H), 3.70 – 3.56 (m, 6H), 3.46 – 3.43 (m, 1H), 3.41 (s, 3H), 3.14 – 3.04 (m, 1H), 2.70 – 2.61 (m, 4H), 2.41 (s, 3H), 2.15 (dd, J = 34.5, 11.4 Hz, 4H), 1.74 – 1.57 (m, 2H), 1.52 – 1.38 (m, 2H), 1.30 (d, J = 6.6 Hz, 3H). | 480.3 |
| 257 | 4 | ¹H NMR (400 MHz, MeOD) δ 9.31 (s, 1H), 8.39 (d, J = 5.1 Hz, 1H), 7.58 (s, 1H), 7.05 (d, J = 4.9 Hz, 1H), 6.96 (s, 1H), 4.19 – 4.03 (m, 1H), 3.72 – 3.63 (m, 1H), 3.59 (dd, J = 9.4, 5.2 Hz, 1H), 3.47 – 3.43 (m, 1H), 3.42 (s, 3H), 3.17 – 3.06 (m, 1H), 2.41 (s, 3H), 2.25 – 2.07 (m, 4H), 1.73 – 1.59 (m, 2H), 1.52 – 1.40 (m, 2H), 1.30 (d, J = 6.6 Hz, 3H). | 396.2 |
| 258 | 4 | ¹H NMR (400 MHz, MeOD) δ 9.27 (d, J = 2.1 Hz, 1H), 8.36 (s, 1H), 7.59 (s, 2H), 6.88 (s, 1H), 4.12 – 4.02 (m, 1H), 3.67 – 3.59 (m, 1H), 3.58 – 3.53 (m, 1H), 3.44 – 3.39 (m, 1H), 3.38 (s, 3H), 3.12 – 3.02 (m, 1H), 2.32 (s, 3H), 2.21 – 2.00 (m, 4H), 1.69 – 1.55 (m, 2H), 1.49 – 1.36 (m, 2H), 1.27 (d, J = 6.6 Hz, 3H). | 396.3 |
| 259 | 4 | ¹H NMR (400 MHz, MeOD) δ 8.87 (s, 1H), 8.11 (dd, J = 5.2, 0.8 Hz, 1H), 7.00 – 6.92 (m, 2H), 6.84 (s, 1H), 4.16 – 4.05 (m, 1H), 3.86 – 3.79 (m, 4H), 3.70 – 3.61 (m, 1H), 3.58 (dd, J = 9.4, 5.2 Hz, 1H), 3.54 – 3.50 (m, 4H), 3.46 – 3.43 (m, 1H), 3.41 (s, 3H), 3.11 (tt, J = 12.0, 3.3 Hz, 1H), 2.24 – 2.05 (m, 4H), 1.73 – 1.55 (m, 2H), 1.52 – 1.39 (m, 2H), 1.30 (d, J = 6.6 Hz, 3H). | 467.3 |
| 260 | 4 | ¹H NMR (400 MHz, CD₃OD) δ 8.53 (s, 1H), 7.72 (s, 1H), 6.49 (s, 1H), 4.13 – 4.03 (m, 1H), 3.86 (s, 3H), 3.69 – 3.61 (m, 1H), 3.58 (dd, J = 9.4, 5.2 Hz, 1H), 3.47 – 3.42 (m, 1H), 3.41 (s, 3H), 3.15 – 3.04 (m, 1H), 2.31 (s, 3H), 2.22 – 2.13 (m, 2H), 2.13 – 2.02 (m, 2H), 1.71 – 1.54 (m, 2H), 1.51 – 1.38 (m, 2H), 1.29 (d, J = 6.6 Hz, 3H) | 399.2 |
| 261 | 4 | ¹H NMR (400 MHz, CD₃OD) δ 8.89 (s, J = 0.8 Hz, 1H), 7.20 (s, 1H), 6.71 (s, 1H), 4.14 – 4.04 (m, 1H), 3.70 – 3.60 (m, 1H), 3.58 (dd, J = 9.5, 5.2 Hz, 1H), 3.43 (dd, J = 7.9, 4.4 Hz, 1H), 3.41 (s, 3H), 3.13 – 2.99 (m, 1H), 2.52 (s, 3H), 2.22 – 2.13 (m, 2H), 2.13 – 2.03 (m, 2H), 1.68 – 1.54 (m, 2H), 1.50 – 1.37 (m, 2H), 1.29 (d, J = 6.6 Hz, 3H) | 386 |
| 262 | 4 | ¹H NMR (500 MHz, MeOD) δ 8.74 (s, 1H), 7.96 (d, J = 0.6 Hz, 1H), 7.79 (d, J = 0.7 Hz, 1H), 6.62 (s, 1H), 4.34 (t, J = 5.3 Hz, 2H), 4.28-4.19 (m, 1H), 3.79-3.76 (m, 2H), 3.64 (tt, J = 10.9, 4.4 Hz, 1H), 3.34 (s, 3H), 3.09 (tt, J = 12.2, 3.4 Hz, 1H), 2.86-2.73 (m, 1H), 2.38-2.23 (m, 1H), 2.21-2.13 (m, 2H), 2.13-2.04 (m, 2H), 1.69-1.53 (m, 2H), 1.50-1.42 (m, 2H), 1.40 (d, J = 6.7 Hz, 3H). | 467.2 |
| 263 | 4 | ¹H NMR (500 MHz, MeOD) δ 8.90 (s, 1H), 8.88 (d, J = 1.6 Hz, 1H), 8.16 (dd, J = 8.2, 2.2 Hz, 1H), 8.12 (d, J = 8.1 Hz, 1H), 6.89 (s, 1H), 4.31-4.22 (m, 1H), 3.66 (tt, J = 10.7, 4.2 Hz, 1H), 3.14 (tt, J = 12.1, 3.5 Hz, 1H), 2.99 (s, 3H), 2.86-2.73 (m, 1H), 2.39-2.27 (m, 1H), 2.25-2.17 (m, 2H), 2.15-2.06 (m, 2H), 1.73-1.57 (m, 2H), 1.52-1.43 (m, 2H), 1.42 (d, J = 6.7 Hz, 3H). | 477.2 |

FIG. 2 (Cont'd)

| No. | General Scheme | NMR | MS |
|---|---|---|---|
| 264 | 4 | $^1$H NMR (500 MHz, MeOD) δ 8.73 (s, 1H), 7.95 (s, 1H), 7.78 (s, 1H), 6.62 (s, 1H), 4.13 (s, 2H), 4.11 – 4.05 (m, 1H), 3.68 – 3.60 (m, 1H), 3.58 (dd, J = 9.4, 5.2 Hz, 1H), 3.45 – 3.42 (m, 1H), 3.41 (s, 3H), 3.13 – 3.04 (m, 1H), 2.22 – 2.13 (m, 2H), 2.13 – 2.01 (m, 2H), 1.70 – 1.57 (m, 2H), 1.50 – 1.40 (m, 2H), 1.29 (d, J = 6.6 Hz, 3H), 1.20 (s, 6H). | 443.2 |
| 265 | 4 | $^1$H NMR (500 MHz, MeOD) δ 8.73 (s, 1H), 8.03 (s, 1H), 7.79 (s, 1H), 6.61 (s, 1H), 4.12 – 4.03 (m, 1H), 3.78 (s, 2H), 3.68 – 3.60 (m, 1H), 3.58 (dd, J = 9.4, 5.2 Hz, 1H), 3.46 – 3.42 (m, 1H), 3.41 (s, 3H), 3.12 – 3.03 (m, 1H), 2.21 – 2.13 (m, 2H), 2.13 – 2.04 (m, 2H), 1.69 – 1.56 (m, 2H), 1.60 (s, 6H), 1.50 – 1.38 (m, 2H), 1.29 (d, J = 6.6 Hz, 3H). | 443.2 |
| 266 | 5 (see Example 32) | $^1$H NMR (500 MHz, MeOD) δ 8.74 (s, 1H), 8.07 (s, 1H), 7.85 (s, 1H), 6.64 (s, 1H), 4.31 (s, 2H), 4.13 – 4.03 (m, 1H), 3.69 – 3.60 (m, 1H), 3.58 (dd, J = 9.4, 5.2 Hz, 1H), 3.45 – 3.42 (m, 1H), 3.41 (s, J = 4.0 Hz, 3H), 3.13 – 3.03 (m, 1H), 2.21 – 2.14 (m, 2H), 2.12 – 2.04 (m, 2H), 1.70 – 1.57 (m, 2H), 1.51 – 1.39 (m, 2H), 1.39 – 1.34 (m, 2H), 1.34 – 1.31 (m, 2H), 1.29 (d, J = 6.6 Hz, 3H). | 450.1 |
| 267 | 4 | $^1$H NMR (400 MHz, MeOD) δ 9.31 (d, J = 2.1 Hz, 1H), 9.07 (s, 1H), 7.83 (d, J = 2.1 Hz, 1H), 7.05 (s, 1H), 4.17 – 4.06 (m, 1H), 3.70 – 3.61 (m, 1H), 3.59 (dd, J = 9.5, 5.3 Hz, 1H), 3.46 – 3.43 (m, 1H), 3.42 (s, 3H), 3.18 – 3.07 (m, 1H), 2.70 (s, 3H), 2.25 – 2.06 (m, 4H), 1.73 – 1.59 (m, 2H), 1.52 – 1.39 (m, 2H), 1.30 (d, J = 6.7 Hz, 3H). | 397.1 |
| 268 | 4 | $^1$H NMR (400 MHz, MeOD) δ 8.77 (s, 1H), 8.63 (d, J = 2.1 Hz, 1H), 7.95 (dd, J = 8.1, 2.3 Hz, 1H), 7.36 (d, J = 8.1 Hz, 1H), 6.76 (s, 1H), 4.10 (dd, J = 12.1, 6.0 Hz, 1H), 3.70 – 3.62 (m, 1H), 3.59 (dd, J = 9.4, 5.2 Hz, 1H), 3.46 – 3.42 (m, 1H), 3.42 (s, 3H), 3.17 – 3.07 (m, 1H), 2.56 (s, 3H), 2.15 (dd, J = 37.1, 10.1 Hz, 4H), 1.74 – 1.58 (m, 2H), 1.46 (q, J = 11.0 Hz, 2H), 1.30 (d, J = 6.6 Hz, 3H). | 396.2 |
| 269 | 4 | $^1$H NMR (500 MHz, MeOD) δ 8.93 (d, J = 2.0 Hz, 1H), 8.90 (s, 2H), 8.45 (t, J = 2.1 Hz, 1H), 6.86 (d, J = 10.8 Hz, 1H), 4.15 – 4.06 (m, 1H), 3.71 – 3.62 (m, 1H), 3.59 (dd, J = 9.5, 5.3 Hz, 1H), 3.44 (dd, J = 9.5, 6.0 Hz, 1H), 3.42 (s, 3H), 3.17 – 3.09 (m, 1H), 2.26 – 2.06 (m, 4H), 1.74 – 1.60 (m, 2H), 1.52 – 1.40 (m, 2H), 1.30 (d, J = 6.6 Hz, 3H). | 425.2 |
| 270 | 4 | $^1$H NMR (500 MHz, MeOD) δ 9.04 (s, 1H), 8.09 (s, 1H), 6.79 (s, 1H), 4.14 – 4.06 (m, 1H), 4.05 (s, 2H), 3.68 – 3.61 (m, 1H), 3.59 (dd, J = 9.4, 5.2 Hz, 1H), 3.46 – 3.42 (m, 1H), 3.41 (s, 3H), 3.14 – 3.06 (m, 1H), 2.25 – 2.14 (m, 2H), 2.13 – 2.04 (m, 2H), 1.70 – 1.56 (m, 2H), 1.51 – 1.39 (m, 2H), 1.30 (d, J = 6.6 Hz, 3H), 0.17 (s, J = 3.4 Hz, 9H). | 458.1 |

FIG. 2 (Cont'd)

| No. | General Scheme | NMR | MS |
|---|---|---|---|
| 271 | 4 | $^1$H NMR (500 MHz, MeOD) δ 8.68 (s, 1H), 8.34 (d, J = 1.8 Hz, 1H), 7.80 (dd, J = 8.8, 2.5 Hz, 1H), 6.92 (d, J = 8.3 Hz, 1H), 6.64 (s, 1H), 4.09 (dd, J = 11.9, 6.0 Hz, 2H), 3.70 – 3.62 (m, 2H), 3.58 (dd, J = 9.4, 5.2 Hz, 4H), 3.45 – 3.42 (m, 1H), 3.41 (s, 2H), 3.11 (dd, J = 13.8, 10.4 Hz, 2H), 2.63 – 2.53 (m, 4H), 2.36 (s, 3H), 2.14 (dd, J = 42.1, 11.0 Hz, 4H), 1.70 – 1.60 (m, 2H), 1.49 – 1.41 (m, 2H), 1.29 (d, J = 6.6 Hz, 3H). | 480.2 |
| 272 | 4 | $^1$H NMR (500 MHz, MeOD) δ 9.03 (d, J = 2.1 Hz, 1H), 8.87 (s, 1H), 8.83 (d, J = 2.1 Hz, 1H), 8.34 (t, J = 2.1 Hz, 1H), 6.89 (s, 1H), 4.17 – 4.07 (m, 1H), 3.70 – 3.63 (m, 1H), 3.59 (dd, J = 9.4, 5.3 Hz, 1H), 3.47 – 3.43 (m, 1H), 3.18 – 3.10 (m, 1H), 2.62 (s, 3H), 2.26 – 2.07 (m, 4H), 1.76 – 1.60 (m, 2H), 1.54 – 1.39 (m, 2H), 1.30 (d, J = 6.6 Hz, 3H). | 475.3 |
| 273 | 4 | $^1$H NMR (500 MHz, MeOD) δ 9.12 (d, J = 2.1 Hz, 1H), 8.96 (d, J = 2.1 Hz, 1H), 8.93 (s, 1H), 8.49 (t, J = 2.1 Hz, 1H), 6.94 (s, 1H), 4.27 (dd, J = 12.7, 6.9 Hz, 1H), 3.72-3.60 (m, 1H), 3.29 (s, 3H), 3.19-3.12 (m, 1H), 2.87-2.71 (m, 1H), 2.40-2.26 (m, 1H), 2.25-2.16 (m, 2H), 2.14-2.04 (m, 2H), 1.74-1.57 (m, 2H), 1.55-1.43 (m, 2H), 1.42 (d, J = 6.7 Hz, 3H). | 498 |
| 274 | 4 | $^1$H NMR (500 MHz, MeOD) δ 8.74 (s, 1H), 7.97 (s, 1H), 7.80 (s, 1H), 6.63 (s, 1H), 6.43 (t, J = 75.5 Hz, 1H), 4.34 (t, J = 5.3 Hz, 2H), 4.19-4.07 (m, 2H), 3.83 (dd, J = 9.3, 6.0 Hz, 1H), 3.78 (t, J = 5.3 Hz, 2H), 3.65 (tt, J = 10.7, 4.1 Hz, 1H), 3.35 (s, 3H), 3.10 (tt, J = 12.3, 3.7 Hz, 1H), 2.20-2.04 (m, 4H), 1.71-1.56 (m, 2H), 1.53-1.41 (m, 2H), 1.35 (d, J = 6.6 Hz, 3H). | 465.3 |
| 275 | 4 | $^1$H NMR (500 MHz, MeOD) δ 9.04 (d, J = 1.9 Hz, 1H), 8.89 (s, 1H), 8.84 (d, J = 1.9 Hz, 1H), 8.35 (t, J = 2.1 Hz, 1H), 6.91 (s, 1H), 6.43 (t, J = 75.4 Hz, 1H), 4.21-4.14 (m, 1H), 4.11 (dd, J = 9.6, 4.6 Hz, 1H), 3.85 (dd, J = 9.7, 6.4 Hz, 1H), 3.66 (tt, J = 10.9, 4.4 Hz, 1H), 3.19-3.11 (m, 1H), 2.63 (s, 3H), 2.26-2.05 (m, 4H), 1.73-1.60 (m, 2H), 1.53-1.43 (m, 2H), 1.36 (d, J = 6.7 Hz, 3H). | 511 |
| 276 | 4 | $^1$H NMR (400 MHz, CD$_3$OD) δ 8.73 (s, 1H), 8.04 – 7.80 (m, 2H), 6.63 (s, 1H), 4.14 – 4.03 (m, 1H), 3.70 – 3.61 (m, 1H), 3.58 (dd, J = 9.4, 5.2 Hz, 1H), 3.46 – 3.42 (m, 1H), 3.41 (s, 3H), 3.15 – 3.02 (m, 1H), 2.22 – 2.13 (m, 2H), 2.13 – 2.03 (m, 2H), 1.71 – 1.56 (m, 2H), 1.51 – 1.37 (m, 2H), 1.29 (d, J = 6.6 Hz, 3H). | 371.2 |
| 277 | 4 | $^1$H NMR (400 MHz, MeOD) δ 8.74 (s, 1H), 8.13 (s, 1H), 7.85 (d, J = 0.7 Hz, 1H), 6.64 (s, 1H), 5.65 (s, 2H), 4.15 – 4.02 (m, 1H), 3.69 – 3.61 (m, 1H), 3.58 (dd, J = 9.4, 5.2 Hz, 1H), 3.45 – 3.42 (m, 1H), 3.41 (s, 3H), 3.13 – 3.04 (m, 1H), 2.53 (s, 3H), 2.22 – 2.05 (m, 4H), 1.70 – 1.55 (m, 2H), 1.51 – 1.38 (m, 2H), 1.29 (d, J = 6.6 Hz, 3H). | 467 |
| 278 | 4 | $^1$H NMR (500 MHz, MeOD) δ 9.04 (d, J = 2.0 Hz, 1H), 8.89 (s, 1H), 8.84 (d, J = 2.1 Hz, 1H), 8.35 (t, J = 2.1 Hz, 1H), 6.90 (s, 1H), 4.33-4.21 (m, 1H), 3.66 (tt, J = 8.6, 4.7 Hz, 1H), 3.19-3.11 (m, 1H), 2.85-2.72 (m, 1H), 2.62 (s, 3H), 2.39-2.27 (m, 1H), 2.25-2.06 (m, 4H), 1.73-1.53 (m, 2H), 1.53-1.44 (m, 2H), 1.42 (d, J = 6.7 Hz, 3H). | 513 |

FIG. 2 (Cont'd)

| No. | General Scheme | NMR | MS |
|---|---|---|---|
| 279 | 4 | $^1$H NMR (500 MHz, MeOD) δ 9.01 (d, J = 1.7 Hz, 1H), 8.95 (s, 1H), 8.31 (dd, J = 8.2, 2.2 Hz, 1H), 8.11 (d, J = 8.2 Hz, 1H), 6.94 (s, 1H), 4.16-4.08 (m, 1H), 3.67 (tt, J = 10.9, 4.3 Hz, 1H), 3.60 (dd, J = 9.4, 5.3 Hz, 1H), 3.45 (dd, J = 9.5, 6.0 Hz, 1H), 3.42 (s, 3H), 3.26 (s, 3H), 3.14 (tt, J = 12.1, 3.4 Hz, 1H), 2.25-2.05 (m, 4H), 1.75-1.58 (m, 2H), 1.54-1.40 (m, 2H), 1.31 (d, J = 6.6 Hz, 3H). | 460 |
| 280 | 4 | $^1$H NMR (500 MHz, MeOD) δ 8.73 (s, 1H), 8.06 (s, 1H), 7.85 (s, 1H), 6.62 (s, 1H), 4.68 (t, J = 6.6 Hz, 2H), 4.14-4.00 (m, 1H), 3.74 (t, J = 6.5 Hz, 2H), 3.64 (tt, J = 10.9, 4.3 Hz, 1H), 3.58 (dd, J = 9.4, 5.2 Hz, 1H), 3.45-3.42 (m, 1H), 3.41 (s, 3H), 3.08 (tt, J = 11.9, 3.4 Hz, 1H), 2.80 (s, 3H), 2.21-2.04 (m, 4H), 1.69-1.52 (m, 2H), 1.49-1.39 (m, 2H), 1.29 (d, J = 6.6 Hz, 3H). | 477.1 |
| 281 | 4 | $^1$H NMR (400 MHz, CD$_3$OD) δ 9.15 (d, J = 5.3 Hz, 1H), 9.09 (s, 1H), 8.75 (s, 1H), 8.17 (s, 1H), 7.92 (s, 1H), 7.53 – 7.39 (m, 1H), 6.65 (s, 1H), 5.54 (s, 2H), 4.14 – 4.02 (m, 1H), 3.69 – 3.60 (m, 1H), 3.58 (dd, J = 9.4, 5.2 Hz, 1H), 3.48 – 3.41 (m, 1H), 3.41 (s, 3H), 3.15 – 3.00 (m, 1H), 2.22 – 2.13 (m, 2H), 2.13 – 2.01 (m, 2H), 1.70 – 1.55 (m, 2H), 1.52 – 1.37 (m, 2H), 1.29 (d, J = 6.6 Hz, 3H). | 463.2 |
| 282 | 4 | $^1$H NMR (400 MHz, CD$_3$OD) δ 8.78 (s, 1H), 8.12 (s, 1H), 7.87 (s, 1H), 6.66 (s, 1H), 4.14 – 4.02 (m, 1H), 3.69 – 3.60 (m, 1H), 3.58 (dd, J = 9.5, 5.2 Hz, 1H), 3.55 – 3.46 (m, 8H), 3.47 – 3.42 (m, 1H), 3.41 (s, J = 0.5 Hz, 3H), 3.14 – 2.96 (m, 1H), 2.21 – 2.13 (m, 2H), 2.13 – 2.03 (m, 2H), 1.83 (s, 6H), 1.70 – 1.56 (m, 2H), 1.52 – 1.37 (m, 2H), 1.29 (d, J = 6.6 Hz, 3H). | 526.1 |
| 283 | 4 | $^1$H NMR (400 MHz, CD$_3$OD) δ 8.78 (s, 1H), 8.13 (s, 1H), 7.90 (s, 1H), 6.66 (s, 1H), 4.13 – 4.05 (m, 1H), 4.01 (t, J = 7.8 Hz, 2H), 3.70 – 3.60 (m, 1H), 3.58 (dd, J = 9.4, 5.2 Hz, 1H), 3.45 – 3.42 (m, 1H), 3.43 – 3.40 (m, 2H), 3.41 (s, 3H), 3.14 – 3.03 (m, 1H), 2.20 – 2.14 (m, 2H), 2.14 – 2.04 (m, 4H), 1.80 (s, 6H), 1.71 – 1.55 (m, 2H), 1.51 – 1.37 (m, 2H), 1.29 (d, J = 6.6 Hz, 3H). | 496.1 |
| 284 | 5 | $^1$H NMR (400 MHz, CD$_3$OD) δ 8.71 (s, 1H), 8.06 (s, 1H), 7.76 (s, 1H), 6.60 (s, 1H), 4.09 – 4.00 (m, 1H), 3.65 – 3.57 (m, 1H), 3.54 (dd, J = 9.4, 5.2 Hz, 1H), 3.42 – 3.38 (m, 1H), 3.38 (s, J = 3.8 Hz, 3H), 3.09 – 3.01 (m, 1H), 2.17 – 2.10 (m, 2H), 2.10 – 2.01 (m, 2H), 1.84 (s, 6H), 1.66 – 1.53 (m, 2H), 1.47 – 1.34 (m, 2H), 1.26 (d, J = 6.6 Hz, 3H). | 457.2 |
| 285 | 4 | $^1$H NMR (400 MHz, MeOD) δ 8.74 (s, 1H), 8.13 (s, 1H), 7.85 (d, J = 0.7 Hz, 1H), 6.64 (s, 1H), 5.65 (s, 2H), 4.15 – 4.02 (m, 1H), 3.69 – 3.61 (m, 1H), 3.58 (dd, J = 9.4, 5.2 Hz, 1H), 3.45 – 3.42 (m, 1H), 3.41 (s, 3H), 3.13 – 3.04 (m, 1H), 2.53 (s, 3H), 2.22 – 2.05 (m, 4H), 1.70 – 1.55 (m, 2H), 1.51 – 1.38 (m, 2H), 1.29 (d, J = 6.6 Hz, 3H). | 467.1 |

FIG. 2 (Cont'd)

| No. | General Scheme | NMR | MS |
|---|---|---|---|
| 286 | 5 | ¹H NMR (500 MHz, MeOD) δ 8.65 (s, 1H), 8.00 (d, J = 0.7 Hz, 1H), 7.81 (s, 1H), 6.53 (s, 1H), 5.19 (tt, J = 8.2, 5.3 Hz, 1H), 4.62 – 4.55 (m, 1H), 4.50 (dd, J = 9.1, 5.0 Hz, 1H), 4.41 – 4.31 (m, 1H), 4.25 (dd, J = 10.5, 5.3 Hz, 1H), 4.05 – 3.91 (m, 1H), 3.58 – 3.50 (m, 1H), 3.48 (dd, J = 9.4, 5.2 Hz, 1H), 3.35 – 3.32 (m, 1H), 3.31 (s, 3H), 2.98 (ddd, J = 12.1, 7.8, 3.4 Hz, 1H), 2.11 – 1.96 (m, 4H), 1.85 (s, 3H), 1.59 – 1.47 (m, 2H), 1.39 – 1.29 (m, 2H), 1.19 (d, J = 6.6 Hz, 3H). | 468.1 |
| 287 | 5 | ¹H NMR (500 MHz, DMSO-d6) δ 8.96 (s, 1H), 8.33 (d, J = 0.6 Hz, 1H), 8.00 (s, 1H), 6.66 (s, 1H), 6.54 (d, J = 7.7 Hz, 1H), 5.27 (dt, J = 14.2, 7.0 Hz, 1H), 4.60 (d, J = 4.5 Hz, 2H), 4.36 – 4.28 (m, 4H), 3.99 (dt, J = 13.2, 6.7 Hz, 1H), 3.53 – 3.40 (m, 2H), 3.31 (s, 3H), 3.28 (dd, J = 9.5, 7.0 Hz, 2H), 3.15 (s, 3H), 2.99 – 2.90 (m, 1H), 2.07 – 1.91 (m, 4H), 1.59 – 1.45 (m, 2H), 1.36 – 1.25 (m, 2H), 1.19 (d, J = 6.6 Hz, 3H). | 504.1 |
| 288 | 4 | ¹H NMR (400 MHz, MeOD) δ 8.75 (s, 1H), 8.06 (s, 1H), 7.85 (s, 1H), 6.63 (s, 1H), 4.68 (t, J = 6.5 Hz, 2H), 4.28-4.18 (m, 1H), 3.74 (t, J = 6.5 Hz, 2H), 3.64 (tt, J = 10.2, 3.8 Hz, 1H), 3.09 (tt, J = 12.4, 3.3 Hz, 1H), 2.89-2.70 (m, 4H), 2.38-2.23 (m, 1H), 2.21-2.04 (m, 4H), 1.70-1.52 (m, 2H), 1.52-1.42 (m, 2H), 1.40 (d, J = 6.7 Hz, 3H). | 515.1 |
| 289 | 4 | ¹H NMR (500 MHz, MeOD) δ 8.74 (s, 1H), 7.99 (s, 1H), 7.79 (s, 1H), 6.62 (s, 1H), 5.09-5.00 (m, 1H), 4.27-4.18 (m, 1H), 4.14 (dd, J = 15.1, 8.1 Hz, 1H), 4.08-4.04 (m, 2H), 3.92 (td, J = 8.4, 5.8 Hz, 1H), 3.63 (tt, J = 10.6, 4.2 Hz, 1H), 3.08 (tt, J = 12.2, 3.5 Hz, 1H), 2.85-2.72 (m, 1H), 2.55-2.46 (m, 1H), 2.42-2.22 (m, 2H), 2.20-2.03 (m, 4H), 1.69-1.52 (m, 2H), 1.50-1.41 (m, 2H), 1.39 (d, J = 6.7 Hz, 3H). | 479.1 |
| 290 | 4 | ¹H NMR (500 MHz, MeOD) δ 8.74 (s, 1H), 8.00 (s, 1H), 7.80 (s, 1H), 6.62 (s, 1H), 5.07 (td, J = 8.4, 3.9 Hz, 1H), 4.28-4.19 (m, 1H), 4.15 (dd, J = 15.2, 7.9 Hz, 1H), 4.09-4.04 (m, 2H), 3.93 (td, J = 8.4, 5.7 Hz, 1H), 3.64 (tt, J = 10.7, 4.3 Hz, 1H), 3.09 (tt, J = 11.9, 3.3 Hz, 1H), 2.86-2.71 (m, 1H), 2.56-2.46 (m, 1H), 2.42-2.23 (m, 2H), 2.21-2.03 (m, 4H), 1.69-1.53 (m, 2H), 1.50-1.42 (m, 2H), 1.40 (d, J = 6.7 Hz, 3H). | 479.1 |
| 291 | 5 | ¹H NMR (400 MHz, MeOD) δ 8.72 (s, 1H), 8.08 (s, 1H), 7.82 (s, 1H), 6.59 (s, 1H), 5.07 – 5.00 (m, 1H), 4.08 – 3.99 (m, 1H), 3.84 (td, J = 7.3, 1.5 Hz, 2H), 3.60 (td, J = 6.8, 1.7 Hz, 2H), 3.54 (dd, J = 9.5, 5.1 Hz, 1H), 3.42 – 3.39 (m, 1H), 3.38 – 3.29 (m, 1H), 3.04 (ddd, J = 14.8, 7.8, 3.1 Hz, 1H), 2.86 – 2.81 (m, 2H), 2.38 – 2.22 (m, 2H), 2.16 – 2.01 (m, 4H), 1.66 – 1.54 (m, 2H), 1.49 – 1.36 (m, 2H), 1.26 (d, J = 6.6 Hz, 3H). | 522.1 |
| 292 | 6 | ¹H NMR (400 MHz, MeOD) δ 8.70 (s, 1H), 8.07 (d, J = 0.6 Hz, 1H), 7.78 (d, J = 0.7 Hz, 1H), 6.59 (s, 1H), 5.46 (s, 2H), 4.09 – 3.99 (m, 1H), 3.65 – 3.57 (m, 1H), 3.54 (dd, J = 9.4, 5.2 Hz, 1H), 3.42 – 3.38 (m, 1H), 3.38 – 3.36 (m, 3H), 3.09 – 3.00 (m, 1H), 2.54 (s, 3H), 2.09 (ddd, J = 16.4, 12.3, 3.4 Hz, 4H), 1.68 – 1.53 (m, 2H), 1.47 – 1.34 (m, 2H), 1.26 (d, J = 6.6 Hz, 3H). | 467.1 |

FIG. 2 (Cont'd)

| No. | General Scheme | NMR | MS |
|---|---|---|---|
| 293 | 5 | ¹H NMR (500 MHz, MeOD) δ 8.64 (s, 1H), 7.99 (s, 1H), 7.81 (s, 1H), 6.53 (s, 1H), 5.23 – 5.15 (m, 1H), 4.79 – 4.76 (m, 1H), 4.74 – 4.69 (m, 3H), 4.52 – 4.46 (m, 1H), 4.45 – 4.37 (m, 2H), 4.28 (dd, J = 10.9, 5.5 Hz, 1H), 4.01 – 3.86 (m, 2H), 3.59 – 3.50 (m, 1H), 3.48 (dd, J = 9.4, 5.2 Hz, 1H), 3.36 – 3.32 (m, 1H), 3.31 (s, 3H), 3.02 – 2.93 (m, 1H), 2.10 – 1.94 (m, 4H), 1.60 – 1.46 (m, 2H), 1.40 – 1.29 (m, 2H), 1.19 (d, J = 6.6 Hz, 3H). | 510.1 |
| 294 | 5 | ¹H NMR (500 MHz, MeOD) δ 8.75 (s, 1H), 8.08 (s, 1H), 7.92 (s, 1H), 6.64 (s, 1H), 5.39 – 5.27 (m, 1H), 4.13 – 4.03 (m, 1H), 3.68 – 3.60 (m, 1H), 3.58 (dd, J = 9.4, 5.2 Hz, 1H), 3.46 – 3.42 (m, 2H), 3.41 (s, 3H), 3.33 (dd, J = 3.7, 2.0 Hz, 2H), 3.12 – 3.04 (m, 1H), 2.22 – 2.05 (m, 4H), 1.69 – 1.57 (m, 2H), 1.49 – 1.40 (m, 2H), 1.36 – 1.24 (m, 8H). | 562.2 |
| 295 | 5 | ¹H NMR (400 MHz, CD₃OD) δ 8.77 (s, 1H), 8.11 (s, 1H), 7.87 (s, J = 9.5 Hz, 1H), 6.65 (s, 1H), 4.14 – 4.02 (m, 1H), 3.70 – 3.60 (m, 1H), 3.58 (dd, J = 9.4, 5.2 Hz, 1H), 3.45 – 3.42 (m, 1H), 3.41 (s, J = 3.8 Hz, 3H), 3.14 – 2.99 (m, 1H), 2.71 (s, 3H), 2.21 – 2.12 (m, 2H), 2.12 – 2.00 (m, 2H), 1.84 (s, 6H), 1.70 – 1.55 (m, 2H), 1.51 – 1.36 (m, 2H), 1.29 (d, J = 6.6 Hz, 3H). | 470.1 |
| 296 | 4 | ¹H NMR (500 MHz, MeOD) δ 8.75 (s, 1H), 8.13 (s, 1H), 7.86 (s, 1H), 6.64 (s, 1H), 5.65 (s, 2H), 4.29-4.16 (m, 1H), 3.69-3.58 (m, 1H), 3.09 (tt, J = 12.3, 3.4 Hz, 1H), 2.85-2.72 (m, 1H), 2.52 (s, 3H), 2.36-2.23 (m, 1H), 2.22-2.13 (m, 2H), 2.13-2.03 (m, 2H), 1.69-1.52 (m, 2H), 1.51-1.42 (m, 2H), 1.40 (d, J = 6.6 Hz, 3H). | 505.1 |
| 297 | 4 | ¹H NMR (400 MHz, MeOD) δ 9.01 (dd, J = 2.2, 0.7 Hz, 1H), 8.96 (s, 1H), 8.31 (dd, J = 8.2, 2.2 Hz, 1H), 8.11 (dd, J = 8.2, 0.7 Hz, 1H), 6.95 (s, 1H), 4.33-4.22 (m, 1H), 3.66 (tt, J = 11.3, 4.7 Hz, 1H), 3.26 (s, 3H), 3.15 (tt, J = 11.5, 3.5 Hz, 1H), 2.84-2.72 (m, 1H), 2.39-2.26 (m, 1H), 2.25-2.16 (m, 2H), 2.16-2.05 (m, 2H), 1.73-1.57 (m, 2H), 1.53-1.43 (m, 2H), 1.42 (d, J = 6.6 Hz, 3H). | 498 |
| 298 | 5 | ¹H NMR (400 MHz, MeOD) δ 8.96 (d, J = 1.9 Hz, 1H), 8.90 (d, J = 2.2 Hz, 1H), 8.86 (s, 1H), 8.50 (t, J = 2.1 Hz, 1H), 6.83 (s, 1H), 4.23 (dd, J = 12.2, 6.6 Hz, 1H), 3.68-3.61 (m, 1H), 3.15-3.08 (m, 1H), 2.77 (ddd, J = 15.1, 11.7, 5.0 Hz, 1H), 2.37-2.22 (m, 1H), 2.22-2.13 (m, 2H), 2.12-2.02 (m, 2H), 1.71-1.51 (m, 2H), 1.52-1.40 (m, 2H), 1.38 (d, J = 6.7 Hz, 3H). | 464 |
| 299 | 5 | ¹H NMR (400 MHz, MeOD) δ 9.18 (s, 2H), 9.00 (s, 1H), 7.01 (s, 1H), 4.34-4.22 (m, 1H), 3.66 (tt, J = 10.9, 4.4 Hz, 1H), 3.15 (tt, J = 11.2, 3.2 Hz, 1H), 2.87-2.69 (m, 1H), 2.42-2.26 (m, 1H), 2.26-2.16 (m, 2H), 2.16-2.06 (m, 2H), 1.75-1.56 (m, 2H), 1.54-1.44 (m, 2H), 1.42 (d, J = 6.7 Hz, 3H). | 465 |

FIG. 2 (Cont'd)

| No. | General Scheme | NMR | MS |
|---|---|---|---|
| 300 | 7 (see Example 37) | $^1$H NMR (500 MHz, MeOD) δ 8.66 (s, 1H), 7.46 (d, J = 8.2 Hz, 2H), 7.31 (d, J = 8.1 Hz, 2H), 6.62 (s, 1H), 4.06 – 3.94 (m, 1H), 3.66 (tt, J = 11.7, 3.9 Hz, 1H), 3.62 – 3.58 (m, 4H), 3.49 (dd, J = 9.4, 5.2 Hz, 1H), 3.45 (s, 2H), 3.36 – 3.32 (m, 1H), 3.31 (s, 3H), 3.08 – 3.01 (m, 1H), 2.42 – 2.36 (m, 4H), 2.16 – 2.07 (m, 2H), 2.00 – 1.91 (m, 2H), 1.84 (s, 3H), 1.66 – 1.54 (m, 2H), 1.39 – 1.28 (m, 2H), 1.20 (d, J = 6.6 Hz, 3H). | 521.2 |
| 301 | 7 | $^1$H NMR (500 MHz, MeOD) δ 8.66 (s, 1H), 7.46 (d, J = 8.2 Hz, 2H), 7.31 (d, J = 8.2 Hz, 2H), 6.61 (s, 1H), 4.04 – 3.95 (m, 1H), 3.65 – 3.57 (m, 4H), 3.49 (dd, J = 9.4, 5.2 Hz, 1H), 3.46 (s, 2H), 3.36 – 3.32 (m, 1H), 3.31 (s, 3H), 3.27 – 3.23 (m, 1H), 3.05 – 2.98 (m, 1H), 2.88 (s, 3H), 2.46 – 2.33 (m, 4H), 2.17 – 2.02 (m, 4H), 1.68 – 1.54 (m, 2H), 1.47 – 1.36 (m, 2H), 1.20 (d, J = 6.6 Hz, 3H). | 557.1 |
| 302 | 4 | $^1$H NMR (500 MHz, MeOD) δ 8.77 (s, 1H), 8.14 (s, 1H), 7.88 (s, 1H), 6.65 (s, 1H), 5.14 (p, J = 7.2 Hz, 1H), 4.15 – 4.06 (m, 1H), 4.03 – 3.99 (m, 2H), 3.85 – 3.80 (m, 2H), 3.70 – 3.62 (m, 1H), 3.60 (dd, J = 9.4, 5.2 Hz, 1H), 3.48 – 3.44 (m, 1H), 3.43 (s, 3H), 3.35 (s, 1H), 3.30 (d, J = 9.7 Hz, 1H), 3.15 – 3.04 (m, 1H), 2.22 – 2.08 (m, 4H), 1.72 – 1.58 (m, 2H), 1.52 – 1.40 (m, 2H), 1.31 (d, J = 6.6 Hz, 3H). | 508.1 |
| 303 | 4 | $^1$H NMR (400 MHz, CD$_3$OD) δ 8.70 (s, J = 0.8 Hz, 1H), 8.02 (s, 1H), 7.80 (s, 1H), 6.62 (s, 1H), 4.26 (d, J = 7.3 Hz, 2H), 4.12 – 4.02 (m, 1H), 3.69 – 3.60 (m, 1H), 3.58 (dd, J = 9.7, 5.0 Hz, 1H), 3.50 – 3.42 (m, 2H), 3.41 (s, J = 0.9 Hz, 3H), 3.28 – 3.19 (m, 1H), 3.14 – 3.02 (m, 2H), 2.50 – 2.41 (m, 1H), 2.21 (dd, J = 17.1, 6.2 Hz, 1H), 2.19 – 2.03 (m, 4H), 1.70 – 1.55 (m, 2H), 1.50 – 1.36 (m, 2H), 1.29 (d, J = 6.2 Hz, 3H). | 468.1 |
| 304 | 5 | $^1$H NMR (500 MHz, MeOD) δ 8.93 (d, J = 2.6 Hz, 2H), 8.85 (d, J = 2.0 Hz, 1H), 8.40 (t, J = 2.1 Hz, 1H), 6.88 (s, 1H), 4.31-4.22 (m, 1H), 3.69-3.62 (m, 1H), 3.18-3.10 (m, 1H), 2.97 (s, 3H), 2.85-2.73 (m, 1H), 2.39-2.26 (m, 1H), 2.25-2.17 (m, 2H), 2.14-2.06 (m, 2H), 1.72-1.57 (m, 2H), 1.52-1.43 (m, 2H), 1.41 (d, J = 6.6 Hz, 3H). | 477 |
| 305 | 4 | $^1$H NMR (500 MHz, MeOD) δ 8.65 (s, 1H), 8.55 – 8.30 (m, 3H), 8.07 (s, 1H), 7.76 (s, 1H), 6.54 (s, 1H), 5.47 (s, 2H), 4.04 – 3.91 (m, 1H), 3.59 – 3.50 (m, 1H), 3.47 (dt, J = 12.1, 6.1 Hz, 1H), 3.37 – 3.32 (m, 1H), 3.31 (s, 3H), 2.98 (ddd, J = 12.2, 7.9, 3.6 Hz, 1H), 2.11 – 1.94 (m, 4H), 1.60 – 1.46 (m, 2H), 1.40 – 1.27 (m, 2H), 1.19 (d, J= 6.6 Hz, 3H). | 463.1 |
| 306 | 4 | $^1$H NMR (500 MHz, MeOD) δ 8.64 (s, 1H), 8.41 (s, 1H), 8.25 (d, J = 1.0 Hz, 1H), 8.04 (s, 1H), 7.74 (s, 1H), 6.53 (s, 1H), 5.41 (s, 2H), 4.03 – 3.93 (m, 1H), 3.58 – 3.50 (m, 1H), 3.48 (dd, J = 9.4, 5.2 Hz, 1H), 3.35 – 3.32 (m, 1H), 3.31 (s, 3H), 2.98 (tt, J = 12.2, 3.5 Hz, 1H), 2.45 (s, 3H), 2.11 – 1.95 (m, 4H), 1.59 – 1.47 (m, 2H), 1.39 – 1.29 (m, 2H), 1.19 (d, J = 6.6 Hz, 3H). | 477.1 |

FIG. 2 (Cont'd)

| No. | General Scheme | NMR | MS |
|---|---|---|---|
| 307 | 7 | ¹H NMR (500 MHz, MeOD) δ 8.78 (s, 1H), 7.58 (d, J = 8.2 Hz, 2H), 7.43 (d, J = 8.1 Hz, 2H), 6.74 (s, 1H), 4.17 – 4.06 (m, 1H), 3.74 – 3.71 (m, 4H), 3.61 (dd, J = 9.4, 5.2 Hz, 1H), 3.58 (s, 2H), 3.48 – 3.44 (m, 1H), 3.43 (s, 3H), 3.22 – 3.13 (m, 1H), 2.56 – 2.46 (m, 4H), 2.32 – 2.06 (m, 4H), 1.80 – 1.65 (m, 2H), 1.64 – 1.52 (m, 2H), 1.32 (d, J = 6.6 Hz, 3H). | 560.5 |
| 308 | 4 | ¹H NMR (500 MHz, MeOD) δ 9.00 (s, 1H), 7.43 (s, 2H), 6.94 (s, 1H), 4.18 – 4.07 (m, 1H), 3.72 – 3.64 (m, 1H), 3.63 – 3.57 (m, 1H), 3.46 (dd, J = 6.3, 3.2 Hz, 1H), 3.44 (s, 3H), 3.13 (tt, J = 12.1, 3.5 Hz, 1H), 2.58 (s, 6H), 2.27 – 2.06 (m, 4H), 1.74 – 1.60 (m, 2H), 1.54 – 1.42 (m, 2H), 1.32 (d, J = 6.6 Hz, 3H). | 410.6 |
| 309 | 4 | ¹H NMR (500 MHz, MeOD) δ 9.00 (s, 1H), 8.38 (d, J = 5.4 Hz, 1H), 7.55 (s, 1H), 7.48 (d, J = 5.3 Hz, 1H), 6.93 (s, 1H), 6.16-5.89 (m, 1H), 4.38-4.25 (m, 1H), 3.65 (tt, J = 11.1, 4.4 Hz, 1H), 3.11 (tt, J = 12.2, 3.4 Hz, 1H), 2.57 (s, 3H), 2.24-2.15 (m, 2H), 2.14-2.06 (m, 2H), 1.72-1.57 (m, 2H), 1.52-1.40 (m, 2H), 1.34 (d, J = 6.9 Hz, 3H). | 402 |
| 310 | 5 | ¹H NMR (500 MHz, MeOD) δ 8.89 (s, 2H), 8.51 (d, J = 1.8 Hz, 1H), 8.10 (t, J = 2.0 Hz, 1H), 6.87 (s, 1H), 4.32-4.22 (m, 1H), 3.72-3.61 (m, 1H), 3.19-3.11 (m, 4H), 3.09 (s, 3H), 2.86-2.73 (m, 1H), 2.39-2.27 (m, 1H), 2.24-2.16 (m, 2H), 2.15-2.06 (m, 2H), 1.73-1.57 (m, 2H), 1.53-1.44 (m, 2H), 1.42 (d, J = 6.7 Hz, 3H). | 491.1 |
| 311 | 5 | ¹H NMR (500 MHz, MeOD) δ 8.90 (d, J = 2.1 Hz, 1H), 8.89 (s, 1H), 8.52 (d, J = 1.9 Hz, 1H), 8.11 (t, J = 2.1 Hz, 1H), 6.88 (s, 1H), 4.31-4.23 (m, 1H), 3.88-3.49 (m, 9H), 3.19-3.11 (m, 1H), 2.86-2.73 (m, 1H), 2.40-2.27 (m, 1H), 2.25-2.17 (m, 2H), 2.15-2.05 (m, 2H), 1.74-1.57 (m, 2H), 1.53-1.44 (m, 2H), 1.42 (d, J = 6.7 Hz, 3H). | 533.2 |
| 312 | 4 | ¹H NMR (500 MHz, MeOD) δ 8.76 (s, 1H), 8.14 (s, 1H), 7.86 (d, J = 0.6 Hz, 1H), 6.65 (s, 1H), 6.43 (t, J = 75.5 Hz, 1H), 5.66 (s, 2H), 4.17-4.07 (m, 2H), 3.83 (dd, J = 9.3, 6.1 Hz, 1H), 3.64 (tt, J = 10.9, 4.3 Hz, 1H), 3.09 (tt, J = 12.2, 3.5 Hz, 1H), 2.53 (s, 3H), 2.21-2.13 (m, 2H), 2.13-2.05 (m, 2H), 1.68-1.56 (m, 2H), 1.51-1.40 (m, 2H), 1.35 (d, J = 6.6 Hz, 3H). | 503 |
| 313 | 4 | ¹H NMR (500 MHz, MeOD) δ 8.97 (s, 1H), 8.38 (d, J = 5.3 Hz, 1H), 7.54 (s, 1H), 7.47 (d, J = 5.4 Hz, 1H), 6.91 (s, 1H), 6.43 (t, J = 75.4 Hz, 1H), 4.20-4.14 (m, 1H), 4.14-4.08 (m, 1H), 3.84 (dd, J = 9.7, 6.4 Hz, 1H), 3.66 (tt, J = 10.9, 4.2 Hz, 1H), 3.13 (tt, J = 12.4, 3.7 Hz, 1H), 2.57 (s, 3H), 2.24-2.15 (m, 2H), 2.15-2.05 (m, 2H), 1.71-1.58 (m, 2H), 1.52-1.42 (m, 2H), 1.36 (d, J = 6.7 Hz, 3H). | 432.1 |

FIG. 2 (Cont'd)

| No. | General Scheme | NMR | MS |
|---|---|---|---|
| 314 | 4 | ¹H NMR (400 MHz, CD₃OD) δ 8.74 (s, 1H), 8.13 (s, 1H), 7.94 (d, J = 7.8 Hz, 2H), 7.87 (s, 1H), 7.50 (d, J = 8.1 Hz, 2H), 6.64 (s, 1H), 5.52 (s, 2H), 4.14 – 4.02 (m, 1H), 3.72 – 3.60 (m, 1H), 3.58 (dd, J = 10.0, 4.9 Hz, 1H), 3.45 – 3.42 (m, 1H), 3.41 (s, 3H), 3.09 (s, 3H), 3.14 – 3.01 (m, 1H), 2.22 – 2.13 (m, 2H), 2.13 – 2.03 (m, 2H), 1.71 – 1.55 (m, 2H), 1.51 – 1.38 (m, 2H), 1.29 (d, J = 6.6 Hz, 3H). | 539 |
| 315 | 4 | ¹H NMR (400 MHz, CD₃OD) δ 8.75 (s, 1H), 8.04 (s, 1H), 7.84 (s, 1H), 6.62 (s, 1H), 5.15 (t, J = 9.0 Hz, 1H), 4.12 – 4.04 (m, 1H), 3.69 – 3.62 (m, 1H), 3.61 – 3.55 (m, 2H), 3.54 – 3.46 (m, 1H), 3.45 – 3.42 (m, 1H), 3.41 (s, 3H), 3.13 – 3.03 (m, 1H), 2.79 – 2.60 (m, 2H), 2.22 – 2.13 (m, 2H), 2.13 – 2.03 (m, 2H), 1.71 – 1.56 (m, 2H), 1.50 – 1.38 (m, 2H), 1.29 (d, J = 6.6 Hz, 3H). | 545.1 |
| 316 | 7 (see Example 38) | ¹H NMR (500 MHz, DMSO) δ 8.99 (s, 1H), 7.66 (d, J = 8.1 Hz, 2H), 7.41 (d, J = 8.2 Hz, 2H), 6.84 (s, 1H), 6.71 (d, J = 7.7 Hz, 1H), 4.14 – 4.02 (m, 1H), 3.93 (br s, 1H), 3.67 – 3.63 (m, 4H), 3.57 (dd, J = 9.5, 5.4 Hz, 1H), 3.54 (s, 2H), 3.37 (s, 3H), 3.35 (dd, J = 9.6, 6.9 Hz, 2H), 3.21 (d, J = 4.5 Hz, 3H), 3.17 – 3.06 (m, 1H), 2.49 – 2.39 (m, 4H), 2.26 – 2.07 (m, 4H), 1.77 – 1.61 (m, 2H), 1.61 – 1.48 (m, 2H), 1.38 – 1.28 (m, 2H), 1.26 (d, J = 8.3 Hz, 3H). | 589.2 |
| 317 | 4 | ¹H NMR (500 MHz, MeOD) δ 8.90 (s, 1H), 8.88 (d, J = 1.6 Hz, 1H), 8.16 (dd, J = 8.1, 2.2 Hz, 1H), 8.12 (d, J = 8.1 Hz, 1H), 6.88 (s, 1H), 6.43 (t, J = 75.4 Hz, 1H), 4.20-4.13 (m, 1H), 4.11 (dd, J = 9.7, 4.6 Hz, 1H), 3.84 (dd, J = 9.6, 6.4 Hz, 1H), 3.70-3.62 (m, 1H), 3.19-3.09 (m, 1H), 2.99 (s, 3H), 2.23-2.16 (m, 2H), 2.14-2.07 (m, 2H), 1.73-1.58 (m, 2H), 1.52-1.43 (m, 2H), 1.36 (d, J = 6.7 Hz, 3H). | 475.2 |
| 318 | 5 | ¹H NMR (400 MHz, CD₃OD) δ 8.77 (s, 1H), 8.16 (s, 1H), 7.88 (s, 1H), 6.66 (s, 1H), 4.60 (d, J = 6.2 Hz, 1H), 4.44 (t, J = 6.5 Hz, 2H), 4.28 (d, J = 6.2 Hz, 1H), 4.11 – 3.97 (m, 1H), 3.71 (s, 1H), 3.66 – 3.57 (m, 1H), 3.55 (dd, J = 9.5, 5.1 Hz, 1H), 3.52 – 3.43 (m, 1H), 3.42 – 3.39 (m, 1H), 3.38 (s, 3H), 3.11 – 2.98 (m, 1H), 2.84 (s, 1H), 2.61 (t, J = 6.6 Hz, 1H), 2.20 – 2.10 (m, 2H), 2.10 – 2.03 (m, 2H), 2.01 (t, J = 7.1 Hz, 2H), 1.80 (s, 3H), 1.78 (s, 3H), 1.69 – 1.50 (m, 2H), 1.48 – 1.34 (m, 2H), 1.26 (d, J = 6.6 Hz, 3H). | 552.7 |
| 319 | 5 | ¹H NMR (400 MHz, CD₃OD) δ 8.78 (s, 1H), 8.13 (s, J = 12.1 Hz, 1H), 7.88 (s, J = 10.0 Hz, 1H), 6.66 (s, 1H), 4.14 – 4.03 (m, 1H), 3.85 – 3.68 (m, 4H), 3.68 – 3.61 (m, 1H), 3.62 – 3.55 (m, 1H), 3.47 – 3.42 (m, 1H), 3.41 (s, 3H), 3.15 – 3.02 (m, 1H), 3.02 – 2.89 (m, 1H), 2.81 (s, 2H), 2.60 (s, 1H), 2.23 – 2.13 (m, 2H), 2.13 – 2.03 (m, 2H), 1.82 (s, 6H), 1.71 – 1.54 (m, 2H), 1.50 – 1.37 (m, 2H), 1.32 – 1.25 (m, 5H). | 552.7 |

FIG. 2 (Cont'd)

| No. | General Scheme | NMR | MS |
|---|---|---|---|
| 320 | 5 | ¹H NMR (400 MHz, CD₃OD) δ 8.76 (s, 1H), 8.13 (s, 1H), 7.87 (s, 1H), 6.66 (s, 1H), 4.14 – 4.02 (m, 1H), 3.70 – 3.61 (m, 1H), 3.58 (dd, J = 9.4, 5.2 Hz, 1H), 3.47 – 3.42 (m, 1H), 3.41 (s, 3H), 3.14 – 3.03 (m, 1H), 2.40 (t, J = 11.3 Hz, 2H), 2.24 – 2.13 (m, 2H), 2.13 – 2.03 (m, 2H), 1.83 (s, 6H), 1.71 – 1.56 (m, 2H), 1.45 (dd, J = 23.5, 10.7 Hz, 2H), 1.35 – 1.24 (m, 3H), 1.22 – 0.17 (m, 10H). | 554.7 |
| 321 | 4 | ¹H NMR (400 MHz, MeOD) δ 8.78 (s, 1H), 8.63 (d, J = 2.1 Hz, 1H), 7.95 (dd, J = 8.1, 2.3 Hz, 1H), 7.37 (d, J = 8.1 Hz, 1H), 6.77 (s, 1H), 6.43 (t, J = 75.4 Hz, 1H), 4.21-4.06 (m, 2H), 3.84 (dd, J = 9.5, 6.2 Hz, 1H), 3.66 (tt, J = 11.1, 4.5 Hz, 1H), 3.13 (tt, J = 11.8, 3.2 Hz, 1H), 2.56 (s, 3H), 2.25-2.04 (m, 4H), 1.75-1.55 (m, 2H), 1.55-1.40 (m, 2H), 1.35 (d, J = 6.6 Hz, 3H). | 432.2 |
| 322 | 6 | ¹H NMR (400 MHz, CD₃OD) δ 8.73 (s, 1H), 8.06 (s, 1H), 7.82 (s, 1H), 7.74 (s, 1H), 7.53 (dd, J = 9.3, 2.3 Hz, 1H), 6.62 (s, 1H), 6.54 (d, J = 9.3 Hz, 1H), 5.15 (s, 2H), 4.14 – 4.01 (m, 1H), 3.69 – 3.60 (m, 1H), 3.60 – 3.54 (m, 4H), 3.46 – 3.41 (m, 1H), 3.41 (s, 3H), 3.14 – 3.01 (m, 1H), 2.23 – 2.12 (m, 2H), 2.12 – 2.01 (m, 2H), 1.71 – 1.54 (m, 2H), 1.49 – 1.37 (m, 2H), 1.29 (d, J = 6.6 Hz, 3H). | 503.1 |
| 323 | 6 | ¹H NMR (400 MHz, CD₃OD) δ 8.74 (s, 1H), 8.04 (s, 1H), 7.82 (s, 1H), 6.62 (s, 1H), 4.69 – 4.55 (m, 1H), 4.16 – 4.02 (m, 1H), 3.71 – 3.60 (m, 1H), 3.58 (dd, J = 9.4, 5.2 Hz, 1H), 3.47 – 3.42 (m, 1H), 3.41 (s, 3H), 3.40 – 3.32 (m, 4H), 3.14 – 3.02 (m, 1H), 2.76 – 2.59 (m, 2H), 2.54 – 2.41 (m, 2H), 2.23 – 2.13 (m, 2H), 2.13 – 2.03 (m, 2H), 1.71 – 1.53 (m, 2H), 1.51 – 1.35 (m, 2H), 1.29 (d, J = 6.6 Hz, 3H). | 492.2 |
| 324 | 6 | ¹H NMR (400 MHz, CD₃OD) δ 8.73 (s, 1H), 7.95 (s, 1H), 7.83 (s, 1H), 6.61 (s, 1H), 4.28 (d, J = 5.1 Hz, 2H), 4.20 – 4.12 (m, 1H), 4.12 – 4.02 (m, 1H), 3.70 – 3.60 (m, 1H), 3.60 – 3.53 (m, 1H), 3.47 – 3.42 (m, 1H), 3.42 (s, 3H), 3.16 – 3.00 (m, 1H), 2.35 – 1.96 (m, 8H), 1.69 – 1.55 (m, 2H), 1.50 – 1.38 (m, 2H), 1.29 (d, J = 6.6 Hz, 3H). | 468.2 |
| 325 | See Example 40 | ¹H NMR (500 MHz, DMSO-D₂O) δ 9.04 (s, 1H), 8.36 (d, J = 5.3 Hz, 1H), 7.50 (s, 1H), 7.44 (dd, J = 5.3, 1.4 Hz, 1H), 6.97 (s, 1H), 4.03 – 3.95 (m, 1H), 3.46 (dd, J = 9.6, 5.7 Hz, 1H), 3.29 (dd, J = 9.6, 6.3 Hz, 1H), 3.26 (s, 3H), 3.17 – 3.01 (m, 1H), 2.47 (s, 3H), 2.08 – 2.01 (m, 2H), 1.85 – 1.76 (m, 2H), 1.76 – 1.64 (m, 4H), 1.16 (d, J = 6.7 Hz, 3H). Major Dias. Described | 464.5 |
| 326 | 5 | ¹H NMR (400 MHz, MeOD) δ 8.77 (s, 1H), 8.12 (s, 1H), 7.89 (s, 1H), 6.65 (s, 1H), 4.70 – 4.50 (m, 4H), 4.11 (s, 2H), 4.05 (dt, J = 12.2, 6.1 Hz, 1H), 3.67 – 3.57 (m, 1H), 3.55 (dd, J = 9.4, 5.2 Hz, 1H), 3.50 (s, 2H), 3.44 – 3.39 (m, 1H), 3.38 (s, 3H), 3.06 (tt, J = 11.9, 3.3 Hz, 1H), 2.20 – 2.02 (m, 4H), 1.75 (s, 6H), 1.67 – 1.54 (m, 2H), 1.48 – 1.34 (m, 2H), 1.26 (d, J = 6.6 Hz, 3H). | 538.2 |

FIG. 2 (Cont'd)

| No. | General Scheme | NMR | MS |
|---|---|---|---|
| 327 | 5 | $^1$H NMR (400 MHz, MeOD) δ 8.75 (s, 1H), 8.09 (s, 1H), 7.85 (s, 1H), 6.63 (s, 1H), 4.33 – 3.82 (m, 5H), 3.66 – 3.51 (m, 2H), 3.43 – 3.39 (m, 1H), 3.37 (s, 3H), 3.10 – 3.01 (m, 1H), 2.90 (d, J = 11.7 Hz, 2H), 2.17 – 2.02 (m, 4H), 1.88 – 1.69 (m, 8H), 1.69 – 1.53 (m, 4H), 1.47 – 1.35 (m, 2H), 1.27 – 1.24 (m, 3H). | 552.2 |
| 328 | 5 | $^1$H NMR (400 MHz, CD$_3$OD) δ 8.74 (s, 1H), 8.12 (d, J = 13.5 Hz, 1H), 7.84 (s, 1H), 6.62 (s, 1H), 4.05 (dd, J = 12.3, 6.0 Hz, 1H), 4.01 – 3.45 (m, 6H), 3.42 – 3.39 (m, 1H), 3.38 (s, 3H), 3.20 – 2.97 (m, 3H), 2.17 – 2.04 (m, 4H), 1.84 (s, 3H), 1.78 (s, 3H), 1.66 – 1.54 (m, 2H), 1.46 – 1.36 (m, 2H), 1.26 (d, J = 6.6 Hz, 3H), 1.21 – 0.81 (m, 6H). | 554.3 |
| 329 | 4 | $^1$H NMR (400 MHz, MeOD) δ 8.71 (s, 1H), 8.41 (s, 1H), 8.18 (s, 1H), 8.12 (s, 1H), 7.82 (s, 1H), 6.60 (s, 1H), 5.47 (s, 2H), 4.11 – 3.98 (m, 1H), 3.65 – 3.52 (m, 2H), 3.42 – 3.39 (m, 1H), 3.38 (s, 3H), 3.11 – 2.99 (m, 1H), 2.52 (s, 3H), 2.20 – 2.00 (m, 4H), 1.67 – 1.51 (m, 2H), 1.47 – 1.34 (m, 2H), 1.26 (d, J = 6.6 Hz, 3H). | 477.3 |
| 330 | 4 | $^1$H NMR (400 MHz, MeOD) δ 8.71 (s, 1H), 8.04 (s, 1H), 7.86 (s, 1H), 6.59 (s, 1H), 5.23 (tt, J = 8.0, 5.4 Hz, 1H), 4.47 – 4.30 (m, 4H), 4.10 – 4.00 (m, 1H), 3.68 (d, J = 0.5 Hz, 3H), 3.66 – 3.57 (m, 1H), 3.54 (dd, J = 9.5, 5.1 Hz, 1H), 3.42 – 3.38 (m, 1H), 3.38 (s, 3H), 3.04 (tt, J = 12.1, 3.3 Hz, 1H), 2.18 – 1.98 (m, 4H), 1.66 – 1.52 (m, 2H), 1.46 – 1.33 (m, 2H), 1.25 (d, J = 6.6 Hz, 3H). | 484.2 |
| 331 | 6 (See Example 33) | $^1$H NMR (400 MHz, MeOD) δ 8.77 (s, 1H), 8.16 (s, 1H), 7.89 (s, 1H), 6.64 (s, 1H), 4.10 – 4.00 (m, 1H), 3.93 – 3.51 (m, 5H), 3.43 – 3.39 (m, 1H), 3.38 (s, 2H), 3.10 – 2.80 (m, 4H), 2.19 – 2.02 (m, 4H), 1.82 (s, 5H), 1.66 – 1.53 (m, 2H), 1.46 – 1.35 (m, 2H), 1.26 (d, J = 6.6 Hz, 3H) | 574.2 |
| 332 | 6 | $^1$H NMR (400 MHz, CD$_3$OD) δ 8.67 (s, 1H), 7.94 (s, 1H), 7.75 (d, J = 0.7 Hz, 1H), 7.71 – 7.46 (m, 2H), 6.56 (s, 1H), 5.26 (s, 2H), 4.10 – 3.96 (m, 1H), 3.64 – 3.56 (m, 1H), 3.54 (dd, J = 9.4, 5.2 Hz, 1H), 3.42 – 3.38 (m, 1H), 3.37 (s, 3H), 3.09 – 2.95 (m, 1H), 2.17 – 2.08 (m, 2H), 2.08 – 2.00 (m, 2H), 1.66 – 1.48 (m, 2H), 1.46 – 1.34 (m, 2H), 1.25 (d, J = 6.6 Hz, 3H). | 451.2 |
| 333 | 6 | $^1$H NMR (400 MHz, CD$_3$OD) δ 8.71 (s, 1H), 7.98 (s, 1H), 7.81 (s, 1H), 6.61 (s, 1H), 6.07 (s, 1H), 5.41 (s, 2H), 4.12 – 4.03 (m, 1H), 3.78 (s, 3H), 3.69 – 3.60 (m, 1H), 3.57 (dd, J = 9.4, 5.2 Hz, 1H), 3.46 – 3.41 (m, 1H), 3.41 (s, 3H), 3.12 – 3.01 (m, 1H), 2.18 (s, 3H), 2.17 – 2.12 (m, 2H), 2.12 – 2.02 (m, 2H), 1.71 – 1.56 (m, 2H), 1.52 – 1.37 (m, 2H), 1.29 (d, J = 6.6 Hz, 3H). | 479.2 |
| 334 | 4 | $^1$H NMR (400MHz, CD$_3$OD) δ 9.44 - 9.21 (m, 2H), 9.14 (br s, 1H), 7.36 (s, 1H), 4.25 - 4.13 (m, 1H), 3.75 - 3.65 (m, 1H), 3.64 - 3.57 (m, 1H), 3.57 - 3.49 (m, 1H), 3.45 (s, 3H), 3.23 (br t, J=11.2 Hz, 1H), 3.07 (br s, 3H), 2.28 - 2.09 (m, 4H), 1.74 (q, J=12.8 Hz, 2H), 1.50 (q, J=12.0 Hz, 2H), 1.37 (d, J=6.4 Hz, 3H). | 440.3 |

FIG. 2 (Cont'd)

| No. | General Scheme | NMR | MS |
|---|---|---|---|
| 335 | 4 | 1H-NMR (400 MHz, CD$_3$OD) δ 9.01 (s, 1H), 8.08 (d, J=1.2 Hz, 1H), 7.63 (d, J=1.2 Hz, 1H), 6.93 (s, 1H), 4.15-4.09 (m, 1H), 3.67-3.65 (m, 1H), 3.61-3.57 (m, 1H), 3.46-3.43 (m, 1H), 3.42 (s, 3H), 3.13-3.09 (m, 1H), 2.99 (s, 3H), 2.62 (s, 3H), 2.22-2.19 (m, 2H), 2.12-2.10 (m, 2H), 1.69-1.63 (m, 2H), 1.48-1.44 (m, 2H), 1.30 (d, J=6.8 Hz, 3H). | 453.3 |
| 336 | 4 | $^1$H NMR (400MHz, CD$_3$OD) δ 8.95 (d, J=1.2 Hz, 1H), 8.92 (s, 1H), 8.25 (dd, J=2.4, 8.0 Hz, 1H), 8.01 (d, J=8.0 Hz, 1H), 6.91 (s, 1H), 4.14-4.09 (m, 1H), 3.69-3.61 (m, 1H), 3.60-3.57 (m, 1H), 3.46-3.43 (m, 1H), 3.42 (s, 3H), 3.17-3.11 (m, 1H), 2.69 (s, 3H), 2.22-2.19 (m, 2H), 2.12-2.09 (m, 2H), 1.70-1.65 (m, 2H), 1.51-1.42 (m, 2H), 1.30 (d, J=6.8 Hz, 3H). | 475.2 |
| 337 | 5 | $^1$H NMR (400MHz, CD$_3$OD) δ 8.87 (s, 1H), 7.94 (d, J=5.6 Hz, 1H), 6.81 - 6.76 (m, 2H), 6.72 - 6.69 (m, 1H), 4.17 - 4.07 (m, 1H), 4.07 - 3.99 (m, 1H), 3.73 - 3.57 (m, 2H), 3.48 - 3.44 (m, 1H), 3.43 (s, 3H), 3.17 - 3.07 (m, 1H), 2.25 - 2.16 (m, 2H), 2.16 - 2.07 (m, 2H), 1.74 - 1.59 (m, 2H), 1.53 - 1.40 (m, 2H), 1.32 (d, J=6.8 Hz, 3H), 1.25 (d, J=6.4 Hz, 6H). | 439.3 |
| 338 | 5 | $^1$H NMR (400MHz, CD$_3$OD) δ 8.90 (s, 1H), 8.15 (d, J=5.2 Hz, 1H), 7.04 (s, 1H), 7.00 (d, J=5.2 Hz, 1H), 6.88 (s, 1H), 4.21 - 4.05 (m, 1H), 3.75 - 3.70 (m, 4H), 3.70 - 3.58 (m, 2H), 3.48 - 3.44 (m, 1H), 3.43 (s, 3H), 3.39 - 3.35 (m, 4H), 3.18 – 3.06 (m, 1H), 2.89 (s, 3H), 2.25 – 2.17 (m, 2H), 2.16 -2.06 (m, 2H), 1.74 - 1.60 (m, 2H), 1.54 - 1.41 (m, 2H), 1.32 (d, J=6.4 Hz, 3H). | 544.4 |
| 339 | 5 | $^1$H NMR (400MHz, CD$_3$OD) δ 8.84 (s, 1H), 7.97 (d, J=5.4 Hz, 1H), 6.80 - 6.75 (m, 2H), 6.58 (s, 1H), 4.07 (sxt, J=6.1 Hz, 1H), 3.68 - 3.52 (m, 2H), 3.52 - 3.42 (d, 4H), 3.43 - 3.40 (s, 1H), 3.39 (s, 3H), 3.13 - 3.02 (m, 1H), 2.16 (br d, J=12.2 Hz, 2H), 2.11 - 1.99 (m, 6H), 1.68 - 1.54 (m, 2H), 1.49 - 1.36 (m, 2H), 1.27 (d, J=6.8 Hz, 3H). | 451.3 |
| 340 | 5 | $^1$H NMR (400 MHz, CDCl$_3$) δ 8.77 (s, 1H), 8.17 (d, J=5.2 Hz, 1H), 6.83 (d, J=6.4 Hz, 1H), 6.65 (s, 1H), 6.11 (s, 1H), 4.85 (d, J=7.2 Hz, 1H), 4.26-4.23 (m, 2H), 4.10-4.02 (m, 1H), 3.89-3.83 (m, 2 H), 3.75-3.65 (m, 1H), 3.58-3.46 (m, 4H), 3.37 (s, 3H), 3.15-3.01 (m, 1H), 2.23-2.06 (m, 4H), 1.54-1.38 (m, 5H), 1.28 (d, J=8 Hz, 3H). | 480.3 |
| 341 | 4 | $^1$H NMR (400MHz, CD$_3$OD) δ 8.91 (s, 1H), 8.11 (d, J=5.6 Hz, 1H), 7.20 (dd, J=1.2, 5.2 Hz, 1H), 6.98 (s, 1H), 6.86 (s,1H), 5.08 (s, 1H), 4.62 (s, 1H), 4.21 - 4.06 (m, 1H), 3.74 - 3.57 (m, 2H), 3.50 - 3.40 (m, 4H), 3.18 - 3.02 (m, 1H), 2.90 -2.70 (m, 2H), 2.50 - 2.37 (m, 2H), 2.34 (s, 3H), 2.20 -2.15 (m, 2H), 2.14-2.10(m, 4H), 1.95- 1.80 (m, 2H), 1.74 - 1.58 (m, 2H), 1.54 -1.40 (m, 2H), 1.32 (d, J=6.4 Hz, 3H). | 495.4 |

FIG. 2 (Cont'd)

| No. | General Scheme | NMR | MS |
|---|---|---|---|
| 342 | 4 | ¹H NMR (400MHz, CD₃OD) δ 8.93 (s, 1H), 8.11 (d, J=5.4 Hz, 1H), 7.19 (d, J=5.4 Hz, 1H), 7.00 (s, 1H), 6.86 (s, 1H),5.20 ( s, 1H), 4.61 s, 1H), 4.19 - 4.02 (m, 1H), 3.77 - 3.55 (m, 2H), 3.52 - 3.39 (m, 4H), 3.19- 3.06 (m, 1H), 2.97 -2.82 (m, 1H),2.63 - 2.36 (m, 3H), 2.32 (s, 3H), 2.26-2.16 (m, J=13.7 Hz, 2H), 2.15-2.08 (m, 2H), 2.06-1.85 (m, 2H), 1.76 - 1.58 (m, 4H), 1.56- 1.39 (m, 2H), 1.32 (d, J=6.4 Hz, 3H). | 495.4 |
| 343 | 4 | ¹H NMR (400MHz, CD₃OD) δ 8.89 (s, 1H), 8.10 (d, J=5.6 Hz, 1H), 7.16 (dd, J=1.6, 5.6 Hz, 1H), 6.94 - 6.91 (m, 1H), 6.84 (s, 1H), 5.30 - 5.21 (m, 1H), 4.17 - 4.06 (m, 1H), 3.71 - 3.57 (m, 2H), 3.48 - 3.44 (m, 1H), 3.43 (s, 3H), 3.16 - 3.06 (m, 1H), 2.25 - 2.16 (m, 2H), 2.15 - 2.06 (m, 2H), 1.73 - 1.59 (m, 2H), 1.53 - 1.41 (m, 2H), 1.37 (d, J=6.0 Hz, 6H), 1.31 (d, J=6.8 Hz, 3H). | 440.3 |
| 344 | 5 | ¹H NMR (400 MHz, CDCl₃) δ 8.82 (s, 1H), 8.22 (d, J=5.2 Hz, 1H), 6.85 (d, J=6.4 Hz, 1H), 6.76 (s, 1H), 6.65 (s, 1H), 4.88 (d, J=7.2 Hz, 1H), 4.34-4.23 (m, 1H), 4.13-4.03 (m,2H), 3.92-3.86 (m, 2 H), 3.74-3.65 (m, 2H), 3.54-3.49 (m, 2H), 3.36-3.27 (m, 2H), 3.12 (s, 3H), 2.87-2.97 (m, 1H), 2.33-2.23 (m, 2H), 2.14-2.06 (m, 5H), 1.64-1.56 (m, 2H), 1.56-1.43 (m, 4H), 1.34 (d, J=6.4 Hz, 3H). | 508.3 |
| 345 | 4 | ¹H NMR (400MHz, CD₃OD) δ 8.91 (s, 1H), 8.11 (d, J=5.6 Hz, 1H), 7.21 (dd, J=1.6, 5.6 Hz, 1H), 7.03 - 7.01 (m, 1H), 6.85 (s, 1H), 4.48 - 4.43 (m, 2H), 4.16 - 4.08 (m, 1H), 3.82 - 3.76 (m, 2H), 3.72 - 3.58 (m, 2H), 3.46 - 3.45 (m, 1H), 3.45 (s, 3H), 3.43 (s, 3H), 3.16 - 3.05 (m, 1H), 2.25 - 2.16 (m, 2H), 2.15 - 2.07 (m, 2H), 1.73 - 1.58 (m, 2H), 1.53 - 1.40 (m, 2H), 1.32 (d, J=6.8 Hz, 3H). | 456.3 |
| 346 | 4 | ¹H NMR (400 MHz, MeOD) δ 8.86 (s, 1H), 8.08 (d, J = 5.2 Hz, 1H), 6.96 – 6.90 (m, 2H), 6.82 (s, 1H), 4.29 – 4.15 (m, 1H), 3.82 – 3.74 (m, 4H), 3.68 – 3.57 (m, 1H), 3.52 – 3.46 (m, 4H), 3.15 – 3.02 (m, 1H), 2.83 – 2.68 (m, 1H), 2.37 – 2.22 (m, 1H), 2.20 – 2.00 (m, 4H), 1.68 – 1.52 (m, 2H), 1.49 – 1.40 (m, 2H), 1.38 (d, J = 6.7 Hz, 3H). | 505.2 |
| 347 | 5 | ¹H NMR (400 MHz, MeOD) δ 9.17 (s, 2H), 8.98 (s, 1H), 6.98 (s, 1H), 4.35-4.18 (m, 1H), 3.66 (tt, J = 10.9, 4.4 Hz, 1H), 3.23-3.08 (m, 1H), 3.02 (s, 3H), 2.88-2.69 (m, 1H), 2.42-2.25 (m, 1H), 2.25-2.15 (m, 2H), 2.16-2.03 (m, 2H), 1.75-1.54 (m, 2H), 1.54-1.44 (m, 2H), 1.42 (d, J = 6.7 Hz, 3H). | 478 |
| 348 | 6 | ¹H NMR (400 MHz, CD₃OD) δ 8.75 (s, 1H), 8.04 (s, 1H), 7.85 (s, 1H), 6.63 (s, 1H), 5.16 (t, J = 9.0 Hz, 1H), 4.14 – 4.02 (m, 1H), 3.69 – 3.61 (m, 1H), 3.61 – 3.55 (m, 2H), 3.54 – 3.45 (m, 1H), 3.46 – 3.42 (m, 1H), 3.41 (s, 3H), 3.13 – 3.03 (m, 1H), 2.80 – 2.59 (m, 2H), 2.23 – 2.13 (m, 2H), 2.13 – 2.04 (m, 2H), 1.71 – 1.56 (m, 2H), 1.51 – 1.38 (m, 2H), 1.29 (d, J = 6.6 Hz, 3H). | 454.5 |

FIG. 2 (Cont'd)

| No. | General Scheme | NMR | MS |
|---|---|---|---|
| 349 | 6 | $^1$H NMR (400 MHz, CD$_3$OD) δ 8.65 (s, 2H), 6.65 (s, 2H), 4.16 – 4.05 (m, 2H), 3.71 – 3.62 (m, 2H), 3.59 (dd, J = 9.4, 5.2 Hz, 2H), 3.47 – 3.43 (m, 2H), 3.42 (s, 6H), 3.17 – 3.06 (m, 2H), 2.24 – 2.15 (m, 4H), 2.15 – 2.05 (m, 4H), 1.75 – 1.61 (m, 4H), 1.53 – 1.39 (m, 4H), 1.30 (d, J = 6.6 Hz, 6H). | 617.7 |
| 350 | 3 | $^1$H NMR (400MHz, CDCl$_3$) δ = 8.82 (s, 1H), 8.24 (d, J=5.2 Hz, 1H), 6.86 (d, J=5.2 Hz, 1H), 6.76 (s, 1H), 6.65 (s, 1H), 4.57 (d, J=7.2 Hz, 1H), 4.03 (qd, J=6.4, 13.2 Hz, 1H), 3.92 - 3.85 (m, 4H), 3.76 (br s, 1H), 3.63 - 3.54 (m, 4H), 3.20 - 3.08 (m, 1H), 2.30 - 2.12 (m, 4H), 1.69 - 1.63 (m, 1H), 1.58 - 1.46 (m, 3H), 1.33 (d, J=6.4 Hz, 6H). | 437.3 |
| 351 | 4 | $^1$H NMR (400 MHz, CD$_3$OD) δ 8.76 (s, 1H), 8.11 (s, 1H), 7.91 (s, 1H), 6.64 (s, 1H), 6.04 (tt, JHF=56.8 Hz, JHH=4.8 Hz, 1H), 5.63-5.56 (m, 1H), 5.10-5.05 (m, 4H), 4.17-4.12 (m, 1H), 3.68-3.60 (m, 1H), 3.13-3.06 (m, 1H), 2.37-2.27 (m, 1H), 2.18-2.14 (m, 2H), 2.11-1.98 (m, 3H), 1.68-1.56 (m, 2H), 1.50-1.42 (m, 2H), 1.35 (d, J=6.8 Hz, 3H). | 447.3 |
| 352 | 4 | $^1$H NMR (400 MHz, CD$_3$OD) δ 8.76 (s, 1H), 7.56 (d, J=8.0 Hz, 2H), 7.40 (d, J=8.0 Hz, 2H), 6.70 (s, 1H), 6.05 (tt, JHF=56.8 Hz, JHH=4.8 Hz, 1H), 4.18 - 4.13 (m, 1H), 3.68 - 3.63 (m, 1H), 3.57 (s, 2H), 3.15 - 3.09 (m, 1H), 2.65 - 2.28 (m, 12H), 2.20 - 2.17 (m, 2H), 2.08 - 2.01 (m, 3H), 1.70 - 1.57 (m, 2H), 1.51-1.42 (m, 2H), 1.35 (d, J=6.8 Hz, 3H). | 513.4 |
| 353 | 4 | $^1$H NMR (400 MHz, CD$_3$OD): δ 9.02 (s, 1H), 8.07 (s, 1H), 7.63 (s, 1H), 6.92 (s, 1H), 4.28-4.23 (m, 1H), 3.68-3.63 (m, 1H), 3.15-3.09 (m, 1H), 2.99 (s, 3H), 2.80-2.75 (m, 1H), 2.62 (s, 3H), 2.36-2.28 (m, 1H), 2.21-2.18 (m, 2H), 2.12-2.10 (m, 2H), 1.68-1.51 (m, 2H), 1.51-1.44 (m, 2H), 1.41 (d, J=6.8 Hz, 3H). | 491.3 |
| 354 | 4 | $^1$H NMR (400MHz, CD$_3$OD) δ 8.87 (s, 1H), 7.95 (d, J=5.6 Hz, 1H), 6.82 - 6.77 (m, 2H), 6.70 (s, 1H), 4.21 - 4.02 (m,1H), 3.73 - 3.58 (m, 2H), 3.48 - 3.44 (m, 1H), 3.43 (s, 3H), 3.19 - 3.14 (m, 1H), 2.25 - 2.06 (m, 4H), 1.71 - 1.56 (m, 2H), 1.54 -1.39 (m, 2H), 1.31 (d, J=6.4 Hz, 3H). | 411.3 |
| 355 | 3 | $^1$H NMR (400MHz, CDCl$_3$-d) δ 8.82 (s, 1H), 8.23 (d, J=5.4 Hz, 1H), 6.84 (d, J=5.4 Hz, 1H), 6.75 (s, 1H), 6.65 (s, 1H), 5.03 (br t, J=5.6 Hz, 1H), 3.89 - 3.84 (m, 4H), 3.74 (br s, 1H), 3.68 - 3.63 (m, 2H), 3.62 - 3.53 (m, 7H), 3.43 (s, 3H), 3.13 (br t, J=11.6 Hz, 1H), 2.30 - 2.05 (m, 4H), 1.60 - 1.40 (m, 4H). | 453.3 |
| 356 | 3 | $^1$H NMR (400MHz, CDCl$_3$-d) δ 8.81 (s, 1H), 8.22 (d, J=5.2 Hz, 1H), 6.83 (d, J=5.0 Hz, 1H), 6.74 (s, 1H), 6.66 (s, 1H), 4.89 (br d, J=6.4 Hz, 1H), 4.44 (br s, 1H), 4.09 - 3.96 (m, 2H), 3.93 - 3.79 (m, 6H), 3.73 (br s, 1H), 3.59 - 3.48 (m, 4H), 3.10 (br t, J=11.8 Hz, 1H), 2.42 - 2.28 (m, 1H), 2.26 - 2.11 (m, 4H), 2.01 - 1.91 (m, 1H), 1.55 - 1.41 (m, 4H). | 465.3 |

FIG. 2 (Cont'd)

| No. | General Scheme | NMR | MS |
|---|---|---|---|
| 357 | 5 | ¹H NMR (400MHz, CDCl₃) δ 8.78 (s, 1H), 8.22 (d, J=5.2 Hz, 1H), 6.90 (d, J=5.2 Hz, 1H), 6.82 (s, 1H), 6.62 (s, 1H), 4.89 (d, J=7.8 Hz, 1H), 4.22 (br s, 4H), 4.14 - 4.06 (m, 1H), 3.73 (br s, 1H), 3.55 - 3.46 (m, 2H), 3.42 (s, 3H), 3.09 (br d, J=5.1 Hz, 5H), 2.22 (br d, J=12.2 Hz, 2H), 2.15 (br d, J=12.2 Hz, 2H), 1.61 (br s, 2H), 1.49 (br d, J=11.4 Hz, 2H), 1.33 (d, J=6.4 Hz, 3H). | 515.4 |
| 358 | 4 | ¹H NMR (400MHz, CD₃OD) δ 8.90 (s, 1H), 8.07 (d, J=6.4 Hz, 1H), 7.22 (dd, J=1.6, 5.6 Hz, 1H), 7.05 – 7.02 (m, 1H), 6.85 (s, 1H), 5.68 - 5.60 (m, 1H), 5.03 (t, J=7.2 Hz, 2H), 4.77 – 4.70 (m, 2H), 4.16 – 4.07 (m, 1H), 3.72 - 3.57 (m, 2H), 3.49 - 3.44 (m, 1H), 3.43 (s, 3H), 3.16 – 3.05 (m, 1H), 2.25 - 2.06 (m, 4H), 1.73 - 1.58 (m, 2H), 1.53 - 1.40 (m, 2H), 1.32 (d, J=6.4 Hz, 3H) | 454.3 |
| 359 | 3 | ¹H NMR (400 MHz, CDCl₃) δ 8.81 (s, 1H), 8.32 (d, J=5.2 Hz, 1H), 6.84 (d, J=5.2 Hz, 1H), 6.75 (s, 1H), 6.64 (s, 1H), 4.83-4.80 (m, 1H), 3.98-3.88 (m, 4H), 3.79-3.66 (m, 1H), 3.58-3.54 (m, 4H), 3.43-3.32 (m, 2H), 3.20-3.08 (m, 1H), 2.34-2.23 (m, 2H), 2.15-2.06 (m, 2H), 1.65-1.60 (m, 2H), 1.55-1.38 (m, 4H), 0.84-0.71 (m, 1H), 0.56-0.47 (m, 2H), 0.18-0.12 (m, 2H). | 463.3 |
| 360 | 4 | ¹H NMR (400 MHz, CDCl₃) δ 8.89 (s, 1H), 8.79 (s,1H), 8.07 (d, J=8.0 Hz, 1H), 8.02-8.00 (m, 1H), 6.70 (s, 1H), 4.89-4.85 (m, 1H), 4.74 (d, J=7.2 Hz, 1H), 4.28-4.25 (m, 1H), 3.75-3.74 (m, 1H), 3.17-3.12 (m, 1H), 2.79 (d, J=5.6 Hz, 3H), 2.29-2.15 (m, 5H), 1.66-1.63 (m, 2H), 1.53-1.50 (m, 5H), 1.47 (d, J=2.8 Hz, 3H). | 513.3 |
| 361 | 4 | ¹H NMR (400MHz, CD₃OD) δ 9.03 (s, 1H), 8.58 (d, J=5.2 Hz, 1H), 8.27 (s, 1H), 7.75 (br d, J=5.2 Hz, 1H), 6.95 (s, 1H), 4.17 – 4.06 (m, 1H), 3.72 - 3.56 (m, 2H), 3.48 - 3.44 (m, 1H), 3.42 (s, 3H), 3.19 – 3.05 (m, 1H), 3.00 (s, 3H), 2.26 – 2.16 (m, 2H), 2.16 – 2.07 (m, 2H), 1.73 - 1.58 (m, 2H), 1.53 - 1.40 (m, 2H), 1.31 (d, J=6.4 Hz, 3H). | 439.3 |
| 362 | 3 | ¹H NMR (400 MHz, CDCl₃) δ 8.82 (s, 1H), 8.23 (d, J=4.8 Hz, 1H), 8.84 (d, J=4.8 Hz, 1H), 6.75 (s, 1H), 6.67 (s, 1H), 4.89 (d, J=6.8 Hz, 1H), 4.45-4.44 (m, 1H), 4.08-4.00 (m, 2H), 3.93-3.80 (m, 6H), 3.78-3.69 (m, 1H), 3.63-3.53 (m, 4H), 3.16-3.05 (m, 1H), 2.43-2.32 (m, 1H), 2.26-2.13 (m, 4H), 2.03-1.92 (m, 1H), 1.55-1.43 (m, 4H). | 465.3 |
| 363 | 3 | ¹H NMR (400MHz, DMSO-d6) δ 9.05 (s, 1H), 8.12 (d, J=5.6 Hz, 1H), 7.15 (t, J=5.7 Hz, 1H), 7.02 - 6.96 (m, 3H), 4.63 (d, J=4.4 Hz, 1H), 3.77 - 3.64 (m, 4H), 3.57 - 3.46 (m, 7H), 3.05 - 2.93 (m, 1H), 2.72 - 2.57 (m, 3H), 2.14 - 1.90 (m, 4H), 1.62 - 1.44 (m, 2H), 1.39 - 1.24 (m, 2H). | 491.3 |
| 364 | 4 | ¹H NMR (400 MHz, MeOD) δ 8.69 (s, 1H), 7.97 (s, 1H), 7.78 (s, 1H), 6.58 (s, 1H), 5.01 – 4.93 (m, 1H), 4.09 – 3.99 (m, 1H), 3.83 – 3.78 (m, 1H), 3.70 (dd, J = 11.5, 5.1 Hz, 3H), 3.65 – 3.51 (m, 3H), 3.50 – 3.46 (m, 1H), 3.41 – 3.38 (m, 1H), 3.38 (s, 3H), 3.08 – 3.00 (m, 1H), 2.44 – 2.37 (m, 2H), 2.17 – 2.01 (m, 4H), 1.64 – 1.54 (m, 2H), 1.46 – 1.38 (m, 11H), 1.25 (d, J = 6.6 Hz, 3H). | 540.4 |

FIG. 2 (Cont'd)

| No. | General Scheme | NMR | MS |
|---|---|---|---|
| 365 | 4 | ¹H NMR (400 MHz, MeOD) δ 8.69 (s, 1H), 7.96 (s, 1H), 7.78 (s, 1H), 6.58 (s, 1H), 5.03 – 4.89 (m, 1H), 4.10 – 3.99 (m, 1H), 3.85 – 3.76 (m, 1H), 3.69 (dd, J = 11.5, 5.0 Hz, 1H), 3.64 – 3.52 (m, 3H), 3.51 – 3.44 (m, 1H), 3.42 – 3.38 (m, 1H), 3.38 (s, 3H), 3.09 – 3.00 (m, 1H), 2.45 – 2.35 (m, 2H), 2.16 – 2.01 (m, 4H), 1.67 – 1.52 (m, 2H), 1.44 (s, 9H), 1.42 – 1.29 (m, 2H), 1.25 (d, J = 6.6 Hz, 3H). | 540.3 |
| 366 | 5 | ¹H NMR (400 MHz, CD₃OD) δ 8.77 (s, 1H), 8.13 (s, 1H), 7.88 (s, 1H), 6.66 (s, 1H), 4.13 – 4.04 (m, 1H), 3.69 – 3.60 (m, 1H), 3.58 (dd, J = 9.4, 5.2 Hz, 1H), 3.51 – 3.46 (m, 4H), 3.46 – 3.42 (m, 1H), 3.41 (s, 3H), 3.14 – 3.03 (m, 2H), 3.14 – 2.94 (m, 1H), 2.23 – 2.13 (m, 2H), 2.13 – 2.02 (m, 2H), 1.84 (s, 6H), 1.72 – 1.55 (m, 2H), 1.52 – 1.39 (m, 2H), 1.29 (d, J = 6.6 Hz, 3H), 1.16 (s, 6H). | 554.7 |
| 367 | 5 | ¹H NMR (400 MHz, CD₃OD) δ 8.77 (s, 1H), 8.14 (s, 1H), 7.88 (s, 1H), 6.66 (s, 1H), 4.14 – 4.03 (m, 1H), 4.02 – 3.70 (m, 4H), 3.70 – 3.61 (m, 1H), 3.58 (dd, J = 9.5, 5.2 Hz, 1H), 3.46 – 3.42 (m, 1H), 3.41 (s, 3H), 3.27 – 3.15 (m, 2H), 3.14 – 3.03 (m, 1H), 2.22 – 2.14 (m, 2H), 2.14 – 2.04 (m, 2H), 1.87 (s, 3H), 1.81 (s, 3H), 1.72 – 1.55 (m, 2H), 1.52 – 1.38 (m, 2H), 1.29 (d, J = 6.6 Hz, 3H), 1.05 (s, 6H). | 554.7 |
| 368 | 6 | ¹H NMR (400 MHz, CD₃OD) δ 8.73 (s, 1H), 7.95 (s, J = 0.7 Hz, 1H), 7.83 (s, J = 0.7 Hz, 1H), 6.61 (s, 1H), 4.27 (d, J = 5.2 Hz, 2H), 4.19 – 4.11 (m, 1H), 4.11 – 4.01 (m, 1H), 3.69 – 3.60 (m, 1H), 3.58 (dd, J = 9.4, 5.2 Hz, 1H), 3.43 (dd, J = 8.2, 4.8 Hz, 1H), 3.41 (s, 3H), 3.13 – 3.01 (m, 1H), 2.33 – 1.96 (m, 8H), 1.71 – 1.54 (m, 2H), 1.51 – 1.38 (m, 2H), 1.29 (d, J = 6.6 Hz, 3H). | 468.5 |
| 369 | 4 | ¹H NMR (400MHz, CD₃OD) δ 8.90 (s, 1H), 8.11 (d, J=5.2 Hz, 1H), 7.21 - 7.18 (m, 1H), 6.99 - 6.97 (m, 1H), 6.85 (s, 1H), 5.22 - 5.13 (m, 1H), 4.18 - 4.06 (m, 1H), 3.72 - 3.57 (m, 2H), 3.48 - 3.44 (m, 1H), 3.43 (s, 3H), 3.21 - 3.07 (m, 3H), 2.89 - 2.79 (m, 2H), 2.25 - 2.16 (m, 2H), 2.15 - 2.05 (m, 4H), 1.84 - 1.72 (m, 2H), 1.70 - 1.59 (m, 2H), 1.53 - 1.40 (m, 2H), 1.32 (d, J=6.4 Hz, 3H). | 481.4 |
| 370 | 5 | ¹H NMR (400MHz, CD₃OD) δ 8.78 (s, 1H), 7.58 (d, J=8.0 Hz, 2H), 7.43 (d, J=8.0 Hz, 2H), 6.72 (s, 1H), 4.31 - 4.22 (m, 1H), 3.71 - 3.54 (m, 7H), 3.18 - 3.08 (m, 1H), 2.91 - 2.74 (m, 1H), 2.56 - 2.50 (m, 2H), 2.50 - 2.45 (m, 2H), 2.39 - 2.27 (m, 1H), 2.25 - 2.17 (m, 2H), 2.16 - 2.06 (m, 5H), 1.73 - 1.57 (m, 2H), 1.55 - 1.45 (m, 2H), 1.43 (d, J=6.8Hz, 3H). | 559.4 |
| 371 | 5 | ¹H NMR (400MHz, CD₃OD) δ 8.55 (d, J=15.3 Hz, 1H), 6.32 (d, J=8.9 Hz, 1H), 4.49 - 4.32 (m, 1H), 4.00 - 3.90 (m, 1H), 3.83 (br t, J=13.6 Hz, 1H), 3.58 - 3.42 (m, 2H), 3.35 - 3.26 (m, 4H), 3.18 - 2.84 (m, 3H), 2.70 - 2.55 (m, 1H), 2.09 - 1.87 (m, 8H), 1.83 - 1.65 (m, 2H), 1.65 - 1.39 (m, 3H), 1.39 - 1.25 (m, 2H), 1.17 (d, J=6.6 Hz, 3H). | 430.4 |

FIG. 2 (Cont'd)

| No. | General Scheme | NMR | MS |
|---|---|---|---|
| 372 | 5 (separated by SFC) | ¹H NMR (400MHz, CD₃OD) δ 8.65 (d, J=15.5 Hz, 1H), 6.42 (d, J=9.4 Hz, 1H), 4.58 - 4.43 (m, 1H), 4.06 (sxt, J=6.1 Hz, 1H), 3.9 - 3.86 (m, 1H), 3.70 - 3.50 (m, 2H), 3.46 - 3.36 (m, 4H), 3.28 - 2.90 (m, 3H), 2.82 - 2.64 (m, 1H), 2.19 - 1.98 (m, 8H), 1.90 - 1.72 (m, 2H), 1.72 - 1.51 (m, 3H), 1.49 - 1.33 (m, 2H), 1.27 (d, J=6.6 Hz, 3H). | 430.4 |
| 373 | 5 (separated by SFC) | ¹H NMR (400MHz, CD₃OD) δ = 8.56 (s, 1H), 7.90 (d, J=6.4 Hz, 1H), 6.34 (s, 1H), 6.27 (d, J=6.4 Hz, 1H), 4.06 -3.92 (m, 1H), 3.89 - 3.61 (m, 2H), 3.58 - 3.37 (m, 4H), 3.37 - 3.28 (m, 4H), 3.03 - 2.87 (m, 1H), 2.34 (s, 4H), 2.19 - 1.88 (m,5H), 1.59 - 1.39 (m, 2H), 1.39 - 1.23 (m, 2H), 1.18 (d, J=6.8 Hz, 3H). | 466.3 |
| 374 | 5 (separated by SFC) | ¹H NMR (400MHz, CD₃OD) δ = 8.56 (s, 1H), 7.90 (d, J=6.4 Hz, 1H), 6.34 (s, 1H), 6.27 (d, J=6.4 Hz, 1H), 4.08 - 3.92 (m, 1H), 3.89 - 3.61 (m, 2H), 3.59 - 3.37 (m, 4H), 3.36 - 3.27 (m, 4H), 3.07 - 2.89 (m, 1H), 2.34 (s, 4H), 2.20 - 1.89 (m, 5H), 1.57 - 1.40 (m, 2H), 1.39 - 1.23 (m, 2H), 1.18 (d, J=6.4 Hz, 3H). | 466.3 |
| 375 | 5 (separated by SFC) | ¹H NMR (400MHz, CD₃OD) δ 8.68 (s, 1H), 6.49 (s, 1H), 4.14 - 4.06 (m, 1H), 3.84 - 3.72 (m, 2H), 3.69 - 3.54 (m,3H), 3.52 - 3.40 (m, 5H), 3.31 - 3.26 (m, 1H), 3.17 - 3.01 (m, 1H), 2.95 (s, 3H), 2.46 - 2.32 (m, 1H), 2.23 - 2.03 (m, 5H), 1.71 -1.53 (m, 2H), 1.51 - 1.36 (m, 2H), 1.30 (d, J=6.4 Hz, 3H). | 452.3 |
| 376 | 5 (separated by SFC) | ¹H NMR (400MHz, CD₃OD) δ 8.56 (s, 1H), 6.37 (s, 1H), 4.05 - 3.90 (m, 1H), 3.75-3.60 (m, 2H), 3.59 - 3.42 (m,3H), 3.41 - 3.27 (m, 5H), 3.20 - 3.15 (m, 1H), 3.05-2.90 (m, 1H), 2.83 (s, 3H), 2.35 -2.20 (m, 1H), 2.09 - 1.90 (m, 5H), 1.60-1.42 (m, 2H), 1.41 - 1.23 (m, 2H), 1.18 (d, J=6.8 Hz, 3H). | 452.3 |
| 377 | 5 (separated by SFC) | ¹H NMR (400MHz, CD₃OD) δ 8.69 (s, 1H), 8.02 (d, J=6.4 Hz, 1H), 6.62 (d, J=6.6 Hz, 1H), 6.46 (s, 1H), 4.75 - 4.56 (m, 1H), 4.55 - 4.32 (m, 1H), 4.15 - 4.01 (m, 1H), 3.70 - 3.53 (m, 2H), 3.49 - 3.38 (m, 4H), 3.19 - 2.98 (m, 4H), 2.44 (s, 3H), 2.23 - 2.01 (m, 5H), 2.0 - 1.8 (m, 2H), 1.77 - 1.53 (m, 3H), 1.52 - 1.37 (m, 2H), 1.30 (d, J=6.6 Hz, 3H). | 480.2 |
| 378 | 5 (separated by SFC) | ¹H NMR (400MHz, CD₃OD) δ 8.69 (s, 1H), 8.02 (d, J=6.5 Hz, 1H), 6.62 (d, J=6.4 Hz, 1H), 6.46 (s, 1H), 4.72-4.57 (m, 1H), 4.52 - 4.36 (m, 1H), 4.16 - 4.03 (m, 1H), 3.70 - 3.54 (m, 2H), 3.47 - 3.39 (m, 4H), 3.16 - 3.00 (m, 4H), 2.45 (s, 3H), 2.23 - 2.03 (m, 5H), 1.97 - 1.81 (m, 2H), 1.76 - 1.54 (m, 3H), 1.51 - 1.36 (m, 2H), 1.30 (d, J=6.6 Hz, 3H). | 480.2 |
| 379 | 4 | ¹H NMR (500 MHz, MeOD) δ 8.62 (s, 1H), 7.87 (s, 1H), 7.68 (s, 1H), 6.51 (s, 1H), 4.21 – 4.07 (m, 3H), 4.03 – 3.92 (m, 1H), 3.80 – 3.72 (m, 1H), 3.70 – 3.63 (m, 1H), 3.58 – 3.50 (m, 1H), 3.48 (dd, J = 9.4, 5.2 Hz, 1H), 3.36 – 3.32 (m, 1H), 3.31 (s, 3H), 2.98 (tt, J = 12.0, 3.5 Hz, 1H), 2.11 – 1.90 (m, 5H), 1.84 – 1.67 (m, 2H), 1.64 – 1.47 (m, 3H), 1.40 – 1.28 (m, 2H), 1.19 (d, J = 6.6 Hz, 3H). | 455.3 |

FIG. 2 (Cont'd)

| No. | General Scheme | NMR | MS |
|---|---|---|---|
| 380 | 4 | ¹H NMR (400 MHz, MeOD) δ 8.68 (s, 1H), 7.93 (d, J = 0.7 Hz, 1H), 7.74 (d, J = 0.7 Hz, 1H), 6.58 (s, 1H), 4.28 – 4.12 (m, 3H), 4.10 – 4.00 (m, 1H), 3.86 – 3.79 (m, 1H), 3.76 – 3.69 (m, 1H), 3.65 – 3.57 (m, 1H), 3.54 (dd, J = 9.4, 5.2 Hz, 1H), 3.42 – 3.38 (m, 1H), 3.38 (s, 3H), 3.05 (tt, J = 12.0, 3.5 Hz, 1H), 2.18 – 1.96 (m, 5H), 1.92 – 1.73 (m, 2H), 1.72 – 1.53 (m, 3H), 1.47 – 1.34 (m, 2H), 1.26 (d, J = 6.6 Hz, 3H). | 455.2 |
| 381 | Analogous to Example 34 | ¹H NMR (500 MHz, MeOD) δ 8.86 (s, 1H), 8.33 (s, 1H), 8.28 (d, J = 5.4 Hz, 1H), 7.46 (d, J = 1.4 Hz, 1H), 7.39 (dd, J = 5.4, 1.5 Hz, 1H), 6.84 (s, 1H), 4.05 – 3.92 (m, 1H), 3.47 (dt, J = 11.9, 5.9 Hz, 1H), 3.34 (dd, J = 9.5, 5.9 Hz, 1H), 3.31 (s, 3H), 3.06 (ddt, J = 19.2, 11.4, 3.7 Hz, 1H), 2.48 (s, 3H), 2.02 (ddd, J = 9.2, 6.2, 4.4 Hz, 2H), 1.76 – 1.63 (m, 4H), 1.61 – 1.53 (m, 2H), 1.24 (s, 3H), 1.20 (d, J = 6.6 Hz, 3H). | 410.2 |
| 382 | Analogous to Example 34 | ¹H NMR (500 MHz, MeOD) δ 8.72 (s, 1H), 8.05 (s, 1H), 7.85 (s, 1H), 6.65 (s, 1H), 4.47 (t, J = 6.5 Hz, 2H), 4.16 – 3.99 (m, 1H), 3.56 (dd, J = 9.4, 5.2 Hz, 1H), 3.43 (dd, J = 9.4, 5.8 Hz, 1H), 3.40 (s, 3H), 3.10 (dd, J = 9.8, 6.0 Hz, 1H), 3.06 (dd, J = 8.1, 4.9 Hz, 2H), 1.97 – 1.87 (m, 4H), 1.84 – 1.75 (m, 2H), 1.63 – 1.49 (m, 2H), 1.28 (d, J = 6.6 Hz, 3H), 1.26 (s, 3H). | 438.2 |
| 383 | 5 | ¹H NMR (400MHz, CD₃OD) δ 8.96 (d, J=15.6 Hz, 1H), 7.04 (d, J=10.4 Hz, 1H), 4.24 - 4.11 (m, 1H), 4.09 - 3.98 (m,1H), 3.92 - 3.74 (m, 2H), 3.73 - 3.59 (m, 2H), 3.54 - 3.40 (m, 6H), 3.25 - 3.14 (m, 1H), 2.55 - 2.058 (m, 8H), 1.77 - 1.62 (m, 2H), 1.54 - 1.40 (m, 2H), 1.35 (d, J=6.4 Hz, 3H). | 416.3 |
| 384 | 4 | ¹H NMR (400MHz, CD₃OD) δ 9.06 (s, 1H), 8.60 (d, J=5.2 Hz, 1H), 8.29 (d, J=1.2 Hz, 1H), 7.78 (dd, J=2.0, 5.2 Hz, 1H), 6.98 (s, 1H), 4.34 - 4.19 (m, 1H), 3.73 - 3.63 (m, 1H), 3.20 - 3.09 (m, 1H), 3.01 (s, 3H), 2.90 - 2.70 (m, 1H), 2.43 - 2.28 (m, 1H), 2.27 - 2.18 (m, 2H), 2.11 (br s, 2H), 1.76 - 1.57 (m, 2H), 1.55 - 1.46 (m, 2H), 1.44 (d, J=6.8 Hz, 3H). | 477.3 |
| 385 | 4 | 1H-NMR (400 MHz, CD₃OD) δ 9.02 (s, 1H), 8.08 (s, 1H), 7.63 (s, 1H), 6.93 (s, 1H), 6.43 (t, JHF=75.2 Hz, 1H), 4.17 - 4.09 (m, 2H), 3.86 - 3.82 (m, 1H), 3.67 - 3.65 (m, 1H), 3.15 - 3.09 (m, 1H), 2.99 (s, 3H), 2.62 (s, 3H), 2.21 - 2.18 (m, 2H), 2.11 - 2.09 (m, 2H), 1.71 - 1.59 (m, 2H), 1.52 - 1.43 (m, 2H), 1.35 (d, J=6.8 Hz, 3H). | 489.3 |
| 386 | 5 | ¹H NMR (400 MHz, CDCl₃) δ 8.85 (s, 1H), 8.15 (d, J=5.6 Hz, 1H), 7.03 (d, J=5.2 Hz, 1H), 6.85 (s, 1H), 6.66 (s, 1H), 5.56-5.46 (m, 1H), 4.90 (d, J=7.2 Hz, 1H), 4.16-4.03 (m, 1H), 3.79-3.68 (m, 1H), 3.56-3.45 (m, 2H), 3.42 (s, 3H), 3.26-3.05 (m, 5H), 3.02-2.91(m, 1H), 2.27-2.10 (m, 5H), 2.05-1.95 (m, 1H), 1.68-1.44 (m, 5H), 1.33 (d, J=6.4 Hz, 3H). | 467.3 |

FIG. 2 (Cont'd)

| No. | General Scheme | NMR | MS |
|---|---|---|---|
| 387 | 4 (separated by SFC) | $^1$H NMR (400MHz, CD$_3$OD) δ 8.76 (s, 1H), 8.12 (s, 1H), 7.92 (s, 1H), 6.65 (s, 1H), 5.66 - 5.56 (m, 1H), 5.13 - 5.06 (m, 4H), 4.17 - 3.98 (m, 1H), 3.76 - 3.58 (m, 1H), 3.17 - 3.06 (m, 1H), 2.68 - 2.50 (m, 1H), 2.41 - 2.31 (m, 7H), 2.25 - 2.15 (m, 2H), 2.14 - 2.05 (m, 2H), 1.70 - 1.55 (m, 2H), 1.50 - 1.38 (m, 2H), 1.32 (d, J=6.4 Hz, 3H). | 440.2 |
| 388 | 4 (separated by SFC) | $^1$H NMR (400MHz, CD$_3$OD) δ 8.74 (s, 1H), 8.10 (s, 1H), 7.90 (s, 1H), 6.63 (s, 1H), 5.64 - 5.55 (m, 1H), 5.12 - 5.03 (m, 4H), 4.12 - 4.00 (m, 1H), 3.69 - 3.58 (m, 1H), 3.15 - 3.02 (m,1 H), 2.65 - 2.58 (m, 1H), 2.40 - 2.30 (m, 7H), 2.23 - 2.13 (m, 2H), 2.12 - 2.04 (m, 2H), 1.68 - 1.53 (m, 2H), 1.50 - 1.36 (m, 2H), 1.30 (d, J=6.4 Hz, 3H) | 440.2 |
| 389 | 5 | $^1$H NMR (400MHz, CD$_3$OD) δ 8.91 (s, 1H), 8.11 (d, J=5.4 Hz, 1H), 7.22 - 7.16 (m, 1H), 7.01 (s, 1H), 6.84 (s, 1H), 5.12 (br s, 1H), 4.12 (sxt, J=6.2 Hz, 1H), 3.72 - 3.56 (m, 2H), 3.50 - 3.45 (m, 1H), 3.44 (s, 3H), 3.21 (dd, J=2.4 , 12.8 Hz, 1H), 3.16 - 3.05 (m, 1H), 3.00 - 2.80 (m, 3H), 2.25 - 2.03 (m, 5H), 1.99 - 1.80 (m, 2H), 1.73 - 1.57 (m, 3H), 1.53 - 1.41 (m, 2H), 1.32 (d, J=6.8 Hz, 3H). | 481.4 |
| 390 | 5 | $^1$H NMR (400MHz, CD$_3$OD) δ 8.91 (s, 1H), 8.11 (d, J=5.2 Hz, 1H), 7.19 (d, J=4.8 Hz, 1H), 7.01 (s, 1H), 6.85 (s, 1H), 5.12 - 5.05 (m, 1H), 4.17 - 4.07 (m, 1H), 3.72 - 3.57 (m, 2H), 3.48 - 3.44 (m, 1H), 3.43 (s, 3H), 3.23 - 3.03 (m, 2H), 2.97 - 2.73 (m, 3H), 2.26 - 2.00 (m, 5H), 1.98 - 1.76 (m, 2H), 1.73 - 1.55 (m, 3H), 1.53 - 1.39 (m, 2H), 1.32 (d, J=6.4 Hz, 3H). | 481.4 |
| 391 | Analogous to Example 34 | $^1$H NMR (500 MHz, MeOD) δ 9.05 (s, 1H), 8.40 (d, J = 5.4 Hz, 1H), 7.74 (s, 1H), 7.68 (d, J = 5.3 Hz, 1H), 7.03 (s, 1H), 4.17 – 4.07 (m, 1H), 3.57 (dd, J = 9.5, 5.4 Hz, 1H), 3.45 (dd, J = 9.5, 5.8 Hz, 1H), 3.41 (s, 3H), 3.16 - 3.08 (m, 1H), 2.64 (s, 3H), 2.00 - 1.90 (m, 4H), 1.85 – 1.75 (m, 2H), 1.65 – 1.54 (m, 2H), 1.30 (d, J = 6.7 Hz, 3H), 1.27 (s, 3H). | 410.2 |
| 392 | 4 | $^1$H NMR (400 MHz, CD$_3$OD) δ 8.72 (s, 1H), 7.97 (s, 1H), 7.79 (s, 1H), 6.61 (s, 1H), 4.12 – 4.04 (m, 1H), 4.07 (d, J = 7.3 Hz, 2H), 3.97 – 3.91 (m, 2H), 3.69 – 3.60 (m, 1H), 3.58 (dd, J = 9.4, 5.2 Hz, 1H), 3.45 – 3.42 (m, 1H), 3.41 (s, 3H), 3.40 – 3.35 (m, 2H), 3.12 – 3.02 (m, 1H), 2.23 – 2.13 (m, 3H), 2.13 – 2.03 (m, 2H), 1.69 – 1.55 (m, 2H), 1.54 – 1.33 (m, 6H), 1.29 (d, J = 6.6 Hz, 3H). | 469.2 |
| 393 | 5 | $^1$H NMR (400 MHz, CD$_3$OD) δ 8.79 (s, 1H), 8.12 (s, 1H), 7.88 (s, 1H), 6.67 (s, 1H), 6.42 (t, J = 75.5 Hz, 1H), 4.20 – 4.04 (m, 2H), 3.83 (dd, J = 9.2, 6.0 Hz, 1H), 3.71 – 3.59 (m, 1H), 3.59 – 3.35 (m, 8H), 3.15 – 3.02 (m, 1H), 2.22 – 2.13 (m, 2H), 2.13 – 2.04 (m, 2H), 1.83 (s, 6H), 1.70 – 1.54 (m, 2H), 1.54 – 1.38 (m, 2H), 1.34 (d, J = 6.6 Hz, 3H). | 562.1 |

FIG. 2 (Cont'd)

| No. | General Scheme | NMR | MS |
|---|---|---|---|
| 394 | 6 (See Example 36) | $^1$H NMR (400 MHz, CD$_3$OD) δ 8.75 (s, 1H), 8.04 (s, 1H), 7.84 (s, 1H), 6.62 (s, 1H), 5.18 (t, J = 8.8 Hz, 1H), 4.14 – 4.02 (m, 1H), 3.69 – 3.51 (m, 4H), 3.46 – 3.42 (m, 1H), 3.41 (s, 3H), 3.13 – 3.03 (m, 1H), 2.95 (s, 3H), 2.73 – 2.63 (m, 1H), 2.59 – 2.47 (m, 1H), 2.22 – 2.13 (m, 2H), 2.13 – 2.02 (m, 2H), 1.70 – 1.55 (m, 2H), 1.50 – 1.38 (m, 2H), 1.29 (d, J = 6.6 Hz, 3H). | 468.2 |
| 395 | 6 | $^1$H NMR (400 MHz, CD$_3$OD) δ 8.73 (s, 1H), 8.02 (s, 1H), 7.80 (s, 1H), 6.61 (s, 1H), 4.25 (dd, J = 7.2, 1.3 Hz, 2H), 4.13 – 4.03 (m, 1H), 3.68 – 3.60 (m, 1H), 3.58 (dd, J = 9.4, 5.2 Hz, 1H), 3.53 (dd, J = 10.3, 8.0 Hz, 1H), 3.46 – 3.42 (m, 1H), 3.41 (s, 3H), 3.35 – 3.32 (m, 1H), 3.13 – 3.04 (m, 1H), 3.04 – 2.94 (m, 1H), 2.80 (s, 3H), 2.53 (dd, J = 17.1, 9.1 Hz, 1H), 2.27 (dd, J = 17.1, 6.1 Hz, 1H), 2.21 – 2.13 (m, 2H), 2.13 – 2.03 (m, 2H), 1.68 – 1.55 (m, 2H), 1.51 – 1.38 (m, 2H), 1.29 (d, J = 6.6 Hz, 3H). | 482.1 |
| 396 | 5 | $^1$H NMR (500 MHz, MeOD) δ 8.66 (d, J = 1.6 Hz, 1H), 7.96 (d, J = 12.9 Hz, 1H), 7.74 (d, J = 4.8 Hz, 1H), 6.60 (d, J = 2.2 Hz, 1H), 5.05 – 4.92 (m, 1H), 4.03 – 3.93 (m, 1H), 3.88 – 3.70 (m, 2H), 3.67 – 3.59 (m, 1H), 3.58 – 3.49 (m, 1H), 3.47 (dd, J = 9.4, 5.2 Hz, 1H), 3.36 – 3.32 (m, 1H), 3.31 (s, 3H), 2.99 (ddd, J = 12.0, 7.7, 3.4 Hz, 1H), 2.48 – 2.32 (m, 2H), 2.11 – 1.93 (m, 7H), 1.63 – 1.47 (m, 2H), 1.39 – 1.25 (m, 3H), 1.20 (d, J = 6.6 Hz, 3H). | 482.2 |
| 397 | 5 | $^1$H NMR (500 MHz, MeOD) δ 8.66 (d, J = 1.6 Hz, 1H), 7.96 (d, J = 13.0 Hz, 1H), 7.74 (d, J = 4.9 Hz, 1H), 6.60 (d, J = 2.2 Hz, 1H), 5.05 – 4.91 (m, 1H), 3.97 (ddd, J = 15.7, 11.5, 6.2 Hz, 1H), 3.90 – 3.70 (m, 2H), 3.69 – 3.59 (m, 1H), 3.54 (qd, J = 11.5, 6.1 Hz, 1H), 3.47 (dd, J = 9.4, 5.2 Hz, 1H), 3.39 – 3.32 (m, 1H), 3.31 (s, 3H), 3.03 – 2.95 (m, 1H), 2.49 – 2.29 (m, 2H), 2.11 – 1.95 (m, 7H), 1.59 – 1.48 (m, 2H), 1.40 – 1.29 (m, 2H), 1.29 – 1.25 (m, 1H), 1.20 (d, J = 6.6 Hz, 3H). | 482.2 |
| 398 | 4 | $^1$H NMR (400MHz, CD$_3$OD) δ 8.95 - 8.92 (m, 2H), 8.85 (d, J=2.0 Hz, 1H), 8.40 (t, J=2.0 Hz, 1H), 6.89 (s, 1H), 6.4 (t, JHF=75.6Hz, 1H), 4.22 - 4.09 (m, 2H), 3.85 (m, 1H), 3.71 - 3.62 (m, 1H), 3.20 - 3.14 (m, 1H), 2.97 (s, 3H), 2.25 - 2.06 (m, 4H), 1.74 - 1.58 (m, 2H), 1.53 - 1.41 (m, 2H), 1.36 (d, J=6.4 Hz, 3H). | 475.3 |
| 399 | 4 | $^1$H NMR (400 MHz, CD$_3$OD) δ 8.78 (s, 1H), 8.11 (s, 1H), 7.91 (s, 1H), 6.65 (s, 1H), 5.63-5.56 (m, 1H), 5.09-5.05 (m, 4H), 4.92 (d, J=6.4 Hz, 2H), 4.52 (d, J=6.4 Hz, 2H), 3.67-3.62 (m, 1H), 3.02-2.96 (m, 1H), 2.15-2.09 (m, 4H), 1.78 (s, 3H), 1.66-1.57 (m, 2H), 1.50-1.40 (m, 2H). | 425.3 |
| 400 | 5 (Methylation of Compound 397) | $^1$H NMR (400 MHz, CDCl$_3$) δ 8.85 (s,1H), 8.13 (d, J=5.6 Hz, 1H), 7.03 - 7.01 (m, 1H), 6.90 (s, 1H), 6.64 (s, 1H), 5.55-5.46 (m, 1H), 4.90 (d, J=7.2 Hz, 1H), 4.13-4.07 (m, 1H), 3.79-3.68 (m, 1H), 3.57-3.45 (m, 1H), 3.42 (s, 3H), 3.16-3.04 (m, 1H), 2.97-2.87 (m, 2H), 2.81-2.76 (m, 1H), 2.48-2.33 (m, 5H), 2.27-2.11 (m, 4H), 2.09-1.96 (m, 1H), 1.65-1.42 (m, 5H), 1.33 (d, J=6.4 Hz, 3H). | 481.3 |

FIG. 2 (Cont'd)

| No. | General Scheme | NMR | MS |
|---|---|---|---|
| 401 | 5 | ¹H NMR (400 MHz, CD₃OD) δ 8.87 (s, 1H), 8.09 (d, J=5.2 Hz, 1H), 7.18 (d, J=5.2 Hz, 1H), 6.96 (s, 1H), 6.81 (s, 1H), 5.54-5.46 (m, 1H), 4.13-4.04 (m, 1H), 3.67-3.53 (m, 2H), 3.45-3.48 (m, 1H), 3.40 (s, 3H), 3.26-2.48 (m, 5H), 2.23-2.03 (m, 6H), 1.71-1.55 (m, 2H), 1.52-1.36 (m, 2H), 1.28 (d, J=6.8 Hz, 2H). | 467.3 |
| 402 | 5 | ¹H NMR (400 MHz, CD₃OD) δ 8.89 (s,1H), 8.10 (d, J=5.6 Hz, 1H), 7.20-7.18 (m, 1H), 6.97 (s, 1H), 6.83 (s, 1H), 5.47-5.45 (m, 1H), 4.14-4.06 (m, 1H), 3.71-3.54 (m, 2H), 3.50-3.47 (m, 1H), 3.45 (s, 3H), 3.16-3.03 (m, 1H), 2.96-2.85 (m, 3H), 2.53-2.36 (m, 5H), 2.26-2.17 (m, 2H), 2.14-2.06 (m, 2H), 2.02-1.94 (m, 1H), 1.73-1.57 (m, 2H), 1.51-1.38 (m, 2H), 1.30 (d, J=6.4 Hz, 3H). | 481.3 |
| 403 | 5 (Methylation of SY-5782) | ¹H NMR (400MHz, CD₃OD) δ 8.89 (s, 1H), 8.08 (d, J=5.4 Hz, 1H), 7.16 (dd, J=1.2, 5.4 Hz, 1H), 6.97 (s, 1H), 6.82 (s, 1H), 5.17 (br s, 1H), 4.14 - 4.05 (m, 1H), 3.70 - 3.54 (m, 2H), 3.45 - 3.42 (m, 1H), 3.41 (s, 3H), 3.14 - 3.04 (m, 1H), 2.84 (br s, 1H), 2.61 - 2.33 (m, 3H), 2.30 (s, 3H), 2.18 (br d, J=12.6 Hz, 2H), 2.09 (br d, J=11.2 Hz, 2H), 2.01 - 1.84 (m, 2H), 1.74 - 1.55 (m, 4H), 1.52 - 1.37 (m, 2H), 1.29 (d, J=6.8 Hz, 3H). | 495.4 |
| 404 | 5 (Methylation of SY-5783) | ¹H NMR (400MHz, DMSO-d6) δ 8.91 (s, 1H), 8.12 (dd, J=0.8, 5.4 Hz, 1H), 7.22 (dd, J=1.6, 5.6 Hz, 1H), 6.94 (dd, J=0.8, 1.8 Hz, 1H), 6.91 (s, 1H), 6.39 (d, J=7.6 Hz, 1H), 5.15 - 5.05 (m, 1H), 4.31 (d, J=4.5 Hz, 1H), 4.11 - 3.97 (m, 1H), 3.59 - 3.46 (m, 2H), 3.39 - 3.35 (m, 1H), 3.34 (s, 2H), 3.04 - 2.99 (m, 1H), 2.93 - 2.87 (m, 1H), 2.59 - 2.53 (m, 1H), 2.21 (s, 3H), 2.18 - 1.92 (m, 7H), 1.83 - 1.72 (m, 1H), 1.68 - 1.52 (m, 3H), 1.50 - 1.28 (m, 3H), 1.24 (d, J=6.8 Hz, 3H). | 495.4 |
| 405 | 4 | ¹H NMR (500 MHz, MeOD) δ 8.89 (s, 1H), 8.12 (dd, J = 5.2, 0.6 Hz, 1H), 7.01 – 6.92 (m, 2H), 6.86 (s, 1H), 6.43 (t, J = 75.4 Hz, 1H), 4.18 – 4.06 (m, 2H), 3.84 – 3.81 (m, 4H), 3.70 – 3.59 (m, 1H), 3.55 – 3.48 (m, 4H), 3.16 – 3.07 (m, 1H), 2.22 – 2.05 (m, 4H), 1.71 – 1.57 (m, 2H), 1.55 – 1.42 (m, 2H), 1.35 (d, J = 6.7 Hz, 3H). | 503.2 |
| 406 | See Example 35 | ¹H NMR (500 MHz, MeOD) δ 10.35 (s, 1H), 9.69 (s, 1H), 9.48 (s, 1H), 8.26 (s, 1H), 7.22 – 7.05 (m, 1H), 6.72 – 6.58 (m, 4H), 5.74 – 5.59 (m, 1H), 5.22 (tt, J = 11.4, 3.1 Hz, 1H), 5.15 – 5.06 (m, 1H), 5.04 – 4.98 (m, 1H), 4.96 (s, 3H), 4.27 – 4.16 (m, 2H), 4.08 – 3.97 (m, 4H), 3.72 – 3.53 (m, 2H), 2.92 – 2.80 (m, 3H). | 425.1 |
| 407 | 4 | ¹H NMR (400MHz, CD₃OD) δ 9.18 (s, 1H), 8.99 (s, 1H), 7.00 (s, 1H), 5.45 (t, J=75.6, 1H), 4.24-4.16 (m, 1H), 4.15-4.10 (m, 1H), 3.90-3.84 (m, 1H), 3.73-3.63 (m, 1H), 3.22-3.11 (m, 1H), 3.03 (s, 3H), 2.26-2.17 (m, 2H), 2.16-2.06 (m, 2H), 1.76-1.61 (m, 2H), 1.55-1.43 (m, 2H), 1.37 (d, J=6.4 Hz, 3H). | 476.3 |
| 408 | 5 | ¹H NMR (400MHz, CD₃OD) δ 8.76 (s, 1H), 8.16 (s, 1H), 7.86 (s, 1H), 6.65 (s, 1H), 4.12-4.06 (m, 1H), 3.68-3.56 (m, 2H), 3.48-3.42 (m, 3H), 3.41 (s, 3H), 3.08-3.01 (m, 3H), 2.17-2.14 (m, 2H), 2.11-2.08 (m, 2H), 1.85-1.75 (m, 4H), 1.74-1.72 (m, 2H), 1.71-1.57 (m, 4H), 1.45-1.42 (m, 2H), 1.29 (d, J=6.4 Hz, 3H). | 508.4 |

FIG. 2 (Cont'd)

| No. | General Scheme | NMR | MS |
|---|---|---|---|
| 409 | 5 | ¹H NMR (400MHz, CD₃OD) δ 8.64 ( s, 1H), 6.42 (s, 1H), 4.62 ( s, 1H), 4.16 - 4.01 (m, 3H), 3.70 - 3.54 (m, 2H), 3.47 - 3.40 (m, 4H), 3.14 - 2.82 (m, 4H), 2.20 - 1.99 (m, 5H), 1.84 - 1.72 (m, 2H), 1.61 (m, *J*=11.6 Hz, 3H), 1.49 (m, 9H), 1.47 - 1.37 (m, 2H), 1.30 (d, *J*=6.4 Hz, 3H). | 488.4 |
| 410 | 5 | ¹H NMR (400MHz, CD₃OD) δ 8.62 (s, 1H), 6.40 (s, 1H), 4.16 - 3.98 (m, 3H), 3.69 - 3.52 (m, 2H), 3.45 - 3.38 (m, 4H), 3.13 - 2.74 (m, 4H), 2.16 - 2.00 (m, 5H), 1.83 - 1.68 (m, 2H), 1.65 - 1.53 (m, 3H), 1.46 (m, 9H), 1.44 - 1.35 (m, 2H), 1.27 (d, *J*=6.8 Hz, 3H). | 488.4 |
| 411 | 4 | ¹H NMR (400MHz, CD₃OD) δ 9.02 (s, 1H), 8.57 (d, J=5.2 Hz, 1H), 8.25 (d, J=1.2 Hz, 1H), 7.74 (dd, J=2.0, 5.2 Hz, 1H), 6.94 (s, 1H), 6.62 (s, 1H), 6.43 (s, 1H), 6.63 - 6.23 (m, 1H), 4.21 - 4.07 (m, 2H), 3.84 (dd, J=6.3, 9.5 Hz, 1H), 3.71 - 3.59 (m, 1H), 3.17 - 3.06 (m, 1H), 2.99 (s, 3H), 2.24 - 2.05 (m, 4H), 1.71 - 1.55 (m, 2H), 1.52 - 1.40 (m, 2H), 1.36 (d, J=6.8 Hz, 3H). | 475.3 |
| 412 | 4 | ¹H NMR (400MHz, CD₃OD) δ 8.73 (s, 1H), 6.54 (s, 1H), 6.03 ( s, 1H), 4.30 - 4.20 (m, 1H), 4.10 (s, 2H), 3.72 - 3.57(m, 3H), 3.14 - 3.03 (m, 1H), 2.88 - 2.70 (m, 1H), 2.62 - 2.55 (m, 2H), 2.40 - 2.23 (m, 1H), 2.19 - 2.03 (m, 4H), 1.69 - 1.54 (m, 2H), 1.53 - 1.43 (m, 11H), 1.41 (d, *J*=6.8 Hz, 3H) | 524.1 |
| 413 | 5 | ¹H NMR (400MHz, CD₃OD) δ 8.77 (s, 1H), 7.57 (d, *J*=7.6 Hz, 2H), 7.42 (d, *J*=7.6 Hz, 2H), 6.71 (s, 1H), 6.66 - 6.18(m, 1H), 4.23 - 4.07 (m, 2H),3.90 - 3.82 (m, 1H),3.74 - 3.52 (m, 7H), 3.20 - 3.05 (m, 1H), 2.58 -2.45 (m, 4H), 2.25 - 2.15 (m,2H), 2.14 - 2.05 (m, 5H), 1.75 - 1.55 (m, 2H), 1.55 - 1.41 (m, 2H), 1.40 - 1.33 (m, 3H). | 557.4 |
| 414 | 4 | ¹H NMR (400MHz, CD₃OD) δ 8.99 (s, 1H), 8.35 (s, 1H), 7.99 (s, 1H), 7.21 (s, 1H), 4.16-4.13 (m, 1H), 3.69-3.64 (m, 4H), 3.54-3.53 (m, 6H), 3.42 (s, 3H), 3.24-3.15 (m, 1H), 2.14-2.12 (m, 4H), 1.74-1.57 (m, 6H), 1.49-1.41 (m, 2H), 1.34 (d, J=6.4 Hz, 3H). | 524.3 |
| 415 | 4 | ¹H NMR (400 MHz, CD₃OD) δ 8.99 (s, 1H), 8.38 (s, 1H), 8.09 (s, 1H), 7.19 (s, 1H), 4.16-4.12 (m, 1H), 4.04-3.99 (m, 1H), 3.69-3.63 (m, 1H), 3.55-3.53 (m, 2H), 3.42 (s, 3H), 3.19-3.15 (m, 1H), 2.16-2.11 (m, 4H), 1.79-1.76 (m, 2H), 1.71-1.68 (m, 2H), 1.67-1.56 (m, 2H), 1.50-1.44 (m, 2H), 1.34 (d, J=6.4 Hz, 3H), 1.34 (d, J=6.8 Hz, 6H). | 496.3 |
| 416 | 5 | ¹H NMR (400 MHz, CD₃OD) δ 8.89 (s, 1H), 7.97 (d, J=5.6 Hz, 1H), 6.86 - 6.83 (m, 1H), 6.81 (s, 1H), 6.79 (s, 1H), 4.51 - 4.40 (m, 1H), 4.17 - 4.06 (m, 1H), 4.04 - 3.96 (m, 2H), 3.92 - 3.84 (m, 1H), 3.76 - 3.55 (m, 3H), 3.51 - 3.45 (m, 1H), 3.43 (s, 3H), 3.20 - 3.05 (m, 1H), 2.39 - 2.27 (m, 1H), 2.26 - 2.07 (m, 4H), 1.99 - 1.87 (m, 1H), 1.74 - 1.58 (m, 2H), 1.54 - 1.40 (m, 2H), 1.32 (d, J=6.4 Hz, 3H). | 467.3 |

FIG. 2 (Cont'd)

| No. | General Scheme | NMR | MS |
|---|---|---|---|
| 417 | 5 | $^1$H NMR (400MHz, CD$_3$OD) δ 8.60 (s, 1H), 6.37 (s, 1H), 4.05 (m, J=6.2 Hz, 1H), 3.66 - 3.52 (m, 2H), 3.41 (m, J=6.0 Hz, 1H), 3.39 (m, 3H), 3.18 - 2.98 (m, 4H), 2.77 - 2.65 (m, 2H), 2.14 - 1.98 (m, 5H), 1.90 - 1.78 (m, 1H), 1.77 - 1.65 (m, 2H), 1.64 - 1.49 (m, 2H), 1.48 - 1.34 (m, 2H), 1.26 (d, J=6.2 Hz, 3H). | 388.3 |
| 418 | 5 | $^1$H NMR (400MHz, CD$_3$OD) δ 8.88 (s, 1H), 7.97 (d, J=5.6 Hz, 1H), 6.83 (d, 1H), 6.80 (s, 1H), 6.77 (s, 1H), 4.53 -4.43 (m, 1H), 4.16 - 4.06 (m, 1H), 4.05 - 3.95 (m, 2H), 3.94 - 3.82 (m, 1H), 3.75 - 3.56 (m, 3H), 3.48 - 3.44 (m, 1H), 3.43 (s,3H), 3.18 - 3.05 (m, 1H), 2.40 - 2.27 (m, 1H), 2.25 -2.16 ( m, 2H), 2.15 - 2.06 (m, 2H), 1.99 - 1.86 (m, 1H), 1.75 - 1.57 (m, 2H),1.54 - 1.40 (m, 2H), 1.32 (d, J=6.4 Hz, 3H). | 467.3 |
| 419 | 4 | $^1$H NMR (500 MHz, MeOD) δ 8.65 (s, 1H), 8.03 (s, 1H), 7.87 (s, 1H), 6.56 (s, 1H), 5.51 (s, 2H), 4.03 – 3.94 (m, 1H), 3.58 – 3.51 (m, 1H), 3.48 (dd, J = 9.4, 5.2 Hz, 1H), 3.35 – 3.32 (m, 1H), 3.31 (s, 3H), 2.99 (tt, J = 12.2, 3.4 Hz, 1H), 2.89 (s, 3H), 2.12 – 1.94 (m, 4H), 1.60 – 1.47 (m, 2H), 1.40 – 1.29 (m, 2H), 1.19 (d, J = 6.6 Hz, 3H). | 463.2 |
| 420 | 4 | $^1$H NMR (500 MHz, MeOD) δ 8.72 (s, 1H), 7.99 (d, J = 0.6 Hz, 1H), 7.78 (d, J = 0.7 Hz, 1H), 6.60 (s, 1H), 4.81 (dd, J = 7.8, 6.3 Hz, 2H), 4.57 (t, J = 6.2 Hz, 2H), 4.49 (d, J= 7.3 Hz, 2H), 4.12 – 4.04 (m, 1H), 3.67 – 3.60 (m, 1H), 3.57 (dd, J = 9.4, 5.2 Hz, 1H), 3.56 – 3.49 (m, 1H), 3.43 (dd, J = 7.9, 4.4 Hz, 1H), 3.41 (s, 3H), 3.12 – 3.00 (m, 1H), 2.21 – 2.12 (m, 2H), 2.12 – 2.02 (m, 2H), 1.68 – 1.56 (m, 2H), 1.49 – 1.38 (m, 2H), 1.29 (d, J = 6.6 Hz, 3H). | 441.3 |
| 421 | 6 | $^1$H NMR (500 MHz, MeOD) δ 8.73 (s, 1H), 7.99 (s, 1H), 7.82 (s, 1H), 6.62 (s, 1H), 4.99 – 4.92 (m, 1H), 4.77 – 4.74 (m, 1H), 4.72 (t, J = 4.8 Hz, 1H), 4.35 – 4.27 (m, 3H), 4.12 – 4.04 (m, 1H), 3.91 (dd, J = 8.9, 6.2 Hz, 1H), 3.69 – 3.64 (m, 1H), 3.64 – 3.60 (m, 1H), 3.58 (dd, J = 9.4, 5.2 Hz, 1H), 3.45 – 3.41 (m, 1H), 3.41 (s, 3H), 3.12 – 3.03 (m, 1H), 2.20 – 2.13 (m, 2H), 2.13 – 2.04 (m, 2H), 1.69 – 1.56 (m, 2H), 1.51 – 1.39 (m, 2H), 1.29 (d, J = 6.6 Hz, 3H). | 499.1 |
| 422 | 6 | $^1$H NMR (500 MHz, MeOD) δ 8.73 (s, 1H), 7.98 (s, J = 0.7 Hz, 1H), 7.81 (s, J = 0.7 Hz, 1H), 6.62 (s, 1H), 5.96 (d, J = 5.0 Hz, 1H), 4.91 – 4.87 (m, 1H), 4.30 (dd, J = 10.2, 5.2 Hz, 1H), 4.16 – 4.12 (m, 1H), 4.12 – 4.04 (m, 1H), 4.01 – 3.91 (m, 2H), 3.68 – 3.61 (m, 1H), 3.58 (dd, J = 9.4, 5.2 Hz, 1H), 3.43 (dd, J = 7.9, 4.4 Hz, 1H), 3.41 (s, 3H), 3.28 – 3.22 (m, 1H), 3.13 – 3.00 (m, 1H), 2.36 – 2.25 (m, 1H), 2.20 – 2.13 (m, 2H), 2.13 – 2.07 (m, 2H), 2.07 – 2.00 (m, 1H), 1.69 – 1.57 (m, 2H), 1.49 – 1.36 (m, 2H), 1.29 (d, J = 6.6 Hz, 3H). | 483.2 |

FIG. 2 (Cont'd)

| No. | General Scheme | NMR | MS |
|---|---|---|---|
| 423 | 6 | ¹H NMR (500 MHz, MeOD) δ 8.98 (s, 1H), 8.42 (d, J = 5.3 Hz, 1H), 8.11 (s, J = 0.9 Hz, 1H), 7.48 (dd, J = 5.3, 1.6 Hz, 1H), 6.90 (s, 1H), 4.35 (s, 2H), 4.13 – 4.08 (m, 1H), 4.08 – 4.03 (m, 4H), 3.70 – 3.62 (m, 1H), 3.59 (dd, J = 9.5, 5.3 Hz, 1H), 3.46 – 3.43 (m, 1H), 3.42 (s, 3H), 3.15 – 3.06 (m, 1H), 2.24 – 2.16 (m, 2H), 2.14 – 2.03 (m, 2H), 1.71 – 1.58 (m, 2H), 1.51 – 1.41 (m, 2H), 1.30 (d, J = 6.6 Hz, 3H). | 481.1 |
| 424 | 4 | ¹H NMR (400 MHz, CD$_3$OD) δ 8.89 (d, J=2 Hz, 1H), 8.88 (s, 1H), 8.21 - 8.18 (m, 1H), 7.96 (d, J=8 Hz, 1H), 6.87 (s, 1H), 6.35 (t, $J_{HF}$=75.2 Hz 1H), 4.12 - 4.04 (m, 2H), 3.81-3.79 (m, 1H), 3.62 - 3.10 (m, 1H), 3.12-3.08 (m, 1H), 2.63 (s, 3H), 2.16-2.13 (m, 2H), 2.06-2.04 (m, 2H), 1.63-1.57 (m, 2H), 1.47-1.37 (m, 2H), 1.30 (d, J=6.8 Hz, 3H). | 511.2 |
| 425 | 4 | ¹H NMR (400MHz, CD$_3$OD) δ 8.71 (s, 1H), 6.53 (s, 1H), 6.02 ( s, 1H), 4.18 - 4.00 (m, 3H), 3.70 - 3.56 (m, 4H), 3.46- 3.43 (m, 1H), 3.42 (s, 3H), 3.13 - 3.01 (m, 1H), 2.61 - 2.51 (m, 2H), 2.21 - 2.02 (m, 4H), 1.69 - 1.55 (m, 2H), 1.51 (s, 9H), 1.48- 1.35 (m, 2H), 1.30 (d, J=6.4 Hz, 3H). | 486.4 |
| 426 | 5 | ¹H NMR (400MHz, CD$_3$OD) δ 8.89 (s, 1H), 8.02 (d, J=5.6 Hz, 1H), 6.94 ( d, J=5.6 Hz, 1H), 6.84 (s, 1H), 6.58 (s,1H),4.88 (s, 4H), 4.58 (s, 1H), 4.25 (s, 4H), 4.17 - 4.05 (m, 1H), 3.71 - 3.58 (m, 2H), 3.48 - 3.44 (m, 1H), 3.43 (s, 3H), 3.16 -3.06 (m, 1H), 2.25 - 2.16 (m, 2H), 2.15 - 2.06 (m, 2H), 1.75 - 1.55 (m, 2H), 1.54 - 1.39 (m, 2H), 1.32 (d, J=6.8 Hz, 3H). | 479.3 |
| 427 | 5 | ¹H NMR (400MHz, CD$_3$OD) δ 8.85 (s, 1H), 8.08 ( d, J=5.2 Hz, 1H), 6.95 (s, 1H), 6.88 (d, J=5.2 Hz, 1H), 6.82 (s,1H), 4.52 (s, 4H), 4.17 - 4.03 (m, 1H), 3.74 - 3.58 (m, 2H), 3.57 - 3.50 (m, 4H), 3.48 - 3.39 (m, 4H), 3.16 - 3.05 (m, 1H), 2.25 -2.16 (m, 2H), 2.15 - 2.06 (m, 2H), 2.00 - 1.89 (m, 4H), 1.75 - 1.55 (m, 2H), 1.53 - 1.39 (m, 2H), 1.31 (d, J=6.4 Hz, 3H). | 507.4 |
| 428 | 3 | ¹H NMR (400MHz, CD$_3$OD) δ 8.76 (s, 1H), 8.12 (s, 1H), 7.91 (s, 1H), 6.64 (s, 1H), 5.70 - 5.55 (m, 1H), 5.14 - 5.05(m, 4H), 4.84 - 4.79 ( m, 2H), 4.70 (t, J=6.4 Hz, 1H), 4.57 (t, J=6.4 Hz, 1H), 4.39 - 4.27 (m, 1H), 3.73 - 3.60 (m, 1H), 3.29 - 3.19(m, 1H), 3.17 - 3.05 (m, 1H), 2.26 - 2.24 (m, 1H), 2.26 - 2.07 (m, 3H), 1.71 - 1.55 (m, 2H), 1.54 - 1.41 (m, 2H), 1.23 (d, J=6.4Hz, 3H). | 439.3 |
| 429 | 3 | ¹H NMR (400MHz, CD$_3$OD) δ8.77 (s, 1H), 8.12 (s, 1H), 7.92 (s, 1H), 6.65 (s, 1H), 5.72 - 5.52 (m, 1H), 5.17 - 5.03 (m, 4H), 4.85 - 4.80 (m, 2H), 4.70 ( t, J=6.4 Hz, 1H), 4.57 (t, J=6.4 Hz, 1H), 4.40 - 4.27 (m, 1H), 3.75 - 3.60 (m, 1H), 3.29 - 3.18(m, 1H), 3.16 - 3.05 (m, 1H), 2.25 - 2.06 (m, 4H), 1.72 - 1.56 (m, 2H), 1.54 - 1.42 (m, 2H), 1.23 (d, J=6.4 Hz, 3H). | 439.3 |

FIG. 2 (Cont'd)

| No. | General Scheme | NMR | MS |
|---|---|---|---|
| 430 | 5 | ¹H NMR (400MHz, CD₃OD) δ 8.83 (s, 1H), 8.05 (d, J=5.2 Hz, 1H), 6.95 (s, 1H), 6.87 (d, J=5.2 Hz, 1H), 6.81 (s, 1H), 4.59 - 4.54 (m, 2H), 4.13 - 4.02 (m, 1H), 3.70 - 3.50 (m, 6H), 3.45 - 3.41 (m, 1H), 3.40 (s, 3H), 3.14 - 3.02 (m, 1H), 2.49 (t, J=8.0 Hz, 2H), 2.21 - 2.04 (m, 4H), 1.95 (t, J=5.2 Hz, 4H), 1.71 - 1.55 (m, 2H), 1.50 - 1.37 (m, 2H), 1.28 (d, J=6.8 Hz, 3H). | 507.4 |
| 431 | 5 | ¹H NMR (400MHz, CD₃OD) δ 8.88 (s, 1H), 7.95 (d, J=5.6 Hz, 1H), 6.83 - 6.78 (m, 2H), 6.75 (s, 1H), 4.17 - 4.07 (m, 1H), 4.04 - 3.92 (m, 3H), 3.71 - 3.55 (m, 4H), 3.48 - 3.44 (m, 1H), 3.43 (s, 3H), 3.17 - 3.05 (m, 1H), 2.25 - 2.16 (m, 2H), 2.15 - 2.07 (m, 2H), 2.06 - 1.97 (m, 2H), 1.73 - 1.39 (m, 6H), 1.34 - 1.34 (m, 1H), 1.31 (d, J=6.8 Hz, 3H). | 481.4 |
| 432 | 5 | ¹H NMR (400MHz, CD₃OD) δ 8.88 (s, 1H), 8.12 (d, J=5.2 Hz, 1H), 6.98 (s, 1H), 6.96 (d, J=5.2 Hz, 1H), 6.86 (s, 1H), 4.17 - 4.07 (m, 1H), 3.75 (s, 3H), 3.72 - 3.55 (m, 10H), 3.48 - 3.44 (m, 1H), 3.43 (s, 3H), 3.17 - 3.07 (m, 1H), 2.25 - 2.16 (m, 2H), 2.16 - 2.06 (m, 2H), 1.73 - 1.58 (m, 2H), 1.53 - 1.40 (m, 2H), 1.32 (d, J=6.8 Hz, 3H). | 524.4 |
| 433 | 5 | ¹H NMR (400MHz, CD₃OD) δ 8.60 (s, 1H), 6.37 (s, 1H), 4.05 (m, J=6.2 Hz, 1H), 3.67 - 3.52 (m, 2H), 3.41 (m, J=6.0 Hz, 1H), 3.39 (m, 3H), 3.18 - 2.96 (m, 4H), 2.79 - 2.64 (m, 2H), 2.16 - 1.95 (m, 5H), 1.88 - 1.65 (m, 3H), 1.64 - 1.50 (m, 2H), 1.47 - 1.33 (m, 2H), 1.26 (d, J=6.8 Hz, 3H). | 388.3 |
| 434 | 5 | ¹H NMR (400MHz, CD₃OD) δ 8.82 (s, 1H), 8.08 (d, J=5.2 Hz, 1H), 6.93 (s, 1H), 6.91 (m, J=5.4 Hz, 1H), 6.80 (s, 1H), 4.08 (m, J=6.2 Hz, 1H), 3.68 - 3.51 (m, 6H), 3.45 - 3.41 (m, 1H), 3.40 (s, 3H), 3.07 (m, J=3.2, 12.0 Hz, 1H), 3.02 - 2.94 (m, 4H), 2.16 (m, J=11.6 Hz, 2H), 2.08 (m, J=10.8 Hz, 2H), 1.68 - 1.54 (m, 2H), 1.50 - 1.37 (m, 2H), 1.28 (d, J=6.4Hz, 3H). | 466.3 |
| 435 | 5 | ¹H NMR (400MHz, CD₃OD) δ 8.67 (s, 1H), 6.47 (s, 1H), 4.09 (m, J=6.2 Hz, 1H), 3.76 (m, J=11.5 Hz, 2H), 3.70 - 3.55 (m, 2H), 3.48 - 3.41 (m, 4H), 3.26 - 3.16 (m, 1H), 3.12 - 3.03 (m, 1H), 2.92 - 2.82 (m, 5H), 2.20 - 2.00 (m, 5H), 1.97 - 1.89 (m, 1H), 1.86 - 1.55 (m, 4H), 1.51 - 1.39 (m, 2H), 1.30 (d, J=6.8 Hz, 3H). | 466.3 |
| 436 | 4 | ¹H NMR (400 MHz, MeOD) δ 8.71 (s, 1H), 8.02 (d, J = 0.7 Hz, 1H), 7.82 (d, J = 0.7 Hz, 1H), 6.60 (s, 1H), 6.59 – 6.21 (m, 1H), 4.65 (t, J = 6.6 Hz, 2H), 4.15 – 4.01 (m, 2H), 3.79 (dd, J = 9.3, 6.1 Hz, 1H), 3.70 (t, J = 6.4 Hz, 2H), 3.65 – 3.55 (m, 1H), 3.07 (ddt, J = 15.5, 7.1, 2.5 Hz, 1H), 2.77 (s, 3H), 2.16 – 2.02 (m, 4H), 1.67 – 1.51 (m, 2H), 1.48 – 1.35 (m, 2H), 1.31 (d, J = 6.7 Hz, 3H). | 513.2 |
| 437 | 4 | ¹H NMR (400 MHz, MeOD) δ 8.71 (s, 1H), 8.02 (s, 1H), 7.82 (s, 1H), 6.61 (s, 1H), 6.59-6.21 (m, 1H), 4.44 (t, J = 6.5 Hz, 2H), 4.15 – 4.02 (m, 2H), 3.80 (dd, J = 9.3, 6.0 Hz, 1H), 3.61 (ddd, J = 14.9, 10.6, 4.1 Hz, 1H), 3.12 – 3.00 (m, 3H), 2.22 – 1.99 (m, 4H), 1.68 – 1.50 (m, 2H), 1.50 – 1.36 (m, 2H), 1.31 (d, J = 6.6 Hz, 3H). | 460.2 |

FIG. 2 (Cont'd)

| No. | General Scheme | NMR | MS |
|---|---|---|---|
| 438 | 6 | $^1$H NMR (400 MHz, CD$_3$OD) δ 8.94 (s, 1H), 8.37 (s, 1H), 8.29 (d, J = 5.4 Hz, 1H), 7.33 (dd, J = 5.4, 1.5 Hz, 1H), 6.87 (s, 1H), 4.53 (t, J = 8.0 Hz, 2H), 4.29 (t, J = 8.1 Hz, 2H), 4.16 – 4.04 (m, 1H), 3.71 – 3.62 (m, 1H), 3.59 (dd, J = 9.4, 5.2 Hz, 1H), 3.44 (dd, J = 8.3, 4.9 Hz, 1H), 3.42 (s, 3H), 3.19 – 3.03 (m, 1H), 2.24 – 2.15 (m, 2H), 2.15 – 2.01 (m, 2H), 1.72 – 1.57 (m, 2H), 1.45 (dd, J = 24.0, 10.8 Hz, 2H), 1.31 (d, J = 6.6 Hz, 3H). | 467.5 |
| 439 | 6 | $^1$H NMR (400 MHz, CD$_3$OD) δ 8.73 (s, 1H), 8.01 (s, 1H), 7.82 (s, 1H), 6.62 (s, 1H), 5.19 – 5.05 (m, 1H), 4.70 – 4.54 (m, 1H), 4.49 – 4.34 (m, 3H), 4.14 – 3.97 (m, 1H), 3.68 – 3.61 (m, 1H), 3.61 – 3.52 (m, 1H), 3.43 (dd, J = 7.4, 3.9 Hz, 1H), 3.41 (s, 3H), 3.13 – 3.01 (m, 1H), 2.80 – 2.63 (m, 1H), 2.59 – 2.46 (m, 1H), 2.22 – 2.13 (m, 2H), 2.13 – 2.03 (m, 2H), 1.69 – 1.54 (m, 2H), 1.51 – 1.38 (m, 2H), 1.29 (d, J = 6.6 Hz, 3H). | 441.5 |
| 440 | 6 | $^1$H NMR (400 MHz, CD$_3$OD) δ 8.76 (s, 1H), 8.19 (s, 1H), 7.81 (s, 1H), 6.64 (s, 1H), 4.14 – 4.02 (m, 1H), 3.69 – 3.60 (m, 1H), 3.58 (dd, J = 9.4, 5.2 Hz, 1H), 3.43 (dd, J = 8.2, 4.7 Hz, 1H), 3.41 (s, 3H), 3.12 – 3.03 (m, 1H), 2.50 (s, 3H), 2.21 – 2.14 (m, 2H), 2.14 – 2.05 (m, 8H), 1.72 – 1.55 (m, 2H), 1.53 – 1.34 (m, 2H), 1.29 (d, J = 6.6 Hz, 3H). | 495.6 |
| 441 | 5 | $^1$H NMR (400MHz, CD$_3$OD) δ 8.69 (s, 1H), 6.51 (s, 1H), 6.09 (s, 1H), 4.27 - 4.19 (m, 1H), 3.79 - 3.55 (m, 9H), 3.16 - 2.94 (m, 2H), 2.87 - 2.66 (m, 2H), 2.63 - 2.53 (m, 2H), 2.51 - 2.26 (m, 3H), 2.24 - 1.98 (m, 5H), 1.90 - 1.63 (m, 1H), 1.60 - 1.43 (m, 4H), 1.41 (d, J=6.8 Hz, 3H). | 536.3 |
| 442 | 5 | $^1$H NMR (400MHz, CD$_3$OD) δ 8.95 (s, 1H), 7.10 (s, 1H), 6.29 (s, 1H), 4.38 - 4.30 (m, 1H), 4.02 - 3.90 (m, 2H), 3.75- 3.61 (m, 1H), 3.52 (t, J=6.0 Hz, 2H), 3.25 - 3.13 (m, 1H), 2.93 - 2.84 (m, 2H), 2.83 - 2.70 (m, 1H), 2.57 - 2.37 (m, 1H), 2.20 -2.06 (m, 4H), 1.82 - 1.56 (m, 2H), 1.55 - 1.37 (m, 5H). | 424.2 |
| 443 | 5 | $^1$H NMR (400MHz, CD$_3$OD) δ 8.93 (s, 1H), 7.07 (s, 1H), 6.27 (s, 1H), 4.21 - 4.08 (m, 1H), 4.00-3.89 (m, 2H), 3.73 -3.60 (m, 1H), 3.59 - 3.49 (m, 4H), 3.43 (s, 3H), 3.24 - 3.13 (m, 1H), 2.91- 2.83 (m, 2H), 2.19 -2.09 (m, 4H), 1.75 -1.60 (m, 2H),1.54 - 1.39 (m, 2H), 1.35 (d, J=6.8 Hz, 3H). | 386.1 |
| 444 | 5 | $^1$H NMR (400MHz, CD$_3$OD) δ 8.82 (s, 1H), 7.74 (d, J=1.2 Hz, 1H), 7.67 (d, J=1.2 Hz, 1H), 6.74 (s, 1H), 4.18 -4.05 (m, 1H), 3.86 - 3.79 (m, 4H), 3.79 - 3.72 (m, 4H), 3.71 - 3.56 (m, 2H), 3.49 - 3.44 (m, 1H), 3.43 (s, 3H), 3.17 - 3.05 (m,1H), 2.24 - 2.15 (m, 2H), 2.14 - 2.06 (m, 2H), 1.74 - 1.56 (m, 2H), 1.53 - 1.39 (m, 2H), 1.31 (d, J=6.4 Hz, 3H). | 500.3 |
| 445 | 5 | $^1$H NMR (400MHz, CD$_3$OD) δ 8.87 (s, 1H), 8.09 (d, J=5.2 Hz, 1H), 6.94 (d, J=5.2 Hz, 1H), 6.86 (s, 1H), 6.85 (s, 1H), 4.54 - 4.47 (m, 2H), 4.17 - 4.06 (m, 1H), 3.91 - 3.84 (m, 2H), 3.71 - 3.57 (m, 2H), 3.48 - 3.44 (m, 1H), 3.43 (s, 3H), 3.16 - 3.05 (m, 3H), 2.25 - 2.16 (m, 2H), 2.15 - 2.07 (m, 2H), 2.04 - 1.87 (m, 4H), 1.73 - 1.58 (m, 2H), 1.53 - 1.40 (m, 2H), 1.31 (d, J=6.8 Hz, 3H). | 493.3 |

FIG. 2 (Cont'd)

| No. | General Scheme | NMR | MS |
|---|---|---|---|
| 446 | 5 | ¹H NMR (400MHz, CD₃OD) δ 8.61 (s, 1H), 6.47 (s, 1H), 4.25 - 4.20 (m, 1H), 3.70 - 3.55 (m, 9H), 3.15 – 3.04 (m, 2H), 2.96 - 2.91 (m, 1H), 2.85 - 2.75 (m, 1H), 2.35 - 2.25 (m, 1H), 2.19 – 2.01 (m, 6H), 1.97 - 1.89 (m, 2H), 1.88 - 1.79 (m, 2H), 1.76 - 1.65 (m, 2H), 1.65 - 1.43 (m, 4H), 1.40 (d, J=6.8 Hz, 3H). | 538.5 |
| 447 | 4 | ¹H NMR (400MHz, DMSO-d₆) δ 8.97 (s, 1H), 8.27 (s, 1H), 7.93 (s, 1H), 6.69 - 6.61 (s, 1H), 5.56 (quin, J=6.8 Hz, 1H), 4.96 (d, J=7.0 Hz, 4H), 4.44 (br s, 1H), 4.31 (br s, 1H), 4.17 - 4.04 (m, 1H), 3.98 - 3.84 (m, 1H), 3.58 - 3.44 (m, 3H), 3.28 - 3.19 (m, 1H), 2.36 - 2.26 (m, 2H), 2.10 - 1.95 (m, 4H), 1.67 - 1.40 (m, 4H), 1.37 (d, J=6.1 Hz, 3H), 1.35 - 1.26 (m, 2H). | 453.3 |
| 448 | 5 | ¹H NMR (400MHz, CD₃OD) δ 8.64 (s, 1H), 6.44 (s, 1H), 4.05 (m, J=6.2 Hz, 1H), 3.73 (m, J=11.8 Hz, 2H), 3.67 - 3.52 (m, 2H), 3.44 - 3.38 (m, 4H), 3.23 - 3.13 (m, 1H), 3.09 - 3.00 (m, 1H), 2.89 - 2.78 (m, 5H), 2.17 - 1.86 (m, 6H), 1.83 - 1.51 (m, 4H), 1.49 - 1.36 (m, 2H), 1.27 (d, J=6.8 Hz, 3H). | 466.3 |
| 449 | 4 | ¹H NMR (400 MHz, CD₃OD) δ 8.48 (s, 1H), 6.45 (s, 1H), 4.19-3.84 (m, 3H), 3.75-3.44 (m, 8H), 3.43-3.37 (m, 1H), 3.28 (s, 3H), 3.03-2.91 (m, 1H), 2.08-1.95 (m, 4H), 1.54-1.43 (m, 8H), 1.4-1.27 (m, 2H), 1.20 (d, J= 6.4 Hz, 3H). | 484.3 |
| 450 | 5 | ¹H NMR (500 MHz, MeOD) δ 8.79 (s, 1H), 8.12 (s, 1H), 7.88 (s, 1H), 6.68 (s, 1H), 4.15-4.06 (m, 1H), 3.67 (tt, J = 10.8, 4.2 Hz, 1H), 3.61 (dd, J = 9.4, 5.2 Hz, 1H), 3.49-3.40 (m, 4H), 3.27-2.91 (m, 5H), 2.23-2.08 (m, 4H), 1.85 (s, 6H), 1.72-1.35 (m, 8H), 1.32 (d, J = 6.6 Hz, 3H), 1.16 (s, 3H). | 554.2 |
| 451 | 5 | ¹H NMR (400 MHz, MeOD) δ 8.75 (s, 1H), 8.10 (d, J = 0.6 Hz, 1H), 7.84 (d, J = 0.5 Hz, 1H), 6.63 (s, 1H), 4.10-3.99 (m, 1H), 3.66-3.58 (m, 1H), 3.58-3.50 (m, 1H), 3.40 (dd, J = 5.7, 3.7 Hz, 1H), 3.39-3.35 (m, 3H), 3.11-2.99 (m, 1H), 2.90 (ddd, J = 12.6, 9.1, 2.5 Hz, 2H), 2.18-1.96 (m, 4H), 1.93-1.69 (m, 7H), 1.68-1.50 (m, 3H), 1.50-1.30 (m, 3H), 1.28 (s, 3H), 1.26 (d, J = 6.6 Hz, 3H), 1.26 (d, J = 6.6 Hz, 3H). | 563.3 |
| 452 | See Example 34 | ¹H NMR (400 MHz, CD₃OD) δ 8.71 (s, 1H), 8.07 (d, J = 0.7 Hz, 1H), 7.87 (s, 1H), 6.63 (s, 1H), 5.56 (dq, J = 7.5, 6.4 Hz, 1H), 5.11 – 4.97 (m, 4H), 4.10 – 3.98 (m, 1H), 3.57 – 3.49 (m, 1H), 3.40 (dd, J = 9.5, 5.8 Hz, 1H), 3.37 (s, 3H), 3.13 – 2.97 (m, 1H), 1.94 – 1.83 (m, 4H), 1.80 – 1.72 (m, 2H), 1.60 – 1.47 (m, 2H), 1.25 (d, J = 6.6 Hz, 3H), 1.22 (s, 3H). | 441.2 |
| 453 | See Example 34 | 8.71 (s, 1H), 8.08 (d, J = 0.7 Hz, 1H), 7.88 (d, J = 0.5 Hz, 1H), 6.63 (s, 1H), 5.65 – 5.50 (m, 1H), 5.09 – 4.97 (m, 4H), 4.11 – 3.95 (m, 1H), 3.53 (dd, J = 9.4, 5.2 Hz, 1H), 3.42 – 3.38 (m, 1H), 3.38 – 3.34 (m, 3H), 3.15 – 3.01 (m, 1H), 2.10 – 1.97 (m, 2H), 1.83 – 1.67 (m, 4H), 1.67 – 1.57 (m, 2H), 1.29 (s, 3H), 1.25 (d, J = 6.6 Hz, 3H). | 441.2 |

FIG. 2 (Cont'd)

| No. | General Scheme | NMR | MS |
|---|---|---|---|
| 454 | 4 | ¹H NMR (400MHz, CD₃OD) δ 8.69 (s, 1H), 6.51 (s, 1H), 6.09 (s, 1H), 4.27 - 4.19 (m, 1H), 3.73 - 3.58 (m, 9H), 3.17 - 2.96 (m, 2H), 2.87 - 2.68 (m, 2H), 2.65 - 2.52 (m, 2H), 2.51 - 2.27 (m, 3H), 2.19 - 1.78 (m, 6H), 1.64 - 1.43 (m, 4H), 1.41 (br d, $J$=6.4 Hz, 3H). | 536.2 |
| 455 | 4 | ¹H NMR (400MHz, CD₃OD) δ 8.70 (s, 1H), 6.51 (s, 1H), 6.09 (s, 1H), 4.27 - 4.19 (m, 1H), 3.79 - 3.55 (m, 9H), 3.16 - 2.94 (m, 2H), 2.87 - 2.66 (m, 2H), 2.63 - 2.53 (m, 2H), 2.51 - 2.26 (m, 3H), 2.24 - 1.98 (m, 5H), 1.94 - 1.79 (m, 1H), 1.71 - 1.44 (m, 4H), 1.41 (d, $J$=6.8 Hz, 3H). | 536.2 |
| 456 | 4 | ¹H NMR (400 MHz, CD₃OD) δ 8.71 (s, 1H), 6.50 (s, 1H), 6.36 (d, $J$=5.2 Hz, 1H), 4.49-4.42 (m, 2H), 4.25-4.20 (m, 2H), 3.66-3.63 (m, 1H), 3.14-2.97 (m, 2H), 2.88-2.70 (m, 1H), 2.43-2.21 (m, 3H), 2.18-1.96 (m, 6H), 1.86-1.74 (m, 1H), 1.73-1.54 (m, 3H), 1.51 (s, 9H), 1.41-1.36 (m, 1H), 1.27 (d, $J$=6.8 Hz, 3H). | 550.3 |
| 457 | 4 | ¹H NMR (400 MHz, CD₃OD) δ 8.62 (s, 1H), 6.41 (s, 1H), 6.27 (d, $J$=5.6 Hz, 1H), 4.40-4.33 (m, 2H), 4.16-4.11 (m, 2H), 3.58-3.54 (m, 1H), 3.04-2.92 (m, 2H), 2.77-2.53 (m, 1H), 2.32-2.13 (m, 3H), 2.08-1.89 (m, 6H), 1.77-1.66 (m,1H), 1.63-1.46 (m, 3H), 1.38 (s, 9H), 1.29-1.31 (m, 1H), 1.30 (d, $J$=6.4 Hz, 3H). | 550.3 |
| 458 | 5 | ¹H NMR (400 MHz, CD₃OD) δ 8.84 (s, 1H), 6.92 (s, 1H), 6.41 (d, $J$=6.0 Hz, 1H), 4.37-4.34 (m, 1H), 4.29-4.22 (m, 2H), 3.62-3.54 (m, 2H), 3.17-3.04 (m, 2H), 2.76-2.62 (m, 2H), 2.44-2.26 (m, 3H), 2.23-1.94 (m, 5H), 1.66-1.43 (m, 3H), 1.38 (d, $J$=6.4 Hz, 3H). | 450.2 |
| 459 | 5 | ¹H NMR (400MHz, CD₃OD) δ 8.74 (s, 1H), 8.07 (s, 1H), 7.79 (s, 1H), 6.63 (s, 1H), 4.15 - 4.06 (m, 1H), 3.72 - 3.57 (m, 2H), 3.54 (t, $J$=4.4 Hz, 3H), 3.47 - 3.45 (m, 1H), 3.43 (s, 3H), 3.17 - 3.02 (m, 1H), 2.66 (s, 2H), 2.26 - 2.05 (m, 8H),1.74 - 1.57 (m, 8H), 1.54 - 1.39 (m, 2H), 1.31 (d, $J$=6.8 Hz, 3H). | 512.3 |
| 460 | 5 | ¹H NMR (400MHz, CD₃OD) δ 8.95 (s, 1H), 7.41 (d, $J$=3.6 Hz, 1H), 7.16 (s, 1H), 7.00 (d, $J$=3.6 Hz, 1H), 4.23 - 4.11(m, 1H), 3.75 - 3.64 (m, 1H), 3.60 - 3.46 (m, 9H), 3.44 (s, 3H), 3.26 - 3.13 (m, 1H), 2.21 - 2.09 (m, 4H), 1.80 - 1.62 (m, 8H),1.55 - 1.41 (m, 2H), 1.36 (d, $J$=6.4 Hz, 3H). | 542.3 |
| 461 | 5 | ¹H NMR (400MHz, CD₃OD) δ 8.70 (s, 1H), 6.49 (s, 1H), 6.32 (d, $J$=5.6 Hz, 1H), 4.13 - 4.02 (m, 1H), 3.88 - 3.79 (m, 2H), 3.68 - 3.54 (m, 2H), 3.46 - 3.40 (m, 4H), 3.10 - 3.00 (m, 1H), 3.00 - 2.90 (m, 1H), 2.36 (d, $J$=16.8 Hz, 1H), 2.20 - 2.04 (m, 6H), 2.00 - 1.88 (m, 1H), 1.82 - 1.71 (m, 1H), 1.66 - 1.52 (m, 2H), 1.50 - 1.37 (m, 2H), 1.29 (d, $J$=6.8 Hz, 3H). | 412.2 |
| 462 | 5 | ¹H NMR (400 MHz, CD₃OD) δ 8.72 (s, 1H), 6.51 (s, 1H), 6.43 – 6.29(m, 1H), 4.84 – 4.76 (m, 1H), 4.19 - 3.98 (m, 1H), 3.71 - 3.52 (m, 2H), 3.47 - 3.39 (m, 4H), 3.16 - 3.00 (m, 2H), 2.60 - 2.22 (m, 2H), 2.21 - 1.76 (m, 11H), 1.67 – 1.51 (m, 2H), 1.51 - 1.37 (m, 2H), 1.29 (d, $J$ = 6.4 Hz, 3H). | 454.2 |

FIG. 2 (Cont'd)

| No. | General Scheme | NMR | MS |
|---|---|---|---|
| 463 | 5 | $^1$H NMR (400 MHz, CD$_3$OD) δ 8.73 (s, 1H), 6.51 (s, 1H), 6.36 (br d, J = 5.6 Hz, 1H), 4.44 – 4.32 (m, 2H), 4.13 - 4.02 (m, 1H), 3.78 - 3.54 (m, 6H), 3.50 - 3.37 (m, 8H), 3.20 - 2.94 (m, 2H), 2.49 – 2.33 (m, 1H), 2.30 - 1.91 (m, 7H), 1.84 - 1.73 (m, 1H), 1.67 - 1.52 (m, 2H), 1.50 - 1.38 (m, 2H), 1.29 (d, J = 6.8 Hz, 3H). | 525.2 |
| 464 | 5 | $^1$H NMR (400 MHz, CD$_3$OD) δ 8.88 (s, 1H), 8.04 (d, J = 5.6 Hz, 1H), 6.87 (d, J = 5.2 Hz, 1H), 6.83 (s, 1H), 6.73 - 6.64 (m, 1H), 6.68 (s, 1H), 4.16 – 4.05 (m, 1H), 4.03 – 3.94 (m, 2H), 3.79 - 3.55 (m, 6H), 3.52 - 3.44 (m, 3H), 3.43 (s, 3H), 3.19 - 3.02 (m, 3H), 2.19 (br d, J = 11.4 Hz, 2H), 2.11 (br d, J = 11.9 Hz, 2H), 1.74 - 1.56 (m, 2H), 1.53 - 1.40 (m, 2H), 1.31 (d, J = 6.8 Hz, 3H). | 493.2 |
| 465 | 5 | $^1$H NMR (400 MHz, CD$_3$OD) δ 8.72 (s, 1H), 6.51 (s, 1H), 6.21 (d, J=4.8 Hz, 1H), 4.13 - 4.02 (m, 1H), 3.68 - 3.55 (m, 2H), 3.52 (br t, J=5.2 Hz, 1H), 3.49 - 3.43 (m, 2H), 3.42 (s, 3H), 3.12 - 3.01 (m, 1H), 3.00 - 2.91 (m, 1H), 2.45 (s, 3H), 2.35 - 2.21 (m, 2H), 2.20 - 1.94 (m, 6H), 1.82 - 1.70 (m, 1H), 1.67 - 1.53 (m, 2H), 1.51 - 1.38 (m, 2H), 1.29 (d, J=6.8 Hz, 3H). | 426.2 |
| 466 | 5 | $^1$H NMR (400 MHz, CD$_3$OD) δ 8.78 (s, 1H), 8.11 (s, 1H), 7.86 (s, 1H), 6.66 (s, 1H), 4.12-4.06 (m, 1H), 3.64-3.56 (m, 3H), 3.54-3.41 (m, 5H), 3.09-2.90 (m, 2H), 2.45-2.03 (m, 11H), 1.82 (s, 6H), 1.64-1.59 (m, 2H), 1.49-1.43 (m, 2H), 1.29 (d, J=6.4 Hz, 3H). | 539.4 |
| 467 | 5 | $^1$H NMR (400MHz, CD$_3$OD) δ 8.68 (s, 1H), 6.46 (s, 1H), 6.30 (d, J=5.6 Hz, 1H), 4.09 - 4.01 (m, 1H), 3.84 - 3.75 (m, 2H), 3.67 - 3.52 (m, 2H), 3.46 - 3.37 (m, 4H), 3.08 - 2.97 (m, 1H), 2.91 (m, J=13.8 Hz, 1H), 2.31 (d, J=17.0 Hz, 1H), 2.17 - 1.99 (m, 6H), 1.97 - 1.84 (m, 1H), 1.80 - 1.68 (m, 1H), 1.64 - 1.49 (m, 2H), 1.48 - 1.34 (m, 2H), 1.27 (d, J=6.8 Hz, 3H). | 412.2 |
| 468 | 5 | $^1$H NMR (400MHz, CD$_3$OD) δ 8.70 (s, 1H), 6.49 (s, 1H), 6.34 (m, J=5.6, 19.6 Hz, 1H), 4.85 - 4.76 (m, 1H), 4.05 (m, J=6.2 Hz, 1H), 3.67 - 3.52 (m, 2H), 3.44 - 3.37 (m, 4H), 3.14 - 2.97 (m, 2H), 2.56 - 2.20 (m, 2H), 2.07 (m, 11H), 1.65 - 1.50 (m, 2H), 1.48 - 1.35 (m, 2H), 1.27 (d, J=6.8 Hz, 3H). | 454.2 |
| 469 | 5 | $^1$H NMR (400MHz, CD$_3$OD) δ 8.70 (s, 1H), 6.48 (s, 1H), 6.34 (br d, J=5.6 Hz, 1H), 4.41 - 4.28 (m, 2H), 4.13 - 3.98 (m, 1H), 3.75 - 3.52 (m, 6H), 3.45 - 3.36 (m, 8H), 3.12 - 2.99 (m, 2H), 2.38 (d, J=16.8 Hz, 1H), 2.25 - 1.90 (m, 7H), 1.82 - 1.71 (m, 1H), 1.65 - 1.50 (m, 2H), 1.49 - 1.35 (m, 2H), 1.27 (d, J=6.8 Hz, 3H). | 525.2 |
| 470 | 6 | $^1$H NMR (400 MHz, CD$_3$OD) δ 8.75 (s, 1H), 8.04 (s, 1H), 7.84 (s, 1H), 6.62 (s, 1H), 5.18 (t, J = 8.8 Hz, 1H), 4.14 – 4.02 (m, 1H), 3.69 – 3.51 (m, 4H), 3.46 – 3.42 (m, 1H), 3.41 (s, 3H), 3.13 – 3.03 (m, 1H), 2.95 (s, 3H), 2.73 – 2.63 (m, 1H), 2.59 – 2.47 (m, 1H), 2.22 – 2.13 (m, 2H), 2.13 – 2.02 (m, 2H), 1.70 – 1.55 (m, 2H), 1.50 – 1.38 (m, 2H), 1.29 (d, J = 6.6 Hz, 3H). | 468.2 |

FIG. 2 (Cont'd)

| No. | General Scheme | NMR | MS |
|---|---|---|---|
| 471 | 6 | $^1$H NMR (400 MHz, CD$_3$OD) δ 8.75 (s, 1H), 8.04 (s, 1H), 7.84 (s, 1H), 6.62 (s, 1H), 5.18 (t, J = 8.8 Hz, 1H), 4.14 – 4.02 (m, 1H), 3.69 – 3.51 (m, 4H), 3.46 – 3.42 (m, 1H), 3.41 (s, 3H), 3.13 – 3.03 (m, 1H), 2.95 (s, 3H), 2.73 – 2.63 (m, 1H), 2.59 – 2.47 (m, 1H), 2.22 – 2.13 (m, 2H), 2.13 – 2.02 (m, 2H), 1.70 – 1.55 (m, 2H), 1.50 – 1.38 (m, 2H), 1.29 (d, J = 6.6 Hz, 3H). | 468.2 |
| 472 | 6 | $^1$H NMR (400 MHz, CD$_3$OD) δ 8.73 (s, 1H), 8.02 (s, 1H), 7.80 (s, 1H), 6.61 (s, 1H), 4.25 (dd, J = 7.2, 1.3 Hz, 2H), 4.13 – 4.03 (m, 1H), 3.68 – 3.60 (m, 1H), 3.58 (dd, J = 9.4, 5.2 Hz, 1H), 3.53 (dd, J = 10.3, 8.0 Hz, 1H), 3.46 – 3.42 (m, 1H), 3.41 (s, 3H), 3.35 – 3.32 (m, 1H), 3.13 – 3.04 (m, 1H), 3.04 – 2.94 (m, 1H), 2.80 (s, 3H), 2.53 (dd, J = 17.1, 9.1 Hz, 1H), 2.27 (dd, J = 17.1, 6.1 Hz, 1H), 2.21 – 2.13 (m, 2H), 2.13 – 2.03 (m, 2H), 1.68 – 1.55 (m, 2H), 1.51 – 1.38 (m, 2H), 1.29 (d, J = 6.6 Hz, 3H). | 482.1 |
| 473 | 6 | $^1$H NMR (400 MHz, CD$_3$OD) δ 8.73 (s, 1H), 8.02 (s, 1H), 7.80 (s, 1H), 6.61 (s, 1H), 4.25 (dd, J = 7.2, 1.3 Hz, 2H), 4.13 – 4.03 (m, 1H), 3.68 – 3.60 (m, 1H), 3.58 (dd, J = 9.4, 5.2 Hz, 1H), 3.53 (dd, J = 10.3, 8.0 Hz, 1H), 3.46 – 3.42 (m, 1H), 3.41 (s, 3H), 3.35 – 3.32 (m, 1H), 3.13 – 3.04 (m, 1H), 3.04 – 2.94 (m, 1H), 2.80 (s, 3H), 2.53 (dd, J = 17.1, 9.1 Hz, 1H), 2.27 (dd, J = 17.1, 6.1 Hz, 1H), 2.21 – 2.13 (m, 2H), 2.13 – 2.03 (m, 2H), 1.68 – 1.55 (m, 2H), 1.51 – 1.38 (m, 2H), 1.29 (d, J = 6.6 Hz, 3H). | 482.1 |
| 474 | 6 | $^1$H NMR (400 MHz, CD$_3$OD) δ 8.73 (s, 1H), 8.01 (s, 1H), 7.82 (s, 1H), 6.62 (s, 1H), 5.20 – 5.11 (m, 1H), 4.65 (ddd, J = 8.5, 7.3, 5.8 Hz, 1H), 4.51 – 4.35 (m, 3H), 4.16 – 4.01 (m, 1H), 3.70 – 3.60 (m, 1H), 3.58 (dd, J = 9.4, 5.1 Hz, 1H), 3.47 – 3.42 (m, 1H), 3.41 (s, 3H), 3.13 – 3.02 (m, 1H), 2.80 – 2.67 (m, 1H), 2.57 – 2.44 (m, 1H), 2.21 – 2.13 (m, 2H), 2.13 – 2.02 (m, 2H), 1.70 – 1.56 (m, 2H), 1.51 – 1.36 (m, 2H), 1.29 (d, J = 6.6 Hz, 3H). | 441.5 |
| 475 | 6 | $^1$H NMR (400 MHz, CD$_3$OD) δ 8.70 (s, 1H), 7.98 (s, 1H), 7.78 (s, 1H), 6.59 (s, 1H), 5.16 – 5.07 (m, 1H), 4.66 – 4.55 (m, 1H), 4.48 – 4.30 (m, 3H), 4.10 – 4.00 (m, 1H), 3.66 – 3.57 (m, 1H), 3.54 (dd, J = 9.4, 5.2 Hz, 1H), 3.43 – 3.38 (m, 1H), 3.38 (s, 3H), 3.10 – 2.98 (m, 1H), 2.78 – 2.66 (m, 1H), 2.52 – 2.40 (m, 1H), 2.18 – 2.10 (m, 2H), 2.10 – 1.99 (m, 2H), 1.67 – 1.51 (m, 2H), 1.49 – 1.35 (m, 2H), 1.26 (d, J = 6.6 Hz, 3H). | 441.5 |
| 476 | 6 | $^1$H NMR (500 MHz, MeOD) δ 8.73 (s, 1H), 8.13–8.12 (m, 1H), 7.91-7.89 (m, 2H), 7.86–7.85 (m, 1H), 7.64–7.61 (m, 2H), 6.63 (s, 1H), 5.50 (s, 2H), 4.10–4.06 (m, 1H), 3.66–3.60 (tt, J = 10.8, 4.2 Hz, 1H), 3.59–3.56 (dd, J = 9.4, 5.2 Hz, 1H), 3.44–3.41 (m, 4H), 3.11–3.04 (m, 4H), 2.17–2.14 (m, 2H) 2.10–2.07 (m, 2H), 1.67–1.57 (m, 2H), 1.47–1.40 (m, 2H), 1.29–1.28 (d, J = 6.6 Hz, 3H). | 539.1 |
| 477 | 5 | $^1$H NMR (400MHz, CD$_3$OD) δ 8.62 (s, 1H), 6.32 (s, 1H), 6.22 (s, 1H), 4.28 ( s, 2H), 4.13 - 4.02 (m, 1H), 3.94 (m, 1H), 3.51 - 3.36 (m, 6H), 2.96-2.81 (m, J=11.8 Hz, 1H), 2.05 - 1.83 (m, 7H), 1.81 - 1.63 (m, 4H), 1.60-1.34 (m, 11H), 1.33-1.19 (m, J=6.8 Hz, 3H), 1.169-1.153 (d, J=6.4 Hz, 3H). | 514.2 |

FIG. 2 (Cont'd)

| No. | General Scheme | NMR | MS |
|---|---|---|---|
| 478 | 5 | $^1$H NMR (400MHz, CD$_3$OD) δ 8.96 (d, J=2.0 Hz, 1H), 8.91 (s, 1H), 8.26 (dd, J1=8.4 Hz, J2=2.4 Hz, 1H), 8.15 (d, J=8.4 Hz, 1H), 6.90 (s, 1H), 4.15-4.10 (m, 1H), 3.65-3.57 (m, 2H), 3.46-3.43 (m, 1H), 3.42 (s, 3H), 3.28 (s, 3H), 3.13-3.11 (m, 1H), 2.21-2.18 (m, 2H), 2.11-2.09 (m, 2H), 1.68-1.63 (m, 2H), 1.50-1.44 (m, 2H), 1.30 (d, J=6.8 Hz, 3H). | 459.2 |
| 479 | 5 (see Example 39) | $^1$H NMR (400 MHz, CD$_3$OD) δ 8.93 (s, 1H), 8.11 (d, J = 5.5 Hz, 1H), 6.94 (d, J = 5.5 Hz, 1H), 6.88 (s, 1H), 6.75 (s, 1H), 4.82 – 4.79 (m, 2H), 4.73 – 4.65 (m, 2H), 4.17 – 4.05 (m, 1H), 3.71 – 3.62 (m, 1H), 3.59 (dd, J = 9.5, 5.2 Hz, 1H), 3.47 – 3.43 (m, 1H), 3.42 (s, 3H), 3.18 – 3.07 (m, 1H), 2.76 (s, 3H), 2.25 – 2.16 (m, 2H), 2.16 – 2.04 (m, 2H), 1.75 – 1.58 (m, 2H), 1.55 – 1.37 (m, 2H), 1.31 (d, J = 6.7 Hz, 3H). | 520.6 |
| 480 | 5 (analogous to Example 39) | $^1$H NMR (400 MHz, CD$_3$OD) δ 8.89 (s, 1H), 8.15 (d, J = 5.3 Hz, 1H), 7.06 – 6.97 (m, 2H), 6.88 (s, 1H), 4.63 (d, J = 6.9 Hz, 2H), 4.54 (d, J = 7.0 Hz, 2H), 4.16 – 4.02 (m, 1H), 3.84 – 3.75 (m, 4H), 3.72 – 3.62 (m, 1H), 3.59 (dd, J = 9.4, 5.3 Hz, 1H), 3.50 – 3.45 (m, 2H), 3.45 – 3.37 (m, 4H), 3.18 – 3.06 (m, 1H), 2.25 – 2.16 (m, 2H), 2.15 – 2.05 (m, 2H), 1.74 – 1.58 (m, 2H), 1.52 – 1.39 (m, 2H), 1.30 (d, J = 6.6 Hz, 3H). | 509.6 |
| 481 | 4 | $^1$H NMR (400 MHz, CD$_3$OD) δ 8.81 (s, 1H), 6.87 (s, 1H), 4.14 – 4.05 (m, 1H), 3.67 – 3.58 (m, 1H), 3.58 – 3.52 (m, 1H), 3.44 – 3.40 (m, 1H), 3.40 (s, 3H), 3.12 – 3.01 (m, 1H), 2.21 – 2.12 (m, 2H), 2.12 – 1.98 (m, 2H), 1.66 – 1.50 (m, 2H), 1.49 – 1.35 (m, 2H), 1.28 (d, J = 6.6 Hz, 3H). | 330.4 |
| 482 | 5 | $^1$H NMR (400MHz, CD$_3$OD) δ 8.67 (s, 1H), 6.49 (s, 1H), 6.13 – 6.13 (m, 1H), 4.16 - 4.01 (m, 1H), 3.79 - 3.53 (m, 10H), 3.48 - 3.38 (m, 4H), 3.11 - 2.94 (m, 2H), 2.64 – 2.53 (m, 2H), 2.52 - 2.29 (m, 2H), 2.20 - 2.04 (m, 4H), 2.04 – 1.94 (m, 1H), 1.92 - 1.78 (m, 1H), 1.69 - 1.53 (m, 2H), 1.50 - 1.37 (m, 2H), 1.30 (d, J = 6.8 Hz, 3H). | 498.3 |
| 483 | 5 | $^1$H NMR (400MHz, CD$_3$OD) δ 8.66 (s, 1H), 6.48 (br s, 1H), 6.07 (br s, 1H), 4.14 - 4.02 (m, 1H), 3.77 - 3.51 (m, 10H), 3.47 - 3.38 (m, 4H), 3.10 - 2.92 (m, 2H), 2.65 – 2.51 (m, 2H), 2.50 - 2.26 (m, 2H), 2.19 - 2.04 (m, 4H), 2.03 - 1.93 (m, 1H), 1.92 - 1.75 (m, 1H), 1.66 – 1.51 (br s, 2H), 1.50 - 1.36 (m, 2H), 1.29 (d, J = 6.4 Hz, 3H). | 498.3 |
| 484 | 5 | $^1$H NMR (400 MHz, CD$_3$OD) δ 8.59 (s, 1H), 6.45 (s, 1H), 4.12 - 4.00 (m, 1H), 3.80 - 3.54 (m, 10H), 3.48 - 3.39 (m, 4H), 3.16 - 3.00 (m, 2H), 2.97 – 2.89 (m, 1H), 2.20 - 2.00 (m, 6H), 1.99 - 1.89 (m, 2H), 1.88 - 1.79 (m, 2H), 1.77 – 1.67 (m, 2H), 1.65 - 1.54 (m, 2H), 1.51 - 1.37 (m, 2H), 1.29 (d, J = 6.8 Hz, 3H). | 500.2 |
| 485 | 5 | $^1$H NMR (400 MHz, CD$_3$OD) δ 8.84 (s, 1H), 8.11 (d, J = 5.2 Hz, 1H), 6.95 - 6.90 (m, 2H), 6.81 (s, 1H), 4.76 - 4.63 (m, 4H), 4.17 – 4.07 (m, 1H), 3.73 - 3.52 (m, 7H), 3.49 - 3.41 (m, 4H), 3.20 – 3.05 (m, 1H), 2.56 - 2.45 (m, 4H), 2.26 - 2.05 (m, 4H), 1.73 – 1.57 (m, 2H), 1.53 - 1.40 (m, 2H), 1.31 (d, J = 6.8 Hz, 3H). | 522.2 |

FIG. 2 (Cont'd)

| No. | General Scheme | NMR | MS |
|---|---|---|---|
| 486 | 5 | ¹H NMR (400 MHz, CD₃OD) δ 8.70 (s, 1H), 6.50 (s, 1H), 6.20 (d, J = 5.2 Hz, 1H), 4.13 – 4.00 (m, 1H), 3.67 - 3.53 (m, 4H), 3.45 - 3.38 (m, 4H), 3.36 - 3.32 (m, 1H), 3.30 - 3.22 (m, 1H), 3.10 - 3.00 (m, 1H), 2.97 – 2.86 (m, 1H), 2.31 - 2.12 (m, 1H), 2.28 - 2.02 (m, 6H), 2.00 - 1.92 (m, 1H), 1.76 – 1.65 (m, 1H), 1.65 - 1.51 (m, 1H), 1.49 - 1.36 (m, 2H), 1.28 (d, J = 6.8 Hz, 3H). | 494.2 |
| 487 | 5 | ¹H NMR (400 MHz, CD₃OD) δ 8.90 (s, 1H), 8.16 (d, J = 5.2 Hz, 1H), 7.04 (s, 1H), 7.02 (d, J = 5.2 Hz, 1H), 6.88 (s, 1H), 4.17 – 4.07 (m, 1H), 4.06 - 3.50 (m, 10H), 3.50 - 3.44 (m, 1H), 3.43 (s, 3H), 3.18 - 3.08 (m, 1H), 2.27 – 2.16 (m, 2H), 2.16 – 2.07 (m, 2H), 1.74 - 1.59 (m, 2H), 1.54 - 1.40 (m, 2H), 1.32 (d, J = 6.8 Hz, 3H). | 598.2 |
| 488 | 6 | ¹H NMR (400 MHz, CD₃OD) δ 8.82 (s, 1H), 8.13 (s, 1H), 7.88 (s, 1H), 7.37 (br s, 1H), 6.69 (s, 1H), 4.12-4.06 (m, 1H), 3.58-3.38 (m, 12H), 3.13-3.09 (m, 2H), 2.81-2.78 (m, 3H), 2.36-2.33 (m, 1H), 2.17-2.07 (m, 1H), 1.83 (s, 6H), 1.27 (d, J=6.4 Hz, 3H). | 548.2 |
| 489 | 4 | ¹H NMR (400 MHz, CD₃OD) δ 8.99 (s, 1H), 8.93 (s, 1H), 8.28 (dd, J1=8.4 Hz, J2=2.4 Hz, 1H), 8.10 (d, J=8.4 Hz, 1H), 6.05 (tt, J1=56.8 Hz, J2=4.8 Hz, 1H), 4.20-4.15 (m, 1H), 3.68-3.63 (m, 1H), 3.26 (s, 3H), 3.13 (t, J=12 Hz, 1H), 2.38-2.28 (m, 1H), 2.26-2.21 (m, 2H), 2.19-2.12 (m, 2H), 2.09-2.02 (m, 1H), 1.70-1.61 (m, 2H), 1.58-1.43 (m, 2H), 1.36 (d, J=6.8 Hz, 3H). | 480.1 |
| 490 | 5 | ¹H NMR (400MHz, CD₃OD) δ 8.94 (s, 1H), 8.45 (d, J=2.6 Hz, 1H), 8.40 (dd, J=1.2, 4.8 Hz, 1H), 8.09 (d, J=5.4 Hz, 1H), 7.72 - 7.65 (m, 1H), 7.51 (m, J=4.8, 8.4 Hz, 1H), 7.39 (m, J=1.6, 5.4 Hz, 1H), 7.28 (s, 1H), 6.90 (s, 1H), 4.11 (m, J=6.2 Hz, 1H), 3.70 - 3.55 (m, 2H), 3.47 - 3.43 (m, 1H), 3.42 (s, 3H), 3.10 (m, J=3.2, 12.0 Hz, 1H), 2.19 (m, J=10.4 Hz, 2H), 2.10 (m, J=10.8 Hz, 2H), 1.72 - 1.56 (m, 2H), 1.53 - 1.39 (m, 2H), 1.30 (d, J=6.8 Hz, 3H). | 475.1 |
| 491 | 5 | ¹H NMR (400MHz, CD₃OD) δ 8.88 (s, 1H), 8.13 (d, J=5.2 Hz, 1H), 7.01 (s, 1H), 6.97 (br d, J=5.2 Hz, 1H), 6.86 (s, 1H), 4.16 - 4.07 (m, 1H), 3.75 - 3.56 (m, 6H), 3.49 - 3.39 (m, 8H), 3.11 (m, J=11.8 Hz, 1H), 2.57 - 2.47 (m, 1H), 2.19 (m, J=12.0 Hz, 2H), 2.10 (m, J=11.8 Hz, 2H), 1.64 (m, J=6.8 Hz, 2H), 1.53 - 1.38 (m, 2H), 1.31 (d, J=6.8 Hz, 3H), 1.14 - 0.99 (m, 4H). | 570.2 |
| 492 | 5 | ¹H NMR (400MHz, CD₃OD) δ 8.71 (s, 1H), 6.51 (s, 1H), 6.21 (d, J=5.3 Hz, 1H), 4.10 - 4.02 (m, 1H), 3.67 - 3.52 (m, 4H), 3.43 (m, J=6.0 Hz, 1H), 3.41 (m, 3H), 3.35 - 3.33 (m, 1H), 3.30 - 3.23 (m, 1H), 3.11 - 3.00 (m, 1H), 2.93 (m, J=17.6 Hz, 1H), 2.30 - 1.91 (m, 8H), 1.76 - 1.67 (m, 1H), 1.66 - 1.52 (m, 2H), 1.49 - 1.36 (m, 2H), 1.28 (d, J=6.8 Hz, 3H). | 494.2 |

FIG. 2 (Cont'd)

| No. | General Scheme | NMR | MS |
|---|---|---|---|
| 493 | 5 | $^1$H NMR (400MHz, CD$_3$OD) δ 8.87 (s, 1H), 8.00 (m, J=5.5 Hz, 1H), 6.91 - 6.76 (m, 2H), 6.61 (s, 1H), 4.73 (m, J=6.1 Hz, 2H), 4.67 (m, J=6.2 Hz, 2H), 4.09 (m, J=6.2 Hz, 1H), 3.75 (m, 2H), 3.69 - 3.48 (m, 4H), 3.45 - 3.38 (m, 4H), 3.14 - 3.03 (m, 1H), 2.34 (t, J=6.8Hz, 2H), 2.17 (m, J=12.8 Hz, 2H), 2.12 - 2.02 (m, 2H), 1.70 - 1.54 (m, 2H), 1.50 - 1.38 (m, 2H), 1.29 (d, J=6.7 Hz, 3H), 1.28 - 1.24 (m, 2H). | 493.2 |
| 494 | 5 | $^1$H NMR (400MHz, CD$_3$OD) δ 8.70 (s, 1H), 6.50 (s, 1H), 6.20 (m, J=5.0 Hz, 1H), 4.05 (m, J=6.2 Hz, 1H), 3.66 - 3.49 (m, 4H), 3.43 - 3.39 (m, 1H), 3.38 - 3.37 (m, 3H), 3.09 - 3.01 (m, 1H), 3.00 - 2.92 (m, 1H), 2.49 (s, 3H), 2.37 - 1.98 (m, 9H), 1.83 - 1.72 (m, 1H), 1.65 - 1.49 (m, 2H), 1.47 - 1.33 (m, 2H), 1.26 (d, J=6.8 Hz, 3H). | 426.2 |
| 495 | 5 | $^1$H NMR (400 MHz, MeOD) δ 8.78 (s, 1H), 8.23 (s, 0.65H), 8.20 (s, 0.35H), 7.90 (s, 1H), 6.66 (s, 1H), 4.75 (brs, 1.3H), 4.64-4.58 (m, 0.7H), 4.06 (dd, J = 12.1, 6.0 Hz, 1H), 3.86 (s, 0.7H), 3.68-3.65 (m, 1.3H), 3.65-3.57 (m, 1H), 3.55 (dd, J = 9.4, 5.2 Hz, 1H), 3.43-3.39 (m, 1H), 3.38 (s, 3H), 3.06 (ddd, J = 12.2, 8.7, 2.6 Hz, 1H), 2.62 (s, 1H), 2.59 (s, 2H), 2.19-2.01 (m, 4H), 1.87 (s, 3.9H), 1.86 (s, 2.1H), 1.68-1.51 (m, 2H), 1.47-1.35 (m, 2H), 1.26 (d, J = 6.6 Hz, 3H). | 579.1 |
| 496 | 5 | $^1$H NMR (400 MHz, MeOD) δ 8.63 (s, 1H), 8.05 (s, 1H), 7.79 (s, 1H), 6.57 (s, 1H), 4.10-3.98 (m, 1H), 3.67-3.56 (m, 1H), 3.56-3.50 (m, 1H), 3.43-3.39 (m, 1H), 3.38 (s, 3H), 3.12-2.98 (m, 1H), 2.48 (brs, 6H), 2.18- 2.01 (m, 4H), 1.83 (s, 6H), 1.68-1.51 (m, 2H), 1.48-1.34 (m, 2H), 1.26 (d, J = 6.6 Hz, 3H). | 593.2 |
| 497 | 4 | $^1$H NMR (400 MHz, CD$_3$OD) δ 8.69 (s, 1H), 6.50 (s, 1H), 4.13 – 4.03 (m, 1H), 4.02 (s, 2H), 3.68 – 3.59 (m, 1H), 3.57 (dd, J = 9.4, 5.2 Hz, 1H), 3.44 – 3.41 (m, 1H), 3.40 (s, J = 2.1 Hz, 3H), 3.12 – 3.02 (m, 1H), 2.18 – 2.04 (m, 4H), 1.66 – 1.52 (m, 2H), 1.49 – 1.37 (m, 2H), 1.28 (d, J = 6.6 Hz, 3H). | 344.1 |
| 498 | 5 (analogous to Example 39) | $^1$H NMR (400 MHz, CD$_3$OD) δ 8.87 (s, 1H), 8.11 (d, J = 5.3 Hz, 1H), 6.99 (s, 1H), 6.91 (dd, J = 5.4, 1.3 Hz, 1H), 6.85 (s, 1H), 4.51 (s, 2H), 4.16 – 4.05 (m, 1H), 3.98 (t, J = 5.6 Hz, 2H), 3.71 – 3.62 (m, 1H), 3.59 (dd, J = 9.4, 5.2 Hz, 1H), 3.47 – 3.42 (m, 1H), 3.42 (s, 3H), 3.17 – 3.07 (m, 1H), 2.74 (t, J = 5.4 Hz, 2H), 2.35 (s, 3H), 2.24 – 2.14 (m, 2H), 2.15 – 2.05 (m, 2H), 1.73 – 1.59 (m, 2H), 1.52 – 1.38 (m, 2H), 1.30 (d, J = 6.6 Hz, 3H). | 517.7 |
| 499 | 5 | $^1$H NMR (400 MHz, CD$_3$OD) δ 8.64 (s, 1H), 6.43 (s, 1H), 6.23 (d, J=5.6 Hz, 1H), 4.16-4.13 (m, 1H), 3.91-3.88 (m, 2H), 3.56-3.51 (m, 1H), 3.08-2.86 (m, 2H), 2.75-2.63 (m, 1H), 2.43-2.32 (m, 1H), 2.28-2.14 (m, 1H), 2.12-1.86 (m, 7H), 1.81-1.70 (m, 1H), 1.56-1.34 (m,4H), 1.30 (d, J=6.4 Hz, 3H). | 450.2 |
| 500 | 5 | $^1$H NMR (400 MHz, CD$_3$OD) δ 8.90 (s,1H), 8.14 (d, J=5.2 Hz, 1H), 6.99 (d, J=7.2 Hz, 1H), 6.87 (s, 1H), 4.32-4.26 (m, 1H), 4.14-4.11 (m, 1H), 3.84-3.73 (m, 2H), 3.71-3.54 (m, 7H), 3.50-3.40 (m, 7H), 3.16-3.08 (m, 1H), 2.28-2.05 (m, 5H), 1.74-1.56 (m, 2H), 1.52-1.40 (m, 2H), 1.32 (d, J=6.8 Hz, 3H). | 550.4 |

FIG. 2 (Cont'd)

| No. | General Scheme | NMR | MS |
|---|---|---|---|
| 501 | 6 | ¹H NMR (400MHz, CD₃OD) δ 8.86 (s, 1H), 8.78 (d, J=2.4 Hz, 1H), 8.25 (dd, J=2.4, 9.6 Hz, 1H), 8.19 (s, 1H), 7.98 (s, 1H), 7.14 (s, 1H), 6.67 (d, J=9.6 Hz, 1H), 5.67 - 5.60 (m, 1H), 5.15 - 5.07 (m, 4H), 4.20 - 4.08 (m, 1H), 3.63 - 3.56 (m, 1H), 3.53 - 3.46 (m, 1H), 3.42 (s, 3H), 1.33 (d, J=6.4 Hz, 3H) | 422.1 |
| 502 | 6 | ¹H NMR (400MHz, CD₃OD) δ 8.80 (s, 1H), 8.18 (s, 1H), 8.15 (s, 1H), 7.96 (s, 1H), 7.09 (s, 1H), 7.01 (d, J=8.8 Hz, 2H), 5.64-5.57 (m, 1H), 5.12-5.06 (m, 4H), 4.15-4.08 (m, 1H), 3.85 (s, 3H), 3.61-3.57 (m, 1H), 3.46-3.42 (m, 1H), 3.40 (s, 3H), 1.31 (d, J=6.8 Hz, 3H). | 435.1 |
| 503 | 6 | ¹H NMR (400MHz, CD₃OD) δ 8.75 (s, 1H), 8.10 (s, 1H), 7.90 (s, 1H), 6.64 (s, 1H), 5.62-5.56 (m, 1H), 5.10-5.03 (m, 4H), 4.10-4.03 (m, 3H), 3.60-3.53 (m, 3H), 3.44-3.39 (m, 5H), 2.03-2.00 (m, 2H), 1.92-1.75 (m, 2H), 1.27 (d, J=6.8 Hz, 3H). | 413.3 |
| 504 | 5 | ¹H NMR (400MHz, CD₃OD) δ = 8.88 (s, 1H), 8.12 (br d, J=4.8 Hz, 1H), 7.03 - 6.94 (m, 2H), 6.85 (s, 1H), 5.41 (m, J=5.2 Hz, 1H), 4.66 (m, J=6.2 Hz, 2H), 4.10 (m, J=5.8 Hz, 1H), 3.83-3.50 (m, J=34.4Hz, 11H), 3.49 - 3.37 (m, J=13.2Hz, 5H), 3.12 (m, J=7.2 Hz, 1H), 2.19 (m, J=13.4 Hz, 2H), 2.10 (m, J=11.8 Hz, 2H), 1.66 (m, 2H), 1.45 (m, J=11.6 Hz, 2H), 1.30 (br d, J=6.8 Hz, 3H). | 566.3 |
| 505 | 4 | ¹H NMR (400MHz, CD₃OD) δ 8.95 (s, 1H), 8.14 (d, J=5.4 Hz, 1H), 7.52 ( d, J=5.4 Hz, 1H), 7.26 (s, 1H), 6.91 (s, 1H), 4.10 (m, J=6.2, 12.2 Hz, 1H), 3.70 - 3.54 (m, 2H), 3.44 (m, J=6.0 Hz, 1H), 3.41 (m, 3H), 3.08 (m, J=3.2, 12.0 Hz, 1H), 2.17 (m, J=12.8 Hz, 2H), 2.09 (m, J=10.8 Hz, 2H), 1.70 - 1.55 (m, 2H), 1.49 - 1.37 (m, 2H), 1.29 (d, J=6.8 Hz, 3H). | 400.1 |
| 506 | 3 | ¹H NMR (500 MHz, MeOD) δ 8.74 (s, 1H), 8.08 (d, J = 0.6 Hz, 1H), 7.87 (s, 1H), 7.42–7.40 (m, 2H), 7.32–7.28 (m, 2H), 7.19–7.16 (m, 1H), 6.54 (s, 1H), 5.61–5.55 (m, 1H), 5.09–5.04 (m, 4H), 3.61–3.55 (m, 1H), 2.87–2.82 (ddd, J = 11.9, 7.7, 3.3 Hz, 1H), 2.08–2.02 (m, 2H), 1.94–1.92 (m, 1H), 1.72–1.69 (m, 1H), 1.61–1.53 (m, 4H), 1.47–1.22 (m, 4H). | 459.1 |
| 507 | 6 | ¹H NMR (500 MHz, MeOD) δ 8.72 (s, 1H), 7.98 (s, 1H), 7.75 (d, J = 0.7 Hz, 1H), 6.61 (s, 1H), 4.18 (s, 2H), 4.10-4.07 (m, 1H), 3.71–3.60 (m, 5H), 3.58 (dd, J = 9.4, 5.2 Hz, 1H), 3.45–3.41 (m, 5H), 3.11–3.07 (m, 1H), 2.71 – 2.69 (m, 4H), 2.18–2.16 (d, J = 11.8 Hz, 2H), 2.11–2.08 (d, J = 12.7 Hz, 2H), 1.66–1.60 (m, 2H), 1.48–1.41 (s, 2H), 1.30–1.29 (d, J = 6.6 Hz, 4H), 1.07 (s, 6H). | 512.2 |
| 508 | 4 | ¹H NMR (400 MHz, CD₃OD) δ 8.81 (s, 1H), 8.61 (s, 1H), 6.61 (s, 1H), 4.62 – 4.51 (m, 1H), 4.17 – 4.01 (m, 1H), 3.73 – 3.61 (m, 1H), 3.58 (dd, J = 9.4, 5.2 Hz, 1H), 3.44 (dd, J = 5.8, 3.7 Hz, 1H), 3.41 (s, 3H), 3.12 (ddt, J = 15.7, 12.2, 3.5 Hz, 1H), 2.39 (s, 3H), 2.22 – 2.14 (m, 2H), 2.13 – 2.04 (m, 2H), 1.73 – 1.57 (m, 2H), 1.53 – 1.39 (m, 2H), 1.34 – 1.24 (m, 3H). | 386.2 |

FIG. 2 (Cont'd)

| No. | General Scheme | NMR | MS |
|---|---|---|---|
| 509 | 5 (analogous to Example 39) | $^1$H NMR (400 MHz, CD$_3$OD) δ 8.88 (s, 1H), 8.13 (d, J = 5.3 Hz, 1H), 7.06 (s, 1H), 6.95 (d, J = 5.3 Hz, 1H), 6.87 (s, 1H), 4.79 (s, 2H), 4.16 – 4.06 (m, 1H), 4.02 (t, J = 5.7 Hz, 2H), 3.71 – 3.62 (m, 1H), 3.59 (dd, J = 9.4, 5.3 Hz, 1H), 3.47 – 3.43 (m, 1H), 3.42 (s, 3H), 3.19 – 3.04 (m, 1H), 2.91 (t, J = 5.6 Hz, 2H), 2.66 (s, 3H), 2.26 – 2.15 (m, 2H), 2.15 – 2.05 (m, 2H), 1.66 (d, J = 12.5 Hz, 2H), 1.46 (q, J = 11.0 Hz, 2H), 1.30 (d, J = 6.6 Hz, 3H). | 534.7 |
| 510 | 4 | $^1$H NMR (500 MHz, MeOD) δ 8.83 (s, 1H), 8.14 (s, 1H), 7.93 (s, 1H), 6.70 (s, 1H), 5.65-5.58 (m, 1H), 5.14-5.05 (m, 4H), 4.84-4.73 (m, 1H), 3.70-3.61 (m, 1H), 3.10 (tt, J = 12.1, 3.5 Hz, 1H), 2.23-2.06 (m, 4H), 1.72-1.63 (m, 1H), 1.63-1.53 (m, 1H), 1.52-1.46 (m, 2H), 1.44 (d, J = 7.0 Hz, 3H). | 451.1 |
| 511 | 6 | $^1$H NMR (400MHz, CD$_3$OD) δ 9.00 (s, 1H), 8.23 (s, 1H), 8.02 (s, 1H), 7.78 (s, 1H), 7.48 (d, J=7.2 Hz, 1H), 7.36 (s, 1H), 7.20 (d, J=7.2 Hz, 1H), 5.74 – 5.56 (m, 1H), 5.16 – 5.06 (m, 4H), 4.29 – 4.18 (m, 1H), 3.64 – 3.48 (m, 2H), 3.42 (s, 3H), 1.34 (d, J=6.4 Hz, 3H). | 422.1 |
| 512 | 4 | $^1$H NMR (400MHz, CD$_3$OD) δ 8.87 (s, 1H), 8.11 (d, J=5.2 Hz, 1H), 7.01 - 6.92 (m, 2H), 6.85 (s, 1H), 4.83 – 4.77 (m, 2H), 4.48 (t, J=6.0 Hz, 2H), 4.17 - 4.05 (m, 1H), 3.73 - 3.63 (m, 1H), 3.63 - 3.53 (m, 5H), 3.48 - 3.44 (m, 1H), 3.43 (s, 3H), 3.41 - 3.34 (m, 1H), 3.18 - 3.07 (m, 1H), 2.81 (d, J=7.2 Hz, 2H), 2.61 - 2.54 (m, 4H), 2.25 - 2.16 (m, 2H), 2.15- 2.06 (m, 2H), 1.74 - 1.57 (m, 2H), 1.54 - 1.41 (m, 2H), 1.31 (d, J=6.8 Hz, 3H). | 536.3 |
| 513 | 4 | $^1$H NMR (400MHz, CD$_3$OD) δ 9.00 (d, J=1.6 Hz, 1H), 8.95 (s, 1H), 8.30 (dd, J=2.4, 8.4 Hz, 1H), 8.12 (d, J=8.4 Hz, 1H), 6.95 (s, 1H), 6.67 - 6.20 (t, J=75.2 Hz, 1H), 4.25 - 4.07 (m, 2H), 3.89 - 3.85 (m, 1H), 3.73 - 3.61 (m, 1H), 3.27 (s, 3H), 3.21 - 3.08 (m, 1H), 2.26 - 2.17 (m, 2H), 2.14 2.05 (m, 2H), 1.76 - 1.58 (m, 2H), 1.55 - 1.42 (m, 2H), 1.37 (d, J=6.8 Hz, 3H). | 496.1 |
| 514 | 5 | $^1$H NMR (400MHz, CD$_3$OD) δ 8.87 (s, 1H), 8.11 (d, J=5.2 Hz, 1H), 6.99 - 6.92 (m, 2H), 6.84 (s, 1H), 4.17 - 4.05 (m, 1H), 3.98 - 3.90 (m, 1H), 3.70 - 3.55(m, J=18.4 Hz, 6H), 3.48 - 3.44 (m, 1H), 3.43 - 3.40 (m, 3H), 3.39-3.34 (m, 4H), 3.22-3.14 (m, 2H), 3.14-3.05 (m, 1H), 2.18 (d, J=12.4 Hz, 2H), 2.09 (m, J=11.6 Hz, 2H), 1.71 - 1.57 (m, 2H), 1.52 - 1.39 (m, 2H), 1.29 (d, J=6.6 Hz, 3H), 1.24-1.17 (d, J=6.8 Hz, 6H), 1.13-1.07 (t, J=6.8 Hz, 3H). | 579.3 |
| 515 | 6 | $^1$H NMR (400MHz, CD$_3$OD) δ 8.76 (s, 1H), 8.11 (s, 1H), 7.90 (s, 1H), 6.65 (s, 1H), 5.58 (m, J=6.8 Hz, 1H), 5.12 - 5.02 (m, 4H), 4.13 - 4.04 (m, 1H), 3.54 (m, J=5.2, 9.4 Hz, 1H), 3.45 - 3.40 (m, 1H), 3.39 - 3.38 (m, 3H), 3.26 - 3.15 (m, 1H), 2.18 (m, J=9.2 Hz, 4H), 2.04 - 1.82 (m, 4H), 1.27 (d, J=6.8 Hz, 3H). | 447.1 |
| 516 | 5 | $^1$H NMR (500 MHz, MeOD) δ 8.78 (s, 1H), 8.14 (s, 1H), 7.87 (s, 1H), 6.66 (s, 1H), 4.51-4.43 (m, 2H), 4.35 (brs, 2H), 4.12-4.03 (m, 1H), 3.74 (brs, 2H), 3.64 (tt, J = 11.1, 4.4 Hz, 1H), 3.58 (dd, J = 9.4, 5.2 Hz, 1H), 3.47-3.42 (m, 1H), 3.41 (s, 3H), 3.37 (brs, 2H), 3.21-2.97 (m, 3H), 2.21-2.03 (m, 4H), 1.84 (s, 6H), 1.68-1.56 (m, 2H), 1.51-1.39 (m, 2H), 1.29 (d, J = 6.6 Hz, 3H). | 568.3 |

FIG. 2 (Cont'd)

| No. | General Scheme | NMR | MS |
|---|---|---|---|
| 517 | 6 | $^1$H NMR (500 MHz, MeOD) δ 8.78 (s, 1H), 8.20 (s, 1H), 7.82 (s, 1H), 6.66 (s, 1H), 6.43 (t, J = 75.5 Hz, 1H), 4.19-4.07 (m, 2H), 3.84 (dd, J = 9.4, 6.1 Hz, 1H), 3.64 (tt, J = 10.8, 4.2 Hz, 1H), 3.10 (tt, J = 12.0, 3.5 Hz, 1H), 2.51 (s, 3H), 2.21-2.04 (m, 10H), 1.69-1.55 (m, 2H), 1.51-1.41 (m, 2H), 1.35 (d, J = 6.6 Hz, 3H). | 531.2 |
| 518 | 5 (analogous to Example 39) | $^1$H NMR (500 MHz, MeOD) δ 8.88 (s, 1H), 8.12 (d, J = 5.3 Hz, 1H), 7.27 (s, 1H), 7.07 (s, 1H), 6.94 (dd, J = 5.3, 1.1 Hz, 1H), 6.88 (s, 1H), 4.71 (s, 2H), 4.14 – 4.06 (m, 1H), 3.88 (t, J = 5.6 Hz, 2H), 3.82 (s, 3H), 3.70 – 3.62 (m, 1H), 3.59 (dd, J = 9.4, 5.3 Hz, 1H), 3.46 – 3.43 (m, 1H), 3.42 (s, 3H), 3.16 – 3.07 (m, 1H), 2.71 (t, J = 5.6 Hz, 2H), 2.24 – 2.16 (m, 2H), 2.16 – 2.05 (m, 2H), 1.74 – 1.60 (m, 2H), 1.51 – 1.38 (m, 2H), 1.30 (d, J = 6.6 Hz, 3H) | 517.7 |
| 519 | 3 | $^1$H NMR (500 MHz, MeOD) δ 8.73 (s, 1H), 8.07 (s, 1H), 7.87 (s, 1H), 7.45–7.40 (m, 3H), 7.31–7.28 (m , 2H), 7.19–7.16 (m, 1H), 6.54 (s, 1H), 5.61–5.55 (m, 1H), 5.08 – 5.04 (m, 4H), 3.61–3.55 (m, 1H), 2.87–2.82 (ddd, J = 11.8, 7.9, 3.2 Hz, 1H), 2.07–2.02 (m, 2H), 1.93–1.91 (m, 1H), 1.71–168 (m, 1H), 1.62–1.52 (m, 4H), 1.46–1.21 (m, 4H). | 459.1 |
| 520 | 6 | $^1$H NMR (400MHz, CD$_3$OD) δ 8.75 (s, 1H), 8.12 (s, 1H), 7.89 (s, 1H), 7.92 (s, 1H), 6.66 (s, 1H), 5.67 - 5.54 (m, 1H), 5.16 - 5.04 (m, 4H), 4.54 - 4.44 (m, 1H), 4.16 - 4.07 (m, 1H), 3.90 - 3.77 (m, 1H), 3.60 - 3.55 (m, 1H), 3.49 -3.44 (m, 1H), 3.42 (s, 3H), 2.43 - 2.27 (m, 1H), 2.22 - 2.10 (m, 2H), 2.10 - 1.98 (m, 1H), 1.91 - 1.68 (m, 2H), 1.30 (d, J=6.8 Hz, 3H). | 413.2 |
| 521 | 6 | $^1$H NMR (400MHz, CD$_3$OD) δ 8.79 - 8.71 (m, 1H), 8.12 (s, 1H), 7.91 (s, 1H), 6.73 (s, 1H), 5.65-5.55 (m, 1H), 5.15 - 5.05 (m, 4H), 4.47 - 4.36 (m, 1H), 4.19 - 4.06 (m, 1H), 3.63 - 3.51 (m, 2H), 3.47 3.43 (m, 1H), 3.41 (s, 3H), 2.62 - 2.47 (m, 1H), 2.25 - 2.12 (m, 1H), 2.06 - 1.90 (m, 2H), 1.88 - 1.70 (m, 2H), 1.29 (d, J=6.8 Hz, 3H). | 413.2 |
| 522 | 6 | $^1$H NMR (400MHz, CD$_3$OD) δ 8.79 (s, 1H), 8.14 (s, 1H), 7.94 (s, 1H), 6.68 (s, 1H), 5.67 - 5.55 (m, 1H), 5.17 - 5.05 (m, 4H), 4.18 - 4.03 (m, 1H), 3.62 - 3.55 (m, 1H), 3.48 - 3.44 (m, 1H), 3.43 (s, 3H), 3.29 - 3.19 (m, 1H), 2.97 - 2.85 (m, 2H), 2.75 - 2.65 (m, 2H), 2.45 - 2.35 (m, 2H), 2.04 - 1.84 (m, 2H), 1.30 (d, J=6.8 Hz, 3H). | 429.3 |
| 523 | 6 | $^1$H NMR (400MHz, CD$_3$OD) δ 8.76 (s, 1H), 8.12 (s, 1H), 7.92 (s, 1H), 6.66 (s, 1H), 5.63-5.56 (m, 1H), 5.11-5.05 (m, 4H), 4.63-4.56 (m, 1H), 4.13-4.05 (m, 1H), 3.58-3.52 (m, 1H), 3.45-3.43 (m, 1H), 3.40 (s, 3H), 3.24-3.17 (m, 1H), 2.15-2.05 (m, 2H), 1.97-1.65 (m, 6H), 1.28 (d, J=6.8 Hz, 3H). | 429.2 |
| 524 | 6 | $^1$H NMR (400MHz, CD$_3$OD) δ 9.00 (s, 1H), 8.32 (s, 1H), 8.03 (s, 1H), 7.19 (s, 1H), 4.64-4.57 (m, 1H), 4.19-4.14 (m, 1H), 4.07-4.02 (m, 2H), 4.00-3.98 (m, 2H), 3.53 (d, J=4.8 Hz, 2H), 3.42 (s, 3H), 3.40- 3.31 (m, 1H), 2.92 (s, 6H), 2.36-2.28 (m, 4H), 1.85-1.77 (m, 4H), 1.33 (d, J=6.4 Hz, 3H). | 490.3 |

FIG. 2 (Cont'd)

| No. | General Scheme | NMR | MS |
|---|---|---|---|
| 525 | 6 | ¹H NMR (400MHz, CD₃OD) δ 9.05 (s, 1H), 8.42 (s, 1H), 8.11 (s, 1H), 7.46 (s, 1H), 4.65-4.60 (m, 1H), 4.17-4.15 (m, 1H), 4.05-4.03 (m, 2H), 4.00-3.98 (m, 2H), 3.58-3.54, (m, 1H), 3.53 (d, J=4.8 Hz, 2H), 3.41 (s, 3H), 3.40- 3.31 (m, 1H), 2.91 (s, 6H), 2.45-2.40 (m, 2H), 2.07-1.97 (m, 6H), 1.33 (d, J=6.4 Hz, 3H). | 490.3 |
| 526 | 6 | ¹H NMR (400MHz, CD₃OD) δ 8.83 (s, 1H), 8.14 (s, 1H), 7.93 (s, 1H), 6.79 - 6.69 (m, 1H), 5.65 - 5.55 (m, 1H), 5.15 - 5.05 (m, 4H), 4.19- 4.02 (m, 1H), 3.81 - 3.73 (m, 1H), 3.70 - 3.62 (m, 1H), 3.61 - 3.54 (m, 1H), 3.53 - 3.44 (m, 2H), 3.43 - 3.40 (m, 3H), 2.68 - 2.41 (m, 2H), 2.32 - 2.19 (m, 2H), 1.34 - 1.27 (d, J=6.8 Hz ,3H) | 426.1 |
| 527 | 4 | ¹H NMR (500 MHz, MeOD) δ 8.82 (s, 1H), 8.13 (s, 1H), 7.92 (s, 1H), 6.69 (s, 1H), 5.64-5.57 (m, 1H), 5.11-5.06 (m, 4H), 4.78 (dt, J = 14.7, 7.1 Hz, 1H), 3.65 (tt, J = 10.6, 4.2 Hz, 1H), 3.10 (tt, J = 12.0, 3.5 Hz, 1H), 2.22-2.05 (m, 4H), 1.71-1.53 (m, 2H), 1.51-1.45 (m, 2H), 1.43 (d, J = 7.0 Hz, 3H). | 451.2 |
| 528 | 3 | ¹H NMR (500 MHz, MeOD) δ 8.76 (s, 1H), 8.11–8.11 (d, J = 0.7 Hz, 1H), 7.90–7.90 (d, J = 0.5 Hz, 1H), 7.28–7.24 (m, 2H), 6.96–6.90 (m, 3H), 6.63 (s, 1H), 5.62–5.57 (m, 1H), 5.10–5.05 (m, 4H), 4.32–4.28 (m, 1H), 4.23–4.20 (dd, J = 9.2, 4.8 Hz, 1H), 4.00–3.97 (dd, J = 9.2, 6.2 Hz, 1H), 3.63–3.57 (m, 1H), 3.07–3.02 (ddd, J = 12.1, 8.6, 3.5 Hz, 1H), 2.16–2.10 (m, 2H), 2.05–1.98 (m, 2H), 1.66–1.55 (m, 2H), 1.45–1.37 (m, 5H). | 489.2 |
| 529 | 3 | ¹H NMR (500 MHz, MeOD) δ 8.77 (s, 1H), 8.46–8.45 (d, J = 5.8 Hz, 2H), 8.08–8.08 (d, J = 0.7 Hz, 1H), 7.87 (s, 1H), 7.50–7.48 (d, J = 6.1 Hz, 2H), 6.55 (s, 1H), 5.61–5.55 (m, 1H), 5.08–5.04 (m, 4H), 3.57–3.52 (m, 1H), 2.76–2.71 (m, 1H), 2.06–1.98 (m, 2H), 1.91–1.87 (m, 1H), 1.57–1.49 (m, 5H), 1.42–1.17 (m, 4H). | 460.2 |
| 530 | 1 | ¹H NMR (400MHz, CD₃OD) δ 8.76 (s, 1H), 8.12 (s, 1H), 7.91 (s, 1H), 6.64 (s, 1H), 5.64 -5.57 (m, 1H), 5.15 - 5.05 (m, 4H), 4.14- 4.06 (m, 1H), 3.63 -3.58 (m, 1H), 3.49 - 3.40 (m, 4H), 3.12 -3.04 (m, 1H), 2.50 - 2.40 (m, 1H), 2.37 (s, 6H), 2.30 - 2.20 (m, 2H), 2.14 - 2.04 (m, 2H), 1.69 - 1.55 (m, 2H), 1.53 - 1.38 (m, 2H), 1.30 (d, J=6.8 Hz, 3H). | 454.2 |
| 531 | 1 | ¹H NMR (400MHz, CD₃OD) δ 8.76 (s, 1H), 8.14 (s, 1H), 7.93 (s, 1H), 6.81 (s, 1H), 5.66 - 5.56 (m, 1H), 5.13 - 5.06 (m, 4H), 4.13 - 4.06 (m, 1H), 3.59 -3.55 (m, 1H), 3.47 - 3.38 (m, 5H), 2.36 - 2.16 (m, 9H), 1.99 - 1.72 (m, 6H), 1.29 (d, J=6.8 Hz, 3H). | 454.2 |
| 532 | 1 | ¹H NMR (400MHz, CD₃OD) δ 8.94 (d, J=2.0 Hz, 1H), 8.89 (s, 1H), 8.24 (dd, J1=8.4 Hz, J2=2.4 Hz, 1H), 8.14 (d, J=8.4 Hz, 1H), 6.88 (s, 1H), 4.14-4.08 (m, 1H), 3.65-3.57 (m, 2H), 3.46-3.43 (m, 1H), 3.42 (s, 3H), 3.28 (s, 3H), 3.10-3.06 (m, 1H), 2.20-2.17 (m, 2H), 2.11-2.08 (m, 2H), 1.68-1.60 (m, 2H), 1.46-1.43 (m, 2H), 1.30 (d, J=6.8 Hz, 3H) | 459.2 |

FIG. 2 (Cont'd)

| No. | General Scheme | NMR | MS |
|---|---|---|---|
| 533 | 5 | ¹H NMR (400MHz, CD₃OD) δ 8.93 (s, , 1H), 8.88 (s, 1H), 8.29 (d,8.4 Hz, 1H), 8.17 (d, J=8.4 Hz, 1H), 6.88 (s, 1H), 4.14 - 4.06 (m, 1H), 3.64 - 3.57 (m, 2H), 3.46 - 3.45 (m, 1H), 3.44 (s, 3H), 3.43 (s, 3H), 3.14 (m, , 1H), 2.19 - 2.08 (m, 4H), 1.69 -1.60 (m, 2H), 1.43 - 1.31 (m, 2H), 1.30 (d, J=6.8 Hz, 3H). | 459.3 |
| 534 | 4 | ¹H NMR (500 MHz, MeOD) δ 8.87 (s, 1H), 8.16 – 8.06 (m, 1H), 6.99 – 6.91 (m, 2H), 6.84 (s, 1H), 4.26 (d, J = 12.5 Hz, 1H), 4.14 – 4.01 (m, 3H), 3.74 – 3.67 (m, 1H), 3.67 – 3.60 (m, 1H), 3.58 (dd, J = 9.4, 5.2 Hz, 1H), 3.43 (dd, J = 9.4, 6.0 Hz, 1H), 3.41 (s, 3H), 3.36 (dd, J = 10.8, 2.4 Hz, 1H), 3.15 – 3.05 (m, 1H), 2.97 – 2.89 (m, 1H), 2.78 (dd, J = 12.4, 10.9 Hz, 1H), 2.23 – 2.15 (m, 2H), 2.13 – 2.07 (m, 2H), 1.70 – 1.59 (m, 2H), 1.50 – 1.40 (m, 2H), 1.30 (d, J = 6.6 Hz, 3H), 1.28 (s, 3H), 1.26 (s, 3H). | 525.2 |
| 535 | 3 | ¹H NMR (500 MHz, MeOD): δ 8.74 (s, 1H), 8.11–8.11 (d, J = 0.7 Hz, 1H), 7.90 (s, 1H), 7.31–7.28 (m, 2H), 7.04–7.01 (m, 2H), 6.63 (s, 1H), 5.62–5.57 (m, 1H), 5.10–5.05 (m, 4H), 4.10–4.06 (dd, J = 13.2, 6.6 Hz, 1H), 3.69–3.64 (m, 1H), 3.17–3.11 (m, 2H), 2.68–2.64 (m, 1H), 2.23–2.18 (m, 1H), 2.14–2.09 (m, 1H), 1.65–1.60 (m, 2H), 1.53–1.48 (m, 2H), 1.22–1.21 (d, J = 6.6 Hz, 3H). | 491.2 |
| 536 | 3 | ¹H NMR (500 MHz, MeOD): δ 8.76 (s, 1H), 8.61–8.61 (d, J = 1.6 Hz, 1H), 8.38–8.38 (d, J = 3.4 Hz, 1H), 8.08–8.08 (d, J = 0.7 Hz, 1H), 7.91–7.89 (dt, J = 8.0, 1.8 Hz, 1H), 7.87–7.87 (d, J = 0.4 Hz, 1H), 7.41–7.38 (dd, J = 7.5, 4.8 Hz, 1H), 6.56 (s, 1H), 5.61– 5.55 (m, 1H), 5.08–5.04 (m, 4H), 4.93–4.89 (m, 1H), 3.58–3.53 (m, 1H), 2.82–2.77 (m, 1H), 2.06–2.03 (m, 2H), 1.95–1.92 (m, 1H), 1.64 –1.57 (m, 4H), 1.55–1.49 (m, 1H), 1.46–1.41 (m, 1H), 1.34–1.24 (m, 2H). | 460.2 |
| 537 | 4 | ¹H NMR (400 MHz, CD₃OD) δ 8.81 (s, 1H), 8.11 (s, 1H), 7.86 (s, 1H), 6.68 (s, 1H), 4.73 (dd, J = 14.5, 7.3 Hz, 2H), 4.53 (s, 1H), 3.66 – 3.43 (m, 6H), 3.17 – 2.96 (m, 4H), 2.63 (s, 1H), 2.26 – 1.94 (m, 6H), 1.80 (s, 6H), 1.76 – 1.37 (m, 11H). | 550.1 |
| 538 | 4 | ¹H NMR (400 MHz, CD₃OD) δ 8.71 (s, 1H), 7.63 – 7.50 (m, 2H), 7.25 – 7.18 (m, 2H), 6.65 (s, 1H), 6.42 (dd, J = 3.1, 0.8 Hz, 1H), 4.07 (dd, J = 12.0, 6.0 Hz, 1H), 3.71 – 3.51 (m, 2H), 3.45 – 3.35 (m, 4H), 3.16 – 3.01 (m, 1H), 2.13 (dd, J = 40.7, 11.0 Hz, 4H), 1.71 – 1.56 (m, 2H), 1.43 (dd, J = 23.3, 10.3 Hz, 2H), 1.27 (d, J = 6.6 Hz, 3H). | 421.1 |
| 539 | 4 | ¹H NMR (400 MHz, CD₃OD) δ 8.68 (s, 1H), 7.70 (d, J = 1.0 Hz, 1H), 7.42 (d, J = 8.4 Hz, 1H), 7.30 (dd, J = 8.4, 1.6 Hz, 1H), 7.22 (d, J = 3.1 Hz, 1H), 6.63 (s, 1H), 6.49 – 6.43 (m, 1H), 4.07 (dd, J = 11.9, 6.0 Hz, 1H), 3.70 – 3.52 (m, 2H), 3.47 – 3.35 (m, 4H), 3.09 (ddd, J = 12.0, 8.6, 3.5 Hz, 1H), 2.13 (dd, J = 39.7, 11.1 Hz, 4H), 1.74 – 1.57 (m, 2H), 1.43 (d, J = 13.1 Hz, 2H), 1.27 (d, J = 6.6 Hz, 3H). | 421.1 |

FIG. 2 (Cont'd)

| No. | General Scheme | NMR | MS |
|---|---|---|---|
| 540 | 5 | ¹H NMR (400MHz, CD₃OD) δ 8.99 (s, 1H), 8.95 (s, 1H), 8.29 (dd, J=2.4, 8.3 Hz, 1H), 8.17 (d, J=8.4 Hz, 1H), 6.94 (s, 1H), 4.28 (m, J=6.4 Hz, 1H), 3.72 - 3.61 (m, 1H), 3.29 (s, 3H), 3.21 - 3.10 (m, 1H), 2.89 - 2.72 (m, 1H), 2.42 - 2.28 (m, 1H), 2.22 (d, J=13.2 Hz, 2H), 2.12 (m, J=9.8 Hz, 2H), 1.75 - 1.56 (m, 2H), 1.55 - 1.45 (m, 2H), 1.43 (d, J=6.8 Hz, 3H). | 497.1 |
| 541 | 5 | ¹H NMR (400MHz, CD₃OD) δ 8.99 (d, J=1.6 Hz, 1H), 8.95 (s, 1H), 8.29 (dd, J=2.4, 8.3 Hz, 1H), 8.17 (d, J=8.4 Hz, 1H), 6.94 (s, 1H), 4.33 - 4.22 (m, 1H), 3.73 - 3.61 (m, 1H), 3.29 (s, 3H), 3.14 (m, J=3.2, , 1H), 2.88 - 2.72 (m, 1H), 2.34 (m, 1H), 2.22 (br d, J=13.1 Hz, 2H), 2.16 - 2.06 (m, 2H), 1.74 - 1.56 (m, 2H), 1.54 - 1.45 (m, 2H), 1.43 (d, J=6.8 Hz, 3H). | 497.1 |
| 542 | 6 | ¹H NMR (400 MHz, CD₃OD), δ 8.81 (s, 1H), 8.14 (s, 1H), 7.93 (s, 1H), 6.71 (s, 1H), 5.66 - 5.57 (m, 1H), 5.13 - 5.06 (m, 4H), 4.17 - 4.08 (m, 1H), 3.61 - 3.50 (m, 2H), 3.63 - 3.49 (m, 1H), 3.49 - 3.38 (m, 5H), 2.99 - 2.86 (m, 2H), 2.58 - 2.46 (m, 2H), 2.24 - 2.07 (m, 2H), 1.31 (d, J=6.4 Hz, 3H). | 445.1 |
| 543 | 6 | ¹H NMR (400 MHz, CD₃OD), δ 8.82 (s, 1H), 8.15 (s, 1H), 7.95 (s, 1H), 6.76 (s, 1H), 5.66 - 5.57 (m, 1H), 5.15 - 5.06 (m, 4H), 4.19 - 4.09 (m, 1H), 3.60 - 3.53 (m, 1H), 3.52 - 3.39 (m, 5H), 3.21 - 3.12 (m, 2H), 3.02 - 2.90 (m, 2H), 2.63 - 2.47 (m, 2H), 2.23 - 2.14 (m, 2H), 1.30 (d, J=6.8 Hz, 3H). | 445.1 |
| 544 | 3 | ¹H NMR (500 MHz, MeOD) δ 8.77 (s, 1H), 8.52–8.50 (ddd, J = 5.0, 1.7, 0.9 Hz, 1H), 8.08–8.08 (d, J = 0.7 Hz, 1H), 7.87–7.87 (m, 1H), 7.78–7.74 (m, 1H), 7.51–7.49 (d, J = 8.0 Hz, 1H), 7.27–7.25 (ddd, J = 7.5, 5.0, 1.1 Hz, 1H), 6.54 (s, 1H), 5.61–5.55 (m, 1H), 5.08–5.04 (m, 4H), 4.92–4.88 (q, J = 7.0 Hz, 1H), 3.56–3.50 (m, 1H), 2.76–2.70 (tt, J = 11.8, 3.4 Hz, 1H), 2.04–2.00 (m, 1H), 1.98–1.94 (m, 1H), 1.87–1.84 (m, 1H), 1.58–1.57 (d, J = 7.1 Hz, 3H), 1.54–1.46 (m, 2H), 1.42–1.34 (m, 1H), 1.30–1.18 (m, 2H). | 460.1 |
| 545 | 3 | ¹H NMR (500 MHz, MeOD) δ 8.77 (s, 1H), 8.52–8.50 (ddd, J = 5.0, 1.7, 0.9 Hz, 1H), 8.08–8.08 (d, J = 0.7 Hz, 1H), 7.87–7.87 (d, J = 0.5 Hz, 1H), 7.78–7.74 (td, J = 7.7, 1.8 Hz, 1H), 7.51–7.49 (d, J = 8.0 Hz, 1H), 7.27–7.25 (ddd, J = 7.5, 5.0, 1.1 Hz, 1H), 6.54 (s, 1H), 5.61 – 5.55 (m, 1H), 5.08 – 5.04 (m, 4H), 4.92– 4.88 (q, J = 7.0 Hz, 1H), 3.56–3.51 (td, J = 10.7, 5.3 Hz, 1H), 2.76–2.71 (ddd, J = 11.9, 8.4, 3.4 Hz, 1H), 2.03–1.94 (m, 2H), 1.87–1.85 (d, J = 11.3 Hz, 1H), 1.58–1.47 (m, 5H), 1.42–1.16 (m, 4H). | 460.2 |
| 546 | 4 | ¹H NMR (500 MHz, MeOD): δ 8.87 (s, 1H), 8.12– 8.11 (dd, J = 5.2, 0.6 Hz, 1H), 6.98–6.97 (m, 2H), 6.88 (s, 1H), 4.13–4.09 (m, 1H), 4.06– 4.05 (m, 1H), 3.84–3.82 (m, 4H), 3.59–3.56 (dd, J = 9.5, 5.3 Hz, 1H), 3.53–3.51 (m, 4H), 3.45–3.42 (dd, J = 9.5, 5.9 Hz, 1H), 3.41 (s, 3H), 3.25–3.20 (tt, J = 11.0, 3.2 Hz, 1H), 2.03–1.97 (m, 2H), 1.91–1.89 (m, 4H), 1.77–1.71 (m, 2H), 1.30–1.28 (d, J = 6.6 Hz, 3H). | 467.2 |

FIG. 2 (Cont'd)

| No. | General Scheme | NMR | MS |
|---|---|---|---|
| 547 | 4 | $^1$H NMR (500 MHz, MeOD): δ 8.78 (s, 1H), 8.14–8.14 (d, J = 0.6 Hz, 1H), 7.89–7.89 (d, J = 0.5 Hz, 1H), 6.71 (s, 1H), 4.11–4.07 (m, 1H), 4.04 (m, 1H), 3.58–3.30(m, 11H), 3.23–2.18 (m, 3H), 2.01–1.96 (m, 2H), 1.89–1.83 (m, 10H), 1.76–1.70 (m, 2H), 1.29–1.28 (d, J = 6.6 Hz, 3H). | 526.3 |
| 548 | 4 (analogous to Example 34) | $^1$H NMR (500 MHz, MeOD) δ 8.89 (s, 1H), 8.14 (d, J = 5.9 Hz, 1H), 7.03 – 6.95 (m, 2H), 6.89 (s, 1H), 4.18 – 4.06 (m, 1H), 3.89 – 3.78 (m, 4H), 3.62 – 3.56 (m, 1H), 3.57 – 3.50 (m, 4H), 3.49 – 3.43 (m, 1H), 3.42 (s, 3H), 3.17 – 3.08 (m, 1H), 2.01 – 1.90 (m, 4H), 1.89 – 1.77 (m, 2H), 1.67 – 1.53 (m, 2H), 1.31 (d, J = 6.7 Hz, 3H), 1.28 (s, 3H). | 481.2 |
| 549 | 4 (analogous to Example 34) | $^1$H NMR (500 MHz, MeOD) δ 8.96 (s, 1H), 8.03 (d, J = 5.9 Hz, 1H), 7.14 (d, J = 7.9 Hz, 1H), 7.12 (s, 1H), 6.99 (s, 1H), 4.16 – 4.04 (m, 1H), 3.89 – 3.83 (m, 4H), 3.63 – 3.58 (m, 4H), 3.56 (dd, J = 10.3, 4.9 Hz, 1H), 3.44 (dd, J = 9.5, 5.9 Hz, 1H), 3.41 (s, 3H), 3.20 – 3.11 (m, 1H), 2.14 – 2.07 (m, 2H), 1.86 – 1.72 (m, 4H), 1.71 – 1.62 (m, 2H), 1.33 (s, 3H), 1.29 (d, J = 6.7 Hz, 3H). | 481.2 |
| 550 | 4 | $^1$H NMR (400 MHz, MeOD) δ 8.73 (s, 1H), 8.45 (s, 1H), 7.86 (d, J = 1.1 Hz, 1H), 7.63 (dt, J = 8.5, 5.0 Hz, 2H), 6.69 (s, 1H), 4.07 (dd, J = 12.0, 6.0 Hz, 1H), 3.68 – 3.49 (m, 2H), 3.44 – 3.34 (m, 4H), 3.27 (dt, J = 3.3, 1.6 Hz, 3H), 3.07 (tt, J = 12.0, 3.4 Hz, 1H), 2.21 – 2.12 (m, 2H), 2.10 – 2.02 (m, 2H), 1.70 – 1.55 (m, 2H), 1.42 (td, J = 13.2, 2.3 Hz, 2H), 1.27 (d, J = 6.6 Hz, 3H) | 422.2 |
| 551 | 4 | $^1$H NMR (400 MHz, CD$_3$OD) δ 8.79 (s, 1H), 8.15 (t, J = 1.5 Hz, 1H), 7.87 (d, J = 7.9 Hz, 1H), 7.80 – 7.71 (m, 1H), 7.57 (t, J = 7.8 Hz, 1H), 6.74 (s, 1H), 4.07 (dd, J = 12.0, 6.0 Hz, 1H), 3.67 – 3.51 (m, 2H), 3.47 – 3.35 (m, 4H), 3.07 (ddd, J = 12.0, 7.7, 3.4 Hz, 1H), 2.63 – 2.58 (m, 3H), 2.16 (d, J = 11.6 Hz, 2H), 2.07 (d, J = 10.6 Hz, 2H), 1.70 – 1.54 (m, 2H), 1.42 (q, J = 11.0 Hz, 2H), 1.27 (d, J = 6.6 Hz, 3H). | 463.21 |
| 552 | 4 | $^1$H NMR (400MHz,CD$_3$OD) δ 8.76 (s, 1H), 8.42 (s, 2H), 7.81 (d,J = 1.2Hz, 2H), 7.73 (d,J = 8.3Hz, 2H), 7.60 (dd,J = 8.3, 1.5Hz, 2H), 6.71 (s, 2H), 4.52 (s, 1H), 4.12 – 4.00 (m, 2H), 3.70 – 3.50 (m, 4H), 3.47 – 3.35 (m, 8H), 3.07 (ddd,J = 12.1, 8.6, 3.5Hz, 2H), 2.11 (dd,J = 36.8, 11.1Hz, 8H), 1.70 – 1.53 (m, 4H), 1.41 (q,J = 10.9Hz, 4H), 1.26 (d,J = 6.6Hz, 6H). | 422.2 |
| 553 | 4 | $^1$H NMR (500 MHz, MeOD) δ 8.75 (s, 1H), 8.18 (s, 1H), 7.76 (s, 1H), 7.67 (d, J = 6.2 Hz, 1H), 7.50 (dd, J = 8.4, 1.6 Hz, 1H), 6.70 (s, 1H), 4.14 – 4.04 (m, 1H), 3.70 – 3.62 (m, 1H), 3.59 (dd, J = 9.4, 5.2 Hz, 1H), 3.47 – 3.43 (m, 1H), 3.42 – 3.40 (m, 3H), 3.11 (tt, J = 12.0, 3.4 Hz, 1H), 2.27 – 2.14 (m, 2H), 2.10 (ddd, J = 15.5, 5.6, 3.8 Hz, 2H), 1.72 – 1.59 (m, 2H), 1.52 – 1.39 (m, 2H), 1.30 (d, J = 6.6 Hz, 3H). | 0 |

FIG. 2 (Cont'd)

| No. | General Scheme | NMR | MS |
|---|---|---|---|
| 554 | 4 | ¹H NMR (500 MHz, MeOD) δ 8.80 (d, J = 2.0 Hz, 1H), 8.16 (s, 1H), 7.89 (d, J = 1.6 Hz, 1H), 6.68 (s, 1H), 4.25 (d, J = 46.3 Hz, 1H), 4.10 (dd, J = 12.0, 6.0 Hz, 1H), 3.69 – 3.51 (m, 3H), 3.48 – 3.41 (m, 3H), 3.17 – 3.04 (m, 1H), 2.88 – 2.55 (m, 2H), 2.15 (dd, J = 39.8, 10.8 Hz, 3H), 1.92 – 1.71 (m, 6H), 1.71 – 1.58 (m, 2H), 1.53 – 1.36 (m, 2H), 1.31 (d, J = 6.6 Hz, 2H). | 526.3 |
| 555 | 4 | ¹H NMR (500 MHz, MeOD) δ 10.34 (d, J = 1.9 Hz, 1H), 9.70 (s, 1H), 9.44 (s, 1H), 8.22 (s, 1H), 5.79 (d, J = 45.9 Hz, 1H), 5.64 (dd, J = 12.0, 6.0 Hz, 1H), 5.46 – 5.06 (m, 5H), 5.06 – 4.92 (m, 4H), 4.71 – 4.59 (m, 1H), 4.43 – 4.08 (m, 2H), 3.80 – 3.57 (m, 4H), 3.46 – 3.28 (m, 7H), 3.25 – 3.11 (m, 2H), 3.08 – 2.88 (m, 3H). | 526.3 |
| 556 | 4 | ¹H NMR (400 MHz, CD₃OD) δ 8.77 (s, 1H), 8.13 (s, 1H), 7.87 (s, 1H), 6.65 (s, 1H), 4.13 – 4.03 (m, 1H), 3.68 – 3.60 (m, 1H), 3.58 (dd, J = 9.5, 5.2 Hz, 1H), 3.46 – 3.42 (m, 1H), 3.41 (s, 3H), 3.13 – 3.03 (m, 1H), 2.85 – 2.75 (m, 1H), 2.75 – 2.65 (m, 1H), 2.21 – 2.13 (m, 2H), 2.13 – 2.04 (m, 2H), 1.85 (s, 3H), 1.82 (s, 3H), 1.71 – 1.56 (m, 2H), 1.43 (dt, J = 13.4, 6.7 Hz, 2H), 1.29 (d, J = 6.6 Hz, 3H), 1.21 – 0.78 (m, 6H). Some protons obscured by broad morpholine peak | 584.2 |
| 557 | 4 | ¹H NMR (400 MHz, CD₃OD) δ 8.89 (s, 1H), 8.11 (d, J = 5.8 Hz, 1H), 7.31 – 7.19 (m, 1H), 6.98 – 6.91 (m, 2H), 6.85 (s, 1H), 6.42 (t, J = 75.4 Hz, 1H), 4.27 (d, J = 12.5 Hz, 1H), 4.20 – 4.00 (m, 3H), 3.84 (dd, J = 9.5, 6.3 Hz, 1H), 3.75 – 3.59 (m, 2H), 3.36 (dd, J = 10.8, 2.4 Hz, 1H), 3.17 – 3.05 (m, 1H), 2.94 (td, J = 12.3, 3.6 Hz, 1H), 2.78 (dd, J = 12.4, 11.0 Hz, 1H), 2.24 – 2.13 (m, 2H), 2.13 – 1.98 (m, 2H), 1.74 – 1.57 (m, 2H), 1.54 – 1.40 (m, 2H), 1.35 (d, J = 6.6 Hz, 3H), 1.28 (s, 3H), 1.26 (s, 3H). | 561.2 |
| 558 | Diasteromer separation on chiral column of Compound 534 | ¹H NMR (400 MHz, CD₃OD) δ 8.88 (s, 1H), 8.16 – 8.05 (m, 1H), 6.99 – 6.92 (m, 2H), 6.85 (s, 1H), 4.27 (d, J = 12.4 Hz, 1H), 4.15 – 4.00 (m, 3H), 3.76 – 3.61 (m, 2H), 3.59 (dd, J = 9.4, 5.2 Hz, 1H), 3.46 – 3.42 (m, 1H), 3.41 (s, 3H), 3.36 (dd, J = 10.7, 2.3 Hz, 1H), 3.16 – 3.06 (m, 1H), 2.94 (td, J = 12.3, 3.6 Hz, 1H), 2.78 (dd, J = 12.5, 10.9 Hz, 1H), 2.23 – 2.15 (m, 2H), 2.14 – 2.05 (m, 2H), 1.73 – 1.59 (m, 2H), 1.52 – 1.41 (m, 2H), 1.30 (d, J = 6.6 Hz, 3H), 1.28 (s, 3H), 1.26 (s, 3H). | 525.2 |
| 559 | Diasteromer separation on chiral column of Compound 534 | ¹H NMR (400 MHz, CD₃OD) δ 8.90 (s, 1H), 8.18 – 8.05 (m, 1H), 7.01 – 6.93 (m, 2H), 6.87 (s, 1H), 4.29 (d, J = 12.4 Hz, 1H), 4.17 – 4.04 (m, 3H), 3.78 – 3.63 (m, 2H), 3.61 (dd, J = 9.4, 5.2 Hz, 1H), 3.48 – 3.45 (m, 1H), 3.43 (s, 3H), 3.38 (dd, J = 10.7, 2.4 Hz, 1H), 3.19 – 3.08 (m, 1H), 2.96 (td, J = 12.3, 3.7 Hz, 1H), 2.80 (dd, J = 12.5, 10.9 Hz, 1H), 2.26 – 2.17 (m, 2H), 2.16 – 2.05 (m, 2H), 1.76 – 1.59 (m, 2H), 1.56 – 1.42 (m, 2H), 1.32 (d, J = 6.6 Hz, 3H), 1.30 (s, 3H), 1.28 (s, 3H). | 525.2 |

FIG. 2 (Cont'd)

| No. | General Scheme | NMR | MS |
|---|---|---|---|
| 560 | 4 | $^1$H NMR (400 MHz, CD$_3$OD) δ 8.74 (s, 1H), 8.10 (d, J = 0.7 Hz, 1H), 7.85 (d, J = 0.6 Hz, 1H), 6.66 (s, 1H), 4.15 – 3.96 (m, 1H), 3.53 (dd, J = 9.4, 5.2 Hz, 2H), 3.45 – 3.35 (m, 6H), 3.15 – 3.03 (m, 2H), 2.11 – 1.99 (m, 2H), 1.85 – 1.56 (m, 13H), 1.32 – 1.20 (m, 6H). | 540.3 |
| 561 | 4 | $^1$H NMR (400 MHz, CD$_3$OD) δ 8.74 (s, 1H), 8.09 (d, J = 0.6 Hz, 1H), 7.84 (d, J = 0.5 Hz, 1H), 6.65 (s, 1H), 4.05 (dd, J = 12.0, 5.7 Hz, 1H), 3.53 (dd, J = 9.5, 5.2 Hz, 2H), 3.45 – 3.34 (m, 6H), 3.08 (d, J = 15.8 Hz, 2H), 1.89 (s, 4H), 1.77 (d, J = 20.7 Hz, 8H), 1.56 (d, J = 13.3 Hz, 2H), 1.27 – 1.21 (m, 6H). | 540.3 |
| 562 | 4 | $^1$H NMR (400 MHz, CD$_3$OD) δ 8.70 (s, 1H), 7.30 (t, J = 7.9 Hz, 1H), 7.14 – 7.01 (m, 2H), 6.91 (dd, J = 8.2, 1.9 Hz, 1H), 6.66 (s, 1H), 4.09 (dd, J = 12.0, 6.0 Hz, 1H), 3.92 – 3.80 (m, 4H), 3.70 – 3.53 (m, 2H), 3.47 – 3.37 (m, 4H), 3.21 – 3.16 (m, 4H), 3.10 (td, J = 12.2, 6.3 Hz, 1H), 2.14 (dd, J = 34.3, 11.1 Hz, 4H), 1.71 – 1.58 (m, 2H), 1.51 – 1.39 (m, 2H), 1.29 (d, J = 6.6 Hz, 3H). | 466.2 |
| 563 | 4 | $^1$H NMR (500 MHz, MeOD) δ 10.32 (s, 1H), 9.75 (d, J = 0.7 Hz, 1H), 9.37 (d, J = 0.6 Hz, 1H), 8.21 (s, 1H), 5.64 (dd, J = 11.9, 6.0 Hz, 1H), 5.25 – 5.08 (m, 2H), 5.03 – 4.94 (m, 4H), 4.64 (ddd, J = 12.1, 8.7, 3.4 Hz, 1H), 3.72 (ddd, J = 8.4, 6.7, 4.2 Hz, 3H), 3.65 (s, 7H), 3.19 (tt, J = 13.1, 10.2 Hz, 2H), 3.00 (dd, J = 23.9, 11.2 Hz, 2H), 2.85 (d, J = 6.6 Hz, 3H), 2.77 – 2.68 (m, 2H), 2.61 (dt, J = 7.3, 4.4 Hz, 2H). | 521.3 |
| 564 | 4 | $^1$H NMR (500 MHz, MeOD) δ 8.75 (s, 1H), 8.12–8.12 (d, J = 0.7 Hz, 1H), 7.91–7.91 (d, J = 0.5 Hz, 1H), 6.69 (s, 1H), 5.63–5.57 (m, 1H), 5.10–5.05 (m, 4H), 4.11–4.07 (m, 1H), 4.04 (m, 1H), 3.58–3.55 (dd, J = 9.4, 5.2 Hz, 1H), 3.45–3.42 (dd, J = 9.4, 5.8 Hz, 1H), 3.40 (s, 3H), 3.22–3.16 (m, 1H), 2.05–1.96 (m, 2H), 1.89–1.87 (m, 4H), 1.76–1.70 (m, 2H), 1.29–1.28 (d, J = 6.6 Hz, 3H). | 427.2 |
| 565 | 6 | $^1$H NMR (500 MHz, MeOD): δ 8.81 (s, 1H), 8.72–8.72 (d, J = 1.8 Hz, 1H), 8.05–8.03 (dd, J = 8.1, 2.3 Hz, 1H), 7.59– 7.57 (d, J = 8.2 Hz, 1H), 6.79 (s, 1H), 4.14–4.09 (m, 1H), 3.72 (s, 2H), 3.69–3.63 (m, 1H), 3.60–3.56 (dd, J = 9.4, 5.2 Hz, 1H), 3.45–3.42 (m, 4H), 3.15 – 3.10 (m, 1H), 2.63 (bs, 11H), 2.21– 2.19 (d, J = 9.9 Hz, 2H), 2.11–2.09 (d, J = 9.0 Hz, 2H), 1.71– 1.62 (ddd, J = 21.3, 15.5, 10.1 Hz, 2H), 1.49–1.42 (dd, J = 24.3, 11.1 Hz, 2H), 1.31–1.29 (d, J = 6.6 Hz, 3H). | 494.2 |
| 566 | 6 | $^1$H NMR (400 MHz, CD$_3$OD) δ 8.97 (s, 1H), 8.53 (d, J = 5.3 Hz, 1H), 7.60 (s, 1H), 7.55 (d, J = 5.3 Hz, 1H), 6.93 (s, 1H), 5.09 (dd, J = 8.5, 5.9 Hz, 2H), 4.97 (t, J = 6.3 Hz, 2H), 4.55 – 4.43 (m, 1H), 4.17 – 4.02 (m, 1H), 3.71 – 3.61 (m, 1H), 3.59 (dd, J = 9.4, 5.3 Hz, 1H), 3.47 – 3.43 (m, 1H), 3.41 (s, 3H), 3.17 – 3.05 (m, 1H), 2.24 – 2.15 (m, 2H), 2.15 – 2.04 (m, 2H), 1.73 – 1.57 (m, 2H), 1.52 – 1.38 (m, 2H), 1.30 (d, J = 6.6 Hz, 3H). | 438.2 |

FIG. 2 (Cont'd)

| No. | General Scheme | NMR | MS |
|---|---|---|---|
| 567 | 4 | ¹H NMR (400 MHz, dmso) δ 8.77 (s, 1H), 8.25 (s, 1H), 7.93 (s, 1H), 6.66 (s, 1H), 4.60 (d, J = 8.7 Hz, 2H), 4.24 (d, J = 8.5 Hz, 2H), 4.13 – 4.02 (m, 1H), 3.68 – 3.60 (m, 1H), 3.58 (dd, J = 9.5, 5.2 Hz, 1H), 3.52 (s, 2H), 3.46 – 3.42 (m, 1H), 3.41 (s, 3H), 3.16 (q, J = 7.4 Hz, 2H), 3.12 – 3.02 (m, 1H), 2.22 – 2.13 (m, 2H), 2.13 – 2.04 (m, 2H), 1.69 – 1.56 (m, 2H), 1.51 – 1.38 (m, 2H), 1.36 (t, J = 7.4 Hz, 3H), 1.29 (d, J = 6.6 Hz, 3H). | 557.1 |
| 568 | 4 (analogous to Example 34) | ¹H NMR (500 MHz, MeOD) δ 8.77 (s, 1H), 8.02 (dd, J = 5.2, 0.6 Hz, 1H), 6.87 (dd, J = 6.9, 1.5 Hz, 2H), 6.76 (s, 1H), 4.05 – 3.95 (m, 1H), 3.74 – 3.68 (m, 4H), 3.47 (dd, J = 9.4, 5.3 Hz, 1H), 3.44 – 3.39 (m, 4H), 3.34 (dd, J = 9.5, 5.9 Hz, 1H), 3.31 (s, 3H), 3.02 (ddd, J = 15.8, 11.1, 4.6 Hz, 1H), 1.82 (ddd, J = 16.9, 15.2, 7.4 Hz, 4H), 1.69 (dt, J = 13.6, 2.5 Hz, 2H), 1.48 – 1.38 (m, 4H), 1.19 (d, J = 6.6 Hz, 3H), 0.87 (t, J = 7.5 Hz, 3H). | 495.2 |
| 569 | 4 (analogous to Example 34) | ¹H NMR (500 MHz, MeOD) δ 8.87 (s, 1H), 8.11 (dd, J = 5.1, 0.8 Hz, 1H), 6.98 – 6.95 (m, 2H), 6.87 (s, 1H), 4.16 – 4.02 (m, 1H), 3.86 – 3.78 (m, 4H), 3.57 (dd, J = 9.4, 5.3 Hz, 1H), 3.54 – 3.50 (m, 4H), 3.44 (dd, J = 9.4, 5.9 Hz, 1H), 3.41 (s, 3H), 3.17 (tt, J = 11.4, 3.9 Hz, 1H), 2.10 – 2.00 (m, 2H), 1.89 (d, J = 12.8 Hz, 2H), 1.83 – 1.74 (m, 2H), 1.71 (q, J = 7.5 Hz, 2H), 1.64 – 1.51 (m, 2H), 1.29 (d, J = 6.6 Hz, 3H), 0.95 (t, J = 7.5 Hz, 3H). | 495.2 |
| 570 | 6 | ¹H NMR (400 MHz, CD₃OD) δ 8.76 (s, 1H), 8.13 (s, 1H), 7.92 (s, 1H), 6.65 (s, 1H), 5.66 - 5.57 (m, 1H), 5.12 - 5.07 (m, 4H), 4.14 - 4.04 (m, 1H), 3.63 - 3.56 (m, 1H), 3.51 - 3.35 (m, 6H), 2.17 - 2.08 (m, 1H), 1.95 - 1.82 (m, 2H), 1.77 - 1.60 (m, 2H), 1.46 - 1.36 (m, 1H), 1.32 (dd, J=1.2, 6.8Hz, 3H), 1.07 (d, J=7.2 Hz, 6H). | 455.2 |
| 571 | 6 | ¹H NMR (400 MHz, CD₃OD) δ 8.76 (s, 1H), 8.13 (s, 1H), 7.93 (s, 1H), 6.68 (s, 1H), 5.66 - 5.57 (m, 1H), 5.14 - 5.06 (m, 4H), 4.15 - 4.04 (m, 1H), 3.63 - 3.56 (m, 1H), 3.51 - 3.43 (m, 3H), 3.42 (s, 3H), 2.07 - 1.97 (m, 1H), 1.96 - 1.70 (m, 4H), 1.66 - 1.59 (m, 1H), 1.31 (dd, J=1.2, 6.8 Hz, 3H), 1.12 (s, 3H), 1.01 (s, 3H). | 455.2 |
| 572 | 5 | ¹H NMR (400 MHz, CD₃OD) δ 9.09 (d, J=2.0 Hz, 1H), 9.01 (d, J=2.0 Hz, 1H), 8.94 (s, 1H), 8.53 (t, J=2.0 Hz, 1H), 6.94 (s, 1H), 4.19 - 4.08 (m, 1H), 3.73 - 3.58 (m, 2H), 3.50 - 3.45 (m, 1H), 3.44 (s, 3H), 3.31 (s, 3H), 3.21 - 3.11 (m, 1H), 2.28 - 2.19 (m, 2H), 2.18 - 2.07 (m, 2H), 1.77 - 1.61 (m, 2H), 1.55 - 1.41 (m, 2H), 1.32 (d, J=6.8 Hz, 3H). | 459.1 |
| 573 | 5 | ¹H NMR (400 MHz, CD₃OD) δ = 9.09 (d, J=2.0 Hz, 1H), 9.01 (d, J=2.0 Hz, 1H), 8.94 (s, 1H), 8.53 (t, J=2.0 Hz, 1H), 6.94 (s, 1H), 4.18 - 4.08 (m, 1H), 3.73 - 3.64 (m, 1H), 3.64 - 3.58 (m, 1H), 3.49 - 3.45 (m, 1H), 3.44 (s, 3H), 3.31 (s, 3H), 3.20 - 3.11 (m, 1H), 2.28 - 2.18 (m, 2H), 2.17 - 2.07 (m, 2H), 1.77 - 1.61 (m, 2H), 1.54 - 1.42 (m, 2H), 1.32 (d, J=6.8 Hz, 3H). | 459.1 |

FIG. 2 (Cont'd)

| No. | General Scheme | NMR | MS |
|---|---|---|---|
| 574 | 5 | $^1$H NMR (400 MHz, CD$_3$OD) δ 9.02 (s, 1H), 8.65 (d, J=4.0, 1H), 8.30 (s, 1H) 8.32 - 8.26 (m, 1H), 7.84 (dd, J=5.14, 1.71 Hz, 1H), 6.99 (s, 1H), 4.18 -4.04 (m, 1H), 3.70 - 3.56 (m, 2H), 3.47 - 3.40 (m, 4H), 3.30 (s, 3H), 3.15 - 3.06 (m, 1H), 2.24 - 2.05 (m, 4H), 1.71 - 1.57 (m, 2H), 1.51 - 1.39 (m, 2H), 1.30 (d, J=6.60 Hz, 3H). | 459.2 |
| 575 | 5 | $^1$H NMR (400 MHz, CD$_3$OD) δ 9.05 (s, 1H), 8.67 (d, J = 5.1 Hz, 1H), 8.32 (d, J = 1.5 Hz, 1H), 7.87 (dd, J = 1.5, 5.2Hz, 1H), 7.02 (s, 1H), 4.13 (sxt, J = 6.3 Hz, 1H), 3.73 - 3.57 (m, 2H), 3.50 - 3.45 (m, 1H), 3.44 (s, 3H), 3.32 (s, 3H), 3.13 (tt, J = 3.2, 12.0 Hz, 1H), 2.22 -2.12 (m, 4H), 1.75 - 1.59 (m, 2H), 1.54 -1.41 (m, 2H), 1.32 (d, J = 6.8 Hz, 3H). | 459.2 |
| 576 | 5 | $^1$H NMR (400MHz, CD$_3$OD) δ = 8.60 (s, 1H), 6.36 (s, 1H), 4.11 - 3.98 (m, 1H), 3.74-3.73(m, 4H), 3.67 - 3.53 (m, 2H), 3.46 - 3.37 (m, 4H), 3.09 - 2.99 (m, 1H), 2.94 - 2.86 (m, 1H), 2.85 - 2.77 (m, 1H), 2.17 - 1.83 (m, 12H), 1.76 - 1.52 (m, 6H), 1.49 - 1.36 (m, 2H), 1.28 (d, J=6.8 Hz, 3H) | 534.3 |
| 577 | 5 | $^1$H NMR (400MHz, CD$_3$OD) δ 8.57 (s, 1H), 6.43 (s, 1H), 4.09 - 4.01 (m, 1H), 3.75 - 3.52 (m, 6H), 3.45 - 3.37 (m, 4H), 3.12 - 2.93 (m, 3H), 2.17 - 1.88 (m, 12H), 1.87 - 1.77 (m, 2H), 1.75 - 1.68 (m, 2H), 1.65 - 1.52 (m, 2H), 1.49 - 1.35 (m, 2H), 1.27 (d, J=6.8 Hz, 3H). | 534.3 |
| 578 | 5 | $^1$H NMR (400MHz, CD$_3$OD) δ 8.58 (s, 1H), 6.34 (s, 1H), 4.82 - 4.79 (m, 4H), 4.45 (s, 2H), 4.14 (s, 2H), 4.09 - 3.96 (m, 1H), 3.71 - 3.51 (m, 2H), 3.45 - 3.37 (m, 4H), 3.09 - 2.98 (m, 1H), 2.94 - 2.81 (m, 1H), 2.42 - 2.28 (m, 1H), 2.13 -2.05 (m, 4H), 2.01 - 1.92 (m, 2H), 1.88 - 1.77 (m, 2H), 1.69 - 1.50 (m, 6H), 1.49 - 1.35 (m, 2H), 1.27 (d, J=6.8 Hz, 3H). | 512.4 |
| 579 | 5 | $^1$H NMR (400MHz, CD$_3$OD) δ 8.56 (s, 1H), 6.40 (s, 1H), 4.80 (s, 4H), 4.42 (s, 2H), 4.14 (s, 2H), 4.10 - 4.00 (m, 1H), 3.67 - 3.53 (m, 2H), 3.44 - 3.38 (m, 4H), 3.09 - 2.98 (m, 2H), 2.60 - 2.55 (m, 1H), 2.15 - 1.96 (m, 6H), 1.95 - 1.85 (m, 2H), 1.83 - 1.73 (m, 2H), 1.72 - 1.52 (m, 4H), 1.48 - 1.35 (m, 2H), 1.27 (d, J=6.8 Hz, 3H). | 512.4 |
| 580 | 5 | $^1$H NMR (400 MHz, DMSO-$d_6$) δ 9.20 (s, 1H), 8.63 (d, J = 5.1 Hz, 1H), 8.23 (s, 1H), 7.92 (dd, J = 1.6, 5.1 Hz, 1H), 7.20 (br d, J = 7.8 Hz, 1H), 7.11 (s, 1H), 4.63 (d, J = 4.4 Hz, 1H), 4.53 (s, 1H), 4.27 - 4.05 (m, 1H), 3.55 - 3.43 (m, 1H), 3.24 - 3.14 (m, 3H), 3.00 (tt, J = 3.2, 12.0 Hz, 1H), 2.83 - 2.69 (m, 1H), 2.45 - 2.35 (m, 1H), 2.07 (br d, J = 12.7 Hz, 2H), 2.00 - 1.89 (m, 2H), 1.64 - 1.45 (m, 2H), 1.39 - 1.34 (m, 1H), 1.33 (br d, J = 6.5 Hz, 3H), 1.30 - 1.20 (m, 2H). | 497.1 |

FIG. 2 (Cont'd)

| No. | General Scheme | NMR | MS |
|---|---|---|---|
| 581 | 5 | $^1$H NMR (400 MHz, DMSO-$d_6$) δ 9.20 (s, 1H), 8.64 (d, J = 5.1 Hz, 1H), 8.24 (s, 1H), 7.92 (d, J = 5.0 Hz, 1H), 7.20 (br d, J = 7.5 Hz, 1H), 7.11 (s, 1H), 4.64 (d, J = 4.4 Hz, 1H), 4.53 (s, 1H), 4.24 - 4.10 (m, 1H), 3.56 - 3.44 (m, 1H), 3.20 (s, 3H), 3.07 - 2.93 (m, 1H), 2.86 - 2.70 (m, 1H), 2.45 - 2.36 (m, 1H), 2.14 - 2.02 (m, 2H), 2.01 - 1.89 (m, 2H), 1.64 - 1.45 (m, 2H), 1.39 - 1.34 (m, 1H), 1.33 (br d, J = 6.4 Hz, 3H), 1.31 - 1.19 (m, 2H). | 497.1 |
| 582 | 4 | $^1$H NMR (400MHz, CD$_3$OD) δ 9.10 (s, 1H), 9.01 (s, 1H), 8.95 (s, 1H), 8.54 (s, 1H), 6.95 (s, 1H), 4.36 - 4.22 (m, 1H), 3.75 - 3.61 (m, 1H), 3.31 (br s, 3H), 3.20 - 3.10 (m, 1H), 2.90 - 2.70 (m, 1H), 2.45 - 2.27 (m, 1H), 2.27 - 2.17 (m, 2H), 2.17 - 2.05 (m, 2H), 1.77 - 1.58 (m, 2H), 1.56 - 1.46 (m, 2H), 1.44 (br d, J=6.4 Hz, 3H). | 497.1 |
| 583 | 4 | $^1$H NMR (400MHz, CD$_3$OD) δ 9.09 (d, J=2.0 Hz, 1H), 9.01 (d, J=2.0 Hz, 1H), 8.95 (s, 1H), 8.53 (t, J=2.0 Hz, 1H), 6.95 (s, 1H), 4.37 - 4.16 (m, 1H), 3.81 - 3.57 (m, 1H), 3.31 (s, 3H), 3.22 - 3.10 (m, 1H), 2.93 - 2.72 (m, 1H), 2.43 - 2.28 (m, 1H), 2.27 - 2.18 (m, 2H), 2.18 - 2.06 (m, 2H), 1.76 - 1.57 (m, 2H), 1.55 - 1.46 (m, 2H), 1.44 (d, J=6.4 Hz, 3H). | 497.1 |
| 584 | 4 | $^1$H NMR (400 MHz, CD$_3$OD) δ 8.99 (s, 1H), 8.65 (d, J = 5.2 Hz, 1H), 7.98 (s, 1H), 7.87 (d, J = 5.2 Hz, 1H), 7.00 (s, 1H), 4.17 – 4.06 (m, 1H), 3.71 – 3.61 (m, 1H), 3.59 (dd, J= 9.5, 5.3 Hz, 1H), 3.44 (dd, J = 8.3, 4.8 Hz, 1H), 3.42 (s, 3H), 3.17 – 3.07 (m, 1H), 2.26 – 2.16 (m, 2H), 2.16 – 2.05 (m, 2H), 1.75 – 1.59 (m, 2H), 1.52 – 1.39 (m, 2H), 1.30 (d, J = 6.6 Hz, 3H). | 450.2 |
| 585 | Diastereomer separation on chiral column of Compound 556 | $^1$H NMR (400 MHz, CD$_3$OD) δ 8.77 (s, 1H), 8.13 (s, 1H), 7.87 (s, 1H), 6.65 (s, 1H), 4.14 – 4.03 (m, 1H), 3.69 – 3.60 (m, 1H), 3.58 (dd, J = 9.4, 5.2 Hz, 1H), 3.47 – 3.42 (m, 1H), 3.41 (s, 3H), 3.14 – 3.02 (m, 1H), 2.87 – 2.75 (m, 1H), 2.75 – 2.60 (m, 1H), 2.23 – 2.13 (m, 2H), 2.13 – 2.01 (m, 2H), 1.85 (s, 3H), 1.82 (s, 3H), 1.69 – 1.56 (m, 2H), 1.52 – 1.37 (m, 2H), 1.29 (d, J = 6.6 Hz, 3H), 1.20 – 0.83 (m, 6H). Missing morpholine signals, peaks too broad to be integrated properly. | 584.3 |
| 586 | Diastereomer separation on chiral column of Compound 556 | $^1$H NMR (400 MHz, CD$_3$OD) δ 8.77 (s, 1H), 8.13 (s, 1H), 7.87 (s, 1H), 6.65 (s, 1H), 4.14 – 4.02 (m, 1H), 3.72 – 3.61 (m, 1H), 3.58 (dd, J = 9.4, 5.2 Hz, 1H), 3.45 – 3.42 (m, 1H), 3.41 (s, 3H), 3.16 – 2.99 (m, 1H), 2.88 – 2.75 (m, 1H), 2.75 – 2.57 (m, 1H), 2.23 – 2.13 (m, 2H), 2.13 – 2.03 (m, 2H), 1.85 (s, 3H), 1.82 (s, 3H), 1.72 – 1.55 (m, 2H), 1.51 – 1.35 (m, 2H), 1.29 (d, J = 6.5 Hz, 3H), 1.14 – 0.80 (m, 6H). Missing morpholine signals, peak too broad to be integrated properly | 584.3 |
| 587 | 6 | $^1$H NMR (400MHz, CD$_3$OD) δ = 8.76 (s, 1H), 8.13 (s, 1H), 7.93 (s, 1H), 6.67 (s, 1H), 5.62 (m, J=6.9 Hz, 1H), 5.13 - 5.06 (m, 4H), 4.15 - 4.05 (m, 1H), 3.85 (m, 1H), 3.59 (m, J=5.2, 9.5 Hz, 1H), 3.48 - 3.43 (m, 1H), 3.42 (d, J=1.2 Hz, 3H), 3.23 (m, J=11.6 Hz, 1H), 2.00 (m, J=13.2 Hz, 1H), 1.94 - 1.71 (m, 5H), 1.67 (m, J=4.4, 11.8 Hz, 1H), 1.33 - 1.28 (m, 3H), 1.04 (d, J=6.4 Hz, 3H). | 441.1 |

FIG. 2 (Cont'd)

| No. | General Scheme | NMR | MS |
|---|---|---|---|
| 588 | 6 | ¹H NMR (400MHz, CD₃OD) δ 8.77 (s, 1H), 8.14 (s, 1H), 7.93 (s, 1H), 6.76 (s, 1H), 5.61 (m, J=6.8 Hz, 1H), 5.13 - 5.06 (m, 4H), 4.15 -4.14 (m, J=6.0 Hz, 1H), 3.60-3.54 (dd, J=5.2, 9.3 Hz, 1H), 3.53 - 3.43 (m, 3H), 3.41 (s, 3H), 2.25 - 2.12 (m, 2H), 1.94 - 1.79 (m, 3H), 1.73 - 1.62 (m, 2H), 1.30 (d, J=6.8 Hz, 3H), 1.11 (d, J=7.2 Hz, 3H). | 441.1 |
| 589 | 6 | ¹H NMR (400MHz, CD₃OD) δ = 8.76 (s, 1H), 8.12 (s, 1H), 7.92 (s, 1H), 6.64 (s, 1H), 5.61 (m, J=6.8 Hz, 1H), 5.10 (m, 2H), 5.08 (m, J=2.4 Hz, 2H), 4.09 (m, J=6.4 Hz, 1H), 3.59 (m, J=5.2, 9.4 Hz, 1H), 3.48 - 3.42 (m, 4H), 3.24 - 3.15 (m, 2H), 2.21 - 2.06 (m, 3H), 1.74 - 1.43 (m, 3H), 1.41 - 1.33 (m, 1H), 1.31 (m, J=6.8 Hz, 3H), 1.09 (d, J=6.4 Hz, 3H). | 441.1 |
| 590 | 6 | ¹H NMR (400MHz, CD₃OD) δ 8.82 (s, 1H), 8.15 (s, 1H), 7.94 (s, 1H), 6.74 (s, 1H), 5.61 (m, J=6.8 Hz, 1H), 5.10 (m, 2H), 5.09 - 5.06 (m, 2H), 4.59 (s, 1H), 4.20 - 4.06 (m, 1H), 3.64 - 3.53 (m, 1H), 3.51 - 3.43 (m, 2H), 3.41 (s, 3H), 3.36 (m, 2H), 3.29 - 3.23 (m, 1H), 2.53 - 2.31 (m, 4H), 1.30 (d, J=6.8 Hz, 3H). | 460.1 |
| 591 | 5 | ¹H NMR (400 MHz, CD₃OD) δ 8.784 (s, 1H) 8.14 (s, 1H), 7.88 (s, 1H), 6.67 (s, 1H), 4.14-4.08 (m, 1H), 3.67-3.58 (m, 2H), 3.47-3.43 (m, 4H), 3.13-2.74 (m, 3H), 2.28 (s, 3H), 2.20-2.17 (d, J=12.0 Hz, 2H), 2.12-2.10 (d, J=13.6 Hz, 2H), 1.85 (s, 6H), 1.66-1.64 (m, 2H), 1.51-1.42 (dd, J=23.6 Hz, J=11.2 Hz, 2H), 1.32-1.26 (d, J=6.8 Hz, 3H), 1.06-0.78 (m, 6H). | 553.3 |
| 592 | 6 | ¹H NMR (400MHz, CD₃OD) δ 8.82 (s, 1H), 8.15 (s, 1H), 7.93 (s, 1H), 6.70 (s, 1H), 5.65 -5.58 (m, 1H), 5.15 - 5.05 (m, 4H), 4.17 - 4.03 (m, 1H), 3.75 - 3.63 (m, 1H), 3.60 - 3.53 (m, 1H), 3.49 - 3.36 (m, 6H), 2.90-2.83 (m, 1H), 2.70 - 2.56 (m, 1H), 2.32 - 2.23 (m, 1H), 2.22 - 2.10 (m, 1H), 1.30 (dd, J=2.4, 6.4 Hz, 3H). | 426.1 |
| 593 | 5 | ¹H NMR (400MHz, CD₃OD) δ 8.81 (s, 1H), 8.20 - 8.12 (m, 1H), 8.14 (s, 1H), 7.89 (s, 1H), 6.69 (s, 1H), 6.67 - 6.20 (t, J=75.6 Hz 1H), 4.23 - 4.10 (m, 2H), 3.91 - 3.81 (m, 1H), 3.78 - 3.38 (m, 3H), 3.28 - 2.87 (m, 3H), 2.47 - 2.15 (m, 8H), 2.13 - 2.03 (m, 2H), 1.84 (s, 6H), 1.71 - 1.56 (m, 2H), 1.55 - 1.41 (m, 2H), 1.36 (d, J=6.4 Hz, 3H). | 575.4 |
| 594 | 6 | ¹H NMR (400 MHz, CD₃OD) δ 9.05 (s, 1H), 8.34 (s, 1H), 8.02 (s, 1H), 7.82 - 7.79 (m, 1H), 7.10 (s, 1H), 4.14 (sxt, J = 6.2 Hz, 1H), 3.85 - 3.73 (m, 1H), 3.71 - 3.46 (m, 5H), 3.42 - 3.38 (m, 1H), 3.38 - 3.34 (m, 1H), 3.90 - 3.34 (m, 5H), 3.08 (ddd, J = 2.6, 10.4, 16.2 Hz, 2H), 2.92 - 2.68 (m, 2H), 2.36 (br d, J = 12.5 Hz, 1H), 2.25 - 2.10 (m, 1H), 1.85 (s, 6H), 1.81 (s, 1H), 1.32 (d, J = 6.6 Hz, 3H). | 548.2 |
| 595 | 6 | ¹H NMR (400 MHz, CD₃OD) δ 9.06 (s, 1H), 8.32 (s, 1H), 7.99 (s, 1H), 7.66 (br d, J = 7.3 Hz, 1H), 6.90 (d, J = 5.6 Hz, 1H), 4.24 - 4.02 (m, 1H), 3.68 - 3.35 (m, 13H), 2.88 (br s, 2H), 2.35 - 2.23 (m, 1H), 2.19 - 2.03 (m, 2H), 1.97 (br dd, J = 3.5, 10.1 Hz, 1H), 1.85 (s, 1H), 1.83 (s, 6H), 1.32 (d, J = 6.7 Hz, 2H), 1.28 (d, J = 6.7 Hz, 2H), 1.19 (t, J = 7.1 Hz, 1H). | 548.2 |

FIG. 2 (Cont'd)

| No. | General Scheme | NMR | MS |
|---|---|---|---|
| 596 | 6 | ¹H NMR (400 MHz, CD₃OD) δ 8.73 (s, 1H), 8.14 (s, 1H), 7.88 (s, 1H), 6.63 (s, 1H), 5.80 (s, 2H), 4.13 – 4.03 (m, 1H), 3.68 – 3.60 (m, 1H), 3.58 (dd, J = 9.4, 5.2 Hz, 1H), 3.46 – 3.42 (m, 1H), 3.41 (s, 3H), 3.12 – 3.03 (m, 1H), 2.74 (s, 3H), 2.21 – 2.13 (m, 2H), 2.13 – 2.04 (m, 2H), 1.70 – 1.54 (m, 2H), 1.51 – 1.37 (m, 2H), 1.29 (d, J = 6.6 Hz, 3H). | 483.2 |
| 597 | Diasteromer separation on chiral column of Compound 557 | ¹H NMR (400 MHz, CD₃OD) δ 8.89 (s, 1H), 8.12 (d, J = 5.9 Hz, 1H), 7.02 – 6.93 (m, 2H), 6.86 (s, 1H), 6.43 (t, J = 75.4 Hz, 1H), 4.27 (d, J = 12.5 Hz, 1H), 4.20 – 3.98 (m, 4H), 3.85 – 3.78 (m, 1H), 3.77 – 3.62 (m, 2H), 3.42 – 3.33 (m, 2H), 3.20 – 3.09 (m, 1H), 3.02 – 2.88 (m, 1H), 2.79 (dd, J = 12.5, 10.9 Hz, 1H), 2.23 – 2.14 (m, 2H), 2.14 – 2.05 (m, 2H), 1.70 – 1.57 (m, 2H), 1.53 – 1.44 (m, 2H), 1.35 (d, J = 6.6 Hz, 2H), 1.28 (s, 3H), 1.26 (s, 3H). | 561.2 |
| 598 | Diasteromer separation on chiral column of Compound 557 | ¹H NMR (400 MHz, CD₃OD) δ 8.86 (s, 1H), 8.09 (d, J = 5.8 Hz, 1H), 7.01 – 6.90 (m, 2H), 6.83 (s, 1H), 6.39 (t, J = 75.4 Hz, 1H), 4.29 – 4.19 (m, 1H), 4.20 – 3.94 (m, 4H), 3.81 (dd, J = 9.4, 6.3 Hz, 1H), 3.75 – 3.57 (m, 2H), 3.34 (d, J = 2.7 Hz, 1H), 3.15 – 3.02 (m, 1H), 2.96 – 2.85 (m, 1H), 2.81 – 2.69 (m, 1H), 2.24 – 2.11 (m, 2H), 2.11 – 2.00 (m, 2H), 1.71 – 1.49 (m, 2H), 1.49 – 1.37 (m, 2H), 1.32 (d, J = 6.6 Hz, 3H), 1.24 (s, 3H), 1.23 (s, 3H). | 561.3 |
| 599 | 6 | ¹H NMR (400 MHz, CD₃OD) δ 8.77 (s, 1H), 8.25 (d, J = 0.7 Hz, 1H), 7.83 (d, J = 0.7 Hz, 1H), 7.12 (t, J = 51.6 Hz, 1H), 6.65 (s, 1H), 4.08 (dd, J = 11.9, 6.0 Hz, 1H), 3.69 – 3.55 (m, 2H), 3.46 – 3.38 (m, 4H), 3.14 – 3.03 (m, 1H), 2.21 – 2.03 (m, 10H), 1.63 (d, J = 9.8 Hz, 2H), 1.50 – 1.38 (m, 2H), 1.29 (dd, J = 6.7, 2.9 Hz, 3H). | 531.4 |
| 600 | 6 | ¹H NMR (400 MHz, CD₃OD) δ 8.75 (s, 1H), 8.20 (s, 1H), 7.81 (s, 1H), 6.64 (s, 1H), 4.08 (dd, J = 12.0, 6.1 Hz, 1H), 3.60 (ddd, J = 14.6, 9.0, 4.7 Hz, 2H), 3.46 – 3.39 (m, 4H), 3.22 – 3.03 (m, 2H), 2.22 – 2.02 (m, 11H), 1.63 (d, J = 12.0 Hz, 2H), 1.52 – 1.41 (m, 2H), 1.41 – 1.26 (m, 10H), 1.20 (s, 1H). | 523.2 |
| 601 | 6 | ¹H NMR (400 MHz, CD₃OD) δ 8.76 (s, 1H), 8.20 (s, 1H), 7.81 (s, 1H), 6.64 (s, 1H), 5.12 (dd, J = 7.7, 5.5 Hz, 1H), 4.08 (dd, J = 12.2, 6.0 Hz, 1H), 3.97 – 3.86 (m, 2H), 3.69 – 3.55 (m, 2H), 3.46 – 3.39 (m, 3H), 3.08 (t, J = 12.2 Hz, 1H), 2.40 – 1.91 (m, 14H), 1.63 (d, J = 14.0 Hz, 2H), 1.45 (t, J = 11.5 Hz, 2H), 1.29 (d, J = 6.6 Hz, 3H). | 551.3 |
| 602 | 6 | ¹H NMR (400 MHz, CD₃OD) δ 8.71 (s, 1H), 8.16 (s, 1H), 7.78 (s, 1H), 6.60 (s, 1H), 5.09 (dd, J = 7.8, 5.4 Hz, 1H), 4.05 (dd, J = 12.1, 5.9 Hz, 1H), 3.95 – 3.75 (m, 2H), 3.68 – 3.46 (m, 2H), 3.46 – 3.33 (m, 4H), 3.13 – 2.91 (m, 1H), 2.36 – 1.91 (m, 14H), 1.58 (tdd, J = 10.2, 8.4, 5.4 Hz, 2H), 1.40 (q, J = 10.8 Hz, 2H), 1.25 (d, J = 6.6 Hz, 3H). | 551.3 |

FIG. 2 (Cont'd)

| No. | General Scheme | NMR | MS |
|---|---|---|---|
| 603 | 6 | ¹H NMR (400 MHz, CD₃OD) δ 8.77 (s, 1H), 8.27 (d, J = 0.6 Hz, 1H), 7.84 (d, J = 0.6 Hz, 1H), 6.66 (s, 1H), 4.08 (dd, J = 11.9, 5.9 Hz, 1H), 3.71 – 3.54 (m, 2H), 3.51 – 3.39 (m, 4H), 3.14 – 3.03 (m, 1H), 2.17 (s, 7H), 2.09 (d, J = 10.6 Hz, 2H), 1.63 (d, J = 9.8 Hz, 2H), 1.44 (dd, J = 23.8, 10.9 Hz, 2H), 1.29 (d, J = 6.6 Hz, 3H). | 549.2 |
| 604 | 6 | ¹H NMR (400 MHz, CD₃OD) δ 8.87 (s, 1H), 8.72 (s, 1H), 8.17 (s, 1H), 7.77 (s, 1H), 6.61 (s, 1H), 4.10 – 4.00 (m, 1H), 3.66 – 3.51 (m, 2H), 3.43 – 3.36 (m, 4H), 3.04 (ddd, J = 12.1, 7.7, 3.5 Hz, 1H), 2.17 – 2.01 (m, 10H), 1.59 (dt, J = 12.8, 7.6 Hz, 2H), 1.41 (q, J = 10.8 Hz, 2H), 1.26 (d, J = 6.6 Hz, 3H). | 481.2 |
| 605 | 5 (analogous to Example 38) | ¹H NMR (500 MHz, MeOD) δ 8.85 (s, 1H), 8.07–8.08 (d, J = 5.4 Hz, 1H), 6.96 (s, 1H), 6.88–6.87 (dd, J = 5.4, 1.4 Hz, 1H), 6.83 (s, 1H), 4.12–4.08 (m, 1H), 3.88–3.83 (dt, J = 8.7, 4.1 Hz, 2H), 3.68–3.62 (m, 1H), 3.60–3.57 (dd, J = 9.4, 5.2 Hz, 1H), 3.48–3.41 (m, 6H), 3.15–3.08 (m, 1H), 2.20–2.18 (d, J = 9.8 Hz, 2H), 2.12–2.09 (d, J = 14.0 Hz, 2H), 1.69–1.63 (m, 6H), 1.49–1.42 (m, 2H), 1.30–1.27 (m, 6H). | 495.1 |
| 606 | 5 | ¹H NMR (400MHz, CD₃OD) δ 8.60 (s, 1H), 6.36 (s, 1H), 4.11 - 3.98 (m, 1H), 3.70 - 3.54 (m, 6H), 3.46 - 3.38 (m, 4H), 3.09 - 2.99 (m, 1H), 2.95 - 2.85 (m, 1H), 2.82 - 2.72 (m, 1H), 2.53 - 2.39 (m, 4H), 2.33 (s, 3H), 2.16 - 1.95 (m, 6H), 1.90 - 1.80 (m, 2H), 1.75 - 1.54 (m, 6H), 1.49 - 1.36 (m, 2H), 1.28 (d, J=6.8Hz, 3H). | 513.3 |
| 607 | 5 | ¹H NMR (400MHz, CD₃OD) δ 8.58 (s, 1H), 6.44 (s, 1H), 4.10 - 4.02 (m, 1H), 3.70 - 3.52 (m, 6H), 3.46 - 3.37 (m, 4H), 3.13 - 3.00 (m, 2H), 2.95 -2.93 (m, 1H), 2.47 -2.43 (m, 3H), 2.51 - 2.38 (m, 1H), 2.32 (s, 2H), 2.30 (s, 1H), 2.17 - 1.98 (m, 6H), 1.97 - 1.88 (m, 2H), 1.87 - 1.78 (m, 2H), 1.75 -1.68 (m, 2H), 1.64 - 1.53 (m, 2H), 1.49 - 1.36 (m, 2H), 1.28 (d, J = 6.8 Hz, 3H). | 513.3 |
| 608 | 5 | ¹H NMR (400MHz, CD₃OD) δ 8.82 (s, 1H), 8.16 (s, 1H), 7.93 (s, 1H), 6.70 (s, 1H), 4.71 - 4.65 (m, 2H), 4.60 - 4.55 (m, 2H), 4.30 - 4.18 (m, 1H), 4.15 (s, 2H), 3.70 - 3.59 (m, 1H), 3.53 (s, 2H), 3.16 - 3.04 (m, 1H), 2.89 - 2.72 (m, 1H), 2.38 - 2.24 (m, 1H), 2.23 - 2.04 (m, 4H), 1.79 (s, 6H), 1.70 - 1.54 (m, 1H), 1.71 - 1.53 (m, 1H), 1.52 - 1.43 (m, 2H), 1.41 (d, J=6.8 Hz, 3H). | 576.3 |
| 609 | 6 | ¹H NMR (400 MHz, CD₃OD) δ 8.76 (s, 1H), 8.11 (s, 1H), 7.91 (s, 1H), 6.67 (s, 1H), 5.65 - 5.52 (m, 1H), 5.12 - 5.03 (m, 4H), 4.29 - 4.17 (m, 1H), 3.15 - 3.02 (m, 1H), 2.88 - 2.70 (m, 1H), 2.41 - 2.20 (m, 1H), 1.99 - 1.72 (m, 6H), 1.64 - 1.49 (m, 2H), 1.40 (d, J = 6.8, 3H), 1.26 (s, 3H). | 479.2 |
| 610 | 6 | ¹H NMR (400 MHz, CD₃OD) δ 8.77 (s, 1H), 8.12 (s, 1H), 7.92 (s, 1H), 6.68 (s, 1H), 5.66 - 5.53 (m, 1H), 5.13 - 5.03 (m, 5H), 4.30 - 4.19 (m, 1H), 3.19 - 3.08 (m, 1H), 2.84 - 2.68 (m, 1H), 2.41 - 2.23 (m, 1H), 2.16 - 2.03 (m, 2H), 1.87 - 1.61 (m, 7H), 1.40(d, J = 6.8, 3H), 1.32 (s, 3H). | 479.2 |

FIG. 2 (Cont'd)

| No. | General Scheme | NMR | MS |
|---|---|---|---|
| 611 | 4 | ¹H NMR(400MHz, CD₃OD) δ 8.80 (s, 1 H), 7.14-7.10 (d, J=3.6 Hz 1 H),7.00-6.94 (d, J=4.0 Hz, 1 H), 6.63 (s, 1 H),4.15-4.05 (m, 1 H),3.70-3.62 (m, 1 H), 3.61 - 3.57 (m, 1 H) 3.47 - 3.44 (m, 1 H), 3.43 (s, 3 H) 3.13 - 3.03 (m, 1 H) 2.52 (s, 3 H) 2.22 - 2.14 (m, 2 H) 2.13 - 2.05 (m, 2 H) 1.96 - 1.86 (s, 6 H) 1.69 - 1.55 (m, 2 H) 1.51 - 1.39 (m, 2 H) 1.32 - 1.28 (d, J=6.8 Hz, 3 H). | 511.3 |
| 612 | 5 | ¹H NMR (400 MHz, CD₃OD) δ 8.79 (s, 1H), 8.16 (s, 1H), 7.90 (s, 1H), 6.68-6.70 (d, J=4.8 Hz, 1H), 4.60 (s, 1H), 4.12-4.08 (m, 1H), 3.66-3.60 (m, 2H), 3.60-3.50 (t, J=9.6 Hz, 1H), 3.47-3.43 (m, 4H), 3.11-3.08 (m, 1H), 2.65-2.62 (m, 2H), 2.20-2.09 (m, 4H), 1.84 (s, 6H), 1.77-1.73 (m, 4H), 1.64-1.63 (m, 2H), 1.62-1.32 (m, 2H), 1.32-1.30 (d, J=6.8 Hz, 3H). | 510.2 |
| 613 | 5 | ¹H NMR (400MHz, CD₃OD) δ 8.83 (s, 1H), 8.17 (s, 1H), 7.95 (s, 1H), 6.72 (s, 1H), 6.50 (t, J=75.2 Hz , 1H), 4.74 - 4.67 (m, 2H), 4.63 - 4.55 (m, 2H), 4.23 - 4.08 (m, 4H), 3.90 - 3.81 (m, 1H), 3.71 - 3.61 (m, 1H), 3.55 (s, 2H), 3.20 - 3.05(m, 1H), 2.24 - 2.07 (m, 4H), 1.81 (s, 6H), 1.72 - 1.58 (m, 2H), 1.57 - 1.43 (m, 2H), 1.37 (d, J=6.4 Hz, 3H). | 574.3 |
| 614 | 6 | ¹H NMR (400MHz, CD₃OD) δ 8.78 (s, 1H), 8.12 (s, 1H), 7.91 (s, 1H), 6.68 (s, 1H), 5.64 - 5.57 (m, 1H), 5.14 - 5.04 (m, 4H), 4.13 - 4.05 (m, 1H), 3.92 - 3.79 (m, 1H), 3.64 - 3.54 (m, 1H), 3.49 - 3.38 (m, 5H), 2.61 - 2.49 (m, 1H), 2.23 - 1.96 (m, 3H), 1.88 - 1.66 (m, 2H), 1.31 (dd, J=2.8, 6.4 Hz, 3H). | 563.2 |
| 615 | 4 | ¹H NMR (500 MHz, MeOD) δ 8.75 (s, 1H), 8.11–8.11 (d, J = 0.6 Hz, 1H), 7.91 (s, 1H), 6.66 (s, 1H), 5.62–5.57 (m, 1H), 5.10–5.05 (m, 4H), 4.10–4.07 (m, 1H), 3.58–3.55 (dd, J = 9.4, 5.2 Hz, 1H), 3.45–3.42 (m, 1H), 3.41 (s, 3H), 3.17–3.12 (m, 1H), 2.05–2.02 (m, 2H), 1.90–1.87 (m, 2H), 1.82–1.68 (m, 4H), 1.61–1.54 (m, 2H), 1.29–1.28 (d, J = 6.6 Hz, 3H), 0.96–0.93 (t, J = 7.5 Hz, 3H). | 455.3 |
| 616 | 4 | ¹H NMR (500 MHz, MeOD): δ 8.75 (s, 1H), 8.11–8.11 (d, J = 0.5 Hz, 1H), 7.91 (s, 1H), 6.66 (s, 1H), 5.63–5.57 (m, 1H), 5.10–5.05 (m, 4H), 4.11–4.06 (m, 1H), 3.58–3.55 (dd, J = 9.4, 5.2 Hz, 1H), 3.45–3.42 (dd, J = 9.4, 5.8 Hz, 1H), 3.40 (s, 3H), 3.13–3.07 (m, 1H), 1.95–1.89 (m, 4H), 1.80–1.76 (dt, J = 13.6, 2.5 Hz, 2H), 1.55–1.48 (m, 4H), 1.29–1.28 (d, J = 6.6 Hz, 3H), 0.98–0.95 (t, J = 7.5 Hz, 3H). | 455.2 |
| 617 | 4 | ¹H NMR (500 MHz, MeOD) δ 8.75 (s, 1H), 8.12–8.11 (d, J = 0.6 Hz, 1H), 7.91 (s, 1H), 6.66 (s, 1H), 5.63–5.57 (m, 1H), 5.10–5.05 (m, 4H), 4.11–4.04 (m, 1H), 3.59–3.56 (dd, J = 9.4, 5.2 Hz, 1H), 3.45–3.39 (m, 4H), 3.11–3.05 (tt, J = 11.6, 4.0 Hz, 1H), 1.98–1.86 (m, 4H), 1.79–1.76 (m, 2H), 1.65–1.55 (m, 3H), 1.29–1.28 (d, J = 6.6 Hz, 3H), 0.98–0.97 (d, J = 6.9 Hz, 6H). | 469.4 |

FIG. 2 (Cont'd)

| No. | General Scheme | NMR | MS |
|---|---|---|---|
| 618 | 4 | $^1$H NMR (500 MHz, MeOD) δ 8.75 (s, 1H), 8.12 (s, 1H), 7.91 (s, 1H), 6.69 (s, 1H), 5.63–5.57 (m, 1H), 5.10–5.05 (m, 4H), 4.11–4.07 (m, 1H), 3.57–3.54 (dd, J = 9.4, 5.3 Hz, 1H), 3.46 – 3.43 (m, 1H), 3.41 (s, 3H), 3.24–3.19 (tt, J = 9.8, 3.9 Hz, 1H), 2.13–2.09 (m, 1H), 2.04–2.02 (m, 4H), 1.93–1.84 (m, 2H), 1.51–1.46 (m, 2H), 1.29–1.28 (d, J = 6.6 Hz, 3H), 0.96–0.95 (d, J = 6.7 Hz, 6H). | 469.4 |
| 619 | 6 | $^1$H NMR (400 MHz, CD$_3$OD) δ 8.98 (s, 1H), 8.46 (d, J = 5.2 Hz, 1H), 7.91 (d, J = 1.5 Hz, 1H), 7.50 (dd, J = 5.3, 1.7 Hz, 1H), 6.91 (s, 1H), 4.17 – 3.97 (m, 1H), 3.70 – 3.62 (m, 1H), 3.59 (dd, J = 9.4, 5.3 Hz, 1H), 3.47 – 3.43 (m, 1H), 3.42 (s, 3H), 3.18 – 3.05 (m, 1H), 2.26 – 2.17 (m, 2H), 2.16 – 2.02 (m, 2H), 1.78 – 1.61 (m, 2H), 1.59 (s, 6H), 1.53 – 1.40 (m, 2H), 1.30 (d, J = 6.6 Hz, 3H). | 440.2 |
| 620 | 4 | $^1$H NMR (400 MHz, CD$_3$OD) δ 8.78 (s, 1H), 8.14 (s, 1H), 7.88 (s, 1H), 6.67 (s, 1H), 4.09 (dd, J = 12.0, 6.1 Hz, 1H), 3.69 – 3.54 (m, 3H), 3.47 – 3.40 (m, 3H), 3.18 – 2.67 (m, 6H), 2.34 (d, J = 11.4 Hz, 1H), 2.14 (dd, J = 33.3, 12.3 Hz, 4H), 1.96 – 1.58 (m, 10H), 1.36 (ddd, J = 30.3, 26.3, 12.2 Hz, 8H), 1.15 (s, 1H). | 540.2 |
| 621 | 4 | $^1$H NMR (400 MHz, CD$_3$OD) δ 8.78 (s, 1H), 8.09 (d, J = 0.6 Hz, 1H), 7.85 (d, J = 0.5 Hz, 1H), 6.65 (s, 1H), 4.08 (dd, J = 12.0, 6.0 Hz, 1H), 3.69 – 3.55 (m, 3H), 3.46 – 3.39 (m, 4H), 3.15 – 3.02 (m, 2H), 2.95 (s, 2H), 2.13 (dd, J = 29.9, 10.8 Hz, 4H), 1.83 (d, J = 24.4 Hz, 6H), 1.51 (ddd, J = 35.4, 33.8, 10.3 Hz, 8H), 1.29 (d, J = 6.6 Hz, 3H), 1.16 (s, 3H). | 554.2 |
| 622 | 6 | $^1$H NMR (400 MHz, CD$_3$OD) δ 8.78 (s, 1H), 8.15 (d, J = 0.7 Hz, 1H), 7.91 (d, J = 0.7 Hz, 1H), 6.67 (s, 1H), 4.08 (dt, J = 12.5, 6.3 Hz, 1H), 3.91 – 3.79 (m, 2H), 3.70 – 3.55 (m, 2H), 3.50 – 3.39 (m, 4H), 3.19 – 3.02 (m, 2H), 2.12 (ddd, J = 14.3, 12.8, 2.7 Hz, 4H), 1.81 (d, J = 2.3 Hz, 6H), 1.71 – 1.56 (m, 2H), 1.44 (td, J = 13.0, 2.2 Hz, 2H), 1.36 – 1.24 (m, 6H). | 526.4 |
| 623 | 4 | $^1$H NMR (400MHz, CD$_3$OD) δ 8.73 (s, 1H), 8.08 (s, 1H), 7.79 (s, 1H), 7.58 - 7.54 (m, 1H), 6.63 (s, 1H), 4.14 - 4.01 (m, 1H), 3.70 - 3.54 (m, 2H), 3.46 - 3.39 (m, 4H), 3.16 - 3.01 (m, 1H), 2.22 - 2.13 (m, 5H), 2.11 (br s, 8H), 1.71 - 1.54 (m, 2H), 1.52 - 1.37 (m, 2H), 1.29 (d, J = 6.8, 3H). | 494.2 |
| 624 | 1 | $^1$H NMR (400MHz, CD$_3$OD) δ 8.80 (s, 1H), 8.13 (s, 1H), 7.92 (s, 1H), 7.46 - 7.30 (m, 1H), 6.67 (s, 1H), 5.65 - 5.57 (m, 1H), 5.14 - 5.05 (m, 4H), 4.14 - 4.05 (m, 1H), 3.61 - 3.50 (m, 2H), 3.48 - 3.42 (m, 1H), 3.41 - 3.37 (m, 3H), 3.20 - 3.04 (m, 1H), 2.86 - 2.75 (m, 3H), 2.40 - 2.31 (m, 1H), 2.18 - 2.06 (m, 1H), 1.29 (d, J = 6.8 Hz, 3H). | 449.4 |
| 625 | 5 | $^1$H NMR(400MHz, CD$_3$OD) δ 8.80 (s, 1 H), 8.25(s, 1 H), 7.90 (s, 1 H), 6.67 (s, 1 H), 4.14-4.05 (m, 1 H), 3.71-3.57 (m, 2 H), 3.48 - 3.42 (m, 4 H), 3.17 - 3.06 (m, 1 H), 2.75-2.71 (s, 3 H), 2.23 – 2.16 (m, 10 H), 1.71 – 1.58 (m, 2 H), 1.53 – 1.40 (m, 2 H), 1.33 - 1.29 (d, J=6.8 Hz, 3 H). | 511.2 |

FIG. 2 (Cont'd)

| No. | General Scheme | NMR | MS |
|---|---|---|---|
| 626 | 4 | ¹H NMR (400MHz, CD₃OD) δ 9.17 (s, 1H), 8.50 (s, 1H), 8.10 (s, 1H), 7.28 (s, 1H), 4.43 - 4.26 (m, 1H), 3.72 - 3.61 (m, 1H), 3.52 - 3.34 (m, 2H), 3.26 - 3.08 (m, 3H), 3.06 - 2.91 (m, 2H), 2.86 (s, 3H), 2.84 - 2.69 (m, 1H), 2.58 - 2.38 (m, 1H), 2.22 - 2.08 (m, 4H), 1.87 (s, 6H), 1.78 - 1.60 (m, 2H), 1.55 - 1.39 (m, J=6.8 Hz, 5H). | 577.3 |
| 627 | 4 | ¹H NMR (400MHz, DMSO-$d_6$) δ 9.15 (s, 1H), 8.7 (d, J=5.6 Hz, 1H), 8.17 (d, J=1.3 Hz, 1H), 8.05 -7.60 (m, 1H), 7.17 (s, 1H), 6.94 (d, J=7.6 Hz, 1H), 4.63 (d, J=4.4 Hz, 1H), 4.06 -3.96 (m, 1H), 3.55 - 3.43 (m, 2H), 3.31 (d, J=1.2 Hz, 6H), 3.04 - 2.94 (m, 1H), 2.12 - 1.90 (m, 4H), 1.68 - 1.47 (m, 2H), 1.40 - 1.14 (m, 6H). | 460.2 |
| 628 | 4 | ¹H NMR (400 MHz, CD₃OD) δ 8.70 (s, 1H), 8.05 (s, 1H), 7.77 (s, 1H), 6.81 - 6.72 (m, 1H), 6.59 (s, 1H), 4.13 - 4.00 (m, 1H), 3.69 - 3.50 (m, 2H), 3.44 - 3.38 (m, 4H), 3.11 - 2.94 (m, 1H), 2.33 - 2.24 (m, 3H), 2.20 - 2.00 (m, 10H), 1.67 - 1.34 (m, 4H), 1.28 (d, J = 6.8 Hz, 3H). | 494.3 |
| 629 | 4 | ¹H NMR (500 MHz, MeOD) δ 8.86 (s, 1H), 8.11 (d, J = 5.3 Hz, 1H), 6.99 – 6.89 (m, 2H), 6.83 (s, 1H), 4.17 – 4.01 (m, 1H), 3.87 – 3.75 (m, 4H), 3.65 (tt, J = 10.9, 4.2 Hz, 1H), 3.58 (dd, J = 9.5, 5.3 Hz, 1H), 3.55 – 3.48 (m, 4H), 3.43 (dd, J = 9.5, 6.0 Hz, 1H), 3.16 – 3.03 (m, 1H), 2.26 – 2.13 (m, 2H), 2.13 – 2.05 (m, 2H), 1.70 – 1.54 (m, 2H), 1.53 – 1.36 (m, 2H), 1.30 (d, J = 6.6 Hz, 3H). | 470.2 |
| 630 | 4 | ¹H NMR (500 MHz, MeOD) δ 8.74 (s, 1H), 8.10 (s, 1H), 7.90 (s, 1H), 6.63 (s, 1H), 5.63 – 5.52 (m, 1H), 5.12 – 5.03 (m, 4H), 4.11 – 4.02 (m, 1H), 3.70 – 3.60 (m, 1H), 3.57 (dd, J = 9.4, 5.2 Hz, 1H), 3.42 (dd, J = 9.4, 5.9 Hz, 1H), 3.12 – 3.00 (m, 1H), 2.20 – 2.12 (m, 2H), 2.12 – 2.06 (m, 2H), 1.69 – 1.55 (m, 2H), 1.50 – 1.38 (m, 2H), 1.29 (d, J = 6.6 Hz, 3H). | 430.2 |
| 631 | 6 | ¹H NMR (400 MHz, CD₃OD) δ 8.75 (s, 1H), 8.15 (s, 1H), 7.82 (s, 1H), 6.64 (s, 1H), 4.08 (dd, J = 12.1, 5.7 Hz, 1H), 3.78 – 3.72 (m, 3H), 3.69 – 3.55 (m, 3H), 3.49 – 3.40 (m, 6H), 3.11 (d, J = 20.0 Hz, 2H), 2.21 – 2.04 (m, 8H), 1.99 (s, 1H), 1.92 (s, 1H), 1.63 (d, J = 10.1 Hz, 2H), 1.44 (d, J = 13.1 Hz, 2H), 1.29 (d, J = 6.6 Hz, 3H). | 566.3 |
| 632 | 4 | ¹H NMR (500 MHz, MeOD) δ 8.88 (s, 1H), 8.00–7.99 (d, J = 5.6 Hz, 1H), 6.94–6.92 (dd, J = 5.6, 1.5 Hz, 1H), 6.84 (s, 1H), 6.58 (s, 1H), 4.12–4.09 (m, 1H), 4.01–3.99 (d, J = 8.6 Hz, 2H), 3.95–3.93 (d, J = 8.4 Hz, 2H), 3.68–3.62 (m, 1H), 3.60–3.57 (dd, J = 9.4, 5.3 Hz, 1H), 3.45–3.41 (m, 4H), 3.14–3.08 (tt, J = 12.1, 3.5 Hz, 1H), 2.20–2.17 (m, 2H), 2.11–2.09 (m, 2H), 1.70–1.57 (m, 5H), 1.49–1.42 (m, 2H), 1.30–1.49 (d, J = 6.6 Hz, 3H). | 467.4 |

FIG. 2 (Cont'd)

| No. | General Scheme | NMR | MS |
|---|---|---|---|
| 633 | 4 | $^1$H NMR (500 MHz, MeOD) δ 8.87 (s, 1H), 8.05–8.04 (d, J = 5.4 Hz, 1H), 6.96 (s, 1H), 6.87–6.86 (dd, J = 5.4, 1.3 Hz, 1H), 6.83 (s, 1H), 4.13–4.07 (m, 1H), 3.78–3.74 (m, 1H), 3.68–3.57 (m, 3H), 3.45–3.41 (m, 4H), 3.15–3.08 (tt, J = 12.1, 3.5 Hz, 1H), 2.20–2.18 (m, 2H), 2.11–2.09 (m, 2H), 1.94–1.87 (m, 1H), 1.75–1.61 (m, 5H), 1.49–1.42 (m, 2H), 1.30–1.29 (d, J = 6.7 Hz, 3H), 1.26 (s, 3H). | 495.3 |

PYRROLOTRIAZINE COMPOUNDS AND METHODS OF INHIBITING TAM KINASES

CROSS-REFERENCE TO RELATED APPLICATION

This application is a U.S. National Phase Application under 35 U.S.C. § 371 of International Application No. PCT/US2018/055070, filed Oct. 9, 2018, which claims the benefit of the filing date of U.S. Provisional Application No. 62/570,381, filed Oct. 10, 2017, the entire contents of each of which is hereby incorporated by reference herein.

BACKGROUND

The TAM receptor tyrosine kinases (TYRO3, AXL and MERTK; the "TAM kinases") constitute a family of receptor tyrosine kinases (RTKs) that play several important roles in normal macrophage physiology, including regulation of cytokine secretion and clearance of apoptotic cells. TAM kinases have also been suggested as emerging targets in cancer therapy (see, e.g., Akalu et al., *Immunol. Rev.* 276 (1):165-177, 2017).

SUMMARY

The present disclosure provides compounds represented by structural Formula I:

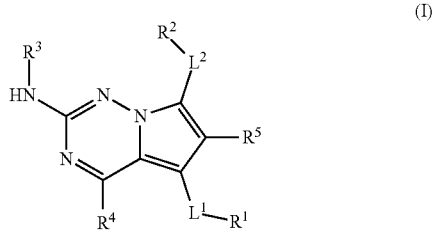

(I)

or a pharmaceutically acceptable salt thereof, wherein:
$L^1$ is a bond, —O—, —S(O)$_2$—, —N(R$^6$)—, —N(R$^6$)—C(O)—*, —C(O)—N(R$^6$)—*, —N(R$^6$)—S(O)$_2$—*, —S(O)$_2$—N(R$^6$)—*, —O—C(O)—*, —C(O)—O—*, —O—C(O)—N(R$^6$)—*, —NR$^6$—C(O)—NR$^6$—*, or —(C$_1$-C$_6$ alkyl)-P(O)—*, wherein "*" is a point of attachment to $R^1$;
$R^1$ is hydrogen, —C$_1$-C$_6$ alkyl, —(C$_0$-C$_6$ alkylene)-aryl, —(C$_0$-C$_6$ alkylene)-heteroaryl, —(C$_0$-C$_6$ alkylene)-heterocyclyl, or —(C$_0$-C$_6$ alkylene)-carbocyclyl, wherein any alkyl or alkylene portion of $R^1$ is optionally substituted with up to six (e.g., 1, 2, 3, 4, 5, or 6) independently selected monovalent substituents and any aryl, heteroaryl, heterocyclyl, or carbocyclyl portion of $R^1$ is optionally substituted with up to four (e.g., 1, 2, 3, or 4) independent substituents;
$L^2$ is a bond, —O—, —S(O)$_2$—, —N(R)—, —N(R)—C(O)-†, C(O)—N(R$^6$)-†, —N(R$^6$)—S(O)$_2$-†, —S(O)$_2$—N(R$^6$)-†, —O—C(O)-†, —O—C(O)—N(R$^6$)-†, —N(R$^6$)—C(O)—NR$^6$-†, or —(C$_1$-C$_6$ alkyl)-P(O)-†, wherein "†" is a point of attachment to $R^2$; $R^2$ is hydrogen, —C$_1$-C$_6$ alkyl, —(C$_0$-C$_6$ alkylene)-aryl, —(C$_0$-C$_6$ alkylene)-heteroaryl, —(C$_0$-C$_6$ alkylene)-heterocyclyl, or —(C$_0$-C$_6$ alkylene)-carbocyclyl, wherein any alkyl or alkylene portion of $R^2$ is optionally substituted with up to six (e.g., 1, 2, 3, 4, 5, or 6) independently selected monovalent substituents and any aryl, heteroaryl, heterocyclyl, or carbocyclyl portion of $R^1$ is optionally substituted with up to four (e.g., 1, 2, 3, or 4) independently selected substituents;
$R^3$ is hydrogen, —C$_1$-C$_8$ alkyl, —C$_2$-C$_8$ alkenyl, —C$_2$-C$_8$ alkynyl, —(C$_2$-C$_6$ alkylene)-O—(C$_1$-C$_6$ alkyl), —(C$_0$-C$_8$ alkylene)-aryl, —(C$_0$-C$_8$ alkylene)-carbocyclyl, —(C$_0$-C$_8$ alkylene)-heterocyclyl, or —(C$_0$-C$_8$ alkylene)-heteroaryl, wherein any alkyl, alkenyl, alkynyl or alkylene portion of $R^3$ is optionally substituted with up to six (e.g., 1, 2, 3, 4, 5, or 6) independently selected monovalent substituents and any aryl, heteroaryl, heterocyclyl, or carbocyclyl portion of $R^3$ is optionally substituted with up to four (e.g., 1, 2, 3, or 4) independently selected substituents;
$R^4$ is hydrogen, halogen, —CN, a 4- to 8-membered heterocyclyl, —C$_1$-C$_6$ alkyl, —C$_1$-C$_6$ haloalkyl, —C$_3$-C$_8$ cycloalkyl, —O—(C$_1$-C$_6$ alkyl), —O—(C$_1$-C$_6$ haloalkyl) or —O—(C$_3$-C$_8$ cycloalkyl), where the cycloalkyl and heterocyclyl are optionally substituted with up to 4 independently selected substituents;
$R^5$ is hydrogen, halogen, —CN, a 4- to 8-membered heterocyclyl, —C$_1$-C$_6$ alkyl, —C$_1$-C$_6$ haloalkyl, —C$_3$-C$_8$ cycloalkyl, —O—(C$_1$-C$_6$ alkyl), —O—(C$_1$-C$_6$ haloalkyl), or —O—(C$_3$-C$_8$ cycloalkyl), where the cycloalkyl and heterocyclyl are optionally substituted with up to 4 independently selected substituents; and
$R^6$ is hydrogen, —C$_1$-C$_6$ alkyl, aryl, heteroaryl, heterocyclyl, or carbocyclyl, wherein $R^6$ is optionally substituted with up to four independently selected substituents.

In some embodiments, a compound and/or composition described herein may be used to inhibit a TAM kinase, at least at a site of interest (e.g., in a tissue, in a cell, in a subcellular location, etc.). In some embodiments, a provided compound and/or composition may be used to inhibit cell proliferation. In some embodiments, a provided compound and/or composition may be used to inhibit activity of one or more kinases, such as a kinase of the TAM kinase family. In some embodiments, a provided compound and/or composition may be used to inhibit an activity of one or more kinases, such as MERTK, AXL and TYRO3. In some embodiments, a provided compound and/or composition has increased specificity for TAM kinases relative to FLT3. In some embodiments, a provided compound and/or composition may be used to inhibit TAM kinases and does not inhibit FLT3 (e.g., does not substantially inhibit FLT3).

In some embodiments, a provided compound and/or composition is contacted with and/or administered to cells, such as cancer cells. In some embodiments, the cancer cells may be cells of a breast cancer, ovarian cancer, glioblastoma, pancreatic ductal adenocarcinoma, non-small cell lung cancer (NSCLC), colorectal cancer (CRC), a blood cancer (e.g., a leukemia or lymphoma), gastric cancer, prostate cancer, pituitary adenoma, melanoma or rhabdomyosarcoma. In some embodiments, the compound and/or composition is administered to a cancer resistant to a checkpoint inhibitor. In some embodiments, a provided compound and/or composition is co-administered with a checkpoint inhibitor. In some embodiments, a provided compound and/or composition is administered to a cancer associated with elevated myeloid infiltration.

BRIEF DESCRIPTION OF THE DRAWINGS

FIG. 2 is a table showing the $^1$H NMR spectra peak values, the mass spectrometry values, and the general synthetic schemes utilized to make each of the compounds in FIG. 1.

DETAILED DESCRIPTION

Figure 1:
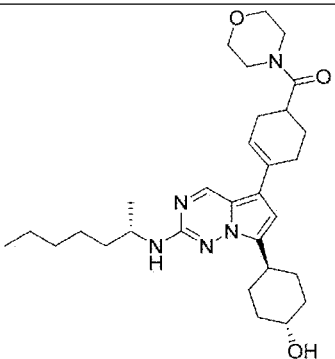
FIG. 1 is a table of exemplary compounds of Formula I.
Figure 1:
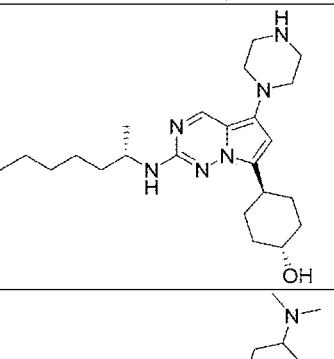
Figure 1:
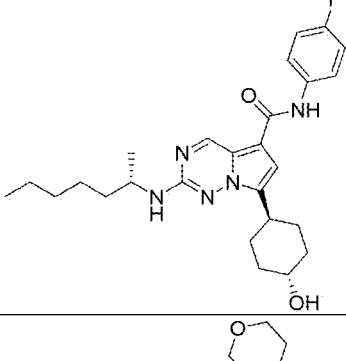
Figure 1:
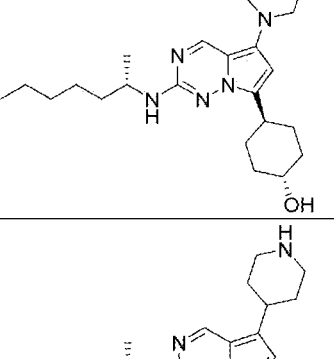
Figure 1:
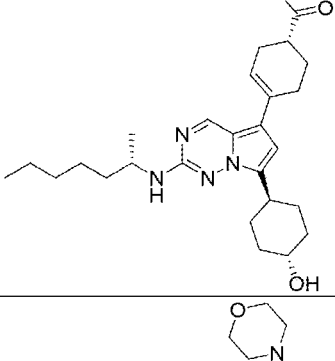
Figure 1:
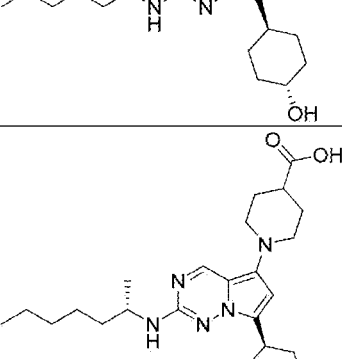
Figure 1:
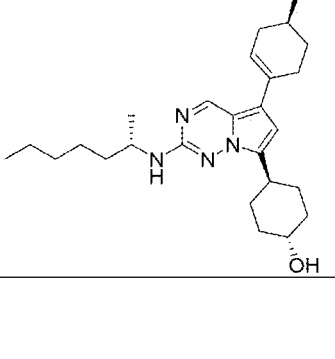
Figure 1:
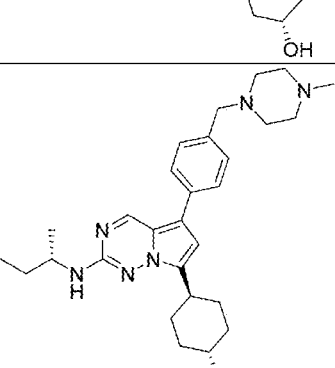
Figure 1:
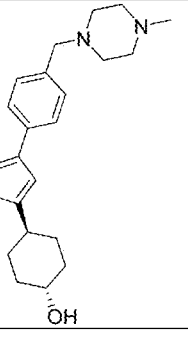
Figure 1:
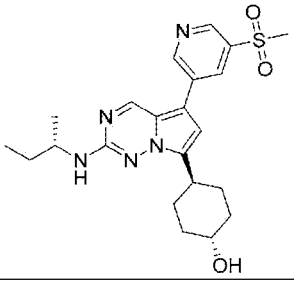
Figure 1:
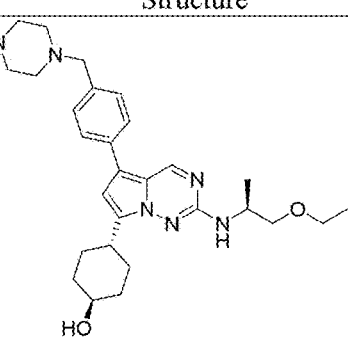
Figure 1:
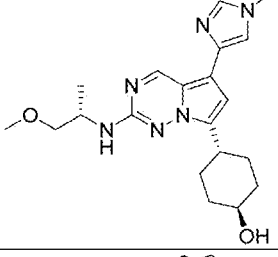
Figure 1:
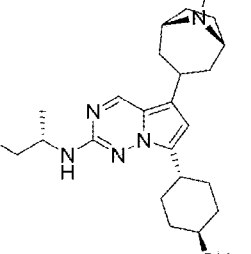
Figure 1:
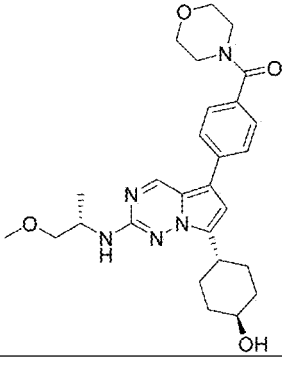
Figure 1:
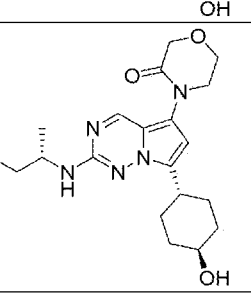
Figure 1:
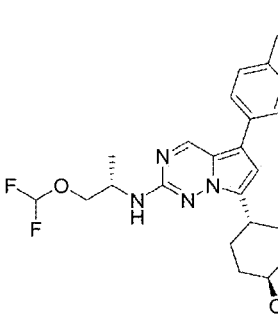
Figure 1:
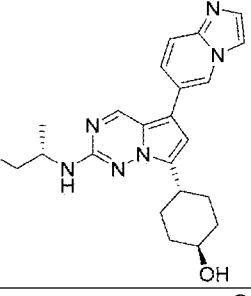
Figure 1:
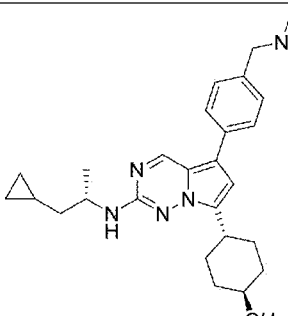
Figure 1:
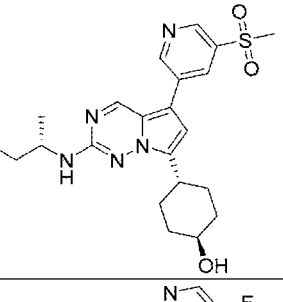
Figure 1:
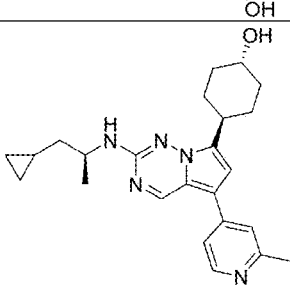
Figure 1:
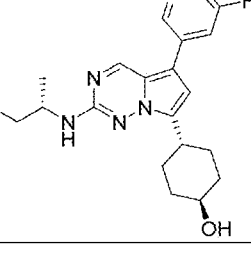
Figure 1:
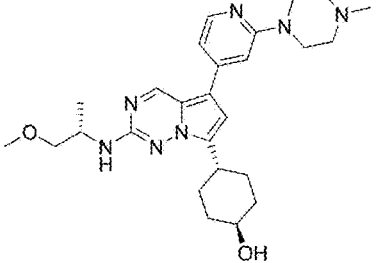
Figure 1:
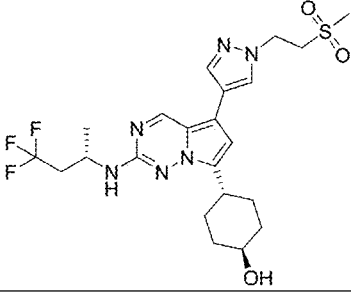
Figure 1:
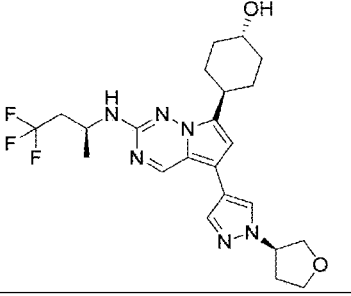
Figure 1:
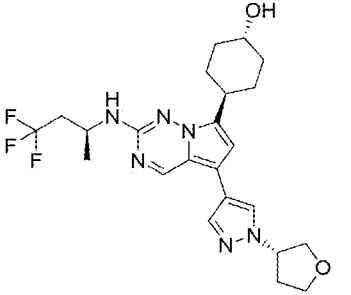
Figure 1:
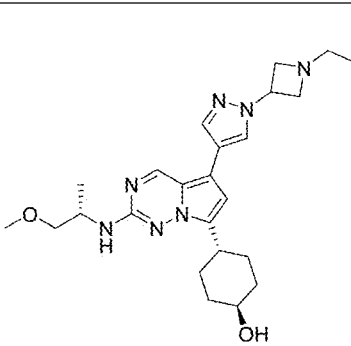
Figure 1:
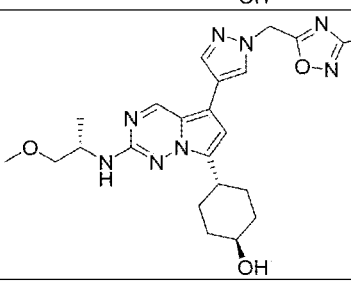
Figure 1:
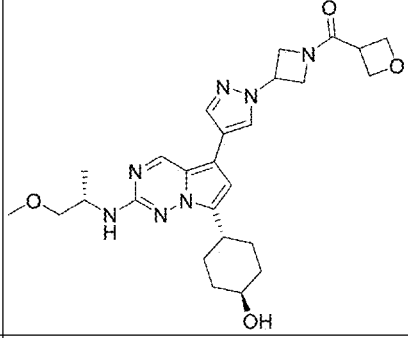
Figure 1:
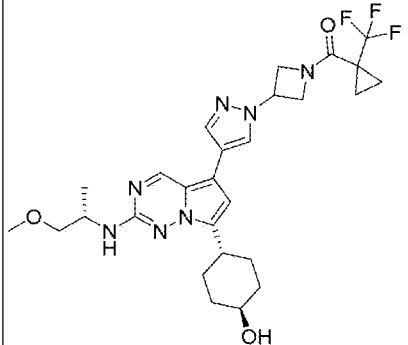
Figure 1:
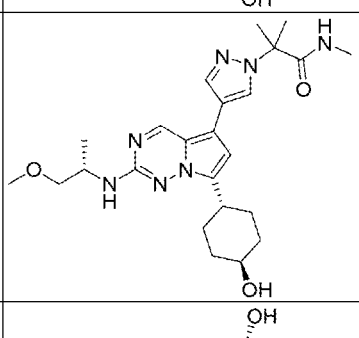
Figure 1:
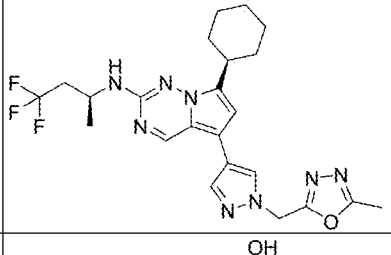
Figure 1:
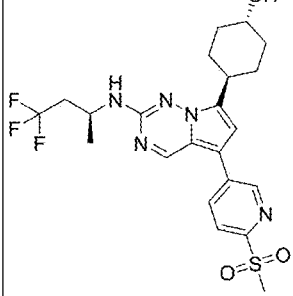
Figure 1:
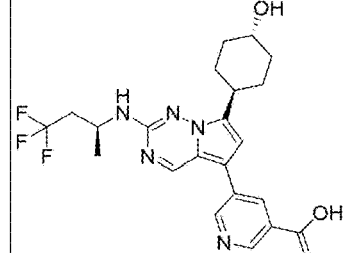
Figure 1:
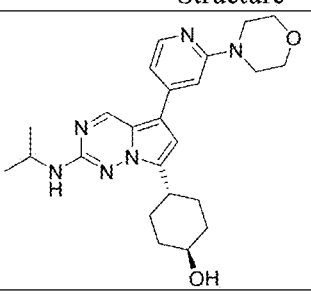
Figure 1:
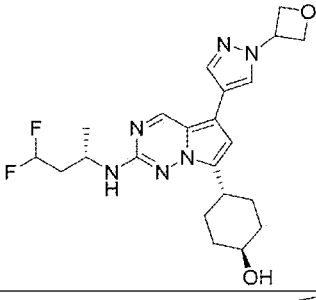
Figure 1:
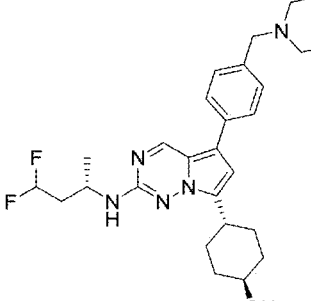
Figure 1:
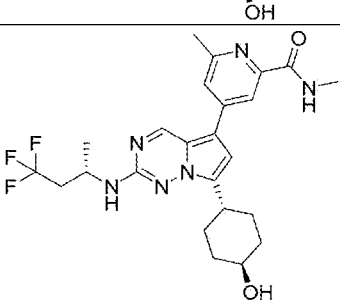
Figure 1:
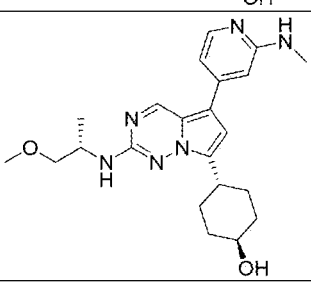
Figure 1:
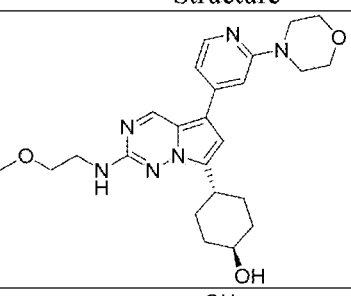
Figure 1:
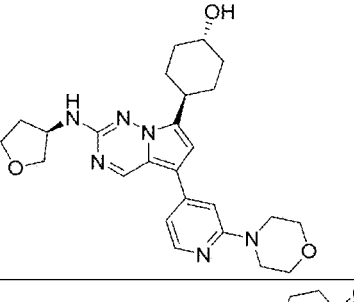
Figure 1:
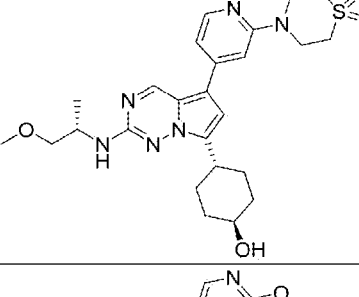
Figure 1:
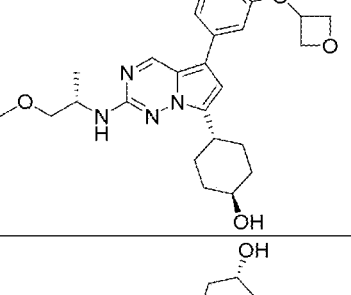
Figure 1:
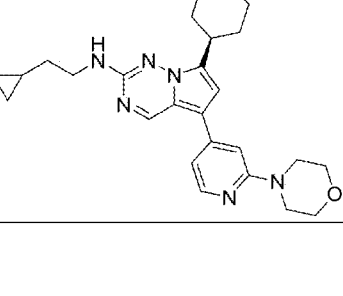
Figure 1:
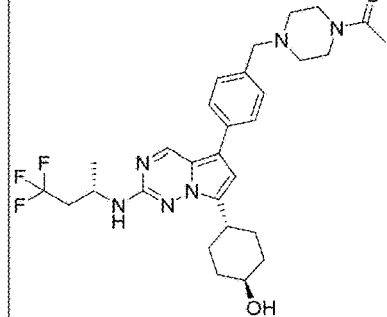
Figure 1:
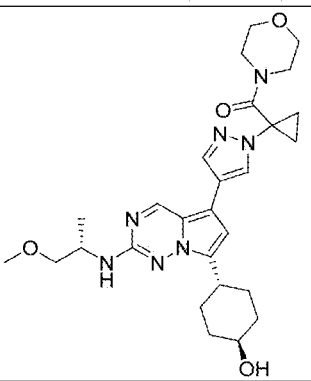
Figure 1:
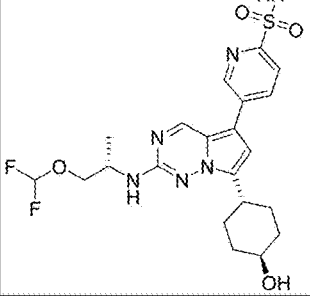
Figure 1:
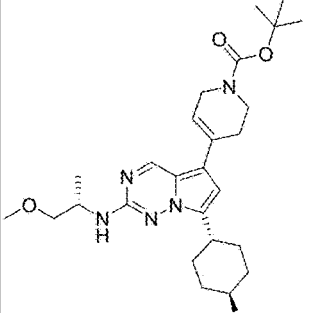
Figure 1:
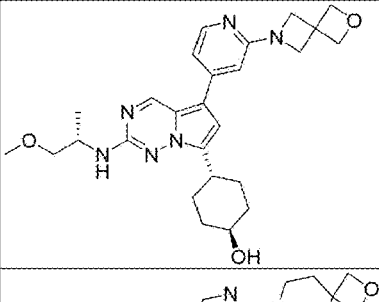
Figure 1:
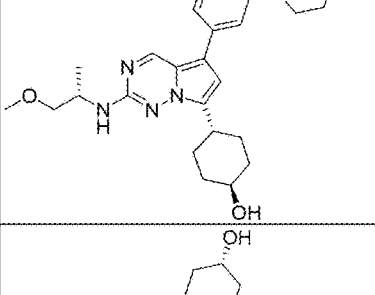
Figure 1:
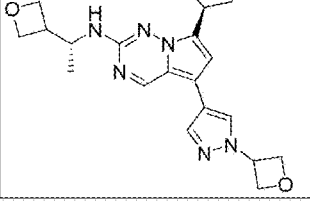
Figure 1:
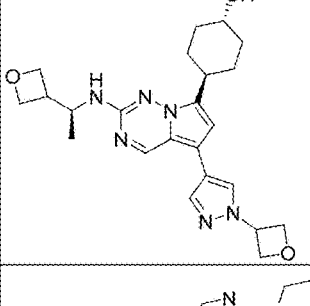
Figure 1:
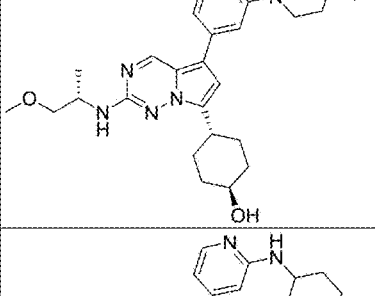
Figure 1:
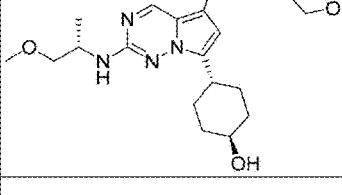
Figure 1:
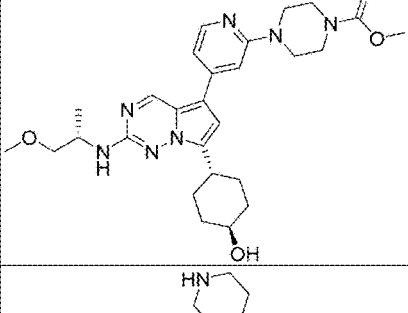
Figure 1:
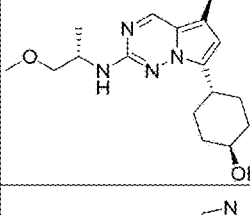
Figure 1:
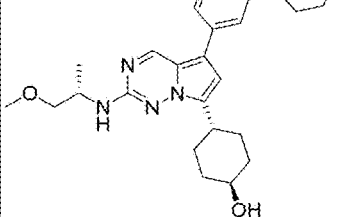
Figure 1:
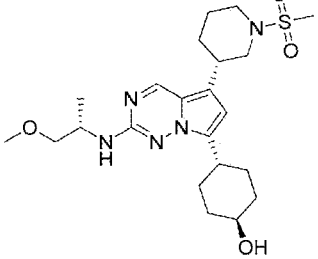
Figure 1:
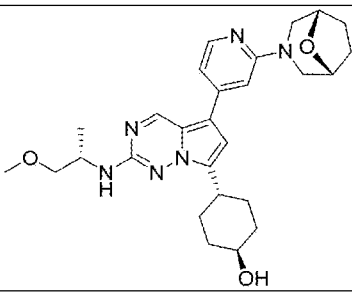
Figure 1:
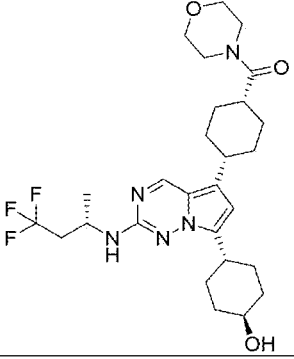
Figure 1:
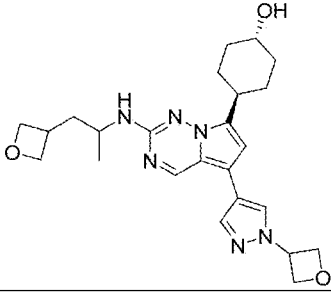
Figure 1:
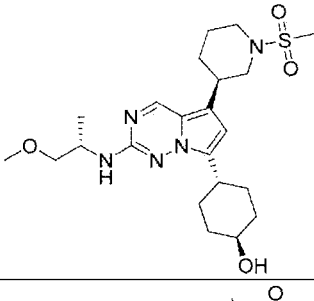
Figure 1:
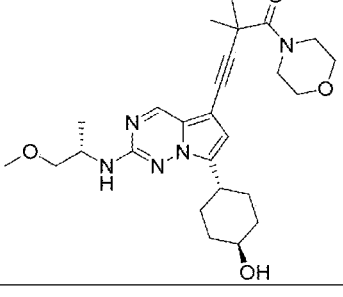
Figure 1:
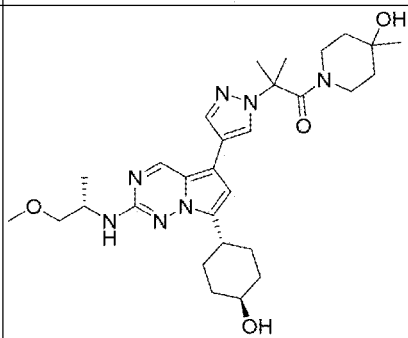
Figure 1:
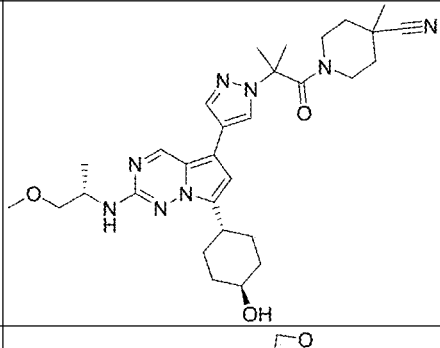
Figure 1:
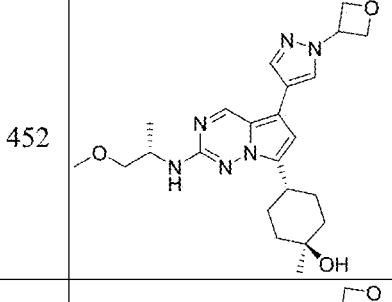
Figure 1:
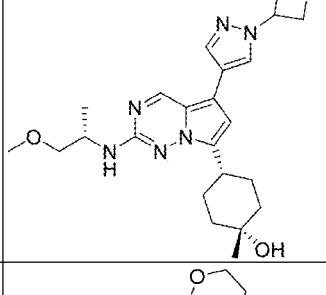
Figure 1:
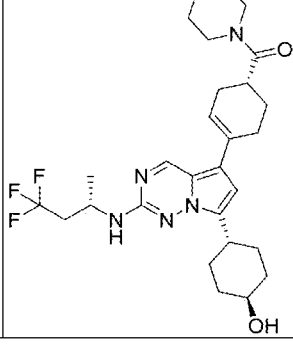
Figure 1:
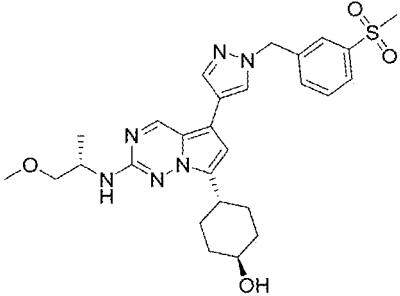
Figure 1:
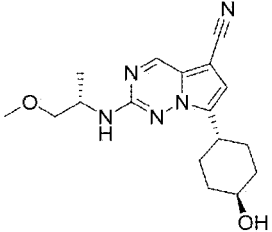
Figure 1:
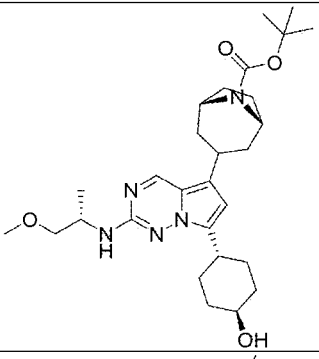
Figure 1:
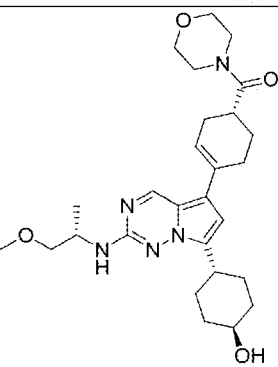
Figure 1:
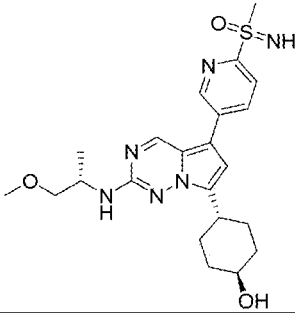
Figure 1:
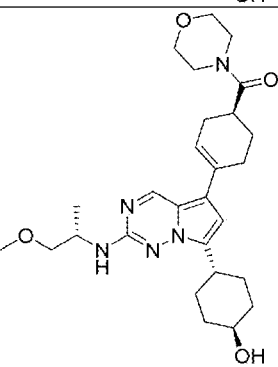
Figure 1:
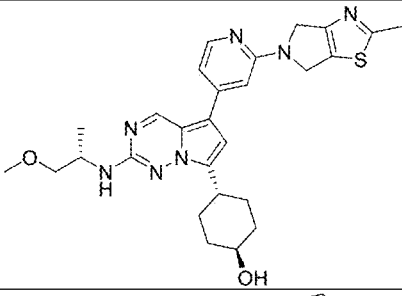
Figure 1:
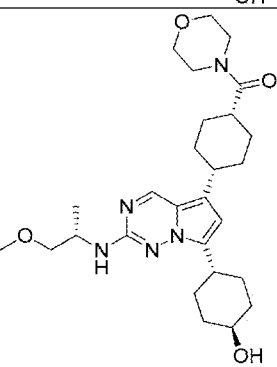
Figure 1:
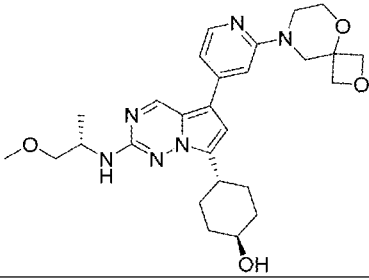
Figure 1:
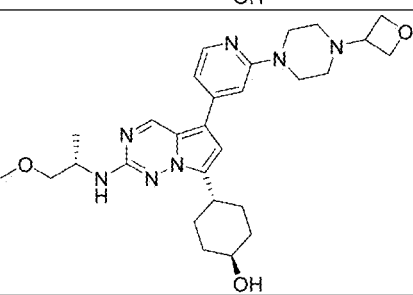
Figure 1:
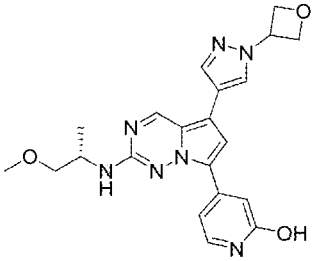
Figure 1:
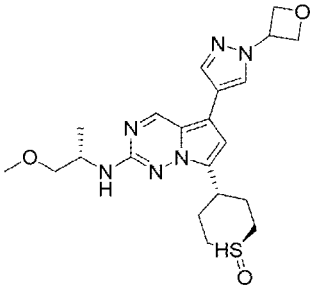
Figure 1:
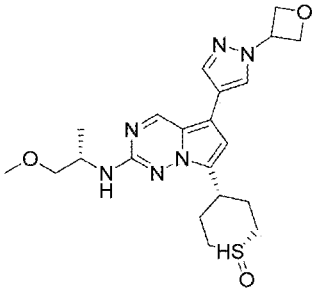
Figure 1:
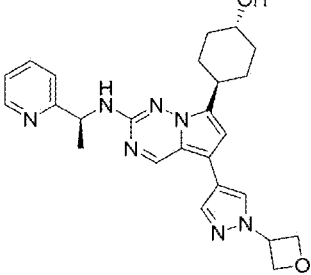
Figure 1:
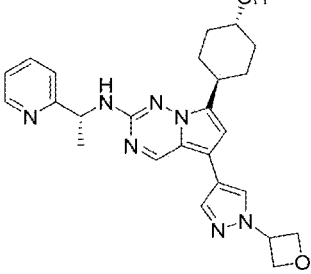
Figure 1:
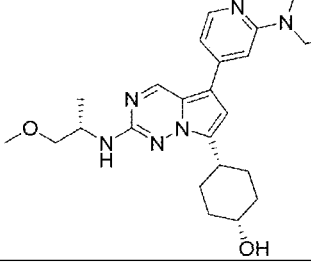
Figure 1:
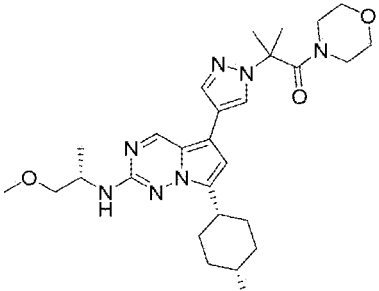
Figure 1:
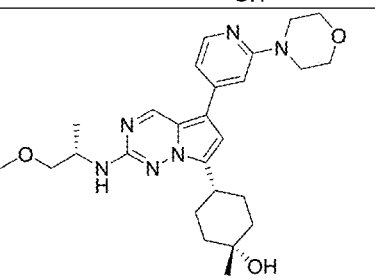
Figure 1:
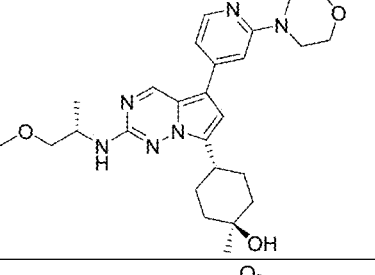
Figure 1:
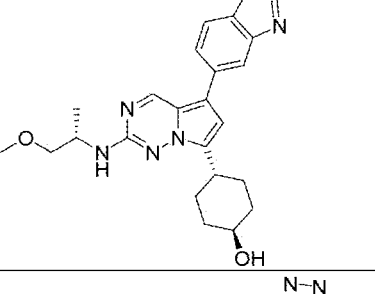
Figure 1:
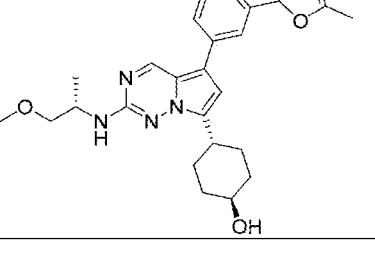
Figure 1:
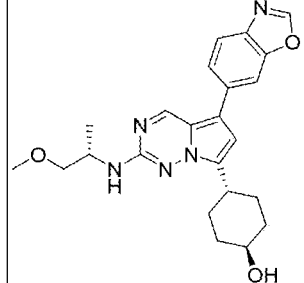
Figure 1:
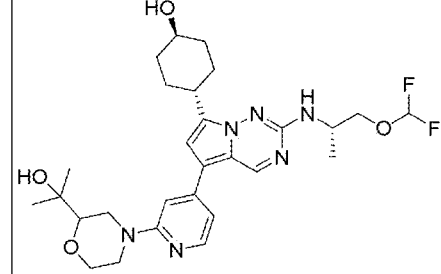
Figure 1:
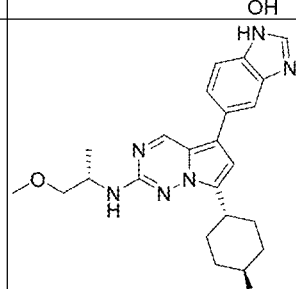
Figure 1:
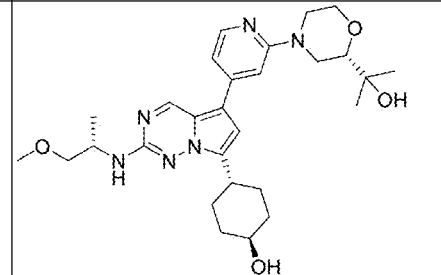
Figure 1:
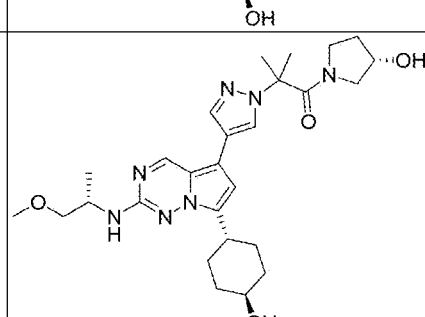
Figure 1:
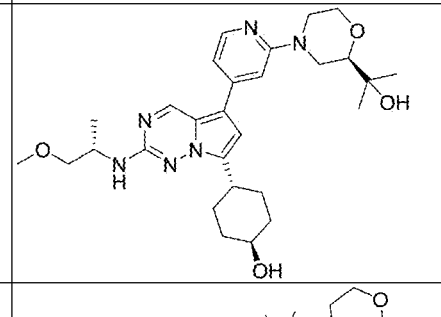
Figure 1:
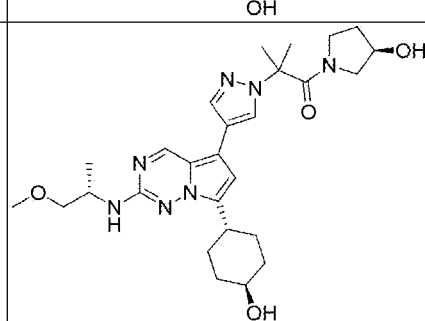
Figure 1:
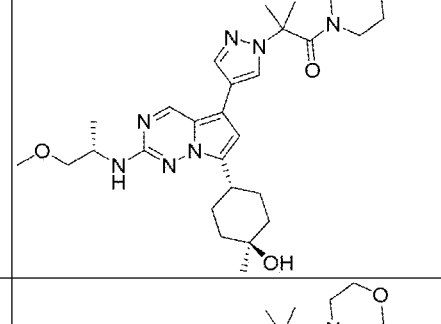
Figure 1:
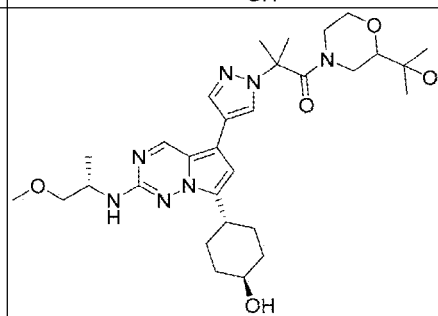
Figure 1:
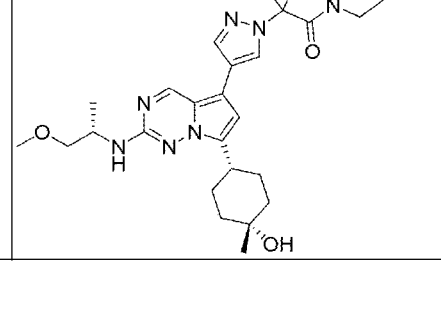
Figure 1:
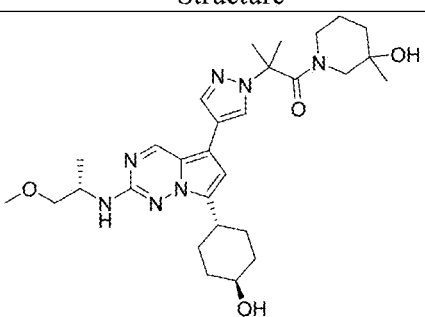

The "TAM receptors" (named for TYRO3, AXL, and MERTK) are a family of receptor tyrosine kinases (RTKs) that play important roles in normal macrophage physiology, including regulation of cytokine secretion and clearance of apoptotic cells. The TAM kinases are characterized by two immunoglobulin-like domains, which mediate ligand-binding, and two fibronectin type III domains at the extracellular N-terminus; by a single-pass transmembrane domain; and by a cytoplasmic tail containing a tyrosine kinase domain. TAM kinases are expressed in many systems, including the nervous, reproductive, vascular, and immune systems (Rothlin et al., *Annu. Rev. Immunol.* 33:355-391, 2015). Expression within the immune system is heterogeneous among macrophage subsets, being mostly restricted to anti-inflammatory M2 macrophages, which contribute to the immunosuppression present in the tumor microenvironment. By inhibiting TAM kinases on tumor-infiltrating macrophages, the immunosuppressive environment can be reduced, thereby increasing effector killer immune cell function and promoting tumor regression.

Current CD8+ T cell- and natural killer (NK) cell-directed immunotherapies have shown promise but only in a limited percentage of patients. The reason for this limitation is not well understood, but it may be that the immunosuppressive environment is inhibiting efficacy. Since M2 macrophages contribute significantly to this environment, reversing the M2 phenotype may increase responsiveness to CD8+ T cell- and NK cell-directed immunotherapies. Therefore, we expect the TAM kinase inhibitors disclosed herein to be useful in treating cancers where checkpoint inhibitors have shown limited efficacy, and particularly where there is high myeloid infiltration. Methods of using the TAM kinase inhibitors disclosed herein, alone or in combination with checkpoint inhibitors, to treat cancer, including pancreatic ductal adenocarcinomas, ovarian cancers, triple-negative breast cancers (TNBCs), glioblastomas, and colorectal cancers, are within the scope of the invention and are discussed further below.

In addition to the expression profiles referenced above, over- or ectopic expression of one or more TAM kinases has been reported in multiple human cancer types, including brain cancer (e.g., glioblastoma), breast cancer (e.g., TNBC), colon and colorectal cancers, gastric cancer, leukemias, liver cancer, lung cancer (e.g., NSCLC), lymphomas, ovarian cancer, pituitary adenomas, prostate cancer, renal cancer, rhabdomyosarcomas, skin cancer (e.g., melanoma), and thyroid malignancies (see, e.g., Graham et al., *Nature Reviews Cancer* $_{14}$(12):769-785, 2014 and Linger et al., *Adv. Cancer Res.* 100:35, 2008). The overexpression of MERTK in at least some cancer cells results in increased survival and resistance to apoptosis, resulting in oncogenesis (Nguyen et al., *J. Biol. Chem.* 289(37):25737-25749, 2014; and Linger et al., *Blood* 122(9):1599-1609, 2013). Elevated TAM kinase expression has also been associated with cancer progression, resistance to targeted therapies, and metastasis (see, e.g., Debruyne et al., *Oncogene* 35(28):3681-3691, 2016; Giles et al., *Mol. Cancer Ther.* 12(11):2541-2558, 2013; and Meyer et al., *Sci. Signal.* 6(287), 2013). At least one report has indicated TAM kinase signaling in NK cells promotes metastasis (Paolino et al., *Nature* 407(7493):508-512, 2014). While the compositions and methods of the invention are not limited to those that achieve a beneficial therapeutic outcome by any particular mechanism of action, it may be that at least some of the anti-tumoral activity results from inhibition of TAM kinase signaling on NK cells.

The following definitions apply to the compositions and methods described herein unless the context clearly indicates otherwise. It will be clear to one of ordinary skill in the art that the definitions apply to grammatical variants of these terms, some of which are particularly mentioned below (e.g., "administration" and "administering"). The chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito, 1999, and "March's Advanced Organic Chemistry," 5$^{th}$ Ed., Ed. Smith and March, John Wiley & Sons, New York, 2001.

The term "about," when used in reference to a value, signifies any value or range of values within plus-or-minus 10% of the stated value (e.g., within plus-or-minus 1%, 2%, 3%, 4%, 5%, 6%, 7%, 8%, 9% or 10% of the stated value). For example, a dose of about 10 mg means any dose as low as 10% less than 10 mg (9 mg), any dose as high as 10% more than 10 mg (11 mg), and any dose or dosage range therebetween (e.g., 9-11 mg; 9.1-10.9 mg; 9.2-10.8 mg; and so on).

The term "administration" and variants thereof, such as "administering," typically refer to the administration of a compound described herein or a composition containing it (e.g., a pharmaceutical composition) to a subject (e.g., a human patient) or system (e.g., a cell- or tissue-based system maintained ex vivo). One of ordinary skill in the art will be aware of a variety of routes that may, in appropriate circumstances, be utilized for administration to a subject or system. For example, the route of administration may be oral (i.e., by swallowing a pharmaceutical composition) or parenteral. More specifically, the route of administration can be bronchial (e.g., by bronchial instillation), by mouth (i.e., oral), dermal (which may be or comprise topical application to the dermis or intradermal, interdermal, or transdermal administration), intragastric or enteral (i.e., directly to the stomach or intestine, respectively), intramedullary, intramuscular, intranasal, intraperitoneal, intrathecal, intravenous (or intra-arterial), intraventricular, by application to or injection into a specific organ (e.g., intrahepatic), mucosal (e.g., buccal, rectal, sublingual, or vaginal), subcutaneous, tracheal (e.g., by intratracheal instillation), or ocular (e.g., topical, subconjunctival, or intravitreal). Administration can involve intermittent dosing (e.g., a plurality of doses separated in time) and/or periodic dosing (e.g., doses separated by a common period of time (e.g., every so many hours, daily, weekly, twice per week, etc.)). In other embodiments, administration may involve continuous dosing (e.g., perfusion) for a selected period of time.

The terms "aliphatic" and "aliphatic group" mean a branched, unbranched (i.e., straight-chain) or cyclic hydrocarbon group that is substituted or unsubstituted and either completely saturated or having one or more units of unsaturation. The cyclic aliphatic group is a monocyclic or bicyclic hydrocarbon group that is not aromatic and that has a single point of attachment to the molecule (i.e., compound) of which it is a part. We may refer to such cyclic groups as "cycloaliphatic," "carbocycle," "carbocyclyl," or "cycloalkyl"). Unless otherwise specified, aliphatic groups contain 1-10 aliphatic carbon atoms ("$C_1$-$C_{10}$"). Aliphatic groups in the present compounds can contain, for example, 1-6 aliphatic carbon atoms ("$C_1$-$C_6$"); 1-5 aliphatic carbon atoms ("$C_1$-$C_5$"); 1-4 aliphatic carbon atoms ("$C_1$-$C_4$"); 1-3 aliphatic carbon atoms ("$C_1$-$C_3$"); or 1-2 aliphatic carbon atoms ("$C_1$-$C_2$"). In some embodiments, a cycloaliphatic hydrocarbon group has 3-6 aliphatic carbon atoms ("$C_3$-$C_6$"). Thus, suitable aliphatic groups include, but are not limited to, substituted or unsubstituted alkyl, alkenyl, and alkynyl groups and hybrids thereof such as (cycloalkyl)alkyl, (cycloalkenyl)alkyl and (cycloalkyl)alkenyl.

The term "alkyl" means a branched or unbranched (i.e., straight) chain, saturated, monovalent hydrocarbon group containing 1 to 10 carbon atoms. Suitable alkyl groups include methyl, ethyl, n- and iso-propyl, n-, sec-, iso- and tert-butyl, and neopentyl. The term "alkylene" means a branched or unbranched (i.e., straight chain) bivalent alkyl group. Exemplary alkylenes include —$CH_2$—, —$CH_2CH_2$—, —$CH(CH_3)$—, —$CH_2CH(CH_3)$—, —$CH(CH_3)CH_2$—, etc. In some embodiments, an "alkylene chain" is a polymethylene group, i.e., —$(CH_2)_n$—, wherein n is a positive integer, preferably from 1 to 6 (e.g., 1, 2, 3, 4, 5, or 6, or 1-4, 1-3, 1-2, 2-3, etc.). A substituted alkylene chain is a bivalent alkyl group in which one or more hydrogen atoms are replaced with a substituent.

The term "alkenyl" means a monovalent branched or unbranched (i.e., straight) chain of, unless otherwise specified, 2 to 10 carbon atoms ("$C_2$-$C_{10}$") containing at least one carbon-carbon double bond. Alkenyl groups are exemplified by ethenyl, propenyl, butenyl, pentenyl, hexenyl, and so forth. The term "alkenylene" means a bivalent alkenyl group. A substituted alkenylene chain is a bivalent alkenyl group containing at least one double bond in which one or more hydrogen atoms are replaced with a substituent.

The term "alkynyl" means a monovalent branched or unbranched (i.e., straight) chain of from 2 to 10 carbon atoms ("$C_2$-$C_{10}$") containing at least one carbon-carbon triple bond. Suitable alkynyl groups include ethynyl, propynyl, butynyl, pentynyl, hexynyl, and so forth.

The terms "aryl" and "aryl ring" describe monocyclic, bicyclic and tricyclic ring systems having a total of six to 14 ring atoms, each of which is carbon. Further, at least one ring in the system is aromatic, and each ring in the system contains three to seven ring members. In certain embodiments, these terms refer to an aromatic ring system that includes, but is not limited to, phenyl (Ph), biphenyl, naphthyl, and anthracyl, which may bear one or more substituents. In some embodiments, an aromatic ring is fused to one or more non-aromatic rings (e.g., indanyl, naphthimidyl, and ortetrahydronaphthyl).

Two events or entities are "associated" with one another if one or more features of the first (e.g., its presence, level and/or form) are correlated with a feature of the second. For example, a first entity (e.g., a polypeptide (e.g., a TAM kinase or a combination thereof), gene expression profile, genetic signature (i.e., a single or combined group of genes in a cell with a uniquely characteristic pattern of gene expression), metabolite, or event (e.g., myeloid infiltration)) is associated with a particular disease, if its presence, level and/or form correlates with the incidence of, severity of, and/or susceptibility to the disease (e.g., a cancer disclosed herein). Associations are typically assessed across a relevant population. Two or more entities are physically "associated" with one another if they interact, directly or indirectly, so that they are and/or remain in physical proximity with one another in a given circumstance (e.g., within a cell maintained under physiological conditions (e.g., within cell culture) or within a pharmaceutical composition). Entities that are physically associated with one another can be covalently linked to one another or non-covalently associated by, for example, hydrogen bonds, van der Waals forces, hydrophobic interactions, magnetism, or combinations thereof.

The terms "binding" and variants thereof (such as "bound" and "bind(s)") typically refer to a covalent or non-covalent association of two or more entities (e.g., a compound and an agent within a pharmaceutical composition or a compound and its target within a cell). "Direct" binding occurs when the two entities physically contact one another (e.g., through a chemical bond) whereas indirect binding occurs when at least one of the entities physically contact one or more intermediate entities that bring them into physical proximity with one another (e.g., within a complex). Binding can be assessed in a variety of contexts (e.g., in full or partial isolation or in more complex, naturally occurring or model systems (e.g., in a tissue, organ, or cell)).

The term "biologically active" describes an agent (e.g., a compound described herein) that produces an observable biological effect or result in a biological system or model thereof (e.g., in a human, other animal, or a system maintained in vitro). The "biological activity" of such an agent can result from binding between the agent and a target (e.g., a TAM kinase), and it may result in modulation (e.g., induction, enhancement, or inhibition) of a biological pathway or event (e.g., cellular activity (e.g., immunostimulation) or proliferation). The presence of biological activity and, optionally, its extent, can be assessed using known and/or standard methods to detect an immediate or downstream product or event associated with the biological activity.

The term "biological sample" refers to a sample obtained or derived from a biological source of interest (e.g., a tissue or organism (e.g., an animal or human patient) or cell culture). The biological sample can contain a biological cell, tissue or fluid or any combination thereof. For example, a biological sample can be or can comprise ascites; blood; blood cells; bodily fluid(s), any of which may include or exclude cells; bone marrow; cerebrospinal fluid (CSF); feces; flexural fluid; free floating nucleic acids; gynecological fluids; immune infiltrates; lymph; peritoneal fluid; plasma; saliva; sputum; surgically-obtained specimens; tissue scraped or swabbed from the skin or a mucus membrane (e.g., in the nose, mouth, or vagina); tissue or fine needle biopsy samples; urine; washings or lavages such as a ductal lavage or broncheoalveolar lavage; or other body fluids, tissues, secretions, and/or excretions. A biological sample may include cancer cells or immune cells, such as NK cells and/or macrophages, which are found in many tissues and organs, including the spleen and lymph nodes. Cells (e.g., NK cells, macrophages, and cancer cells) within the sample may have been obtained from an individual for whom a treatment is intended. Samples used in the form in which they were obtained may be referred to as "primary" samples, and samples that have been further manipulated (e.g., by adding or removing one or more components of the sample) may be referred to as "secondary" or "processed" samples. Such processed samples may contain or be enriched for a particular cell type (e.g., a TAM kinase-expressing cell such as a macrophage or tumor cell), cellular component (e.g., a membrane fraction), or cellular material (e.g., one or more cellular proteins, including one or more of the TAM kinases, DNA, or RNA (e.g., mRNA), which may have been subjected to amplification).

The term "cancer" refers to a disease in which cells exhibit an aberrant growth phenotype characterized by loss of control of cell proliferation to an extent that will be detrimental to a patient having the disease. A cancer can be classified by the type of tissue in which it originated (histological type) and/or by the primary site in the body in which the cancer first developed. Based on histological type, cancers are generally grouped into six major categories: carcinomas; sarcomas; myelomas; leukemias; lymphomas; and mixed types. A cancer treated as described herein may be of any one of these types and may comprise cells that are precancerous (e.g., benign), malignant, pre-metastatic, metastatic, and/or non-metastatic. A patient who has a malignancy or malignant lesion has a cancer. The present disclosure specifically identifies certain cancers to which its teachings may be particularly relevant, and one or more of these cancers may be characterized by a solid tumor or by a hematologic tumor, which may also be known as a blood cancer (e.g., a type described herein). Although not all cancers manifest as solid tumors, we may use the terms "cancer cell" and "tumor cell" interchangeably to refer to any malignant cell.

The term "carrier" refers to a diluent, adjuvant, excipient, or other vehicle with which a compound or composition is administered. The carrier can be a sterile or sterilizable liquid, such as a water (e.g., water for injection) or a natural or synthetic oil (e.g., a petroleum-based or mineral oil, an animal oil, or a vegetable oil (e.g., a peanut, soybean, sesame, or canola oil)). The carrier can also be a solid; a liquid that includes one or more solid components (e.g., a salt, for example, a "normal saline"); a mixture of solids; or a mixture of liquids.

The term "comparable" refers to two or more items (e.g., agents, entities, situations, sets of conditions, etc.) that are not identical to one another but are sufficiently similar to permit comparison therebetween so that one of ordinary skill in the art will appreciate that conclusions may reasonably be drawn based on differences or similarities observed. In some embodiments, comparable sets of conditions, circumstances, individuals, or populations are characterized by a plurality of substantially identical features and one or a small number of varied features. One of ordinary skill in the art will understand, in context, what degree of identity is required in any given circumstance for two or more items to be considered comparable. For example, two items are comparable to one another when they have in common a sufficient number and type of substantially identical features to warrant a reasonable conclusion that any differences in results obtained or phenomena observed with the items are caused by or are indicative of the variation in those features that are varied. In some embodiments, a comparable item serves as a "control." For example, a "control subject/population" can be an untreated individual/population who is afflicted with the same disease as an individual/population being treated.

The term "combination therapy" refers to those situations in which a subject is exposed to two or more therapeutic regimens (e.g., two or more therapeutic agents) to treat a single disease (e.g., a cancer). The two or more regimens may be administered simultaneously or sequentially (e.g., all "doses" of a first regimen are administered prior to administration of any dose(s) of a second regimen by the same or a different route of administration). For clarity, combination therapy does not require that individual agents be administered together in a single composition (or even necessarily at the same time), although in some embodiments, two or more agents (e.g., compounds described herein) may be administered together in a single composition or even as a combination compound (e.g., associated in a single chemical complex or covalent entity).

The term "compound" means a chemical compound (e.g., a compound represented by a structural Formula depicted herein, a sub-genus thereof, or a species thereof). Any given compound can be biologically and/or therapeutically active (e.g., when contained in a pharmaceutical composition in a therapeutically effective amount) and can be provided and/or utilized (e.g., used in a biological assay, administered to a patient, incorporated into a medicament, or otherwise used as described herein) in any of a variety of forms: unless the context clearly indicates otherwise, the references herein to a "compound" encompass the compound per se, a stereoisomeric form thereof (e.g., an optical and/or structural isomer), a tautomer, or an isotopic form thereof. The stereoisomers of any referenced or depicted structure can be enantiomers and diastereomers (e.g., cis/trans isomers and conformational isomers). These include the R and S configurations for each asymmetric center, Z and E double bond isomers, and Z and E conformational isomers. Compositions containing a single type of stereochemical isomer as well as enantiomeric, diastereomeric, and geometric (or conformational) mixtures of the present compounds are within the scope of the invention. Where a compound contains an isotopic substitution, it can be, e.g., $^2$H or $^3$H for H; $^{11}$C, $^{13}$C or $^{14}$C for $^{12}$C; $^{13}$N or $^{15}$N for $^{14}$N; $^{17}$O or $^{18}$O for $^{16}$O; $^{36}$C; for $^{35}$C; $^{18}$F for $^{19}$F; $^{131}$I for $^{127}$I; etc. Such compounds have use, for example, as analytical tools, as probes in biological assays, and/or as therapeutic or prophylactic agents for use in accordance with the present invention. In particular, an isotopic substitution of deuterium (2H) for hydrogen is known to potentially slow down metabolism, shift metabolism to other sites on the compound, slow down racemization and/or have other effects on the pharmacokinetics of the compound that may be therapeutically beneficial.

The terms "dosage form," "formulation," and "preparation" are used to refer to compositions containing a compound or other biologically and/or therapeutically active agent that are suitable for administration to a patient. The term "unit dosage form" refers to a physically discrete unit of a compound or other biologically and/or therapeutically active agent (e.g., a therapeutic or diagnostic agent) formulated for administration to a subject. Typically, each such unit contains a predetermined quantity of the active agent, which may be the amount prescribed for a single dose (i.e., an amount expected to correlate with a desired outcome when administered as part of a therapeutic regimen) or a fraction thereof. One of ordinary skill in the art will appreciate that the total amount of a therapeutic composition or agent administered to a particular subject is determined by one or more attending physicians and may involve administration of multiple unit dosage forms.

The term "dosing regimen" refers to the unit dosage form(s) administered to, or prescribed for, a subject, and typically includes more than one dose separated by periods of time (e.g., as described elsewhere herein). The dosage form(s) administered within a dosing regimen can be of the same unit dose amount or of different amounts. For example, a dosing regimen can comprises a first dose in a first dose amount, followed by one or more additional doses in a second dose amount that is the same as or different from the first dose amount.

The term "halogen" means F, Cl, Br, or I.

The term "heteroalkyl" refers to an alkyl group in which one or more carbon atoms is replaced with a heteroatom selected from oxygen (O), sulfur (S), or nitrogen (N).

The term "heteroar-," used alone or as part of a e.g. longer term such as "heteroaryl" or "heteroaryl ring/group," refer to optionally substituted (i.e., substituted or unsubstituted) mono-, bi-, or tricyclic chemical groups having 5 to 14 ring atoms (e.g., 5, 6, or 9 ring atoms); 6, 10, or 14 π electrons shared in a cyclic array; and in addition to carbon atoms, from one to five heteroatoms. A heteroaryl group is both heterocyclic and aromatic and can be, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, and pteridinyl. In a heteroar-, a heteroaryl ring can also be fused to one or more aryl, cycloaliphatic, or heterocyclyl rings (e.g., it can be indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, 5,6,7,8-tetrahydroquinolinyl, 5,6,7,8-tetrahydroisoquinolinyl, and pyrido[2,3-b]-1,4-oxazin-3(4H)-one. When a heteroaryl ring is fused to an aryl ring, the term "heteroaro" is used to refer to that heteroaryl ring.

The term "heteroatom" refers to oxygen, sulfur, nitrogen, phosphorus, and silicon, including any oxidized forms of those atoms; and the quaternized form of any basic nitrogen or a substitutable nitrogen of a heterocyclic ring; for example N (as in 3,4-dihydro-2H-pyrrolyl-

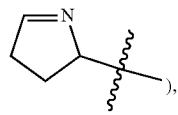 [SMILES: *C1CCC=N1]

NH (as in pyrrolidinyl-

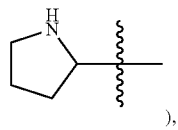

NR^ (as in N-substituted 2-pyrrolidinyl-

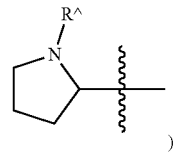

or $^+$NR^ (as in N-substituted 1-pyrrolidinyl-

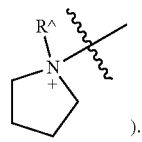

As used immediately above and elsewhere herein, "⁓" appearing across or at the end of a bond indicates a point of attachment between two atoms. For example, in the ring structures just shown, ⁓ indicates that the ring carbon or ring nitrogen is bound to an undepicted structure on which the ring is a substituent.

The terms "heterocycle," "heterocyclyl," and "heterocyclic radical/ring," are used interchangeably and refer to a stable 4- to 7-membered monocyclic, 7-11-membered bicyclic, or 10-16-membered tricyclic heterocyclic chemical structure that is either saturated or partially unsaturated, and that has, in addition to carbon atoms, one or more (e.g., 1-4) heteroatoms, as defined herein. A heterocyclic ring can be attached to its pendant group at any heteroatom or carbon atom that results in a stable structure, and any of the ring atoms can be optionally substituted (i.e., substituted or unsubstituted). As shown above and for example, in a saturated or partially unsaturated ring having 0-3 heteroatoms selected from oxygen, sulfur or nitrogen, the nitrogen moiety may be N (as in 3,4-dihydro-2H-pyrrolyl-), NH (as in pyrrolidinyl-), NR^ (as in N-substituted 2-pyrrolidinyl) or $^+$NR^ (as in N-substituted 1-pyrrolidinyl). Examples of a saturated or partially unsaturated heterocycle include, without limitation, tetrahydrofuranyl, tetrahydrothiophenyl, pyrrolidinyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl, as well as chemical structures in which a heterocyclyl ring is fused to one or more aryl, heterocyclyl, or cycloaliphatic rings (e.g., indolinyl, 3H-indolyl, chromanyl, 1,2,3,4-tetrahydroisoquinolinyl and 1,2,3,4-tetrahydroquinolinyl). When a heterocyclic ring is fused to an aryl ring, we refer to that heterocyclic ring using the term "heterocyclo." A "saturated heterocyclic ring" refers to a saturated ring having one or more heteroatoms, wherein the ring is monocyclic or fused to one or more saturated cycloaliphatic rings.

"Improve(s)," "increase(s)" or "reduce(s)/decrease(s)" are terms used to characterize the manner in which a value has changed relative to a reference value. For example, a measurement obtained from a patient (or a biological sample obtained therefrom) prior to treatment can be increased or reduced/decreased relative to that measurement obtained during or after treatment in the same patient, a control patient, on average in a patient population, or biological sample(s) obtained therefrom. The value may be improved in either event, depending on whether an increase or decrease is associated with a positive therapeutic outcome.

The term "inhibitor" refers to an agent, including a compound described herein, whose presence (e.g., at a certain level or in a certain form) correlates with a decrease in the expression or activity of another agent (i.e., the inhibited agent or target) or a decrease in the occurrence of an event (e.g., tumor progression or metastasis). In some embodiments, an inhibitor exerts its influence on a target by binding to the target, directly or indirectly. In other embodiments, an inhibitor exerts its influence by binding and/or otherwise altering a regulator of the target, so that the expression and/or activity of the target is reduced. Inhibition can be assessed in silico, in vitro (e.g., in a cell, tissue, or organ culture or system), or in vivo (e.g., in a patient or animal model).

A compound described herein can contain one or more "optionally substituted" moieties. By "substituted," we mean that one or more hydrogens of the designated moiety are replaced with a suitable substituent. Unless otherwise indicated, an "optionally substituted" group may have a suitable substituent at each substitutable position of the group, and when more than one position in any given structure is substituted with more than one substituent selected from a specified group, the substituent may be either the same or different at every position. As a designated moiety within an optionally substituted compound may be, but is not necessarily, substituted, such moieties are described as substituted when a suitable substituent is present and "unsubstituted" when any such substituent is absent.

For example, "optionally substituted phenyl" encompasses "substituted phenyl" and "unsubstituted phenyl;" an "optionally substituted alkyl" encompasses "substituted alkyl" and "unsubstituted alkyl;" a substitutable carbon atom may be a "substituted carbon atom" or an "unsubstituted carbon atom;" and so forth. Combinations of substituents are those that result in the formation of stable or chemically feasible compounds. The term "stable" refers to compounds that are not substantially altered when subjected to conditions that allow for their production, detection, and, in certain embodiments, their recovery, purification, and use for one or more of the purposes disclosed herein.

Suitable monovalent substituents on a substitutable carbon atom of an optionally substituted group can be, independently, deuterium, halogen; $-(CH_2)_{0-4}R^{\circ}$; $-(CH_2)_{0-4}OR^{\circ}$; $-O(CH_2)_{0-4}R^{\circ}$; $-O-(CH_2)_{0-4}C(O)OR^{\circ}$; $-(CH_2)_{0-4}CH(OR^{\circ})_2$; $-(CH_2)_{0-4}SR^{\circ}$; $-(CH_2)_{0-4}Ph$, which may be substituted with $R^{\circ}$; $-(CH_2)_{0-4}O(CH_2)_{0-1}Ph$ which may be substituted with $R^{\circ}$; $-CH=CHPh$, which may be substituted with $R^{\circ}$; $-(CH_2)_{0-4}O(CH_2)_{0-1}$-pyridyl which may be substituted with $R^{\circ}$; $-NO_2$; $-CN$; $-N_3$; $-(CH_2)_{0-4}N(R^{\circ})_2$; $-(CH_2)_{0-4}N(R^{\circ})C(O)R^{\circ}$; $-N(R^{\circ})C(S)R^{\circ}$; $-(CH_2)_{0-4}N(R^{\circ})C(O)NR^{\circ}_2$; $-N(R^{\circ})C(S)NR^{\circ}_2$; $-(CH_2)_{0-4}N(R^{\circ})C(O)OR^{\circ}$; $-N(R^{\circ})N(R^{\circ})C(O)R^{\circ}$; $-N(R^{\circ})N(R^{\circ})C(O)NR^{\circ}_2$; $-N(R^{\circ})N(R^{\circ})C(O)OR^{\circ}$; $-(CH_2)_{0-4}C(O)R^{\circ}$; $-C(S)R^{\circ}$; $-(CH_2)_{0-4}C(O)OR^{\circ}$; $-(CH_2)_{0-4}-C(O)-N(R^{\circ})-S(O)_2-R^{\circ}$; $-C(NCN)NR^{\circ}_2$; $-(CH_2)_{0-4}C(O)SR^{\circ}$; $-(CH_2)_{0-4}C(O)OSiR^{\circ}_3$; $-(CH_2)_{0-4}OC(O)R^{\circ}$; $-OC(O)(CH_2)_{0-4}SR^{\circ}$; $SC(S)SR^{\circ}$; $-(CH_2)_{0-4}SC(O)R^{\circ}$; $-(CH_2)_{0-4}C(O)NR^{\circ}_2$; $-C(S)NR^{\circ}_2$; $-C(S)SR^{\circ}$; $-(CH_2)_{0-4}OC(O)NR^{\circ}_2$; $-C(O)N(OR^{\circ})R^{\circ}$; $-C(O)C(O)R^{\circ}$; $-C(O)CH_2C(O)R^{\circ}$; $-C(NOR^{\circ})R^{\circ}$; $-(CH_2)_{0-4}SSR^{\circ}$; $-(CH_2)_{0-4}S(O)_2R^{\circ}$; $-(CH_2)_{0-4}S(O)_2OR^{\circ}$; $-(CH_2)_{0-4}OS(O)_2R^{\circ}$; $-S(O)_2NR^{\circ}_2$; $-(CH_2)_{0-4}S(O)R^{\circ}$; $-N(R^{\circ})S(O)_2NR^{\circ}_2$; $-N(R^{\circ})S(O)_2R^{\circ}$; $-N(OR^{\circ})R^{\circ}$; $-C(NOR^{\circ})NR^{\circ}_2$; $-C(NH)NR^{\circ}_2$; $-P(O)_2R^{\circ}$; $-P(O)R^{\circ}_2$; $-P(O)(OR^{\circ})_2$; $-OP(O)R^{\circ}_2$; $-OP(O)(OR^{\circ})_2$; $-OP(O)(OR^{\circ})R^{\circ}$; $-SiR^{\circ}_3$; $-(C_{1-4}$ straight or branched alkylene)$O-N(R^{\circ})_2$; or $-(C_{1-4}$ straight or branched alkylene)$C(O)O-N(R^{\circ})_2$, wherein each $R^{\circ}$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 3-6-membered saturated, partially unsaturated, or aryl ring having 0-4 heteroatoms independently selected from N, O, or S, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), may be, independently, halogen, $-(CH_2)_{0-2}R^{\bullet}$, $-(haloR^{\bullet})$, $-(CH_2)_{0-2}OH$, $-(CH_2)_{0-2}OR^{\bullet}$, $-(CH_2)_{0-2}CH(OR^{\bullet})_2$, $-O(haloR^{\bullet})$, $-CN$, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-OSiR^{\bullet}_3$, $-C(O)SR^{\bullet}$, $-(C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 independently selected heteroatoms (e.g., N, O, or S). Suitable divalent substituents on a saturated carbon atom of $R^{\circ}$ include $=O$ and $=S$.

Suitable divalent substituents on a saturated carbon atom of an optionally substituted moiety include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, and $-S(C(R^*_2))_{2-3}S-$, wherein each independent occurrence of $R^*$ is selected from hydrogen, $C_{1-6}$ aliphatic, which may be substituted as defined below, or an unsubstituted 5-6-membered saturated, partially unsaturated, or aryl ring having 0-4 independently selected heteroatoms (e.g., N, O, or S). Suitable divalent substituents that are bound to vicinal substitutable carbons of an optionally substituted moiety include: $-O(CR^*_2)_{2-3}O-$, wherein each independent occurrence of $R^*$ is selected from hydrogen, $C_{1-6}$ aliphatic, which may be substituted as defined below, or an unsubstituted 5-6-membered saturated, partially unsaturated, or aryl ring having 0-4 independently selected heteroatoms (e.g., N, O, or S).

Suitable substituents on the aliphatic group of $R^*$ include halogen, $-R^{\bullet}$, -(halo$R^{\bullet}$), $-OH$, $-OR^{\bullet}$, $-O(haloR^{\bullet})$, $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 independently selected heteroatoms (e.g., N, O, or S).

Suitable substituents on a substitutable nitrogen of an "optionally substituted" group include $-R^{\dagger}$, $-NR^{\dagger}_2$, $-C(O)R^{\dagger}$, $-C(O)OR^{\dagger}$, $-C(O)C(O)R^{\dagger}$, $-C(O)CH_2C(O)R^{\dagger}$, $-S(O)_2R^{\dagger}$, $-S(O)_2NR^{\dagger}_2$, $-C(S)NR^{\dagger}_2$, $-C(NH)NR^{\dagger}_2$, or $-N(R^{\dagger})S(O)_2R^{\dagger}$; wherein each $R^{\dagger}$ is independently hydrogen, $C_{1-6}$ aliphatic which may be substituted as defined below, unsubstituted $-OPh$, or an unsubstituted 3-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on an aliphatic group of $R^{\dagger}$ are, independently, halogen, $-R^{\bullet}$, -(halo$R^{\bullet}$), $-OH$, $-OR^{\bullet}$, $-O(haloR^{\bullet})$, $-CN$, $-C(O)OH$, $-C(O)OR^{\bullet}$, $-NH_2$, $-NHR^{\bullet}$, $-NR^{\bullet}_2$, or $-N_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from N, O, or S. Suitable divalent substituents on a saturated carbon atom of $R^{\dagger}$ include $=O$ and $=S$.

"Partially unsaturated" refers to a ring moiety other than an aryl or heteroaryl that includes at least one double or triple bond and may include multiple sites of unsaturation.

A "pharmaceutical composition" is a composition in which an active agent (e.g., an active pharmaceutical ingredient (e.g., a compound) is formulated together with one or more pharmaceutically acceptable carriers. The active agent can be present in a unit dose amount appropriate for administration in a therapeutic regimen that shows a statistically significant probability of achieving a predetermined therapeutic effect when administered to a relevant population. The pharmaceutical composition may be specially formulated for administration in solid or liquid form, including forms made for oral or parenteral administration. For oral administration, the pharmaceutical composition can be formulated, for example, as an aqueous or non-aqueous solution or suspension or as a tablet or capsule. For systemic absorption through the mouth, the composition can be formulated for buccal administration, sublingual administration, or as a paste for application to the tongue. For parenteral administration, the composition can be formulated, for example, as a sterile solution or suspension for subcutaneous, intramuscular, intravenous, intra-arterial, intraperitoneal, or epidural injection. Pharmaceutical compositions comprising an active agent (e.g., a compound described herein) can also be formulated as sustained-release formulations or as a cream, ointment, controlled-release patch, or spray for topical application. Creams, ointments, foams, gels, and pastes can also be applied to mucus membranes lining the nose, mouth, vagina, and rectum. Any of the compounds described herein and any pharmaceutical composition containing such a compound may also be referred to as a "medicament."

The terms "patient" and "subject" refer to any organism to which a compound described herein is administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.). In some embodiments, a subject is suffering from a disease (e.g., a cancer) described herein.

The term "pharmaceutically acceptable," when applied to a carrier used to formulate a composition disclosed herein (e.g., a pharmaceutical composition), means a carrier that is compatible with the other ingredients of the composition and not deleterious to a patient (e.g., it is non-toxic in the amount required and/or administered (e.g., in a unit dosage form)).

The term "pharmaceutically acceptable salt" refers to a salt that is, within the scope of sound medical judgment, suitable for use in contact with the tissues of humans (e.g., patients) and lower animals without unacceptable toxicity, irritation, allergic response and the like, and that can be used in a manner commensurate with a reasonable benefit/risk ratio. Many pharmaceutically acceptable salts are well known in the art (see, e.g., Berge et al., *J. Pharm. Sci.* 66:1-19, 1977; incorporated herein by reference) and, as noted, the invention encompasses pharmaceutically acceptable salt forms of each compound described herein.

A "polypeptide" is a polymer of amino acid residues, regardless of length, source, or post-translational modification; it encompasses but is not limited to full-length, naturally occurring proteins. Where a polypeptide is bound by (e.g., specifically bound) or otherwise interacts with a composition described herein, we may refer to that polypeptide as the composition's "target."

The terms "prevent(s)," "prevention," and "prophylaxis/prophylactic," when used in connection with the occurrence of disease (e.g., a cancer), refer to reducing the risk of developing the disease and/or to delaying the onset of one or more signs or symptoms thereof. Prevention can be considered complete when onset has been delayed for a predefined period of time.

The term "reference" describes a standard or control relative to which a comparison is made. For example, in some embodiments, an agent, animal, cell, individual, population, sample (e.g., biological sample), sequence or value of interest is compared with a reference or control agent, animal, cell, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by one of ordinary skill in the art, a reference or control is determined or characterized under comparable conditions or circumstances to those under assessment, and one of ordinary skill in the art will appreciate when sufficient similarities are present to justify reliance on and/or comparison to a particular possible reference or control.

The term "response" with respect to a treatment may refer to any beneficial alteration in a subject's condition that occurs as a result of, or correlates with, treatment. Such an alteration may include stabilization of the condition (e.g., prevention of deterioration that would have taken place in the absence of the treatment), amelioration of symptoms of the condition, and/or improvement in the prospects for cure of the condition, etc. The response may be a cellular response (e.g., a tumor's response) and can be measured using a wide variety of criteria, including clinical criteria and objective criteria, known in the art. Techniques for assessing a response include, but are not limited to, assay assessment, clinical examination, positron emission tomography, X-ray, CT scan, MRI, ultrasound, endoscopy, laparoscopy, assessing the presence or level of tumor markers in a sample obtained from a subject, cytology, and/or histology. Regarding measuring tumor response, methods and guidelines for assessing response to treatment are discussed in Therasse et al. (*J. Natl. Cancer Inst.*, 92(3):205-216, 2000). The exact response criteria can be selected by one of ordinary skill in the art in any appropriate manner, provided that when comparing groups of cancers and/or patients, the groups to be compared are assessed based on the same or comparable criteria for determining response rate.

The term "specific," as used herein with reference to an agent (e.g., a compound) having an activity (e.g., inhibition of a target), means that the agent discriminates between potential target entities or states. For example, an agent binds "specifically" to its intended target (or otherwise specifically inhibits its target) if it preferentially binds or otherwise inhibits the expression or activity of that target in the presence of one or more alternative targets. Although the invention is not so limited, a specific and direct interaction can depend upon recognition of a particular structural feature of the target (e.g., an epitope, a cleft, or a binding site). Specificity need not be absolute; the degree of specificity need only be enough to result in an effective treatment without unacceptable side effects. The specificity of an agent can be evaluated by comparing the effect of the agent on an intended target or state relative to its effect on a distinct target or state. The effects on the intended and distinct targets can each be determined or the effect on the intended target can be determined and compared to a reference standard developed at an earlier time (e.g., a reference specific binding agent or a reference non-specific binding agent). In some embodiments, the agent does not detectably bind the competing alternative target under conditions in which it detectably (and, preferably, significantly) binds its intended target and/or does not detectably inhibit the expression or activity of the competing target under conditions in which it detectably (and, preferably, significantly) inhibits the expression or activity of its intended target. In some embodiments, a compound of the invention may exhibit, with respect to its target(s), a higher on-rate, lower off-rate, increased affinity, decreased dissociation, and/or increased stability compared with the competing alternative target, and any of these parameters can be assessed in methods of the invention.

The term "substantially" refers to the qualitative condition of exhibiting a characteristic or property of interest to a total or near-total extent or degree. One of ordinary skill in the art will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. For example, a chemical reaction may be characterized as substantially complete even though the yield is well below 100%. Certain features may also be described as being "substantially identical," meaning they are about the same and/or exhibit about the same activity. For example, two nearly identical compounds that produce about the same effect on an event (e.g., cellular proliferation) may be described as substantially similar. With regard to the purity of a compound or composition, "substantially pure" is defined below.

An individual who is "susceptible to" a disease (e.g., a cancer) has a greater than average risk for developing the disease. In some embodiments, such an individual does not display any symptoms of the disease. In some embodiments, such an individual has not been diagnosed with the disease. In some embodiments, such an individual has been exposed to conditions associated with development of the disease (e.g., exposure to a carcinogen). In some embodiments, a risk of developing a disease is a population-based risk.

A "sign or symptom is reduced" when one or more objective signs or subjective symptoms of a particular disease are reduced in magnitude (e.g., intensity, severity, etc.) and/or frequency. A delay in the onset of a particular sign or symptom is one form of reducing the frequency of that sign or symptom. Reducing a sign or symptom can be achieved by, e.g., a "therapeutically active" compound.

A "therapeutic regimen" refers to a dosing regimen that, when administered across a relevant population, is correlated with a desired therapeutic outcome.

A "therapeutically effective amount" refers to an amount that produces the desired effect for which it is administered. In some embodiments, the term refers to an amount that is sufficient, when administered to a population suffering from or susceptible to a disease in accordance with a therapeutic dosing regimen, to treat the disease. One of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount measured in one or more specific tissues (e.g., a tissue affected by the disease) or fluids (e.g., blood, saliva, urine, etc.).

The term "treatment" (also "treat(s)" or "treating") refers to any use of a pharmaceutical composition or administration of a therapy that partially or completely alleviates, ameliorates, relives, inhibits, reduces the severity of, and/or reduces incidence of one or more signs or symptoms of a particular disease (e.g., a cancer). In some embodiments, such treatment may be of a subject who exhibits only early signs or symptoms of the disease. Alternatively or additionally, such treatment may be of a subject who exhibits one or more established signs or symptoms of the relevant disease. In some embodiments, treatment may be of a subject who has been diagnosed as suffering from the relevant disease. The term "treatment" is distinguished from "prophylaxis," which relates, for example, to delaying onset of one or more signs or symptoms of the particular disease and/or to administration to a subject who does not exhibit signs of the relevant disease and/or to a subject known to have one or more susceptibility factors that are statistically correlated with increased risk of development of the relevant disease.

The term "unsaturated," as used herein with regard to a compound or a moiety therein, means that the compound or the moiety therein has one or more units of unsaturation (e.g., a carbon-carbon double bond (i.e., —C═C—) or a carbon-carbon triple bond (i.e., —C≡C—)).

As described herein, compounds within the present invention can have a structure represented by Formula I:

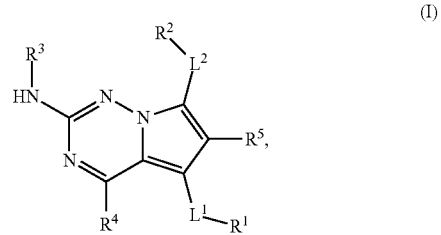

(stated more simply, "a compound of Formula I"), wherein each of $L^1$, $R^1$, $L^2$, $R^2$, $R^3$, $R^4$, and $R^5$ is as defined herein and further described in classes and subclasses, both singly and in combination.

In some embodiments, when $L^2$ is a bond and $R^2$ is aryl or heteroaryl, $R^3$ is other than optionally substituted phenyl, and the compound is other than:

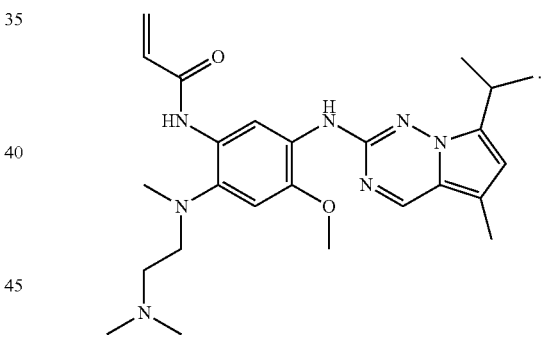

In some embodiments, $L^1$ is a bond, —O—, —S(O)$_2$—, —N(R$^6$)—, —N(R$^6$)—C(O)—*, —C(O)—N(R$^6$)—*, —N(R$^6$)—S(O)$_2$—*, —S(O)$_2$—N(R$^6$)—*, —O—C(O)—*, —C(O)—O—*, —O—C(O)—N(R$^6$)—*, —NR$^6$—C(O)—NR$^6$—*, or —(C$_1$-C$_6$ alkyl)-P(O)—*, wherein "*" is a point of attachment to $R^1$. In some embodiments, $L^1$ is a bond.

In some embodiments, $R^1$ is hydrogen, C$_1$-C$_6$ alkyl, —(C$_0$-C$_6$ alkylene)-aryl, —(C$_0$-C$_6$ alkylene)-heteroaryl, —(C$_0$-C$_6$ alkylene)-heterocyclyl, or —(C$_0$-C$_6$ alkylene)-carbocyclyl, wherein any alkyl or alkylene portion of $R^1$ is optionally substituted with up to six independently selected monovalent substituents and any aryl, heteroaryl, heterocyclyl, or carbocyclyl portion of $R^1$ is optionally substituted with up to four independent substituents. In some embodiments, $R^1$ is heteroaryl (e.g., —(C$_0$ alkylene)-heteroaryl) substituted with one to four independent substituents.

In some embodiments, $L^2$ is a bond, —O—, —S(O)$_2$—, —N(R$^6$)—, —N(R$^6$)—C(O)-†, C(O)—N(R)-†, —N(R$^6$)—S(O)$_2$-†, —S(O)$_2$—N(R$^6$)—†, —O—C(O)-†, —C(O)—N ($R^6$)—†, —N($R^6$)—C(O)—$NR^6$-†, or —($C_1$-$C_6$ alkyl)-P(O)-†, wherein "†" is a point of attachment to $R^2$.

In some embodiments, $R^2$ is hydrogen, $C_1$-$C_6$ alkyl, —($C_0$-$C_6$ alkylene)-aryl, —($C_0$-$C_6$ alkylene)-heteroaryl, —($C_0$-$C_6$ alkylene)-heterocyclyl, or —($C_0$-$C_6$ alkylene)-carbocyclyl, wherein any alkyl or alkylene portion of $R^2$ is optionally substituted with up to six (e.g., 1, 2, 3, 4, 5, or 6) independently selected monovalent substituents and any aryl, heteroaryl, heterocyclyl, or carbocyclyl portion of $R^1$ is optionally substituted with up to four independent substituents. In some compounds of these embodiments, $R^2$ is aryl (e.g., —($C_0$ alkylene)-aryl), heteroaryl (e.g., —($C_0$ alkylene)-heteroaryl), -heterocyclyl (e.g., —($C_0$ alkylene)-heterocyclyl), or carbocyclyl (e.g. —($C_0$ alkylene)-carbocyclyl), where any aryl, heteroaryl, heterocyclyl, or carbocyclyl is optionally substituted with up to four independent substituents.

In some embodiments, $R^3$ is hydrogen, —$C_1$-$C_8$ alkyl, —$C_2$-$C_8$ alkenyl, —$C_2$-$C_8$ alkynyl, —($C_2$-$C_6$ alkylene)-O—($C_1$-$C_6$ alkyl), —($C_0$-$C_8$ alkylene)-aryl, —($C_0$-$C_8$ alkylene)-carbocyclyl, —($C_0$-$C_8$ alkylene)-heterocyclyl, or —($C_0$-$C_8$ alkylene)-heteroaryl, wherein any alkyl, alkenyl, alkynyl or alkylene portion of $R^3$ is optionally substituted with up to six (e.g., 1, 2, 3, 4, 5, or 6) independently selected monovalent substituents and any aryl, heteroaryl, heterocyclyl, or carbocyclyl portion of $R^3$ is optionally substituted with up to four independent substituents. In some compounds, $R^3$ is $C_2$-$C_4$ alkyl, ($C_2$-$C_4$ alkylene)-O—($C_1$-$C_3$ alkyl), —($C_0$-$C_4$ alkylene)-aryl, —($C_0$-$C_4$ alkylene)-carbocyclyl, —($C_0$-$C_4$ alkylene)-heterocyclyl, or —($C_0$-$C_4$ alkylene)-heteroaryl, where any alkyl, alkenyl, alkynyl or alkylene portion of $R^3$ is optionally substituted with up to six independently selected monovalent substituents; and any aryl, heteroaryl, heterocyclyl, or carbocyclyl portion of $R^3$ is optionally substituted with up to four independent substituents.

In some embodiments, $R^4$ is hydrogen, halogen, —CN, a 4- to 8-membered heterocyclyl, —$C_1$-$C_6$ alkyl, —$C_1$-$C_6$ haloalkyl, —$C_3$-$C_8$ cycloalkyl, —O—($C_1$-$C_6$ alkyl), —O—($C_1$-$C_6$ haloalkyl) or —O—($C_3$-$C_8$ cycloalkyl), wherein the cycloalkyl and heterocyclyl is optionally substituted with up to four independently selected substituents. In some embodiments, $R^4$ is hydrogen.

In some embodiments, $R_5$ is hydrogen, halogen, —CN, a 4- to 8-membered heterocyclyl, —$C_1$-$C_6$ alkyl, —$C_1$-$C_6$ haloalkyl, $C_3$-$C_8$ cycloalkyl, —O—($C_1$-$C_6$ alkyl), —O—($C_1$-$C_6$ haloalkyl), or —O—($C_3$-$C_8$ cycloalkyl), wherein the cycloalkyl and heterocyclyl is optionally substituted with up to 4 independently selected substituents. In some embodiments, $R_5$ is hydrogen.

In some embodiments, $R^6$ is hydrogen, —$C_1$-$C_6$ alkyl, aryl, heteroaryl, heterocyclyl, or carbocyclyl, wherein $R^6$ is optionally substituted with up to four independent substituents. In some embodiments, $R^6$ is hydrogen or —$C_1$-$C_4$ alkyl.

In some embodiments, $L^1$ is a bond, —NH—, —O—, or —C(O)—NH—*. In some embodiments, $L^1$ is a bond.

In some embodiments, $R^1$ is carbocyclyl, heterocyclyl, heteroaryl, aryl, or $C_1$-$C_6$ alkyl; and, in any one or more of these embodiments, $R^1$ can be optionally substituted.

In some embodiments, $R^1$ is methyl, cyclopentyl, cyclohexyl, cyclohex-3-en-4-yl, phenyl, piperidin-4-yl, piperazin-1-yl, piperidin-1-yl, piperidin-4-yl, pyridin-3-yl, pyrrolidin-3-yl, 3,6-dihydro-2H-pyran-4-yl, tetrahydro-2H-pyran-4-yl, or 1,2,3,6-tetrahydropyridin-4-yl; and in any one or more of these embodiments, $R^1$ can be optionally substituted.

In some embodiments, $R^1$ is piperidin-3-yl, pyrazol-3-yl, pyrazol-4-yl, 1,2,3-triazol-4-yl, imidazol-4-yl, isoindolin-4-yl, isoindolin-5-yl, pyridin-2-yl, pyridin-4-yl, pyrimdin-5-yl, oxazol-5-yl, indolin-5-yl, indolin-6-yl, indol-6-yl, pyridazin-5-yl, pyrrolidin-1-yl, morpholin-4-yl, 2-oxa-6-azaspiro[3.4]octan-6-yl, 8-azabicyclo[3.2.1]oct-2-ene-3-yl, 8-azabicyclo[3.2.1]octan-3-yl, thien-3-yl, thien-2-yl, 3,6-dihydropyridin-4-yl, benzo[d]imidazol-5-yl, benzo[d]oxazol-5-yl, benzo[d]oxazol-6-yl, isoxazol-4-yl, or imidazo[1,2-a]pyridin-6-yl; and in any one or more of these embodiments, $R^1$ is optionally substituted.

In some embodiments, $R^1$ is pyrazol-4-yl, or pyridin-4-yl, wherein $R^1$ is substituted with fluoro, —CN; $C_1$-$C_4$ alkyl optionally substituted with one or more substitutents selected from cyano, hydroxy, and halo; —($C_0$-$C_3$ alkylene)-COOH, —O—($C_1$-$C_3$ alkylene)-O—($C_1$-$C_4$ alkyl), —($C_1$-$C_3$ alkylene)-O—($C_1$-$C_4$ alkyl), —O—($C_1$-$C_4$ alkyl), —($C_0$-$C_4$ alkylene)-S(O)$_2$—($C_1$-$C_3$ alkyl), —S(O)(=NH)—($C_1$-$C_4$ alkyl), —C(O)NH$_2$, —($C_0$-$C_3$ alkylene)-C(O)—NH—($C_1$-$C_4$ alkyl), —($C_0$-$C_3$ alkylene)-C(O)—O—($C_1$-$C_4$ alkyl), —($C_0$-$C_3$ alkylene)-C(O)—($C_1$-$C_4$ alkyl), —($C_0$-$C_3$ alkylene)-C(O)—NH—S(O)$_2$—($C_1$-$C_4$ alkyl), —NH—($C_1$-$C_4$ alkyl), —S(O)$_2$—NH—($C_1$-$C_4$ alkyl), -(cyclopropyl)-C(O)—NH—($C_1$-$C_4$ alkyl), -(cyclopropyl)-(cyano-substituted $C_1$-$C_3$ alkyl), —($C_0$-$C_4$ alkylene)-aryl, —($C_0$-$C_4$ alkylene)-heteroaryl, —O-heteroaryl, —($C_0$-$C_4$ alkylene)-heterocyclyl, —($C_0$-$C_3$ alkylene)-C(O)-heterocyclyl, —C(O)—($C_0$-$C_3$ alkylene)-heterocyclyl, —($C_0$-$C_3$ alkylene)-NH-heterocyclyl, —($C_0$-$C_3$ alkylene)-C(O)—NH-heterocyclyl, -(cyclopropyl)-C(O)-(heterocyclyl), —O-heterocyclyl, wherein the aryl, heterocyclyl or heteroaryl portion of an $R^1$ substituent is optionally substituted. In some aspects of these embodiments the aryl, heterocyclyl or heteroaryl portion of an $R^1$ substituent is optionally substituted with one or more substituents selected from —OH, —CN, =O, $C_1$-$C_4$ alkyl, halo-substituted $C_1$-$C_4$ alkyl, hydroxy-substituted $C_1$-$C_4$ alkyl, —S(O)$_2$—($C_1$-$C_4$ alkyl), —S(O)$_2$-cyclopropyl, cyclopropyl, —S(O)$_2$—($C_1$-$C_4$ haloalkyl), —C(O)—O—($C_1$-$C_4$ alkyl), —C(O)—N($C_1$-$C_4$ alkyl)$_2$, —C(O)—NH($C_1$-$C_4$ alkyl), —C(O)—($C_1$-$C_4$ alkyl), oxetanyl, —C(O)-oxetanyl, —C(O)—O-oxetanyl, —CH$_2$-oxetanyl, tetrahydrofuranyl, or morpholinyl.

In some embodiments, $R^1$ is 8-azabicyclo[3.2.1]oct-2-ene-3-yl, wherein $R^1$ is unsubstituted or substituted with $C_1$-$C_4$ alkyl, halo-substituted $C_1$-$C_4$ alkyl, —C(O)—O—($C_1$-$C_4$ alkyl), —C(O)—($C_1$-$C_4$ alkyl), or —C(O)-heteroaryl, and in any one or more of these embodiments, the heteroaryl portion of an $R^1$ substituent is optionally substituted.

In some embodiments, $R^1$ is cyclohexyl, wherein $R^1$ is substituted with —C(O)— heterocyclyl, or —COOH; and the heterocyclyl substituent is optionally substituted with oxo, or $C_1$-$C_4$ alkyl.

In some embodiments, $R^1$ is methyl, 4-(morpholin-4-ylsulfonyl)phenyl, 4-(4-methylpiperazin-1-ylmethyl)phenyl, 4-fluorophenyl, 1-methylpiperdin-4-yl, 4-(morpholin-4-ylcarbonyl)cyclohexyl, 1-(morpholin-4-ylcarbonyl)cyclohex-3-en-4-yl, 4-(piperidin-4-ylcarbonyl)piperazin-1-yl, 4-(piperidin-4-ylcarbonyl)piperidin-1-yl, 4-dimethylaminopiperidin-1-yl, 4-dimethylaminomethylpiperidin-1-yl, 3-dimethylaminopiperidin-1-yl, 3-hydroxypiperidin-1-yl, pyrrolidin-3-yl, cyclopentyl, 4-(dimethylaminomethylcarbonyl)piperazin-1-yl, 4-(2-dimethylaminoethylcarbonyl)piperazin-1-yl, 4-(oxetan-3-ylmethylcarbonyl)piperazin-1-yl, piperidin-4-yl, 4-hydroxycarbonylpiperidin-1-yl, 5-methylsulfonylpyridin-3-yl, 4-hydroxycarbonylcyclohex-1-ene-1-yl, 4-hydroxycarbonylcyclohexyl, 4-(4-methylpiperazin-1-yl)carbonylcyclohexyl, 3,6-dihydro-2H-pyran-4-yl, tetrahydro-2H-pyran-4-yl, 1,2,3,6-tetrahydropyridin-4-yl, 4-(hydroxycarbonylmethyl)phenyl, or 4-(2H-tetrazo-5-yl)phenyl.

In some embodiments, $R^1$ is —CN, —CH$_2$CN, 1-((1-oxetan-3-ylcarbonyl)azetidin-3-yl)pyrazol-4-yl, 1-(1-(1,1-dioxothiomorpholin-4-ylcarbonyl)-1-methylethan-1-yl)pyrazol-4-yl, 1-(1-(1-trifluoromethylcyclopropylcarbonyl)azetidin-3-yl)pyrazol-4-yl, 1-(1-(2,2,2-trifluoroethan-1-yl)azetidin-3-yl)pyrazol-4-yl, 1-(1-(2,2-dimethylmorpholin-4-ylcarbonyl)-1-methylethan-1-yl)pyrazol-4-yl, 1-(1-(2,6-dimethylmorpholin-4-ylcarbonyl)-1-methylethan-1-yl)pyrazol-4-yl, 1-(1-(2-oxa-6-azaspiro[3.3]heptan-6-ylcarbonyl)-1-methylethan-1-yl)pyrazol-4-yl, 1-(1-(2-oxa-6-azaspiro[3.4]octan-6-ylcarbonyl)-1-methylethan-1-yl)pyrazol-4-yl, 1-(1-(3,3,3-trifluoropropan-1-yl)azetidin-3-yl)pyrazol-4-yl, 1-(1-(8-oxa-3-azabicyclo[3.2.1]octan-3-ylcarbonyl)-1-methylethan-1-yl)pyrazol-4-yl, 1-(1-(azetidin-1-ylcarbonyl)-1-methylethan-1-yl)pyrazol-4-yl, 1-(1-(ethan-2-ylsulfonyl)-3-(cyanomethyl)azetidin-3-yl)pyrazol-4-yl, 1-(1-(hexahydro-1H-furo[3,4-c]pyrrol-5-ylcarbonyl)-1-methylethan-1-yl)pyrazol-4-yl, 1-(1-(isopropylaminocarbonyl)cyclopropyl)pyrazol-4-yl, 1-(1-(morpholin-4-ylcarbonyl)-1-methylethan-1-yl)pyrazol-4-yl, 1-(1-(morpholin-4-ylcarbonyl)cyclopropyl)pyrazol-4-yl, 1-(1-(pyrrolidin-1-ylcarbonyl)cyclopropyl)pyrazol-4-yl, 1-(1,1-dioxotetrahydro-2H-thiopyran-4-yl)pyrazol-4-yl, 1-(1,3-dimethylpyrazol-5-yl)pyrazol-4-yl, 1-(1-acetylazetidin-3-yl)pyrazol-4-yl, 1-(1-acetylpyrrolidin-3-yl)pyrazol-4-yl, 1-(1-cyanocyclopropylmethyl)pyrazol-4-yl, 1-(1H-pyrazol-4-ylmethyl)pyrazol-4-yl, 1-(1-hydroxy-3-chloropropan-2-yl)pyrazol-4-yl, 1-(1-hydroxylcarbonyl-1-methylethan-1-yl)pyrazol-4-yl, 1-(1-methoxycarbonylazetidin-3-yl)pyrazol-4-yl, 1-(1-methyl-2(1H)-pyridinon-5-ylmethyl)pyrazol-4-yl, 1-(1-methyl-2-oxopyrrolidin-4-ylmethyl)pyrazol-4-yl, 1-(1-methylaminocarbonyl-1-methylethan-1-yl)pyrazol-4-yl, 1-(1-methylsulfonylazetidin-3-yl)pyrazol-4-yl, 1-(1-t-butoxycarbonylpyrrolidin-3-yl)pyrazol-4-yl, 1-(2-(1,3,4-oxadiazol-2-yl)propan-2-yl)pyrazol-4-yl, 1-(2-(2-(2-hydroxypropan-2-yl)morpholin-4-ylcarbonyl)propan-2-yl)pyrazol-4-yl, 1-(2-(2,5-dioxa-8-azaspiro[3.5]nonan-8-ylcarbonyl)propan-2-yl)pyrazol-4-yl, 1-(2-(2-methyl-1,3,4-oxadiazol-5-yl)propan-2-yl)pyrazol-4-yl, 1-(2-(2-methyl-4,6-dihydro-5H-pyrrolo[3,4-d]thiazol-5-ylcarbonyl)propan-2-yl)pyrazol-4-yl, 1-(2-(2-methyl-6,7-dihydrothiazolo[4,5-c]pyridin-5-ylcarbonyl)propan-2-yl)pyrazol-4-yl, 1-(2-(3,5-dimethylpiperazin-1-ylcarbonyl)propan-2-yl)pyrazol-4-yl, 1-(2-(3-hydroxy-3-methylazetidin-1-ylcarbonyl)propan-2-yl)pyrazol-4-yl, 1-(2-(3-hydroxy-3-methylpiperidin-1-ylcarbonyl)propan-2-yl)pyrazol-4-yl, 1-(2-(3-hydroxy-3-methylpyrrolidin-1-ylcarbonyl)propan-2-yl)pyrazol-4-yl, 1-(2-(3-hydroxypyrrolidin-1-ylcarbonyl)propan-2-yl)pyrazol-4-yl, 1-(2-(4-cyano-4-methylpiperidin-1-ylcarbonyl)propan-2-yl)pyrazol-4yl, 1-(2-(4-hydroxy-4-methylpiperidin-1-ylcarbonyl)propan-2-yl)pyrazol-4-yl, 1-(2-(4-methyloxazol-2-yl)propan-2-yl)pyrazol-4-yl, 1-(2-(4-methylpiperazin-1-ylcarbonyl)propan-2-yl)pyrazol-4-yl, 1-(2-(5-(morpholin-4-yl)-1,3,4-oxadiazol-2-yl)propan-2-yl)pyrazol-4-yl, 1-(2-(5-(tetrahydrofuran-2-yl)-1,3,4-oxadiazol-2-yl)propan-2-yl)pyrazol-4-yl, 1-(2-(5-cyclopropyl-1,3,4-oxadiazol-2-yl)propan-2-yl)pyrazol-4-yl, 1-(2-(5-difluoromethyl-1,3,4-oxadiazol-2-yl)propan-2-yl)pyrazol-4-yl, 1-(2-(5-isopropyl-1,3,4-oxadiazol-2-yl)propan-2-yl)pyrazol-4-yl, 1-(2-(5-methyl-1,3,4-thiadiazol-2-yl)propan-2-yl)pyrazol-4-yl, 1-(2-(5-methyloxazol-2-yl)propan-2-yl)pyrazol-4-yl, 1-(2-(5-trifluoromethyl-1,3,4-oxadiazol-2-yl)propan-2-yl)pyrazol-4-yl, 1-(2-(methyl)-2-(morpholin-4-yl)propan-3-yl)pyrazol-4-yl, 1-(2-(methyl)-3-(morpholin-4-yl)propan-2-yl)pyrazol-4-yl, 1-(2-(pyrrolidin-1-ylcarbonyl)propan-2-yl)pyrazol-4-yl, 1-(2-cyanoethyl)pyrazol-4-yl, 1-(2-hydroxy-2-methylpropan-1-yl)pyrazol-4-yl, 1-(2-methoxyethyl)pyrazol-4-yl, 1-(2-methyl-3-hydroxypropan-2-yl)pyrazol-4-yl, 1-(2-methylpropyl)pyrazol-4-yl, 1-(2-methylpyridin-4-yl)piperdin-3-yl, 1-(2-methylpyrimidin-4-yl)pyrrolidin-3-yl, 1-(2-methylsulfonylethan-1-yl)pyrazol-4-yl, 1-(2-morpholin-4-ylethyl)pyrazol-4-yl, 1-(2-oxopyrrolidin-3-yl)pyrazol-4-yl, 1-(2-oxopyrrolidin-4-ylmethyl)pyrazol-4-yl, 1-(3-methyl-1,2,4-oxadiazol-5-ylmethyl)pyrazol-4-yl, 1-(3-methylsulfonylphenylmethyl)pyrazol-4-yl, 1-(4-methylpiperazin-1-ylcarbonylmethyl)pyrazol-4-yl, 1-(4-methylpyrimindin-2-yl)piperidin-4-yl, 1-(4-methylsulfonylphenylmethyl)pyrazol-4-yl, 1-(5-methyl-1,2,4-oxadiazol-3-ylmethyl)pyrazol-4-yl, 1-(5-methyl-1,3,4-oxadiazol-2-ylmethyl)pyrazol-4-yl, 1-(5-methylpyrazin-2-ylmethyl)pyrazol-4-yl, 1-(5-oxopyrrolidin-2-ylmethyl)pyrazol-4-yl, 1-(6-hydroxyhexahydrofuro[3,2-b]furan-3-yl)pyrazol-4-yl, 1-(6-methylpyrazin-2-ylmethyl)pyrazol-4-yl, 1-(ethoxycarbonylmethyl)pyrazol-4-yl, 1-(hexahydrofuro[2,3-b]furan-3-yl)pyrazol-4-yl, 1-(hydroxycarbonylmethyl)pyrazol-4-yl, 1-(isopropylaminocarbonylmethyl)pyrazol-4-yl, 1-(isopropylcarbonylmethyl)pyrazol-4-yl, 1-(methylaminocarbonylmethyl)pyrazol-4-yl, 1-(methylsulfonylaminocarbonylmethyl)pyrazol-4-yl, 1-(methylsulfonylmethyl)pyrazol-4-yl, 1-(morpholin-4-ylcarbonylmethyl)pyrazol-4-yl, 1-(oxetan-2-ylmethyl)pyrazol-4-yl, 1-(oxetan-3-ylmethyl)pyrazol-4-yl, 1-(pyrazin-2-ylmethyl)pyrazol-4-yl, 1-(pyridazin-4-ylmethyl)pyrazol-4-yl, 1-(pyridin-3-ylmethyl)pyrazol-4-yl, 1-(pyrrolidin-1-ylcarbonylmethyl)pyrazol-4-yl, 1-(t-butoxycarbonyl)3,6-dihydropyridin-4-yl, 1-(t-butoxycarbonyl)piperidin-3-yl, 1-(tetrahydrofuran-2-ylmethyl)pyrazol-4-yl, 1-(tetrahydrofuran-3-yl)pyrazol-4-yl, 1-(tetrahydrofuran-3-ylaminocarbonylmethyl)pyrazol-4-yl, 1-(tetrahydropyran-4-yl)pyrazol-4-yl, 1-(tetrahydropyran-4-ylmethyl)pyrazol-4-yl, 1,3-dimethylpyrazol-4-yl, 1-acetylpiperidin-3-yl, 1-acetylpyrrolidin-3-yl, 1-difluoromethylpyrazol-4-yl, 1H-benzo[d]imidazol-6-yl, 1H-indol-5-yl, 1H-indol-6-yl, 1H-pyrazol-4-yl, 1-methyl-1,2,3-triazol-4-yl, 1-methylimidazol-4-yl, 1-methylpyrazol-3-yl, 1-methylpyrazol-4-yl, 1-methylsulfonylpiperidin-3-yl, 1-methylsulfonylpyrrolidin-3-yl, 1-oxetan-3-ylpyrazol-4-yl, 1-oxoisoindolin-4-yl, 1-oxoisoindolin-5-yl, 1-t-butylpyrazol-4-yl, 2-(1,1-dioxothiomorpholin-4-yl)pyridin-4-yl, 2-(1-methylpiperidin-3-yloxy)pyridin-4-yl, 2-(1-methylpiperidin-4-yloxy)pyridin-4-yl, 2-(1-methylpyrrolidin-3-yloxy)pyridin-4-yl, 2-(2-methoxyethan-1-yloxy)pyridin-4-yl, 2-(3-methoxypropan-2-ylamino)-7-(4-hydroxycyclohexyl)pyrrolo[2,1-f]-1,2,4-triazin-5-yl, 2-(3-oxopiperazin-1-yl)pyridin-4-yl, 2-(4-acetylpiperazin-1-yl)pyridin-4-yl, 2-(4-methylpiperazin-1-yl)pyridin-4-yl, 2-(4-methylsulfonylpiperazin-1-yl)pyridin-4-yl, 2-(morpholin-4-yl)pyridin-4-yl, 2-(oxetan-3-yloxy)pyridin-4-yl, 2-(piperidin-3-yloxy)pyridin-4-yl, 2-(piperidin-4-yloxy)pyridin-4-yl, 2-(pyrrolidin-3-yloxy)pyridin-4-yl, 2,6-dimethylpyridin-4-yl, 2-hydroxycarbonylpyrimidin-5-yl, 2-isopropoxypyridin-4-yl, 2-isopropylaminopyridin-4-yl, 2-methyl-2-(morpholin-4-ylcarbonyl)but-3-yn-4-yl, 2-methylaminocarbonyl-6-methylpyridin-4-yl, 2-methylaminocarbonylpyridin-4-yl, 2-methylaminocarbonylpyrimidin-5-yl, 2-methylaminopyridin-4-yl, 2-methyloxazol-5-yl, 2-methylpyridin-4-yl, 2-morpholin-4-ylpyridin-4-yl, 2-oxoindolin-5-yl, 2-oxoindolin-6-yl, 2-oxopyrrolidin-1-yl, 2-pyrrolidin-1-ylpyridin-4-yl, 3-(1-pyrrolidin-1-ylethyl)phenyl, 3-(3,3-difluoropyrrolidin-1-ylmethyl)phenyl, 3-(3-fluoropyrrolidin-1-ylmethyl)phenyl, 3-(5-methyl-1,3,4-oxadiazol-2-yl)phenyl, 3-(morpholin-4-yl)phenyl, 3-(morpholin-4-ylmethyl)phenyl, 3-(pyrrolidin-1-ylmethyl)phenyl, 3-fluoro-4-cyanophenyl, 3-methylisoxazol-4-yl, 3-methylpyridazin-5-yl, 3-oxomorpholin-4-yl, 4-(1-(1,1-dioxothiomorpholin-4-ylcarbonyl)cyclopropyl)phenyl, 4-(1-(1-methylpiperazin-4-yl)cyclopentyl)phenyl, 4-(1-(hydroxycarbonyl)cyclopropyl)phenyl, 4-(1-(morpholin-4-ylcarbonyl)cyclopropyl)phenyl, 4-(1,1-dioxothiomorpholin-4-ylcarbonyl)cyclohexyl, 4-(1,1-dioxothiomorpholin-4-ylcarbonyl)phenyl, 4-(1-morpholin-4-ylcyclopentyl)phenyl, 4-(1-morpholin-4-ylethyl)phenyl, 4-(1-pyrrolidin-1-ylethyl)phenyl, 4-(2-oxa-6-azaspiro[3.3]hepatan-6-ylcarbonyl)cyclohexyl, 4-(4-(4-methylpyrimidin-2-yl)piperazin-1-ylmethyl)phenyl, 4-(4,4-difluoropiperdin-1-ylcarbonyl)cylohexyl, 4-(4-acetylpiperazin-1-ylmethyl)phenyl, 4-(4-methylpiperazin-1-ylcarbonyl)phenyl, 4-(5-methyl-1,3,4-oxadiazol-2-yl)phenyl, 4-(morpholin-4-ylcarbonyl)phenyl, 4-(morpholin-4-ylmethyl)phenyl, 4-(pyrrolidin-1-ylcarbonyl)phenyl, 4-(pyrrolidin-1-ylmethyl)phenyl, 4-hydroxycarbonylphenyl, 4-methylpyridin-2-yl, 4-methylpyridin-3-yl, 5-(2-(5-methyl-1,3,4-oxadiazol-2-yl)propan-2-yl)thien-2-yl, 5-(2-(morpholin-4-ylcarbonyl)propan-2-yl)thien-2-yl, 5-(4-methylpiperazin-1-ylcarbonyl)pyridin-3-yl, 5-(morpholin-4-ylcarbonyl)thien-3-yl, 5-(morpholin-4-ylmethyl)pyridin-3-yl, 5-(pyrrolidin-1-ylcarbonyl)pyridin-3-yl, 5-(S-imino(methyl)sulfinyl)pyridin-2-yl, 5-(S-imino(methyl)sulfinyl)pyridin-3-yl, 5-aminocarbonylpyridin-3-yl, 5-cyanopyridin-3-yl, 5-dimethylaminocarbonylpyridin-3-yl, 5-fluoropyridin-3-yl, 5-hydroxycarbonylpyridin-3-yl, 5-methylaminocarbonylpyridin-3-yl, 5-methylaminosulfonylpyridin-3-yl, 5-methylpyridin-2-yl, 5-methylpyridin-3-yl, 6-(1-methyl-4,5,6,7-tetrahydro-1H-pyrazolo[3,4-c]pyridin-6-yl)pyridin-4-yl, 6-(1-methylpiperazin-4-yl)pyridin-3-yl, 6-(2-(2-hydroxypropan-2yl)morpholin-4-yl)pyridin-4-yl, 6-(2,5-dioxa-8-azaspiro[3.5]nonan-8-yl)pyridin-4-yl, 6-(2-hydroxypropan-2-yl)pyridin-4-yl, 6-(2-methyl-4,5,6,7-tetrahydro-3H-imidazo[4,5-c]pyridin-5-yl)pyridin-4-yl, 6-(2-methyl-4,5,6,7-tetrahydrothiazolo[5,4-c]pyridin-5-yl)pyridin-4-yl, 6-(2-methyl-5,6-dihydro-4H-pyrrolo[3,4-d]thiazol-5-yl)pyridin-4-yl, 6-(2-oxa-6-azaspiro[3.3]heptan-6-yl)pyridin-4-yl, 6-(2-oxa-6-azaspiro[3.4]octan-6-yl)pyridin-4-yl, 6-(2-oxa-7-azaspiro[3.5]nonan-7-yl)pyridin-4-yl, 6-(2-oxo-oxazol-3-yl)pyridin-4-yl, 6-(3-methyl-3-hydroxyazetidin-1-yl)pyridin-4-yl, 6-(3-methyl-3-hydroxypyrrolidin-1-yl)pyridin-4-yl, 6-(3-oxa-7-azaspiro[3.5]nonan-7-yl)pyridin-4-yl, 6-(3-oxomorpholin-4-yl)pyridin-4-yl, 6-(4-(cyclopropylsulfonyl)piperazin-1-yl)pyridin-4-yl, 6-(4-(N-isopropyl-N-ethylaminocarbonyl)piperazin-1-yl)pyridin-4-yl, 6-(4-(oxetan-3-ylcarbonyl)piperazin-1-yl)pyridin-4-yl, 6-(4-(oxetan-3-ylmethyl)piperazin-1-yl)pyridin-4-yl, 6-(4-(oxetan-3-yloxycarbonyl)piperazin-1-yl)pyridin-4-yl, 6-(4-(oxtean-3-yl)piperazin-1-yl)pyridin-4-yl, 6-(4-methoxycarbonylpiperazin-1-yl)pyridin-4-yl, 6-(4-methyl-4-hydroxypiperidin-1-yl)pyridin-4-yl, 6-(4-methylpiperaizin-1-ylmethyl)pyridin-4-yl, 6-(4-methylpiperazin-1-ylcarbonyl)pyridin-3-yl, 6-(4-trifluoromethylsulfonylpiperazin-1-yl)pyridin-4-yl, 6-(8-oxa-3-azabicyclo[3.2.1]octan-3-yl)pyridin-4-yl, 6-(hexahydro-1H-furo[3,4-c]pyrrol-5-yl)pyridin-4-yl, 6-(isopropylaminocarbonyl)pyridin-3-yl, 6-(methylaminocarbonyl)pyridin-3-yl, 6-(morpholin-4-yl)pyridin-4-yl, 6-(morpholin-4-ylcarbonyl)pyridin-3-yl, 6-(morpholin-4-ylmethyl)pyridin-3-yl, 6-(oxetan-3-yl)pyridin-4-yl, 6-(piperazin-1-yl)pyridin-4-yl, 6-(pyridin-3-yloxy)pyridin-4-yl, 6-(S-imino(methyl)sulfinyl)pyridin-4-yl, 6-(S-methyl-S-iminosulfinyl)pyridin-3-yl, 6-(tetrahydropyran-3-ylamino)pyridin-4-yl, 6-(tetrahydropyran-4-ylamino)pyridin-4-yl, 6-fluoropyridin-4-yl, 6-methylaminosulfonylpyridin-3-yl, 6-methylpyridin-2-yl, 6-methylpyridin-3-yl, 6-methylpyridin-4-yl, 6-methylsulfonylpyridin-3-yl, 6-methylsulfonylpyridin-4-yl, 7-oxo-2-oxa-6-azaspiro[3.4]octan-6-yl, 8-(1,1,1-trifluoroethan-2-yl)-8-azabicyclo[3.2.1]oct-2-en-3-yl, 8-(acetyl)-8-azabicyclo[3.2.1]oct-2-en-3-yl, 8-(morpholin-4-yl-carbonyl)-8-azabicyclo[3.2.1]oct-6-en-7-yl, 8-azabicyclo[3.2.1]oct-2-ene-3-yl, 8-methyl-8-azabicyclo[3.2.1]oct-2-en-3-yl, 8-methyl-8-azabicyclo[3.2.1]octan-3-yl, 8-t-butoxycarbonyl-8-azabicyclo[3.2.1]oct-2-ene-3-yl, 8-t-butoxycarbonyl-8-azabicyclo[3.2.1]octan-3-yl, benzo[d]oxazol-5-yl, benzo[d]oxazol-6-yl, imidazo[1,2-a]pyridin-6-yl, or piperdin-3-yl.

In some embodiments, $R^1$ is 1-(1-(1,1-dioxothiomorpholin-4-ylcarbonyl)-1-methylethan-1-yl)pyrazol-4-yl, 1-(1-(1-trifluoromethylcyclopropylcarbonyl)azetidin-3-yl)pyrazol-4-yl, 1-(1-(2,2,2-trifluoroethan-1-yl)azetidin-3-yl)pyrazol-4-yl, 1-(1-(2,2-dimethylmorpholin-4-ylcarbonyl)-1-methylethan-1-yl)pyrazol-4-yl, 1-(1-(2,6-dimethylmorpholin-4-ylcarbonyl)-1-methylethan-1-yl)pyrazol-4-yl, 1-(1-(2-oxa-6-azaspiro[3.3]heptan-6-ylcarbonyl)-1-methylethan-1-yl)pyrazol-4-yl, 1-(1-(2-oxa-6-azaspiro[3.4]octan-6-ylcarbonyl)-1-methylethan-1-yl)pyrazol-4-yl, 1-(1-(3,3,3-trifluoropropan-1-yl)azetidin-3-yl)pyrazol-4-yl, 1-(1-(8-oxa-3-azabicyclo[3.2.1]octan-3-ylcarbonyl)-1-methylethan-1-yl)pyrazol-4-yl, 1-(1-(azetidin-1-ylcarbonyl)-1-methylethan-1-yl)pyrazol-4-yl, 1-(1-(hexahydro-1H-furo[3,4-c]pyrrol-5-ylcarbonyl)-1-methylethan-1-yl)pyrazol-4-yl, 1-(1-(isopropylaminocarbonyl)cyclopropyl)pyrazol-4-yl, 1-(1-(morpholin-4-ylcarbonyl)-1-methylethan-1-yl)pyrazol-4-yl, 1-(1-(morpholin-4-ylcarbonyl)cyclopropyl)pyrazol-4-yl, 1-(1-(pyrrolidin-1-ylcarbonyl)cyclopropyl)pyrazol-4-yl, 1-(1,1-dioxotetrahydro-2H-thiopyran-4-yl)pyrazol-4-yl, 1-(1,3-dimethylpyrazol-5-yl)pyrazol-4-yl, 1-(1-acetylazetidin-3-yl)pyrazol-4-yl, 1-(1-cyanocyclopropylmethyl)pyrazol-4-yl, 1-(1-ethylsulfonyl-3-cyanomethylazetidin-3-yl)pyrazol-4-yl, 1-(1H-pyrazol-4-ylmethyl)pyrazol-4-yl, 1-(1-hydroxylcarbonyl-1-methylethan-1-yl)pyrazol-4-yl, 1-(1-methoxycarbonylazetidin-3-yl)pyrazol-4-yl, 1-(1-methyl-2(1H)-pyridinon-5-ylmethyl)pyrazol-4-yl, 1-(1-methyl-2-oxopyrrolidin-4-ylmethyl)pyrazol-4-yl, 1-(1-methylaminocarbonyl-1-methylethan-1-yl)pyrazol-4-yl, 1-(1-methylsulfonylazetidin-3-yl)pyrazol-4-yl, 1-(1-morpholin-4-ylcarbonyl-1-methylethan-1-yl)pyrazol-4-yl, 1-(1-t-butoxycarbonylpyrrolidin-3-yl)pyrazol-4-yl, 1-(2-(1,3,4-oxadiazol-2-yl)propan-2-yl)pyrazol-4-yl, 1-(2-(2-(2-hydroxypropan-2-yl)morpholin-4-ylcarbonyl)propan-2-yl)pyrazol-4-yl, 1-(2-(2,5-dioxa-8-azaspiro[3.5]nonan-8-ylcarbonyl)propan-2-yl)pyrazol-4-yl, 1-(2-(2-methyl-1,3,4-oxadiazol-5-yl)propan-2-yl)pyrazol-4-yl, 1-(2-(2-methyl-4,6-dihydro-5H-pyrrolo[3,4-d]thiazol-5-ylcarbonyl)propan-2-yl)pyrazol-4-yl, 1-(2-(2-methyl-6,7-dihydrothiazolo[4,5-c]pyridin-5-ylcarbonyl)propan-2-yl)pyrazol-4-yl, 1-(2-(3,5-dimethylpiperazin-1-ylcarbonyl)propan-2-yl)pyrazol-4-yl, 1-(2-(3-hydroxy-3-methylazetidin-1-ylcarbonyl)propan-2-yl)pyrazol-4-yl, 1-(2-(3-hydroxy-3-methylpiperidin-1-ylcarbonyl)propan-2-yl)pyrazol-4-yl, 1-(2-(3-hydroxy-3-methylpyrrolidin-1-ylcarbonyl)propan-2-yl)pyrazol-4-yl, 1-(2-(3-hydroxypyrrolidin-1-ylcarbonyl)propan-2-yl)pyrazol-4-yl, 1-(2-(4-cyano-4-methylpiperidin-1-ylcarbonyl)propan-2-yl)pyrazol-4yl, 1-(2-(4-hydroxy-4-methylpiperidin-1-ylcarbonyl)propan-2-yl)pyrazol-4-yl, 1-(2-(4-methylpiperazin-1-ylcarbonyl)propan-2-yl)pyrazol-4-yl, 1-(2-(5-(tetrahydrofuran-2-yl)-1,3,4-oxadiazol-2-yl)propan-2-yl)pyrazol-4-yl, 1-(2-(5-difluoromethyl-1,3,4-oxadiazol-2-yl)propan-2-yl)pyrazol-4-yl, 1-(2-(5-isopropyl-1,3,4-oxadiazol-2-yl)propan-2-yl)pyrazol-4-yl, 1-(2-(5-methyl-1,3,4-thiadiazol-2-yl)propan-2-yl)pyrazol-4-yl, 1-(2-(5-trifluoromethyl-1,3,4-oxadiazol-2-yl)propan-2-yl)pyrazol-4-yl, 1-(2-(methyl)-2-(morpholin-4-yl)propan-3-yl)pyrazol-4-yl, 1-(2-(methyl)-3-(morpholin-4-yl)propan-2-yl)pyrazol-4-yl, 1-(2-(morpholin-4-ylcarbonyl)propan-2-yl)pyrazol-4-yl, 1-(2-cyanoethyl)pyrazol-4-yl, 1-(2-methoxyethyl)pyrazol-4-yl, 1-(2-methylsulfonylethan-1-yl)pyrazol-4-yl, 1-(2-morpholin-4-ylethyl)pyrazol-4-yl, 1-(2-oxopyrrolidin-3-yl)pyrazol-4-yl, 1-(2-oxopyrrolidin-4-ylmethyl)pyrazol-4-yl, 1-(3-methyl-1,2,4-oxadiazol-5-ylmethyl)pyrazol-4-yl, 1-(3-methylsulfonylphenylmethyl)pyrazol-4-yl, 1-(4-methylsulfonylphenylmethyl)pyrazol-4-yl, 1-(5-methyl-1,2,4-oxadiazol-3-ylmethyl)pyrazol-4-yl, 1-(5-methyl-1,3,4-oxadiazol-2-ylmethyl)pyrazol-4-yl, 1-(5-methylpyrazin-2-ylmethyl)pyrazol-4-yl, 1-(5-oxopyrrolidin-2-ylmethyl)pyrazol-4-yl, 1-(6-hydroxyhexahydrofuro[3,2-b]furan-3-yl)pyrazol-4-yl, 1-(6-methylpyrazin-2-ylmethyl)pyrazol-4-yl, 1-(ethoxycarbonylmethyl)pyrazol-4-yl, 1-(hexahydrofuro[2,3-b]furan-3-yl)pyrazol-4-yl, 1-(hydroxycarbonylmethyl)pyrazol-4-yl, 1-(isopropylaminocarbonylmethyl)pyrazol-4-yl, 1-(methylsulfonylaminocarbonylmethyl)-pyrazol-4-yl, 1-(methylsulfonylmethyl)pyrazol-4-yl, 1-(morpholin-4-ylcarbonyl)cyclohex-3-en-4-yl, 1-(morpholin-4-ylcarbonylmethyl)pyrazol-4-yl, 1-(oxetan-2-ylmethyl)pyrazol-4-yl, 1-(oxetan-3-ylmethyl)pyrazol-4-yl, 1-(pyrazin-2-ylmethyl)pyrazol-4-yl, 1-(pyridazin-4-ylmethyl)pyrazol-4-yl, 1-(pyridin-3-ylmethyl)pyrazol-4-yl, 1-(pyrrolidin-1-ylcarbonylmethyl)pyrazol-4-yl, 1-(t-butoxycarbonyl)3,6-dihydropyridin-4-yl, 1-(tetrahydrofuran-3-yl)pyrazol-4-yl, 1-(tetrahydrofuran-3-ylaminocarbonylmethyl)pyrazol-4-yl, 1,2,3,6-tetrahydropyridin-4-yl, 1-difluoromethylpyrazol-4-yl, 1H-benzo[d]imidazol-6-yl, 1H-indol-6-yl, 1H-pyrazol-4-yl, 1-methylpyrazol-4-yl, 1-oxetan-3-ylpyrazol-4-yl, 1-t-butylpyrazol-4-yl, 2-(1,1-dioxothiomorpholin-4-ylpyridin-4-yl, 2-(1-methylpiperidin-3-yloxy)pyridin-4-yl, 2-(1-methylpiperidin-4-yloxy)pyridin-4-yl, 2-(2-methoxyethan-1-yloxy)pyridin-4-yl, 2-(3-oxopiperazin-1-yl)pyridin-4-yl, 2-(4-acetylpiperazin-1-yl)pyridin-4-yl, 2-(4-methylpiperazin-1-yl)pyridin-4-yl, 2-(4-methylsulfonylpiperazin-1-yl)pyridin-4-yl, 2-(morpholin-4-yl)pyridin-4-yl, 2-(oxetan-3-yloxy)pyridin-4-yl, 2-hydroxycarbonylpyrimidin-5-yl, 2-isopropoxypyridin-4-yl, 2-isopropylaminopyridin-4-yl, 2-methylaminocarbonyl-6-methylpyridin-4-yl, 2-methylaminocarbonylpyridin-4-yl, 2-methylaminocarbonylpyrimidin-5-yl, 2-methylaminopyridin-4-yl, 2-methylpyridin-4-yl, 2-morpholin-4-ylpyridin-4-yl, 2-pyrrolidin-1-ylpyridin-4-yl, 3-(1-pyrrolidin-1-ylethyl)phenyl, 3-(3-fluoropyrrolidin-1-ylmethyl)phenyl, 3-(5-methyl-1,3,4-oxadiazol-2-yl)phenyl, 3-(morpholin-4-yl)phenyl, 3,6-dihydro-2H-pyran-4-yl, 3-methylisoxazol-4-yl, 4-(1-(1,1-dioxothiomorpholin-4-ylcarbonyl)cyclopropyl)phenyl, 4-(1-morpholin-4-ylethyl)phenyl, 4-(1-pyrrolidin-1-ylethyl)phenyl, 4-(2H-tetrazol-5-yl)phenyl, 4-(4,4-difluoropiperdin-1-ylcarbonyl)cyclohexyl, 4-(4-acetylpiperazin-1-ylmethyl)phenyl, 4-(4-methylpiperazin-1-ylcarbonyl)phenyl, 4-(4-methylpiperazin-1-ylmethyl)phenyl, 4-(4-methylpiperazin-1-ylmethyl)phenyl, 4-(morpholin-4-ylcarbonyl)cyclohexyl, 4-(morpholin-4-ylmethyl)phenyl, 4-(morpholin-4-ylsulfonyl)phenyl, 4-(pyrrolidin-1-ylcarbonyl)phenyl, 4-(pyrrolidin-1-ylmethyl)phenyl, 4-hydroxycarbonylcyclohex-1-ene-1-yl, 5-(2-(morpholin-4-ylcarbonyl)propan-2-yl)thien-2-yl, 5-(morpholin-4-ylcarbonyl)pyridin-3-yl, 5-(morpholin-4-ylcarbonyl)thien-3-yl, 5-dimethylaminocarbonylpyridin-3-yl, 5-hydroxycarbonylpyridin-3-yl, 5-methylaminocarbonylpyridin-3-yl, 5-methylaminosulfonylpyridin-3-yl, 5-methylsulfonylpyridin-3-yl, 6-(1-methyl-4,5,6,7-tetrahydro-1H-pyrazolo[3,4-c]pyridin-6-yl)pyridin-4-yl, 6-(2-(2-hydroxypropan-2-yl)morpholin-4-yl)pyridin-4-yl, 6-(2,5-dioxa-8-azaspiro[3.5]nonan-8-yl)pyridin-4-yl, 6-(2-hydroxypropan-2-yl)pyridin-4-yl, 6-(2-methyl-4,5,6,7-tetrahydro-3H-imidazo[4,5-c]pyridin-5-yl)pyridin-4-yl, 6-(2-methyl-4,5,6,7-tetrahydrothiazolo[5,4-c]pyridin-5-yl)pyridin-4-yl, 6-(2-methyl-5,6-dihydro-4H-pyrrolo[3,4-d]thiazol-5-yl)pyridin-4-yl, 6-(2-oxa-6-azaspiro[3.3]heptan-6-yl)pyridin-4-yl, 6-(2-oxa-6-azaspiro[3.4]octan-6-yl)pyridin-4-yl, 6-(2-oxa-7-azaspiro[3.5]nonan-7-yl)pyridin-4-yl, 6-(2-oxo-oxazol-3-yl)pyridin-4-yl, 6-(3-oxa-7-azaspiro[3.5]nonan-7-yl)pyridin-4-yl, 6-(3-oxomorpholin-4-yl)pyridin-4-yl, 6-(4-(cyclopropylsulfonyl)piperazin-1-yl)pyridin-4-yl, 6-(4-(N-isopropyl-N-ethylaminocarbonyl)piperazin-1-yl)pyridin-4-yl, 6-(4-(oxetan-3-ylmethyl)piperazin-1-yl)pyridin-4-yl, 6-(4-(oxetan-3-yloxycarbonyl)piperazin-1-yl)pyridin-4-yl, 6-(4-(oxtean-3-yl)piperazin-1-yl)pyridin-4-yl, 6-(4-methoxycarbonylpiperazin-1-yl)pyridin-4-yl, 6-(4-methyl-4-hydroxypiperidin-1-yl)pyridin-4-yl, 6-(4-methylpiperazin-1-ylcarbonyl)pyridin-3-yl, 6-(4-methylpiperazin-1-yl)pyridin-4-yl, 6-(4-trifluoromethylsulfonylpiperazin-1-yl)pyridin-4-yl, 6-(8-oxa-3-azabicyclo[3.2.1]octan-3-yl)pyridin-4-yl, 6-(hexahydro-1H-furo[3,4-c]pyrrol-5-yl)pyridin-4-yl, 6-(methylaminocarbonyl)pyridin-3-yl, 6-(morpholin-4-yl)pyridin-4-yl, 6-(morpholin-4-ylcarbonyl)pyridin-3-yl, 6-(oxetan-3-yl)pyridin-4-yl, 6-(piperazin-1-yl)pyridin-4-yl, 6-(pyridin-3-yloxy)pyridin-4-yl, 6-(S-imino(methyl)sulfinyl)pyridin-4-yl, 6-(S-methyl-S-iminosulfinyl)pyridin-3-yl, 6-(tetrahydropyran-3-ylamino)pyridin-4-yl, 6-(tetrahydropyran-4-ylamino)pyridin-4-yl, 6-fluoropyridin-4-yl, 6-methylaminosulfonylpyridin-3-yl, 6-methylpyridin-3-yl, 6-methylsulfonylpyridin-3-yl, 6-trifluoromethylpyridin-4-yl, 8-(1,1,1-trifluoroethan-2-yl)-8-azabicyclo[3.2.1]oct-2-en-3-yl, 8-(acetyl)-8-azabicyclo[3.2.1]oct-2-en-3-yl, 8-(morpholin-4-yl-carbonyl)-8-azabicyclo[3.2.1]oct-6-en-7-yl, 8-azabicyclo[3.2.1]oct-2-ene-3-yl, 8-t-butoxycarbonyl-8-azabicyclo[3.2.1]octan-3-yl, benzo[d]oxazol-5-yl, benzo[d]oxazol-6-yl, or imidazo[1,2-a]pyridin-6-yl.

In some embodiments, $L^2$ is a bond.

In some embodiments, $R^2$ is optionally substituted heterocyclyl. In some of these embodiments, $R^2$ is an optionally substituted tetrahydropyranyl, piperidinyl, hexahydrothiopyranyl, or tetrahydroindazolyl. In some aspects of these embodiments, $R^2$ is a heterocyclyl optionally substituted with one or more substituent selected from oxo, hydroxyl, fluoro, methoxy, methyl, amino, imino, methylamino and dimethylamino. In some aspects of these embodiments, $R^2$ is tetrahydropyran-4-yl, 1-oxohexahydrothiopyran-4-yl, 1-imino-1-oxohexahydrothiopyran-4-yl, 2-oxopiperdin-4-yl, 2-oxopiperdin-5-yl, hexahydrothiopyran-4-yl, 4,5,6,7-tetrahydro-1H-indazol-4-yl or 4,5,6,7-tetrahydro-1H-indazol-5-yl.

In some embodiments, $R^2$ is optionally substituted aryl or heteroaryl. In some aspects of these embodiments, $R^2$ is an optionally substituted pyridinyl or phenyl. In some aspects of these embodiments, $R^2$ is 2-hydroxypyridin-4-yl or 4-methoxyphenyl.

In some embodiments, $R^2$ is optionally substituted $C_3$-$C_8$ cycloalkyl. In some aspects of these embodiments, $R^2$ is an optionally substituted cyclohexyl. In some aspects of these embodiments, $R^2$ is a substituted cyclohexyl. In some aspects of these embodiments, $R^2$ is a substituted cyclohexyl, wherein two substituents on the same ring carbon atom are taken together to form an optionally substituted heterocyclic ring that is spiro fused to the cyclohexyl. In some aspects of these embodiments, R² is an optionally substituted cyclopentyl.

In some embodiments, R² is 4-hydroxycyclohexyl or 4-methyl-4-hydroxycyclohexyl.

In some embodiments, R² is 4-methoxycyclohexyl, 4-aminocyclohexyl, 4-methylcarbonylaminocyclohexyl, 4-methylsylfonylaminocyclohexyl, 4-(1,2-dioxo-4-methyl-aminocyclobut-3-enylamino)cyclohexyl, 4-(2-cyano-3-methylguanidinyl)cyclohexyl, 2,4-dioxo-1,3-diazaspiro[4.5]decan-8-yl, 4-oxocyclohexyl, 3-hydroxycyclopentyl, 4-fluorocyclohexyl, 4,4-difluorocyclohexyl, 3,3-dimethyl-4-hydroxycyclohexyl, 3,3-difluoro-4-hydroxycyclohexyl, 3-methyl-4-hydroxycyclohexyl, 4-isopropyl-4-hydroxycyclohexyl, 4-ethyl-4-hydroxycyclohexyl, or 4-dimethylaminocyclohexyl.

In some embodiments, R² is 4-hydroxycyclohexyl, 4-methylcarbonylaminocyclohexyl, 4-methylsylfonylaminocyclohexyl, 4-(1,2-dioxo-4-methylaminocyclobut-3-enylamino)cyclohexyl, 4-(2-cyano-3-methylguanidinyl)cyclohexyl, 2,4-dioxo-1,3-diazaspiro[4.5]decan-8-yl, 3-methyl-4-hydroxycyclohexyl, 4-fluorocyclohexyl, 4-isopropyl-4-hydroxycyclohexyl, 4-ethyl-4-hydroxycyclohexyl, or 4,5,6,7-tetrahydro-1H-indazol-5-yl.

In some embodiments, R³ is —C₃-C₈ alkyl, —(C₂-C₆ alkylene)-O—(C₁-C₆ alkyl), phenyl, C₃-C₆ cycloalkyl, or saturated heterocyclyl, wherein each R³ is optionally substituted with 1-2 substituents independently selected from halo, —OH, —C₁-C₄ alkyl, and —O—C₁-C₄ alkyl.

In some embodiments, R³ is —C₃-C₈ alkyl, —(C₂-C₆ alkylene)-O—(C₁-C₆ alkyl), C₃-C₆ cycloalkyl, —(C₂-C₆ alkylene)-C₃-C₆ cycloalkyl, —(C₂-C₆ alkylene)-saturated heterocyclyl, or saturated heterocyclyl, wherein each R³ is optionally substituted with 1-5 substituents independently selected from deuterium, halo, —OH, —CN, —C₁-C₄ alkyl, —(C₁-C₄ alkylene)-O—(C₁-C₄ alkyl), —O—C₁-C₄ alkyl, —N(C₁-C₄ alkyl)₂.

In some embodiments, R³ is n-butyl, isopropyl, butan-2-yl, heptan-2-yl, 1,3-dimethoxypropan-2-yl, 3-methoxypropan-2-yl, pentan-2-yl, 4-methylpentan-2-yl, pentan-3-yl, cyclopentyl, 4-chlorophenyl, tetrahydrofuran-3-yl, 3-hydroxypropan-2-yl, 3,3-dimethylcyclobutyl, 2,2-dimethylcyclobutyl, or 1-ethylcyclobutyl.

In some embodiments, R³ is 1-(methoxymethyl)cyclopropanyl, 3,3-(difluoromethoxy)propan-2-yl, 3-(tetrahydrofuran-2-yl)propan-2-yl, 3,3,3-trifluoropropan-2-yl, 3,3-difluoropropan-2-yl, 3-cyanopropan-2-yl, 3-cyclopropylpropan-2-yl, 3-ethoxypropan-2-yl, 4,4,4-trifluorobutan-2-yl, 4-fluorobutan-2-yl, 4-methoxybutan-2-yl, 4-difluoromethoxybutan-2-yl, 4,4-difluorobutan-2-yl, 2-methoxyethan-1-yl, 2-cyclopropanylethan-1-yl, 3,3,3-trifluoropropan-1-yl, 3-dimethylaminopropan-2-yl, 1-methyltetrahydrofuran-3-yl, 2-(oxetan-3-yl)ethan-2-yl, 3-(oxetan-3-yl)propan-2-yl, 2-(pyridin-2-yl)ethan-2-yl, 2-(pyridin-3-yl)ethan-2-yl, 2-(pyridin-4-yl)ethan-2-yl, 2-(phenyl)ethan-2-yl, 3-(4-fluorophenyl)propan-2-yl, 3-trideuteromethoxypropan-2-yl, or 3-(phenoxy)propan-2-yl.

In some embodiments, R³ is isopropyl, n-butanyl, heptan-2-yl, propan-2-yl, 3-methoxypropan-2-yl, 3,3-(difluoromethoxy)propan-2-yl, 3,3-difluoropropan-2-yl, 3-cyclopropylpropan-2-yl, 4,4,4-trifluorobutan-2-yl, 4-fluorobutan-2-yl, 4,4-difluorobutan-2-yl, 2-methoxyethan-1-yl, 2-cyclopropanylethan-1-yl, or 3,3,3-trifluoropropan-1-yl.

In some embodiments, R⁴ is hydrogen.

In some embodiments, both L¹ and L² are bonds; R⁴ and R⁵ are hydrogen, and the compound has structural Formula II:

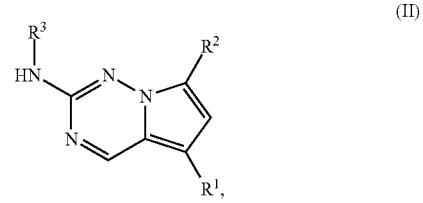

(II)

or a pharmaceutically acceptable salt thereof, wherein R¹, R², and R³ are as defined for Formula I, including the specific listings of moieties for each of those variables set forth above.

In some embodiments of Formula II, R¹ is pyridin-3-yl, pyridin-4-yl, pyrazol-4-yl, cyclohexyl, or 8-azabicyclo[3.2.1]oct-2-ene-3-yl, wherein R¹ is optionally substituted with up to four independently selected substituents. In some compound of this embodiment, R¹ is optionally substituted with up to four substituents independently selected from halo, hydroxy, —CN, —(C₁-C₄ alkyl optionally substituted with one or more substituents selected from cyano, hydroxy and halo), —C(O)NH₂, —COOH, —(C₀-C₃ alkylene)-C(O)—(C₁-C₄ alkyl), —(C₀-C₃ alkylene)-C(O)—NH—(C₁-C₄ alkyl), —(C₀-C₃ alkylene)-C(O)—NH—S(O)₂—(C₁-C₄ alkyl), —(C₀-C₃ alkylene)-C(O)—O—(C₁-C₄ alkyl), —(C₀-C₃ alkylene)-COOH, —(C₀-C₄ alkylene)-S(O)₂—(C₁-C₃ alkyl), —(C₁-C₃ alkylene)-O—(C₁-C₄ alkyl), —S(O)(=NH)—(C₁-C₄ alkyl), —S(O)₂—NH—(C₁-C₄ alkyl), -(cyclopropyl)-(cyano-substituted C₁-C₃ alkyl), -(cyclopropyl)-C(O)—NH—(C₁-C₄ alkyl), —(C₀-C₃ alkylene)-C(O)-heterocyclyl, —C(O)—(C₀-C₃ alkylene)-heterocyclyl, -(cyclopropyl)-C(O)-heterocyclyl, —(C₀-C₄ alkylene)-heterocyclyl, —(C₀-C₃ alkylene)-C(O)—NH-heterocyclyl, —(C₀-C₄ alkylene)-aryl, and —(C₀-C₄ alkylene)-heteroaryl, wherein the heterocyclyl or heteroaryl portion of the R¹ substitutent is optionally further substituted.

In some embodiments of Formula II, R¹ is 1-((1-oxetan-3-ylcarbonyl)azetidin-3-yl)pyrazol-4-yl, 1-(1-(1,1-dioxothiomorpholin-4-ylcarbonyl)-1-methylethan-1-yl)pyrazol-4-yl, 1-(1-(1-trifluoromethylcyclopropylcarbonyl)azetidin-3-yl)pyrazol-4-yl, 1-(1-(2,2,2-trifluoroethan-1-yl)azetidin-3-yl)pyrazol-4-yl, 1-(1-(2,2-dimethylmorpholin-4-ylcarbonyl)-1-methylethan-1-yl)pyrazol-4-yl, 1-(1-(2,6-dimethylmorpholin-4-ylcarbonyl)-1-methylethan-1-yl)pyrazol-4-yl, 1-(1-(2-oxa-6-azaspiro[3.3]heptan-6-ylcarbonyl)-1-methylethan-1-yl)pyrazol-4-yl, 1-(1-(2-oxa-6-azaspiro[3.4]octan-6-ylcarbonyl)-1-methylethan-1-yl)pyrazol-4-yl, 1-(1-(3,3,3-trifluoropropan-1-yl)azetidin-3-yl)pyrazol-4-yl, 1-(1-(8-oxa-3-azabicyclo[3.2.1]octan-3-ylcarbonyl)-1-methylethan-1-yl)pyrazol-4-yl, 1-(1-(azetidin-1-ylcarbonyl)-1-methylethan-1-yl)pyrazol-4-yl, 1-(1-(ethan-2-ylsulfonyl)-3-(cyanomethyl)azetidin-3-yl)pyrazol-4-yl, 1-(1-(hexahydro-1H-furo[3,4-c]pyrrol-5-ylcarbonyl)-1-methylethan-1-yl)pyrazol-4-yl, 1-(1-(isopropylaminocarbonyl)cyclopropyl)pyrazol-4-yl, 1-(1-(morpholin-4-ylcarbonyl)-1-methylethan-1-yl)pyrazol-4-yl, 1-(1-(morpholin-4-ylcarbonyl)cyclopropyl)pyrazol-4-yl, 1-(1-(pyrrolidin-1-ylcarbonyl)cyclopropyl)pyrazol-4-yl, 1-(1,1-dioxotetrahydro-2H-thiopyran-4-yl)pyrazol-4-yl, 1-(1,3-dimethylpyrazol-5-yl)pyrazol-4-yl, 1-(1-acetylazetidin-3-yl)pyrazol-4-yl, 1-(1-acetylpyrrolidin-3-yl)pyrazol-4-yl, 1-(1-cyanocyclopropylmethyl)pyrazol-4-yl, 1-(1H-pyrazol-4-ylmethyl)pyrazol-4-yl, 1-(1-hydroxy-3-chloropropan-2-yl)pyrazol-4-yl, 1-(1-hydroxylcarbonyl-1-methylethan-1-yl)pyrazol-4-yl, 1-(1-methoxycarbonylazetidin-3-yl)pyrazol-4-yl, 1-(1-methyl-2(1H)-pyridinon-5-ylmethyl)pyrazol-4-yl, 1-(1-methyl-2-oxopyrrolidin-4-ylmethyl)pyrazol-4-yl, 1-(1-methylaminocarbonyl-1-methylethan-1-yl)pyrazol-4-yl, 1-(1-methylsulfonylazetidin-3-yl)pyrazol-4-yl, 1-(1-t-butoxycarbonylpyrrolidin-3-yl)pyrazol-4-yl, 1-(2-(1,3,4-oxadiazol-2-yl)propan-2-yl)pyrazol-4-yl, 1-(2-(2-(2-hydroxypropan-2-yl)morpholin-4-ylcarbonyl)propan-2-yl)pyrazol-4-yl, 1-(2-(2,5-dioxa-8-azaspiro[3.5]nonan-8-ylcarbonyl)propan-2-yl)pyrazol-4-yl, 1-(2-(2-methyl-1,3,4-oxadiazol-5-yl)propan-2-yl)pyrazol-4-yl, 1-(2-(2-methyl-4,6-dihydro-5H-pyrrolo[3,4-d]thiazol-5-ylcarbonyl)propan-2-yl)pyrazol-4-yl, 1-(2-(2-methyl-6,7-dihydrothiazolo[4,5-c]pyridin-5-ylcarbonyl)propan-2-yl)pyrazol-4-yl, 1-(2-(3,5-dimethylpiperazin-1-ylcarbonyl)propan-2-yl)pyrazol-4-yl, 1-(2-(3-hydroxy-3-methylazetidin-1-ylcarbonyl)propan-2-yl)pyrazol-4-yl, 1-(2-(3-hydroxy-3-methylpiperidin-1-ylcarbonyl)propan-2-yl)pyrazol-4-yl, 1-(2-(3-hydroxy-3-methylpyrrolidin-1-ylcarbonyl)propan-2-yl)pyrazol-4-yl, 1-(2-(3-hydroxypyrrolidin-1-ylcarbonyl)propan-2-yl)pyrazol-4-yl, 1-(2-(4-cyano-4-methylpiperidin-1-ylcarbonyl)propan-2-yl)pyrazol-4yl, 1-(2-(4-hydroxy-4-methylpiperidin-1-ylcarbonyl)propan-2-yl)pyrazol-4-yl, 1-(2-(4-methyloxazol-2-yl)propan-2-yl)pyrazol-4-yl, 1-(2-(4-methylpiperazin-1-ylcarbonyl)propan-2-yl)pyrazol-4-yl, 1-(2-(5-(morpholin-4-yl)-1,3,4-oxadiazol-2-yl)propan-2-yl)pyrazol-4-yl, 1-(2-(5-(tetrahydrofuran-2-yl)-1,3,4-oxadiazol-2-yl)propan-2-yl)pyrazol-4-yl, 1-(2-(5-cyclopropyl-1,3,4-oxadiazol-2-yl)propan-2-yl)pyrazol-4-yl, 1-(2-(5-difluoromethyl-1,3,4-oxadiazol-2-yl)propan-2-yl)pyrazol-4-yl, 1-(2-(5-isopropyl-1,3,4-oxadiazol-2-yl)propan-2-yl)pyrazol-4-yl, 1-(2-(5-methyl-1,3,4-thiadiazol-2-yl)propan-2-yl)pyrazol-4-yl, 1-(2-(5-methyloxazol-2-yl)propan-2-yl)pyrazol-4-yl, 1-(2-(5-trifluoromethyl-1,3,4-oxadiazol-2-yl)propan-2-yl)pyrazol-4-yl, 1-(2-(methyl)-2-(morpholin-4-yl)propan-3-yl)pyrazol-4-yl, 1-(2-(methyl)-3-(morpholin-4-yl)propan-2-yl)pyrazol-4-yl, 1-(2-(pyrrolidin-1-ylcarbonyl)propan-2-yl)pyrazol-4-yl, 1-(2-cyanoethyl)pyrazol-4-yl, 1-(2-hydroxy-2-methylpropan-1-yl)pyrazol-4-yl, 1-(2-methoxyethyl)pyrazol-4-yl, 1-(2-methyl-3-hydroxypropan-2-yl)pyrazol-4-yl, 1-(2-methylpropyl)pyrazol-4-yl, 1-(2-methylsulfonylethan-1-yl)pyrazol-4-yl, 1-(2-morpholin-4-ylethyl)pyrazol-4-yl, 1-(2-oxopyrrolidin-3-yl)pyrazol-4-yl, 1-(2-oxopyrrolidin-4-ylmethyl)pyrazol-4-yl, 1-(3-methyl-1,2,4-oxadiazol-5-ylmethyl)pyrazol-4-yl, 1-(3-methylsulfonylphenylmethyl)pyrazol-4-yl, 1-(4-methylpiperazin-1-ylcarbonylmethyl)pyrazol-4-yl, 1-(4-methylsulfonylphenylmethyl)pyrazol-4-yl, 1-(5-methyl-1,2,4-oxadiazol-3-ylmethyl)pyrazol-4-yl, 1-(5-methyl-1,3,4-oxadiazol-2-ylmethyl)pyrazol-4-yl, 1-(5-methylpyrazin-2-ylmethyl)pyrazol-4-yl, 1-(5-oxopyrrolidin-2-ylmethyl)pyrazol-4-yl, 1-(6-hydroxyhexahydrofuro[3,2-b]furan-3-yl)pyrazol-4-yl, 1-(6-methylpyrazin-2-ylmethyl)pyrazol-4-yl, 1-(ethoxycarbonylmethyl)pyrazol-4-yl, 1-(hexahydrofuro[2,3-b]furan-3-yl)pyrazol-4-yl, 1-(hydroxycarbonylmethyl)pyrazol-4-yl, 1-(isopropylaminocarbonylmethyl)pyrazol-4-yl, 1-(isopropylcarbonylmethyl)pyrazol-4-yl, 1-(methylaminocarbonylmethyl)pyrazol-4-yl, 1-(methylsulfonylaminocarbonylmethyl)pyrazol-4-yl, 1-(methylsulfonylmethyl)pyrazol-4-yl, 1-(morpholin-4-ylcarbonylmethyl)pyrazol-4-yl, 1-(oxetan-2-ylmethyl)pyrazol-4-yl, 1-(oxetan-3-ylmethyl)pyrazol-4-yl, 1-(pyrazin-2-ylmethyl)pyrazol-4-yl, 1-(pyridazin-4-ylmethyl)pyrazol-4-yl, 1-(pyridin-3-ylmethyl)pyrazol-4-yl, 1-(pyrrolidin-1-ylcarbonylmethyl)pyrazol-4-yl, 1-(tetrahydrofuran-2-ylmethyl)pyrazol-4-yl, 1-(tetrahydrofuran-3-yl)pyrazol-4-yl, 1-(tetrahydrofuran-3-ylaminocarbonylmethyl)pyrazol-4-yl, 1-(tetrahydropyran-4-yl)pyrazol-4-yl, 1-(tetrahydropyran-4-ylmethyl)pyrazol-4-yl, 1,3-dimethylpyrazol-4-yl, 1-difluoromethylpyrazol-4-yl, 1H-pyrazol-4-yl, 1-methylpyrazol-3-yl, 1-methylpyrazol-4-yl, 1-oxetan-3-ylpyrazol-4-yl, 1-t-butylpyrazol-4-yl, 2-(1,1-dioxothiomorpholin-4-yl)pyridin-4-yl, 2-(1-methylpiperidin-3-yloxy)pyridin-4-yl, 2-(1-methylpiperidin-4-yloxy)pyridin-4-yl, 2-(1-methylpyrrolidin-3-yloxy)pyridin-4-yl, 2-(2-methoxyethan-1-yloxy)pyridin-4-yl, 2-(3-oxopiperazin-1-yl)pyridin-4-yl, 2-(4-acetylpiperazin-1-yl)pyridin-4-yl, 2-(4-methylpiperazin-1-yl)pyridin-4-yl, 2-(4-methylsulfonylpiperazin-1-yl)pyridin-4-yl, 2-(morpholin-4-yl)pyridin-4-yl, 2-(oxetan-3-yloxy)pyridin-4-yl, 2-(piperidin-3-yloxy)pyridin-4-yl, 2-(piperidin-4-yloxy)pyridin-4-yl, 2-(pyrrolidin-3-yloxy)pyridin-4-yl, 2,6-dimethylpyridin-4-yl, 2-isopropoxypyridin-4-yl, 2-isopropylaminopyridin-4-yl, 2-methylaminocarbonyl-6-methylpyridin-4-yl, 2-methylaminocarbonylpyridin-4-yl, 2-methylaminopyridin-4-yl, 2-methylpyridin-4-yl, 2-morpholin-4-ylpyridin-4-yl, 2-pyrrolidin-1-ylpyridin-4-yl, 4-(1,1-dioxothiomorpholin-4-ylcarbonyl)cyclohexyl, 4-(2-oxa-6-azaspiro[3.3]heptan-6-ylcarbonyl)cyclohexyl, 4-(4,4-difluoropiperidin-1-ylcarbonyl)cyclohexyl, 4-(4-methylpiperazin-1-yl)carbonylcyclohexyl, 4-(morpholin-4-ylcarbonyl)cyclohexyl, 4-hydroxycarbonylcyclohexyl, 4-methylpyridin-3-yl, 5-(4-methylpiperazin-1-ylcarbonyl)pyridin-3-yl, 5-(morpholin-4-ylmethyl)pyridin-3-yl, 5-(pyrrolidin-1-ylcarbonyl)pyridin-3-yl, 5-(S-imino(methyl)sulfinyl)pyridin-3-yl, 5-aminocarbonylpyridin-3-yl, 5-cyanopyridin-3-yl, 5-dimethylaminocarbonylpyridin-3-yl, 5-fluoropyridin-3-yl, 5-hydroxycarbonylpyridin-3-yl, 5-methylaminocarbonylpyridin-3-yl, 5-methylaminosulfonylpyridin-3-yl, 5-methylpyridin-3-yl, 5-methylsulfonylpyridin-3-yl, 6-(1-methyl-4,5,6,7-tetrahydro-1H-pyrazolo[3,4-c]pyridin-6-yl)pyridin-4-yl, 6-(1-methylpiperazin-4-yl)pyridin-3-yl, 6-(2-(2-hydroxypropan-2yl)morpholin-4-yl)pyridin-4-yl, 6-(2,5-dioxa-8-azaspiro[3.5]nonan-8-yl)pyridin-4-yl, 6-(2-hydroxypropan-2-yl)pyridin-4-yl, 6-(2-methyl-4,5,6,7-tetrahydro-3H-imidazo[4,5-c]pyridin-5-yl)pyridin-4-yl, 6-(2-methyl-4,5,6,7-tetrahydrothiazolo[5,4-c]pyridin-5-yl)pyridin-4-yl, 6-(2-methyl-5,6-dihydro-4H-pyrrolo[3,4-d]thiazol-5-yl)pyridin-4-yl, 6-(2-oxa-6-azaspiro[3.3]heptan-6-yl)pyridin-4-yl, 6-(2-oxa-6-azaspiro[3.4]octan-6-yl)pyridin-4-yl, 6-(2-oxa-7-azaspiro[3.5]nonan-7-yl)pyridin-4-yl, 6-(2-oxo-oxazol-3-yl)pyridin-4-yl, 6-(3-methyl-3-hydroxyazetidin-1-yl)pyridin-4-yl, 6-(3-methyl-3-hydroxypyrrolidin-1-yl)pyridin-4-yl, 6-(3-oxa-7-azaspiro[3.5]nonan-7-yl)pyridin-4-yl, 6-(3-oxomorpholin-4-yl)pyridin-4-yl, 6-(4-(cyclopropylsulfonyl)piperazin-1-yl)pyridin-4-yl, 6-(4-(N-isopropyl-N-ethylaminocarbonyl)piperazin-1-yl)pyridin-4-yl, 6-(4-(oxetan-3-yl)piperazin-1-yl)pyridin-4-yl, 6-(4-(oxetan-3-ylcarbonyl)piperazin-1-yl)pyridin-4-yl, 6-(4-(oxetan-3-ylmethyl)piperazin-1-yl)pyridin-4-yl, 6-(4-(oxetan-3-yloxycarbonyl)piperazin-1-yl)pyridin-4-yl, 6-(4-methoxycarbonylpiperazin-1-yl)pyridin-4-yl, 6-(4-methyl-4-hydroxypiperidin-1-yl)pyridin-4-yl, 6-(4-methylpiperazin-1-ylcarbonyl)pyridin-3-yl, 6-(4-methylpiperazin-1-ylmethyl)pyridin-4-yl, 6-(4-trifluoromethylsulfonylpiperazin-1-yl)pyridin-4-yl, 6-(8-oxa-3-azabicyclo[3.2.1]octan-3-yl)pyridin-4-yl, 6-(hexahydro-1H-furo[3,4-c]pyrrol-5-yl)pyridin-4-yl, 6-(isopropylaminocarbonyl)pyridin-3-yl, 6-(methylaminocarbonyl)pyridin-3-yl, 6-(morpholin-4-yl)pyridin-4-yl, 6-(morpholin-4-ylcarbonyl)pyridin-3-yl, 6-(morpholin-4-ylmethyl)pyridin-3-yl, 6-(oxetan-3-yl)pyridin-4-yl, 6-(piperazin-1-yl)pyridin-4-yl, 6-(pyridin-3-yloxy)pyridin-4-yl, 6-(S-imino(methyl)sulfinyl)pyridin-4-yl, 6-(S-methyl-S-iminosulfinyl)pyridin-3-yl, 6-(tetrahydropyran-3-ylamino)pyridin-4-yl, 6-(tetrahydropyran-4-ylamino)pyridin-4-yl, 6-fluoropyridin-4-yl, 6-methylaminosulfonylpyridin-3-yl, 6-methylpyridin-3-yl, 6-methylpyridin-4-yl, or 6-methylsulfonylpyridin-3-yl.

In some embodiments of Formula II, $R^2$ is cyclohexyl substituted with hydroxy and optionally additionally substituted with one to three substituents independently selected from the group consisting of $C_1$-$C_4$ alkyl and fluoro, or is 4,5,6,7-tetrahydro-1H-indazolyl optionally substituted with one to three substituents independently selected from the group consisting of $C_1$-$C_4$ alkyl and fluoro. In some compound of these embodiments, $R^2$ is 4-hydroxycyclohexyl, 4-methyl-4-hydroxycyclohexyl, 3,3-difluoro-4-hydroxycyclohexyl, 3-fluoro-4-hydroxycyclohexyl, or 4,5,6,7-tetrahydro-1H-indazolyl.

In some embodiments of Formula II, $R^3$ is —$C_3$-$C_8$ alkyl, —($C_2$-$C_6$ alkylene)-O—($C_1$-$C_6$ alkyl), $C_3$-$C_6$ cycloalkyl, or —($C_2$-$C_6$ alkylene)-$C_3$-$C_6$ cycloalkyl, wherein $R^3$ is optionally substituted with 1-5 substituents independently selected from the group consisting of deuterium, halo, and —OH.

In some embodiments, the compound has structural Formula III:

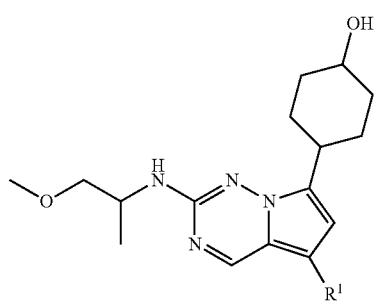

(III)

or a pharmaceutically acceptable salt thereof, wherein $R^1$ is as defined for Formula I, including the specific listings of moieties for that variable set forth above.

In some embodiments, the compound of Formula III has the stereochemistry depicted in Formula IIIa:

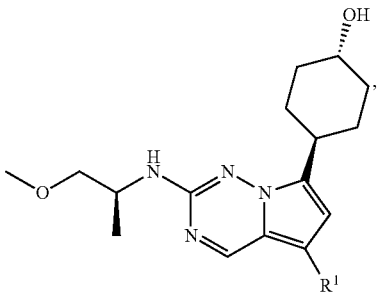

(IIIa)

or is a pharmaceutically acceptable salt thereof, wherein $R^1$ is as defined for Formula I, including the specific moieties for that variable set forth above.

In some embodiments, the compound of Formula III has the stereochemistry depicted in Formula IIIb:

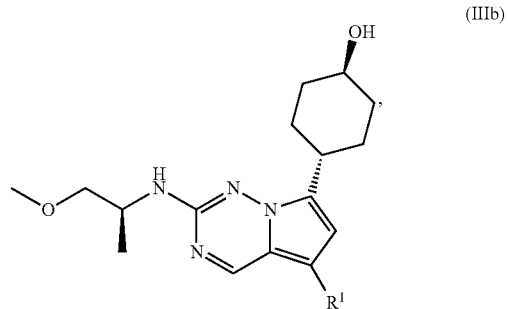

(IIIb)

or a pharmaceutically acceptable salt thereof, wherein $R^1$ is as defined for Formula I, including the specific moieties for that variable set forth above.

In some embodiments, the compound has structural Formula IV:

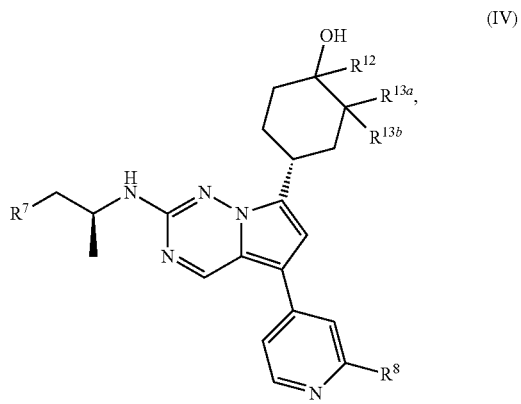

(IV)

or structural Formula V:

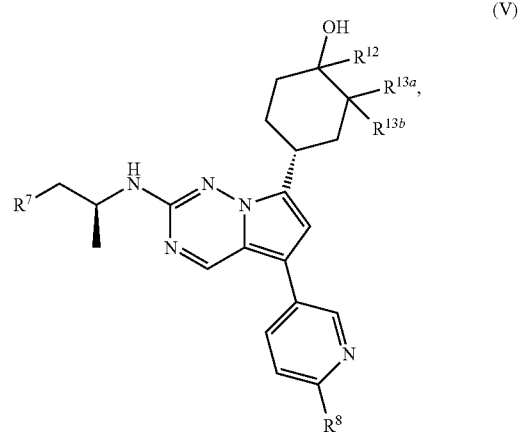

(V)

wherein:

R$^8$ is —(C$_0$-C$_4$ alkylene)-S(O)$_2$—(C$_1$-C$_3$ alkyl), —C(O)—NH—(C$_1$-C$_4$ alkyl), —C$_1$-C$_4$ alkyl optionally substituted with one or more of halo, hydroxy and cyano, —NH—(C$_1$-C$_4$ alkyl), —O—(C$_1$-C$_3$ alkylene)-O—(C$_1$-C$_4$ alkyl), —O—(C$_1$-C$_4$ alkyl), —S(O)(=NH)—(C$_1$-C$_4$ alkyl), —S(O)$_2$—NH—(C$_1$-C$_4$ alkyl), —(C$_0$-C$_3$ alkylene)-C(O)-heterocyclyl, —(C$_0$-C$_3$ alkylene)-NH-heterocyclyl, —(C$_0$-C$_4$ alkylene)-heterocyclyl, —O-heteroaryl, or —O-heterocyclyl, wherein any heterocyclyl, or heteroaryl portion of R$^8$ is optionally further substituted;

R$^7$ is —O—C$_1$-C$_3$ alkyl, C$_1$-C$_3$ haloalkyl, or —O—C$_1$-C$_3$ haloalkyl; and R$^{12}$ is hydrogen, or C$_1$-C$_4$ alkyl; and each of R$^{13a}$ and R$^{13b}$ is independently selected from hydrogen and fluoro.

In some embodiments of Formulae IV or V, R$^8$ is —CH$_3$, —C(O)NHCH$_3$, —C(O)NHCH(CH$_3$)$_2$, —NHCH(CH$_3$)$_2$, —NHCH$_3$, —S(=O)(=NH)—CH$_3$, —S(=O)$_2$—CH$_3$, —S(=O)$_2$—NH—CH$_3$, 1,1-dioxothiomorpholin-4-yl, 1-methyl-1,4,5,7-tetrahydro-6H-pyrazolo[3,4-c]pyridin-6-yl, 1-methylpiperidin-3-yloxy, 1-methylpiperidin-4-yloxy, 1-methylpyrrolidin-3-yloxy, 1-oxa-7-azospiro[3.5]nonan-7-yl, 2-(2-hydroxypropan-2-yl)morpholin-4-yl, 2,5-dioxa-8-azospiro[3.5]nonan-8-yl, 2-methoxyethan-1-yloxy, 2-methyl-4,6-dihydro-5H-pyrrolo[3,4-d]thiazol-5-yl, 2-methyl-6,7-dihydrothiazolo[5,4-c]pyridin-5(4H)-yl, 2-oxa-6-azospiro[3.3]heptan-6-yl, 2-oxa-6-azospiro[3.5]octan-6-yl, 2-oxa-7-azospiro[3.5]nonan-7-yl, 2-oxo-oxazolidin-3-yl, 3-oxomorpholin-4-yl, 3-oxopiperazin-1-yl, 4-(N-ethyl-N-isopropylaminocarbonyl)piperazin-1-yl, 4-(oxetan-3-yl)piperazin-1-yl, 4-(oxetan-3-ylmethyl)piperazin-1-yl, 4-acetylpiperazin-1-yl, 4-cyclopropylsulfonylpiperazin-1-yl, 4-methoxycarbonylpiperazin-1-yl, 4-methylpiperazin-1-yl, 4-methylpiperazin-1-ylmethyl, 4-sulfonylmethylpiperazin-1-yl, 4-trifluoromethylsulfonylpiperazin-1-yl, 8-oxa-3-azabicyclo[3.2.1]octan-3-yl, isopropyloxy, morpholin-4-carbonyl, morpholin-4-yl, morpholin-4-ylmethyl, oxetan-3-yl, oxetan-3-yloxy, piperazin-1-yl, piperidin-3-yloxy, piperidin-4-yloxy, pyridin-3-yloxy, pyrrolidin-1-yl, pyrrolidin-3-yloxy, tetrahydro-1H-furo[3,4-c]pyrrol-5-yl, tetrahydrofuran-3-ylamino, or tetrahydropyran-4-yl.

In some embodiments of Formulae IV or V, R$^8$ is optionally substituted morpholin-4-yl, —S(=O)(=NH)—C$_1$-C$_3$ alkyl, or —S(=O)$_2$—C$_1$-C$_3$ alkyl. In some more specific aspects of these embodiments, R$^8$ is morpholin-4-yl, —S(=O)(=NH)—CH$_3$, or —S(=O)$_2$—CH$_3$.

In some embodiments of Formulae IV or V, R$^7$ is —OCH$_3$, —CF$_3$, or —OCHF$_2$.

In some embodiments of Formulae IV or V, R$^{12}$ is hydrogen or —CH$_3$. In some aspects of these embodiments, R$^{12}$ is hydrogen and each of R$^{13a}$ and R$^{13b}$ is fluoro. In some aspects of these embodiments, each of R$^{12}$ and R$^{13a}$ is hydrogen and R$^{13b}$ is fluoro. In some aspects of these embodiments, each of R$^{12}$, R$^{13a}$ and R$^{13b}$ is hydrogen and the compound has structural formula IVa:

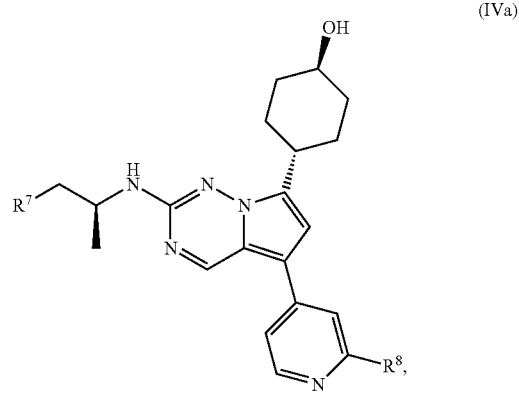

(IVa)

or structural formula Va:

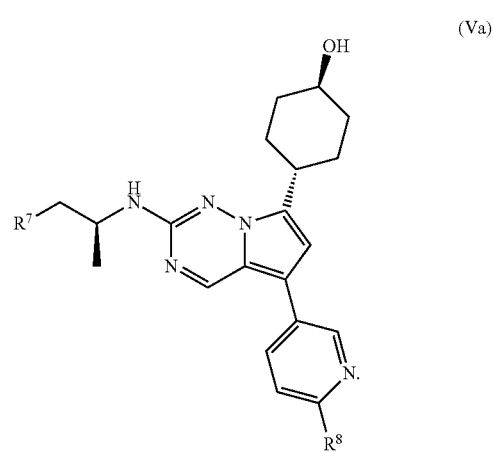

(Va)

In some embodiments, the compound has structural Formula VI:

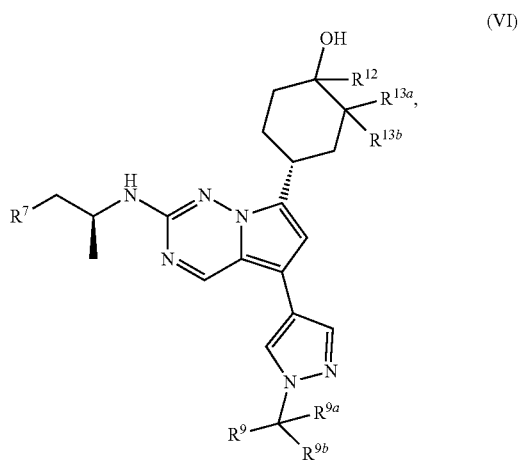

(VI)

wherein:

R$^7$ is —O—C$_1$-C$_3$ alkyl, C$_1$-C$_3$ haloalkyl, or —O—C$_1$-C$_3$ haloalkyl;

each of R$^{9a}$ and R$^{9b}$ are —CH$_3$, or R$^{9a}$ and R$^{9b}$ are taken together with the carbon atom to which they are bound to form cyclopropyl;

$R^9$ is $C_1$-$C_3$ alkyl, $C_1$-$C_3$ hydroxyalkyl, —COOH, —C(O)NH—$C_1$-$C_4$ alkyl, —CH$_2$-heterocyclyl, —C(=O)-heterocyclyl or a 5-membered heteroaryl, wherein the heterocyclyl or heteroaryl portion of $R^9$ is optionally substituted with up to two substituents independently selected from oxo, cyclopropyl, —OH, —CN, —$C_1$-$C_3$ alkyl, and —$C_1$-$C_3$ hydroxyalkyl; and $R^{12}$ is hydrogen, or $C_1$-$C_4$ alkyl; and each of $R^{13a}$ and $R^{13b}$ is independently selected from hydrogen and fluoro.

In some embodiments of Formula VI, $R^7$ is —OCH$_3$, —CF$_3$, or —OCHF$_2$.

In some embodiment of Formula VI, $R^9$ is —CH$_3$, —CH$_2$OH, —COOH, —C(O)NHCH$_3$, —C(O)NHCH(CH$_3$)$_2$, 1,1-dioxothiomorpholin-4-ylcarbonyl, 2-(2-hydroxypropan-2-yl)morpholin-4-ylcarbonyl, 2,2-dimethylmorpholin-4-ylcarbonyl, 2,5-dioxa-8-azaspiro[3.5]nonan-8-ylcarbonyl, 2,6-dimethylmorpholin-4-ylcarbonyl, 2-oxa-6-azaspiro[3.3]heptan-6-ylcarbonyl, 2-oxa-6-azaspiro[3.4]octan-6-ylcarbonyl, 3-hydroxypyrrolidin-1-ylcarbonyl, 4-cyano-4-methylpiperidin-1-ylcarbonyl, 4-hydroxy-4-methylpiperidin-1-ylcarbonyl, 4-methylpiperazin-1-ylcarbonyl, 5-cyclopropyl-1,3,4-oxadiazol-2-yl, 5-methyl-1,3,4-oxadiazol-2-yl, 8-oxa-3-azabicyclo[3.2.1]octan-3-ylcarbonyl, azetidin-1-ylcarbonyl, morpholin-4-ylcarbonyl, morpholin-4-ylmethyl, pyrrolidin-1-ylcarbonyl, or tetrahydro-1H-furo[3,4-c]pyrrol-5(3H)-ylcarbonyl. In some aspects of these embodiments, $R^9$ is morpholin-4-ylcarbonyl, 4-methylpiperazin-1-ylcarbonyl, 2-oxa-6-azaspiro[3.3]heptan-6-ylcarbonyl, 3-methyl-3-hydroxypyrrolidin-1-ylcarbonyl, 5-methyl-1,3,4-oxadiazol-2-yl, or 5-methyl-1,3,4-thiadiazol-2-yl.

In some embodiments of Formula VI, $R^{12}$ is hydrogen or —CH$_3$. In some aspects of these embodiments, $R^{12}$ is hydrogen and each of $R^{13a}$ and $R^{13b}$ is fluoro. In some aspects of these embodiments, each of $R^{12}$ and $R^{13a}$ is hydrogen and $R^{13b}$ is fluoro. In some aspects of these embodiments, each of $R^{12}$, $R^{13a}$ and $R^{13b}$ is hydrogen and the compound has structural formula VIa:

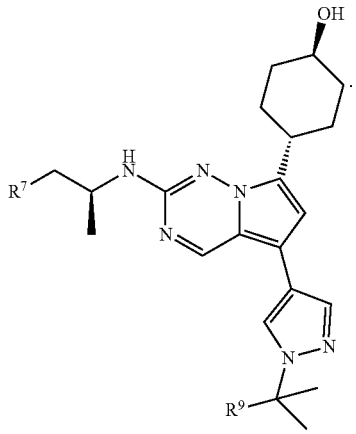

(VIa)

In some embodiments, the compound has structural Formula VII:

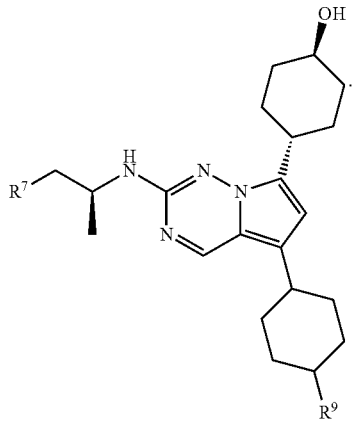

(VII)

wherein:
$R^{7a}$ is $C_1$-$C_4$ alkyl, —O—$C_1$-$C_3$ alkyl, $C_1$-$C_3$ haloalkyl, or —O—$C_1$-$C_3$ haloalkyl;
$R^9$ is —COOH, —C(=O)-heterocyclyl or a 5-membered heteroaryl, wherein $R^9$ is optionally substituted with up to two substituents independently selected from oxo, —OH and —$C_1$-$C_3$ alkyl; and
$R^{12}$ is hydrogen or $C_1$-$C_4$ alkyl; and
each of $R^{13a}$ and $R^{13b}$ are independently selected from hydrogen and fluoro.

In some embodiments of Formula VII, $R^{7a}$ is —(CH$_2$)$_3$CH$_3$, —OCH$_3$, —CF$_3$, or —OCHF$_2$. In some aspects of these embodiments, $R^{7a}$ is —(CH$_2$)$_3$CH$_3$, —OCH$_3$, or —CF$_3$.

In some embodiments of Formula VII, $R^9$ is —COOH, morpholin-4-ylcarbonyl, 4-methylpiperazin-1-ylcarbonyl, 2-oxa-6-azaspiro[3.3]heptan-6-ylcarbonyl, 3-methyl-3-hydroxypyrrolidin-1-ylcarbonyl, 5-methyl-1,3,4-oxadiazol-2-yl, 5-methyl-1,3,4-thiadiazol-2-yl, or 1,1-dioxothiomorpholin-4-ylcarbonyl. In some aspects of these embodiments, $R^9$ is —COOH, morpholin-4-ylcarbonyl, or 1,1-dioxothiomorpholin-4-ylcarbonyl. In some more specific aspects of these embodiments, $R^9$ is morpholin-4-ylcarbonyl.

In some embodiments of Formula VII, $R^{12}$ is hydrogen or —CH$_3$. In some aspects of these embodiments, $R^{12}$ is hydrogen and each of $R^{13a}$ and $R^{13b}$ is fluoro. In some aspects of these embodiments, each of $R^{12}$ and $R^{13a}$ is hydrogen and $R^{13b}$ is fluoro. In some aspects of these embodiments, each of $R^{12}$, $R^{13a}$ and $R^{13b}$ is hydrogen and the compound has structural formula VIIa:

(VIIa)

In other embodiments, this disclosure provides a composition (e.g., a pharmaceutical composition) comprising any of the compounds (as defined herein) described herein.

In some embodiments, a provided compound is a compound depicted in FIG. 1, a pharmaceutically acceptable salt thereof, or other form thereof (e.g., as also described herein).

Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Other pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

For ease of reading, we will not refer to both a compound of the invention and a pharmaceutically acceptable salt thereof when describing each and every composition, method, and use within the scope of the invention. It is to be understood that where a compound of the invention can be used, a pharmaceutically acceptable salt thereof may also be useful, and making that determination is well within the ability of one of ordinary skill in the art. For example, a compound described herein or a pharmaceutically acceptable salt thereof may have an increased specificity for at least one TAM kinase relative to another; may exhibit that specificity relative to FLT3; and so forth as described herein.

In the unlikely event a compound described herein is found in nature, that compound may be provided and/or utilized as described herein in a form different from that in which it is found in nature. For example, a compound described herein can be provided or utilized as a non-naturally occurring racemic mixture or in a non-naturally occurring isotopic form. A composition of the invention (e.g., a pharmaceutical composition) can contain a different concentration of a given compound (either a higher or lower concentration) than a reference composition or source (e.g., a natural source) of the compound and would, therefore, be a non-naturally occurring composition. For example, in some embodiments, a compound is "substantially pure" by virtue of being substantially free of other, distinct chemical compounds, including but not limited to those with which it may have been associated in a reference composition or source (e.g., a natural source). In some embodiments, a composition of the invention contains a compound described herein and less than about 25%, 20%, 15%, 10%, 9%, 8%, 7%, 6%, 5%, 4%, 3%, 2%, 1%, 0.5%, 0.1%, or 0.05%, by weight, of other distinct chemical compounds and/or other materials. In case of doubt, a composition containing a single stereoisomer of a compound differs from a composition containing a racemic mixture of that compound; a particular salt of a compound differs from other salt forms of the compound; compounds having one conformational isomer ((Z) or (E)) of a double bond differ from compounds having the other conformational isomer ((E) or (Z)) of the double bond; and compounds in which one or more atoms are of a different isotope than is present in compounds of a reference preparation differ from that reference preparation.

Any compound described herein can be prepared using methods described herein and/or known in the art. Techniques useful in synthesizing these compounds are accessible to one of ordinary skill in the art, and the discussion below illustrates certain of the diverse methods available for use in assembling them. The discussion is not intended to limit the scope of useful reactions or reaction sequences.

The present compounds are generally prepared according to the Schemes set forth below. Schemes 1-3 are general schemes for producing compounds where $R^4$ and $R^5$ are each hydrogen, $L^2$ is a bond and $R^2$ is 4-hydroxycyclohexyl. Scheme 4 is a more general scheme for synthesizing compounds described herein. The starting material in Scheme 4, 7-bromo-4-chloro-2-(methylthio)pyrrolo[2,1-f][1,2,4]triazine, is commercially available. $L^{1'}$ represents either a precursor to $L^1$ having a leaving group when $L^1$ is other than a bond; or a leaving group when $L^1$ is a bond. X represents a halogen.

Scheme 1

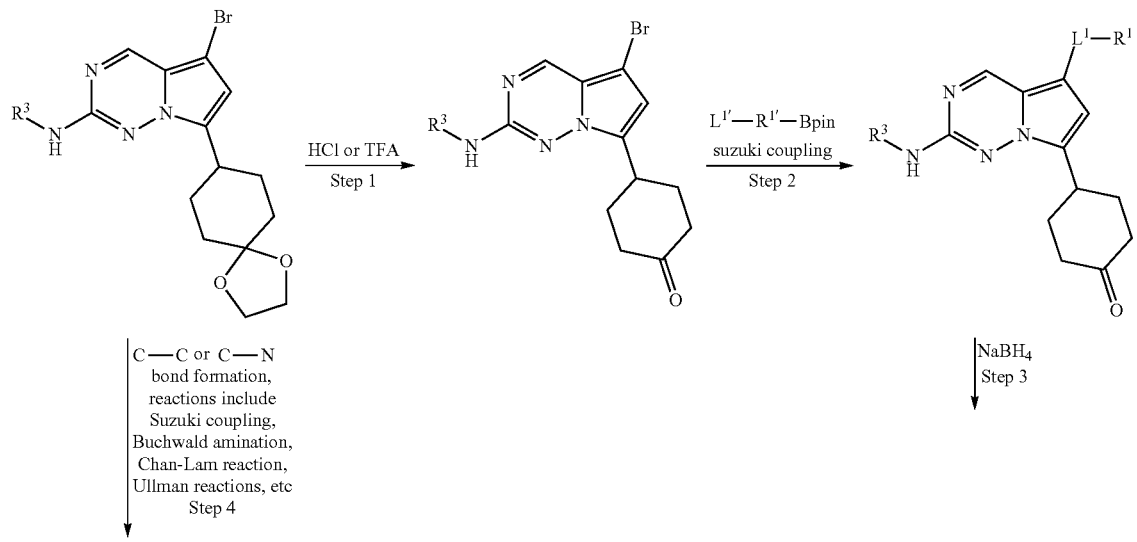

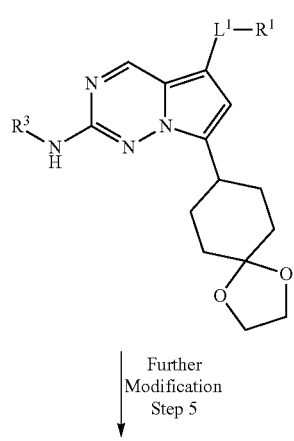
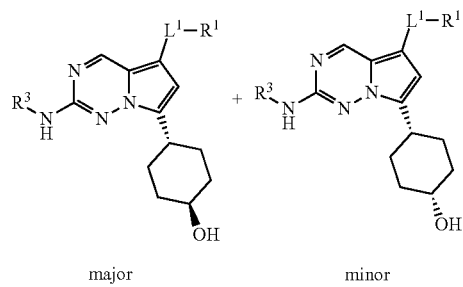
major + minor
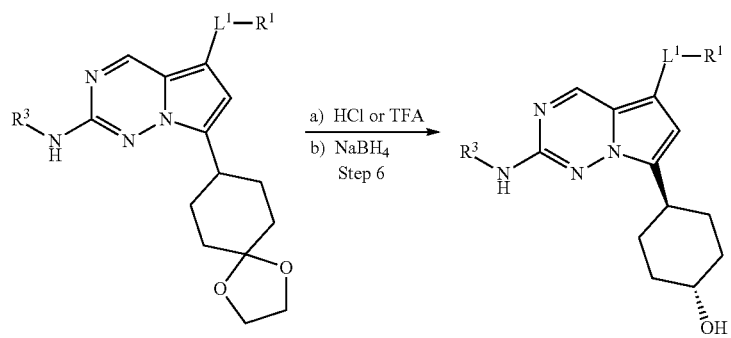
Scheme 2
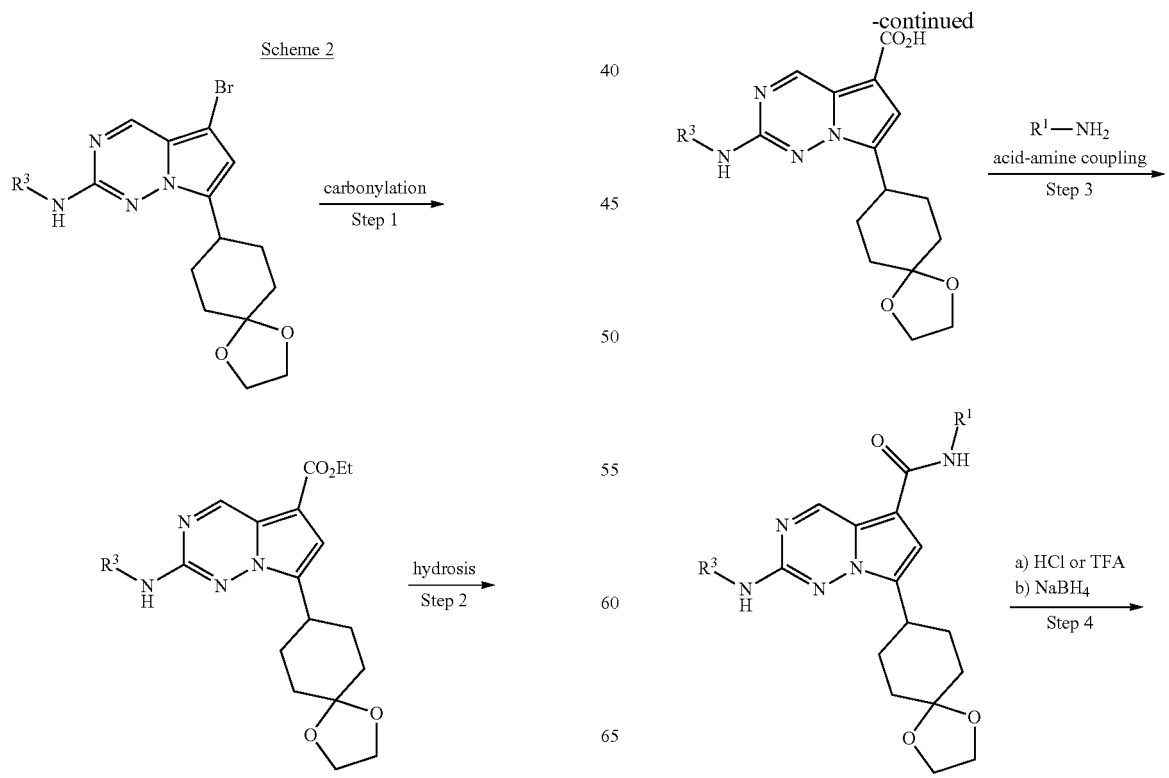

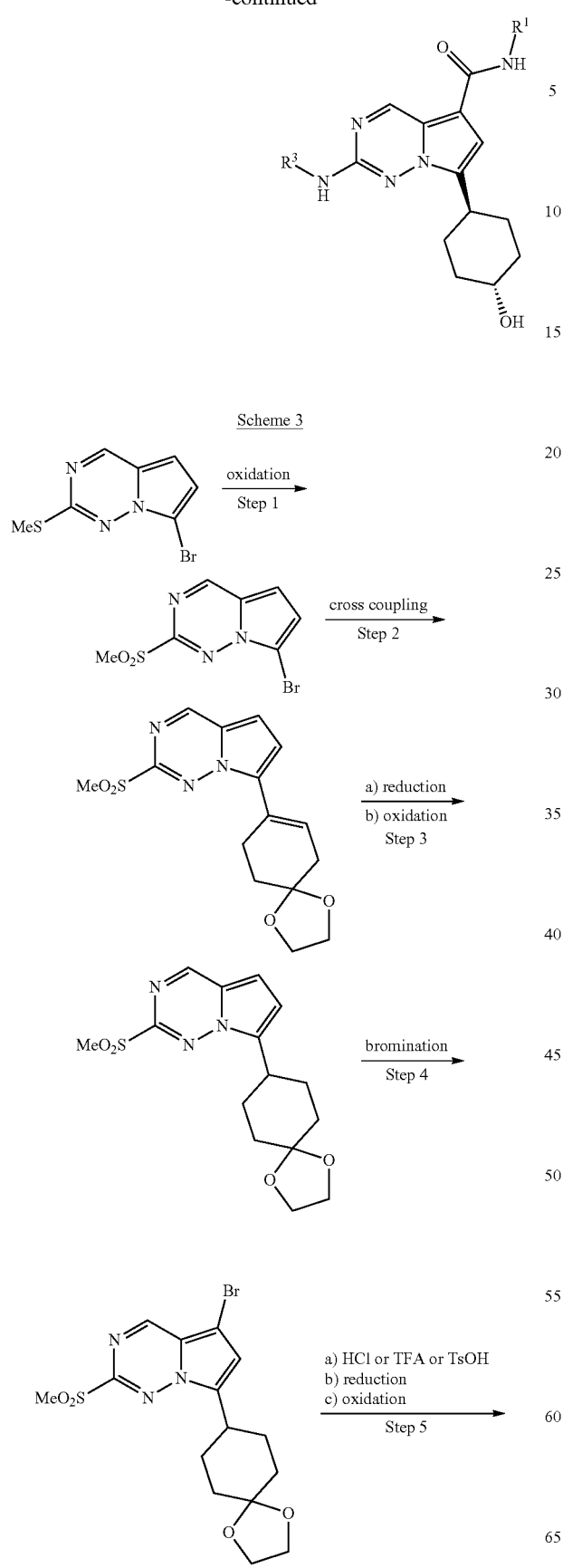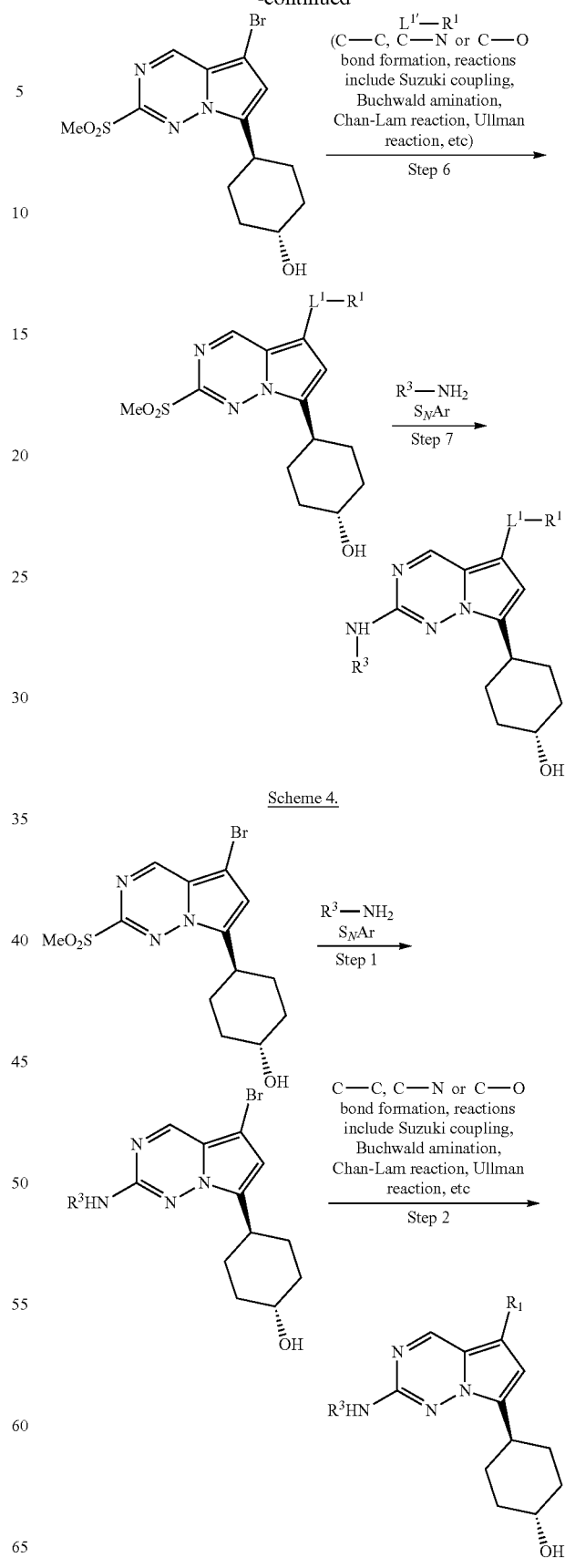

Scheme 5.
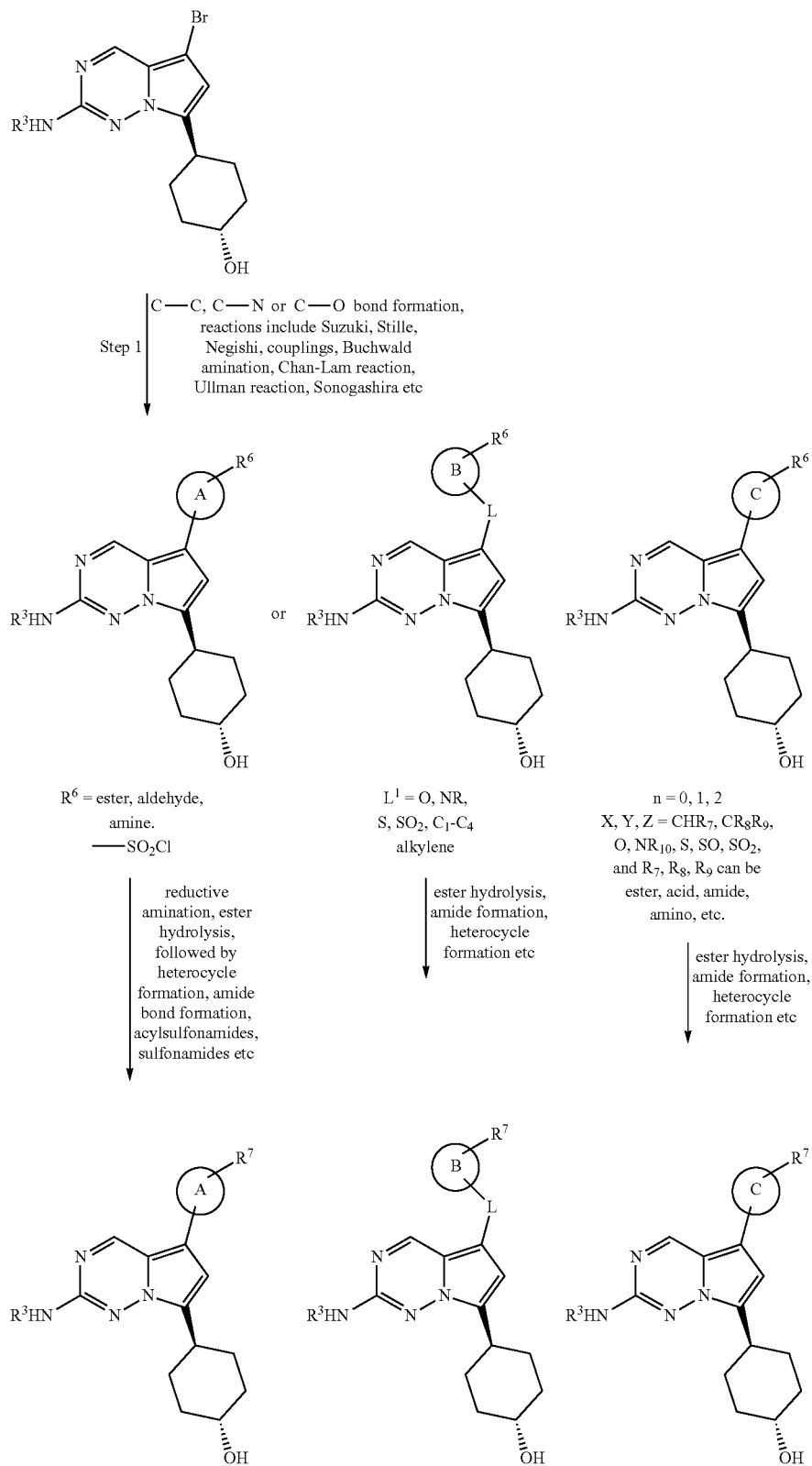

In Scheme 5, ring A represents phenyl; ring B a saturated heterocyclyl ring or a cycloalkyl ring; and ring C a partially saturated carbocyclyl, a partially saturated heterocyclyl, or a heteroaryl ring.

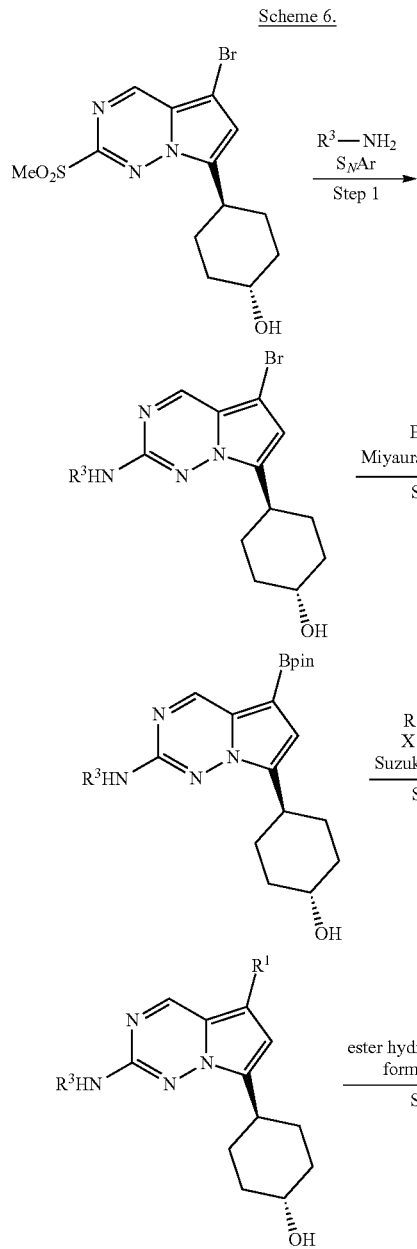

Scheme 6.

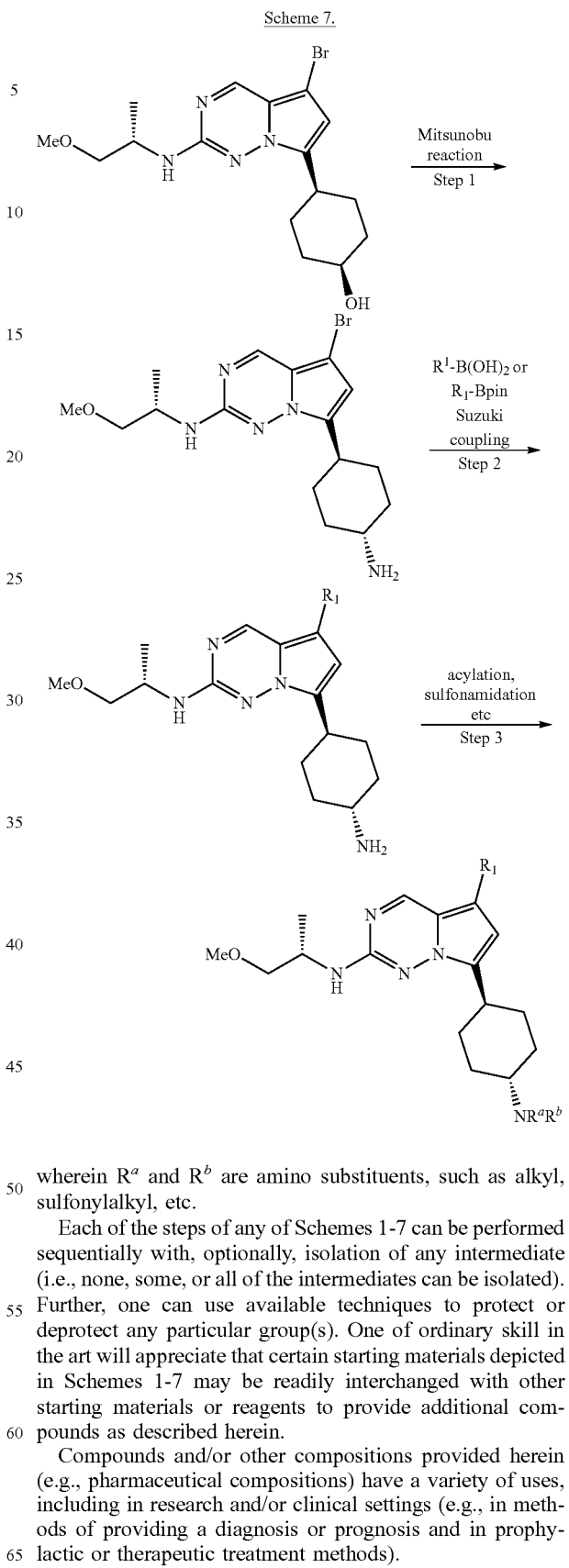

Scheme 7.

wherein $R^a$ and $R^b$ are amino substituents, such as alkyl, sulfonylalkyl, etc.

Each of the steps of any of Schemes 1-7 can be performed sequentially with, optionally, isolation of any intermediate (i.e., none, some, or all of the intermediates can be isolated). Further, one can use available techniques to protect or deprotect any particular group(s). One of ordinary skill in the art will appreciate that certain starting materials depicted in Schemes 1-7 may be readily interchanged with other starting materials or reagents to provide additional compounds as described herein.

Compounds and/or other compositions provided herein (e.g., pharmaceutical compositions) have a variety of uses, including in research and/or clinical settings (e.g., in methods of providing a diagnosis or prognosis and in prophylactic or therapeutic treatment methods).

In some embodiments, the compounds and other compositions described herein are used in preventing or treating a cancer in a patient in need thereof (e.g., in a patient having tumor cells that express or over-express a TAM kinase or any combination of TAM kinases). In various embodiments of these methods, one may carry out a step of obtaining a biological sample from the patient and/or detecting the presence of and/or determining the amount of, or activity of, one or more TAM kinases in a provided biological sample (i.e., these steps are optional). Similarly, and in any embodiment of these methods, one may carry out other tests useful in diagnosing whether the patient has cancer and/or in characterizing the cancer (e.g., its type, grade, susceptibility to treatment, etc. . . . ) (i.e., diagnostic testing is another optional step that can be carried out prior to or in the course of treatment). The methods of treatment require administering to a patient in need thereof a therapeutically effective amount of a compound described herein (e.g., a compound having the structure depicted in Formula I-Formula VII in a pharmaceutically acceptable composition to reduce a sign or symptom of the disease), and TAM kinases can be evaluated in biological samples obtained from the patient at any point(s) in time during the therapeutic regimen.

Each method (e.g., each therapeutic or diagnostic method) that employs a compound described herein and involves administration of the compound to a patient may also be expressed in terms of "use" and vice versa. For example, the invention encompasses: the use of a compound or composition described herein for the treatment of a disease described herein (e.g., a cancer); a compound or composition for use in diagnosing and/or treating a disease (e.g., a cancer); and the use of the compound or composition for the preparation a medicament for treating a disease described herein (e.g., a cancer).

The methods of the invention that concern diagnosing and/or treating a disease described herein (e.g., a cancer) may specifically exclude any one or more of the types of diseases (e.g., any one or more of the types of cancer) described herein. For example, the invention features methods of treating cancer by administering a compound described herein (e.g., a compound of any one of Formulas I-VII) with the proviso that the cancer is not a breast cancer; with the proviso that the cancer is not a breast cancer or a leukemia; with the proviso that the cancer is not a breast cancer, a leukemia, or an ovarian cancer; and so forth, with exclusions selected from any of the diseases/cancer types listed herein and with the same notion of variable exclusion from lists of elements relevant to other aspects and embodiments of the invention (e.g., chemical substituents of a compound described herein or components of kits and pharmaceutical compositions).

A provided compound and/or a composition containing it can have activity against each of TYRO3, AXL and MERTK (e.g., inhibitory activity above a particular level (e.g., a reference level) with respect to each of TYRO3, AXL and MERTK). In some embodiments, a provided compound and/or composition shows specificity for only one or any two (but not all) of TYRO3, AXL and MERTK. In some embodiments, a provided compound and/or composition shows more specificity for one TAM kinase than another TAM kinase or more specificity for a TAM kinase than a non-TAM kinase.

In some embodiments, a provided compound and/or composition is considered to be specific for a given kinase or set of kinases when it shows at least or about 2-fold, 3-fold, 4-fold, 5-fold, 10-fold, 15-fold, 20-fold, 50-fold, 100-fold or more activity for the specific kinase(s) than for one or more appropriate comparator kinase(s) (e.g., for one or more TAM kinases relative to one or more non-TAM kinases, for one or more of TYRO3, AXL and MERTK relative to one or more kinases other than TYRO3, AXL and MERTK, or for one or more of TYRO3, AXL, and MERTK relative to one another). In one specific aspect of these embodiments, a provided compound and/or composition is considered to be specific for a given kinase or set of kinases when it shows at least 2-fold, 3-fold, 4-fold, 5-fold, 10-fold, 15-fold, 20-fold, 50-fold, 100-fold or more activity for the specific kinase(s) than for FLT3. In a more specific aspect of these embodiments, a provided compound and/or composition shows at least 2-fold, 3-fold, 4-fold, 5-fold, 10-fold, 15-fold, 20-fold, 50-fold, 100-fold or lower $IC_{50}$ against the TAM kinase member against which it is most active (e.g., has the lowest $IC_{50}$) than against another kinase (e.g., FLT3). In a more specific embodiment, a provided compound and/or composition shows at least 2-fold, 3-fold, 4-fold, 5-fold, 10-fold, 15-fold, 20-fold, 50-fold, 100-fold or lower $IC_{50}$ against MERTK than against FLT3. One of ordinary skill in the art will recognize the evaluating specificity in terms of "fold difference" is only one applicable measure. In any of the embodiments just described, specificity can be expressed as a "percent difference." For example, a provided compound and/or composition is considered to be specific for a given kinase or set of kinases when it shows at least 101%, 105%, 110%, 120%, 130%, 140%, 150%, 200%, 300%, 400%, 500% or more activity for the specific kinase(s) than for one or more appropriate comparator kinase(s) (e.g., for one or more TAM kinases relative to one or more non-TAM kinases, for one or more of TYRO3, AXL and MERTK relative to one or more kinases other than TYRO3, AXL and MERTK, or for one or more of TYRO3, AXL, and MERTK relative to one another).

The methods of the invention include methods of inhibiting a TAM kinase by exposing the kinase to a compound for a time and under conditions sufficient to allow the compound to inhibit the kinase. The kinase targeted can be one or more of TYRO3, AXL and MERTK. In some embodiments, the kinase is TYRO3. In some embodiments, the kinase is AXL. In some embodiments, the kinase is MERTK. These methods can be carried out in vivo or in vitro, and analysis of TAM kinase activity can be assessed using techniques described herein and/or well known in the art (e.g., an assay of the kinase's ability to phosphorylate its substrate).

In some embodiments, compounds of the present disclosure are administered (e.g., by a route described herein) in a therapeutically effective amount to treat and/or delay the onset of (e.g., prevent) a disease responsive to inhibition of one or more TAM kinases (e.g., TYRO3, AXL and/or MERTK). Thus, a compound described herein is useful (e.g., as a therapeutic) in the treatment of cancer; is useful in preventing cancer; and/or is useful in delaying the onset of cancer or inhibiting its metastasis and, as noted above, each therapeutic or prophylactic application may also be expressed in terms of "use" of a compound described herein. The cancer a patient has been diagnosed as having and/or the cancer cells contacted with a compound or composition described herein can be of the following type: a blood cancer, a bone cancer, a breast cancer (e.g., TNBC), an endocrine cancer (e.g., cancer of the thyroid, parathyroid, or adrenal gland), a gastrointestinal cancer (e.g., a gastric cancer or colorectal cancer), a genitourinary cancer (e.g., a cancer of the bladder, kidney, prostate, cervix, or uterus (e.g., an endometrial cancer)), a head and neck cancer (e.g., cancer of the larynx), a liver cancer, a lung cancer (e.g., a non-small cell lung cancer (NSCLC)), a melanoma (e.g., a skin cancer or a cutaneous or intraocular melanoma), a nervous system or brain cancer (e.g., glioblastoma), an oral cancer (e.g., a cancer of the mouth or throat), an ovarian cancer, a pancreatic cancer (e.g., pancreatic ductal adenocarcinoma), a plasma cell neoplasm or myeloma (typically referred to as a plasmacytoma when plasma cells form a single tumor in bone or soft tissue or multiple myeloma when multiple tumors are formed), or rhabdomyosarcoma. The blood cancer, which may also be referred to as a hematopoietic or hematological cancer or malignancy, can be a leukemia such as acute lymphocytic leukemia (ALL; e.g., B cell ALL or T cell ALL), acute myelocytic leukemia (AML; e.g., B cell AML or T cell AML), chronic myelocytic leukemia (CML; e.g., B cell CML or T cell CML), or chronic lymphocytic leukemia (CLL; e.g., B cell CLL (e.g., hairy cell leukemia) or T cell CLL). The blood cancer can also be a lymphoma such as Hodgkin lymphoma (HL; e.g., B cell HL or T cell HL), non-Hodgkin lymphoma (NHL; e.g., B cell NHL or T cell NHL), follicular lymphoma, chronic lymphocytic leukemia/small lymphocytic lymphoma (CLL/SLL), mantle cell lymphoma (MCL), a marginal zone B cell lymphoma (e.g., splenic marginal zone B cell lymphoma), primary mediastinal B cell lymphoma (e.g., splenic marginal zone B cell lymphoma), primary mediastinal B cell lymphoma, Burkitt lymphoma, lymphoplasmacytic lymphoma (i.e., Waldenstrom's macroglobulinemia), immunoblastic large cell lymphoma, precursor B lymphoblastic lymphoma, or primary central nervous system (CNS) lymphoma. The B cell NHL can be diffuse large cell lymphoma (DLCL; e.g., diffuse large B cell lymphoma), and the T cell NHL can be precursor T lymphoblastic lymphoma or a peripheral T cell lymphoma (PTCL). In turn, the PTCL can be a cutaneous T cell lymphoma (CTCL) such as mycosis fungoides or Sezary syndrome, angioimmunoblastic T cell lymphoma, extranodal natural killer T cell lymphoma, enteropathy type T cell lymphoma, subcutaneous anniculitis-like T cell lymphoma, or anaplastic large cell lymphoma. While the invention is not limited to treating or preventing blood cancers having any particular cause or presentation, stem cells within the bone marrow may proliferate, thereby becoming a dominant cell type within the bone marrow and a target for a compound described herein. Leukemic cells can accumulate in the blood and infiltrate organs such as the lymph nodes, spleen, liver, and kidney. In some embodiments, a compound of the present disclosure is useful in the treatment or prevention of a leukemia or lymphoma. In other embodiments, the cancer is a gastric cancer, prostate cancer, breast cancer (e.g., TNBC), pituitary adenoma, lung cancer (e.g., NSCLC), a melanoma, glioblastoma, ovarian cancer or rhabdomyosarcoma. In some embodiments, the cancer is a hematologic disorder, such as myelodysplastic syndrome (MDS) or myeloproliferative disease (MPS), in which precursor cells in the bone marrow (e.g., stem cells) do not mature properly. Some types of MDS may develop into AML. Patients who have been diagnosed with MDS or MPS that then transforms to AML may be referred to as having AML or AML with myelodysplasia-related changes. A provided compound and/or composition containing it (e.g., a pharmaceutical composition) can also be administered to cells or to a patient who has a benign lesion such as a papilloma or adenoma (e.g., a pituitary adenoma). In some embodiments, the benign lesion is tuberous sclerosis. Although hematologic disorders and benign lesions generally have less serious consequences for a patient than cancer, we may refer to these conditions as a "disease" and any are amenable to treatment and preventative care as described herein.

The present invention provides pharmaceutical compositions comprising a compound as described herein (e.g., a compound of formula I, a sub-genus thereof, or a species thereof), or a pharmaceutically acceptable salt thereof, optionally in combination with a pharmaceutically acceptable carrier. The compound can be any compound depicted in FIG. 1 and as noted herein, reference to any given compound encompasses stereoisomers, tautomers, and isotopic forms.

The invention also encompasses combination therapies. Thus, any given compound described herein can be administered to a subject alone (i.e., as the sole active agent (e.g., TAM kinas inhibitor)) or in combination (i.e., a first compound described herein can be co-administered with a second compound described herein or other therapeutic agent). A combination therapy or co-administration of two or more active pharmaceutical agents includes simultaneous or sequential administration by the same or different routes of administration.

When a provided compound is used in combination with a second therapeutic agent active against the same disease state, the dose of each compound may differ from that when the compound is used alone. Appropriate doses will be readily appreciated by one of ordinary skill in the art. It will be appreciated that the amount of a provided compound required for use in treatment will vary with the nature of the condition being treated and the age and the condition of the patient and will be ultimately at the discretion of the attendant physician or veterinarian. It will be appreciated that, in some embodiments, provided compounds are utilized in combination with (e.g., administered to subjects receiving) therapy (e.g., standard of care therapy) for the treatment of cancer, including but not limited to any of the specific types described herein. In some embodiments, the cancer is associated with elevated levels of myeloid infiltration compared to a reference cell or cancer (e.g., a normal cell or healthy (non-cancerous) tissue).

Alternatively, or additionally, in some embodiments, provided compounds are utilized in combination with (e.g., administered to subjects receiving) immunotherapy. In some embodiments, such immunotherapy comprises or consists of checkpoint inhibitor therapy, vaccine therapy (e.g., cancer vaccine therapy), and/or cell therapy (e.g., CAR-T therapy and/or CAR-NK therapy). In some embodiments, provided combinations are administered to subjects who have or will receive antibody therapy, cell therapy (e.g., CAR-T therapy and/or CAR-NK therapy), chemotherapy, hormone therapy (e.g., therapy that reduces the level of a hormone and/or hormone receptor and/or inhibits hormone-receptor interaction or one or more downstream effects thereof), radiation therapy, and/or surgical therapy. A provided compound and/or composition containing it (e.g., a pharmaceutical composition) can be administered to cancer cells or a cancer patient, including to cells or a patient having any of the types of cancer described above, and such administration can occur in the event the patient is being (or will be) treated with a checkpoint inhibitor and/or in the event the cancer is resistant to a checkpoint inhibitor (i.e., a method or use described herein may be applied to a patient who has received, is receiving, or is scheduled to receive a checkpoint inhibitor). Checkpoint inhibitors include, but are not limited to, PD-1 inhibitors (e.g., avelumab, nivolumab, and pembrolizumab), PD-L1 inhibitors (e.g., atezoliluma and durvalumab), and CTLA4 inhibitors (e.g., ipilumumab). In some embodiments, a compound described herein or a pharmaceutically acceptable salt thereof can be used to treat cancers where checkpoint inhibitors have shown limited efficacy and/or there is high myeloid infiltration, such as pancreatic ductal adenocarcinoma, ovarian cancer, TNBC, glioblastoma, and colorectal cancer.

Compounds of the present disclosure can be prepared and administered in a wide variety of oral and parenteral dosage forms. Thus, the compounds of the present disclosure can be formulated for administration by injection (e.g. intravenously, intramuscularly, intracutaneously, subcutaneously, or intraperitoneally). The compounds can also be formulated for administration by inhalation (e.g., intranasally) or by insufflation. In other embodiments, the compounds described herein can be formulated for topical or transdermal administration (i.e., they can be in a dosage form suitable for administration by the various routes just described).

For preparing pharmaceutical compositions including a compound described herein, pharmaceutically acceptable carriers can be added in either solid or liquid form or a combination thereof. Solid dosage form preparations within the scope of the present invention include powders, tablets, pills, capsules, cachets, suppositories, and dispersible granules. A solid carrier can be a substance that may also act as a diluent, flavoring agent, binder, preservative, tablet disintegrating agent, or an encapsulating material. In powders, the carrier is a finely divided solid in a mixture with the finely divided active component (e.g., a compound described herein, e.g., a compound conforming to the structure of Formula II). In tablets, the active component is mixed with the carrier having the necessary binding properties in suitable proportions and compacted in the shape and size desired. Pharmaceutical compositions, including those formulated as powders and tablets, can contain from about 5% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Tablets, powders, capsules, pills, cachets, and lozenges can be used as solid dosage forms suitable for oral administration. For preparing suppositories, a low melting wax, such as a mixture of fatty acid glycerides or cocoa butter, is melted and the active component is dispersed therein.

Liquid form preparations include solutions, suspensions, and emulsions, for example, water or water/propylene glycol solutions. For parenteral injection, liquid preparations can be formulated in solution in aqueous polyethylene glycol solution. When parenteral application is needed or desired, particularly suitable admixtures for the compounds of the invention are injectable, sterile solutions, preferably oily or aqueous solutions, as well as suspensions, emulsions, or implants, including suppositories. In some embodiments, suitable carriers for parenteral administration will be selected for human administration.

In particular, carriers for parenteral administration include aqueous solutions of dextrose, saline, pure water, ethanol, glycerol, glycerol formal, polyethylene glycol, propylene glycol, peanut oil, sesame oil, polyoxyethylene-block polymers, pyrrolidine, N-methyl pyrrolidione, and the like. Ampoules are convenient unit dosage forms. The compounds of the present disclosure can also be incorporated into liposomes or administered via transdermal pumps or patches. Pharmaceutical admixtures suitable for use in the present disclosure include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical compositions are preferably in unit dosage form. The unit dosage form can be a packaged preparation, the package containing discrete quantities of preparation, such as packeted tablets, capsules, and powders in vials or ampoules. Unit dosage forms can also be capsules, tablets, cachets, lozenges, or the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition (e.g., polysorbate 20, 60, and 80; Pluronic® F-68, F-84, and P-103; cyclodextrin; and polyoxyl 35 castor oil). Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

Compositions of the present invention may additionally include components to provide sustained release and/or comfort (e.g., high molecular weight, anionic mucomimetic polymers, gelling polysaccharides, and finely-divided drug carrier substrates). These components are discussed in detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present disclosure include compositions wherein the active ingredient is contained in a therapeutically effective amount, i.e., in an amount effective to achieve its intended purpose. The actual amount effective for a particular application will depend, inter alia, on the condition being treated. For example, when administered in methods to a subject with cancer, such compositions will contain an amount of active ingredient effective to achieve the desired result.

The dosage and frequency (single or multiple doses) of compound administered can vary depending on a variety of factors, including route of administration; the size, age, sex, health, body weight, body mass index, and diet of the recipient; nature and extent of symptoms of the disease being treated; any concurrent treatment; and complications from any disease or treatment regimen. Other therapeutic regimens or agents can be used in conjunction with the methods and compounds of the present disclosure.

For any compound or pharmaceutical composition described herein, the therapeutically effective amount can be initially determined from, or informed by data generated in, cell culture assays and/or animal models of disease. For example, a dose for humans can be formulated to achieve a concentration that has been found to be effective in animals. The dosage in humans can be adjusted by, for example, monitoring kinase inhibition, the signs an symptoms of the disease being treated, and side effects and subsequently adjusting the dosage upwards or downwards.

Dosages may be varied depending upon the requirements of the patient and the compound being employed. The dose administered to a patient should be sufficient to effect a beneficial therapeutic response in the patient over time. The size of the dose also will also be determined by the existence, nature, and extent of any adverse side effects. Generally, treatment is initiated with smaller dosages, which are less than the optimum dose of the compound. Thereafter, the dosage is increased by small increments until the optimum effect under a desired circumstance is reached. In some embodiments, the concentration of compound is about 0.001% to 10% w/v (e.g., about 0.1% to about 5% w/v). In some embodiments, the concentration range is 0.1% to 5% w/v. Concentrations, dosage amounts, and intervals can be adjusted in each individual patient to provide levels of the administered compound effective for the particular disease being treated. This will provide a therapeutic regimen commensurate with the severity of the patient's disease.

EXAMPLES

The following analytical instruments were used in the synthesis and analysis of compounds of the invention. For liquid chromatography mass spectrometry (LCMS or LC-MS): Shimadzu UFLC MS: LCMS-2020; Agilent Technologies 1200 series MS: Agilent Technologies 6110; Agilent Technologies 1200 series MS: LC/MSD VL; Waters Alliance HPLC system. MS: Waters Micromass ZQ; and Waters 996 PDA detector. For nuclear magnetic resonance (NMR): BRUKER AVANCE III/400 MHz, Varian 400 MHz or BRUKER AVANCE II/500 MHz; for preparatory high performance liquid chromatography (prep-HPLC): Gilson GX-281 systems, instruments GX-A, GX-B, GX-C, GX-D, GX-E, GX-F, GX-G and GX-H; Waters 2767 Sample Manager, MS. Waters Micromass ZQ, Waters 2545 binary gradient module; and Waters 2996 PDA detector.

Example 1: Synthesis of Intermediates

A. 7-bromo-2-(methylthio)pyrrolo[2,1-f][1,2,4]triazine

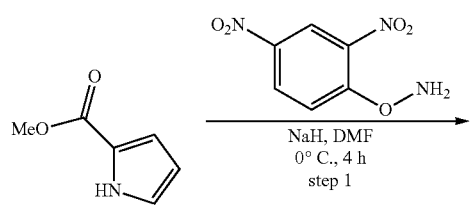

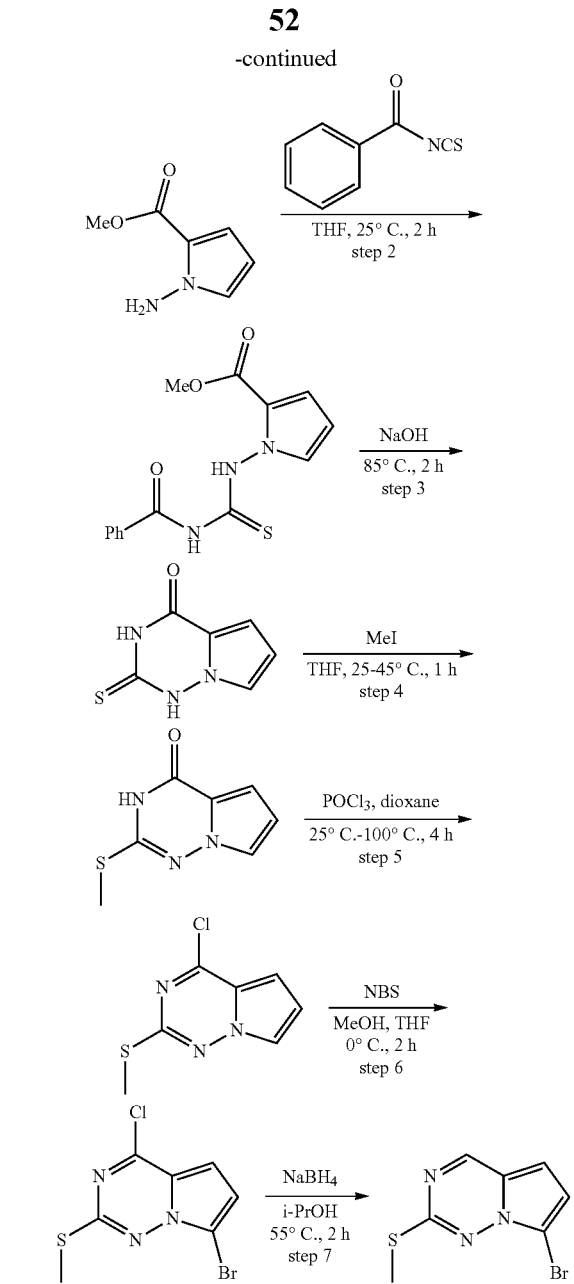

Step 1: methyl 1-amino-1H-pyrrole-2-carboxylate

To a solution of methyl 1H-pyrrole-2-carboxylate (100 g, 799 mmol) in dimethylformamide (DMF; 1.2 L) was added NaH (51.1 g, 1.28 mol, 60% purity) at 0° C. The mixture was stirred at 0° C. for 1 hour, then O-(2,4-dinitrophenyl) hydroxylamine (238.71 g, 1.20 mol) in DMF (300 mL) was added dropwise. The mixture was stirred at 0° C. for 3 hours. The reaction mixture of two batches was combined and poured into aqueous (aq.) sat. sodium thiosulfate solution (10 L). The resulting mixture was extracted with EtOAc (4 L×3). The combined organic layers were washed with brine (2 L×3), dried over Na$_2$SO$_4$, and then filtered. The filtrate was concentrated, then purified by silica gel chromatography to afford methyl 1-amino-1H-pyrrole-2-carboxylate (190 g, crude) as a yellow oil.

Step 2: methyl 1-(3-benzoylthioureido)-1H-pyrrole-2-carboxylate

To a solution of methyl 1-amino-1H-pyrrole-2-carboxylate (95.0 g, 647 mmol) in THF (tetrahydrofuran; 2.0 L) was added a solution of benzoyl isothiocyanate (137 g, 842 mmol) in THF (500 mL) at 25° C. The mixture was stirred at 25° C. for 2 hours. Two batches were combined and concentrated in vacuo. The residue was triturated with MTBE (methyl tert-butyl ether; 1.0 L) then filtered to afford the title compound (352 g, 696 mmol, 54% yield, 60% purity).

Step 3: 2-thioxo-2,3-dihydropyrrolo[2,1-f][1,2,4]triazin-4(1H)-one

A solution of methyl 1-(3-benzoylthioureido)-1H-pyrrole-2-carboxylate (140 g, 461 mmol) in aq. NaOH solution (2.0 M, 923 mL) was stirred at 85° C. for 2 hours. Two batches of the reaction mixture were combined and cooled to 0° C., to which acetic acid (300 mL) was added at 0° C., and the resulting mixture was stirred for another 30 minutes. Precipitate was collected by filtration to afford a white solid, which was triturated in MTBE (2.0 L) and stirred for 20 minutes. The mixture was filtered and washed with MTBE (500 mL). The filtered cake was dried to afford 2-thioxo-2,3-dihydropyrrolo[2,1-f][1,2,4]triazin-4(1H)-one (140 g, 754 mmol, 82% yield, 90% purity).

Step 4: 2-(methylthio)pyrrolo[2,1-f][1,2,4]triazin-4(3H)-one

To a solution of 2-thioxo-2,3-dihydropyrrolo[2,1-f][1,2,4]triazin-4(1H)-one (57.0 g, 341 mmol) in THF (1.7 L) was added MeI (69.6 g, 491 mmol) at 25° C. The mixture was stirred at 45° C. for 1 hour. Three batches were combined and the solvent was removed in vacuo to afford an off-white solid, which was then treated with water (2.0 L) and aq. sat. NaHCO₃(2.0 L). The resulting mixture was stirred for 30 minutes, then filtered to afford the title compound (126 g, crude).

Step 5: 4-chloro-2-(methylthio)pyrrolo[2,1-f][1,2,4]triazine

To a solution of 2-(methylthio)pyrrolo[2,1-f][1,2,4]triazin-4(3H)-one (60.0 g, 331 mmol) in dioxane (630 mL) was added POCl₃ (phosphoryl chloride; 697 g, 4.54 mol, 422 mL) at 25° C. The mixture was heated at 100° C. for 4 hours. The two batches were combined, cooled to 25° C., then poured into water (3.0 L). The pH of the mixture was adjusted to 7 by adding NH₃.H₂O. The mixture was extracted with EtOAc (1.5 L×3). The organic layers were combined, washed with brine (2.0 L), dried over Na₂SO₄, filtered and concentrated in vacuo to give 4-chloro-2-(methylthio)pyrrolo[2,1-f][1,2,4]triazine (110 g, 375 mmol, 57% yield, 68% purity) as a dark brown solid.

Step 6: 7-bromo-4-chloro-2-(methylthio)pyrrolo[2,1-f][1,2,4]triazine

To a solution of 4-chloro-2-(methylthio)pyrrolo[2,1-f][1,2,4]triazine (51.0 g, 255 mmol) in MeOH (1.0 L) and THF (1.5 L) was added NBS (N-bromosuccinimide 45.5 g, 255 mmol) at 0° C. The resulting mixture was stirred at 0° C. for 2 hours. Two batches were combined and the solvent was evaporated under vacuum to afford a yellow solid. The solid was dissolved in dichloromethane (DCM; 1.0 L) and washed with water (1.0 L) then brine (0.5 L), sequentially. The organic layer was dried over Na₂SO₄, filtered and concentrated in vacuo to give 7-bromo-4-chloro-2-(methylthio)pyrrolo[2,1-f][1,2,4]triazine (126.00 g, crude).

Step 7: 7-bromo-2-(methylthio)pyrrolo[2,1-f][1,2,4]triazine

A solution of 7-bromo-4-chloro-2-(methylthio)pyrrolo[2,1-f][1,2,4]triazine (40.0 g, 144 mmol) in isopropanol (400 mL) was heated to 55° C., then treated with NaBH₄ (sodium tetrahydroborate; 11.40 g, 301.33 mmol). The mixture was stirred at 55° C. for 2 hours before three batches were combined. The precipitate was filtered and washed with DCM (500 mL). The filtrate was concentrated in vacuo then re-dissolved in DCM (3.0 L). Dichlorodicyanoquinone (108 g) was then added to the solution over 15 minutes. The reaction mixture was stirred at 25° C. for 30 minutes. Precipitate was filtered through Celite® and washed with DCM (500 mL). Filtrate was concentrated and purified by column chromatography to give a yellow solid (60 g), which was further purified by another column chromatography to afford 7-bromo-2-(methylthio)pyrrolo[2,1-f][1,2,4]triazine (47.7 g, 93% purity) as a yellow solid.

B. (S)-5-bromo-N-(heptan-2-yl)-7-(1,4-dioxaspiro[4.5]decan-8-yl)pyrrolo[2,1-f][1,2,4]triazin-2-amine

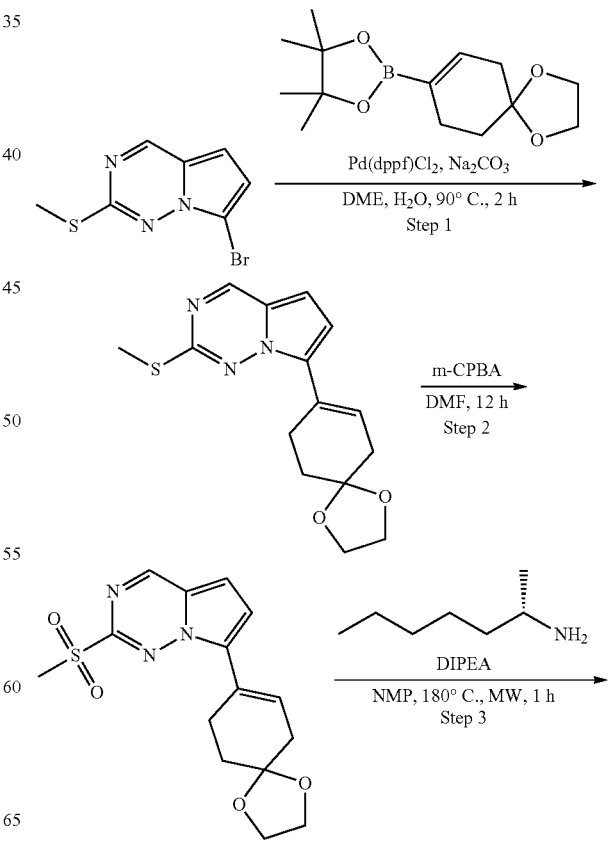

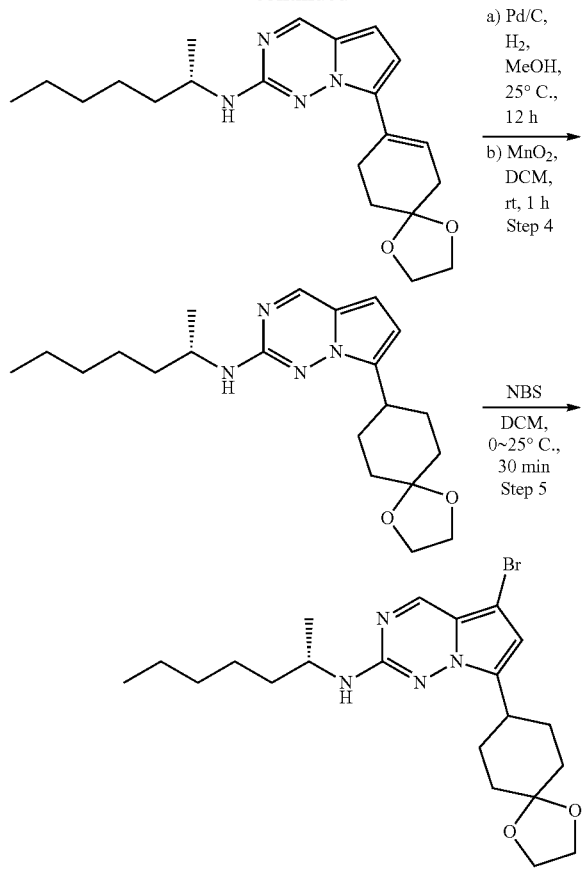

Step 1: 2-(methylthio)-7-(1,4-dioxaspiro[4.5]dec-7-en-8-yl)pyrrolo[2,1-f][1,2,4]triazine A mixture of 7-bromo-2-(methylthio)pyrrolo[2,1-f][1,2,4]triazine (2.5 g, 10 mmol), 2-(1,4-dioxaspiro[4.5]dec-7-en-8-yl)-4,4,5,5-tetramethyl-1,3,2-dioxaborolane (3.4 g, 12.8 mmol), Pd(dppf)Cl$_2$ ([1,1'-Bis(diphenylphosphino)ferrocene]dichloropalladium(II); 375 mg, 0.512 mmol), Na$_2$CO$_3$ (4.3 g, 41 mmol) in DME (37.5 mL) and H$_2$O (15 mL) was degassed and purged with N$_2$ 3 times, and then the mixture was stirred at 90° C. for 2 hours under N$_2$. Upon completion, the reaction mixture was diluted with EtOAc (40 mL) and extracted with water (50 mL). The aqueous layer was separated and extracted with EtOAc (50 mL×3). All organic layers were combined, washed with brine (40 mL×2), dried over anhydrous Na$_2$SO$_4$, filtered and concentrated in vacuo. The residue was purified by silica gel chromatography to give the title compound (2.3 g, 72% yield, 98% purity) as a yellow solid.

Step 2: 2-(methylsulfonyl)-7-(1,4-dioxaspiro[4.5]dec-7-en-8-yl)pyrrolo[2,1-f][1,2,4]triazine To a solution of 2-(methylthio)-7-(1,4-dioxaspiro[4.5]dec-7-en-8-yl)pyrrolo[2,1-f][1,2,4]triazin (2.3 g, 7.6 mmol) in DMF (40 mL) was added m-CPBA (3.1 g, 15 mmol, 80% purity), the mixture was then stirred at 65° C. for 12 hours. Upon completion, the reaction mixture was diluted with water (30 mL) and extracted with ethyl acetate (EtOAc; 30 mL×4). The organic layers were combined, washed with brine (30 mL×2), dried over anhydrous sodium sulfate, filtered and concentrated in vacuo to give the title compound (1.95 g, crude) as a yellow solid.

Step 3: (S)-N-(heptan-2-yl)-7-(1,4-dioxaspiro[4.5]dec-7-en-8-yl)pyrrolo[2,1-f][1,2,4]triazin-2-amine 7-(1,4-dioxaspiro[4.5]dec-7-en-8-yl)-2-methylsulfonyl-pyrrolo[2,1-f][1,2,4]triazine (0.95 g, 2.8 mmol), (2S)-heptan-2-amine (1.14 g, 9.1 mmol), N,N-diisopropyl ethylamine (DIPEA; 1.7 mL, 9.9 mmol) and NMP (N-methyl-2-pyrrolidone; 10 mL) were added into a microwave tube, which was sealed and heated at 180° C. for 1 hour under microwave irradiation. DIPEA (0.247 mL, 1.4 mmol) and (2S)-heptan-2-amine (163 mg, 1.4 mmol) were then added, and the resulting mixture was heated at 180° C. for another 1 hour under microwave irradiation. Upon completion, the reaction mixture was diluted with EtOAc (20 mL) and extracted with water (20 mL). The aqueous layer was separated, extracted with EtOAc (20 mL×3). All organic layers were combined, washed with brine (20 mL×2), dried over anhydrous Na$_2$SO$_4$, filtered and concentrated in vacuo. The residue was purified by column chromatography to give the tittle compound (480 mg, 46% yield, 100% purity) as a light yellow solid.

Step 4a: (S)-N-(heptan-2-yl)-7-(1,4-dioxaspiro[4.5]decan-8-yl)-3,4-dihydropyrrolo[2,1-f][1,2,4]triazin-2-amine To a solution of 7-(1,4-dioxaspiro[4.5]dec-7-en-8-yl)-N-[(1S)-1-methylhexyl]pyrrolo[2,1-f][1,2,4]triazin-2-amine (480 mg, 1.3 mmol) in MeOH (60 mL) was added Pd—C (palladium on carbon; 10% purity, 70 mg) under N$_2$. The suspension was degassed and purged with H$_2$ several times, then stirred under H$_2$ (40 psi) at 25° C. for 12 hours. Upon completion, the reaction mixture was filtered and concentrated in vacuo to afford the title compound (430 mg, crude) as a light yellow oil.

Step 4b: (S)-N-(heptan-2-yl)-7-(1,4-dioxaspiro[4.5]decan-8-yl)pyrrolo[2,1-f][1,2,4]triazin-2-amine To a solution of (S)-N-(heptan-2-yl)-7-(1,4-dioxaspiro[4.5]decan-8-yl)-3,4-dihydropyrrolo[2,1-f][1,2,4]triazin-2-amine (430 mg, 1.2 mmol) in DCM (10 mL) was added MnO$_2$ (399 mg, 4.6 mmol). The resulting mixture was stirred at 25° C. for 1 hour. Upon completion, the reaction mixture was filtered and concentrated in vacuo. The residue was purified by prep-TLC (thin layer chromatography) to give the title compound (250 mg, 58% yield, 99% purity) as a light yellow solid.

Step 5: (S)-5-bromo-N-(heptan-2-yl)-7-(1,4-dioxaspiro[4.5]decan-8-yl)pyrrolo[2,1-f][1,2,4]triazin-2-amine To a solution of 7-(1,4-dioxaspiro[4.5]decan-8-yl)-N-[(1S)-1-methylhexyl]pyrrolo[2,1-f][1,2,4]triazin-2-amine (250 mg, 0.671 mmol) in DCM (10 mL) was added NBS (120 mg, 0.671 mmol) at 0° C. The mixture was stirred at 25° C. for 30 minutes. Upon completion, the reaction mixture was filtered and concentrated in vacuo. The residue was purified by column chromatography to give the title compound (300 mg, 99% yield) as a light yellow oil.

C. 5-bromo-N-butyl-7-(1,4-dioxaspiro[4.5]decan-8-yl)pyrrolo[2,1-f][1,2,4]triazin-2-amine
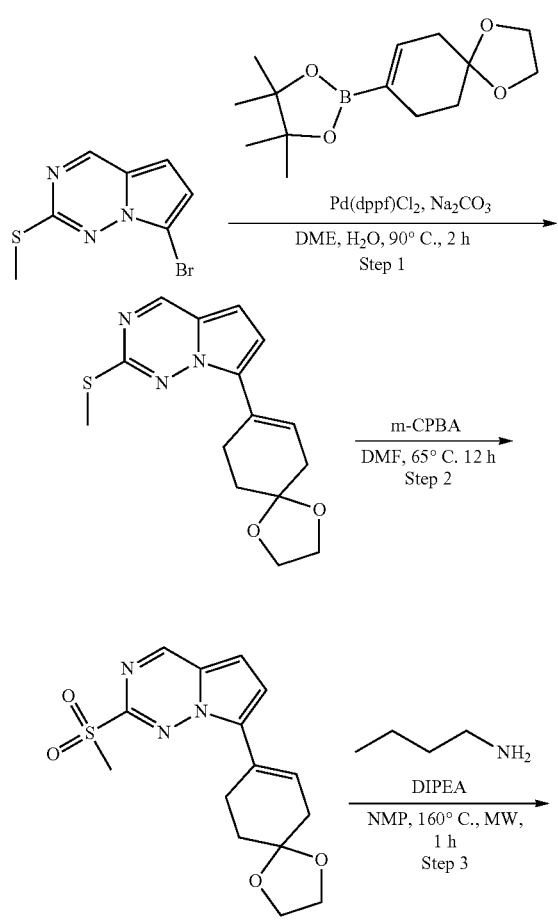
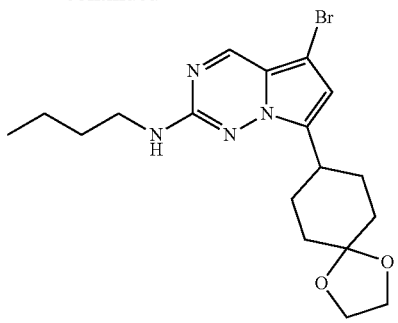
This synthesis was carried out in a manner similar to the synthesis described in Example 1, part B, substituting (S)-pentan-2-amine for n-butylamine at Step 3.
D. cis and trans-4-(5-bromo-2-(methylsulfonyl)pyrrolo[2,1-f][1,2,4]triazin-7-yl)cyclohexan-1-ol
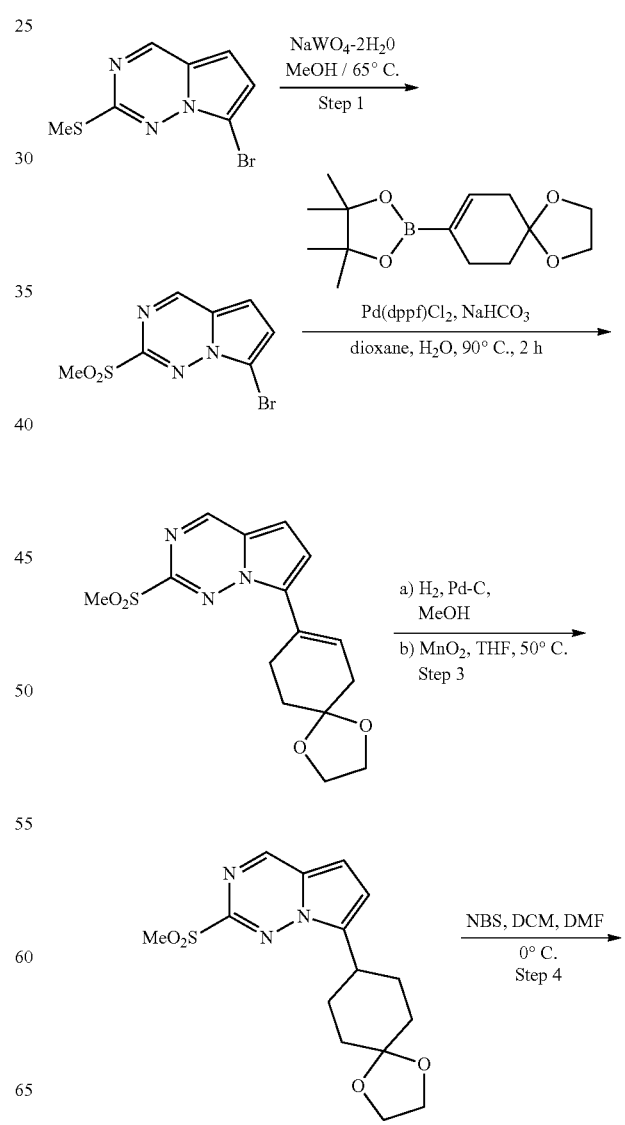

-continued

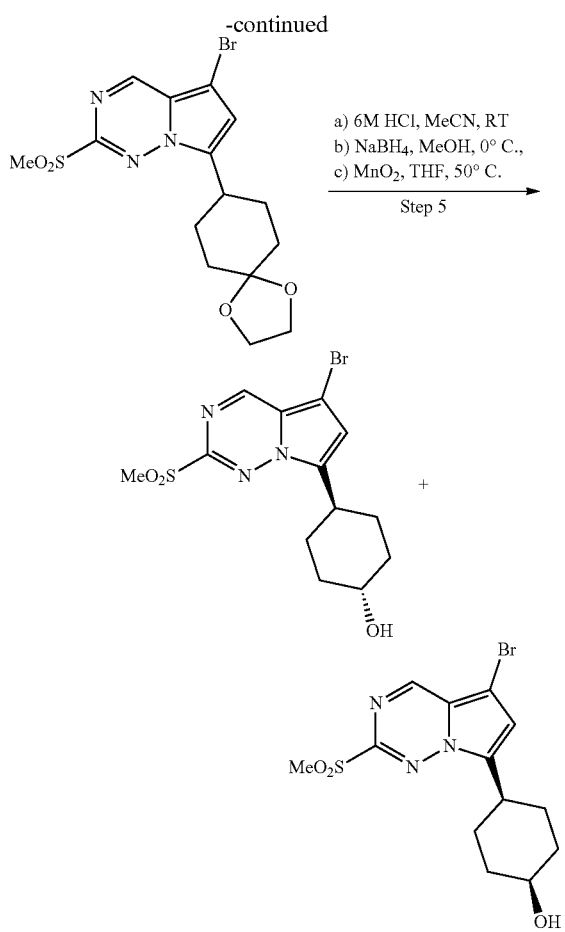

Step 1: 7-bromo-2-(methylsulfonyl)pyrrolo[2,1-f][1,2,4]triazine

A mixture of 7-bromo-2-(methylthio)pyrrolo[2,1-f][1,2,4]triazine (25.0 g, 102 mmol), and sodium tungstate dihydrate (2.08 g, 6.32 mmol) in MeOH (183 mL) was treated with hydrogen peroxide solution (41.6 mL, 408 mmol). The suspension was heated at 65° C. and, within 10 minutes, became homogeneous. After heating for 2 hours, a precipitate formed. The hot mixture was treated with 120 (25 mL) and allowed to cool slowly to RT (heating switched off, but bath maintained). The product was filtered and washed with $H_2O$, flowed by heptane and dried under suction overnight. A bright yellow solid (25.1 g, 89%) was obtained.

Step 2: 2-(methylsulfonyl)-7-(1,4-dioxaspiro[4.5]dec-7-en-8-yl)pyrrolo[2,1-f][1,2,4]triazine A mixture of 7-bromo-2-(methylsulfonyl)pyrrolo[2,1-f][1,2,4]triazine (270 mg, 978 μmol), 1,4-Dioxaspiro[4.5]dec-7-en-8-boronic acid pinacol ester (390 mg, 1.44 mmol) and sodium hydrogenocarbonate (128 μL, 3.29 mmol) was suspended in 1,4-Dioxane (9.7 mL) and $H_2O$ (3 mL), and the mixture was degassed by bubbling $N_2$ through the mixture for 5 min. The mixture was treated with [1,1'-Bis(diphenylphosphino)ferrocene]-dichloropalladium(II) (48.8 mg, 59.7 μmol) and then heated at 90° C. for 30 min. The reaction mixture was cooled to RT, poured into $H_2O$ and extracted with EtOAc (λ3). The combined organic layers were washed ($H_2O$, brine), dried ($Na_2SO_4$) and concentrated in vacuo. The residue was purified by column chromatography (Comnbiflash, 24 g column 0 to 100% EtOAc in hexanes). We obtained 223 mg of product.

Step 3: 2-(methylsulfonyl)-7-(1,4-dioxaspiro[4.5]decan-8-yl)pyrrolo[2,1-f][1,2,4]triazine A suspension of 2-(methylsulfonyl)-7-(1,4-dioxaspiro[4.5]dec-7-en-8-yl)pyrrolo[2,1-f][1,2,4]triazine (190 mg, 567 μmol) and palladium on carbon 10% loading (1.83 g, 1.72 mmol) in THF (7.00 mL) and MeOH (10.0 mL) was evacuated and backfilled with $N_2$ five times. The mixture was then evacuated and backfilled with hydrogen five times and allowed to stir at RT with a balloon of H, After 4.5 hours, the mixture was evacuated and backfilled with $N_2$ (λ3) then filtered over Celite® The reaction was concentrated in vacuo and the residue concentrated from THF. The residue was dissolved in THF (7 mL) and combined with the crude reaction mixture from a 24 mg run. It was treated with activated manganese (IV) oxide (240 mg, 2.83 mmol) and heated at 50° C. for 30 min. After one hour, a second portion of 200 mg of $MnO_2$ was added. This was repeated twice more (four total additions), and the reaction was cooled to RT and filtered through Celite®. The crude material (194 mg) was used "as is" in the next step.

Step 4: 5-bromo-2-(methylsulfonyl)-7-(1,4-dioxaspiro[4.5]decan-8-yl)pyrrolo[2,1-f][1,2,4]triazine A solution of 2-(methyl sulfonyl)-7-(1,4-dioxaspiro[4.5]decan-8-yl)pyrrolo[2,1-f][1,2,4]triazine (194 mg, 575 μmol) in $CH_2Cl_2$ (3.00 mL) was cooled in an ice bath and treated with NBS (105 mg, 592 μmol) dissolved in DMF (1 mL). The reaction mixture was concentrated to remove DCM and partitioned between $H_2O$ and EtOAc. The layers were separated and then the aqueous phase was extracted with EtOAc (×3). The combined organic layers were washed ($H_2O$×3, brine), dried ($Na_2SO_4$) and concentrated in vacuo. The residue was purified by column chromatography (CombiFlash®, 24 g column, Solvent A=50% DCM in hexanes; Solvent B=50% DCM in hexanes containing 10% iPrOH.). We obtained an orange colored gum (193 mg, 80%).

Step 5: (cis)- and (trans)-4-(5-bromo-2-(methylsulfonyl)pyrrolo[2,1-f][1,2,4]triazin-7-yl)cyclohexan-1-ol A solution of 5-bromo-2-(methylsulfonyl)-7-(1,4-dioxaspiro[4.5]decan-8-yl)pyrrolo[2,1-f][1,2,4]triazine (26.0 g, 62.5 mmol) in MeCN (400 mL) and acetone (125 mL) was cooled to 0° C. and treated with hydrochloric acid (65 mL, 390 mmol) and allowed to stir for 2 h. The volatile solvents were removed, and the reaction was dissolved in acetone (500 mL) and treated with further HCl (6M, 25 mL). After stirring for a further 2 h, the reaction mixture was poured carefully into a stirred solution of saturated $NaHCO_3$ and the mixture allowed to stir for 20 min. The solution was extracted with EtOAc (×3), and the organic layers were washed (brine), dried ($Na_2SO_4$) and concentrated in vacuo. Attempted recrystallization of the crude material from hex: EtOAc was unsuccessful. Filtering the hot suspension gave 5.88 g of pure ketone. The remaining material was dissolved in 75 mL acetone and 75 mL MeCN and treated with 50 mL of HCl 6M at 0° C. After 5 min, the ice bath was removed and the mixture was allowed to stir at RT for 30 min. The reaction was worked up as above, and we obtained 17.92 g. The crude material was used "as is" in the next experiment.

A solution of the ketone obtained above (12.1 g, 32.6 mmol) in MeOH (250 mL) was cooled to 0° C., treated with sodium borohydride (5.34 g, 136 mmol), and allowed to stir for 30 min. The mixture was quenched with saturated $NH_4Cl$ and then 1-120 and finally acidified to pH 2-3 with 6 M HCl. The mixture was diluted with EtOAc, the layers separated, and the aq phase extracted with EtOAc (×3). The combined organic layers were washed ($H_2O$, brine), dried ($Na_2SO_4$) and concentrated in vacuo. The residue was purified by column chromatography (CombiFlash®, 330 g column, solvent A=50% DCM in hexanes, solvent B=20% IPA in 50% DCM:hexanes). we obtained a pale yellow solid (7.3 g) as the major product (trans) and a pale yellow solid (that elutes before the major) 900 mg (cis).

E. (trans)-4-(5-bromo-2-(((S)-1-methoxypropan-2-yl)amino)pyrrolo[2,1-f][1,2,4]triazin-7-yl)cyclohexan-1-ol

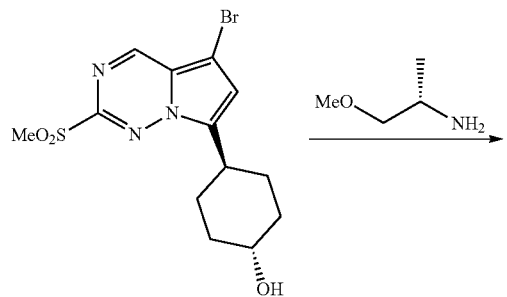

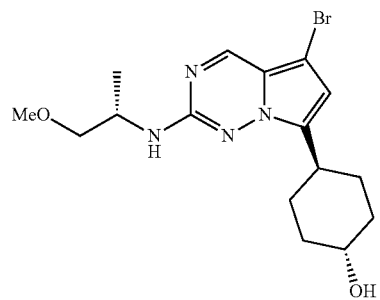

A mixture of (trans)-4-(5-bromo-2-(methylsulfonyl)pyrrolo[2,1-f][1,2,4]triazin-7-yl)cyclohexan-1-ol (3.78 g, 10.1 mmol), (S)-1-methoxy-2-propylamine (5.4 mL, 50.5 mmol) and DIPEA (4.4 mL, 25.3 mmol) in NMP (9.5 mL) was sealed and heated for 4 hours at 135° C. The mixture was cooled to RT, diluted with EtOAc (100 mL), and washed with saturated $NaHCO_3$ (3×), water (3×) and brine (3×). The organic phase was dried with $MgSO_4$, filtered, and then concentrated under reduced pressure. We obtained a pale orange foam (3.77 g, 97%), which was used "as is" in subsequent reactions.

The following intermediates were prepared analogously to the previous intermediates, using the indicated amine:

| Intermediate | Name | Amine | Structure |
|---|---|---|---|
| F | (trans)-4-(5-bromo-2-(((S)-4,4,4-trifluorobutan-2-yl)amino)pyrrolo[2,1-f][1,2,4]triazin-7-yl)cyclohexan-1-ol | | 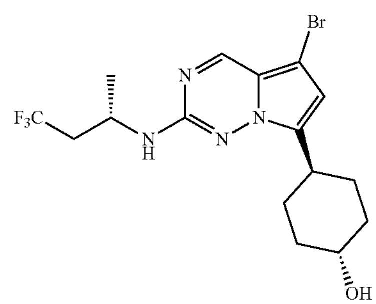 [SMILES: C[C@@H](CC(F)(F)F)Nc1ncc2c(Br)cc([C@H]3CC[C@H](O)CC3)n2n1] |
| G | (trans)-4-(5-bromo-2-(((S)-1-(difluoromethoxy)propan-2-yl)amino)pyrrolo[2,1-f][1,2,4]triazin-7-yl)cyclohexan-1-ol | | 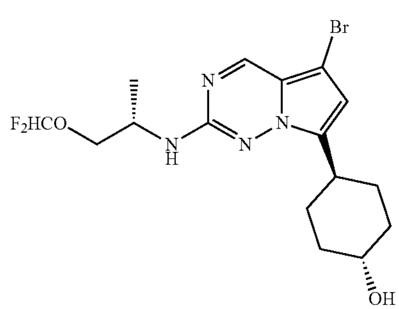 [SMILES: C[C@@H](COC(F)F)Nc1ncc2c(Br)cc([C@H]3CC[C@H](O)CC3)n2n1] |

-continued

| Intermediate | Name | Amine | Structure |
|---|---|---|---|
| H | (trans)-4-(5-bromo-2-(((S)-4-fluorobutan-2-yl)amino)pyrrolo[2,1-f][1,2,4]triazin-7-yl)cyclohexan-1-ol | 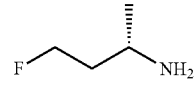 | 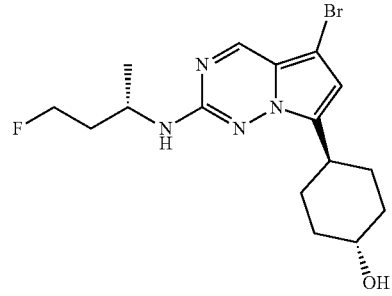 [SMILES: C[C@@H](CCF)Nc1ncc2c(Br)cc([C@H]3CC[C@H](O)CC3)n2n1] |
| I | (trans)-4-(5-bromo-2-(((S)-1-cyclopropylpropan-2-yl)amino)pyrrolo[2,1-f][1,2,4]triazin-7-yl)cyclohexan-1-ol | 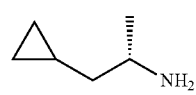 | 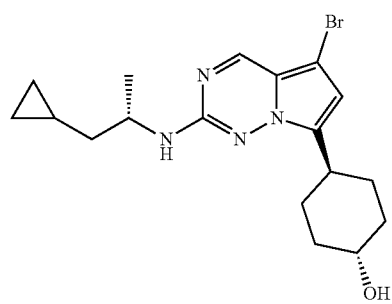 [SMILES: C[C@@H](CC1CC1)Nc1ncc2c(Br)cc([C@H]3CC[C@H](O)CC3)n2n1] |
| J | (cis)-4-(5-bromo-2-(((S)-1-methoxypropan-2-yl)amino)pyrrolo[2,1-f][1,2,4]triazin-7-yl)cyclohexan-1-ol | 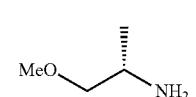 | 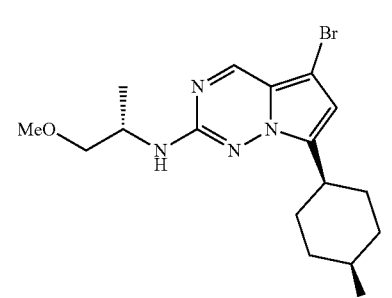 |
| K | (trans)-4-(5-bromo-2-(((S)-1,1,1-trifluoropropan-2-yl)amino)pyrrolo[2,1-f][1,2,4]triazin-7-yl)cyclohexan-1-ol |  | 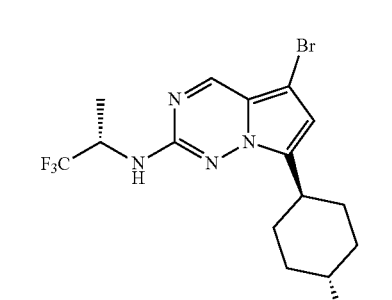 |
| L | (trans)-4-(5-bromo-2-((1,1-difluoropropan-2-yl)amino)pyrrolo[2,1-f][1,2,4]triazin-7-yl)cyclohexan-1-ol |  | 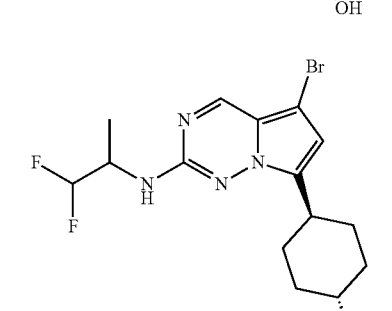 |

-continued

| Intermediate | Name | Amine | Structure |
|---|---|---|---|
| M | (trans)-4-(5-bromo-2-((1-(methoxymethyl)cyclopropyl)amino)pyrrolo[2,1-f][1,2,4]triazin-7-yl)cyclohexan-1-ol | | 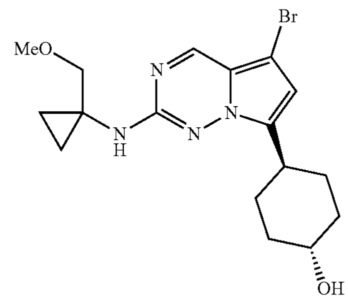 [SMILES: COCC1(Nc2ncc3c(Br)cc([C@H]4CC[C@H](O)CC4)n3n2)CC1] |
| N | (trans)-4-(5-bromo-2-(((S)-4-(difluoromethoxy)butan-2-yl)amino)pyrrolo[2,1-f][1,2,4]triazin-7-yl)cyclohexan-1-ol | | 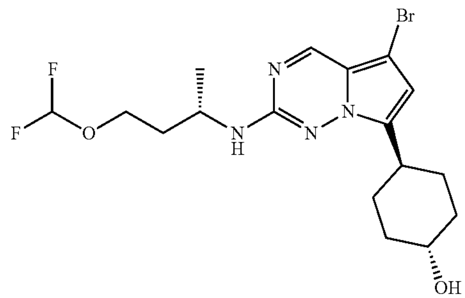 [SMILES: C[C@@H](CCOC(F)F)Nc1ncc2c(Br)cc([C@H]3CC[C@H](O)CC3)n2n1] |
| O | (trans)-4-(5-bromo-2-((1-ethylcyclobutyl)amino)pyrrolo[2,1-f][1,2,4]triazin-7-yl)cyclohexan-1-ol | | 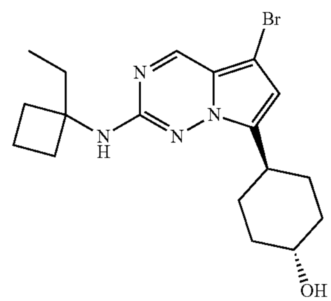 [SMILES: CCC1(Nc2ncc3c(Br)cc([C@H]4CC[C@H](O)CC4)n3n2)CCC1] |
| P | (trans)-4-(5-bromo-2-(((S)-1-ethoxypropan-2-yl)amino)pyrrolo[2,1-f][1,2,4]triazin-7-yl)cyclohexan-1-ol | | 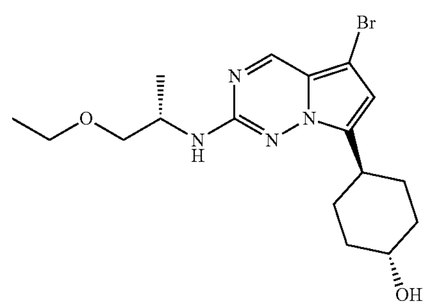 [SMILES: CCOC[C@H](C)Nc1ncc2c(Br)cc([C@H]3CC[C@H](O)CC3)n2n1] |
| Q | (S)-3-((5-bromo-7-((trans)-4-hydroxycyclohexyl)pyrrolo[2,1-f][1,2,4]triazin-2-yl)amino)butanenitrile | | 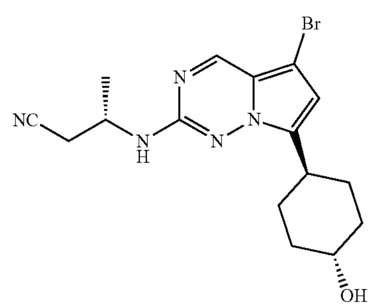 [SMILES: C[C@@H](CC#N)Nc1ncc2c(Br)cc([C@H]3CC[C@H](O)CC3)n2n1] |

-continued

| Intermediate | Name | Amine | Structure |
|---|---|---|---|
| R | (trans)-4-(5-bromo-2-(((S)-4-methoxybutan-2-yl)amino)pyrrolo[2,1-f][1,2,4]triazin-7-yl)cyclohexan-1-ol | methoxy-CH(CH₃)-CH₂-CH₂ with NH₂ | 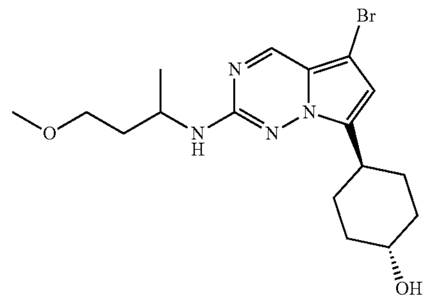 |
| S | (trans)-4-(5-bromo-2-(((S)-1-isopropoxypropan-2-yl)amino)pyrrolo[2,1-f][1,2,4]triazin-7-yl)cyclohexan-1-ol | | 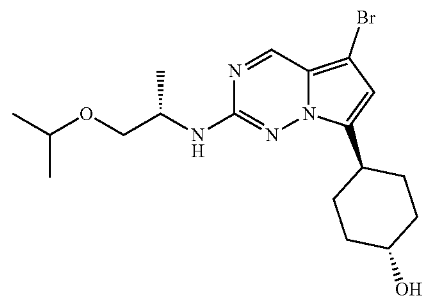 [SMILES: CC(C)OC[C@H](C)Nc1ncc2c(Br)cc([C@H]3CC[C@H](O)CC3)n2n1] |
| T | (trans)-4-(5-bromo-2-((1-(tetrahydrofuran-2-yl)ethyl)amino)pyrrolo[2,1-f][1,2,4]triazin-7-yl)cyclohexan-1-ol | | 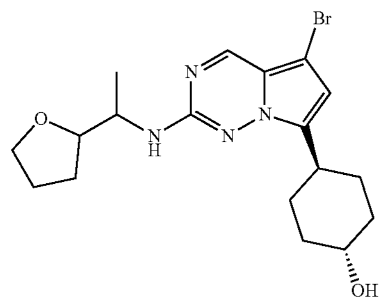 [SMILES: CC(Nc1ncc2c(Br)cc([C@H]3CC[C@H](O)CC3)n2n1)C1CCCO1] |
| U | (trans)-4-(5-bromo-2-(((R)-1,1,1-trifluoropropan-2-yl)amino)pyrrolo[2,1-f][1,2,4]triazin-7-yl)cyclohexanol | | 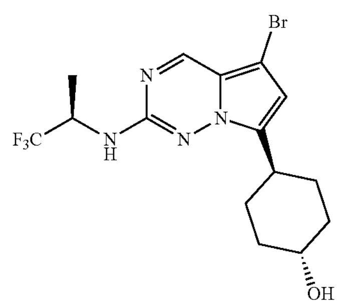 [SMILES: C[C@@H](Nc1ncc2c(Br)cc([C@H]3CC[C@H](O)CC3)n2n1)C(F)(F)F] |
| V | (trans)-4-(5-bromo-2-(((S)-1-phenylethyl)amino)pyrrolo[2,1-f][1,2,4]triazin-7-yl)cyclohexanol | | 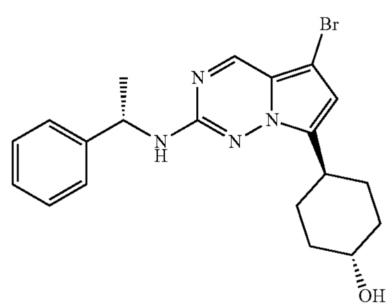 [SMILES: C[C@H](Nc1ncc2c(Br)cc([C@H]3CC[C@H](O)CC3)n2n1)c1ccccc1] |

| Intermediate | Name | Amine | Structure |
|---|---|---|---|
| W | (trans)-4-(5-bromo-2-(((R)-1-phenylethyl)amino)pyrrolo[2,1-f][1,2,4]triazin-7-yl)cyclohexanol | | 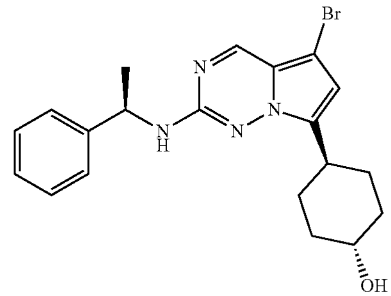 [SMILES: C[C@@H](Nc1ncc2c(Br)cc([C@H]3CC[C@H](O)CC3)n2n1)c1ccccc1] |
| BF | (trans)-4-(5-bromo-2-(((S)-4,4-difluorobutan-2-yl)amino)pyrrolo[2,1-f][1,2,4]triazin-7-yl)cyclohexanol | | 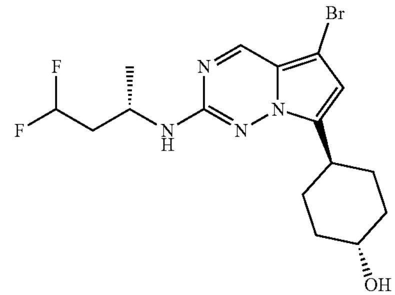 [SMILES: C[C@@H](CC(F)F)Nc1ncc2c(Br)cc([C@H]3CC[C@H](O)CC3)n2n1] |
| BG | (trans)-4-(5-bromo-2-(((S)-1-trideuteromethoxypropan-2-yl)amino)pyrrolo[2,1-f][1,2,4]triazin-7-yl)cyclohexan-1-ol | | 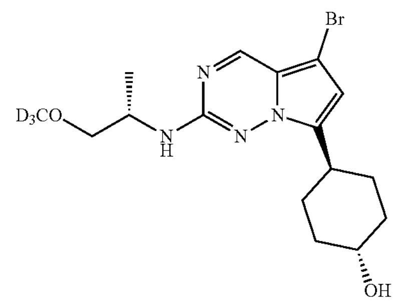 |

X. 1-((4-(4,4,5,5-tetramethyl-1,3,2-dioxaborolan-2-yl)-1H-pyrazol-1-yl)methyl)cyclopropane carbonitrile

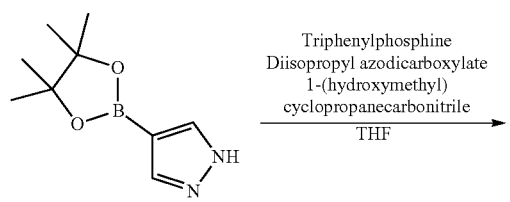

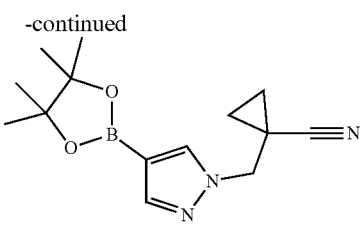

4-(4,4,5,5-tetramethyl-1,3,2-dioxaborolan-2-yl)-1H-pyrazole (200 mg, 1.01 mmol) and triphenylphosphine (397 mg, 1.52 mmol) were added in a 10 mL round-bottomed flask. THF (2.00 mL) was added followed by the 1-(hydroxymethyl)cyclopropanecarbonitrile (107 μL, 1.26 mmol) and the diisopropyl azodicarboxylate (304 μL, 1.52 mmol). The solution was stirred for 48 hours. Upon completion, the solvent was removed in vacuo to give the title compound (1050 mg, crude) as a pale yellow clear oil, which was used "as is" in subsequent steps. 4-((4-(4,4,5,5-tetramethyl-1,3,2-dioxaborolan-2-yl)-1H-pyrazol-1-yl)methyl)pyridazine (Intermediate Y) was prepared analogously using 4-hydroxymethylpyridazine in place of 1-(hydroxymethyl)cyclopropanecarbonitrile.

Z. methyl-2-methyl-2-(4-(4,4,5,5-tetramethyl-1,3,2-dioxaborolan-2-yl)-1H-pyrazol-1-yl)propanoate

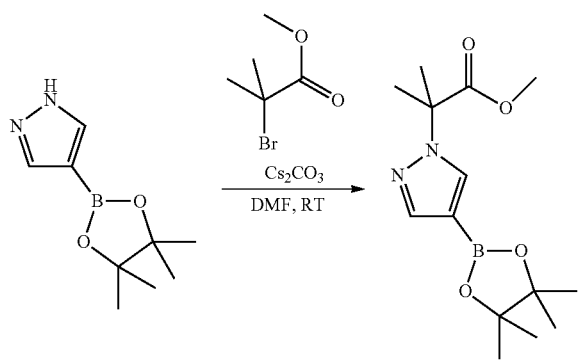

A mixture of pyrazole-4-boronic acid pinacol ester (1.00 g, 5.15 mmol) and cesium carbonate (3.38 g, 10.3 mmol) in DMF (16.0 mL) was treated with methyl alpha-bromoisobutyrate (1.01 mL, 7.73 mmol) and the mixture was allowed to stir at RT for 2 days. The crude mixture was then concentrated to dryness, diluted with EtOAc and water and slowly acidified with 1N HCl (pH=5-6). The organic phase was washed with HCl 1N, then the aqueous phase was extracted three times with EtOAc. The combined organic phases were dried with $Na_2SO_4$, filtered and concentrated under reduced pressure. The crude mixture was purified on a 40 g silica column (dry pack) eluting with (A) hexanes and (B) MTBE (gradient started at 5% and the product started to be collected at 40% MTBE). After evaporation of the volatiles, the title product was obtained as a white solid (988 mg, 61%).

AA. 5-methyl-3-((4-(4,4,5,5-tetramethyl-1,3,2-dioxaborolan-2-yl)-1H-pyrazol-1-yl)methyl)-1,2,4-oxadiazole

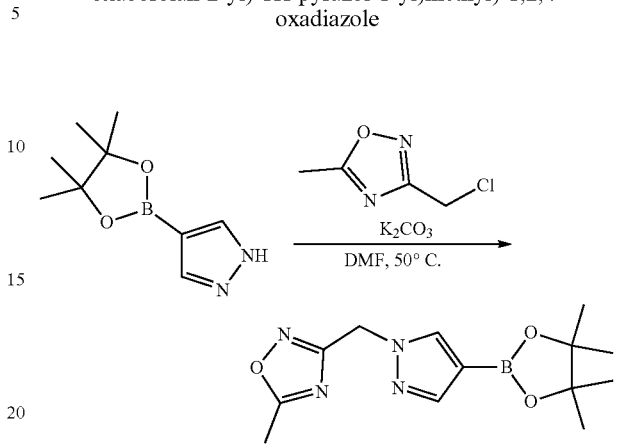

Pyrazole-4-boronic acid pinacol ester (106 mg, 0.535 mmol), 3-(chloromethyl)-5-methyl-1,2,4-oxadiazole (145 mg, 1.07 mmol) and potassium carbonate (142 mg, 1.03 mmol) were added in vial under nitrogen. Anhydrous DMF (1.5 mL) was then added and the reaction mixture was heated to 50° C. overnight. The remaining salts were filtered off and after evaporation of the volatiles under reduced pressure, the title product was used onto the next step (69 mg, 47%).

The following intermediates were prepared analogously to the indicated intermediate using the indicated alkylating agent.

| Intermediate | Name | Analagous Intermediate | Alkylating agent | Structure |
|---|---|---|---|---|
| AB | 1-(2-(methylsulfonyl)ethyl)-4-(4,4,5,5-tetramethyl-1,3,2-dioxaborolan-2-yl)-1H-pyrazole | Z | | 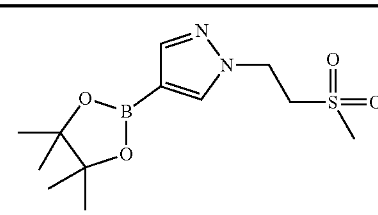 |
| AC | 2-methyl-5-((4-(4,4,5,5-tetramethyl-1,3,2-dioxaborolan-2-yl)-1H-pyrazol-1-yl)methyl)-1,3,4-oxadiazole | AA | | 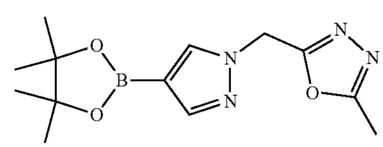 |
| AD | methyl 2-(4-iodo-1H-pyrazol-1-yl)-2-methylpropanoate | Z | | 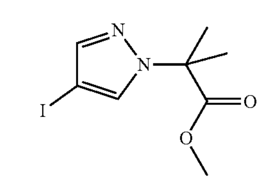 |
| AE | 5-((4-iodo-1H-pyrazol-1-yl)methyl)-3-methyl-1,2,4-oxadiazole | AA | | 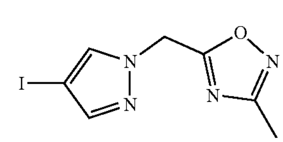 |

| Intermediate | Name | Analagous Intermediate | Alkylating agent | Structure |
|---|---|---|---|---|
| AF | 1-((tetrahydro-2H-pyran-4-yl)methyl)-4-(4,4,5,5-tetramethyl-1,3,2-dioxaborolan-2-yl)-1H-pyrazole | Z (ACN 90° C.) | 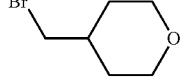 | 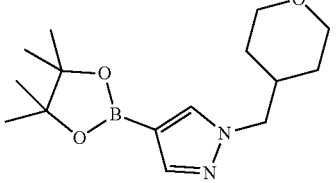 |

AG. (S)-1-((tetrahydrofuran-2 yl)methyl)-4-(4,4,5,5-tetramethyl-1,3,2-dioxaborolan-2 yl)-1H-pyrazole

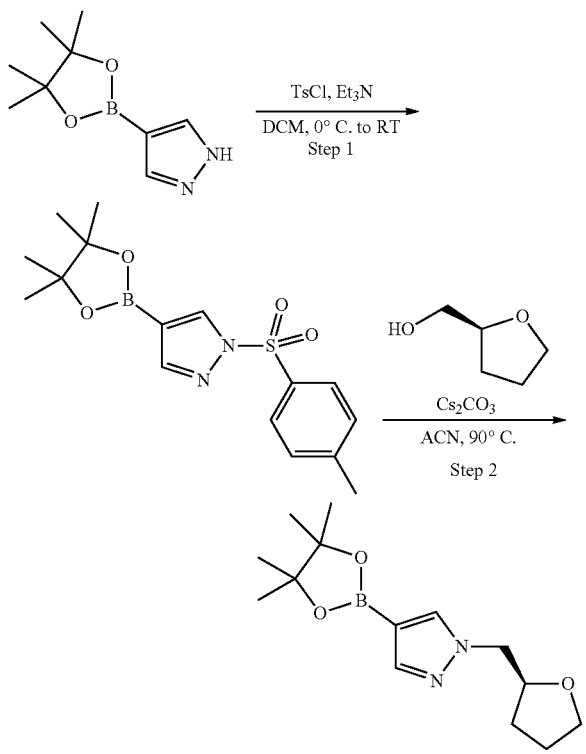

Step 1: 4-(4,4,5,5-tetramethyl-1,3,2-dioxaborolan-2-yl)-1-tosyl-1H-pyrazole

Pyrazole-4-boronic acid pinacol ester (2.00 g, 10.3 mmol) was weighed into around bottom flask, which was then fitted with a stirring bar and capped with a septum. DCM (40.0 mL) was added to the flask and the mixture was left to stir until dissolution occurred. p-toluenesulfonyl chloride (2.38 g, 12.4 mmol) was added to the mixture and the solution was cooled to 0° C. in an ice bath. Triethylamine (TEA; 1.89 mL, 13.4 mmol) was then added to the mixture dropwise via syringe. The mixture was allowed to stir at 0° C. for 10 minutes, then warmed to RT and left to stir overnight. Upon completion, the mixture was quenched with aqueous sodium bicarbonate and diluted with DCM. The phases were separated and the aqueous phase was extracted with DCM (2×). The organic phases were combined and washed with brine, then dried over MgSO$_4$, filtered and concentrated under reduced pressure. The crude was obtained as a white solid (3.42 g, 95%) and was used "as is" in the following reaction.

Step 2: (S)-1-((tetrahydrofuran-2-yl)methyl)-4-(4,4,5,5-tetramethyl-1,3,2-dioxaborolan-2-yl)-1H-pyrazole 4-(4,4,5,5-tetramethyl-1,3,2-dioxaborolan-2-yl)-1H-pyrazole (200 mg, 0.574 mmol), cesium carbonate (207 mg, 0.632 mmol), (S)-(tetrahydrofuran-2-yl)methanol (79.4 mg, 0.747 mmol) were all added to a sealed tube containing 2.0 mL of MeCN. This mixture was heated overnight at 90° C. Upon completion, this mixture was concentrated under reduced pressure and used onto the next reaction as is (160 mg, crude).

The following were prepared analogously, using the alcohol indicated:

| Intermediate | Name | Alcohol | Structure |
|---|---|---|---|
| AH | (R)-1-((tetrahydrofuran-2-yl)methyl)-4-(4,4,5,5-tetramethyl-1,3,2-dioxaborolan-2-yl)-1H-pyrazole | 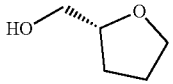 | 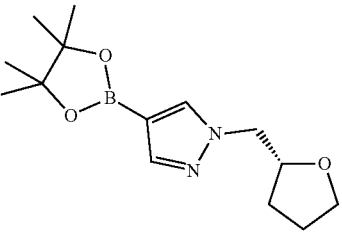 [SMILES: CC1(C)OB(c2cnn(C[C@H]3CCCO3)c2)OC1(C)C] |

-continued

| Intermediate | Name | Alcohol | Structure |
|---|---|---|---|
| AI | (S)-tert-butyl 3-(4-(4,4,5,5-tetramethyl-1,3,2-dioxaborolan-2-yl)-1H-pyrazol-1-yl)pyrrolidine-1-carboxylate | | 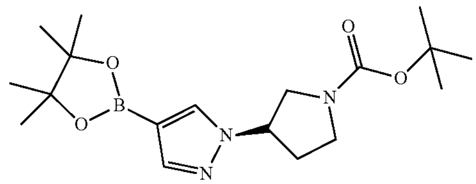 |
| AJ | (S)-tert-butyl 3-(4-(4,4,5,5-tetramethyl-1,3,2-dioxaborolan-2-yl)-1H-pyrazol-1-yl)pyrrolidine-1-carboxylate | | 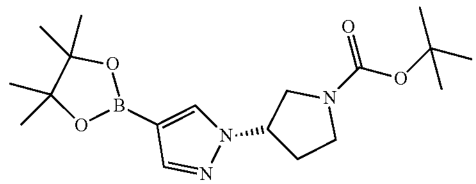 |
| AK | 2-methyl-6-((4-(4,4,5,5-tetramethyl-1,3,2-dioxaborolan-2-yl)-1H-pyrazol-1-yl)methyl)pyrazine | | 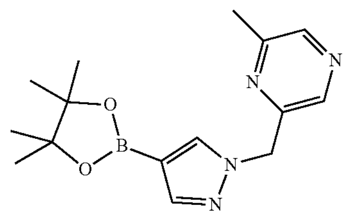 [SMILES: Cc1cncc(Cn2cc(B3OC(C)(C)C(C)(C)O3)cn2)n1] |
| AL | 2-methyl-5-((4-(4,4,5,5-tetramethyl-1,3,2-dioxaborolan-2-yl)-1H-pyrazol-1-yl)methyl)pyrazine | | 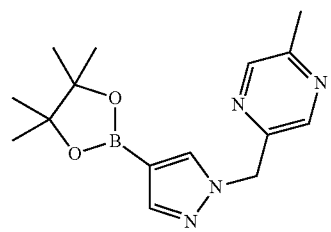 [SMILES: Cc1cnc(Cn2cc(B3OC(C)(C)C(C)(C)O3)cn2)cn1] |
| AM | 2-((4-(4,4,5,5-tetramethyl-1,3,2-dioxaborolan-2-yl)-1H-pyrazol-1-yl)methyl)pyrazine | | 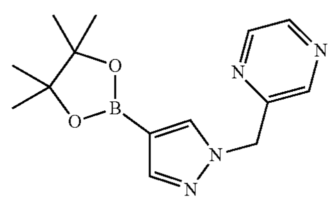 [SMILES: CC1(C)OB(c2cnn(Cc3cnccn3)c2)OC1(C)C] |
| AN | 4-iodo-1-(oxetan-2-ylmethyl)-1H-pyrazole | | 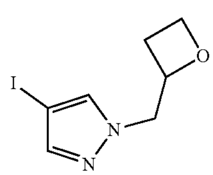 [SMILES: Ic1cnn(CC2CCO2)c1] |
| AO | 1-((3S,3aS,6aR)-hexahydrofuro[2,3-b]furan-3-yl)-4-iodo-1H-pyrazole | | 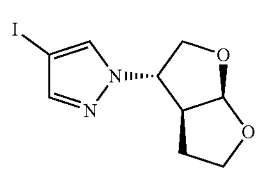 [SMILES: Ic1cnn([C@@H]2CO[C@H]3OCC[C@H]32)c1] |

| Intermediate | Name | Alcohol | Structure |
|---|---|---|---|
| AP | 4-((4-iodo-1H-pyrazol-1-yl)methyl)-1-methylpyrrolidin-2-one | | 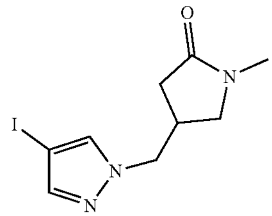 |
| AQ | 3-(4-iodo-1H-pyrazol-1-yl)-1-methylpyrrolidin-2-one | | 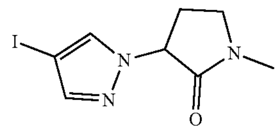 |
| AR | (3R,3aR,6S,6aR)-6-(4-iodo-1H-pyrazol-1-yl)hexahydrofuro[3,2-b]furan-3-ol | | 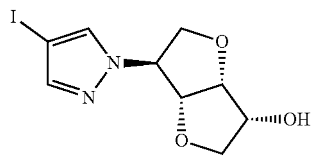 [SMILES: O[C@@H]1CO[C@H]2[C@@H]1OC[C@@H]2n1cc(I)cn1] |
| AS | (S)-5-((4-bromo-1H-pyrazol-1-yl)methyl)pyrrolidin-2-one | | 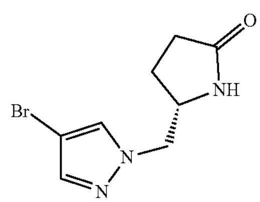 [SMILES: O=C1CC[C@@H](Cn2cc(Br)cn2)N1] |
| AT | (R)-5-((4-bromo-1H-pyrazol-1-yl)methyl)pyrrolidin-2-one | | 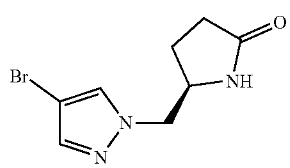 [SMILES: O=C1CC[C@H](Cn2cc(Br)cn2)N1] |
| AU | (S)-3-(4-bromo-1H-pyrazol-1-yl)pyrrolidin-2-one | | 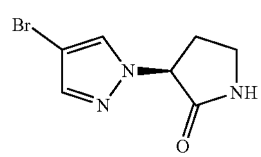 [SMILES: O=C1NCC[C@@H]1n1cc(Br)cn1] |
| AV | (R)-3-(4-bromo-1H-pyrazol-1-yl)pyrrolidin-2-one | | 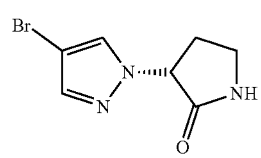 |
| AW | 1-((1H-pyrazol-4-yl)methyl)-4-bromo-1H-pyrazole | | 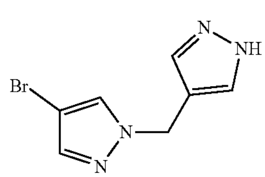 [SMILES: Brc1cnn(Cc2cn[nH]c2)c1] |
| AX | 5-((4-bromo-1H-pyrazol-1-yl)methyl)-1,3-dimethyl-1H-pyrazole | | 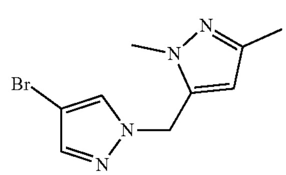 |

-continued

| Intermediate | Name | Alcohol | Structure |
|---|---|---|---|
| AY | 5-((4-bromo-1H-pyrazol-1-yl)methyl)-1-methylpyridin-2(1H)-one | | 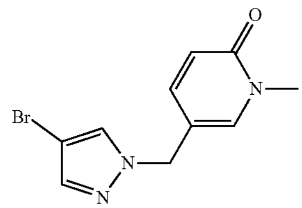 |
| AZ | 4-(4-bromo-1H-pyrazol-1-yl)tetrahydro-2H-thiopyran 1,1-dioxide | | 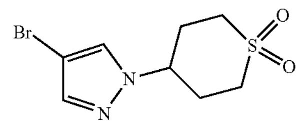 [SMILES: O=S1(=O)CCC(n2cc(Br)cn2)CC1] |
| BA | 4-((4-(4,4,5,5-tetramethyl-1,3,2-dioxaborolan-2-yl)-1H-pyrazol-1-yl)methyl)pyrrolidin-2-one | | 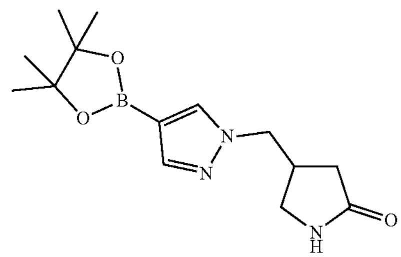 [SMILES: CC1(C)OB(c2cnn(CC3CNC(=O)C3)c2)OC1(C)C] |
| BB | 1-(4-(methylsulfonyl)benzyl)-4-(4,4,5,5-tetramethyl-1,3,2-dioxaborolan-2-yl)-1H-pyrazole | | 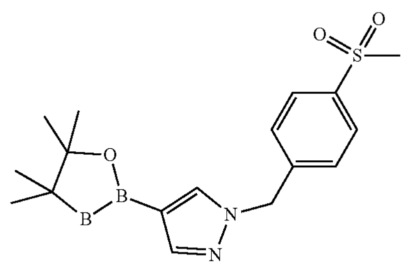 |
| BH | 2-((4-iodo-1H-pyrazol-1-yl)methyl)-5-methyl-1,3,4-thiadiazole | | 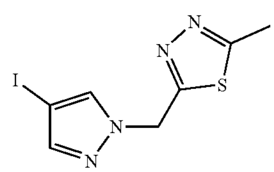 |

BC. Methyl 3-(4-(4,4,5,5-tetramethyl-1,3,2-dioxaborolan-2yl)-1H-pyrazol-1-yl)azetidine-1-carboxylate

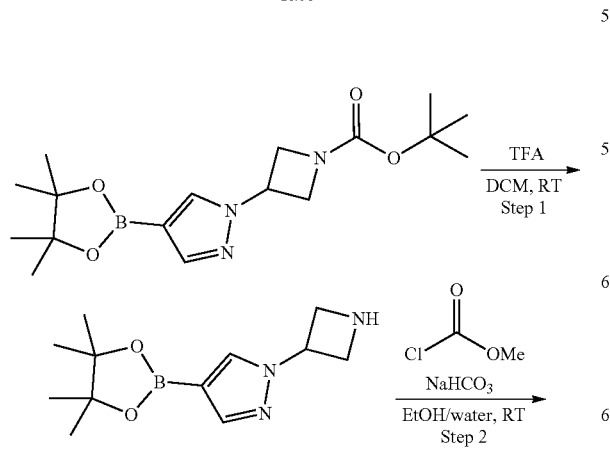

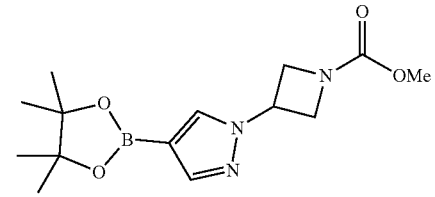

Step 1: 1-(azetidin-3-yl)-4-(4,4,5,5-tetramethyl-1,3,2-dioxaborolan-2-yl)-1H-pyrazole tert-Butyl 3-(4-(4,4,5,5-tetramethyl-1,3,2-dioxaborolan-2-yl)-1H-pyrazol-1-yl)azetidine-1-carboxylate (100 mg, 0.275 mmol) was dissolved in DCM (3.0 mL). TFA (0.425 mL, 5.50 mmol) was then added and the mixture was stirred at RT for 2 hours. Upon completion, the mixture was concentrated and the crude product was used into the next reaction "as is" (65 mg).

Step 2: methyl 3-(4-(4,4,5,5-tetramethyl-1,3,2-dioxaborolan-2-yl)-1H-pyrazol-1-yl)azetidine-1-carboxylate 1-(Azetidin-3-yl)-4-(4,4,5,5-tetramethyl-1,3,2-dioxaborolan-2-yl)-1H-pyrazole (70 mg, 0.281 mmol) was dissolved in a mixture of EtOH (5.0 mL) and water (0.5 mL). Sodium hydrogencarbonate (47.2 mg, 0.562 mmol) and methyl chloroformate (0.03 mL, 0.384 mmol) were then added. The resulting mixture was stirred at RT for 3 hours. Upon completion, the mixture was concentrated and the crude product was used into the next reaction "as is."

BD. 4-(4,4,5,5-tetramethyl-1,3,2-dioxaborolan-2-yl)-1-(1-(2,2,2-trifluoroethyl)azetidin-3-yl)-1H-pyrazole

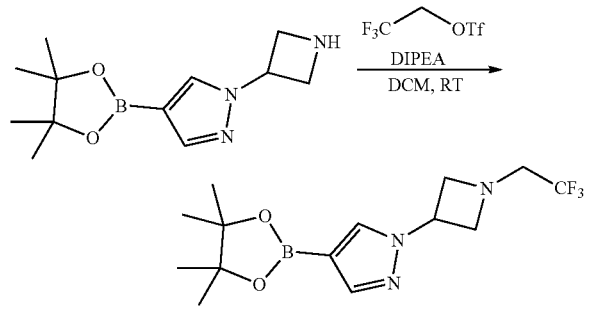

In a flame dried flask, 1-(azetidin-3-yl)-4-(4,4,5,5-tetramethyl-1,3,2-dioxaborolan-2-yl)-1H-pyrazole (71 mg, 0.285 mmol) was dissolved in DCM (3.0 mL). Then, 2,2,2-trifluoroethyl trifluoromethanesulfonate (88.7 mg, 0.371 mmol) and DIPEA (0.055 mL, 0.2314 mmol) were added under nitrogen and the reaction mixture was stirred at RT. Upon completion, the reaction mixture was concentrated under reduced pressure and the crude material was used in the next reaction "as is."

BE. 2-(2-(4-iodo-1H-pyrazol-1-yl)propan-2-yl)-5-methyl-1,3,4-oxadiazole (General Method A)

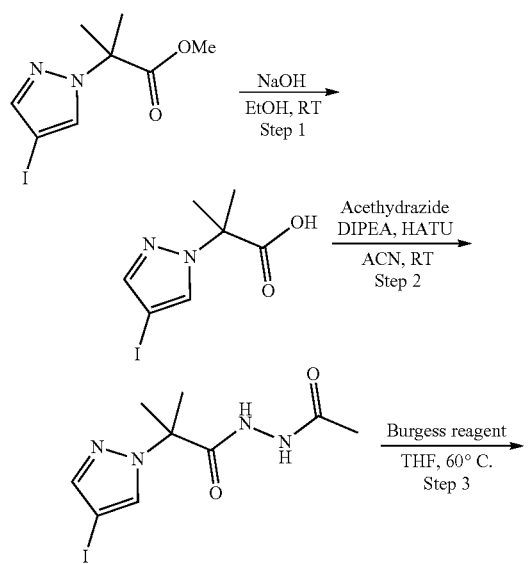

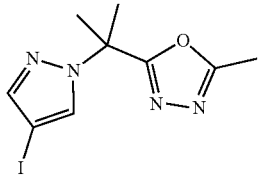

Step 1: 2-(4-iodo-1H-pyrazol-1-yl)-2-methylpropanoic acid

Methyl 2-(4-iodo-1H-pyrazol-1-yl)-2-methylpropanoate (500 mg, 1.70 mmol) was dissolved in EtOH (33.6 mL) and then 1N NaOH (34.0 mL, 34.0 mmol) was added. The resulting mixture was stirred at RT for 1 hour. Upon completion, the reaction was quenched with 36 mL of HCl 1N and then diluted with brine and EtOAc. The aqueous phase was extracted 3× with EtOAc. The combined organic phases were dried with MgSO$_4$, filtered and concentrated under reduce pressure to give the title product (635 mg, crude), as a white solid.

Step 2: N'-acetyl-2-(4-iodo-1H-pyrazol-1-yl)-2-methylpropanehydrazide 2-(4-iodo-1H-pyrazol-1-yl)-2-methylpropanoic acid (175 mg, 625 μmol) was dissolved in dry acetonitrile (ACN; 4.5 mL) and DIPEA (241 μL, 1.37 mmol) was added, followed by acethydrazide (119 mg, 1.56 mmol) and HATU ((dimethylamino)-N,N-dimethyl(3H-[1,2,3]triazolo[4,5-b]pyridine-3-yloxy)methaniminium hexafluorophosphate; 291 mg, 750 μmol). The resulting mixture was stirred overnight at RT. Upon completion, the solvent was removed under reduced pressure and the residue was diluted with EtOAc and successively washed with HCl 1 N, aqueous saturated NaHCO$_3$ and brine. The organic phase was dried with MgSO$_4$, filtered and then concentrated under reduced pressure. The crude residue was directly used in the next step without further purification. The title product was obtained as a white solid (250 mg).

Step 3: 2-(2-(4-iodo-1H-pyrazol-1-yl)propan-2-yl)-5-methyl-1,3,4-oxadiazole

N'-acetyl-2-(4-iodo-1H-pyrazol-1-yl)-2-methylpropanehydrazide (125 mg, 372 μmol) was dissolved in dry THF (5 mL) and then the burgess reagent (232 mg, 930 μmol) was added. The resulting solution was then heated at 60° C. for 15 hours. Upon completion, the reaction was diluted with EtOAc and water and the organic phase was washed with HCl 1N, aqueous saturated NaHCO$_3$ and brine. The organic phase was dried with MgSO$_4$, filtered and concentrated under reduce pressure. The resulting crude white solid (84.5 mg) was directly used in the next step without further purification.

BI: 2-(2-(4-iodo-1H-pyrazol-1-yl)propan-2-yl)-5-methyl-1,3,4-oxadiazole

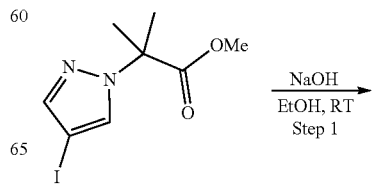

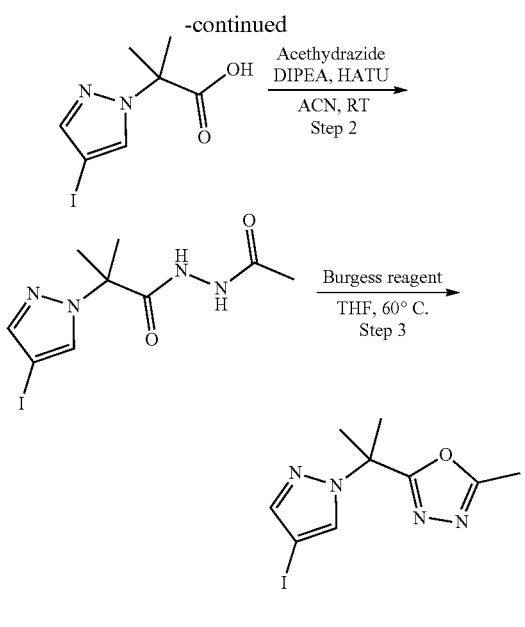

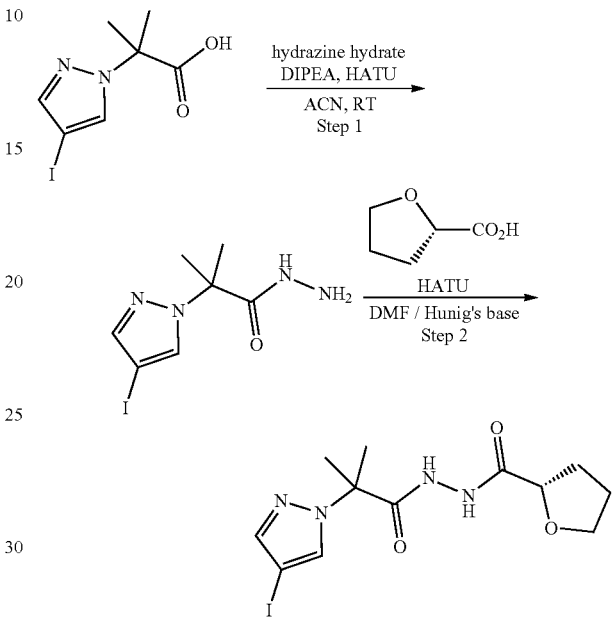

Step 1:
2-(4-iodo-1H-pyrazol-1-yl)-2-methylpropanoic acid

Methyl 2-(4-iodo-1H-pyrazol-1-yl)-2-methylpropanoate (500 mg, 1.70 mmol) was dissolved in EtOH (33.6 mL) and then 1N NaOH (34.0 mL, 34.0 mmol) was added. The resulting mixture was stirred at RT for 1 hour. Upon completion, the reaction was quenched with 36 mL of HCl 1N and then diluted with brine and EtOAc. The aqueous phase was extracted 3× with EtOAc. The combined organic phases were dried with MgSO$_4$, filtered and concentrated under reduce pressure to give the title product (635 mg, crude), as a white solid.

Step 2: N'-acetyl-2-(4-iodo-1H-pyrazol-1-yl)-2-methylpropanehydrazide 2-(4-iodo-1H-pyrazol-1-yl)-2-methylpropanoic acid (175 mg, 625 μmol) was dissolved in dry ACN (4.5 mL) and DIPEA (241 μL, 1.37 mmol) was added, followed by acethydrazide (119 mg, 1.56 mmol) and HATU (291 mg, 750 μmol). The resulting mixture was stirred overnight at RT. Upon completion, the solvent was removed under reduced pressure and the residue was diluted with EtOAc and successively washed with HCl 1N, aqueous saturated NaHCO$_3$ and brine. The organic phase was dried with MgSO$_4$, filtered and then concentrated under reduced pressure. The crude residue was directly used in the next step without further purification. The title product was obtained as a white solid (250 mg).

Step 3: 2-(2-(4-iodo-1H-pyrazol-1-yl)propan-2-yl)-5-methyl-1,3,4-oxadiazole

N'-acetyl-2-(4-iodo-1H-pyrazol-1-yl)-2-methylpropanehydrazide (125 mg, 372 μmol) was dissolved in dry THF (5 mL) and then the burgess reagent (232 mg, 930 μmol) was added. The resulting solution was then heated at 60° C. for 15 hours. Upon completion, the reaction was diluted with EtOAc and water and the organic phase was washed with HCl 1N, aqueous saturated NaHCO$_3$ and brine. The organic phase was dried with MgSO$_4$, filtered and concentrated under reduce pressure. The resulting crude white solid (84.5 mg) was directly used in the next step without further purification.

BJ: (S)-N'-(2-(4-iodo-1H-pyrazol-1-yl)-2-methylpropanoyl)tetrahydrofuran-2-carbohydrazide

Step 1: 2-(4-iodo-1H-pyrazol-1-yl)-2-methylpropanehydrazide

To a solution of 2-(4-iodo-1H-pyrazol-1-yl)-2-methylpropanoic acid (1.33 mL, 3.57 mmol) N,N-Diisopropylethylamine; (1.37 mL, 7.82 mmol) in DMF (25.0 mL) was added HATU (1.62 g, 4.14 mmol). The mixture was stirred for 10 min. Hydrazine (25 mL, 3.57 mmol) was added and the obtained mixture at room temperature (RT) for 10 minutes. The reaction mixture was diluted with EtOAc and washed sat NaHCO$_3$ (×3), dried (MgSO$_4$) and concentrated in vacuo. The residue was purified by silica gel chromatograpy using 20% MeOH, 2.5% NH$_4$OH in DCM. LCMS: m/z=249.9 (M=O)+.

Step 2: (S)-N'-(2-(4-iodo-1H-pyrazol-1-yl)-2-methylpropanoyl)tetrahydrofuran-2-carbohydrazide 2-(4-iodo-M-pyrazol-1-yl)-2-methylpropanebydrazide (200 mg, 680 μmol) was dissolved in DMF (15 mL). To the solution was added DIPEA. (199 μL, 2.04 mmol) and the mixture was cooled to 0° C. and (s)-(+)-tetrahydro-2-furoic acid (49.5 μL, 505 μmol) was added. The solution was then stirred at RT overnight. The mixture was evaporated and purified by flash using 20% MeOH in DCM/DCM (10-50%). LCMS: 393.0 (M+H)+. The diacylhydrazides so obtained were cyclized using the conditions indicated in the Table below.

The following intermediates were prepared analogously to the indicated intermediate using the indicated cyclization conditions:

| Intermediate | General Method | Structure | Cyclization conditions |
|---|---|---|---|
| BK | BI | 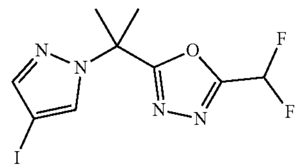 [SMILES: CC(C)(c1nnc(C(F)F)o1)n1cc(I)cn1] | TFAA/Hunig's base/ DMF/ON |
| BL | BI | 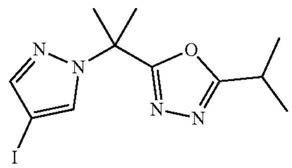 [SMILES: CC(C)c1nnc(C(C)(C)n2cc(I)cn2)o1] | Burgess reagent/ THF/microwave/ 120° C./30 min |
| BM | BJ | 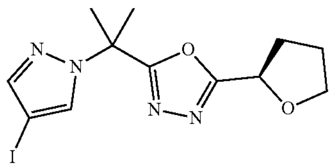 [SMILES: CC(C)(c1nnc([C@H]2CCCO2)o1)n1cc(I)cn1] | Burgess reagent/ THF/microwave/ 120° C./30 min |
| BN | BJ | 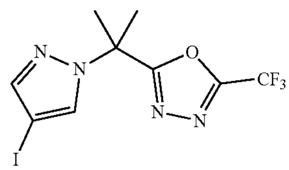 [SMILES: CC(C)(c1nnc(C(F)(F)F)o1)n1cc(I)cn1] | TFAA/DMF/0° C. to RT overnight |
| BO | BJ | 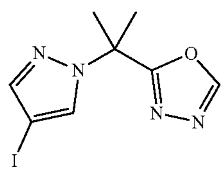 | Burgess reagent/ THF/microwave/ 80° C./60 min |
| BP | BJ (CDI/Hunig's base/DMF/DCM 0° C. then morpholine, microwave 120° C./30 mins | 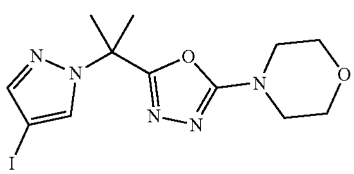 [SMILES: CC(C)(c1nnc(N2CCOCC2)o1)n1cc(I)cn1] | Burgess reagent/ THF/microwave/ 120° C./30 min |

BQ and BR: 2-(4-iodo-H-pyrazol-1yl)-2-methyl-1-morpholinopropan-1-one (Intermediate BQ) and 2-methyl-1-morpholino-2-(4-(4,4,5,5-tetramethyl-1,3,2-dioxaborolan-2-yl)-1H-pyrazol-1 yl)propan-1-one (Intermediate BR)

-continued

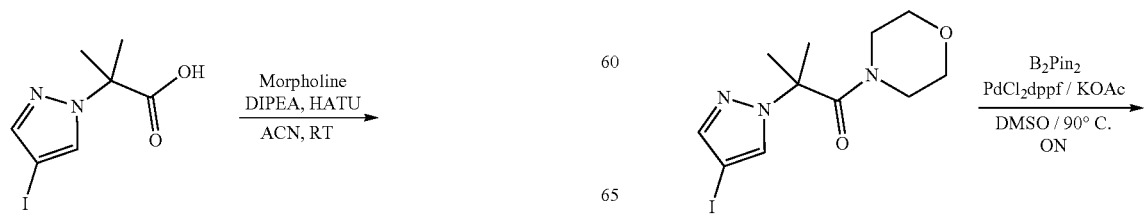

Step 1: 2-(4-iodo-1H-pyrazol-1-yl)-2-methyl-1-morpholinopropan-1-one

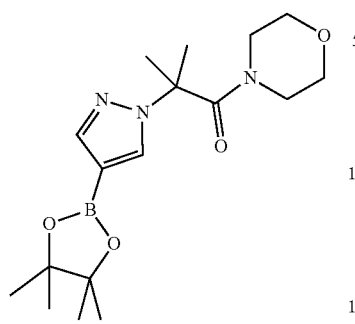

To a solution of 2-(4-iodo-1H-pyrazol-1-yl)-2-methylpropanoic acid (401 mg, 1.43 mmol), morpholine (317 μL, 3.58 mmol) and N,N-Diisopropylethylamine (550 μL, 3.14 mmol) in DMF (10 mL) was added HATU (652 mg, 1.66 mmol). The resulting mixture was stirred at 55° C. overnight. The residue was diluted with 120 and extracted with EtOAc (λ3). The combined layers were washed (H$_2$O λ4), brine, dried (Na$_2$SO) and concentrated. The residue was purified by column chromatography on silica gel, eluting with 0 to 80% EtOAc in hexanes to afford the desired product (347 mg, 69%) H NMR (500 MUz, CDCl$_3$) δ 7.57-7.54 (m, 1H), 7.52 (d, J=0.5 Hz, 1H), 3.48 (s, 8H), 1.78 (s, 6H). LCMS m/z=344.9 (M+H)+.

Step 2: 2-methyl-1-morpholino-2-(4-(4,4,5,5-tetramethyl-1,3,2-dioxaborolan-2-yl)-1H-pyrazol-1-yl)propan-1-one In a flame-dried flask was added DMSO (dimethyl sulfoxide; 2. mL) which was degassed with argon for 10 min (bubbling with a long needle, in a sonication bath), KOAc (142 mg, 1.43 mmol), Bis(pinacolato)diboron (175 mg, 676 μmol) and 2-(3-iodo-1H-pyrrol-1-yl)-2-methyl-1-morpholinopropan-1-one (200 mg, 573 μmol) were then added and the reaction mixture was degassed again for 10 min and then stirred at RT for 20 min. PdCl$_2$dppf was then added and the resulting mixture was stirred overnight at 9% C The residue was diluted with H$_2$O and extracted with EtOAc (×3). The combined layers were washed (sat NH$_4$Cl, sat NaHCO$_3$, brine, dried (Na$_2$SO$_4$) and concentrated. The residue was purified by column chromatography on silica gel, eluting with 0 to 20 IPA in DCM to afford the desired product (143 mg, 72%). LCMS m/z=350.1 (M+H)$^+$.

The following were prepared analogously to BQ and BR:

| Intermediate | Structure | Intermediate | Structure |
|---|---|---|---|
| BS | 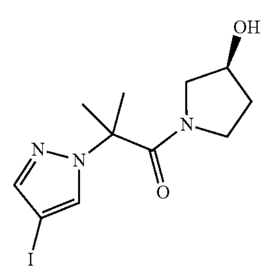 [SMILES: CC(C)(C(=O)N1CC[C@H](O)C1)n1cc(I)cn1] | BU | 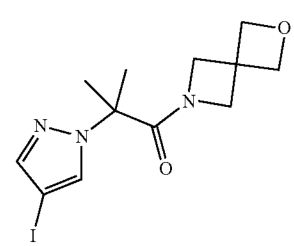 [SMILES: CC(C)(C(=O)N1CC2(COC2)C1)n1cc(I)cn1] |
| BT | 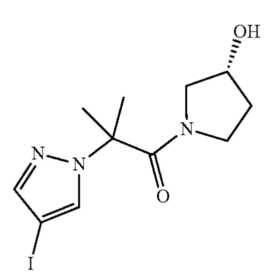 [SMILES: CC(C)(C(=O)N1CC[C@@H](O)C1)n1cc(I)cn1] | BV | 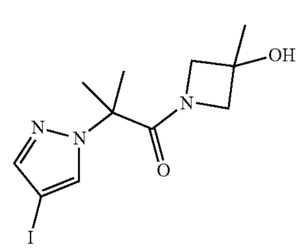 [SMILES: CC1(O)CN(C(=O)C(C)(C)n2cc(I)cn2)C1] |

BW 4-chloro-2-(oxetan-3-yl)pyridine

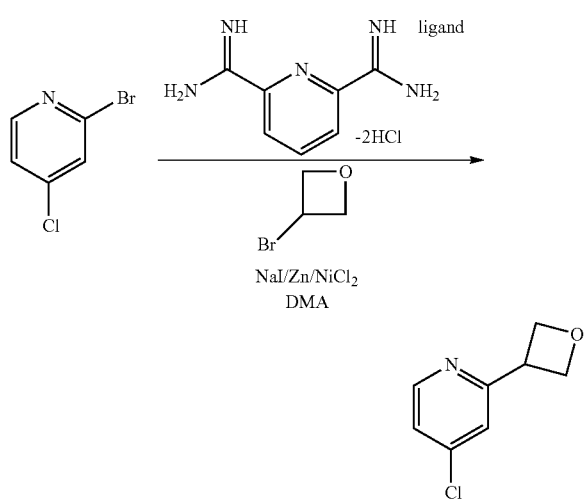

The indicated ligand was prepared as described in *J. Org. Chem.* 82:7085, 2017. In a flame dried 5 mL microwave vial was successively added dimethyl adipate (DMA; 5 mL), ligand (15.3 mg, 65.0 μmol), nickel chloride, dimethoxyethane adduct (14.7 mg, 65.0 μmol), sodium iodide (48.7 mg, 325 μmol) 2-Bromo-4-chloropyridine (286 μL, 1.30 mmol), 3-bromooxetane (162 μL, 1.95 mmol) zinc (173 mg, 2.60 mmol), trifluoroacetic acid (10.0 μL, 130 μmol). The vial was capped and argon was bubbled into the solution for 8 minutes in the sonic bath. The reaction mixture was heated to 60° C. with stirring overnight then filtered through a Celite® pad subsequently washed with EtOAc. The filtrate was then washed with 5% aq $NH_{40}H$. The organic layer was washed with brine, dried over $MgSO_4$, and filtered, and concentrated in vacuo. The residue was purified by column chromatography (silica gel and eluting with 10 to 100% EtOAc in heptane). We obtained a pale yellow oil (41.0 mg, 19%). LCMS m/z=350.1 (M+H)+.

BX: 2-(4-bromopyridin-2-yl)propan-2-ol

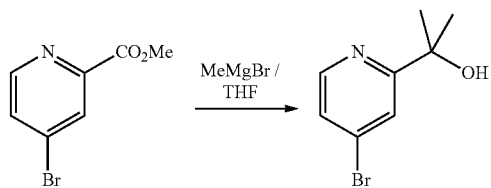

Methyl 4-bromopicolinate (500 mg, 2.31 mmol) was dissolved in dry THF (10 mL) under argon at 0° C. and MeMgBr (1.70 mL, 5.09 mmol) was added dropwise After 30 min, the solution was stirred for hour at RT then stored "as is" at −17° C. overnight. The resulting solution was diluted with water and extracted with EtOAc (×2). The organic phase was dried with $MgSO_4$ filtered and then concentrated under reduced pressure. The residue was purified on a 12 g silica column eluting with 5 to 100% EtOAc in hexanes. The desired product was obtained as a colorless oil (256 mg, 51%). LCMS m/z=215.8/217.8 (M+H)+.

BY: 1-((5-bromopyridin-2-yl)methyl)-4-methylpiperazine

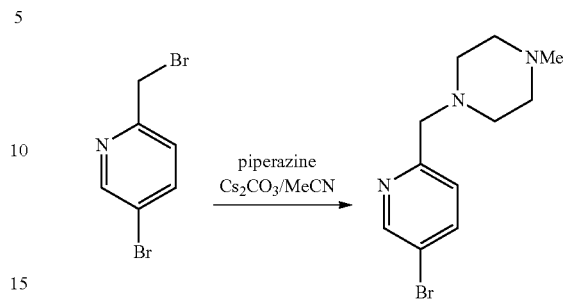

To a solution of 5-Bromo-2-(bromomethyl)pyridine (70.0 mg, 279 μmol) in MeCN (1 mL), cesium carbonate (137 mg, 418 μmol) was added. The resulting slurry was stirred at RT and 1-methylpiperazine (46.4 μL, 418 μmol) was added. The mixture was stirred at RT for 1 hour. The so-obtained solution of the crude product (also containing the quaternary salt) was used "as is" in the next step.

Preparation of Amines:

Amine for Intermediate F:
(S)-4,4,4-trifluorobutan-2-amine hydrochloride

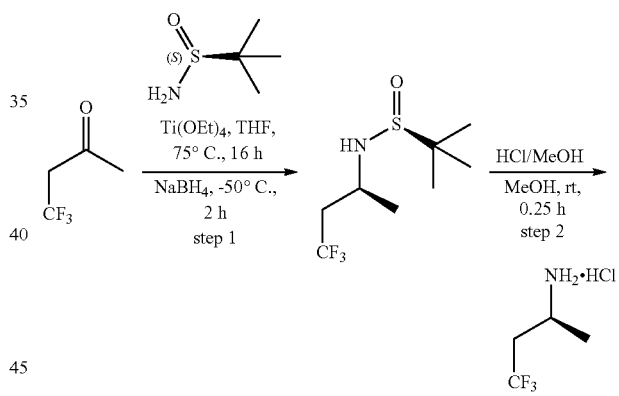

Step 1: (S)-2-methyl-N-((S)-4,4,4-trifluorobutan-2-yl)propane-2-sulfinamide

A mixture of 4,4,4-trifluorobutan-2-one (5 g, 39.7 mmol, 1 eq), 2-methylpropane-2-sulfinamide (4.8 g, 39.7 mmol, 1.0 eq) and $Ti(OEt)_4$ (16.4 mL, 79.3 mmol, 2 eq) in THF (30 mL) was degassed and purged with $N_2$ 3 times, and then the mixture was heated to 75° C. for 16 hours. TLC indicated that one new spot was formed (UV=254 nm), then the mixture was cooled to RT and then cooled to −50° C., $NaBH_4$ (6.0 g, 158.6 mmol, 4.0 eq) was added slowly to the mixture at −50° C., the mixture was stirred at this temperature for 2 hours. Upon completion, the reaction mixture was poured into ice water of saturated $Na_2CO_3$ (200 mL) and diluted with DCM (200 mL). The mixture was then filtered, and the filtrate was extracted with DCM (200 mL×3). The combined organic layers were washed with brine (200 mL×2), dried over anhydrous $Na_2SO_4$, concentrated in vacuo to give a residue. The residue was purified by column chromatography (SiO$_2$, Petroleum ether/EtOAc=10/1 to 5/1) to give the tittle compound (5.3 g, 58% yield,) as a yellow solid. LCMS: (ES+) m/z (M+H)$^+$=232.0.

Step 2: (S)-4,4,4-trifluorobutan-2-amine hydrochloride

To a solution of 2-methyl-N-(3,3,3-trifluoro-1-methylpropyl)propane-2-sulfinamide (1 g, 4.3 mmol, 1 eq) in DCM (2 mL) was added HCl/EtOAc (4 M, 2 mL, 1.85 eq). The mixture was stirred at 25° C. for 0.25 hours. Upon completion, the reaction mixture was concentrated under reduced pressure to give a residue. The residue was purified by re-crystallized from DCM (5 mL) to afford 4,4,4-trifluorobutan-2-amine hydrochloride (0.6 g, 84.84% yield) as a white solid, confirmed by $^1$H NMR.

Amine for Intermediate G:
(S)-1-(difluoromethoxy)propan-2-amine hydrochloride

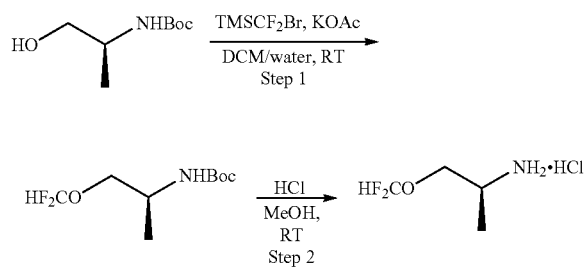

Step 1: (S)-tert-butyl (1-(difluoromethoxy)propan-2-yl)carbamate

To a solution of (S)-tert-butyl (1-hydroxypropan-2-yl) carbamate (2.40 g, 13.4 mmol) and potassium acetate (3.99 g, 40.3 mmol) in DCM (9.60 mL)/water (9.60 mL) was added (bromodifluoromethyl)trimethylsilane (3.19 mL, 20.1 mmol). The resulting mixture was stirred at RT for 7 days. Upon completion, DCM and water were added. The aqueous layer was extracted 3 times with DCM. The combined organic layers were washed with brine, dried over Na$_2$SO$_4$, filtered and concentrated under reduced pressure (3 g, crude).

Step 2: (S)-1-(difluoromethoxy)propan-2-amine hydrochloride

To a solution of (S)-tert-butyl (1-(difluoromethoxy)propan-2-yl)carbamate (3 g, 13.3 mmol) in MeOH (25 mL) was added hydrochloric acid (33.5 mL, 134 mmol). The resulting mixture was stirred at RT for 3 hours. Upon completion, the volatiles were evaporated under reduced pressure. The residue was triturated with MTBE and filtered to give (S)-1-(difluoromethoxy)propan-2-amine hydrochloride (1.29 g, crude).

Amine for Intermediate H:
(S)-1-fluoropropan-2-amine hydrochloride salt

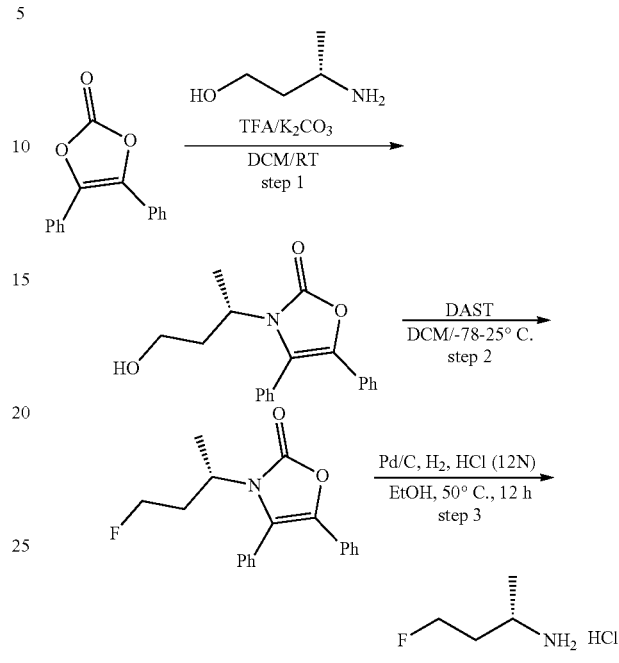

Step 1: (S)-3-(4-hydroxybutan-2-yl)-4,5-diphenyloxazol-2(3H)-one

A mixture of (S)-3-Aminobutan-1-ol (4.25 mL, 42.0 mmol) and 4,5-diphenyl-1,3-dioxol-2-one (10.0 g, 42.0 mmol) in DMF (125 mL) was allowed to stir at RT overnight. The reaction was diluted with H$_2$O and extracted with EtOAc (×5), and the combined organic layers washed (H$_2$O×5, brine), dried (Na$_2$SO$_4$) and concentrated in vacuo. The residue was treated with TFA (39.0 mL, 504 mmol) and the solution was allowed to stir for 2 hours. The solution was concentrated and the residue taken up in MeOH and treated with K$_2$CO$_3$ (11.9 mL, 210 mmol) and the mixture was allowed to stir for 1 hour. The mixture was concentrated and the residue was diluted with H$_2$O and extracted with EtOAc (×3), and the combined organic layers washed (H$_2$O×2, brine), dried (Na$_2$SO$_4$) and concentrated in vacuo. The residue was purified by column chromatography (0 to 100% EtOAc in hexanes) to give a colorless solid (7.60 g, 59%).

Step 2: (S)-3-(1-fluoropropan-2-yl)-4,5-diphenyloxazol-2(3H)-one

A solution of (S)-3-(4-hydroxybutan-2-yl)-4,5-diphenyloxazol-2(3H)-one (1.00 g, 3.23 mmol) in Toluene (10 mL) was treated with 2-pyridinesulfonyl fluoride (603 mg, 3.56 mmol) followed by 1,8-diazabicyclo[5.4.0]undec-7-ene (DBU) (971 μL, 6.37 mmol) dropwise at RT overnight. The mixture was diluted with 8 mL DCM and stirring continued for a further 24 h. The DCM was removed in vacuo, and the residue was diluted with H$_2$O and extracted with EtOAc (×3). The combined organic layers were washed (H$_2$O, brine), dried (Na$_2$SO$_4$) and concentrated in vacuo. The residue was purified by column chromatography (Combiflash, 12 g column, 0 to 100% EtOAc in hexanes). We obtained a colorless solid (411 mg, 41%).

Step 3: (S)-1-fluoropropan-2-amine hydrochloride salt

A solution of (S)-3-(4-fluorobutan-2-yl)-4,5-diphenyloxazol-2(3H)-one (405 mg, 1.30 mmol) in MeOH (10 mL) containing HCl (542 μL, 6.50 mmol) and palladium 10% wt on activated carbon (400 mg) was hydrogenated under a balloon at 50° C. overnight. The mixture was filtered through Celite® and the residue concentrated. ¹H NMR showed a mixture, and was consistent with the desired product and diphenylethane. The crude material was used "as is" in subsequent steps. Assume theoretical yield.

Amine for Intermediate N:
(S)-4-(difluoromethoxy)butan-2-amine hydrochloride

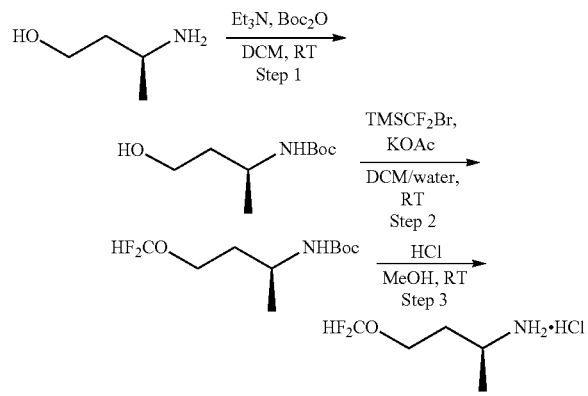

Step 1: (S)-tert-butyl (4-hydroxybutan-2-yl)carbamate

To a solution of (S)-3-Aminobutan-1-ol (2.00 g, 22.4 mmol) in DCM (10.0 mL) was added TEA (4.74 mL, 33.7 mmol) and di-tert-butyl dicarbonate (5.67 mL, 24.7 mmol). The resulting mixture was stirred at RT for 16 hours. Upon completion, ice water was added, then the aqueous layer was extracted twice with DCM. The combined organic layers were washed with brine, dried over $Na_2SO_4$, filtered, and concentrated under reduced pressure to give the title compound (4.12 g, crude).

Step 2: (S)-tert-butyl (4-(difluoromethoxy)butan-2-yl)carbamate

To a solution of (S)-tert-butyl (4-hydroxybutan-2-yl)carbamate (1.00 g, 5.28 mmol) and potassium acetate (1.57 g, 15.9 mmol) in DCM (3.78 mL)/water (3.78 mL) was added (bromodifluoromethyl)trimethylsilane (1.26 mL, 7.93 mmol). The resulting mixture was stirred at RT for 4 days. Upon completion, DCM and water were added. The aqueous layer was extracted three times with DCM. The combined organic layers were washed with brine, dried over $Na_2SO_4$, filtered and concentrated under reduced pressure to give the title compound (1.26 g, crude).

Step 3: (S)-4-(difluoromethoxy)butan-2-amine hydrochloride

To a solution of (S)-tert-butyl (4-(difluoromethoxy)butan-2-yl)carbamate (630 mg, 2.63 mmol) in MeOH (9.41 mL) was added hydrochloric acid (6.58 mL, 26.3 mmol). The resulting mixture was stirred at RT for 4 hours. Upon completion, the volatiles were evaporated under reduced pressure. The residue was triturated with MTBE and filtered to give (S)-4-(difluoromethoxy)butan-2-amine hydrochloride (399 mg, crude).

Amine for Intermediate BF:
(S)-4,4-difluorobutan-2-amine hydrochloride

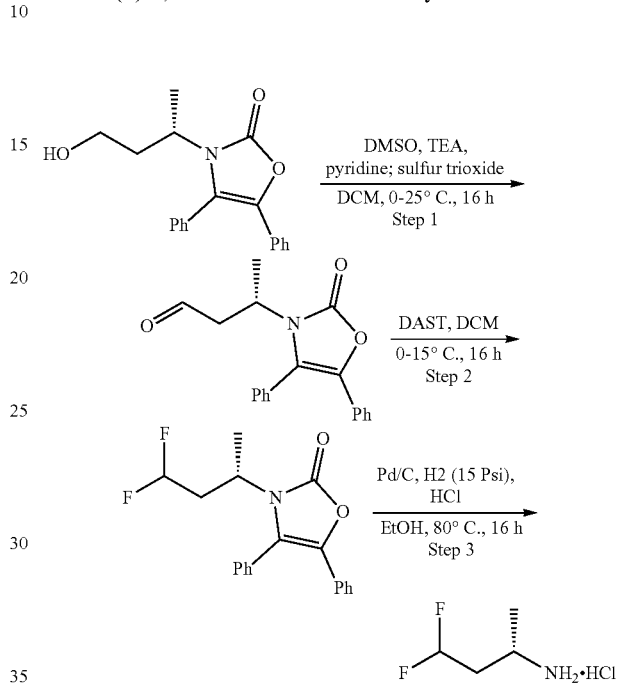

Step 1: (S)-3-(2-oxo-4,5-diphenyloxazol-3(2H)-yl)butanal

To a solution of 3-[(1S)-3-hydroxy-1-methyl-propyl]-4,5-diphenyl-oxazol-2-one (5 g, 16.16 mmol, 1 eq) in DCM (50 mL) was added DMSO (3.79 mL, 48.5 mmol, 3 eq), TEA (6.75 mL, 48.5 mmol, 3 eq) and pyridine; sulfur trioxide (5.14 g, 32.3 mmol, 2 eq) at 0° C. Then the mixture was stirred at 25° C. for 16 hours. Upon completion, the mixture was concentrated in vacuo. The residue was diluted with water (50 mL) and extracted with EtOAc (3×30 mL). The combined organic layer was washed with brine (2×20 mL), dried over $Na_2SO_4$ and concentrated in vacuo. The residue was purified by column chromatography ($SiO_2$, Petroleum ether/EtOAc=6:1) to give the title compound (2.7 g, 54% yield) as a white solid.

Step 2: (S)-3-(4,4-difluorobutan-2-yl)-4,5-diphenyloxazol-2(3H)-one

To a solution of (3S)-3-(2-oxo-4,5-diphenyl-oxazol-3-yl) butanal (2.3 g, 7.5 mmol, 1 eq) in dry DCM (45 mL) was added DAST (12.1 g, 74.8 mmol, 9.9 mL, 10 eq) at 0° C. Then the mixture was stirred at 15° C. for 16 hours. On completion, the mixture was quenched by sat. $NaHCO_3$(50 mL), and extracted with DCM (50 mL×2). The combined organic layer was washed with water (30 mL) and brine (30 mL), dried over $Na_2SO_4$ and concentrated in vacuo. The residue was purified by column chromatography ($SiO_2$, Petroleum ether/EtOAC=20/1) to give the title compound (1.9 g, 76% yield) as a yellow oil.

Step 3: (S)-4,4-difluorobutan-2-amine hydrochloride

To a solution of 3-[(1S)-3,3-difluoro-1-methyl-propyl]-4,5-diphenyl-oxazol-2-one (2.2 g, 6.68 mmol, 1 eq) in EtOH (80 mL) was added HCl (12 M, 2.78 mL, 5 eq) and Pd/C (2.83 g, 1.34 mmol, 5% purity, 0.2 eq) under $N_2$. The suspension was degassed under vacuum and purged with $H_2$ several times. The mixture was stirred under $H_2$ (15 psi) at 80° C. for 16 hours. Upon completion, the mixture was filtered and the filtrated was concentrated in vacuo to give a crude product. To the residue was added 20 mL of petroleum ether/EtOAc (1:1) and 1 N HCl (30 mL). The aqueous layer was extracted with petroleum ether/EtOAc (1:1) (20 mL×2). The combined organic was washed with 1 N HCl (30 mL). The organic phase was discarded. The aqueous layer was combined and lyophilized to give the title compound (950 mg, 98% yield) as a white solid.

Amine for Intermediate BG: (S)-1-(D3)-methoxy-propan-2-amine (TFA salt)

To a solution of of (S)-2-(Boc-amino)-1-propanol (1) (1.00 g, 5.71 mmol) in DMF (12 mL) at 0° C. was added sodium hydride (750 mg, 18.7 mmol) and the reaction was stirred for 30 min. The mixture was a white paste but still mixable. Iodomethane-d3 (497 μL, 7.99 mmol) was added dropwise at 0° C. and then the reaction was allowed to warm up to RT and further stirred 4 hours. The reaction was diluted with water and extracted (2×) with EtOAC. The organic phase was washed with brine and dried over $MgSO_4$, filtered and then concentrated under reduced pressure. The residue was purified by silica gel column chromatography on a 30 g column eluting with 10% to 60% EtOAc in hexanes, affording a colorless oil (638 mg, 58%). The product was diluted in DCM (5 mL) and treated with TFA (3 mL) was added. After stirring at RT for 3 h, toluene was added and concentrated under reduce pressure. This was repeated 3 times. The amine salt so obtained was used directly in the next step.

Example 2: Synthesis of Compound 102 and 103

Compounds 102 and 103 (as shown in FIG. 1) were synthesized according to General Scheme 1, above. The step numbers indicated below correspond to the steps shown in that scheme.

Step 1: (S)-4-(5-bromo-2-(heptan-2-ylamino)pyrrolo[2,1-f][1,2,4]triazin-7-yl)cyclohexanone To a solution of 5-bromo-7-(1,4-dioxaspiro[4.5]decan-8-yl)-N-[(1S)-1-methylhexyl]pyrrolo[2,1-f][1,2,4]triazin-2-amine (180 mg, 0.399 mmol) in MeCN (5.0 mL) was added aq. HCl (6 M, 5.0 mL). The mixture was stirred at 25° C. for 1 hour. Upon completion, the reaction mixture was adjusted pH by $NaHCO_3$ to 6-7, then extracted with EtOAc (30 mL×3). The organic layers were combined, washed with water (30 mL), brine (30 mL×2), dried over anhydrous $Na_2SO_4$, filtered and concentrated in vacuo to give the tittle compound (210 mg, crude) as a light yellow solid.

Step 2: (S)-4-(2-(heptan-2-ylamino)-5-(4-(morpholinosulfonyl)phenyl)pyrrolo[2,1-f][1,2,4]triazin-7-yl)cyclohexanone A mixture of 4-[5-bromo-2-[[(1S)-1-methylhexyl]amino]pyrrolo[2,1-f][1,2,4]triazin-7-yl]cyclohexanone (100 mg, 0.246 mmol), 4-[4-(4,4,5,5-tetramethyl-1,3,2-dioxaborolan-2-yl)phenyl]sulfonylmorpholine (95 mg, 0.270 mmol), $Pd(PPh_3)_4$ (terakis(triphenylphosphine) palladium(0); 28 mg, 0.025 mmol), $Na_2CO_3$ (78 mg, 0.737 mmol) in dioxane (6.0 mL) and $H_2O$ (2.0 mL) was degassed and purged with $N_2$ for 3 times, and then stirred at 80° C. for 2 hours under $N_2$ atmosphere (atm). Upon completion, the reaction mixture was diluted with DCM (20 mL) and extracted with DCM (20 mL×3). The organic layers were combined, washed with water (20 mL), brine (20 mL×2) sequentially, dried over anhydrous $Na_2SO_4$, filtered and concentrated in vacuo. The residue was purified by prep-TLC to give the tittle compound (62 mg, 0.112 mmol, 46% yield) as a light yellow solid.

Step 3: (1S,4r)-4-(2-((S)-heptan-2-ylamino)-5-(4-(morpholinosulfonyl)phenyl)pyrrolo[2,1-f][1,2,4]triazin-7-yl)cyclohexanol and (1R,4s)-4-(2-((S)-heptan-2-ylamino)-5-(4-(morpholinosulfonyl)phenyl)pyrrolo[2,1-f][1,2,4]triazin-7-yl)cyclohexanol To a solution of 4-[2-[[(1S)-1-methylhexyl]amino]-5-(4-morpholinosulfonylphenyl)pyrrolo[2,1-f][1,2,4]triazin-7-yl]cyclohexanone (54 mg, 0.098 mmol) in MeOH (20.0 mL) was added $NaBH_4$ (19 mg, 0.390 mmol) at 0° C. The mixture was stirred at 0° C. for 1 hour. Upon completion, the reaction mixture was quenched by aq. sat. $NH_4Cl$ (30 mL). The mixture was then extracted with DCM (20 mL×3). The organic layers were combined, dried over anhydrous $Na_2SO_4$, filtered and concentrated in vacuo. The residue was purified by prep-HPLC. The eluent was concentrated to remove organic solvent, treated with aq. HCl (0.2 M, 0.5 mL) and then lyophilized to give 4-[2-[[(1S)-1-methylhexyl]amino]-5-(4-morpholino-sulfonylphenyl)pyrrolo[2,1-f][1,2,4]triazin-7-yl]cyclohexanol as HCl salt (37 mg, 67% yield, 98% purity) and 4-[2-[[(1S)-1-methylhexyl]amino]-5-(4-morpholinosulfonylphenyl)pyr-rolo[2,1-f][1,2,4]triazin-7-yl]cyclohexanol as HCl salt (3.2 mg, 5.9% yield, 99% purity) as light yellow solids. The structure and purity of the title compounds were confirmed by $^1H$ NMR and LCMS.

Example 3: Synthesis of Compound 106

Compound 106 (as shown in FIG. 1) was synthesized according to General Scheme 1, above. The step numbers indicated below correspond to the steps shown in that scheme.

Step 4: (S)-N5-(4-fluorophenyl)-N2-(heptan-2-yl)-7-(1,4-dioxaspiro[4.5]decan-8-yl)pyrrolo[2,1-f][1,2,4]triazine-2,5-diamine A mixture of 5-bromo-7-(1,4-dioxaspiro[4.5]decan-8-yl)-N-[(1S)-1-methylhexyl]pyrrolo[2,1-f][1,2,4]triazin-2-amine (80 mg, 0.177 mmol), 4-fluoroaniline (30 mg, 0.266 mmol), $Cs_2CO_3$ (116 mg, 0.355 mmol), Brettphos-Pd-$G_3$ (16 mg, 0.018 mmol; "Brettphos" being dicyclohexyl(2,4,6-triisopropyl-3,6-dimethoxy-[1,1-biphenyl]-2-yl)phosphine) in dioxane (5 mL) was degassed and purged with $N_2$ for 3 times, and then stirred at 60° C. for 12 hours under $N_2$ atm. After that, 4-fluoroaniline (30 mg, 0.266 mmol), Brettphos-Pd-G3 (16 mg, 0.018 mmol) and $Cs_2CO_3$ (58 mg, 0.177 mmol) were added to the mixture. Then the mixture was stirred at 60° C. for 4 hours under $N_2$ atm. Upon completion, the reaction mixture was concentrated in vacuo. The residue was diluted with EtOAc (30 mL) and extracted with EtOAc (20 mL×3). The organic layers were combined, washed with water (20 mL), brine (20 mL×2), dried over anhydrous $Na_2SO_4$, filtered and concentrated in vacuo. The residue was purified by prep-TLC to give the title compound (110 mg, crude) as a yellow oil.

Step 6a: (S)-4-(5-((4-fluorophenyl)amino)-2-(heptan-2-ylamino)pyrrolo[2,1-f][1,2,4]triazin-7-yl)cyclohexanone To a solution of 7-(1,4-dioxaspiro[4.5]decan-8-yl)-N5-(4-fluorophenyl)-N2-[(1S)-1-methylhexyl]pyrrolo[2,1-f][1,2,4]triazine-2,5-diamine (100 mg, 0.208 mmol), ACN (5 mL) was added aq. HCl (6 M, 5 mL). The mixture was stirred at 25° C. for 30 minutes. Upon completion, the reaction mixture was added $NaHCO_3$ to adjust pH to 6-7, and then extracted with EtOAc (20 mL×3). The combined organic layers were washed with brine (20 mL×2), dried over anhydrous $Na_2SO_4$, filtered and concentrated in vacuo to give the tittle compound (90 mg, crude) as a red solid.

Step 6b: (1S,4r)-4-(5-((4-fluorophenyl)amino)-2-((S)-heptan-2-ylamino)pyrrolo[2,1-f][1,2,4]triazin-7-yl)cyclohexanol hydrochloride To a solution of 4-[5-(4-fluoroanilino)-2-[[(1S)-1-methylhexyl]amino]-pyrrolo[2,1-f][1,2,4]triazin-7-yl]cyclohexanone (85 mg, 0.194 mmol) in MeOH (5 mL) was added $NaBH_4$ (29 mg, 0.777 mmol). The mixture was stirred at 0° C. for 30 minutes. Upon completion, the reaction mixture was quenched by addition saturated $NH_4Cl$ (30 mL) at 0° C., and then extracted with DCM (20 mL×3). The combined organic layers were dried over anhydrous $Na_2SO_4$, filtered and concentrated in vacuo to give a residue. The residue was purified by prep-HPLC. The eluent was concentrated to remove organic solvent, adjusted by aq. HCl (0.2 M, 0.5 mL), and lyophilized to give the title compound (8 mg, 8.5% yield, 98% purity) as a red solid. The structure and purity of the title compound were confirmed by LCMS and $^1$H NMR.

Example 4: Synthesis of Compound 115

Compound 115 (as shown in FIG. 1) was synthesized according to General Scheme 1, above. The step numbers indicated below correspond to the steps shown in that scheme.

Step 4: 5-[4-(dimethylamino)-1-piperidyl]-7-(1,4-dioxaspiro[4.5]decan-8-yl)-N-[(1S)-1-methylhexyl]pyrrolo[2,1-f][1,2,4]triazin-2-amine A mixture of (S)-5-bromo-N-(heptan-2-yl)-7-(1,4-dioxaspiro[4.5]decan-8-yl)pyrrolo[2,1-f][1,2,4]triazin-2-amine (90 mg, 0.199 mmol), N,N-dimethylpiperidin-4-amine (38 mg, 0.299 mmol), t-BuONa (29 mg, 0.299 mmol), SPhos-Pd-G2 (14 mg, 0.020 mmol) in dioxane (9.0 mL) was degassed and purged with $N_2$ (×3), and then stirred at 90° C. for 30 hours under $N_2$ atm. Upon completion, the reaction mixture was cooled to RT, partitioned between EtOAc (30 mL) and water (15 mL). The organic phase was separated, washed with brine (5 mL×2), dried over anhydrous $Na_2SO_4$, filtered and concentrated in vacuo. The residue was purified by prep-TLC to afford the title compound (60 mg, crude) as a yellow solid.

Step 6a: 4-[5-[4-(dimethylamino)-1-piperidyl]-2-[[(1S)-1-methylhexyl]amino]pyrrolo[2,1-f][1,2,4]triazin-7-yl]cyclohexanone To a solution of 5-[4-(dimethylamino)-1-piperidyl]-7-(1,4-dioxaspiro[4.5]decan-8-yl)-N-[(1S)-1-methylhexyl]pyrrolo[2,1-f][1,2,4]triazin-2-amine (60 mg, 0.120 mmol) in ACN (4.0 mL) was added aq. HCl (6 M, 4 mL). The mixture was stirred at 25° C. for 1 hour. Upon completion, the reaction mixture was adjusted pH to 8 by $NaHCO_3$, diluted with water (10 mL) and extracted with EtOAc (15 mL×2). Organic layers were combined, washed with brine (10 mL×2), dried over anhydrous $Na_2SO_4$, filtered and concentrated in vacuo to give the title compound (30 mg, crude) as a yellow solid.

Step 6b: 4-[5-[4-(dimethylamino)-1-piperidyl]-2-[[(1S)-1-methylhexyl]amino]pyrrolo[2,1-f][1,2,4]triazin-7-yl]cyclohexanol hydrochloride To a solution of 4-[5-[4-(dimethylamino)-1-piperidyl]-2-[[(1S)-1-methylhexyl]amino]pyrrolo[2,1-f][1,2,4]triazin-7-yl]cyclohexanone (30 mg, 0.066 mmol) in MeOH (1.0 mL) was added $NaBH_4$ (2.5 mg, 0.066 mmol). The mixture was stirred at −40° C. for 0.5 hour. Upon completion, to the reaction mixture was added with sat. aq. $NaHCO_3$ (5 mL), extracted with EtOAc (5 mL×2). The organic layers were combined, washed with brine (5 mL), dried over anhydrous $Na_2SO_4$, filtered and concentrated in vacuo. The residue was purified by prep-HPLC. The eluent was concentrated to remove organic solvent, treated with aq. HCl (0.1 M, 2 mL), and lyophilized to give the title compound (1.2 mg, 3.6% yield, 97% purity) as a red solid. The structure and purity of the title compound were confirmed by LCMS and $^1$H NMR.

Example 5: Synthesis of Compound 116

Compound 116 (as shown in FIG. 1) was synthesized according to General Scheme 1, above. The step numbers indicated below correspond to the steps shown in that scheme.

Step 4: (S)-tert-butyl 4-(2-(heptan-2-ylamino)-7-(1,4-dioxaspiro[4.5]decan-8-yl)pyrrolo[2,1-f][1,2,4]triazin-5-yl)-5,6-dihydropyridine-1(2H)-carboxylate A mixture of 5-bromo-7-(1,4-dioxaspiro[4.5]decan-8-yl)-N-[(1S)-1-methylhexyl]pyrrolo[2,1-f][1,2,4]triazin-2-amine (60 mg, 0.133 mmol), tert-butyl 4-(4,4,5,5-tetramethyl-1,3,2-dioxaborolan-2-yl)-3,6-dihydro-2H-pyridine-1-carboxylate (82 mg, 0.266 mmol), $Na_2CO_3$ (42.3 mg, 0.399 mmol), Pd(dppf)$Cl_2$.$CH_2Cl_2$ (5.4 mg, 0.0067 mmol) in DME (3 mL) and $H_2O$ (1 mL) was degassed and purged with $N_2$ for 3 times, and then stirred at 90° C. for 2 hours under $N_2$ atm. Upon completion, the reaction mixture was diluted with EtOAc (20 mL), and then extracted with EtOAc (20 mL×3) and water (20 mL). The organic layers were combined, washed with brine (20 mL×2), dried over anhydrous $Na_2SO_4$, filtered and concentrated in vacuo. The residue was purified by prep-TLC to give the tittle compound (50 mg, 0.087 mmol, 66% yield, 96% purity) as a yellow solid Step 5: (S)-tert-butyl 4-(2-(heptan-2-ylamino)-7-(1,4-dioxaspiro[4.5]decan-8-yl)pyrrolo[2,1-f][1,2,4]triazin-5-yl)piperidine-1-carboxylate To a solution of tert-butyl 4-[7-(1,4-dioxaspiro[4.5]decan-8-yl)-2-[[(1S)-1-methylhexyl]amino]pyrrolo[2,1-f][1,2,4]

triazin-5-yl]-3,6-dihydro-2H-pyridine-1-carboxylate (50 mg, 0.090 mmol) in MeOH (10 mL) was added Pd/C (5% purity, 30 mg) under $N_2$. The suspension was degassed under vacuum and purged with $H_2$ several times. The mixture was stirred under $H_2$ (15 psi) at 25° C. for 12 hours. Upon completion, the reaction mixture was filtered and concentrated in vacuo to give a mixture of the desired product and over-reduced byproduct (35 mg in total, crude). To a solution of the mixture (35 mg, 0.063 mmol) in DCM (5 mL) was added $MnO_2$ (27 mg, 0.314 mmol). The mixture was stirred at 25° C. for 12 hours. Upon completion, the reaction mixture was filtered and concentrated in vacuo. The residue was purified by prep-TLC to give the tittle compound (18 mg, 52% yield) as a yellow solid.

Step 6a: (S)-4-(2-(heptan-2-ylamino)-5-(piperidin-4-yl)pyrrolo[2,1-f][1,2,4]triazin-7-yl)cyclohexanone To a solution of tert-butyl 4-[7-(1,4-dioxaspiro[4.5]decan-8-yl)-2-[[(1S)-1-methylhexyl]amino]pyrrolo[2,1-f][1,2,4]triazin-5-yl]piperidine-1-carboxylate (45 mg, 0.081 mmol) in MeCN (3 mL) was added aq. HCl (6 M, 3 mL). The mixture was stirred at 25° C. for 30 minutes. Upon completion, the reaction mixture was added $NaHCO_3$ to adjust pH to 6-7, and then extracted with EtOAc (20 mL×3). Organic layers were combined, washed with brine (20 mL×2), dried over anhydrous $Na_2SO_4$, filtered and concentrated in vacuo to give the title compound (40 mg, crude).

Step 6b: (1S,4r)-4-(2-((S)-heptan-2-ylamino)-5-(piperidin-4-yl)pyrrolo[2,1-f][1,2,4]triazin-7-yl)cyclohexanol hydrochloride To a solution of 4-[2-[[(1S)-1-methylhexyl]amino]-5-(4-piperidyl)pyrrolo[2,1-f][1,2,4]triazin-7-yl]cyclohexanone (40 mg, 0.097 mmol) in MeOH (5 mL) was added $NaBH_4$ (15 mg, 0.389 mmol). The mixture was stirred at 0° C. for 30 minutes. Upon completion, the reaction mixture was quenched by aq. sat. $NH_4Cl$ (20 mL) at 0° C., then diluted with EtOAc (30 mL), and extracted with EtOAc (30 mL×3). Organic layers were combined, washed with brine (20 mL×2), dried over anhydrous $Na_2SO_4$, filtered and concentrated in vacuo. The residue was purified by prep-HPLC. The eluent was concentrated to remove organic solvent, then treated with aq. HCl (0.2M, 0.5 mL) and lyophilized to give the title compound (19.4 mg, 44% yield, 99% purity) as HCl salt as a yellow solid. The structure and purity of the title compound were confirmed by LCMS and $^1H$ NMR.

Example 6: Synthesis of Compound 111

Compound 111 (as shown in FIG. 1) was synthesized according to General Scheme 2, above. The step numbers indicated below correspond to the steps shown in that scheme.

Step 1: (S)-ethyl 2-(heptan-2-ylamino)-7-(1,4-dioxaspiro[4.5]decan-8-yl)pyrrolo[2,1-f][1,2,4]triazine-5-carboxylate To a solution of 5-bromo-7-(1, 4-dioxaspiro[4.5]decan-8-yl)-N-[(1S)-1-methylhexyl]pyrrolo[2,1-f][1,2,4]triazin-2-amine (0.1 g, 0.22 mmol) in EtOH (15 mL) was added cyclopentyl(diphenyl)phosphane:iron (0.06 g, 0.11 mmol), benzonitrile:dichloropalladium (0.02 g, 0.055 mmol) and TEA (0.09 mL, 0.66 mmol). The suspension was degassed and purged with CO for several times. The mixture was stirred under CO (3 MPa) at 130° C. for 48 hours. The reaction mixture was cooled to RT and concentrated in vacuo. The residue was partitioned between EtOAc (30 mL) and water (20 mL) and separated. The aqueous layer was extracted with EtOAc (25 mL×2). All organic layers were combined, washed with brine (20 mL), dried over $Na_2SO_4$, filtered and concentrated in vacuo. The residue was purified by prep-TLC to afford the title compound (0.08 g, 82% yield) as a yellow oil.

Step 2: (S)-2-(heptan-2-ylamino)-7-(1,4-dioxaspiro[4.5]decan-8-yl)pyrrolo[2,1-f][1,2,4]triazine-5-carboxylic acid To a solution of (S)-ethyl 2-(heptan-2-ylamino)-7-(1,4-dioxaspiro[4.5]decan-8-yl)pyrrolo[2,1-f][1,2,4]triazine-5-carboxylate (0.08 g, 0.18 mmol) in MeOH (4 mL) was added aq. NaOH (4 M, 2 mL). The mixture was stirred at 45° C. for 3 hours. The reaction mixture was quenched by addition HCl (1 M) and adjusted pH to 2. The resulting mixture was then diluted with water (10 mL) and extracted with EtOAc (10 mL×3). All organic layers were combined, washed with brine (10 mL), dried over $Na_2SO_4$, filtered and concentrated in vacuo. The residue was purified by prep-TLC to afford the title compound (0.04 g, 58% yield) as a yellow solid.

Step 3: (S)-N-(4-fluorophenyl)-2-(heptan-2-ylamino)-7-(1,4-dioxaspiro[4.5]decan-8-yl)pyrrolo[2,1-f][1,2,4]triazine-5-carboxamide To a solution of (S)-2-(heptan-2-ylamino)-7-(1,4-dioxaspiro[4.5]decan-8-yl)pyrrolo[2,1-f][1,2,4]triazine-5-carboxylic acid (0.04 g, 0.096 mmol) in DMF (2 mL) was added HATU (0.04 g, 0.12 mmol). The mixture was stirred at 60° C. for 0.5 hour, before treated with DIPEA (0.05 g, 0.38 mmol, 0.067 mL) and 4-fluoroaniline (0.013 g, 0.012 mmol). The resulting mixture was then stirred at 60° C. for another 0.5 hour then cooled to RT. The mixture was diluted with water (10 mL) and extracted with EtOAc (10 mL×3). All organic layers were combined, washed with brine (10 mL), dried over $Na_2SO_4$, filtered and concentrated in vacuo. The residue was purified by prep-TLC to afford the title compound (21 mg, 32% yield, 75% purity) as a yellow oil.

Step 4a: N-(4-fluorophenyl)-2-[[(1S)-1-methylhexyl]amino]-7-(4-oxocyclohexyl)pyrrolo[2,1-f][1,2,4]triazine-5-carboxamide To a solution of (S)-N-(4-fluorophenyl)-2-(heptan-2-ylamino)-7-(1,4-dioxaspiro[4.5]decan-8-yl)pyrrolo[2,1-f][1,2,4]triazine-5-carboxamide (21 mg, 0.031 mmol) in DCM (1 mL) was added TFA (0.38 mL, 5.1 mmol). The mixture was stirred at RT for 3 hours. The reaction mixture was quenched by sat. aq. $NaHCO_3$ solution (5 mL), then extracted with DCM (5 mL×3). Organic layers were combined, washed with brine (5 mL), dried over $Na_2SO_4$, filtered and concentrated in vacuo. The residue was purified by prep-TLC to afford the title compound (15 mg, 92% yield, 88% purity) as a yellow solid.

Step 4b: N-(4-fluorophenyl)-7-(4-hydroxycyclohexyl)-2-[[(1S)-1-methylhexyl]amino]pyrrolo[2,1-f][1,2,4]triazine-5-carboxamide To a solution of N-(4-fluorophenyl)-2-[[(1S)-1-methylhexyl]amino]-7-(4-oxocyclohexyl)pyrrolo[2,1-f][1,2,4]triazine-5-carboxamide (15 mg, 0.03 mmol) in MeOH (1 mL)

was added NaBH₄ (2.4 mg, 0.06 mmol) at −40° C. and stirred at −40° C. for 0.5 hour. The reaction mixture was quenched by water (0.2 mL), and then concentrated in vacuo. The residue was purified by prep-HPLC. The eluent was concentrated to remove organic solvent and lyophilized to afford the title product (2.4 mg, 5.6% yield, 98% purity) as a yellow solid. The structure and purity were confirmed by LCMS and ¹H NMR.

Example 7: Synthesis of Compound 124

Compound 124 (as shown in FIG. 1) was synthesized according to General Scheme 3, above. The step numbers indicated below correspond to the steps shown in that scheme.

Step 6: trans-4-(5-(4-((4-methylpiperazin-1-yl)methyl)phenyl)-2-(methylsulfonyl)pyrrolo[2,1-f][1,2,4]triazin-7-yl)cyclohexan-1-ol A mixture of 4-(5-bromo-2-(methylsulfonyl)pyrrolo[2,1-f][1,2,4]triazin-7-yl)cyclohexan-1-ol (134 mg, 0.358 mmol), NaHCO₃ (103 mg, 1.23 mmol), and 1-Methyl-4-[4-(4,4,5,5-tetramethyl-1,3,2-dioxaborolan-2-yl)benzyl]piperazine (115 mg, 0.346 mmol) was suspended in 1,4-Dioxane (3.6 mL) and H₂O (1.2 mL) and the mixture was degassed by bubbling N₂ through the mixture for 5 min. The mixture was treated with [1,1'-Bis(diphenylphosphino)ferrocene]dichloropalladium(II) (17.9 mg, 0.0219 mmol) and then heated at 90'C for 30 min. The reaction mixture was cooled to RT and poured into H₂O and extracted with EtOAc (×3). The combined organic layers were washed with H₂O, brine sequentially, dried over anhydrous Na₂SO₄, filtered and concentrated in vacuo. The aqueous phase was basified by aq. NaOH (1 M) and extracted with DCM (×3). The combined layers were washed with brine, dried over anhydrous Na₂SO₄, filtered and concentrated in vacuo. The residue was taken up in MeOH and absorbed onto 2.5 g of Silicycle SCX functionalized silica. The pad was washed with MeOH (ca 30 mL) and the product was eluted with NH₃ in MeOH (7M). The fractions containing the product were concentrated to give an orange residue which was used directly without further purification (153 mg, 88%).

Step 7: trans-4-(2-(((S)-1-methoxypropan-2-yl)amino)-5-(4-((4-methylpiperazin-1-yl)methyl)phenyl)pyrrolo[2,1-f][1,2,4]triazin-7-yl)cyclohexan-1-ol To a microwave tube was added trans-4-(5-(4-((4-methylpiperazin-1-yl)methyl)phenyl)-2-(methylsulfonyl)pyrrolo[2,1-f][1,2,4]triazin-7-yl)cyclohexan-1-ol (50.0 mg, 0.103 mmol) (mixture of cis/trans diastereoisomers), NMP (0.104 mL), DIPEA (0.046 mL, 0.258 mmol) and (S)-1-Methoxy-2-propylamine (93.1 mg, 1.03 mmol). The resulting mixture was heated at 160° C. under microwave irradiation for 3 hours. The reaction mixture was partitioned between EtOAc and water and separated. The aqueous layer was extracted with EtOAc (×2). All organic layers were combine, washed with brine, dried over anhydrous Na₂SO₄, filtered and concentrated in vacuo. The residue was purified by preparative HPLC to give the title compound (14 mg, 27%) as a single diastereomer. The structure and purity were confirmed by LCMS and ¹H NMR.

Example 8: Synthesis of Compound 122 (as shown in FIG. 1)

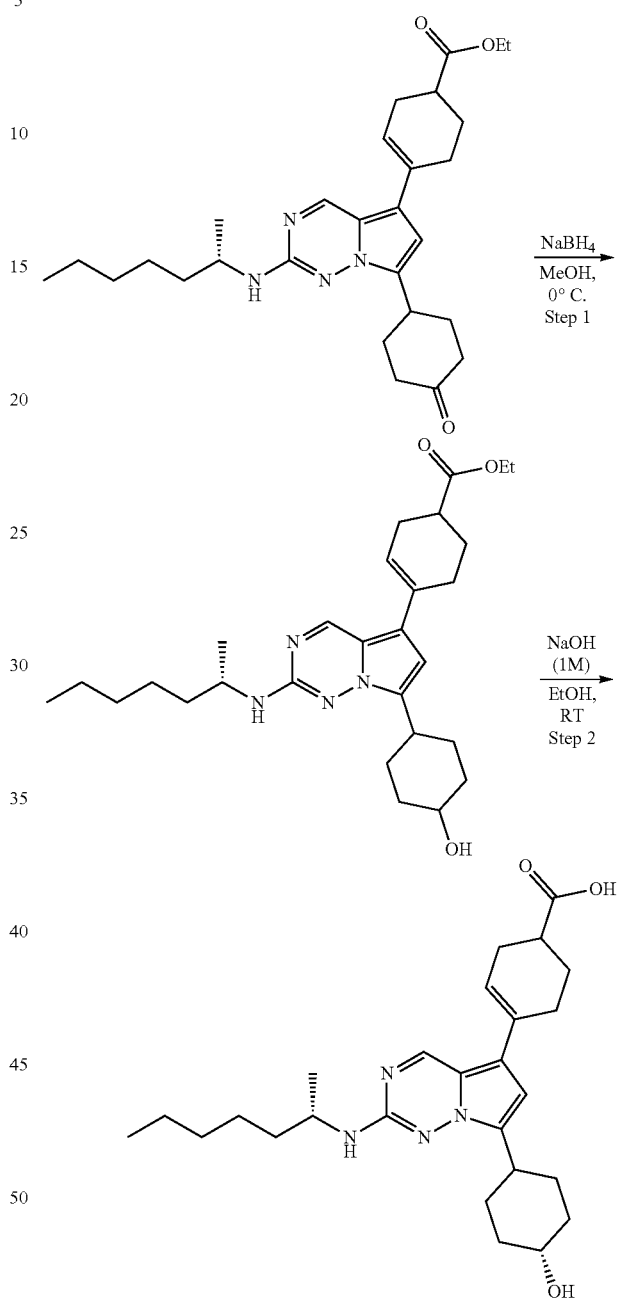

Step 1: ethyl 4-(2-((S)-heptan-2-ylamino)-7-(4-hydroxycyclohexyl)pyrrolo[2,1-f][1,2,4]triazin-5-yl)cyclohex-3-enecarboxylate To a solution of ethyl 4-(2-((S)-heptan-2-ylamino)-7-(4-oxocyclohexyl)pyrrolo[2,1-f][1,2,4]triazin-5-yl)cyclohex-3-enecarboxylate (54.0 mg, 112 μmol) in MeOH (3.00 mL) was added sodium borohydride (17.7 mg, 449 μmol) at 0° C. The resulting mixture was stirred at 0° C. for 1 hour. Upon completion, 1M HCl and EtOAc were added. The aqueous layer was extracted 3 times with EtOAc. The combined organic layers were washed with brine, dried over Na$_2$SO$_4$, filtered and concentrated under reduced pressure to give the tittle compound (50 mg, crude) as a yellow solid.

Step 2: 4-(2-((S)-heptan-2-ylamino)-7-((trans)-4-hydroxycyclohexyl)pyrrolo[2,1-f][1,2,4]triazin-5-yl)cyclohex-3-enecarboxylic acid To a solution of ethyl 4-(2-((S)-heptan-2-ylamino)-7-(4-hydroxycyclohexyl)pyrrolo[2,1-f][1,2,4]triazin-5-yl)cyclohex-3-enecarboxylate (50.0 mg, crude) in EtOH (2.30 mL) was added sodium hydroxide (1M) (2.30 mL, 2.30 mmol). The resulting mixture was stirred at RT for 2.5 hours. Upon completion, 1M HCl and EtOAc were added. The aqueous layer was extracted 3 times with EtOAc. The combined organic layers were washed with brine, dried over Na$_2$SO$_4$, filtered and concentrated under reduced pressure. The residue was purified by prep-HPLC with AmF/ACN (ammonium formate/acetonitrile) and lyophilized to give 4-(2-((S)-heptan-2-ylamino)-7-((trans)-4-hydroxycyclohexyl)pyrrolo[2,1-f][1,2,4]triazin-5-yl)cyclohex-3-enecarboxylic acid (3.2 mg, 6.8%) as a yellow solid. The structure and purity of the title compound was confirmed by H NMR and LCMS.

Example 9: Synthesis of Compounds 125 and 109 (as shown in FIG. 1)

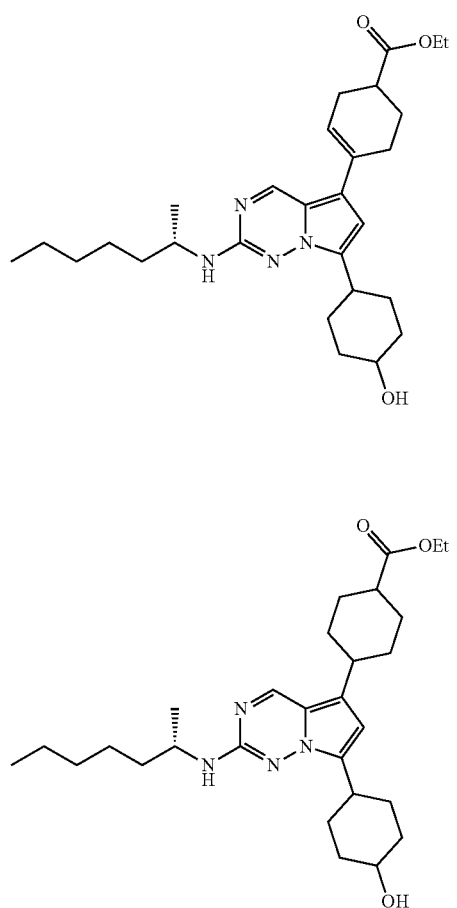

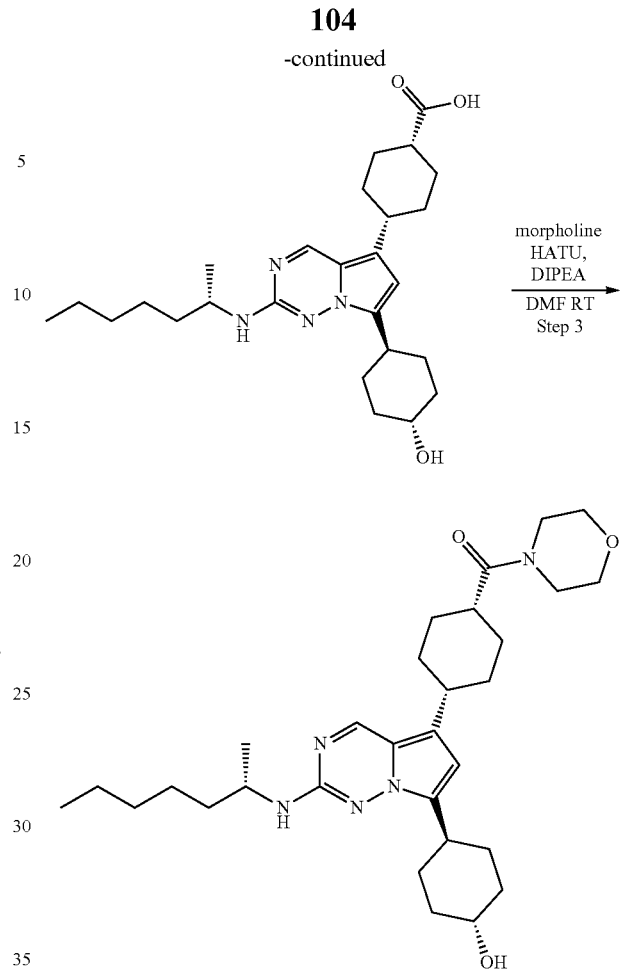

Step 1: (S)-ethyl 4-(2-(heptan-2-ylamino)-7-(4-hydroxycyclohexyl)pyrrolo[2,1-f][1,2,4]triazin-5-yl)cyclohexanecarboxylate Ethyl 4-(2-((S)-heptan-2-ylamino)-7-(4-hydroxycyclohexyl)pyrrolo[2,1-f][1,2,4]triazin-5-yl)cyclohex-3-enecarboxylate was synthesized according to general procedure 1 using ethyl 4-(4,4,5,5-tetramethyl-1,3,2-dioxaborolan-2-yl)cyclohex-3-enecarboxylate. To a solution of ethyl 4-(2-((S)-heptan-2-ylamino)-7-(4-hydroxycyclohexyl)pyrrolo[2,1-f][1,2,4]triazin-5-yl)cyclohex-3-enecarboxylate (245 mg, 508 μmol) in MeOH (12.3 mL) was added palladium on activated carbon (120 mg). The resulting mixture was purged with hydrogen three times and was then stirred at RT for 15 hours. Upon completion, the reaction material was filtered and concentrated under reduced pressure to give (S)-ethyl 4-(2-(heptan-2-ylamino)-7-(4-hydroxycyclohexyl)-3,4-dihydropyrrolo[2,1-f][1,2,4]triazin-5-yl)cyclohexanecarboxylate (195 mg, crude).

To a solution of (S)-ethyl 4-(2-(heptan-2-ylamino)-7-(4-hydroxycyclohexyl)-3,4-dihydropyrrolo[2,1-f][1,2,4]triazin-5-yl)cyclohexanecarboxylate (534 mg, crude) in THF (16.2 mL) was added activated manganese(IV) oxide (102 mg, 1.20 mmol). The resulting mixture was stirred at 50° C. for 1 hour. Upon completion, the reaction material was filtered over Celite® with EtOAc and concentration under reduced pressure to give the title compound (565 mg, crude).

Step 2: (cis)-4-(2-((S)-heptan-2-ylamino)-7-((trans)-4-hydroxycyclohexyl)pyrrolo[2,1-f][1,2,4]triazin-5-yl)cyclohexanecarboxylic acid To a solution of (S)-ethyl 4-(2-(heptan-2-ylamino)-7-(4-hydroxycyclohexyl)pyrrolo[2,1-f][1,2,4]triazin-5-yl)cyclohexanecarboxylate (565 mg, crude) in EtOH (26 mL) was added sodium hydroxide (1M) (26 mL, 26 mmol). The resulting mixture was stirred at RT for 16 hours. Upon completion, 1M HCl and EtOAc were added. The aqueous layer was extracted 3 times with EtOAc. The combined organic layers were washed with brine, dried over Na$_2$SO$_4$, filtered and concentrated under reduced pressure. The residue was purified by prep-HPLC with AmF/ACN and lyophilized to give (cis)-4-(2-((S)-heptan-2-ylamino)-7-((trans)-4-hydroxycyclohexyl)pyrrolo[2,1-f][1,2,4]triazin-5-yl)cyclohexanecarboxylic acid (90 mg) as a yellow solid. The structure and purity of the title compound was confirmed by $^1$H NMR and LCMS.

Step 3: ((cis)-4-(2-((S)-heptan-2-ylamino)-7-((trans)-4-hydroxycyclohexyl)pyrrolo[2,1-f][1,2,4]triazin-5-yl)cyclohexyl)(morpholino)methanone To a solution of (cis)-4-(2-((S)-heptan-2-ylamino)-7-((trans)-4-hydroxycyclohexyl)pyrrolo[2,1-f][1,2,4]triazin-5-yl)cyclohexanecarboxylic acid (30.0 mg, 65.7 µmol), N,N-diisopropylethylamine (57.8 µL, 328 µmol) and morpholine (29.0 µL, 328 µmol) in dry DMF (1.50 mL) was added HATU (25.8 mg, 65.7 µmol). The resulting mixture was stirred at RT for 2 hours. Upon completion, water and EtOAc were added. The aqueous layer was extracted 3 times with EtOAc. The combined organic layers were washed with brine, dried over Na$_2$SO$_4$, filtered and concentrated under reduced pressure. The residue was purified by flash chromatography on C18 silica with AmF/ACN and lyophilized to give ((cis)-4-(2-((S)-heptan-2-ylamino)-7-((trans)-4-hydroxycyclohexyl)pyrrolo[2,1-f][1,2,4]triazin-5-yl)cyclohexyl)(morpholino)methanone (23 mg, 67%) as a yellow solid. The structure and purity of the title compound was confirmed by $^1$H NMR and LCMS.

Example 10: Synthesis of Compound 127

Compound 127 (as shown in FIG. 1) was synthesized using the procedure of Example 9 and N-methylpiperazine.

Example 11: Synthesis of Compound 137

Compound 137 (as shown in FIG. 1) was synthesized using the procedure of Example 9 and thiomorpholine 1,1-dioxide.

Example 12: Synthesis of Compounds 131 and 132 (as shown in FIG. 1)

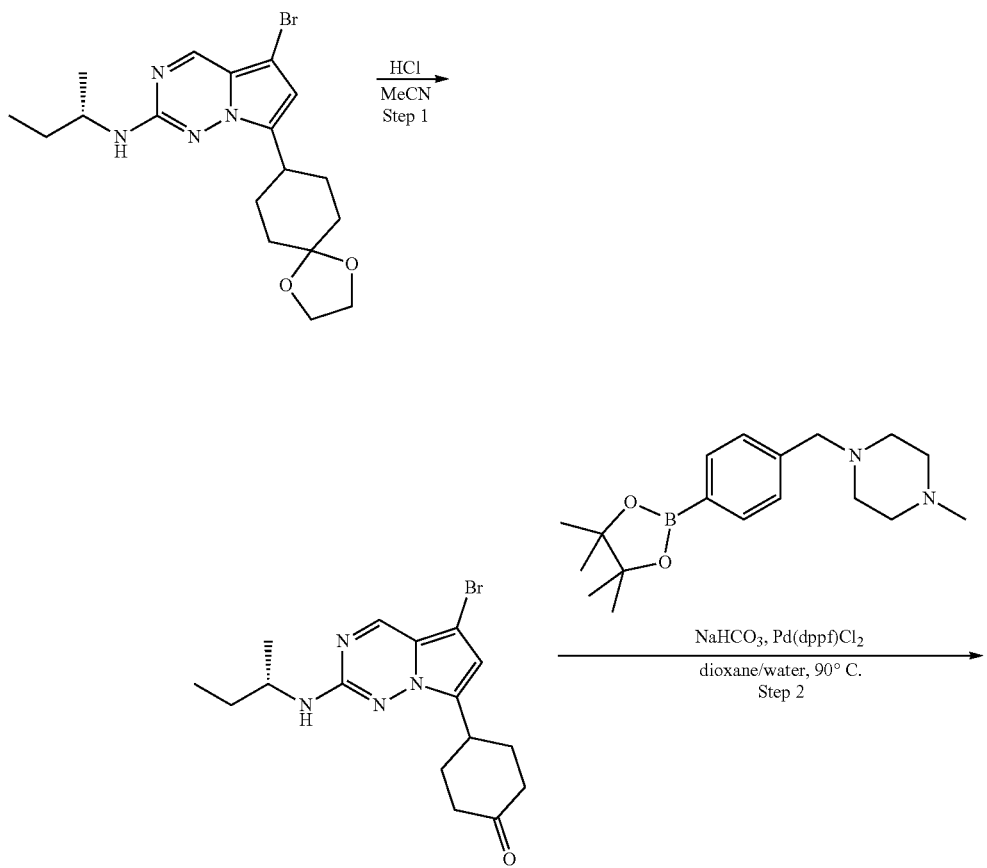

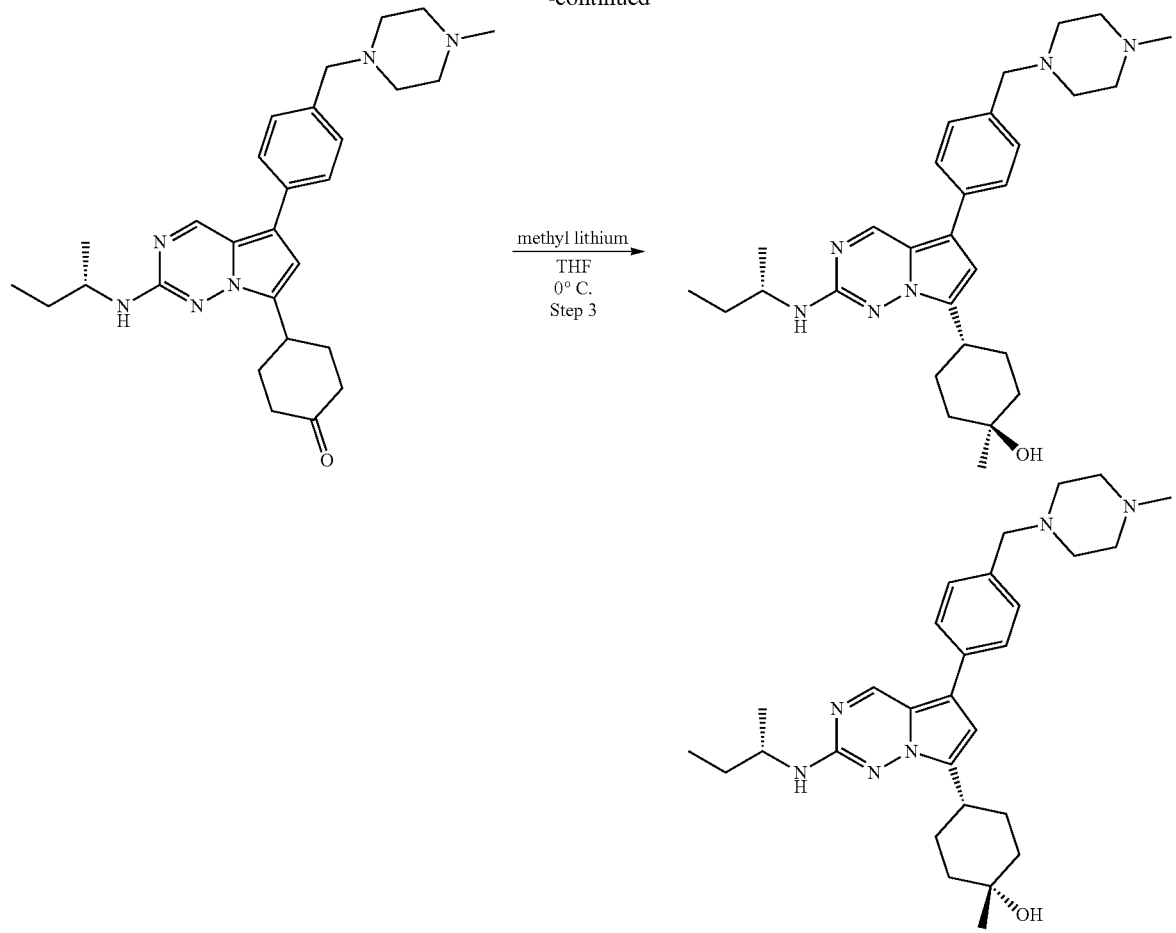

Step 1: (S)-4-(5-bromo-2-(sec-butylamino)pyrrolo[2,1-f][1,2,4]triazin-7-yl)cyclohexanone To a solution of (S)-5-bromo-N-(sec-butyl)-7-(1,4-dioxaspiro[4.5]decan-8-yl)pyrrolo[2,1-f][1,2,4]triazin-2-amine (567 mg, 1.39 mmol) in MeCN (25 mL) was added HCl (6 M, 17 mL). The mixture was stirred at 25° C. for 1 hour. Upon completion, the reaction mixture was adjusted with NaHCO₃ to pH=6-7, then extracted with EtOAC (600 mL×3) and water (600 mL). The combined organic layers were dried over anhydrous MgSO₄, filtered and concentrated in vacuo to give 501 mg of (S)-4-(5-bromo-2-(sec-butylamino)pyrrolo[2,1-f][1,2,4]triazin-7-yl)cyclohexanone (99% yield). The material was subsequently used "as is."

Step 2: (S)-4-(2-(sec-butylamino)-5-(4-((4-methylpiperazin-1-yl)methyl)phenyl)pyrrolo[2,1-f][1,2,4]triazin-7-yl)cyclohexanone To a solution of (S)-4-(5-bromo-2-(sec-butylamino)pyrrolo[2,1-f][1,2,4]triazin-7-yl)cyclohexanone (140 mg, 384 μmol), sodium hydrogenocarbonate (97 mg, 1.15 mol) and 1-methyl-4-[4-(4,4,5,5-tetramethyl-1,3,2-dioxaborolan-2-yl)benzyl]piperazine (127.6 mg, 384 μmol) in dioxane (3.8 mL)/water (1.2 mL) was degassed with nitrogen. [1,1'-bis(diphenylphosphino)ferrocene]dichloropalladium(II) (18.8 mg, 23 μmol) was then added and the resulting mixture was stirred at 90° C. under nitrogen for 2 hours. Upon completion, water and EtOAc were added. The aqueous layer was extracted 3 times with EtOAc. The combined organic layers were washed with brine, dried over Na₂SO₄, filtered and concentrated under reduced pressure. The residue was purified by flash chromatography on silica (5/5 hexanes/EtOAc to 100% EtOAc, then 9/1 to 5/5 EtOAc/MeOH with 1% of Et₃N) to give the title compound (126 mg, 69%).

Step 3: (cis)-4-(2-((S)-sec-butylamino)-5-(4-((4-methylpiperazin-1-yl)methyl)phenyl)pyrrolo[2,1-f][1,2,4]triazin-7-yl)-1-methylcyclohexanol and (trans)-4-(2-((S)-sec-butylamino)-5-(4-((4-methylpiperazin-1-yl)methyl)phenyl)pyrrolo[2,1-f][1,2,4]triazin-7-yl)-1-methylcyclohexanol To a solution of (S)-4-(2-(sec-butylamino)-5-(4-((4-methylpiperazin-1-yl)methyl)phenyl)pyrrolo[2,1-f][1,2,4]triazin-7-yl)cyclohexanone (86.0 mg, 181 μmol) in dry THF (3 mL) was added methyl lithium (200 μL, 320 μmol) under nitrogen at 0° C. The resulting mixture was stirred at 0° C. After 10 minutes, methyl lithium (100 μL, 160 μmol) were added. After 10 minutes, water and EtOAc were then added. The aqueous layer was extracted 3 times with EtOAc. The combined organic layers were washed with brine, dried over Na₂SO₄, filtered and concentrated under reduced pressure. The crude material was again treated with MeLi and worked up, as above. This process was carried out a third time. The residue was purified by prep HPLC with AmF/ACN. The two diastereoisomers were separated and lyophilized, leading to (cis)-4-(2-((S)-sec-butylamino)-5-(4-((4-methylpiperazin-1-yl)methyl)phenyl)pyrrolo[2,1-f][1,2,4]triazin-7-yl)-1-methylcyclohexanol (10 mg, 11%) and (trans)-4-(2-((S)-sec-butylamino)-5-(4-((4-methylpiperazin-1-yl)methyl)phenyl)pyrrolo[2,1-f][1,2,4]triazin-7-yl)-1-methylcyclohexanol (18 mg, 20%) as yellow solids.

Example 13: Synthesis of Compounds 204 and 205 (as shown in FIG. 1)

The mixture of diastereoisomers was obtained from intermediate T using general procedure 4 and 4-(4-(4,4,5,5-tetramethyl-1,3,2-dioxaborolan-2-yl)benzyl)morpholine. The diastereosiomers were separated by chiral HPLC using ChiralPak IB, 250 mm×4.6 mm ID, 5 μm with 7.5:2.5:90 MeOH:DCM:hexane (1 mL/min, 45 bars, 26° C., 20 min).

Example 14: Synthesis of Compounds 211 and 212 (as shown in FIG. 1)

Compounds 211 and 212 were synthesized using the procedure of Example 13 using racemic 4-methoxybutan-2-amine and the diastereomers separated on a chiral column.

Example 15: Synthesis of Compounds 156 and 157 (as shown in FIG. 1)

The mixture of diastereoisomers was obtained from intermediate E using general procedure 4 and racemic 4-(1-(4-(4,4,5,5-Tetramethyl-1,3,2-dioxaborolan-2-yl)phenyl)ethyl)morpholine. The diastereosiomers were separated by chiral HPLC using ChiralPak IA, 250 mm×4.6 mm ID, 5 μm with 2:16:82 MeOH:i-PrOH:hexane (0.8 mL/min, 45.5 bars, 26° C., 25 min).

Example 16: Synthesis of Compound 228 (as shown in FIG. 1)

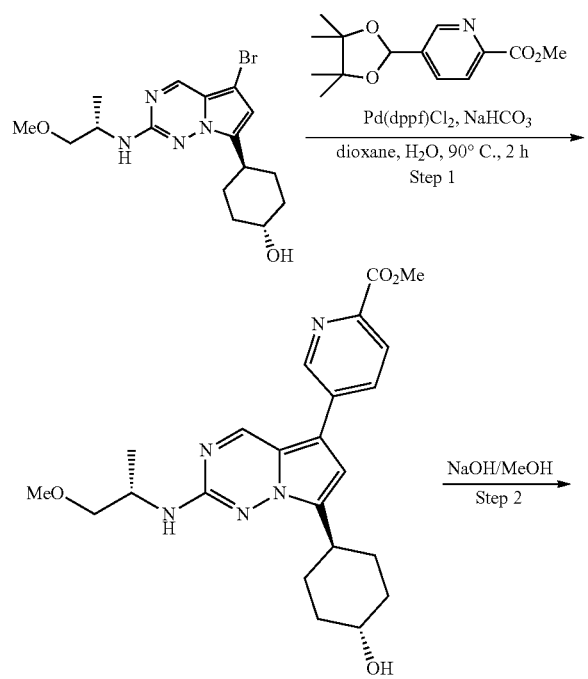

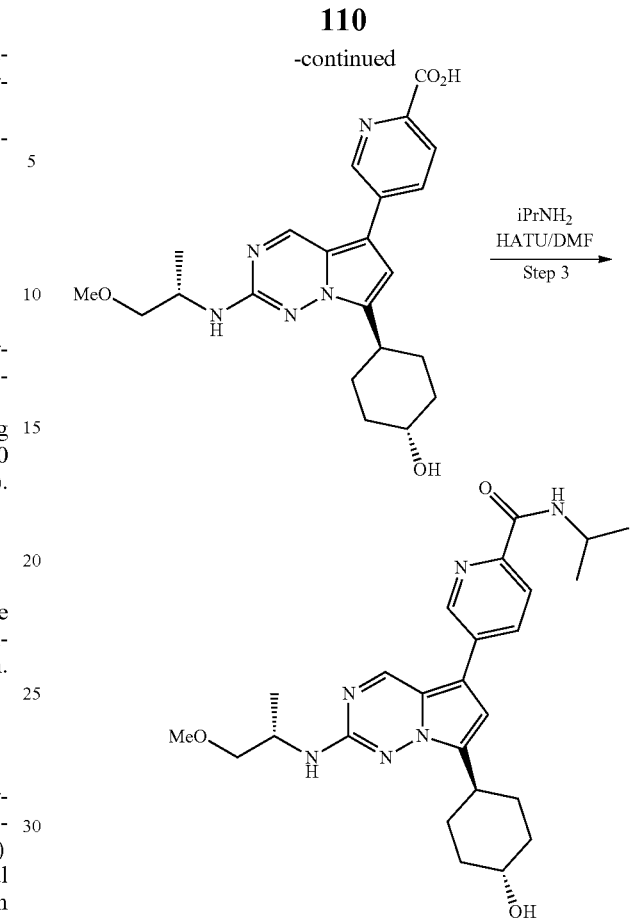

Step 1. Methyl 5-(7-((trans)-4-hydroxycyclohexyl)-2-(((S)-1-methoxypropan-2-yl)amino)pyrrolo[2,1-f][1,2,4]triazin-5-yl)picolinate A mixture of (trans)-4-(5-bromo-2-(((S)-1-methoxypropan-2-yl)amino)pyrrolo[2,1-f][1,2,4]triazin-7-yl)cyclohexan-1-ol (527 mg, 1.37 mmol), (6-(Methoxycarbonyl)pyridin-3-yl)boronic acid (1.06 g, 5.88 mmol) and sodium hydrogenocarbonate (137 μL, 3.52 mmol) in dioxane and $H_2O$ (2.11 mL) was degassed by bubbling $N_2$ through the mixture for 5 min. The mixture was then treated with $PdCl_2$dppf (102 mg, 137 μmol) and heated at 80° C. After heating for 1 h the reaction was treated with 0.5 equiv boronate, and 1 equiv ($NaHCO_3$). The reaction was allowed to heat overnight. The mixture was cooled to RT and then poured into $H_2O$, diluted with EtOAc, and filtered through Celite®. The layers were separated and the aq. phase was extracted with EtOAc (×3). The combined organic layers were washed ($H_2O$, brine), dried ($Na_2SO_4$) and concentrated in vacuo. The residue was purified by column chromatography (Combiflash, 10 g column, 0 to 30% IPA in DCM). we obtained a yellow-orange foam (142 mg).

Step 2: 5-(7-((trans)-4-hydroxycyclohexyl)-2-(((S)-1-methoxypropan-2-yl)amino)pyrrolo[2,1-f][1,2,4]triazin-5-yl)picolinic acid A mixture of methyl 5-(7-((trans)-4-hydroxycyclohexyl)-2-(((S)-1-methoxypropan-2-yl)amino)pyrrolo[2,1-f][1,2,4]triazin-5-yl)picolinate (135 mg, 307 μmol) in MeOH (4 mL) at RT was treated with NaOH (2 mL, 2 mmol) and the mixture was allowed to stir at RT for 30 min. A further 0.5 mL of NaOH was added and stirring continued for 30 min. The mixture was acidified with HCl (6M) and concentrated to dryness (evaporated from toluene×2). The residue was used "as is" in the next experiment.

Step 3: 5-(7-((1r,4S)-4-hydroxycyclohexyl)-2-(((S)-1-methoxypropan-2-yl)amino)pyrrolo[2,1-f][1,2,4]triazin-5-yl)-N-isopropylpicolinamide The crude product obtained above was suspended in DMF, treated with Hunig's base (100 µL) and separated into three 4 mL vials. The reactions were treated with the amines (isopropylamine 30 mg), followed by HATU (154 mg, 0.40 mmol). After stirring at RT for 30 min, the reactions were diluted with 1120 and extracted with EtOAc (×3). The combined organic layers were washed (H₂O, brine), dried (Na₂SO₄) and concentrated in vacuo. The residue was purified by column chromatography (Combiflash, 10 g column, DCM-IPA) to give the title compound as a yellow solid (35.8 mg, 76%).

Example 17: Synthesis of Compound 223 (as shown in FIG. 1)

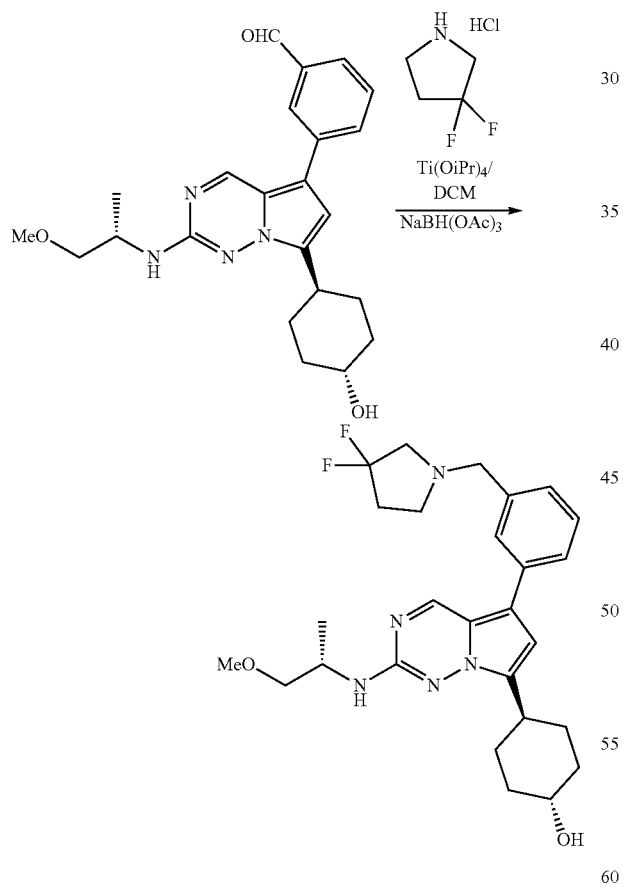

The starting material, (7-(trans)-4-hydroxycyclohexyl)-2-(((S)-1-methoxypropan-2-yl)amino)pyrrolo[2,1-f][1,2,4]triazin-5-yl)benzaldehyde was prepared according to step 1 Example 16, using 3(4,4,5,5-tetramethyl-1,3,2-dioxaborolan-2yl)benzadehyde as the coupling partner. The aldehyde so obtained (70.0 mg, 171 mmol) was dissolved in dry DCM (3 mL) with 3,3-difluoropyrrolidine hydrochloride (50.2 mg, 343 µmol) and then Titanium(IV) isopropoxide (254 µL, 85 µmol) was added. The resulting mixture was stirred for 1.5 hours before the addition of NaBH(OAc)₃ (93.2 mg, 428 µmol). The reaction was then stirred 10 more hours. The reaction was quenched by adding MeOH (1 mL) and then silica powder (about 4 mL) and stirred for 30 minutes before being concentrated to dryness in vacuo. The material was purified by flash chromatography (20 g) silica column eluting with DCM:20% IPA in DCM and then by reverse phase on a 12 g C-18 column eluting with solvent A:=: 10 M ammonium formate (AMF) and solvent B=ACN. We obtained the title compound as a fluffy solid (35.2 mg, 41%).

Example 18: Synthesis of Compound 135 (as shown in FIG. 1)

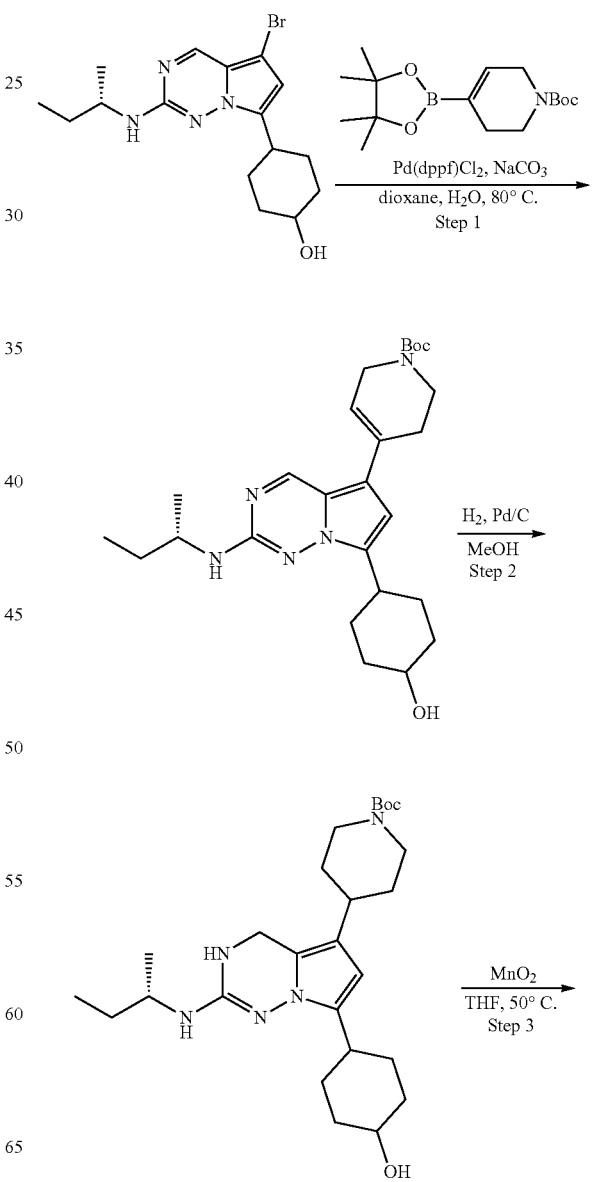

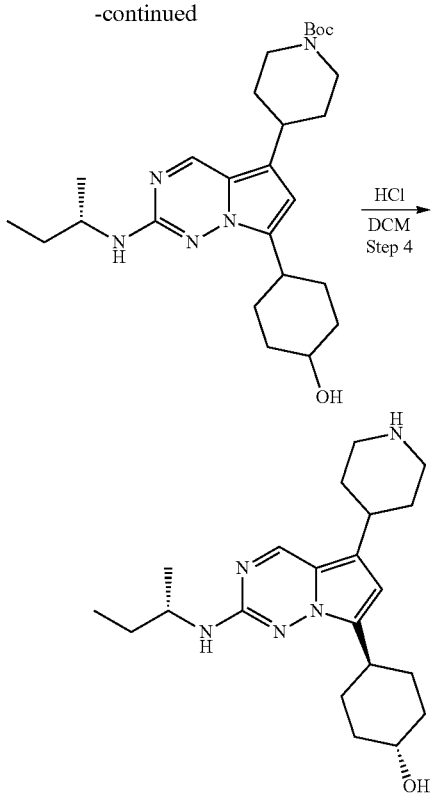

Step 1: (S)-tert-butyl 4-(2-(sec-butylamino)-7-(4-hydroxycyclohexyl)pyrrolo[2,1-f][1,2,4]triazin-5-yl)-5,6-dihydropyridine-1(2H)-carboxylate (S)-4-(5-bromo-2-(sec-butylamino)pyrrolo[2,1-f][1,2,4]triazin-7-yl)cyclohexanol (383 mg, 1.04 mmol), tert-Butyl 4-(4,4,5,5-tetramethyl-1,3,2-dioxaborolan-2-yl)-5,6-dihydropyridine-1(2H)-carboxylate (461 mg, 1.46 mmol), Pd(dppf)Cl$_2$ (77.4 mg, 0.104 mmol) and Na$_2$CO$_3$ (332 mg, 3.12 mmol) were all added to a microwave vial under nitrogen. Then a mixture of degassed (by sparging) dioxane (14.4 mL) and H$_2$O (4.79 mL) was added to the vial and then the mixture was stirred at 80° C. overnight under N$_2$ atm. Upon completion, the reaction mixture was diluted with DCM (100 mL) and water (100 mL) and the layers separated. The aq. phase was extracted with DCM (100 mL×3) and the combined organic layers were dried over Na$_2$SO$_4$, filtered and concentrated under vacuo. The residue was purified by flash chromatography using 0-60% EtOAc in hexanes to give 410 mg of the desired compound in 84% yield.

Step 2: (S)-tert-butyl 4-(2-(sec-butylamino)-7-(4-hydroxycyclohexyl)-3,4-dihydropyrrolo[2,1-f][1,2,4]triazin-5-yl)piperidine-1-carboxylate (S)-tert-butyl-4-(2-(sec-butylamino)-7-(4-hydroxycyclohexyl)pyrrolo[2,1-f][1,2,4]triazin-5-yl)-5,6-dihydropyridine-1(2H)-carboxylate (320 mg, 0.681 mmol) was dissolved in MeOH (16.5 mL). Then, Pd/C (10 wt % loading, 145 mg) was added to the reaction. The reaction was then degassed and put under 1 atm of hydrogen. This was cycled several times and then, the reaction was left to stir under 1 atm of hydrogen till LC-MS showed complete conversion to the desired product. The reaction was then filtered over Celite® and concentrated in vacuo. The residue was purified using 0-100% of 1:1 mixture of DCM:hexanes with 10% isopropanol in 1:1 mixture of DCM:hexanes to give 120 mg of the desired product in 37% yield.

Step 3: (S)-tert-butyl 4-(2-(sec-butylamino)-7-(4-hydroxycyclohexyl)pyrrolo[2,1-f][1,2,4]triazin-5-yl)piperidine-1-carboxylate (S)-tert-butyl 4-(2-(sec-butylamino)-7-(4-hydroxycyclohexyl)-3,4-dihydropyrrolo[2,1-f][1,2,4]triazin-5-yl)piperidine-1-carboxylate (120 mg, 0.253 mmol) was dissolved in THF (10.0 mL). Activated manganese (IV) oxide (100 mg, 1.01 mmol) was added and then reaction was stirred at 50° C. till full conversion was observed. Then the reaction was cooled and filtered over Celite® and concentrated in vacuo. This gave 108 mg of the desired product in 90% yield. It was then used crude in the next step.

Step 4: (trans)-4-(2-((S)-sec-butylamino)-5-(piperidin-4-yl)pyrrolo[2,1-f][1,2,4]triazin-7-yl)cyclohexanol (S)-tert-butyl 4-(2-(sec-butylamino)-7-(4-hydroxycyclohexyl)pyrrolo[2,1-f][1,2,4]triazin-5-yl)piperidine-1-carboxylate (40 mg, 0.0848 mmol) was dissolved in DCM (5.0 mL) and then a 4 M solution of HCl in dioxane was added. The reaction was run till full conversion was observed and then concentrated in vacuo. After, it was concentrated and then the residue from this reaction was purified by prep-HPLC (column: XBridge Prep C18 OBD 30×50 mm, 5 μm; mobile phase: 10 mM AMF buffer-MeCN; B %: 10%-30%, 13 min). The eluent was concentrated to remove organic solvent and the residual aqueous solution was lyophilized to give 6.5 mg of (trans)-4-(2-((S)-sec-butylamino)-5-(piperidin-4-yl)pyrrolo[2,1-f][1,2,4]triazin-7-yl)cyclohexanol in 21% yield.

Example 19: Synthesis of Compound 136 (as shown in FIG. 1)

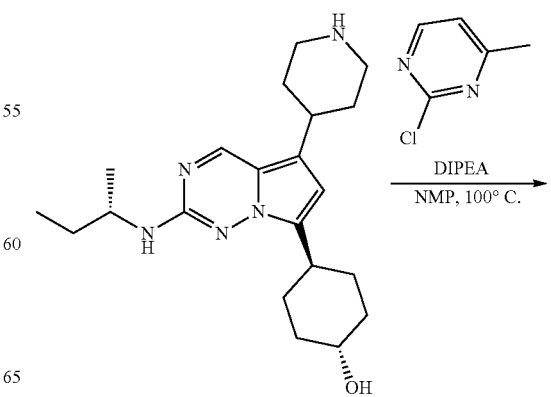

-continued

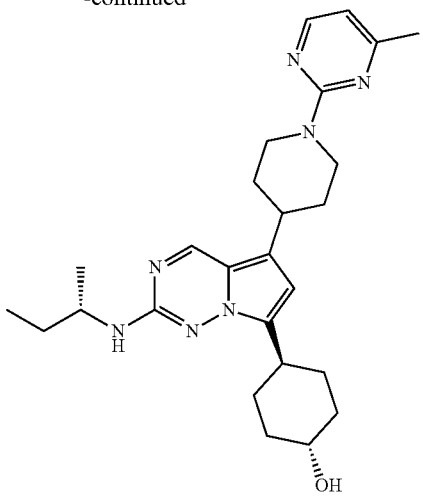

(trans)-4-(2-((S)-sec-butylamino)-5-(piperidin-4-yl)pyrrolo[2,1-f][1,2,4]triazin-7-yl)cyclohexanol (44 mg, 0.118 mmol) was dissolved in NMP (1.0 mL) in a microwave vial then 2-chloro-4-methylpyrimidine (15.2 mg, 0.118 mmol) and DIPEA (0.025 mL, 0.142 mmol) was added. The reaction was then heated to 100° C. overnight. The reaction was then allowed to cool and then it was purified by reverse phase chromatography using 0-100% MeCN in H$_2$O (with 10 mM AMF). The organic solvent was removed under vacuum, and the aqueous phase was lyophilized to give 26.7 mg of (trans)-4-(2-((S)-sec-butylamino)-5-(1-(4-methylpyrimidin-2-yl)piperidin-4-yl)pyrrolo[2,1-f][1,2,4]triazin-7-yl)cyclohexanol in 49% yield.

Example 20: Synthesis of Compound 150-1 (as shown in FIG. 1)

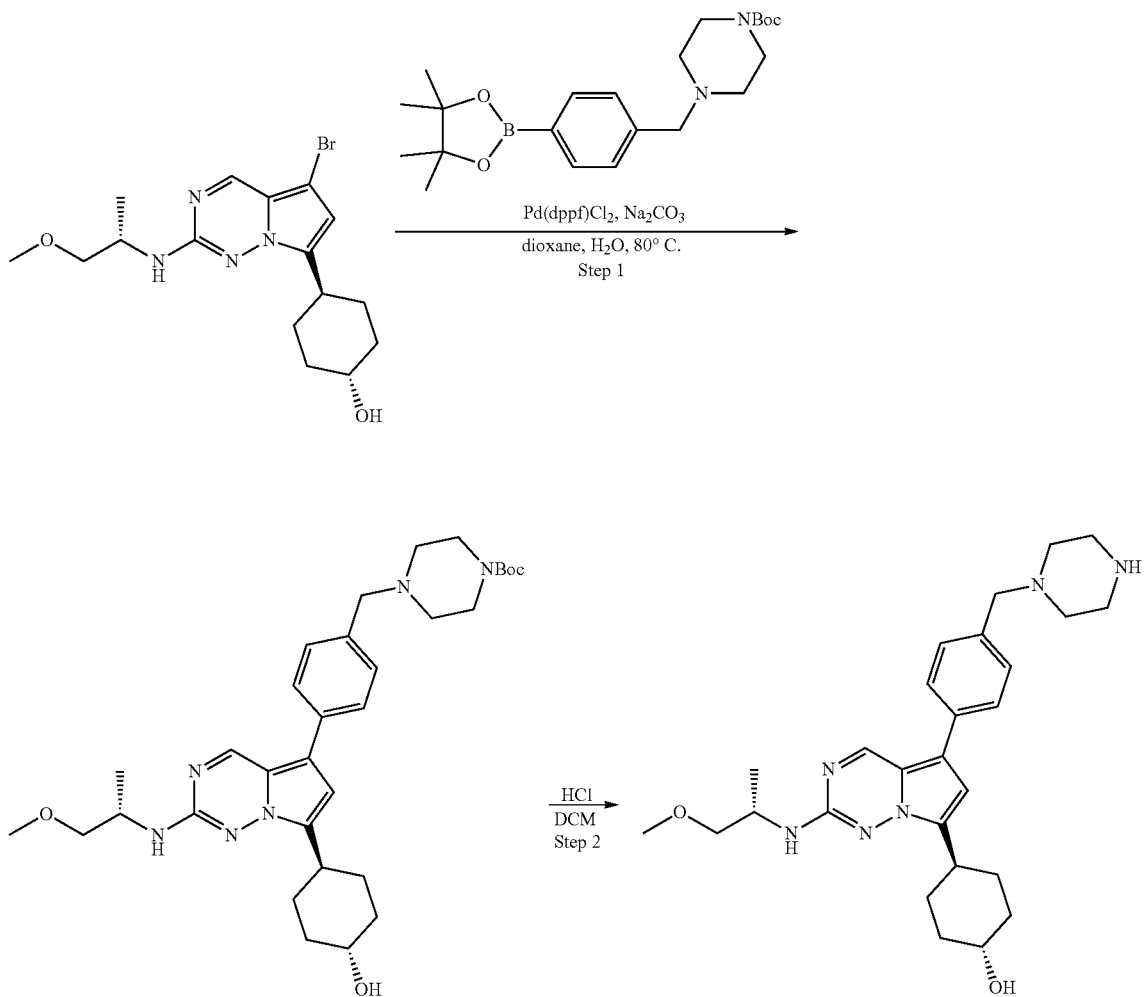

117

Step 1: tert-butyl 4-(4-(7-((trans)-4-hydroxycyclohexyl)-2-(((S)-1-methoxypropan-2-yl)amino)pyrrolo[2,1-f][1,2,4]triazin-5-yl)benzyl)piperazine-1-carboxylate (trans)-4-(5-bromo-2-(((S)-1-methoxypropan-2-yl)amino)pyrrolo[2,1-f][1,2,4]triazin-7-yl)cyclohexanol (250 mg, 0.652 mmol), tert-Butyl 4-(4-(4,4,5,5-tetramethyl-1,3,2-dioxaborolan-2-yl)benzyl)piperazine-1-carboxylate (359 mg, 0.848 mmol), Pd(dppf)Cl$_2$ (24.2 mg, 0.0326 mmol) and Na$_2$CO$_3$ (207 mg, 1.96 mmol) were all added to a microwave vial under nitrogen. Then a mixture of degassed (by sparging) dioxane (6.18 mL) and water (1.95 mL) was added to the vial and then the mixture was stirred at 80° C. overnight under N$_2$ atm. Upon completion, the reaction mixture was diluted with DCM (100 mL) and extracted with DCM (100 mL×3) and water (100 mL). The combined organic layers were dried over Na$_2$SO$_4$, filtered and concentrated under vacuum. The residue from this reaction was purified by flash chromatography using 0-50% MeOH in DCM to give 223 mg the desired product in 59% yield.

Step 2: (trans)-4-(2-(((S)-1-methoxypropan-2-yl)amino)-5-(4-(piperazin-1-ylmethyl)phenyl)pyrrolo[2,1-f][1,2,4]triazin-7-yl)cyclohexanol tert-butyl 4-(4-(7-((trans)-4-hydroxycyclohexyl)-2-(((S)-1-methoxypropan-2-yl)amino)pyrrolo[2,1-f][1,2,4]triazin-5-yl)benzyl)piperazine-1-carboxylate (223 mg, 0.385 mmol) was dissolved in DCM (15 ml). Then a 4 M HCl in dioxane (4 mL, large excess) was added to the reaction and then the reaction was stirred till complete consumption of starting material was observed. It was then concentrated in vacuo. Then it was dissolved in 10 mL of EtOH and a large excess of K$_2$CO$_3$ was added. This was stirred till pH=7 was achieved then the solid was filtered and then organic layer was concentrated to give 173 mg of (trans)-4-(2-(((S)-1-methoxypropan-2-yl)amino)-5-(4-(piperazin-1-ylmethyl)phenyl)pyrrolo[2,1-f][1,2,4]triazin-7-yl)cyclohexanol in 94% yield of a yellow solid. The structure and purity of the title compounds were confirmed by $^1$H NMR and LCMS.

Example 21: Synthesis of Compound 150 (as shown in FIG. 1)

118

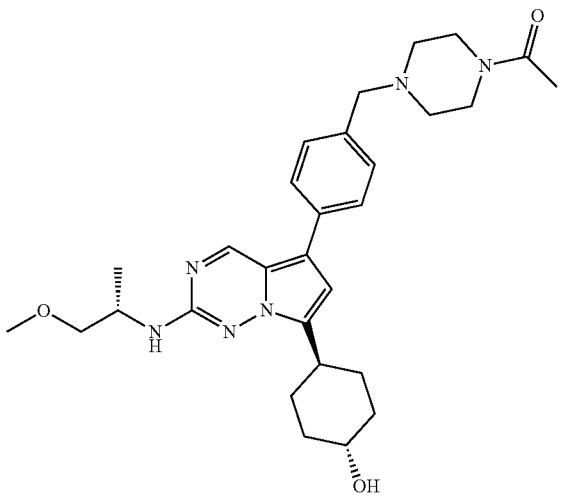

Acetic acid (0.07 mL, 0.125 mmol), HATU (73.7 mg, 0.188 mmol) and DIPEA (0.09 mL, 0.501 mmol) was dissolved in DMF (6.0 mL) and stirred for 30 min. (trans)-4-(2-(((S)-1-methoxypropan-2-yl)amino)-5-(4-(piperazin-1-ylmethyl)phenyl)pyrrolo[2,1-f][1,2,4]triazin-7-yl)cyclohexanol (60 mg, 0.125 mmol) was added to the mixture and this was stirred overnight at RT. Full conversion was observed and then this mixture was directly placed onto a 30 gram C18 column and purified using 0-100% MeCN in a 10 mM ammonium bicarbonate (AmB) buffer. The organic solvent was removed and the aqueous phase was lyophilized to give 29.7 mg of (trans)-4-(2-(((S)-1-methoxypropan-2-yl)amino)-5-(4-(piperazin-1-ylmethyl)phenyl)pyrrolo[2,1-f][1,2,4]triazin-7-yl)cyclohexanol in 46% yield. The structure and purity of the title compounds were confirmed by $^1$H NMR and LCMS.

Example 22: Synthesis of Compound 154 (as shown in FIG. 1)

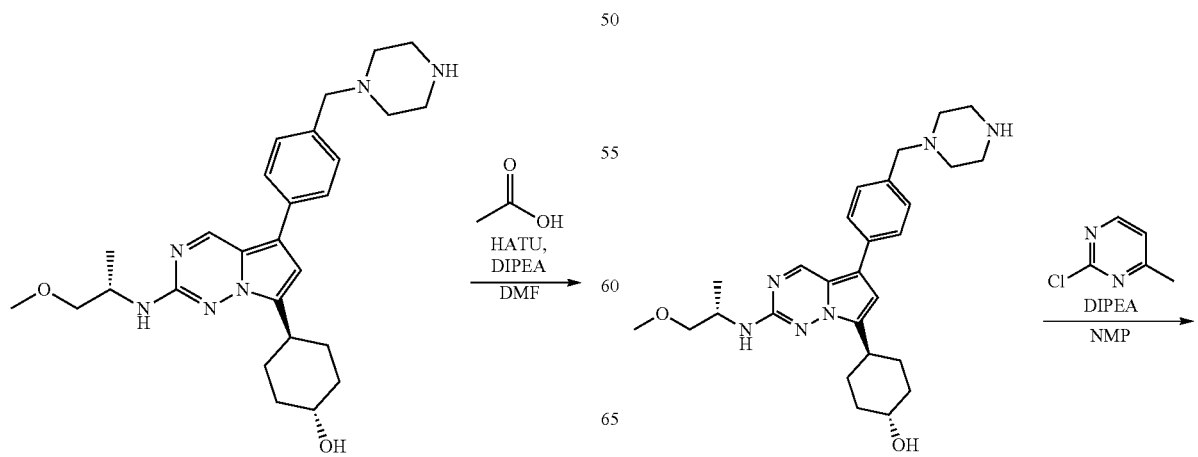

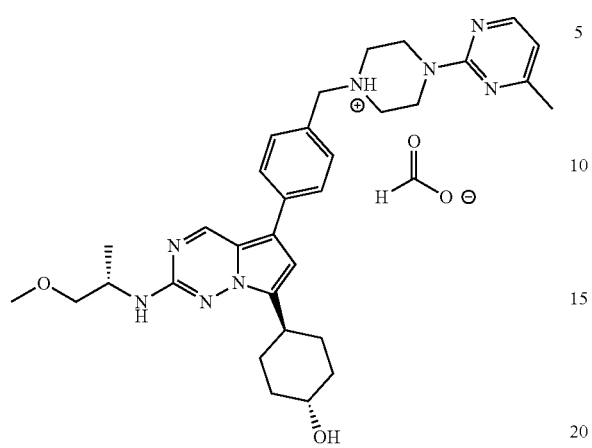

(trans)-4-(2-(((S)-1-methoxypropan-2-yl)amino)-5-(4-(piperazin-1-ylmethyl)phenyl)pyrrolo[2,1-f][1,2,4]triazin-7-yl)cyclohexanol (25 mg, 0.0522 mmol), 2-Cholo-4-methylpyrimidine (6.71 mg, 0.0522 mmol) and DIPEA (0.01 mL, 0.0627 mmol) was dissolved in NMP (1.0 mL). This was heated to 100° C. overnight. Then, full conversion was observed to desired product. Then the mixture was placed directly on a reverse phase column and the desired product was purified using 0-100% MeCN in a 10 mM AMF buffer. The organic solvent was removed under vacuo. Then, the aqueous layer was lyophilized to give 5.3 mg of (trans)-4-(2-(((S)-1-methoxypropan-2-yl)amino)-5-(4-((4-(4-methylpyrimidin-2-yl)piperazin-1-yl)methyl)phenyl)pyrrolo[2,1-f][1,2,4]triazin-7-yl)cyclohexanol as a formate salt in 18% yield. The structure and purity of the title compounds were confirmed by $^1$H NMR and LCMS.

Example 23: Synthesis of Compound 163 (as shown in FIG. 1)

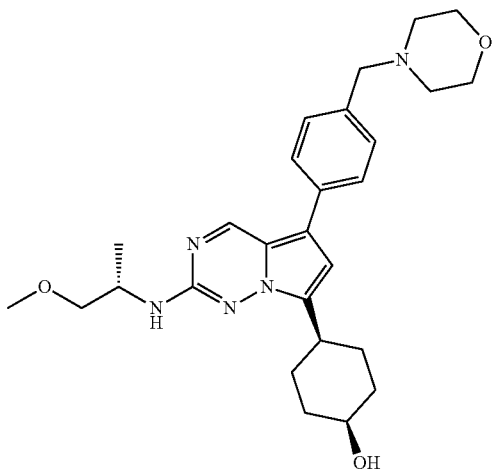

(cis)-4-(5-bromo-2-(((S)-1-methoxypropan-2-yl)amino)pyrrolo[2,1-f][1,2,4]triazin-7-yl)cyclohexanol (70 mg, 0.183 mmol), 4-(Morpholinomethyl)phenylboronic acid (56.5 mg, 0.256 mmol), Pd(dppf)Cl$_2$(6.77 mg, 0.00913 mmol) and Na$_2$CO$_3$ (58.1 mg, 0.548 mmol) were all added to sealed tube under nitrogen. Then a mixture of degassed (by sparging) dioxane (2.63 mL) and water (0.875 mL) was added to the sealed tube and then the mixture was stirred at 80° C. for overnight under N$_2$ atm. Upon completion, the reaction mixture was diluted with DCM (30 mL) and extracted with DCM (30 mL×3) and water (30 mL). The combined organic layers were dried over Na$_2$SO$_4$, filtered and concentrated under vacuum. The residue from this reaction was purified by normal phase chromatography using 0-100% iPrOH in DCM. The pure fractions were concentrated to give 32.1 mg of (cis)-4-(2-(((S)-1-methoxypropan-2-yl)amino)-5-(4-(morpholinomethyl)phenyl)pyrrolo[2,1-f][1,2,4]triazin-7-yl)cyclohexanol in 37% yield. The structure and purity of the title compounds were confirmed by $^1$H NMR and LCMS.

Example 24: Synthesis of Compounds 175 and 176 (as shown in FIG. 1)

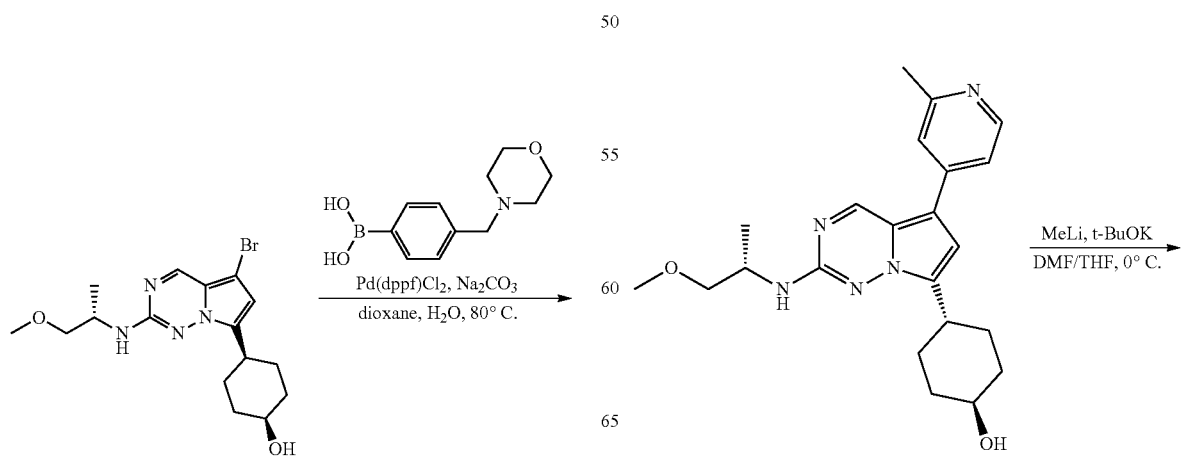

-continued

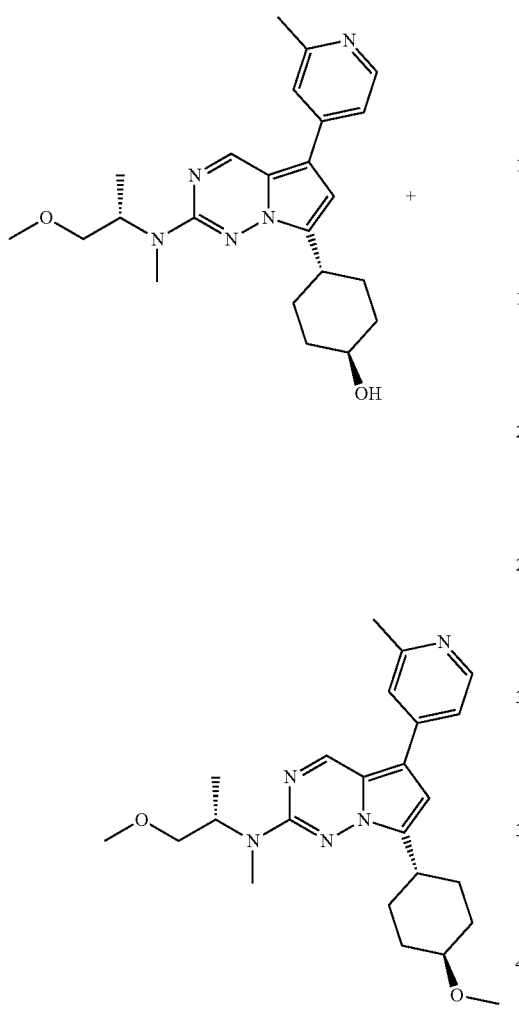

Example 25: Synthesis of Compound 187 (as shown in FIG. 1)

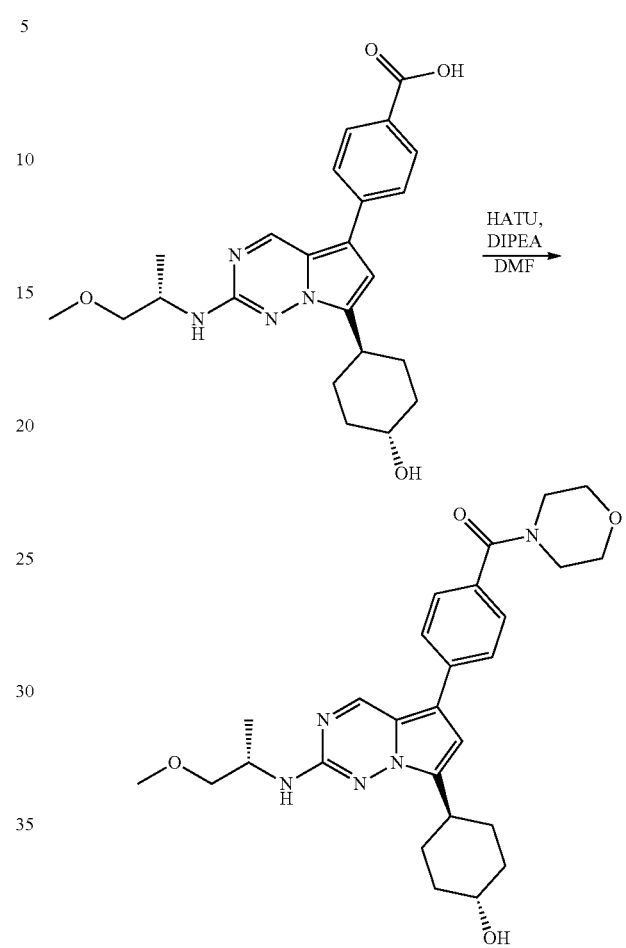

To a solution of (trans)-4-(2-(((S)-1-methoxypropan-2-yl)amino)-5-(2-methylpyridin-4-yl)pyrrolo[2,1-f][1,2,4]triazin-7-yl)cyclohexanol (40.0 mg, 101 μmol) in DMF (800 μL) was added potassium tert-butoxide (1M in THF) (253 μL, 253 μmol) at RT under nitrogen. The mixture was stirred for 10 min. Iodomethane (6.30 μL, 101 μmol) was then added at 0° C. and the resulting mixture mixture was stirred at 0° C. for 2 hours. Upon completion, water and EtOAc were added. The aqueous layer was extracted three times with EtOAc. The combined organic layers were dried over $Na_2SO_4$, filtered and concentrated under reduced pressure. The residue was purified by flash chromatography on silica with DCM/MeOH to give (trans)-4-(2-(((S)-1-methoxypropan-2-yl)(methyl)amino)-5-(2-methylpyridin-4-yl)pyrrolo[2,1-f][1,2,4]triazin-7-yl)cyclohexanol (14 mg, 34%) and 7-((trans)-4-methoxycyclohexyl)-N-((S)-1-methoxypropan-2-yl)-N-methyl-5-(2-methylpyridin-4-yl)pyrrolo[2,1-f][1,2,4]triazin-2-amine (10 mg, 24%) as yellow solids.

The starting material, 4-(7-((trans)-4-hydroxycyclohexyl)-2-(((S)-1-methoxypropan-2-yl)amino)pyrrolo[2,1-f][1,2,4]triazin-5-yl)benzoic acid was prepared according to step 1 of Example 8, using 4-Carboxylphenylboronic acid pinacol ester as the coupling partner. The benzoic acid so obtained, (80.0 mg, 0.188 mmol), HATU (111 mg, 0.283 mmol) and DIPEA (0.133 mL, 0.754 mmol) was dissolved in DMF (10.0 mL) and stirred for 30 min. Then morpholine (0.02 mL, 0.226 mmol) was added to the mixture and this was stirred overnight at RT. Full conversion was observed and then this mixture was concentrated in vacuo and placed directly onto a 25 g silica column and purified using 0-100% iPrOH in DCM. The fractions containing the desired product were concentrated. The product was contaminated with DIPEA. The product was then re-purified (loaded using a few drops of TFA) using a 0-100% MeCN in a 10 mM ammonium formate buffer. The fractions containing the desired product were combined and made basic using solid potassium carbonate. Then the mixture was extracted several times with DCM till no more product was found in the aqueous layer. The organic solvent was removed and then the product was lyophilized to give 25.4 mg of (4-(7-((trans)-4-hydroxycyclohexyl)-2-(((S)-1-methoxypropan-2-yl)amino)pyrrolo[2,1-f][1,2,4]triazin-5-yl)phenyl)(morpholino)methanone in 27% yield.

Example 26: Synthesis of Compound 129 (as shown in FIG. 1)

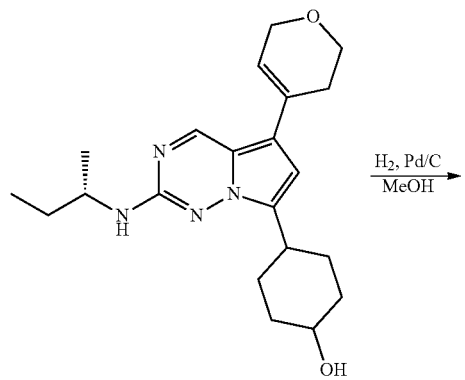

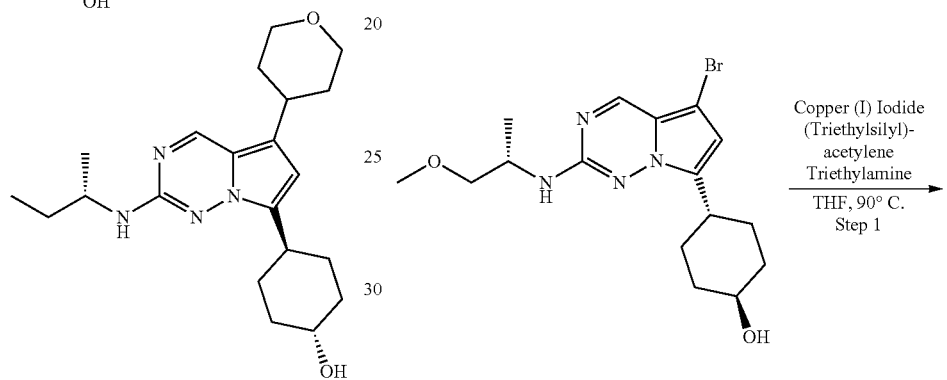

The starting material, (S)-4-(2-(sec-butylamino)-5-(3,6-dihydro-2H-pyran-4-yl)pyrrolo[2,1-f][1,2,4]triazin-7-yl)cyclohexanol was prepared according to step 1 of Example 10, using 3,6-Dihydro-2H-pyran-4-boronic acid pinacol ester as the coupling partner. Then, (S)-4-(2-(sec-butylamino)-5-(3,6-dihydro-2H-pyran-4-yl)pyrrolo[2,1-f][1,2,4]triazin-7-yl)cyclohexanol (80.0 mg, 0.216 mmol), Pd/C (46 mg, 10% wt on carbon) were dissolved in MeOH (5.22 mL). Then, the mixture was degassed and put under 1 atm of hydrogen several times. It was left to stir under 1 atm of hydrogen till complete conversion to the desired product was observed by LC-MS. It was then filtered over Celite® and concentrated in vacuo. The residue from this reaction was purified by prep-HPLC (column: XBridge Prep C18 OBD 30×50 mm, 5 μm; mobile phase: 10 mM AMF buffer-MeCN; B %: 35%-45%, 13 min). The eluent was concentrated to remove organic solvent and the residual aqueous solution was lyophilized to give 18.4 mg of (trans)-4-(2-((S)-sec-butylamino)-5-(tetrahydro-2H-pyran-4-yl)pyrrolo[2,1-f][1,2,4]triazin-7-yl)cyclohexanol in 23% yield. The structure and purity of the title compounds were confirmed by $^1$H NMR and LCMS.

Example 27: Synthesis of Compound 229 (as Shown in FIG. 1)

A solution of cis-4-(5-bromo-2-(((S)-1-methoxypropan-2-yl)amino)pyrrolo[2,1-f][1,2,4]triazin-7-yl)cyclohexan-1-ol (350 mg, 913 μmol) and PPh$_3$ (363 mg, 1.37 mmol) in 2-Me-THF (4.67 mL) was cooled to OC and treated with N,N-Diisopropylethylamine (240 μL, 1.37 mmol) followed by diisopropyl azodicarboxylate (DIAD; 275 μL, 1.37 mmol). After stirring for 45 min, the mixture was treated with diphenoxyphosphoryl azide (DPPA 304 μL, 1.37 mmol) and allowed to warm to RT while stirring overnight. Triphenylphosphine (363 mg, 1.37 mmol) was added and the mixture allowed stir at RT overnight. The mixture was then treated with H$_2$O (200 μL) and was allowed to stir at 50° C. overnight. The reaction was concentrated and the residue was purified by column chromatography (silica gel, 25 g column, 0 to 30% MeOH in DCM). We obtained a yellow solid 127 mg.

Example 28: Synthesis of Compounds 248 and 250 (as shown in FIG. 1)

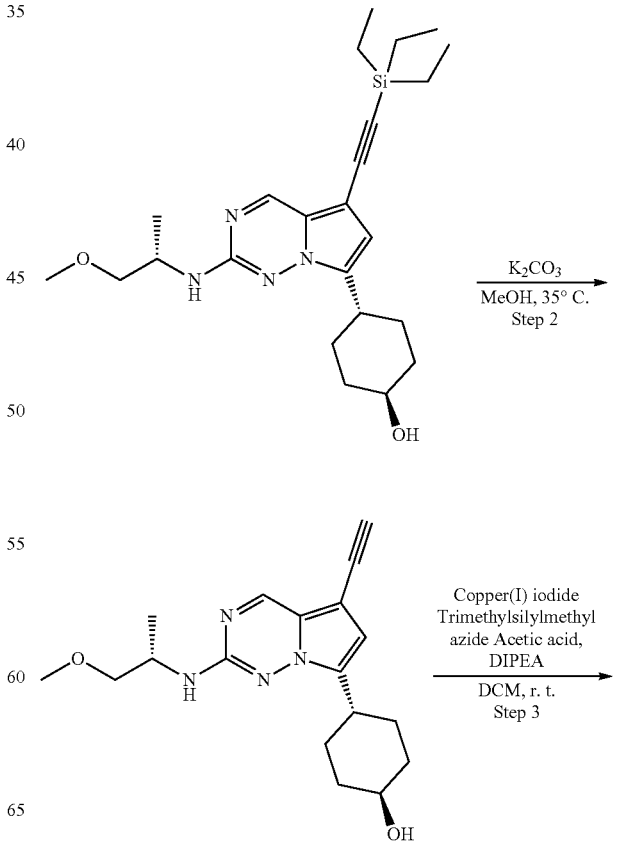

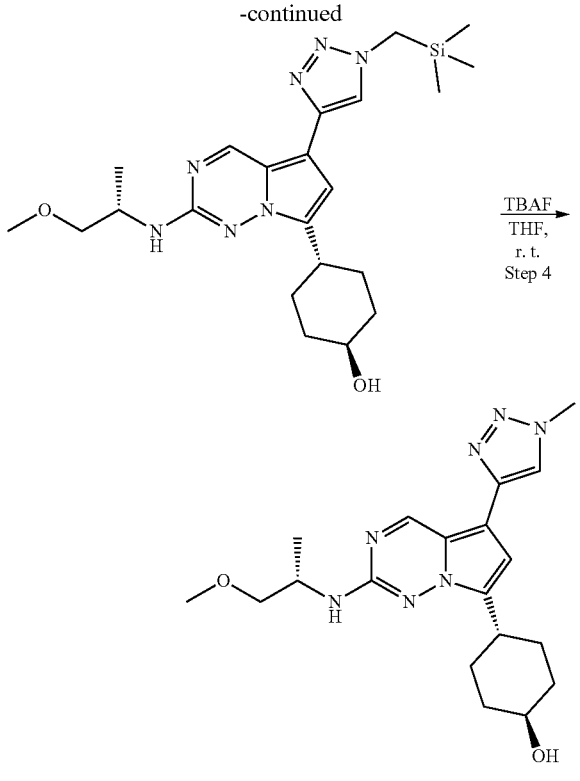

Step 1: ((trans)-4-(2-(((S)-1-methoxypropan-2-yl) amino)-5-((triethylsilyl)ethynyl)pyrrolo [2,1-f][1,2,4]triazin-7-yl)cyclohexanol In a flame dried and inert gas purged microwave vial was added (trans)-4-(5-bromo-2-(((S)-1-methoxypropan-2-yl) amino)pyrrolo[2,1-f][1,2,4]triazin-7-yl)cyclohexanol (60.0 mg, 157 µmol) and TEA (1 mL) and THF (1 mL). The solution was purged with $N_2$ under sonication for 8 minutes. Then the (Triethylsilyl)acetylene (58.1 µL, 313 µmol) was added, followed by 1,1-bis(diphenylphosphino)ferrocene-palladium dichloride (11.6 mg, 15.7 µmol) and copper(I) iodide (6.08 mg, 31.3 µmol). Lastly the microwave vial was capped and again, the solution was purged with inert gas under sonication for 8 minutes. The vial was placed in oil bath and heated at 90° C. for 15 hours. Upon completion, the reaction mixture was diluted with EtOAc (30 mL) and water 30 mL) and then extracted with EtOAc (30 mL×3). The organic layers were combined, washed with sat $NaHCO_3$(30 mL), brine (30 mL×2), dried over anhydrous $MgSO_4$, filtered and concentrated. The crude residue was purified on a 20 g silica column eluting with (A) DCM and (B) 20%, MeOH in DCM. Title compound obtained as a dark yellow oil (63.0 mg, 91%).

Step 2: (trans)-4-(5-ethynyl-2-(((S)-1-methoxypropan-2-yl)amino)pyrrolo[2,1-f][1,2,4]triazin-7-yl)cyclohexanol ((trans)-4-(2-(((S)-1-methoxypropan-2-yl)amino)-5-((triethylsilyl) ethynyl) pyrrolo[2,1-f][1,2,4] triazin-7-yl) cyclohexanol (63.00 mg, 142 µmol) was dissolved in MeOH (3.00 mL) and then finely grinded $K_2CO_3$ (39.3 mg, 285 µmol) was added. The heterogeneous mixture was gently heated to 35° C. for 1.5 hour. Upon completion, the solvent was removed in vacuo and the remaining paste was partitioned in a separatory funnel with water (30 mL) and EtOAc (30 mL). The aqueous layer was extracted with EtOAc (30 mL×3). The organic layers were combined, washed with water (30 mL), brine (30 mL×2), dried over anhydrous $MgSO_4$, filtered and concentrated in vacuo to give the tittle compound (43 mg, crude) as a beige solid.

Step 3: (trans)-4-(2-(((S)-1-methoxypropan-2-yl) amino)-5-(1-((trimethylsilyl)methyl)-1H-1,2,3-triazol-4-yl)pyrrolo[2,1-f][1,2,4]triazin-7-yl)cyclohexanol To a mixture of copper(i) iodide copper(i) iodide (1.25 mg, 6.55 µmol), DIPEA (N,N-diisopropyl ethylamine; 2.29 µL, 13.1 µmol) and acetic acid (0.750 µL, 13.1 µmol) in DCM (1.0 mL) was added (trans)-4-(5-ethynyl-2-(((S)-1-methoxypropan-2-yl) amino)pyrrolo[2,1-f][1,2,4] Triazin-7-yl)cyclohexanol (43.0 mg, 131 µmol) and trimethylsilylmethyl azide (25.3 µL, 170 µmol) at RT. The resultant mixture was stirred for 15 hours. Upon completion the reaction mixture was concentrated in vacuo. The product was purified on a 20 g silica column eluting with 5 to 10% Hexane: MTBE to afford title compound as a white solid (42.0 mg, 70% yield).

Step 4: (trans)-4-(2-(((S)-1-methoxypropan-2-yl) amino)-5-(1-methyl-1H-1,2,3-triazol-4-yl)pyrrolo[2,1-f][1,2,4]triazin-7-yl)cyclohexanol Product (trans)-4-(2-(((S)-1-methoxypropan-2-yl) amino)-5-(1-((trimethylsilyl)methyl)-1H-1,2,3-triazol-4-yl) pyrrolo[2,1-f][1,2,4]triazin-7-yl)cyclohexanol (42.0 mg, 91 µmol) was dissolved in THF (2 mL) followed by the addition of TBAF [1N THF] (184 µL, 184 µmol). Upon completion, the solvent was removed in vacuo and the remaining crude was partitioned in a separatory funnel with water (30 mL) and EtOAc (30 mL). The aqueous layer was extracted with EtOAc (30 mL×3). The organic layers were combined, washed with water (30 mL), brine (30 mL×2), dried over anhydrous $MgSO_4$, filtered and concentrated in vacuo. The crude product was purified on a 30 g C-18 column eluting with (A) water 10 µmol AMF buffer and (B) ACN. The eluent was concentrated to remove organic solvent and then lyophilized to give title compound (35 mg, 40% yield) as a light yellow solid.

Example 29: Synthesis of Compound 192 (as shown in FIG. 1)

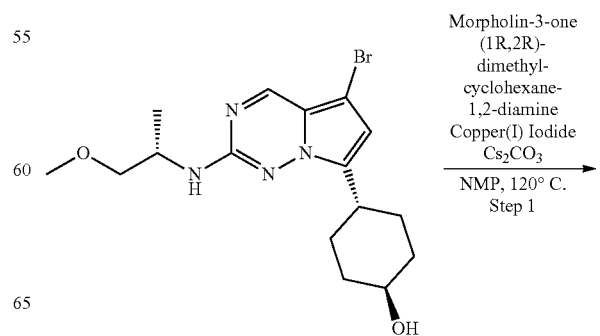

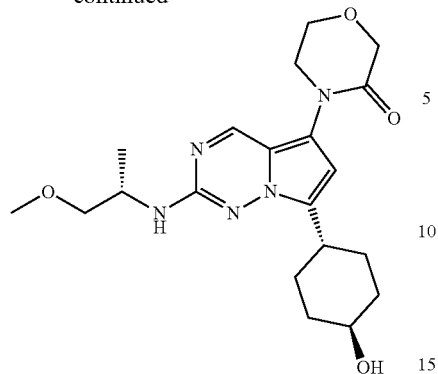

In a flame dried microwave vial and purged with inert gas was quickly introduced the Cs₂CO₃ (128 mg, 391 μmol) and the (trans)-4-(5-bromo-2-(((S)-1-methoxypropan-2-yl) amino)pyrrolo[2,1-f][1,2,4]triazin-7-yl)cyclohexanol (50.0 mg, 130 μmol) and the amide morpholin-3-one (40.8 mg, 391 μmol). The dry NMP (1.50 mL) was added though the septum followed by the (1R,2R)-dimethylcyclohexane-1,2-diamineamine (10.6 μL, 65.2 μmol). The resulting mixture was degassed for 8 minutes under sonication and then the copper(I) iodide (5.07 mg, 26.1 μmol) was added. The reaction heated for 15 hours at 120° C. Upon completion, the solvent was removed in vacuo and the remaining crude was partitioned in a separatory funnel with water (30 mL) and EtOAc (30 mL). The aqueous layer was extracted with EtOAc (30 mL×3). The organic layers were combined, washed with water (30 mL), brine (30 mL×2), dried over anhydrous MgSO₄, filtered and concentrated in vacuo. The crude product was purified on a 30 g C-18 column eluting with water containing 10 mM AMF and ACN. The eluent was concentrated to remove organic solvent and then lyophilized to give title compound (24 mg, 47% yield, 99% purity) as light yellow solids.

Example 30: Synthesis of Compound 177 (as shown in FIG. 1)

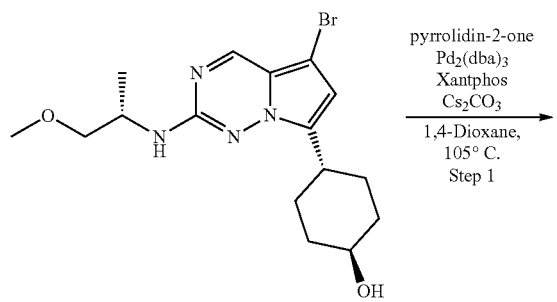

In a microwave vial purged with inert gas, were added (trans)-4-(5-bromo-2-(((S)-1-methoxypropan-2-yl) amino) pyrrolo [2,1-f][1,2,4] triazin-7-yl) cyclohexanol (70.0 mg, 183 μmol), pyrrolidinone (37.7 mg, 438 μmol), cesium carbonate (83.9 mg, 256 μmol), 1,4-dioxane (2.00 mL) and water (1.60 mL). The resulting mixture was degassed by inert gas bubbling. In parallel, in a 2 dram vial purged with inert gas was added tris(dibenzylideneacetone) dipalladium (0) chloroform adduct (9.45 mg, 9.13 μmol) and 4,4-Bis (diphenylphosphino)-9,9-dimethylxanthene (10.8 mg, 18.3 μmol) and 1,4-dioxane (1 mL). This solution was added and the solution was purged with inert gas under sonication for 5 min and then heated for 5 min in an oil bath at 90° C. for catalyst pre-activation. After 5 min, the catalyst solution was syringed out and injected into the coupling partner mix. The solution was heated 15 hours at 105° C. Upon completion, the solvent was removed in vacuo. The residue was purified by flash chromatography on silica (24 g column) eluting with 0 to 100% DCM:20% IPA in DCM and then on a 12 g C-18 column eluting with water containing 10 mM AMF and ACN. The eluent was concentrated to remove organic solvent and then lyophilized to give title compound (4.5 mg, 6% yield, 98% purity) as light yellow solids.

Example 31: Synthesis of Compound 178 (as shown in FIG. 1)

The synthesis was carried out using the same protocol as described in step 1 of Example 30 using 2-oxa-6-azaspiro [3.4]octan-7-one as cross coupling partner. Title compound (7.3 mg, 9% yield, 95% purity) obtained as a light yellow solid.

Example 32: Synthesis of Compound 266 (as shown in FIG. 1)

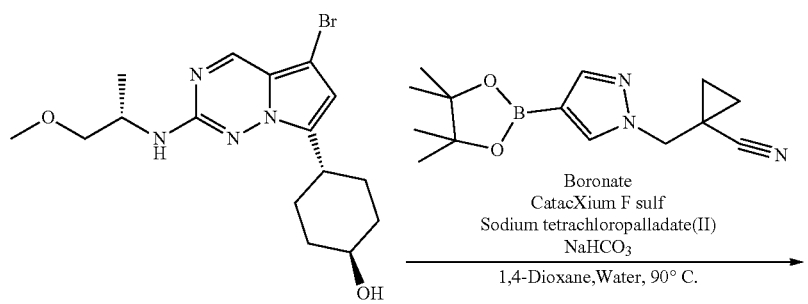

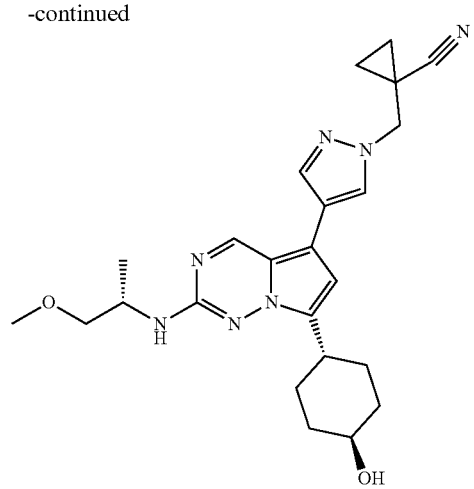

In a vial purged with inert gas, were introduced (trans)-4-(5-bromo-2-(((S)-1-methoxypropan-2-yl) amino) pyrrolo [2,1-f][1,2,4] triazin-7-yl) cyclohexanol (80.0 mg, 0.209 mmol), sodium hydrogenocarbonate (70.2 mg, 0.836 mmol) and the boronate 1-((4-(4,4,5,5-tetramethyl-1,3,2-dioxaborolan-2-yl)-1H-pyrazol-1-yl) methyl) cyclopropane carbonitrile (307 mg, crude). 1,4-dioxane (2 mL) was added and the system was degassed by evacuating and backfilling 3 times with inert gas. In parallel, a second vial was purged with inert gas and water (1.3 mL) was added, and the system degassed as above. CatacXium F sulf (16.2 mg, 0.0209 mmol) and sodium tetrachloropalladate(II) (3.13 mg, 0.0104 mmol) and sodium hydrogenocarbonate (10.5 mg, 0.125 mmol) were added and the solution was heated for 1 hour at 60° C. After heating for 1 h, the ligand-palladium solution was syringed out and injected into the first vial containing the coupling partner mix. The resulting solution was heated 15 hours at 90° C. Upon completion the crude was diluted with EtOAc (30 mL) and washed (2×) with NaHCO₃ and then (6×20 mL) of 1N HCl. The organic phase was set aside and the acid aqueous phase was basified with K₂CO₃ and extracted with EtOAc (3×20 mL) and 2-Methyl THF (3×20 mL). The organic phase was dried with Na₂SO₄ filtered and then concentrated in vacuo. The product was purified on 30 g C-18 column and eluted with water 10 mM AMF and ACN. The eluent was concentrated to remove organic solvent. The product was extracted with EtOAc and sat NaHCO₃. The organic layers were combined, dried over anhydrous MgSO₄, filtered and concentrated in vacuo. The residue was frozen and then lyophilized to give title compound (53 mg, 57% yield) as a light yellow solid.

Example 33: Synthesis of Compound 331

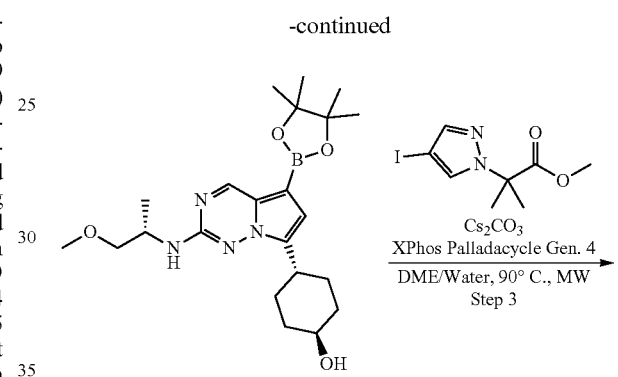

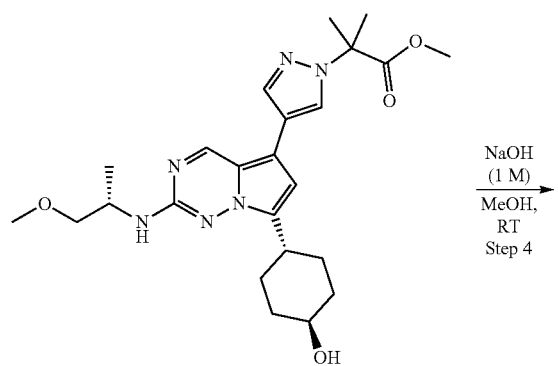

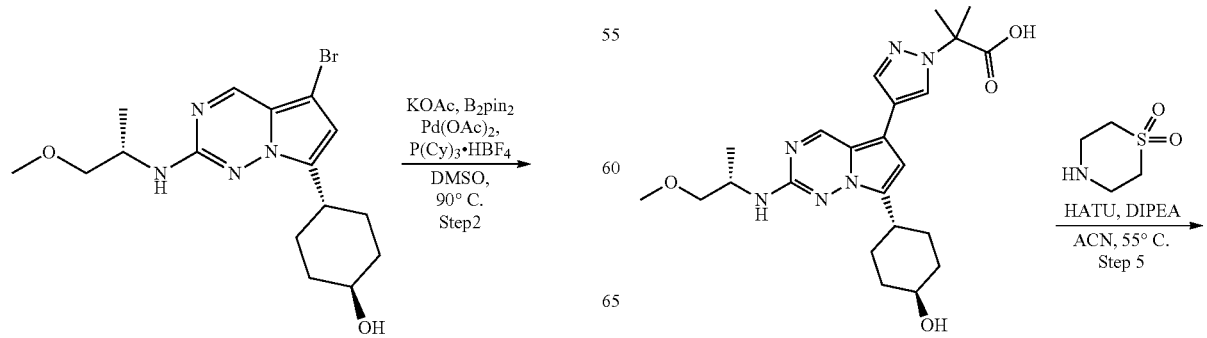

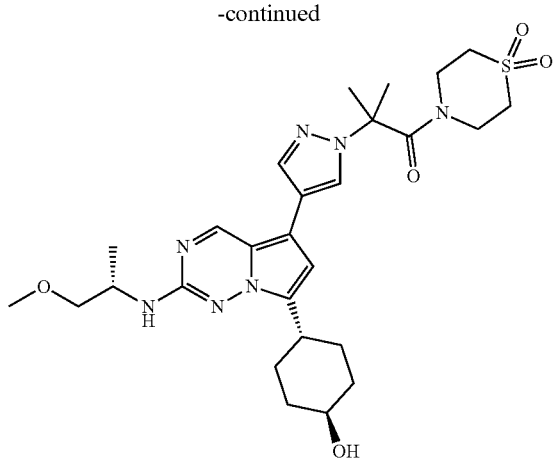

Compound 331 (as shown in FIG. 1) was synthesized according to General Scheme 6, above. The step numbers indicated below correspond to the steps shown in that scheme.

Step 2: (trans)-4-(2-(((S)-1-methoxypropan-2-yl)amino)-5-(4,4,5,5-tetramethyl-1,3,2-dioxaborolan-2-yl)pyrrolo[2,1-f][1,2,4]triazin-7-yl)cyclohexanol In a flame-dried flask was added dry DMSO (5.42 mL) which was degassed with argon for 10 min (bubbling with a long needle, in a sonication bath). Potassium acetate (349 mg, 3.52 mmol), palladium(II) acetate (13.3 mg, 58.7 µmol) and tricyclohexylphosphine tetrafluoroborate (43.7 mg, 117 µmol) were then added and the reaction mixture was degassed again for 10 min and then stirred at RT for 20 min. (trans)-4-(5-bromo-2-(((S)-1-methoxypropan-2-yl)amino)pyrrolo[2,1-f][1,2,4]triazin-7-yl)cyclohexanol (450 mg, 1.17 mmol) and Bis(pinacolato)diboron (913 mg, 3.52 mmol) were then added and the resulting mixture was stirred overnight at 90° C. Upon completion, water and EtOAc were added. The aqueous layer was extracted three times with EtOAc. The combined organic layers were washed with sat. NH₄Cl, sat. NaHCO₃ and brine, dried over Na₂SO₄, filtered and concentrated under reduced pressure. The residue was purified by flash chromatography on silica with DCM/IPA to give title compound (385 mg, 69% yield) as a light yellow solid.

Step 3: Methyl 2-(4-(7-((trans)-4-hydroxycyclohexyl)-2-(((S)-1-methoxypropan-2-yl)amino)pyrrolo[2,1-f][1,2,4]triazin-5-yl)-1H-pyrazol-1-yl)-2-methylpropanoate To a microwave vial was added (trans)-4-(2-(((S)-1-methoxypropan-2-yl)amino)-5-(4,4,5,5-tetramethyl-1,3,2-dioxaborolan-2-yl)pyrrolo[2,1-f][1,2,4]triazin-7-yl)cyclohexanol (385 mg, 895 µmol), methyl 2-(4-iodo-1H-pyrazol-1-yl)-2-methylpropanoate (605 mg, 2.06 mmol) and cesium carbonate (741 mg, 2.24 mmol), followed by DME (8.94 mL) and water (3.89 mL). The resulting mixture was set to 3 cycles of vacuum and argon sparging and XPhos (2-dicyclohexylphosphino-2',4',6'-triisopropylbiphenyl) Palladacycle Gen. 4 (31.4 mg, 35.8 µmol) was then added. The resulting mixture was heated at 90° C. for 10 min under microwave irradiation. Upon completion, water and DCM were added. The aqueous layer was extracted three times with DCM. The combined organic layers were washed with brine, dried over Na₂SO₄, filtered and concentrated under reduced pressure. The residue was purified by flash chromatography on silica with DCM/MeOH to give title compound (330 mg, 78% yield) as a yellow solid.

Step 4: 2-(4-(7-((trans)-4-hydroxycyclohexyl)-2-(((S)-1-methoxypropan-2-yl)amino)pyrrolo[2,1-f][1,2,4]triazin-5-yl)-1H-pyrazol-1-yl)-2-methylpropanoic acid To a solution of methyl 2-(4-(7-((trans)-4-hydroxycyclohexyl)-2-(((S)-1-methoxypropan-2-yl)amino)pyrrolo[2,1-f][1,2,4]triazin-5-yl)-1H-pyrazol-1-yl)-2-methylpropanoate (330 mg, 701 µmol) in MeOH (15.6 mL) was added sodium hydroxide (1 M in water) (16 mL, 96.1 mmol). The resulting mixture was stirred at RT for 3 hours. Upon completion, HCl (1M in water) and EtOAc were added. The aqueous layer was extracted six times with EtOAc. The combined organic layers were washed with brine, dried over Na₂SO₄, filtered and concentrated under reduced pressure to give the title compound (321 mg, crude) as an orange solid.

Step 5: 1-(1,1-dioxidothiomorpholino)-2-(4-(7-((trans)-4-hydroxycyclohexyl)-2-(((S)-1-methoxypropan-2-yl)amino)pyrrolo[2,1-f][1,2,4]triazin-5-yl)-1H-pyrazol-1-yl)-2-methylpropan-1-one To a solution of 2-(4-(7-((trans)-4-hydroxycyclohexyl)-2-(((S)-1-methoxypropan-2-yl)amino)pyrrolo[2,1-f][1,2,4]triazin-5-yl)-1H-pyrazol-1-yl)-2-methylpropanoic acid (50.0 mg, 110 µmol), thiomorpholine-1,1-dioxide (37.0 mg, 274 µmol) and N,N-diisopropylethylamine (42.2 µL, 241 µmol) in ACN (766 µL), was added HATU (51.0 mg, 131 µmol). The resulting mixture was stirred at 55° C. under nitrogen. The residue was purified by flash chromatography on C₁₈ silica with AmF/ACN and lyophilized to give the title compound as a yellow solid. The structure and purity of the title compound was confirmed by ¹H NMR and LCMS.

Example 34: Synthesis of Compounds 452 and 453 (as shown in FIG. 1)

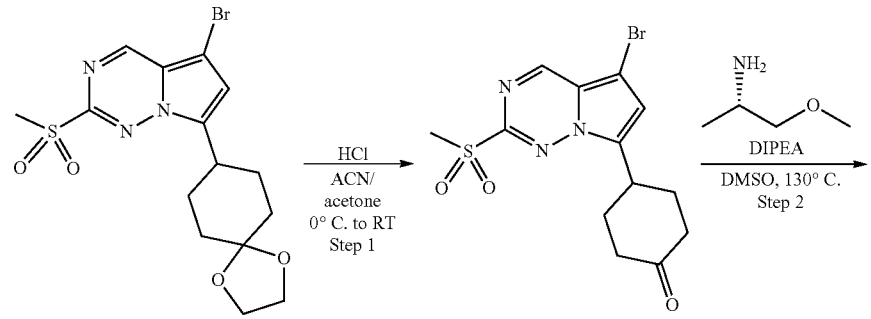

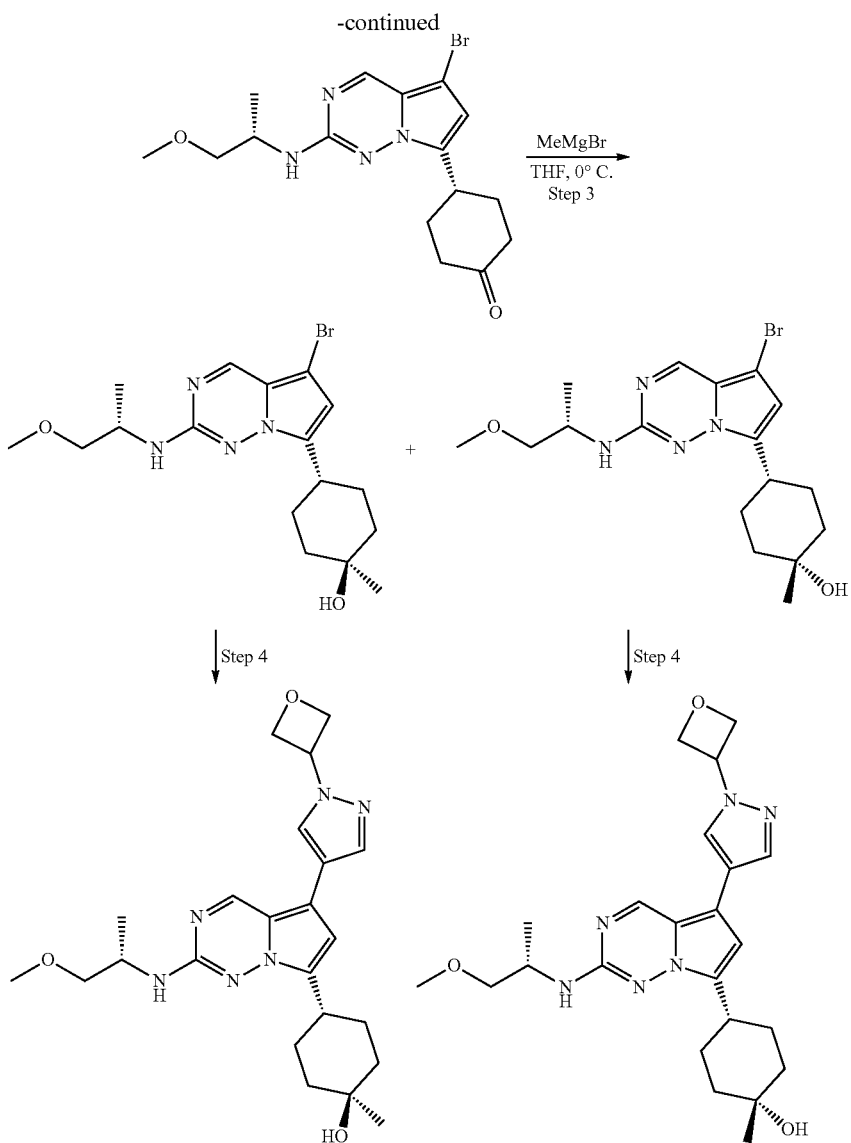

Step 1: 4-(5-bromo-2-(methylsulfonyl)pyrrolo[2,1-f][1,2,4]triazin-7-yl)cyclohexanone A solution of 5-bromo-2-(methylsulfonyl)-7-(1,4-dioxaspiro[4.5]decan-8-yl)pyrrolo[2,1-f][1,2,4]triazine (26.0 g, 62.5 mmol) in ACN (400 mL) and acetone (125 mL) was cooled to 0° C. and treated with hydrochloric acid (65 mL, 390 mmol) and allowed to stir for 2 hours. The reaction mixture was then poured carefully into a stirred solution of saturated NaHCO$_3$ and the mixture was allowed to stir for 20 min. The solution was extracted with EtOAc (×3) and the organic layers were washed (brine), dried (Na$_2$SO$_4$) and concentrated in vacuo. The crude material was then dissolved in 75 mL acetone and 75 mL MeCN and treated with 50 mL of HCl 6M at 0° C. After 5 minutes the ice bath was removed and the mixture was allowed to stir at RT for 30 minutes. The reaction was worked up as above and the crude material (17.92 g) was used as is in the next experiment.

Step 2: (S)-4-(5-bromo-2-((1-methoxypropan-2-yl)amino)pyrrolo[2,1-f][1,2,4]triazin-7-yl)cyclohexanone A mixture of 5-bromo-2-(methylsulfonyl)-7-(1,4-dioxaspiro[4.5]decan-8-yl)pyrrolo[2,1-f][1,2,4]triazine (1.00 g, 2.69 mmol), (S)-1-methoxy-2-propylamine (3.12 mL, 29.3 mmol), and N,N-diisopropylethylamine (1.09 mL, 6.21 mmol) in dry DMSO (3.13 mL) was heated at 130° C. for 2 hours. The reaction mixture was cooled to RT and poured into water and extracted 3 times with EtOAc. The combined organic layers were washed with brine, water, dried (Na$_2$SO$_4$) and concentrated in vacuo. The crude material was used as in subsequent reactions.

Step 3: (trans)-4-(5-bromo-2-(((S)-1-methoxypropan-2-yl)amino)pyrrolo[2,1-f][1,2,4]triazin-7-yl)-1-methylcyclohexanol and (cis)-4-(5-bromo-2-(((S)-1-methoxypropan-2-yl)amino)pyrrolo[2,1-f][1,2,4]triazin-7-yl)-1-methylcyclohexanol A solution of (S)-4-(5-bromo-2-((1-methoxypropan-2-yl)amino)pyrrolo[2,1-f][1,2,4]triazin-7-yl)cyclohexanone (300 mg, 787 µmol) in THF (12.0 mL) was cooled to 0° C. and treated with methylmagnesium bromide (656 µL, 1.97 mmol) dropwise. The solution was allowed to stir overnight and then treated with sat NH₄Cl. The reaction mixture was poured into water and extracted with EtOAc (×3). The combined organic layers were washed (water, brine), dried (Na₂SO₄) and concentrated in vacuo. The residue was purified by column chromatography (Combiflash, 10 g column, 0 to 100% solvent A=50:50 DCM:hexanes, and solvent B=20% IPA in 50:50 DCM:hexanes) to give (trans)-4-(5-bromo-2-(((S)-1-methoxypropan-2-yl)amino)pyrrolo[2,1-f][1,2,4]triazin-7-yl)-1-methylcyclohexanol (66 mg, 21%) and (cis)-4-(5-bromo-2-(((S)-1-methoxypropan-2-yl)amino)pyrrolo[2,1-f][1,2,4]triazin-7-yl)-1-methylcyclohexanol (64 mg, 21%). The relative stereochemistry is unclear at this point and will be left arbitrary.

Step 4: (trans)-4-(2-(((S)-1-methoxypropan-2-yl)amino)-5-(1-(oxetan-3-yl)-1H-pyrazol-4-yl)pyrrolo[2,1-f][1,2,4]triazin-7-yl)-1-methylcyclohexanol A mixture of (trans)-4-(5-bromo-2-(((S)-1-methoxypropan-2-yl)amino)pyrrolo[2,1-f][1,2,4]triazin-7-yl)-1-methylcyclohexanol (60.0 mg, 151 µmol), sodium hydrogenocarbonate (38 mg, 453 µmol) and 1-(oxetan-3-yl)-4-(4,4,5,5-tetramethyl-1,3,2-dioxaborolan-2-yl)-1H-pyrazole (83.1 mg, 332 µmol) in dioxane (1.02 mL) and water (339 µL) was degassed by evacuating and backfilling the flash with argon. The residue was treated with 1,1-bis(diphenylphosphino)ferrocene-palladium dichloride (11.2 mg, 15.1 µmol) and then heated at 80° C. for 4 hours. The reaction mixture was poured into water and extracted with EtOAc (×3). The combined organic layers were washed (water, brine), dried (Na₂SO₄) and concentrated in vacuo. The residue was purified by column chromatography (Combiflash, 50 g column, 10 to 100% IPA in DCM. The residue was evaporated from MeCN, and the residue was lyophylized to give the title product as a fluffy yellow solid (15.6 mg, 23%). The structure and purity was confirmed by ¹H NMR and LCMS.

The diastereoisomer (cis)-4-(2-(((S)-1-methoxypropan-2-yl)amino)-5-(1-(oxetan-3-yl)-1H-pyrazol-4-yl)pyrrolo[2,1-f][1,2,4]triazin-7-yl)-1-methylcyclohexanol was obtained using the same procedure.

Example 35: Synthesis of Compound 406 (as shown in FIG. 1)

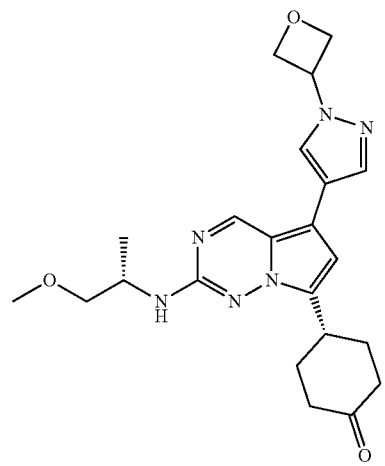

A mixture of (S)-4-(5-bromo-2-((1-methoxypropan-2-yl)amino)pyrrolo[2,1-f][1,2,4]triazin-7-yl)cyclohexanone (250 mg, 656 µmol), sodium hydrogenocarbonate (165 mg, 1.97 mmol) and 1-(oxetan-3-yl)-4-(4,4,5,5-tetramethyl-1,3,2-dioxaborolan-2-yl)-1H-pyrazole (361 mg, 1.44 mmol) in dioxane (4.42 mL) and water (1.47 mL) was degassed by evacuating and backfilling the flash with argon. The residue was treated with 1,1-bis(diphenylphosphino)ferrocene-palladium dichloride (48.6 mg, 65.6 µmol) and then heated at 80° C. for 4 hours. The reaction mixture was poured into water and extracted 3 times with EtOAc. The combined organic layers were washed with water, brine, dried (Na₂SO₄) and concentrated in vacuo. The residue was purified by column chromatography (Combiflash, 50 g column, 10 to 100% IPA in DCM, then 10 g C18 column 10 to 90% MeCN in water containing 10 mM AMF) and lyophilized to give title compound as a light yellow solid (153 mg, 55%). The structure and purity was confirmed by ¹H NMR and LCMS.

Example 36: Synthesis of Compound 394

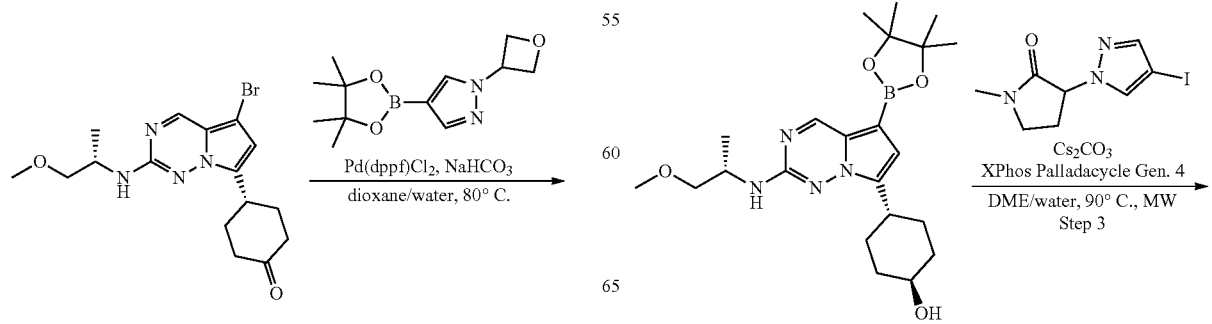

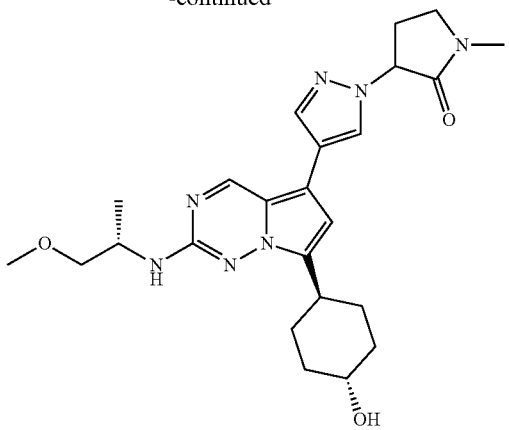

Compound 394 (as shown in FIG. 1) was synthesized according to General Scheme 6, above. The step numbers indicated below correspond to the steps shown in that scheme.

Step 3: 3-(4-(7-((trans)-4-hydroxycyclohexyl)-2-(((S)-1-methoxypropan-2-yl)amino)pyrrolo[2,1-f][1,2,4]triazin-5-yl)-1H-pyrazol-1-yl)-1-methylpyrrolidin-2-one In a conical microwave vial were added 3-(4-iodo-1H-pyrazol-1-yl)-1-methylpyrrolidin-2-one (30.4 mg, 105 µmol), (trans)-4-(2-(((S)-1-methoxypropan-2-yl)amino)-5-(4,4,5,5-tetramethyl-1,3,2-dioxaborolan-2-yl)pyrrolo[2,1-f][1,2,4]triazin-7-yl)cyclohexanol (30.0 mg, 69.7 µmol) and cesium carbonate (57.7 mg, 174 µmol). Then DME (697 µL) and water (303 µL) were added and the resulting mixture was set to 3 cycles of vacuum and argon sparging. XPhos Palladacycle Gen. 4 (3.06 mg, 3.49 µmol) was then added, the vial was sealed and the reaction mixture was irradiated in a microwave apparatus at 90° C. for 10 minutes. After the reaction mixture was cooled to ambient temperature, the crude mixture was concentrated to dryness. The crude mixture was purified on a 12 g silica column (dry pack) eluting with (A) DCM and (B) 20% MeOH in DCM (gradient from 5% to 50%). The product was dissolved in a mixture of ACN/water and was lyophilized affording the title product as a yellow powder (10 mg, 30%). The structure and purity was confirmed by $^1$H NMR and LCMS.

Example 37: Synthesis of Compound 300

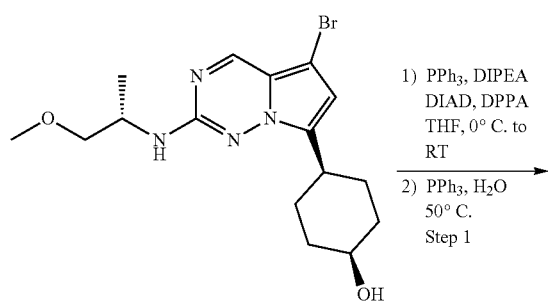

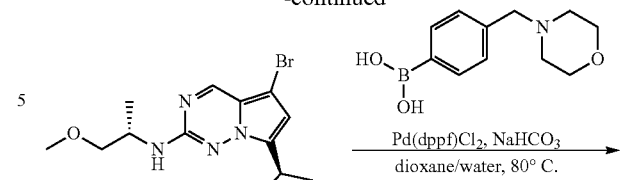

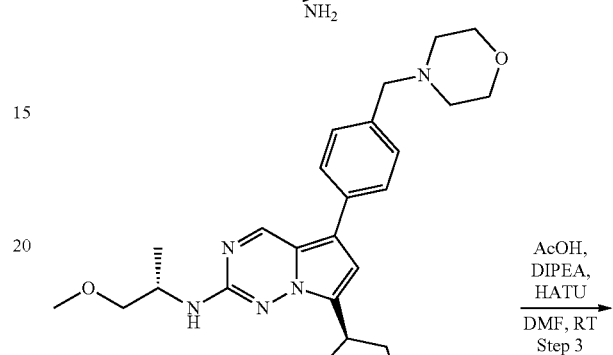

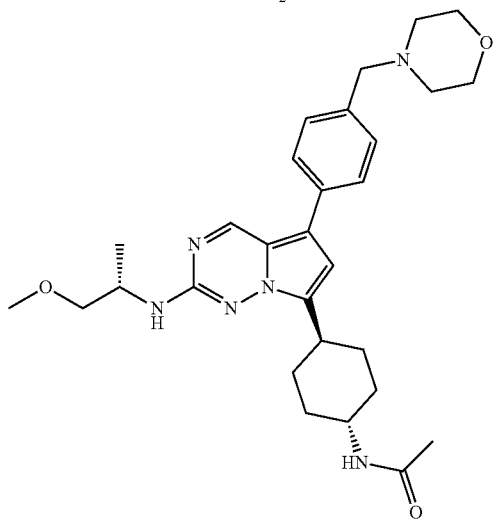

Compound 300 (as shown in FIG. 1) was synthesized according to General Scheme 7, above. The step numbers indicated below correspond to the steps shown in that scheme.

Step 1: 7-((trans)-4-aminocyclohexyl)-5-bromo-N-((S)-1-methoxypropan-2-yl)pyrrolo[2,1-f][1,2,4]triazin-2-amine A solution of (cis)-4-(5-bromo-2-(((S)-1-methoxypropan-2-yl)amino)pyrrolo[2,1-f][1,2,4]triazin-7-yl)cyclohexan-1-ol (259 mg, 677 µmol) and triphenylphosphine (215 mg, 812 µmol) in THF (3.0 mL) was cooled to 0° C. and treated with N,N-diisopropylethylamine (150 µL, 859 µmol) followed by diisopropyl azodicarboxylate (170 µL, 846 µmol). After stirring for 45 min, the mixture was treated with diphenyl phosphoryl azide (180 µL, 812 µmol) and allowed to warm to RT while stirring overnight. The mixture was treated with triphenylphosphine (215 mg, 812 μmol), and allowed to stir overnight. The mixture was then treated with water (100 μL) and the mixture was allowed to stir at 50° C. overnight. The reaction was concentrated and the residue was purified by column chromatography (Combiflash, 25 g column, 0 to 30% MeOH in DCM). The crude was used as is in the next step.

Step 2: 7-((trans)-4-aminocyclohexyl)-N-((S)-1-methoxypropan-2-yl)-5-(4-(morpholinomethyl)phenyl)pyrrolo[2,1-f][1,2,4]triazin-2-amine A mixture of 7-((trans)-4-aminocyclohexyl)-5-bromo-N-((S)-1-methoxypropan-2-yl)pyrrolo[2,1-f][1,2,4]triazin-2-amine (120 mg, 314 μmol), 4-(morpholinomethyl)phenylboronic acid (106 mg, 471 μmol) and sodium hydrogenocarbonate (36.6 μL, 942 μmol) in and H$_2$O (0.1 mL) was degassed by bubbling nitrogen through the mixture for 5 min. The mixture was then treated with 1,1-bis(diphenylphosphino)ferrocene-palladium dichloride (23.3 mg, 31.4 μmol) and heated at 80° C. for 90 min. The reaction mixture was poured into water and extracted with EtOAc (×3). The combined organic layers were washed (water, brine), dried (Na$_2$SO$_4$) and concentrated in vacuo. The residue was purified by Reverse Phase chromatography (C18, 30 g) eluting with MeCN and water containing 10 mM AMF. The desired compound was obtained as a yellow solid (85 mg, 56%).

Step 3: N-((trans)-4-(2-(((S)-1-methoxypropan-2-yl)amino)-5-(4-(morpholinomethyl)phenyl)pyrrolo[2,1-f][1,2,4]triazin-7-yl)cyclohexyl)acetamide 7-((trans)-4-aminocyclohexyl)-N-((S)-1-methoxypropan-2-yl)-5-(4-(morpholinomethyl)phenyl)pyrrolo[2,1-f][1,2,4]triazin-2-amine (40.5 mg, 0.142 mmol), acetic acid (6 μL, 0.105 mmol) and DIPEA (62.1 μL, 0.356 mmol) was dissolved in DMF (3.0 mL). Then, HATU (52.4 mg, 0.134 mmol) was added to the reaction and it was left to stir overnight at RT. Upon completion, the mixture was then loaded directly onto a 60 gram C18 column and the desired product was eluted using 0-100% MeCN in 10 mM AmB. The organic solvent was removed in vacuo, then the aqueous was lyophilized to give title compound as a yellow solid (16.0 mg, 36%). The structure and purity was confirmed by $^1$H NMR and LCMS.

Example 38: Synthesis of Compound 316

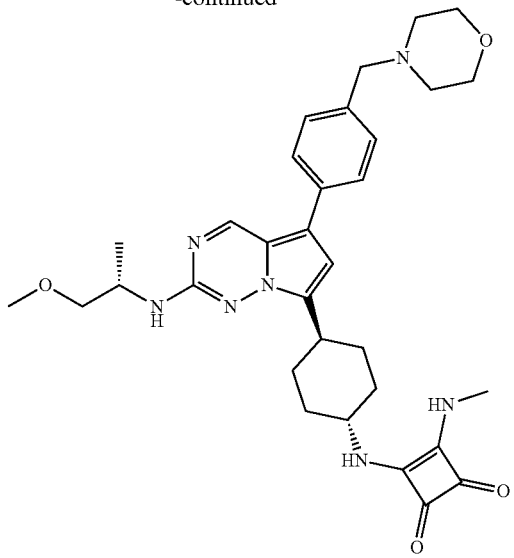

Compound 316 (as shown in FIG. 1) was synthesized according to General Scheme 7, above. The step numbers indicated below correspond to the steps shown in that scheme.

Step 3: 3-(((trans)-4-(2-(((S)-1-methoxypropan-2-yl)amino)-5-(4-(morpholinomethyl)phenyl)pyrrolo[2,1-f][1,2,4]triazin-7-yl)cyclohexyl)amino)-4-(methylamino)cyclobut-3-ene-1,2-dione (the starting material was prepared in example 36)

7-((trans)-4-aminocyclohexyl)-N-((S)-1-methoxypropan-2-yl)-5-(4-(morpholinomethyl)phenyl)pyrrolo[2,1-f][1,2,4]triazin-2-amine (55.0 mg, 0.115 mmol) was dissolved in MeOH (3.0 mL). Then, 3,4-diethoxy-3-cyclobutene-1,2-dione (0.02 mL, 0.128 mmol) was added to the mixture and the reaction was stirred overnight at RT until full consumption was observed. Then, a 2 M solution of methylamine in THF (1.28 mL, 2.57 mmol) was added the reaction was stirred until full conversion to the desired product was observed. The mixture was then concentrated and dissolved in a minimum of DMSO and loaded onto a 60 gram C18 column. The column was run 0-100% MeCN in 10 mM AmB buffer. The product was concentrated and lyophilized to give the title compound as a yellow solid (21.4 mg, 28% yield). The structure and purity was confirmed by $^1$H NMR and LCMS.

Example 39: Synthesis of Compound 479 (as shown in FIG. 1)

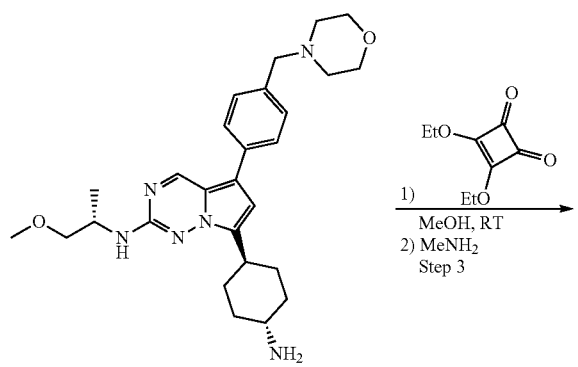

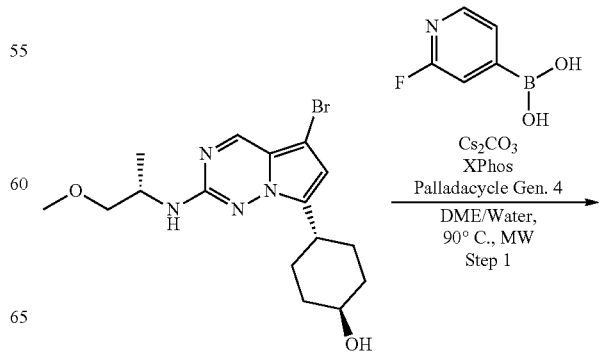

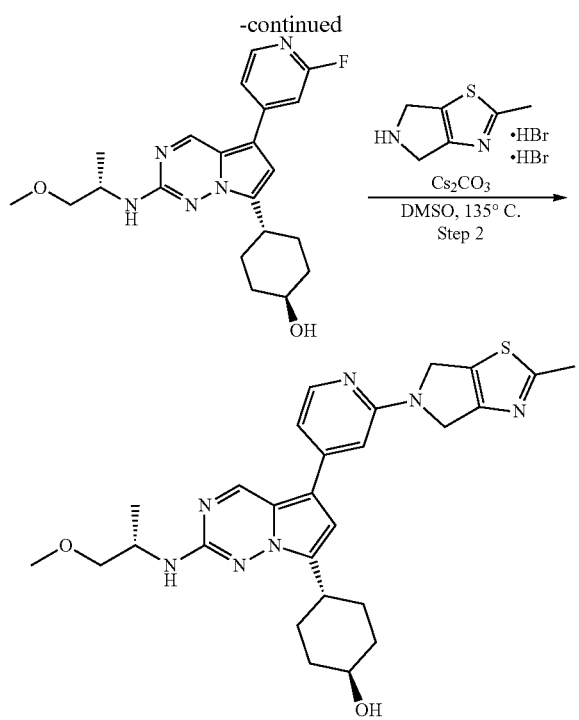

Step 1: (trans)-4-(5-(2-fluoropyridin-4-yl)-2-(((S)-1-methoxypropan-2-yl)amino)pyrrolo[2,1-f][1,2,4]triazin-7-yl)cyclohexanol In a 20 mL microwave vial were added (trans)-4-(5-(2-fluoropyridin-4-yl)-2-(((S)-1-methoxypropan-2-yl)amino)pyrrolo[2,1-f][1,2,4]triazin-7-yl)cyclohexanol (600 mg, 1.57 mmol), cesium carbonate (1.24 g, 3.76 mmol) and 2-fluoropyridin-4-yl-boronic acid (331 mg, 2.35 mmol). DME (10 mL) and water (4 mL) were then added and the resulting mixture was sparged with argon for 8 minutes in the sonication bath. Finally, XPhos Palladacycle Gen. 4 (27.5 mg, 31.3 μmol) was added, the vial was sealed and the reaction mixture was irradiated in a microwave apparatus at 90° C. for 25 min. The mixture was diluted with EtOAc concentrated to dryness. The crude product was purified on a 40 g silica column (dry pack) eluting with (A) DCM and (B) 20% IPA in DCM (gradient from 5% to 60%). The product was dissolved in a minimum of ACN and then water was added. The cloudy solution was frozen and lyophilized, affording the title product as a yellow powder obtained (515 mg, 82%).

Step 2: (trans)-4-(2-(((S)-1-methoxypropan-2-yl)amino)-5-(2-(2-methyl-4H-pyrrolo[3,4-d]thiazol-5(6H)-yl)pyridin-4-yl)pyrrolo[2,1-f][1,2,4]triazin-7-yl)cyclohexanol In a 2.5 mL sealed tube, (trans)-4-(5-(2-fluoropyridin-4-yl)-2-(((S)-1-methoxypropan-2-yl)amino)pyrrolo[2,1-f][1,2,4]triazin-7-yl)cyclohexanol (60.0 mg, 150 μmol) was dissolved in DMSO (1.20 mL) and 2-methyl-4H,5H,6H-pyrrolo[3,4-D][1,3]thiazole dihydrobromide (143 mg, 451 μmol) was added followed by potassium carbonate (83 mg, 601 μmol). The reaction mixture was heated for 16 hours at 135° C. in an oil bath. Next morning, LCMS indicated limited conversion. The reaction was cooled to RT and cesium carbonate (198 mg, 601 μmol) was added. The reaction was then heated again to 135° C. for 2 days. The reaction was then diluted with EtOAc and water and the organic phase was washed with HCl 1N, aqueous saturated NaHCO₃ and then brine. The organic phase was dried with MgSO₄, filtered and concentrated under reduced pressure. The product was purified on a 12 g silica column (dry pack) eluting with (A) DCM and (B) 20% IPA (gradient 10-90%). The residue was then purified on 12 g C-18 column. Product eluted with (A) 10 μM AMF and (B) ACN (gradient 10-90%). The product was concentrated and lyophilized to give the title compound as a yellow solid (19.0 mg, 24%). The structure and purity was confirmed by ¹H NMR and LCMS.

Example 40: Synthesis of Compound 325 (as shown in FIG. 1)

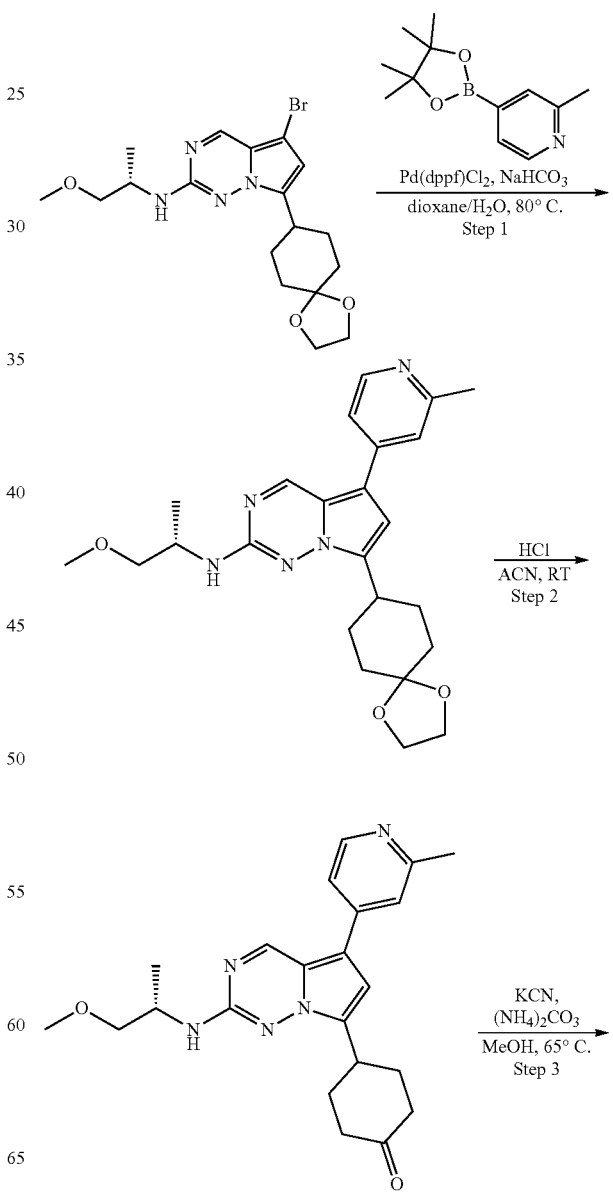

143
-continued

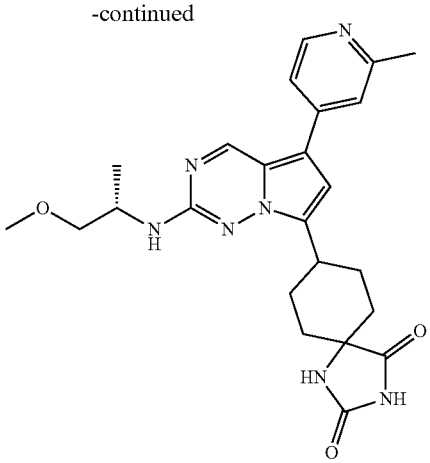

Step 1: (S)-N-(1-methoxypropan-2-yl)-5-(2-methylpyridin-4-yl)-7-(1,4-dioxaspiro[4.5]decan-8-yl)pyrrolo[2,1-f][1,2,4]triazin-2-amine A mixture of (S)-5-bromo-N-(1-methoxypropan-2-yl)-7-(1,4-dioxaspiro[4.5]decan-8-yl)pyrrolo[2,1-f][1,2,4]triazin-2-amine (379 mg, 891 µmol), 2-methyl-4-(4,4,5,5-tetramethyl-1,3,2-dioxaborolan-2-yl)pyridine (421 mg, 1.86 mmol) and sodium hydrogenocarbonate (247 mg, 2.94 mmol) in dioxane (6.00 mL) and water (2.00 mL) was degassed by evacuating and backfilling the flash with argon. The residue was treated with 1,1-bis(diphenylphosphino)ferrocene-palladium dichloride (37.7 mg, 50.8 µmol) and then heated at 80° C. for 4 hours. The reaction mixture was poured into water and extracted with EtOAc (×3). The combined organic layers were washed (water, brine), dried (Na$_2$SO$_4$) and concentrated in vacuo. The residue was purified by column chromatography (Combiflash, 50 g column, 10 to 100% IPA in DCM to give the title product as a yellow orange oil (336 mg/86%).

Step 2: (S)-4-(2-((1-methoxypropan-2-yl)amino)-5-(2-methylpyridin-4-yl)pyrrolo[2,1-f][1,2,4]triazin-7-yl)cyclohexanone A solution of (S)-N-(1-methoxypropan-2-yl)-5-(2-methylpyridin-4-yl)-7-(1,4-dioxaspiro[4.5]decan-8-yl)pyrrolo[2,1-f][1,2,4]triazin-2-amine (336 mg, 768 µmol) in ACN (10.0 mL) was treated with HCl (solution in water, 2.00 mL, 12.0 mmol) and the reaction was allowed to stir for 4 hours. The mixture was poured carefully into saturated NaHCO$_3$ and extracted with three times with EtOAc. The combined organic layers were washed (water, brine) and dried (Na$_2$SO$_4$) and concentrated in vacuo. The residue was purified by column chromatography (Combiflash, 50 g column, 0 to 100% IPA in DCM) to give the title product (221 mg, 73%).

Step 3: (S)-8-(2-((1-methoxypropan-2-yl)amino)-5-(2-methylpyridin-4-yl)pyrrolo[2,1-f][1,2,4]triazin-7-yl)-1,3-diazaspiro[4.5]decane-2,4-dione A mixture of (S)-4-(2-((1-methoxypropan-2-yl)amino)-5-(2-methylpyridin-4-yl)pyrrolo[2,1-f][1,2,4]triazin-7-yl)cyclohexan-1-one (120 mg, 305 µmol), ammonium carbonate (87.9 mg, 915 µmol) and potassium cyanide (31.0 mg, 457 µmol) in MeOH (5.00 mL) was allowed to stir at 65° C.

144 overnight. Upon completion, water and EtOAc were added. The aqueous layer was extracted with EtOAc. The combined organic layers were washed with brine, dried over Na$_2$SO$_4$, filtered and concentrated under reduced pressure. The product was purified on a 10 g silica column eluting with (A) DCM and (B) 20% IPA (dry pack). The product was dispersed in a minimum of ACN and then water was added. Cloudy slurry solution was frozen and lyophilized to give the title product as a yellow powder (41.0 mg, 29%, mixture of diastereoisomers). The structure and purity was confirmed by $^1$H NMR and LCMS.

The synthetic protocols and intermediates described above were used to prepare other compounds disclosed herein as indicated below. The chemical structure, synthesis protocol, and NMR and LC-MS data obtained for exemplary compounds of the invention are shown in the table of FIG. 1. One of ordinary skill in the art will be readily able to make other compounds of the invention based on the general synthesis schemes, intermediate synthesis protocols, and specific compound synthesis protocols set forth herein. In some embodiments, a provided compound is a compound depicted in FIG. 1 or a pharmaceutically acceptable salt thereof.

Example 41: Kinase Activity Assay

IC$_{50}$ values for compound inhibition of AXL, FLT3, MERTK and TYRO3 activity were determined by using a TR-FRET activity assay. A polypeptide substrate with a fluorescent label is phosphorylated on a tyrosine by each enzyme, where the now phosphorylated product is bound by a Europium-labeled antibody specific to that phosphorylation site. The proximity between the antibody and the substrate gives a signal known as TR-FRET. As the enzyme is inhibited by compound, less phosphorylated peptide product is made causing a decrease in overall signal.

Activity assays were performed in a 384-well, small volume, black microplates in an active enzyme volume of 10 µL and final developed volume of 20 µL. Final assay conditions are 50 mM HEPES pH 7.5, 10 mM MgCl$_2$, 1 mM EGTA, 0.01% Brij 35 and 1 mM DTT all at RT. Enzyme, substrate labeled peptide and compound are mixed, and then the reaction is initiated with the addition of ATP at Km concentration for each enzyme. The reaction is allowed to run 60 minutes and then quenched with a 12.5 mM EDTA (ethylenediamine tetraacetic acid) solution. The plate is then developed with the addition of Europium labeled antibody for a final volume of 20 µL and is then incubated for 30 minutes in darkness. Plates are read in a Pherastar plate reader. Data is analyzed in GraphPad PRISM.

The results of these assays are shown in Table 1, below, wherein "No." designates compound number (FIG. 1); "A" represents a value of ≤100 nM; "B" a value of >100 nM and ≤1 µM; "C" a value of >1 µM and ≤10 µM; "D" a value of >10 µM; "ND" is not determined. The ratio of Mer to FLT3 is calculated as follows: FLT3 IC$_{50}$/Mer IC$_{50}$. "+" represents a ratio of >2.0 and <10; "++" represents a ratio of between 10 and 100; and "+++" represents a ratio of >100.

TABLE 1

Activity of Exemplary Compounds against Various Kinases and Ratio of Mer Activity to FLT3 Activity.

| No. | Axl | Flt3 | Mer | Tyro3 | FLT3/Mer |
|---|---|---|---|---|---|
| 101 | A | A | A | ND | + |
| 102 | B | B | A | A | ++ |

TABLE 1-continued

Activity of Exemplary Compounds against Various Kinases and Ratio of Mer Activity to FLT3 Activity.

| No. | Axl | Flt3 | Mer | Tyro3 | FLT3/Mer |
|---|---|---|---|---|---|
| 103 | B | B | A | B | ++ |
| 104 | A | B | A | A | ++ |
| 105 | B | B | A | A | + |
| 106 | D | D | B | ND | ++ |
| 107 | A | B | A | A | +++ |
| 108 | B | B | A | B | +++ |
| 109 | A | B | A | A | ++ |
| 110 | A | B | A | A | ++ |
| 111 | D | C | C | ND | + |
| 112 | B | B | A | A | +++ |
| 113 | A | B | A | A | ++ |
| 114 | A | B | A | A | +++ |
| 115 | B | C | A | B | ++ |
| 116 | A | B | A | A | +++ |
| 117 | B | C | A | B | +++ |
| 118 | A | A | A | A | ++ |
| 119 | B | C | A | A | +++ |
| 120 | B | C | A | A | +++ |
| 121 | B | B | A | A | ++ |
| 122 | A | B | A | A | +++ |
| 123 | C | C | A | B | +++ |
| 124 | A | B | A | A | ++ |
| 125 | B | C | A | B | ++ |
| 126 | B | C | A | B | ++ |
| 127 | A | B | A | A | +++ |
| 128 | A | A | A | A | ++ |
| 129 | B | C | A | A | +++ |
| 130 | A | A | A | A | +++ |
| 131 | A | A | A | A | +++ |
| 132 | A | A | A | A | ++ |
| 133 | A | B | A | A | +++ |
| 134 | A | C | A | A | +++ |
| 135 | A | B | A | A | +++ |
| 136 | B | C | A | B | +++ |
| 137 | A | B | A | A | +++ |
| 138 | B | B | A | A | ++ |
| 139 | A | C | A | A | +++ |
| 140 | A | B | A | A | +++ |
| 141 | A | B | A | A | +++ |
| 142 | A | B | A | A | +++ |
| 143 | A | A | A | A | ++ |
| 144 | A | B | A | A | +++ |
| 145 | A | A | A | A | ++ |
| 146 | B | C | A | A | +++ |
| 147 | B | C | A | A | +++ |
| 148 | A | B | A | A | +++ |
| 149 | B | B | A | A | ++ |
| 150 | A | B | A | A | ++ |
| 150-1 | ND | ND | ND | ND | ND |
| 151 | B | B | A | A | +++ |
| 152 | A | B | A | A | +++ |
| 153 | B | C | A | A | +++ |
| 154 | A | B | A | A | +++ |
| 155 | A | B | A | A | ++ |
| 156 | A | B | A | A | ++ |
| 157 | A | A | A | A | ++ |
| 158 | A | B | A | A | +++ |
| 159 | A | B | A | A | +++ |
| 160 | A | C | A | A | +++ |
| 161 | B | A | A | A | ++ |
| 162 | A | B | A | A | +++ |
| 163 | A | B | A | A | ++ |
| 164 | A | A | A | A | ++ |
| 165 | A | A | A | A | ++ |
| 166 | A | A | A | A | ++ |
| 167 | A | B | A | A | +++ |
| 168 | C | C | A | B | +++ |
| 169 | A | C | A | A | +++ |
| 170 | A | C | A | A | +++ |
| 171 | A | A | A | A | ++ |
| 172 | A | A | A | A | ++ |
| 173 | A | B | A | A | +++ |
| 174 | B | C | A | A | +++ |
| 175 | C | C | B | C | ++ |
| 176 | C | C | C | C | + |
| 177 | C | C | A | B | +++ |
| 178 | C | C | A | B | +++ |
| 179 | B | B | A | A | +++ |
| 180 | B | B | A | A | ++ |
| 181 | B | A | A | A | ++ |
| 182 | A | A | A | A | ++ |
| 183 | B | C | A | A | +++ |
| 184 | B | B | A | A | ++ |
| 185 | A | B | A | A | ++ |
| 186 | B | B | A | A | ++ |
| 187 | A | B | A | A | +++ |
| 188 | A | A | A | A | +++ |
| 189 | A | A | A | A | ++ |
| 190 | A | A | A | A | +++ |
| 191 | B | C | A | A | +++ |
| 192 | C | C | B | C | ++ |
| 193 | A | C | A | A | +++ |
| 194 | B | C | A | A | +++ |
| 195 | B | C | A | A | +++ |
| 196 | A | B | A | A | +++ |
| 197 | A | B | A | A | +++ |
| 198 | B | B | A | A | +++ |
| 199 | A | B | A | A | +++ |
| 200 | B | C | A | A | +++ |
| 201 | B | C | A | A | +++ |
| 202 | B | B | A | A | +++ |
| 203 | A | A | A | A | ++ |
| 204 | C | C | B | B | ++ |
| 205 | C | C | A | A | +++ |
| 206 | B | C | A | A | +++ |
| 207 | A | B | A | A | +++ |
| 208 | B | C | A | A | +++ |
| 209 | B | B | A | A | +++ |
| 210 | B | C | A | A | +++ |
| 211 | B | B | A | A | ++ |
| 212 | B | C | A | B | ++ |
| 213 | A | A | A | A | +++ |
| 214 | B | C | A | A | +++ |
| 215 | B | C | A | A | +++ |
| 216 | A | A | A | A | ++ |
| 217 | B | B | A | A | +++ |
| 218 | B | B | A | A | +++ |
| 219 | B | C | A | A | +++ |
| 220 | A | B | A | A | +++ |
| 221 | A | B | A | A | +++ |
| 222 | A | B | A | A | +++ |
| 223 | B | C | A | A | +++ |
| 224 | B | B | A | A | +++ |
| 225 | A | B | A | A | +++ |
| 226 | B | B | A | A | +++ |
| 227 | B | C | A | A | +++ |
| 228 | B | C | A | A | +++ |
| 229 | A | B | A | A | +++ |
| 230 | B | B | A | A | +++ |
| 231 | B | C | A | A | +++ |
| 232 | B | C | A | A | +++ |
| 233 | B | C | A | A | +++ |
| 234 | B | C | A | A | +++ |
| 235 | B | C | A | A | +++ |
| 236 | ND | ND | ND | ND | ND |
| 237 | B | B | A | A | +++ |
| 238 | B | B | A | A | +++ |
| 239 | A | B | A | A | +++ |
| 240 | B | B | A | A | +++ |
| 241 | B | B | A | A | +++ |
| 242 | A | B | A | A | +++ |
| 243 | A | B | A | A | +++ |
| 244 | A | A | A | A | ++ |
| 245 | B | C | A | A | +++ |
| 246 | A | B | A | A | +++ |
| 247 | B | C | A | A | +++ |
| 248 | B | C | A | A | +++ |
| 249 | A | B | A | A | +++ |

TABLE 1-continued

Activity of Exemplary Compounds against Various Kinases and Ratio of Mer Activity to FLT3 Activity.

| No. | Axl | Flt3 | Mer | Tyro3 | FLT3/Mer |
|---|---|---|---|---|---|
| 250 | B | C | A | A | +++ |
| 251 | B | B | A | A | +++ |
| 252 | B | B | A | A | +++ |
| 253 | C | C | A | A | +++ |
| 254 | B | B | A | A | +++ |
| 255 | A | A | A | A | ++ |
| 256 | A | B | A | A | +++ |
| 257 | C | C | A | B | +++ |
| 258 | B | C | A | A | ++ |
| 259 | A | B | A | A | +++ |
| 260 | B | B | A | A | +++ |
| 261 | B | C | A | A | +++ |
| 262 | A | A | A | A | +++ |
| 263 | A | A | A | A | ++ |
| 264 | A | C | A | A | +++ |
| 265 | A | C | A | A | +++ |
| 266 | A | B | A | A | +++ |
| 267 | B | C | A | A | +++ |
| 268 | B | B | A | A | +++ |
| 269 | A | A | A | A | ++ |
| 270 | A | A | A | A | +++ |
| 271 | A | A | A | A | ++ |
| 272 | B | B | A | A | +++ |
| 273 | A | B | A | A | +++ |
| 274 | A | A | A | A | +++ |
| 275 | A | C | A | A | +++ |
| 276 | A | B | A | A | +++ |
| 277 | A | A | A | A | +++ |
| 278 | A | B | A | A | +++ |
| 279 | A | B | A | A | +++ |
| 280 | A | B | A | A | +++ |
| 281 | A | A | A | A | +++ |
| 282 | A | B | A | A | +++ |
| 283 | A | C | A | A | +++ |
| 284 | B | C | A | A | +++ |
| 285 | A | B | A | A | +++ |
| 286 | A | A | A | A | +++ |
| 287 | A | A | A | A | +++ |
| 288 | A | A | A | A | ++ |
| 289 | A | A | A | A | + |
| 290 | A | A | A | A | ++ |
| 291 | A | B | A | A | +++ |
| 292 | A | B | A | A | +++ |
| 293 | A | B | A | A | +++ |
| 294 | A | A | A | A | +++ |
| 295 | A | C | A | A | +++ |
| 296 | A | A | A | A | ++ |
| 297 | A | A | A | A | ++ |
| 298 | A | C | A | A | +++ |
| 299 | A | C | A | A | +++ |
| 300 | A | B | A | A | +++ |
| 301 | A | A | A | A | +++ |
| 302 | A | B | A | A | +++ |
| 303 | A | B | A | A | +++ |
| 304 | A | C | A | A | +++ |
| 305 | A | B | A | A | +++ |
| 306 | A | B | A | A | +++ |
| 307 | A | A | A | A | +++ |
| 308 | B | C | A | A | +++ |
| 309 | A | B | A | A | +++ |
| 310 | A | B | A | A | +++ |
| 311 | A | B | A | A | +++ |
| 312 | A | A | A | A | +++ |
| 313 | A | B | A | A | +++ |
| 314 | A | A | A | A | +++ |
| 315 | A | B | A | A | +++ |
| 316 | A | A | A | A | ++ |
| 317 | A | A | A | A | +++ |
| 318 | A | C | A | A | +++ |
| 319 | A | C | A | A | +++ |
| 320 | A | C | A | A | +++ |
| 321 | A | A | A | A | +++ |
| 322 | A | B | A | A | +++ |
| 323 | A | B | A | A | +++ |
| 324 | A | B | A | A | +++ |
| 325 | A | C | A | A | +++ |
| 326 | A | C | A | A | +++ |
| 327 | A | C | A | A | +++ |
| 328 | A | C | A | A | +++ |
| 329 | A | B | A | A | +++ |
| 330 | A | B | A | A | +++ |
| 331 | A | B | A | A | +++ |
| 332 | A | B | A | A | +++ |
| 333 | A | B | A | A | +++ |
| 334 | B | C | A | A | +++ |
| 335 | B | C | A | A | +++ |
| 336 | A | B | A | A | +++ |
| 337 | A | B | A | A | +++ |
| 338 | A | B | A | A | +++ |
| 339 | A | B | A | A | +++ |
| 340 | A | B | A | A | +++ |
| 341 | A | B | A | A | +++ |
| 342 | A | B | A | A | +++ |
| 343 | A | C | A | A | +++ |
| 344 | A | B | A | A | +++ |
| 345 | A | C | A | A | +++ |
| 346 | A | A | A | A | +++ |
| 347 | A | A | A | A | +++ |
| 348 | A | B | A | A | +++ |
| 349 | C | C | A | A | +++ |
| 350 | A | A | A | A | +++ |
| 351 | A | A | A | A | ++ |
| 352 | A | A | A | A | ++ |
| 353 | B | B | A | A | +++ |
| 354 | A | B | A | A | +++ |
| 355 | A | A | A | A | + |
| 356 | A | A | A | A | ++ |
| 357 | A | B | A | A | +++ |
| 358 | A | C | A | A | +++ |
| 359 | A | A | A | A | + |
| 360 | A | A | A | A | ++ |
| 361 | A | C | A | A | +++ |
| 362 | A | A | A | A | ++ |
| 363 | A | A | A | A | + |
| 364 | A | A | A | A | +++ |
| 365 | A | B | A | A | +++ |
| 366 | A | C | A | A | +++ |
| 367 | A | C | A | A | +++ |
| 368 | A | B | A | A | +++ |
| 369 | A | B | A | A | +++ |
| 370 | A | A | A | A | + |
| 371 | C | C | A | B | +++ |
| 372 | C | C | B | C | ++ |
| 373 | B | C | A | A | +++ |
| 374 | A | C | A | A | +++ |
| 375 | B | C | A | A | +++ |
| 376 | B | C | A | A | +++ |
| 377 | B | C | A | A | +++ |
| 378 | C | C | A | B | +++ |
| 379 | A | B | A | A | +++ |
| 380 | A | B | A | A | +++ |
| 381 | A | C | A | A | +++ |
| 382 | A | B | A | A | +++ |
| 383 | B | C | A | A | +++ |
| 384 | A | A | A | A | +++ |
| 385 | B | C | A | A | +++ |
| 386 | A | B | A | A | +++ |
| 387 | C | C | B | B | ++ |
| 388 | C | C | B | C | ++ |
| 389 | A | B | A | A | +++ |
| 390 | A | B | A | A | +++ |
| 391 | A | B | A | A | +++ |
| 392 | A | A | A | A | +++ |
| 393 | A | A | A | A | +++ |
| 394 | A | B | A | A | +++ |
| 395 | A | B | A | A | +++ |
| 396 | A | B | A | A | +++ |
| 397 | A | B | A | A | +++ |

TABLE 1-continued

Activity of Exemplary Compounds against Various Kinases and Ratio of Mer Activity to FLT3 Activity.

| No. | Axl | Flt3 | Mer | Tyro3 | FLT3/Mer |
|---|---|---|---|---|---|
| 398 | A | C | A | A | +++ |
| 399 | A | B | A | A | +++ |
| 400 | A | B | A | A | +++ |
| 401 | A | B | A | A | +++ |
| 402 | A | B | A | A | +++ |
| 403 | A | B | A | A | +++ |
| 404 | A | B | A | A | +++ |
| 405 | A | A | A | A | +++ |
| 406 | B | B | A | A | +++ |
| 407 | A | B | A | A | +++ |
| 408 | A | B | A | A | +++ |
| 409 | C | D | A | C | +++ |
| 410 | B | C | A | A | +++ |
| 411 | A | B | A | A | +++ |
| 412 | A | A | A | A | +++ |
| 413 | A | A | A | A | ++ |
| 414 | A | C | A | A | +++ |
| 415 | A | C | A | A | +++ |
| 416 | A | B | A | A | +++ |
| 417 | B | D | A | A | +++ |
| 418 | A | B | A | A | +++ |
| 419 | A | B | A | A | +++ |
| 420 | A | B | A | A | +++ |
| 421 | A | B | A | A | +++ |
| 422 | A | B | A | A | +++ |
| 423 | A | B | A | A | +++ |
| 424 | A | B | A | A | +++ |
| 425 | A | B | A | A | +++ |
| 426 | A | B | A | A | +++ |
| 427 | A | B | A | A | +++ |
| 428 | C | C | B | A | ++ |
| 429 | B | A | A | A | ++ |
| 430 | A | B | A | A | +++ |
| 431 | A | B | A | A | +++ |
| 432 | A | B | A | A | +++ |
| 433 | B | C | A | A | +++ |
| 434 | A | B | A | A | +++ |
| 435 | C | C | A | B | +++ |
| 436 | A | B | A | A | +++ |
| 437 | A | A | A | A | +++ |
| 438 | A | C | A | A | +++ |
| 439 | A | B | A | A | +++ |
| 440 | A | C | A | A | +++ |
| 441 | A | A | A | A | ++ |
| 442 | A | A | A | A | ++ |
| 443 | A | C | A | A | +++ |
| 444 | A | B | A | A | +++ |
| 445 | A | B | A | A | +++ |
| 446 | A | A | A | A | +++ |
| 447 | C | C | C | C | + |
| 448 | A | C | A | A | +++ |
| 449 | B | C | A | A | +++ |
| 450 | A | C | A | A | +++ |
| 451 | A | B | A | A | +++ |
| 452 | A | B | A | A | +++ |
| 453 | A | B | A | A | +++ |
| 454 | A | A | A | A | ++ |
| 455 | A | A | A | A | ++ |
| 456 | A | A | A | A | +++ |
| 457 | A | B | A | A | +++ |
| 458 | A | A | A | A | +++ |
| 459 | A | C | A | A | +++ |
| 460 | A | A | A | A | +++ |
| 461 | A | C | A | A | +++ |
| 462 | A | B | A | A | +++ |
| 463 | A | B | A | A | +++ |
| 464 | A | B | A | A | +++ |
| 465 | A | C | A | A | +++ |
| 466 | A | C | A | A | +++ |
| 467 | A | C | A | A | +++ |
| 468 | A | B | A | A | +++ |
| 469 | A | B | A | A | +++ |
| 470 | A | B | A | A | +++ |
| 471 | A | C | A | A | +++ |
| 472 | A | B | A | A | +++ |
| 473 | A | B | A | A | +++ |
| 474 | A | B | A | A | +++ |
| 475 | A | B | A | A | +++ |
| 476 | A | B | A | A | +++ |
| 477 | A | C | A | A | +++ |
| 478 | A | C | A | A | +++ |
| 479 | A | C | A | A | +++ |
| 480 | A | B | A | A | +++ |
| 481 | C | C | A | B | +++ |
| 482 | A | A | A | A | +++ |
| 483 | A | B | A | A | +++ |
| 484 | B | C | A | A | +++ |
| 485 | A | B | A | A | +++ |
| 486 | A | C | A | A | +++ |
| 487 | B | C | A | A | +++ |
| 488 | A | B | A | A | +++ |
| 489 | A | A | A | A | +++ |
| 490 | A | B | A | A | +++ |
| 491 | A | B | A | A | +++ |
| 492 | A | C | A | A | +++ |
| 493 | A | B | A | A | +++ |
| 494 | A | C | A | A | +++ |
| 495 | A | C | A | A | +++ |
| 496 | A | C | A | A | +++ |
| 497 | B | C | A | A | +++ |
| 498 | A | B | A | A | +++ |
| 499 | A | B | A | A | +++ |
| 500 | A | B | A | A | +++ |
| 501 | B | C | A | A | ++ |
| 502 | B | C | A | A | ++ |
| 503 | B | C | A | A | +++ |
| 504 | A | B | A | A | +++ |
| 505 | A | C | A | A | +++ |
| 506 | C | D | A | A | +++ |
| 507 | A | B | A | A | +++ |
| 508 | A | C | A | A | +++ |
| 509 | A | C | A | A | +++ |
| 510 | B | C | A | A | +++ |
| 511 | C | B | A | A | ++ |
| 512 | A | B | A | A | +++ |
| 513 | A | B | A | A | +++ |
| 514 | A | C | A | A | +++ |
| 515 | B | B | A | A | +++ |
| 516 | A | C | A | A | +++ |
| 517 | A | C | A | A | +++ |
| 518 | A | C | A | A | +++ |
| 519 | A | C | A | A | +++ |
| 520 | B | C | A | A | +++ |
| 521 | B | B | A | A | ++ |
| 522 | B | B | A | A | +++ |
| 523 | A | B | A | A | +++ |
| 524 | A | B | A | A | +++ |
| 525 | B | C | A | A | +++ |
| 526 | C | C | A | A | ++ |
| 527 | B | B | A | A | +++ |
| 528 | A | B | A | A | +++ |
| 529 | B | C | A | A | +++ |
| 530 | B | B | A | A | ++ |
| 531 | B | B | A | A | +++ |
| 532 | A | C | A | A | +++ |
| 533 | A | C | A | A | +++ |
| 534 | A | B | A | A | +++ |
| 535 | A | A | A | A | ++ |
| 536 | B | C | A | A | +++ |
| 537 | A | C | A | A | +++ |
| 538 | B | C | A | A | +++ |
| 539 | B | C | A | A | +++ |
| 540 | A | A | A | A | +++ |
| 541 | A | A | A | A | ++ |
| 542 | C | C | A | A | +++ |
| 543 | C | C | A | A | +++ |
| 544 | C | C | B | A | ++ |
| 545 | C | B | A | A | + |

TABLE 1-continued

Activity of Exemplary Compounds against Various Kinases and Ratio of Mer Activity to FLT3 Activity.

| No. | Axl | Flt3 | Mer | Tyro3 | FLT3/Mer |
|---|---|---|---|---|---|
| 546 | A | B | A | A | +++ |
| 547 | A | B | A | A | +++ |
| 548 | A | B | A | A | +++ |
| 549 | A | B | A | A | +++ |
| 550 | A | B | A | A | +++ |
| 551 | A | C | A | A | +++ |
| 552 | A | B | A | A | +++ |
| 553 | A | B | A | A | +++ |
| 554 | A | C | A | A | +++ |
| 555 | A | C | A | A | +++ |
| 556 | A | C | A | A | +++ |
| 557 | A | B | A | A | +++ |
| 558 | A | B | A | A | +++ |
| 559 | A | B | A | A | +++ |
| 560 | A | B | A | A | +++ |
| 561 | A | B | A | A | +++ |
| 562 | A | A | A | A | +++ |
| 563 | A | B | A | A | +++ |
| 564 | A | A | A | A | ++ |
| 565 | A | B | A | A | +++ |
| 566 | A | B | A | A | +++ |
| 567 | A | C | A | A | +++ |
| 568 | A | B | A | A | +++ |
| 569 | A | B | A | A | +++ |
| 570 | B | B | A | A | ++ |
| 571 | B | B | A | A | ++ |
| 572 | B | D | A | A | +++ |
| 573 | B | D | A | A | +++ |
| 574 | B | C | A | A | +++ |
| 575 | B | C | A | A | +++ |
| 576 | B | C | A | A | +++ |
| 577 | A | C | A | A | +++ |
| 578 | B | C | A | A | +++ |
| 579 | B | C | A | A | +++ |
| 580 | A | A | A | A | +++ |
| 581 | A | A | A | A | +++ |
| 582 | A | C | A | A | +++ |
| 583 | A | B | A | A | +++ |
| 584 | A | C | A | A | +++ |
| 585 | A | C | A | A | +++ |
| 586 | A | C | A | A | +++ |
| 587 | A | B | A | A | +++ |
| 588 | B | B | A | A | ++ |
| 589 | A | B | A | A | +++ |
| 590 | C | C | A | B | +++ |
| 591 | A | C | A | A | +++ |
| 592 | C | C | A | A | +++ |
| 593 | A | B | A | A | +++ |
| 594 | A | C | A | A | +++ |
| 595 | B | C | A | A | +++ |
| 596 | A | B | A | A | +++ |
| 597 | A | B | A | A | +++ |
| 598 | A | B | A | A | +++ |
| 599 | A | C | A | A | +++ |
| 600 | A | C | A | A | +++ |
| 601 | A | C | A | A | +++ |
| 602 | A | C | A | A | +++ |
| 603 | A | C | A | A | +++ |
| 604 | A | C | A | A | +++ |
| 605 | A | B | A | A | +++ |
| 606 | A | C | A | A | +++ |
| 607 | A | C | A | A | +++ |
| 608 | A | A | A | A | ++ |
| 609 | A | A | A | A | ++ |
| 610 | A | A | A | A | ++ |
| 611 | A | B | A | A | +++ |
| 612 | A | B | A | A | +++ |
| 613 | A | A | A | A | +++ |
| 614 | A | B | A | A | +++ |
| 615 | A | B | A | A | +++ |
| 616 | A | B | A | A | +++ |
| 617 | A | B | A | A | +++ |
| 618 | A | B | A | A | +++ |
| 619 | A | B | A | A | +++ |
| 620 | A | C | A | A | +++ |
| 621 | A | B | A | A | +++ |
| 622 | A | C | A | A | +++ |
| 623 | A | C | A | A | +++ |
| 624 | A | A | A | A | ++ |
| 625 | A | B | A | A | +++ |
| 626 | A | A | A | A | ++ |
| 627 | A | C | A | A | +++ |
| 628 | A | C | A | A | +++ |
| 629 | A | B | A | A | +++ |
| 630 | A | B | A | A | +++ |
| 631 | A | C | A | A | +++ |
| 632 | A | B | A | A | +++ |
| 633 | A | B | A | A | +++ |

Example 42: Exemplary Compound in Combination with an Anti-PD1 Antibody Demonstrates Synergy in Reducing Syngeneic Tumor BLAB/c syngeneic mice challenged with colon carcinoma CT-26 cells were used to test the tumor growth inhibitory activity of Compound 124 and an anti-PD1 antibody alone or in combination. CT-26 tumor cells were maintained in vitro as a monolayer culture in RPMI-1640 medium supplemented with 10% heat inactivated fetal bovine serum, 100 U/ml penicillin and 100 µg/ml streptomycin at 37° C. in an atmosphere of 5% $CO_2$ in air. The tumor cells were routinely subcultured twice weekly by trypsin-EDTA treatment. The cells growing in an exponential growth phase were harvested and counted for tumor inoculation. Balb/c female mice (6-8 weeks old; 18-22 g) were inoculated subcutaneously at the right lower flank with CT-26 tumor cells ($3\times10^5$) in 0.1 ml of PBS for tumor development. Treatments were started on day 8 after tumor inoculation when the average tumor size reached approximately 56 $mm^3$.

Figure 3:
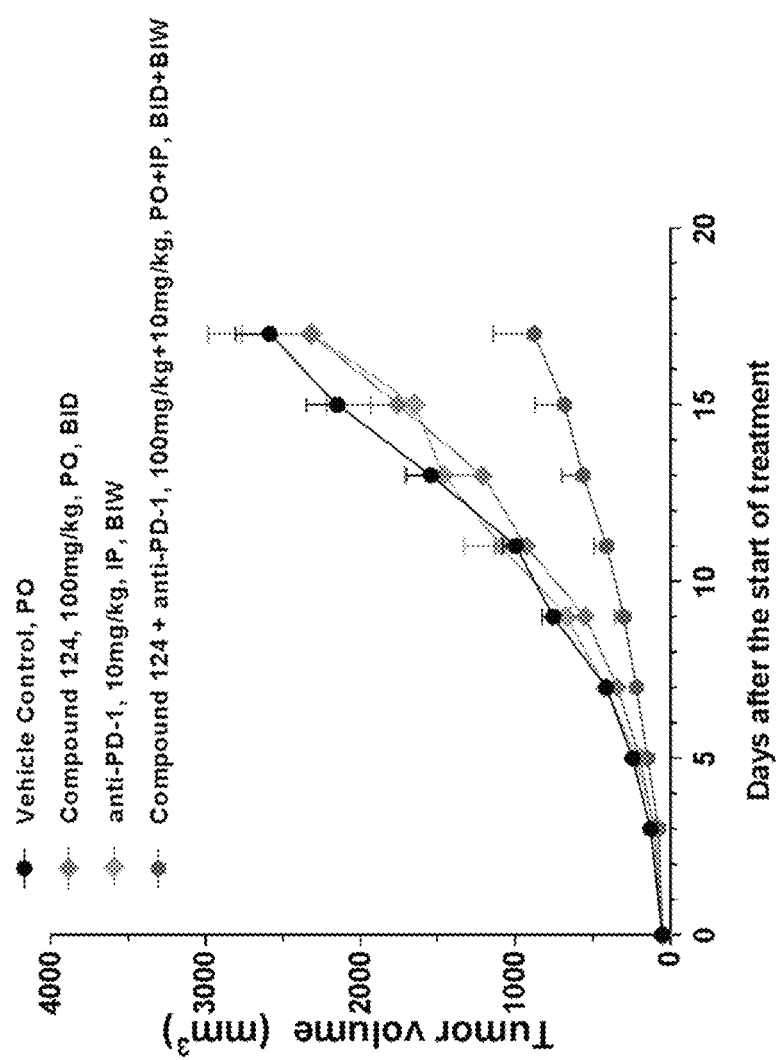
FIG. 3 is a graph demonstrating the effect on tumor volume after administration of Compound 124 (as shown in FIG. 1) alone, an anti-PD-1 antibody alone, or those two agents in combination.

Mice (8 for each regimen) were dosed with one of the following regimens: (1) twice daily oral dosing with 100 mg/kg of Compound 124; (2) biweekly IP injections with 10 mg/kg of anti-PD1 antibody (clone RMP1-14); (3) a combination of twice daily Compound 124 (100 mg/kg) and biweekly anti-PD1 antibody (10 mg/kg) or (4) an orally dosed vehicle control. Subcutaneous tumor volumes were measured three times per week starting at three days post-first dosing using caliper measurements in 2 dimensions (looking down at the tumor, using the calipers to make 2 diameter measurements at right angles to each other). The tumor volume was then calculated using the following standard formula: Tumor Volume=$0.5*A*B^2$, wherein A=longest diameter of the tumor; and B=shortest diameter of the tumor. As shown in FIG. 3, mice treated with a combination of Compound 124 and anti-PD1 demonstrated slower tumor growth than mice treated with either agent as a monotherapy.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists every possible subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

Those skilled in the art will recognize, or be able to ascertain using no more than routine experimentation, many equivalents to the specific embodiments of the disclosure described and claimed herein. Such equivalents are intended to be encompassed by the following claims.

What is claimed is:
1. A compound of structural formula II:

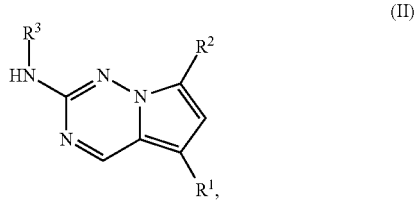

(II)

or a pharmaceutically acceptable salt thereof, wherein:
$R^1$ is pyridin-3-yl, pyridin-4-yl, pyrazol-4-yl, cyclohexyl, or 8-azabicyclo[3.2.1]oct-2-ene-3-yl, wherein $R^1$ is optionally substituted with up to four independently selected substituents;
$R^2$ is cyclohexyl substituted with hydroxy and optionally substituted with one or two additional substituents independently selected from $C_1$-$C_4$ alkyl and fluoro, or is 4,5,6,7-tetrahydro-1H-indazolyl optionally substituted with one to three substituents independently selected from $C_1$-$C_4$ alkyl and fluoro; and
$R^3$ is —$C_3$-$C_8$ alkyl, —($C_2$-$C_6$ alkylene)-O—($C_1$-$C_6$ alkyl), $C_3$-$C_6$ cycloalkyl, or —($C_2$-$C_6$ alkylene)-$C_3$-$C_6$ cycloalkyl, wherein $R^3$ is optionally substituted with 1-5 substituents independently selected from deuterium, halo, and —OH.

2. The compound of claim 1 or the pharmaceutically acceptable salt thereof, wherein $R^1$ is optionally substituted with up to four substituents independently selected from halo, hydroxy, -CN, -($C_1$-$C_4$ alkyl optionally substituted with one or more substituents selected from cyano, hydroxy and halo), -C(O)NH$_2$, -COOH, -($C_0$-$C_3$ alkylene)-C(O)-($C_1$-$C_4$ alkyl), -($C_0$-$C_3$ alkylene)-C(O)-NH-($C_1$-$C_4$ alkyl), -($C_0$-$C_3$ alkylene)-C(O)-NH-S(O)$_2$-($C_1$-$C_4$ alkyl), -($C_0$-$C_3$ alkylene)-C(O)-O-($C_1$-$C_4$ alkyl), -($C_0$-$C_3$ alkylene)-COOH, -($C_0$-$C_4$ alkylene)-S(O)$_2$-($C_1$-$C_3$ alkyl), -($C_1$-$C_3$ alkylene)-O-($C_1$-$C_4$ alkyl), -S(O)(=NH)-($C_1$-$C_4$ alkyl), -S(O)$_2$-NH-($C_1$-$C_4$ alkyl), -(cyclopropyl)-(cyano-substituted $C_1$-$C_3$ alkyl), -(cyclopropyl)-C(O)-NH-($C_1$-$C_4$ alkyl), -($C_1$-$C_3$ alkylene)-C(O)-heterocyclyl, -C(O)-($C_0$-$C_3$ alkylene)-heterocyclyl, -(cyclopropyl)-C(O)-heterocyclyl, -($C_0$-$C_4$ alkylene)-heterocyclyl, -($C_0$-$C_3$ alkylene)-C(O)-NH-heterocyclyl, -($C_0$-$C_4$ alkylene)-aryl, and -($C_0$-$C_4$ alkylene)-heteroaryl, wherein the heterocyclyl or heteroaryl portion of the $R^1$ substituent is optionally further substituted.

3. The compound of claim 1 or the pharmaceutically acceptable salt thereof, wherein $R^1$ is 1-((1-oxetan-3-ylcarbonyl)azetidin-3-yl)pyrazol-4-yl, 1-(1-(1,1-dioxothiomorpholin-4-ylcarbonyl)-1-methylethan-1-yl)pyrazol-4-yl, 1-(1-(1-trifluoromethylcyclopropylcarbonyl)azetidin-3-yl) pyrazol-4-yl, 1-(1-(2,2,2-trifluoroethan-1-yl)azetidin-3-yl) pyrazol-4-yl, 1-(1-(2,2-dimethylmorpholin-4-ylcarbonyl)-1-methylethan-1-yl)pyrazol-4-yl, 1-(1-(2,6-dimethylmorpholin-4-ylcarbonyl)-1-methylethan-1-yl) pyrazol-4-yl, 1-(1-(2-oxa-6-azaspiro[3.3]heptan-6-ylcarbonyl)-1-methylethan-1-yl)pyrazol-4-yl, 1-(1-(2-oxa-6-azaspiro[3.4]octan-6-ylcarbonyl)-1-methylethan-1-yl) pyrazol-4-yl, 1-(1-(3,3,3-trifluoropropan -1-yl)azetidin-3-yl)pyrazol-4-yl, 1-(1-(8-oxa-3-azabicyclo[3.2.1]octan-3-ylcarbonyl)-1-methylethan-1-yl)pyrazol-4-yl, 1-(1-(azetidin-1-ylcarbonyl)-1-methylethan-1-yl)pyrazol-4-yl, 1-(1-(ethan-2-ylsulfonyl)-3-(cyanomethyl)azetidin-3-yl) pyrazol-4-yl, 1-(1-(hexahydro-1H -furo[3,4-c]pyrrol-5-yl-carbonyl)-1-methylethan-1-yl)pyrazol-4-yl, 1-(1-(isopropy-laminocarbonyl)cyclopropyl)pyrazol-4-yl, 1-(1-(morpholin-4-ylcarbonyl)-1-methylethan-1-yl)pyrazol-4-yl, 1-(1-(morpholin-4-ylcarbonyl)cyclopropyl)pyrazol-4-yl, 1-(1-(pyrrolidin-1-ylcarbonyl)cyclopropyl)pyrazol-4-yl, 1-(1,1-dioxotetrahydro-2H-thiopyran-4-yl)pyrazol-4-yl, 1-(1,3-dimethylpyrazol-5-yl)pyrazol-4-yl, 1-(1-acetylazetidin-3-yl)pyrazol-4-yl, 1-(1-acetylpyrrolidin-3-yl)pyrazol-4-yl, 1-(1-cyanocyclopropylmethyl)pyrazol-4-yl, 1-(1H -pyrazol-4-ylmethyl)ppyrazol-4-yl, 1-(1-hydroxy-3-chloropropan-2-yl)pyrazol-4-yl, 1-(1-hydroxylcarbonyl-1-methylethan-1-yl) pyrazol-4-yl, 1-(1-methoxycarbonylazetidin-3-yl)pyrazol -4-yl, 1-(1-methyl-2(1H)-pyridinon-5-ylmethyl)pyrazol-4-yl, 1-(1-methyl-2-oxopyrrolidin-4-ylmethyl)pyrazol-4-yl, 1-(1-methylaminocarbonyl-1-methylethan-1-yl)pyrazol-4-yl, 1-(1-methylsulfonylazetidin-3-yl)pyrazol-4-yl, 1-(1-t-butoxycarbonylpyrrolidin-3-yl)pyrazol-4-yl, 1-(2-(1,3,4-oxadiazol-2-yl)propan-2-yl)pyrazol-4-yl, 1-(2-(2-(2-hydroxypropan-2-yl)morpholin-4-ylcarbonyl)propan-2-yl) pyrazol-4-yl, 1-(2-(2,5-dioxa-8-azaspiro[3.5]nonan-8-ylcarbonyl)propan-2-yl)pyrazol-4-yl, 1-(2-(2-methyl-1,3,4-oxadiazol-5-yl)propan-2-yl)pyrazol -4-yl, 1-(2-(2-methyl-4,6-dihydro-5H-pyrrolo[3,4-d]thiazol-5-ylcarbonyl)propan-2-yl)pyrazol-4-yl, 1-(2-(2-methyl-6,7-dihydrothiazolo[4,5-c] pyridin-5-ylcarbonyl)propan-2-yl)pyrazol-4-yl, 1-(2-(3,5-dimethylpiperazin-1-ylcarbonyl)propan-2-yl)pyrazol-4-yl, 1-(2-(3-hydroxy-3-methylazetidin-1-ylcarbonyl)propan-2-yl)pyrazol-4-yl, 1-(2-(3-hydroxy-3-methylpiperidin-1-yl-carbonyl)propan-2-yl)pyrazol-4-yl, 1-(2-(3-hydroxy-3-methylpyrrolidin-1-ylcarbonyl)propan -2-yl)pyrazol-4-yl, 1-(2-(3-hydroxypyrrolidin-1-ylcarbonyl)propan-2-yl)pyrazol-4-yl, 1-(2-(4-cyano-4-methylpiperidin-1-ylcarbonyl)propan-2-yl)pyrazol-4yl, 1-(2-(4-hydroxy-4-methylpiperidin-1-ylcarbonyl)propan-2-yl)pyrazol-4-yl, 1-(2-(4-methyloxazol-2-yl)propan-2-yl)pyrazol-4-yl, 1-(2-(4-methylpiperazin-1-ylcarbonyl)propan-2-yl)pyrazol-4-yl, 1-(2-(5-(morpholin-4-yl)-1,3,4-oxadiazol-2-yl)propan-2-yl)pyrazol-4-yl, 1-(2-(5-(tetrahydrofuran-2-yl)-1,3,4-oxadiazol-2-yl)propan-2-yl)pyrazol-4-yl, 1-(2-(5-cyclopropyl-1,3,4-oxadiazol-2-yl)propan-2-yl)pyrazol-4-yl, 1-(2-(5-difluoromethyl-1,3,4-oxadiazol-2-yl)propan-2-yl)pyrazol-4-yl, 1-(2-(5-isopropyl-1,3,4-oxadiazol-2-yl)propan-2-yl)pyrazol-4-yl, 1-(2-(5-methyl-1,3,4-thiadiazol-2-yl)propan-2-yl)pyrazol-4-yl, 1-(2-(5-methyloxazol-2-yl)propan-2-yl)pyrazol-4-yl, 1-(2-(5-trifluoromethyl-1,3,4-oxadiazol-2-yl)propan-2-yl)pyrazol-4-yl, 1-(2-(methyl)-2-(morpholin-4-yl)propan-3-yl)pyrazol-4-yl, 1-(2-(methyl)-3-(morpholin-4-yl)propan-2-yl)pyrazol-4-yl, 1-(2-(pyrrolidin-1-ylcarbonyl)propan-2-yl)pyrazol-4-yl, 1-(2-cyanoethyl)pyrazol-4-yl, 1-(2-hydroxy-2-methylpropan-1-yl)pyrazol-4-yl, 1-(2-methoxyethyl)pyrazol-4-yl, 1-(2-methyl-3-hydroxypropan-2-yl)pyrazol-4-yl, 1-(2-methylpropyl)pyrazol-4-yl, 1-(2-methylsulfonylethan-1-yl)pyrazol-4-yl, 1-(2-morpholin-4-ylethyl)pyrazol-4-yl, 1-(2-oxopyrrolidin-3-yl)pyrazol-4-yl, 1-(2-oxopyrrolidin-4-ylmethyl)pyrazol-4-yl, 1-(3-methyl-1,2,4-oxadiazol-5-ylmethyl)ppyrazol-4-yl, 1-(3-methylsulfonylphenylmethyl)pyrazol-4-yl, 1-(4-methylpiperazin-1-ylcarbonylmethylppyrazol-4-yl, 1-(4-methylsulfonylphenylmethyl)pyrazol-4-yl, 1-(5-methyl-1,2,4-oxadiazol-3-ylmethylppyrazol-4-yl, 1-(5-methyl-1,3,4-oxadiazol-2-ylmethylppyrazol-4-yl, 1-(5-methylpyrazin-2-ylmethyl)pyrazol-4-yl, 1-(5-oxopyrrolidin-2-ylmethylpyrazol-4-yl, 1-(6-hydroxyhexahydrofuro[3,2-b]furan-3-yl)pyrazol-4-yl, 1-(6-methylpyrazin-2-ylmethyl)pyrazol-4-yl, 1-(ethoxycarbonylmethyl)pyrazol-4-yl, 1-(hexahydrofuro[2,3-b]furan-3-yl)pyrazol-4-yl, 1-(hydroxycarbonylmethyl)pyrazol-4-yl, 1-(isopropylaminocarbonylmethyl)pyrazol-4-yl, 1-(isopropylcarbonylmethyl)pyrazol-4-yl, 1-(methylaminocarbonylmethyl)pyrazol-4-yl, 1-(methylsulfonylaminocarbonylmethylppyrazol-4-yl, 1-(methylsulfonylmethyl)pyrazol-4-yl, 1-(morpholin-4-ylcarbonylmethyl)pyrazol-4-yl, 1-(oxetan-2-ylmethyl)pyrazol-4-yl, 1-(oxetan-3-ylmethyl)pyrazol-4-yl, 1-(pyrazin-2-ylmethyl)pyrazol-4-yl, 1-(pyridazin-4-ylmethyl)pyrazol-4-yl, 1-(pyridin-3-ylmethyl)ppyrazol-4-yl, 1-(pyrrolidin-1-ylcarbonylmethylppyrazol-4-yl, 1-(tetrahydrofuran-2-ylmethyl)pyrazol-4-yl, 1-(tetrahydrofuran-3-yl)pyrazol-4-yl, 1-(tetrahydrofuran-3-ylaminocarbonylmethylppyrazol-4-yl, 1-(tetrahydropyran-4-yl)pyrazol-4-yl, 1-(tetrahydropyran-4-ylmethyl)pyrazol-4-yl, 1,3-dimethylpyrazol-4-yl, 1-difluoromethylpyrazol-4-yl, 1H-pyrazol-4-yl, 1-methylpyrazol-3-yl, 1-methylpyrazol-4-yl, 1-oxetan-3-ylpyrazol-4-yl, 1-t-butylpyrazol-4-yl, 2-(1,1-dioxothiomorpholin-4-yl)pyridin-4-yl, 2-(1-methylpiperidin-3-yloxy)pyridin-4-yl, 2-(1-methylpiperidin-4-yloxy)pyridin-4-yl, 2-(1-methylpyrrolidin-3-yloxy)pyridin-4-yl, 2-(2-methoxyethan-1-yloxy)pyridin-4-yl, 2-(3-oxopiperazin-l-yl)pyridin-4-yl, 2-(4-acetylpiperazin-1-yl)pyridin-4-yl, 2-(4-methylpiperazin-l-yl)pyridin-4-yl, 2-(4-methylsulfonylpiperazin-1-yl)pyridin-4-yl, 2-(morpholin-4-yl)pyridin-4-yl, 2-(oxetan-3-yloxy)pyridin-4-yl, 2-(piperidin-3-yloxy)pyridin-4-yl, 2-(piperidin-4-yloxy)pyridin-4-yl, 2-(pyrrolidin-3-yloxy)pyridin-4-yl, 2,6-dimethylpyridin-4-yl, 2-isopropoxypyridin-4-yl, 2-isopropylaminopyridin-4-yl, 2-methylaminocarbonyl-6-methylpyridin-4-yl, 2-methylaminopyridin-4-yl, 2-methylpyridin-4-yl, 2-morpholin-4-yl, 2-pyrrolidin-1-ylpyridin-4-yl, 4-(1,1-dioxothiomorpholin-4-ylcarbonyl)cyclohexyl, 4-(2-oxa-6-azaspiro[3.3]heptan-6-ylcarbonyl)cyclohexyl, 4-(4,4-difluoropiperidin-1-ylcarbonyl)cyclohexyl, 4-(4-methylpiperazin-1-yl)carbonylcyclohexyl, 4-(morpholin-4-ylcarbonyl)cyclohexyl, 4-hydroxycarbonylcyclohexyl, 4-methylpyridin-3-yl, 5-(4-methylpiperazin-1-ylcarbonyl)pyridin-3-yl, 5-(morpholin-4-ylmethyl)pyridin-3-yl, 5-(pyrrolidin-1-ylcarbonyl)pyridin-3-yl, 5-(S-imino(methyl)sulfinyl)pyridin-3-yl, 5-aminocarbonylpyridin-3-yl, 5-cyanopyridin-3-yl, 5-dimethylaminocarbonylpyridin-3-yl, 5-fluoropyridin-3-yl, 5-hydroxycarbonylpyridin-3-yl, 5-methylaminocarbonylpyridin-3-yl, 5-methylaminosulfonylpyridin-3-yl, 5-methylpyridin-3-yl, 5-methylsulfonylpyridin-3-yl, 6-(1-methyl-4,5,6,7-tetrahydro-1H-pyrazolo[3,4-c]pyridin-6-yl)pyridin-4-yl, 6-(1-methylpiperazin-4-yl)pyridin-3-yl, 6-(2-(2-hydroxypropan-2yl)morpholin-4-yl)pyridin-4-yl, 6-(2,5-dioxa-8-azaspiro[3.5]nonan-8-yl)pyridin-4-yl, 6-(2-hydroxypropan-2-yl)pyridin-4-yl, 6-(2-methyl-4,5,6,7-tetrahydro-3H-imidazo[4,5-c]pyridin-5-yl)pyridin-4-yl, 6-(2-methyl-4,5,6,7-tetrahydrothiazolo[5,4-c]pyridin-5-yl)pyridin-4-yl, 6-(2-methyl-5,6-dihydro-4H-pyrrolo[3,4-d]thiazol-5-yl)pyridin-4-yl, 6-(2-oxa-6-azaspiro[3.3]heptan-6-yl)pyridin-4-yl, 6-(2-oxa-6-azaspiro[3.4]octan-6-yl)pyridin-4-yl, 6-(2-oxa-7-azaspiro[3.5]nonan-7-yl)pyridin-4-yl, 6-(2-oxo-oxazol-3-yl)pyridin-4-yl, 6-(3-methyl-3-hydroxyazetidin-1-yl)pyridin-4-yl, 6-(3-methyl-3-hydroxypyrrolidin-1-yl)pyridin-4-yl, 6-(3-oxa-7-azaspiro[3.5]nonan-7-yl)pyridin-4-yl, 6-(3-oxomorpholin-4-yl)pyridin-4-yl, 6-(4-(cyclopropylsulfonyl)piperazin-1-yl)pyridin-4-yl, 6-(4-(N-isopropyl-N-ethylaminocarbonyl)piperazin-1-yl)pyridin-4-yl, 6-(4-(oxetan-3-yl)piperazin-1-yl)pyridin-4-yl, 6-(4-(oxetan-3-ylcarbonyl)piperazin-1-yl)pyridin-4-yl, 6-(4-(oxetan-3-ylmethyl)piperazin-1-yl)pyridin-4-yl, 6-(4-(oxetan-3-yloxycarbonyl)piperazin-1-yl)pyridin-4-yl, 6-(4-methoxycarbonylpiperazin-1-yl)pyridin-4-yl, 6-(4-methyl-4-hydroxypiperidin-1-yl)pyridin-4-yl, 6-(4-methylpiperazin-1-ylcarbonyl)pyridin-3-yl, 6-(4-methylpiperazin-1-ylmethyl)pyridin-4-yl, 6-(4-trifluoromethylsulfonylpiperazin-1-yl)pyridin-4-yl, 6-(8-oxa-3-azabicyclo[3.2.]octan-3-yl)pyridin-4-yl, 6-(hexahydro-1H-furo[3,4-c]pyrrol-5-yl)pyridin-4-yl, 6-(isopropylamino-carbonyl)pyridin-3-yl, 6-(methylaminocarbonyl)pyridin-3-yl, 6-(morpholin-4-yl)pyridin-4-yl, 6-(morpholin-4-ylcarbonyl)pyridin-3-yl, 6-(morpholin-4-ylmethyl)pyridin-3-yl, 6-(oxetan-3-yl)pyridin-4-yl, 6-(piperazin-l-yl)pyridin-4-yl, 6-(pyridin-3-yloxy)pyridin-4-yl, 6-(S-imino(methyl)sulfinyl)pyridin-4-yl, 6-(S-methyl-S-iminosulfinyl)pyridin-3-yl, 6-(tetrahydro-pyran-3-ylamino)pyridin-4-yl, 6-(tetrahydropyran-4-ylamino)pyridin-4-yl, 6-fluoropyridin-4-yl, 6-methylaminosulfonylpyridin-3-yl, 6-methylpyridin-3-yl, 6-methylpyridin-4-yl, or 6-methylsulfonylpyridin-3-yl.

4. The compound of claim 1 or the pharmaceutically acceptable salt thereof, wherein $R^2$ is 4-hydroxycyclohexyl optionally substituted with one to three substituents selected from -$CH_3$ and fluoro, or is 4,5,6,7-tetrahydro-1H-indazol-5-yl.

5. The compound of claim 1 or the pharmaceutically acceptable salt thereof, wherein $R^3$ is isopropyl, n-butanyl, heptan-2-yl, propan-2-yl, 3-methoxypropan-2-yl, 3,3-(difluoromethoxy)propan-2-yl, 3,3-difluoropropan-2-yl, 3-cyclopropylpropan-2-yl, 4,4,4-trifluorobutan-2-yl, 4-fluorobutan-2-yl, 4,4-difluorobutan-2-yl, 2-methoxyethan-l-yl, 2-cyclopropanylethan-1-yl, or 3,3,3-trifluoropropan-1-yl.

6. The compound of claim 1, having structural Formula IV:

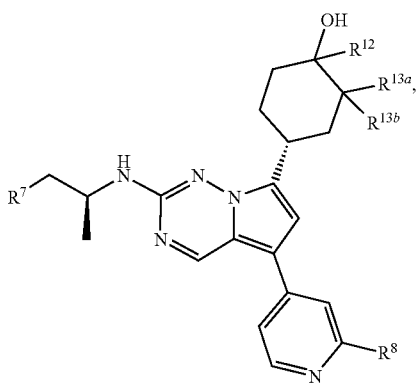

(IV)

or structural Formula V:

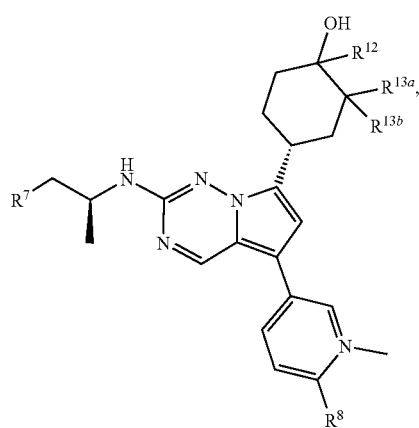

(V)

or a pharmaceutically acceptable salt thereof, wherein:
- $R^8$ is -($C_0$-$C_4$ alkylene)-S(O)$_2$-($C_1$-$C_3$ alkyl), -C(O)-NH-($C_1$-$C_4$ alkyl), -$C_1$-$C_4$ alkyl optionally substituted with one or more of halo, hydroxy and cyano, -NH-($C_1$-$C_4$ alkyl), -O-($C_1$-$C_3$ alkylene)-O-($C_1$-$C_4$ alkyl), -O-($C_1$-$C_4$ alkyl), -S(O)(=NH)-($C_1$-$C_4$ alkyl), -S(O)$_2$-NH-($C_1$-$C_4$ alkyl), -($C_0$-$C_3$ alkylene)-C(O)-heterocyclyl, -($C_0$-$C_3$ alkylene)-NH-heterocyclyl, -($C_0$-$C_4$ alkylene)-heterocyclyl, -O-heteroaryl, or -O-heterocyclyl, wherein any heterocyclyl, or heteroaryl portion of $R^8$ is optionally further substituted;
- $R^7$ is -O-$C_1$-$C_3$ alkyl, $C_1$-$C_3$ haloalkyl, or -O-$C_1$-$C_3$ haloalkyl;
- $R^{12}$ is hydrogen or $C_1$-$C_4$ alkyl; and
- each is $R^{13a}$ and $R^{13b}$ is independently selected from hydrogen and fluoro.

7. The compound of claim 6 or the pharmaceutically acceptable salt thereof, wherein $R^8$ is -CH$_3$, -C(O)NHCH$_3$, -C(O)NHCH(CH$_3$)$_2$, -NHCH(CH$_3$)$_2$, -NHCH$_3$, -S(=O)(=NH)-CH$_3$, -S(=O)$_2$-CH$_3$, -S(=O)$_2$-NH-CH$_3$, 1,1-dioxothiomorpholin-4-yl, 1-methyl -1,4,5,7-tetrahydro-6H-pyrazolo[3,4-c]pyridin-6-yl, 1-methylpiperidin-3-yloxy, 1-methylpiperidin-4-yloxy, 1-methylpyrrolidin-3-yloxy, 1-oxa-7-azospiro[3.5]nonan-7-yl, 2-(2-hydroxypropan-2-yl)morpholin-4-yl, 2,5-dioxa-8-azospiro[3.5]nonan-8-yl, 2-methoxyethan-1-yloxy, 2-methyl-4,6-dihydro-5H-pyrrolo[3,4-d]thiazol-5-yl, 2-methyl-6,7-dihydrothiazolo[5,4-c]pyridin-5(4H)-yl, 2-oxa-6-azospiro[3.3]heptan-6-yl, 2-oxa-6-azospiro[3.5]octan-6-yl, 2-oxa-7-azospiro[3.5]nonan-7-yl, 2-oxo-oxazolidin-3-yl, 3-oxomorpholin-4-yl, 3-oxopiperazin-1-yl, 4-(N-ethyl-N-isopropylaminocarbonyl)piperazin-1-yl, 4-(oxetan-3-yl)piperazin-1-yl, 4-(oxetan-3-ylmethyl)piperazin-1-yl, 4-acetylpiperazin-1-yl, 4-cyclopropylsulfonylpiperazin-1-yl, 4-methoxycarbonylpiperazin-1-yl, 4-methylpiperazin-1-yl, 4-methylpiperazin-1-ylmethyl, 4-sulfonylmethylpiperazin-1-yl, 4-trifluoromethylsulfonylpiperazin-1-yl, 8-oxa-3-azabicyclo[3.2.1]octan-3-yl, isopropyloxy, morpholin-4-carbonyl, morpholin-4-yl, morpholin-4-ylmethyl, oxetan-3-yl, oxetan-3-yloxy, piperazin-1-yl, piperidin-3-yloxy, piperidin-4-yloxy, pyridin-3-yloxy, pyrrolidin-1-yl, pyrrolidin-3-yloxy, tetrahydro-1H-furo[3,4-c]pyrrol-5-yl, tetrahydrofuran-3-ylamino, or tetrahydropyran-4-yl.

8. The compound of claim 6 or the pharmaceutically acceptable salt thereof, wherein $R^8$ is morpholin-4-yl, -S(=O)(=NH)-CH$_3$, or -S(=O)$_2$-CH$_3$.

9. The compound of claim 6 or the pharmaceutically acceptable salt thereof, wherein $R^7$ is -OCH$_3$, -CF$_3$, or -OCHF$_2$.

10. The compound of claim 6 or the pharmaceutically acceptable salt thereof, wherein $R^{12}$ is hydrogen or -CH$_3$.

11. The compound of claim 10, wherein each of $R^{12}$, $R^{13a}$ and $R^{13b}$ is hydrogen and the compound has structural formula IVa

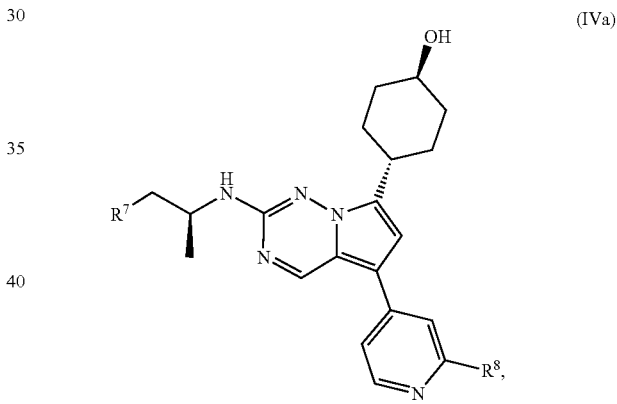

(IVa)

structural formula Va

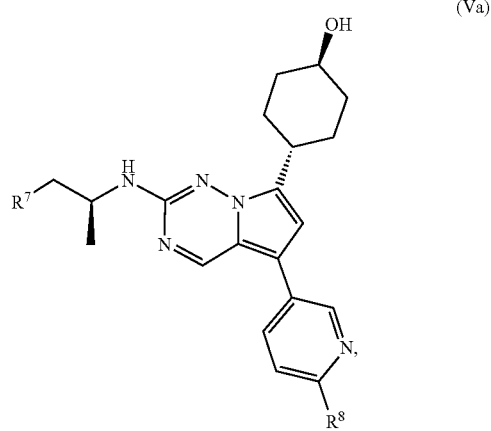

(Va)

or is a pharmaceutically acceptable salt of either of the foregoing.

12. The compound of claim 1, having structural Formula VI:

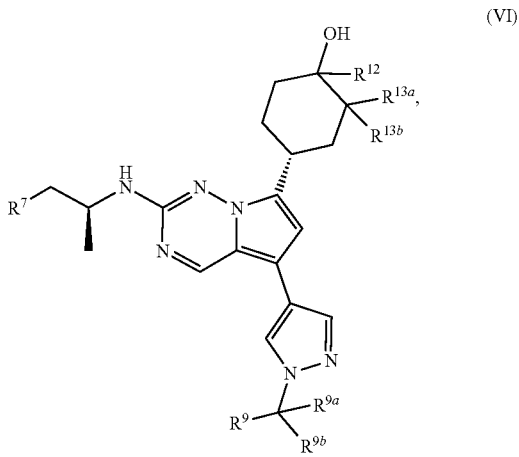

or a pharmaceutically acceptable salt thereof, wherein:
- $R^7$ is -O-$C_1$-$C_3$ alkyl, $C_1$-$C_3$ haloalkyl, or -O-$C_1$-$C_3$ haloalkyl;
- each of $R^{9a}$ and $R^{9b}$ are -$CH_3$, or $R^{9a}$ and $R^{9b}$ are taken together with the carbon atom to which they are bound to form cyclopropyl;
- $R^9$ is $C_1$-$C_3$ alkyl, $C_1$-$C_3$ hydroxyalkyl, -COOH, -C(O)NH-$C_1$-$C_4$ alkyl, -$CH_2$- heterocyclyl, -C(=O)-heterocyclyl or a 5-membered heteroaryl, wherein the heterocyclyl or heteroaryl portion of $R^9$ is optionally substituted with up to two substituents independently selected from oxo, cyclopropyl, -OH, -CN, -$C_1$-$C_3$ alkyl, and -$C_1$-$C_3$ hydroxyalkyl; and
- $R^{12}$ is hydrogen or $C_1$-$C_4$ alkyl; and
- each of $R^{13a}$ and $R^{13b}$ is independently selected from hydrogen and fluoro.

13. The compound of claim 12 or the pharmaceutically acceptable salt thereof, wherein $R^7$ is -$OCH_3$, -$CF_3$, or -$OCHF_2$.

14. The compound of claim 12 or the pharmaceutically acceptable salt thereof, wherein $R^9$ is -$CH_3$, -$CH_2OH$, -COOH, -C(O)$NHCH_3$, -C(O)NHCH($CH_3$)$_2$, 1,1-dioxothiomorpholin-4-ylcarbonyl, 2-(2-hydroxypropan-2-yl)morpholin-4-ylcarbonyl, 2,2-dimethylmorpholin-4-ylcarbonyl, 2,5-dioxa-8-azaspiro[3.5]nonan-8-ylcarbonyl, 2,6-dimethylmorpholin-4-ylcarbonyl, 2-oxa-6-azaspiro[3.3]heptan-6-ylcarbonyl, 2-oxa-6-azaspiro[3.4]octan-6-ylcarbonyl, 3-hydroxypyrrolidin-l-ylcarbonyl, 4-cyano-4-methylpiperidin-1-ylcarbonyl, 4-hydroxy-4-methylpiperidin-1-ylcarbonyl, 4-methylpiperazin-1-ylcarbonyl, 5-cyclopropyl-1,3,4-oxadiazol-2-yl, 5-methyl-1,3,4-oxadiazol-2-yl, 8-oxa-3-azabicyclo[3.2.1]octan-3-ylcarbonyl, azetidin-1-ylcarbonyl, morpholin-4-ylcarbonyl, morpholin-4-ylmethyl, pyrrolidin-1-ylcarbonyl, or tetrahydro-1H-furo[3,4-c]pyrrol-5(3H)-ylcarbonyl.

15. The compound of claim 14 or the pharmaceutically acceptable salt thereof, wherein $R^9$ is morpholin-4-ylcarbonyl, 4-methylpiperazin-1-ylcarbonyl, 2-oxa-6-azaspiro [3.3] heptan-6-ylcarbonyl, 3-methyl-3-hydroxypyrrolidin-1-ylcarbonyl, 5-methyl-1,3,4-oxadiazol-2-yl, or 5-methyl-1,3,4-thiadiazol-2-yl.

16. The compound of claim 12 or the pharmaceutically acceptable salt thereof, wherein $R^{12}$ is hydrogen or -$CH_3$.

17. The compound of claim 16, wherein each of $R^{12}$, $R^{13a}$ and $R^{13b}$ is hydrogen and the compound has structural formula VIa:

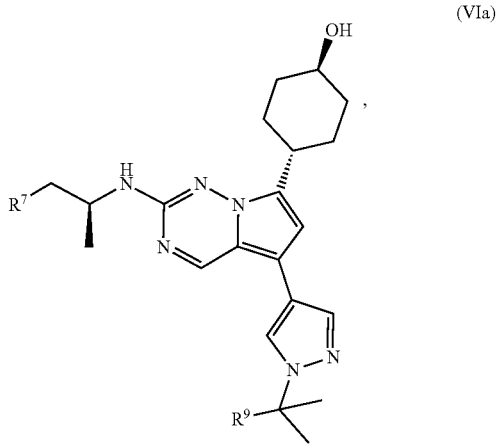

or the pharmaceutically acceptable salt thereof.

18. The compound of claim 1 having structural Formula VII:

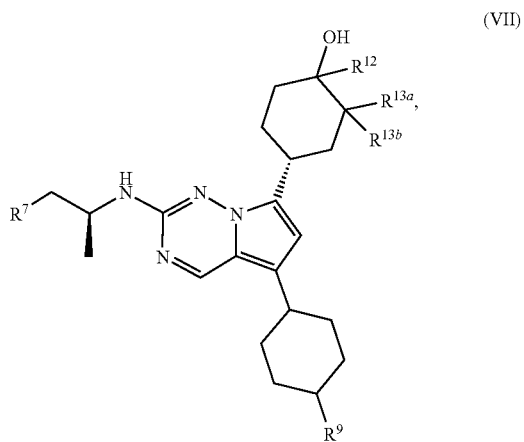

or a pharmaceutically acceptable salt thereof, wherein:
- $R^{7a}$ is $C_1$-$C_4$ alkyl, -O-$C_1$-$C_3$ alkyl, $C_1$-$C_3$ haloalkyl, or -O-$C_1$-$C_3$ haloalkyl;
- $R^9$ is -COOH, -C(=O)-heterocyclyl or a 5-membered heteroaryl, wherein $R^9$ is optionally substituted with up to two substituents independently selected from oxo, -OH and -$C_1$-$C_3$ alkyl; and
- $R^{12}$ is hydrogen, or $C_1$-$C_4$ alkyl; and
- each of $R^{13a}$ and $R^{13b}$ is independently selected from hydrogen and fluoro.

19. The compound of claim 18 or the pharmaceutically acceptable salt thereof, wherein $R^7$a is -($CH_2$)$_3CH_3$, -$OCH_3$, -$CF_3$, or -$OCHF_2$.

20. The compound of claim 19, wherein $R^{7a}$ is -($CH_2$)$_3$$CH_3$, -$OCH_3$, or -$CF_3$.

21. The compound of claim 17 or the pharmaceutically acceptable salt thereof, wherein $R^9$ is -COOH, morpholin-4-ylcarbonyl, 4-methylpiperazin-1-ylcarbonyl, 2-oxa-6- azaspiro[3.3]heptan-6-ylcarbonyl, 3-methyl-3-hydroxypyr-rolidin-1-ylcarbonyl, 5-methyl-1,3,4-oxadiazol-2-yl, 5-methyl-1,3,4-thiadiazol-2-yl, or 1,1-dioxothiomorpholin-4-ylcarbonyl.

22. The compound of claim 21 or the pharmaceutically acceptable salt thereof, wherein $R^9$ is morpholin-4-ylcarbonyl.

23. The compound of claim 17 or the pharmaceutically acceptable salt thereof, wherein $R^{12}$ is hydrogen or -CH$_3$.

24. The compound of claim 18 or the pharmaceutically acceptable salt thereof, wherein each of $R^{12}$, $R^{13a}$ and $R^{13b}$ is hydrogen and the compound has structural formula VIIa:

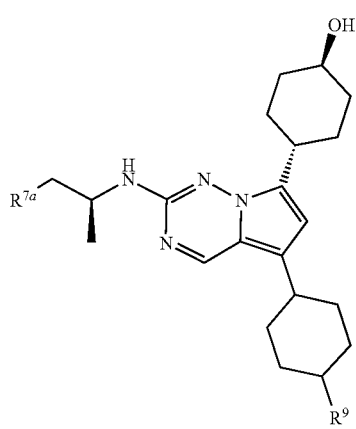

(VIIa)

25. A compound of claim 1, wherein the compound is:

Compound 108

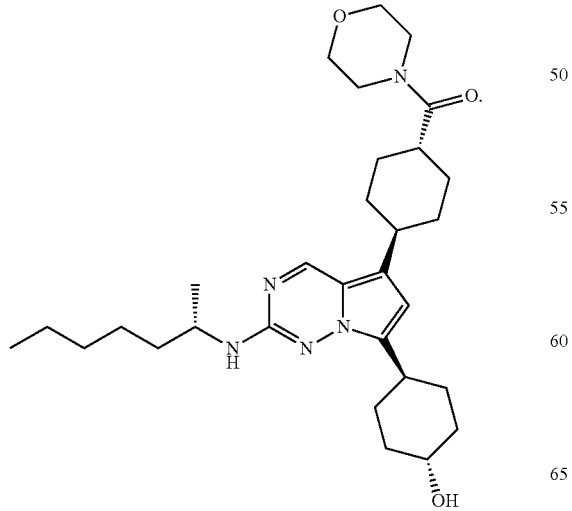

Compound 109

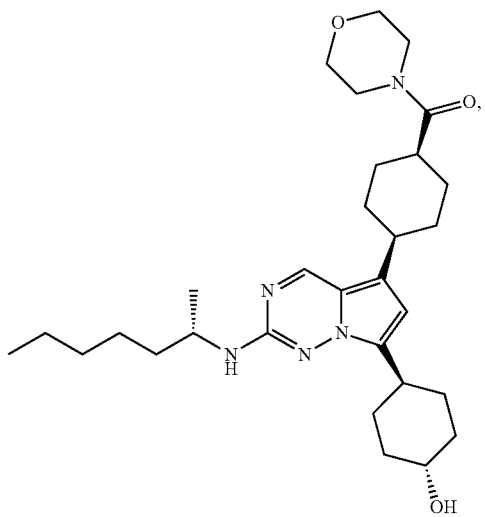

Compound 119

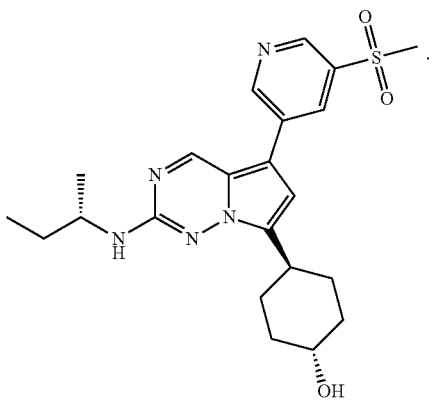

Compound 120

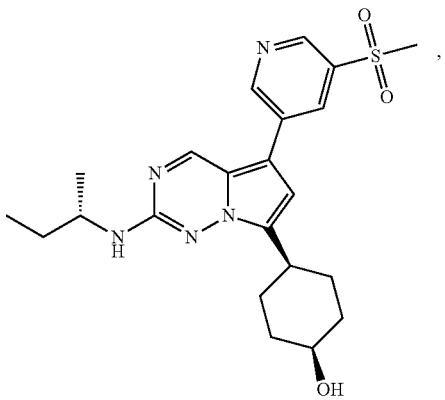

Compound 125
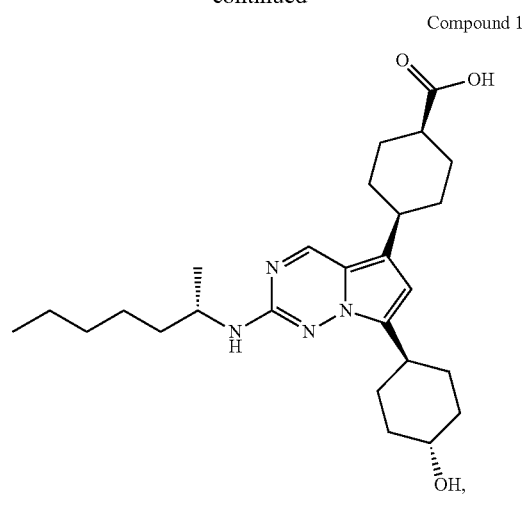
Compound 146
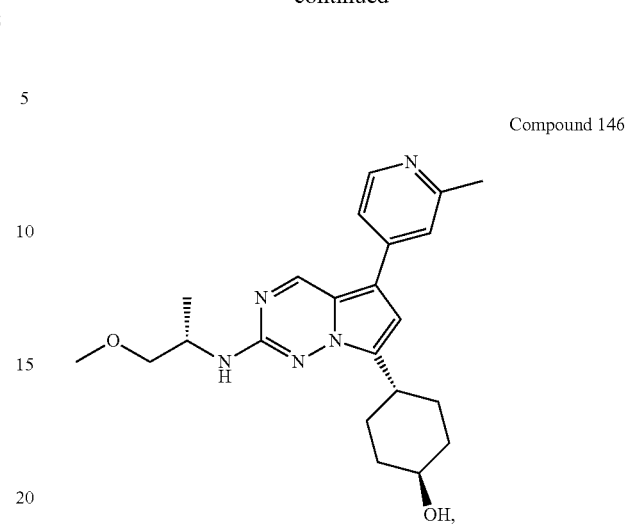
Compound 127
Compound 147
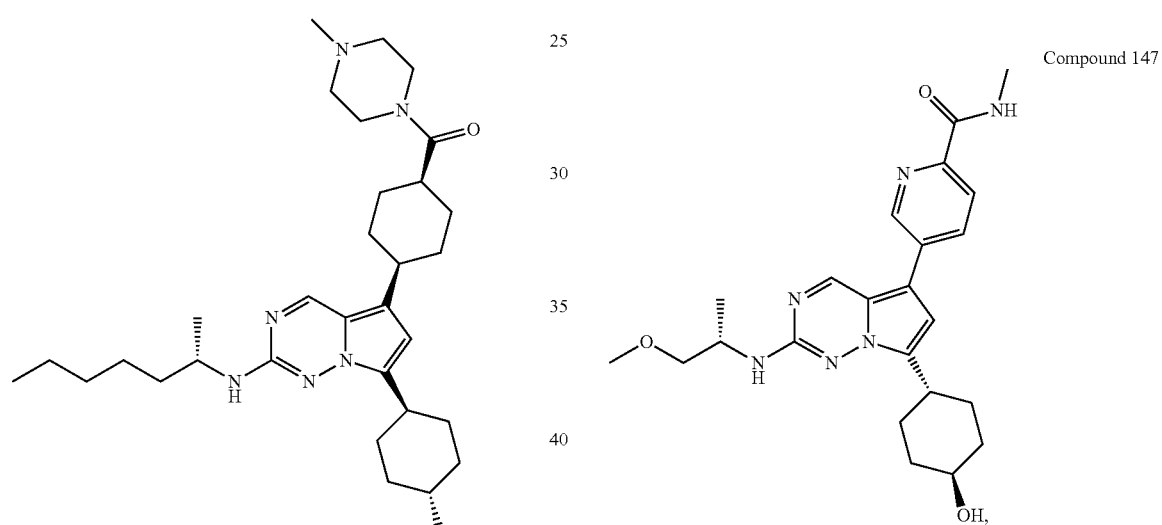
Compound 137
Compound 151
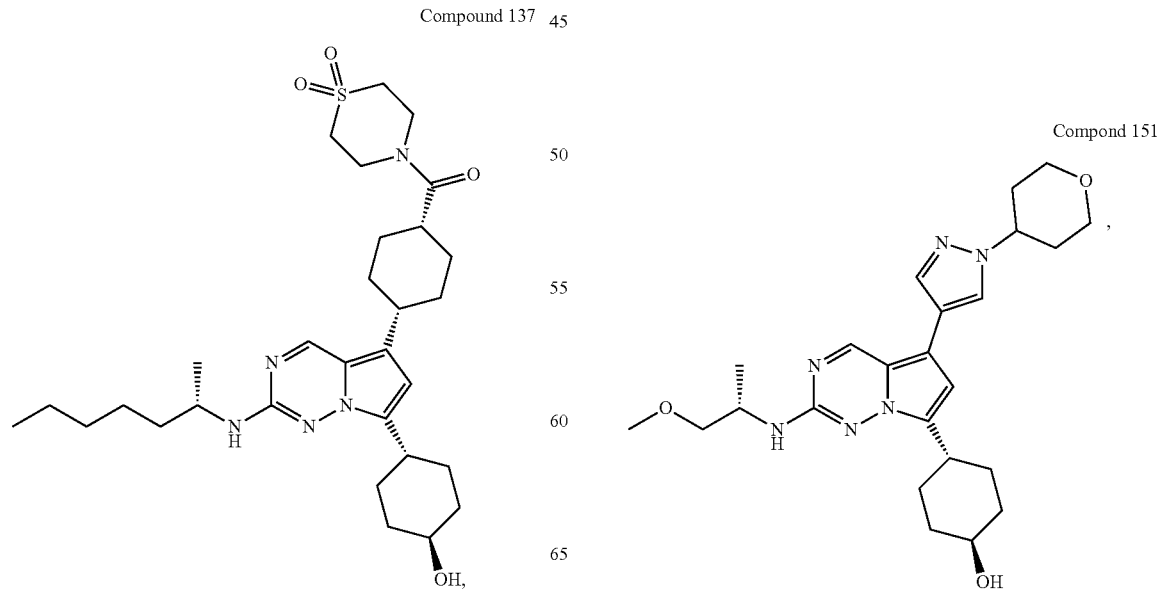

Compound 152
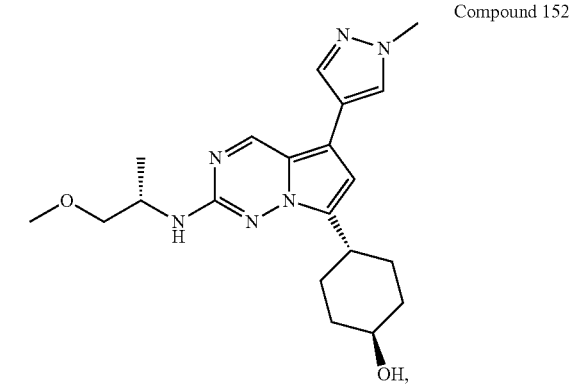
Compound 153
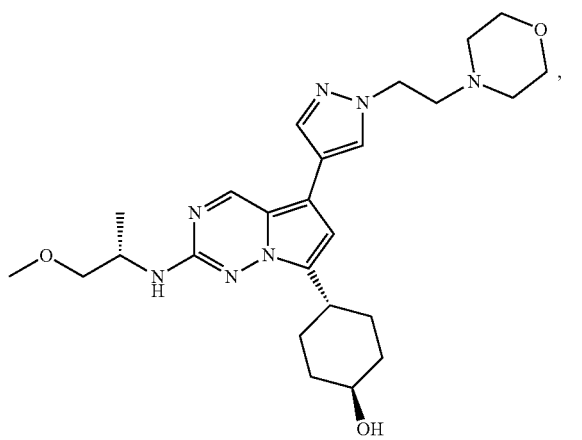
Compound 159
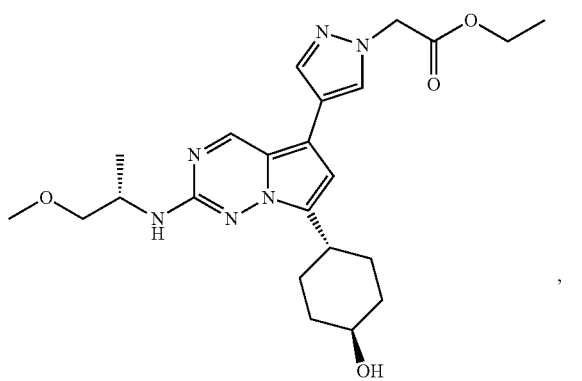
Compound 160
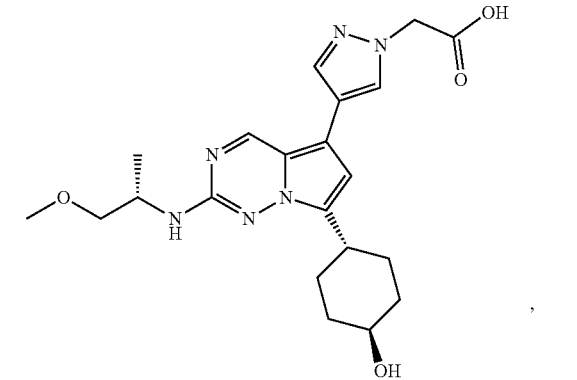
Compound 162
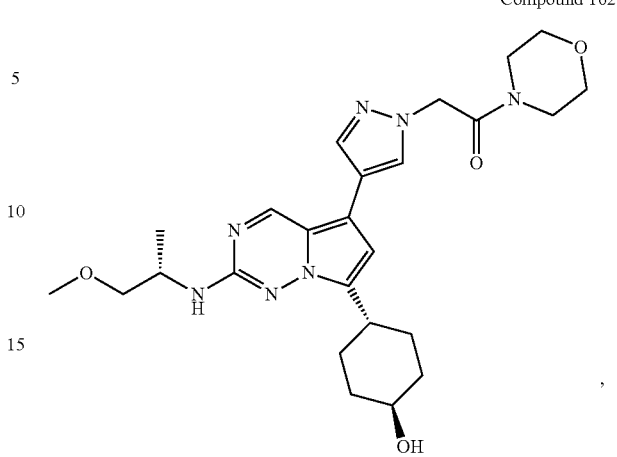
Compound 167
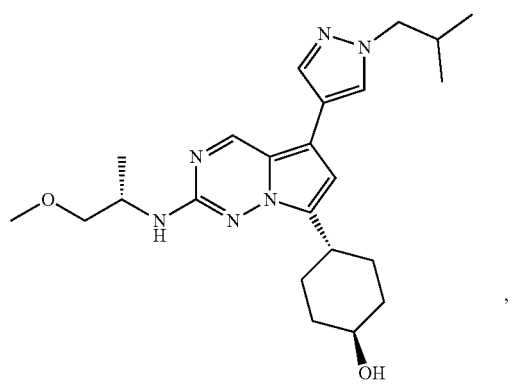
Compound 168
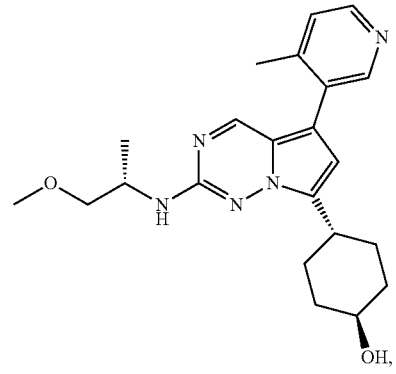
Compound 174
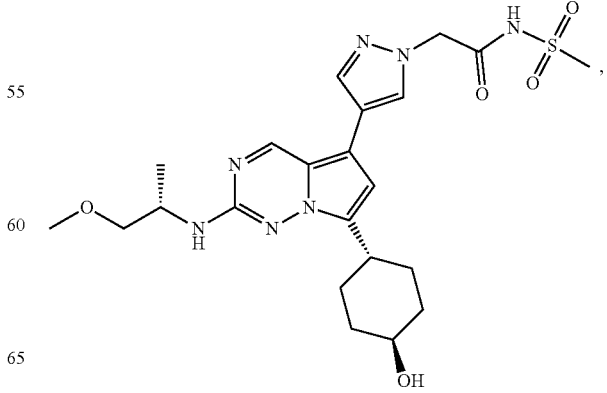

Compound 183
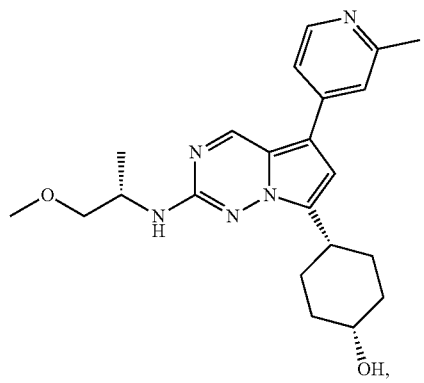
Compound 190
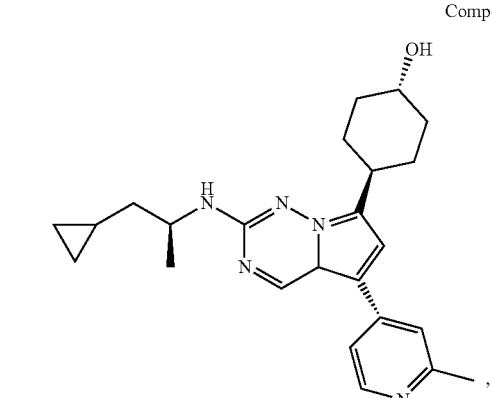
Compound 194
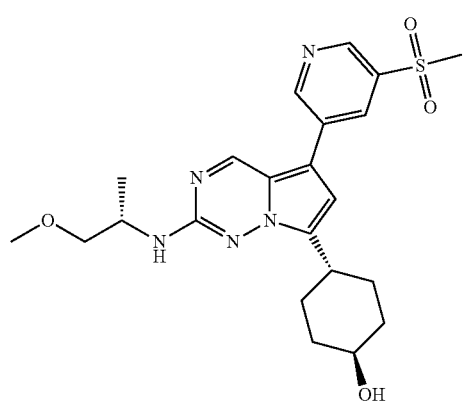
Compound 195
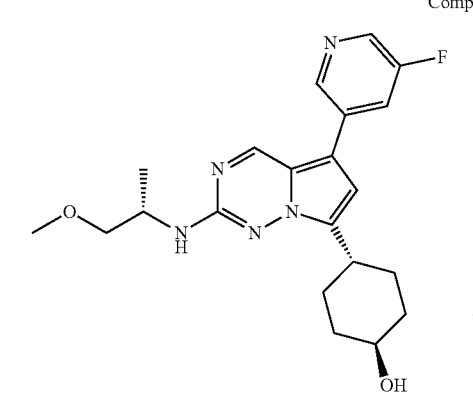
Compound 201
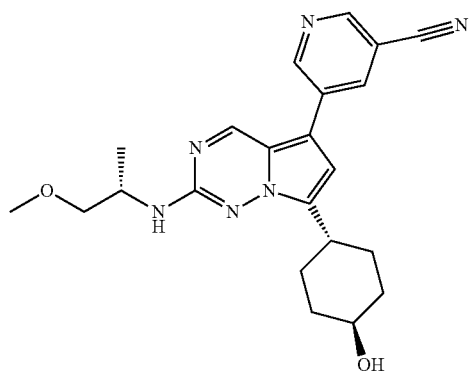
Compound 206
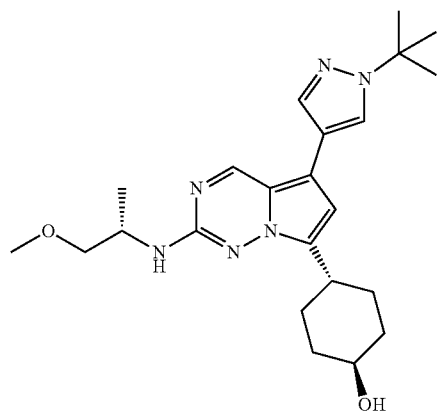
Compound 207
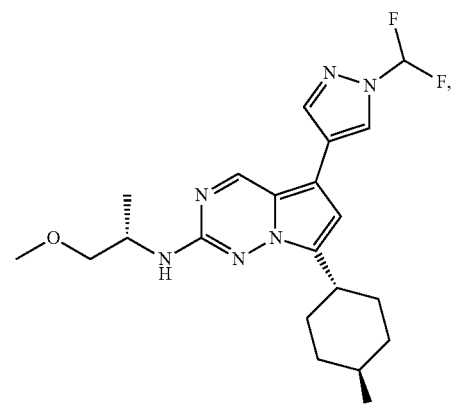
Compound 208
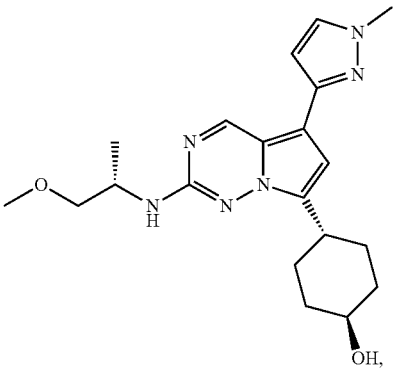

Compound 209
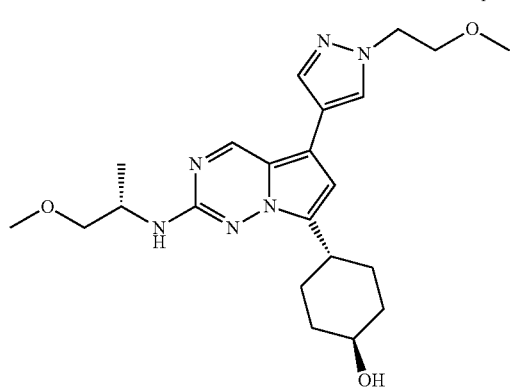
Compound 213
Compound 215
Compound 219
Compound 226
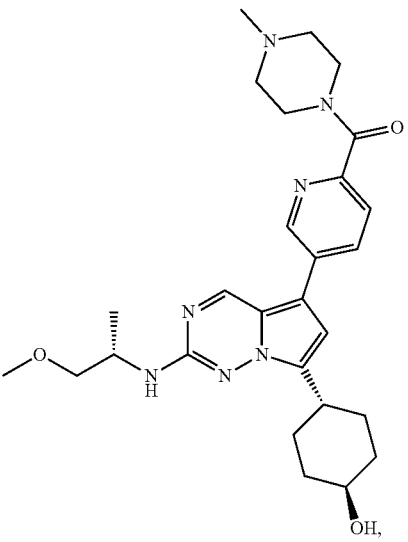
Compound 227
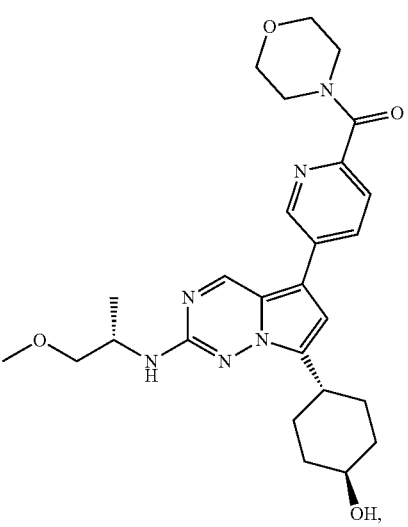
Compound 228
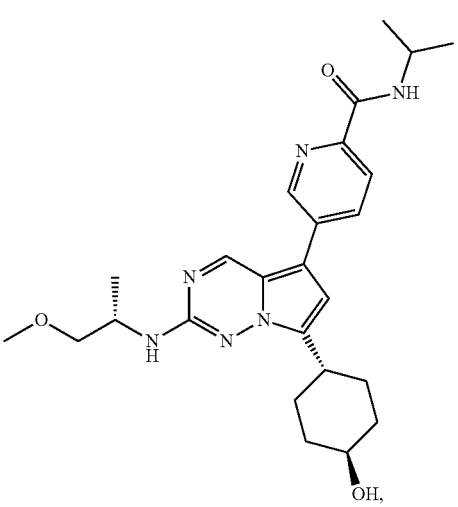

Compound 230
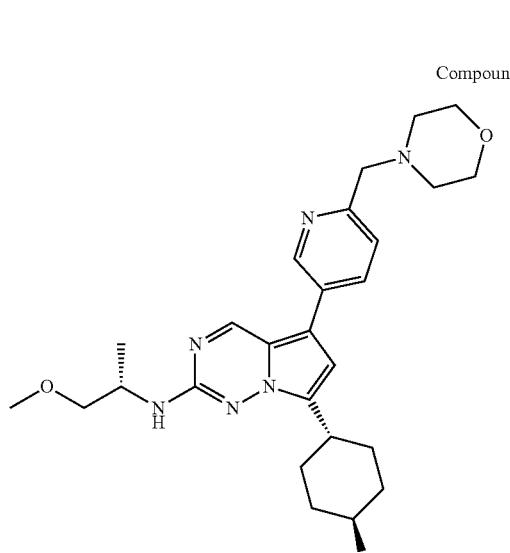
Compound 231
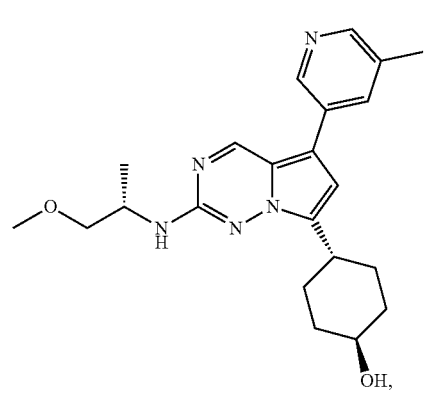
Compound 232
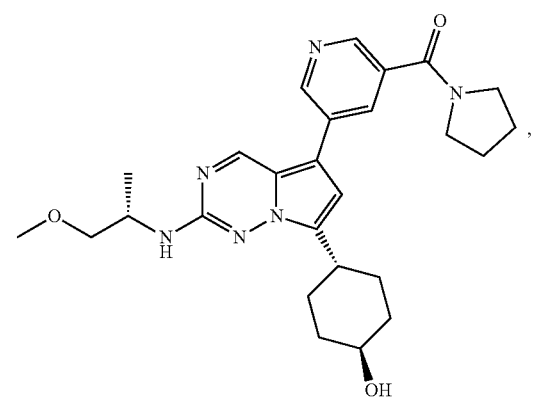
Compound 233
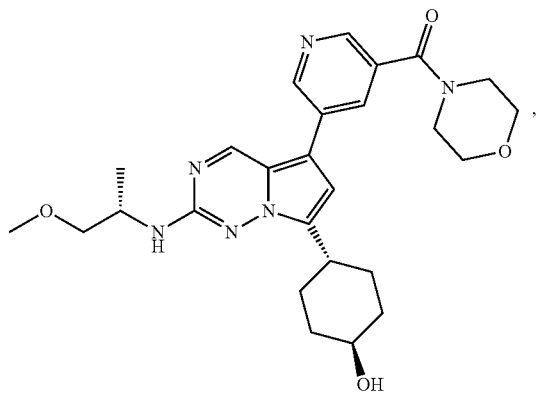
Compound 234
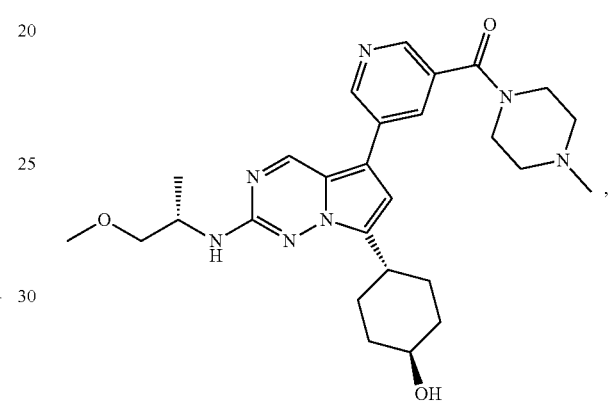
Compound 235
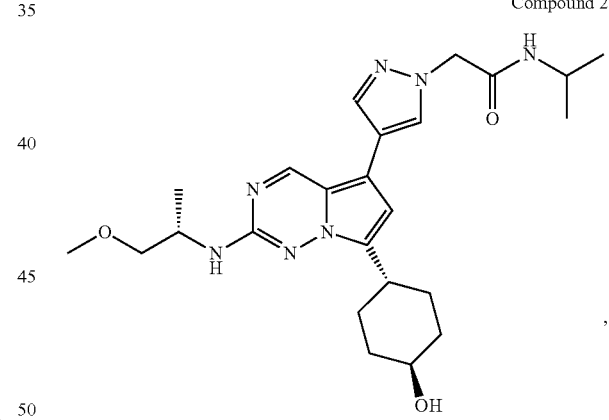
Compound 236
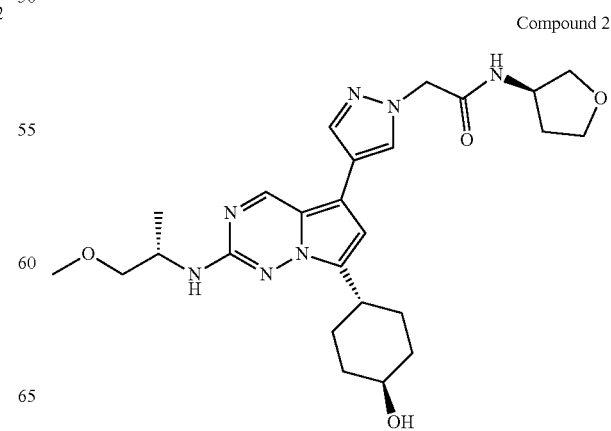

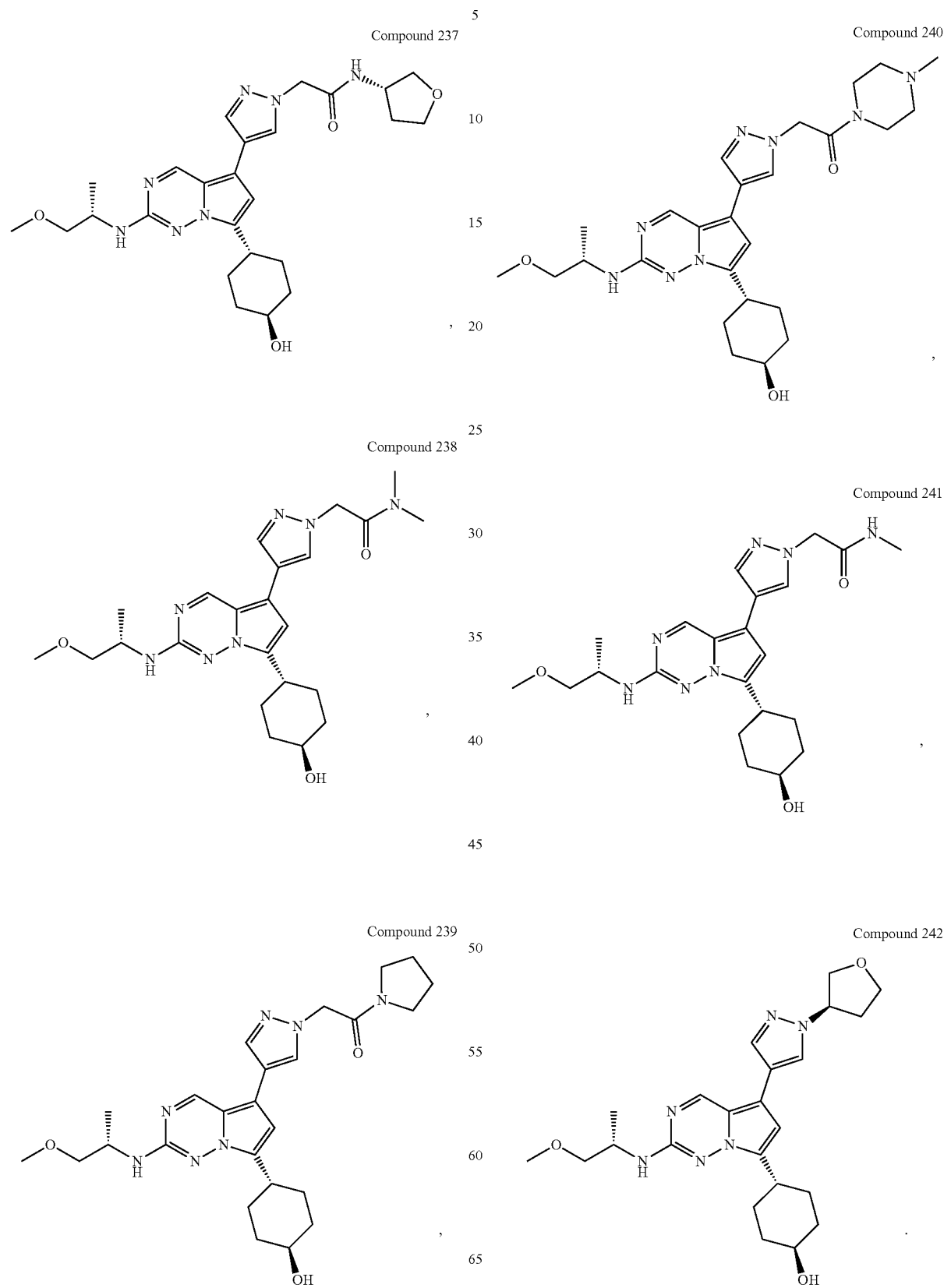

Compound 243
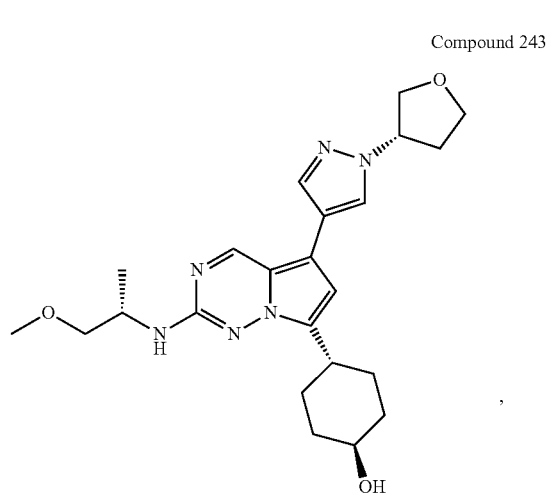
Compound 247
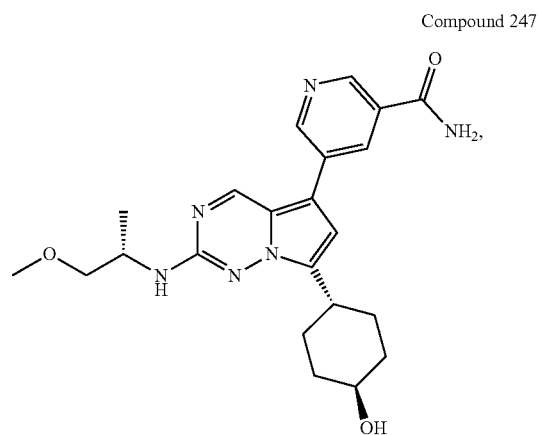
Compound 245
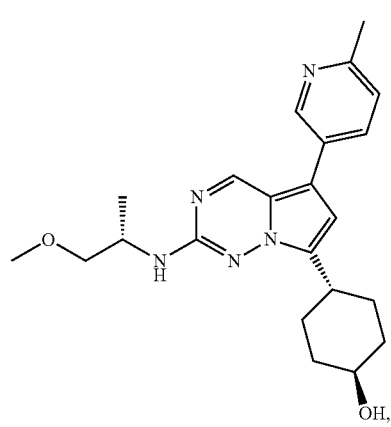
Compound 254
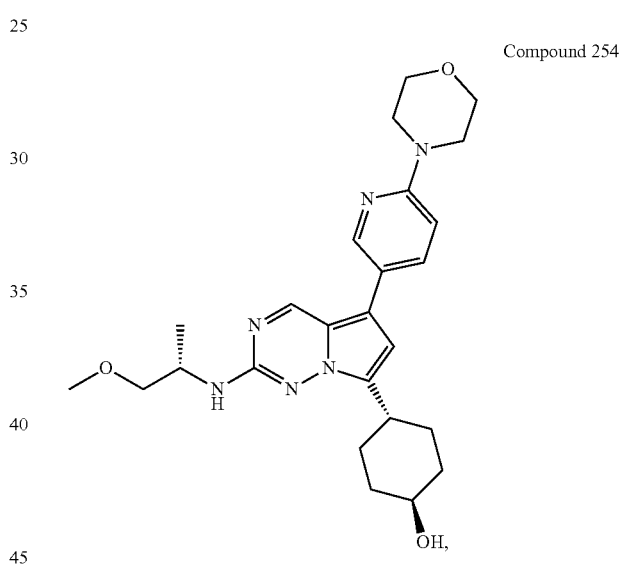
Compound 246
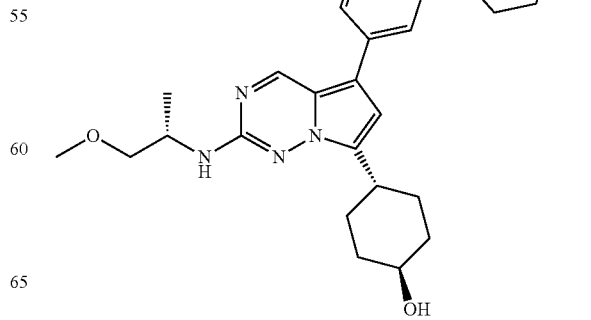
Compound 256

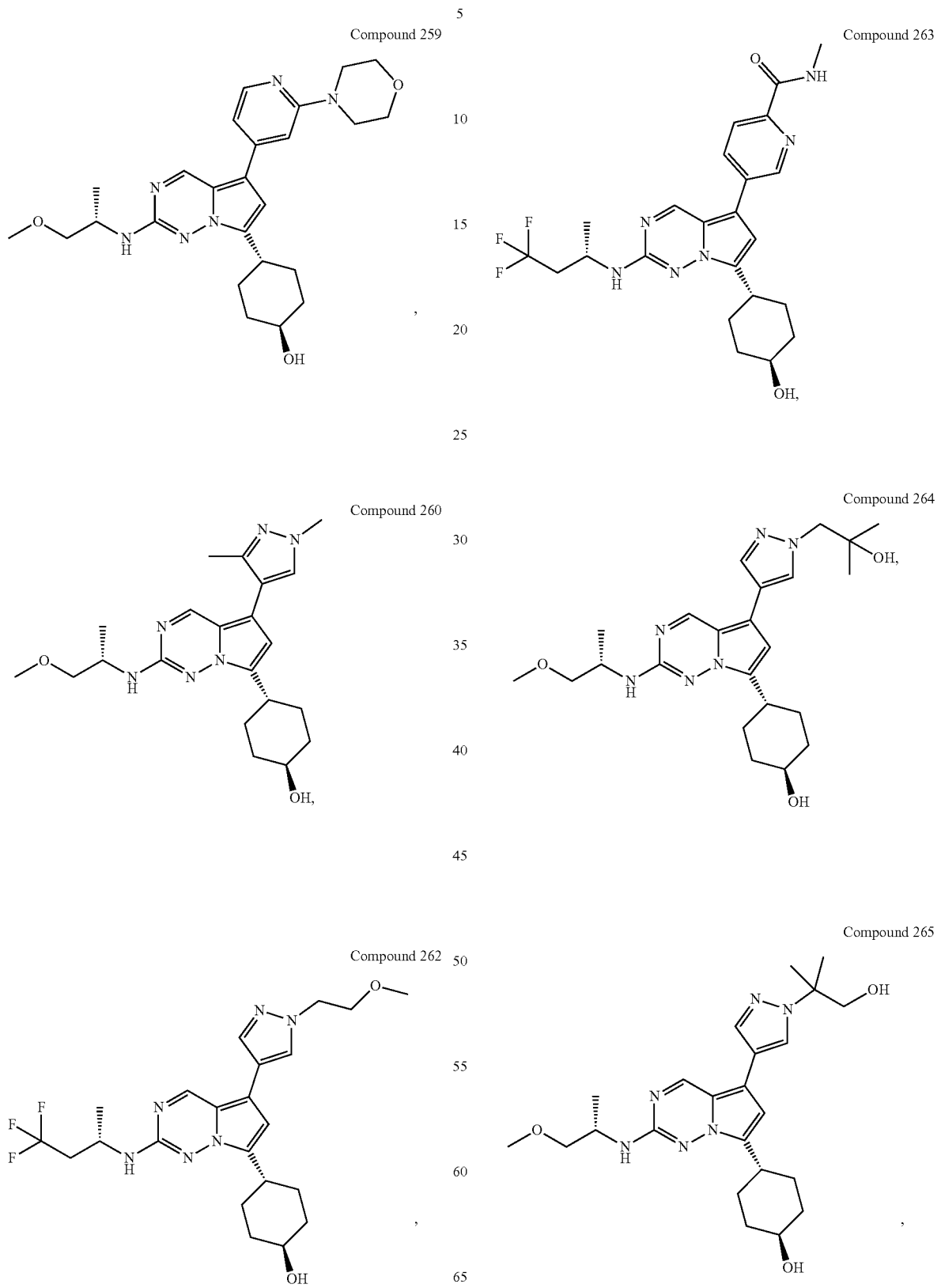

Compound 266
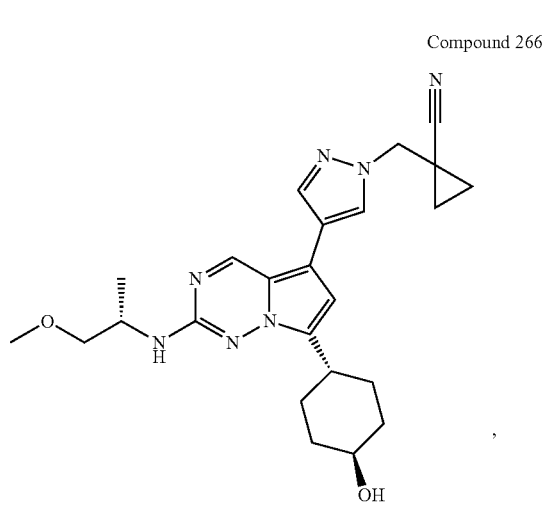
Compound 269
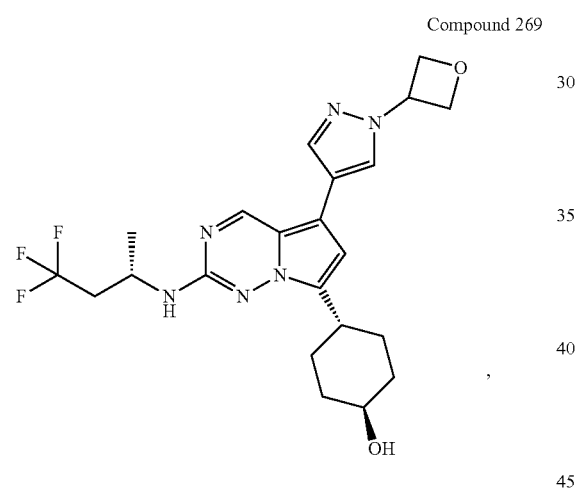
Compound 270
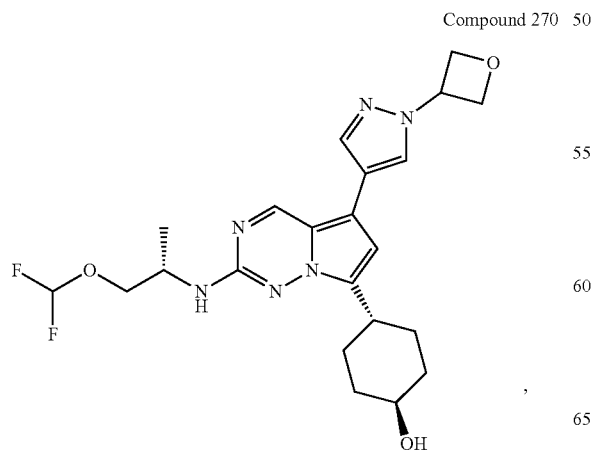
Compound 271
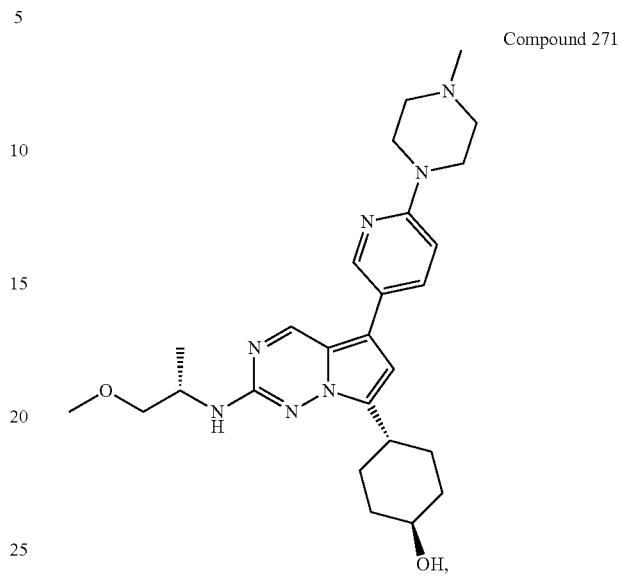
Compound 272
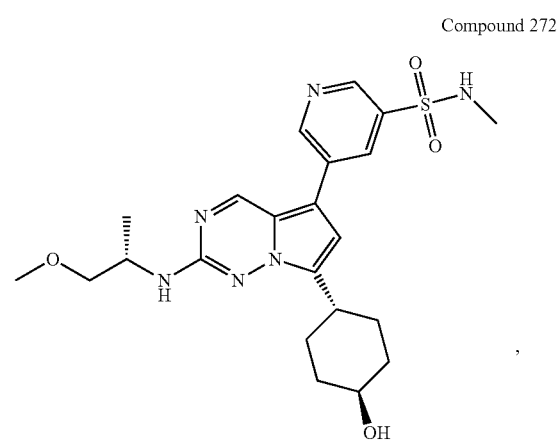
Compound 273
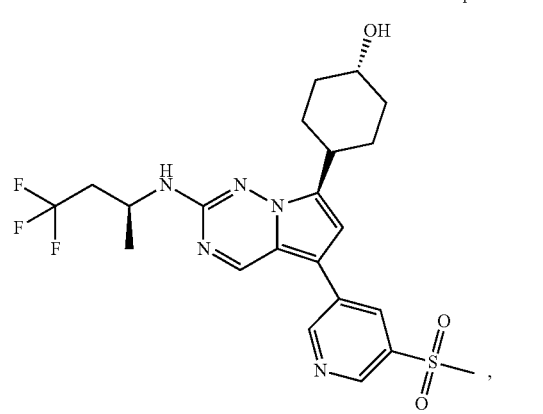

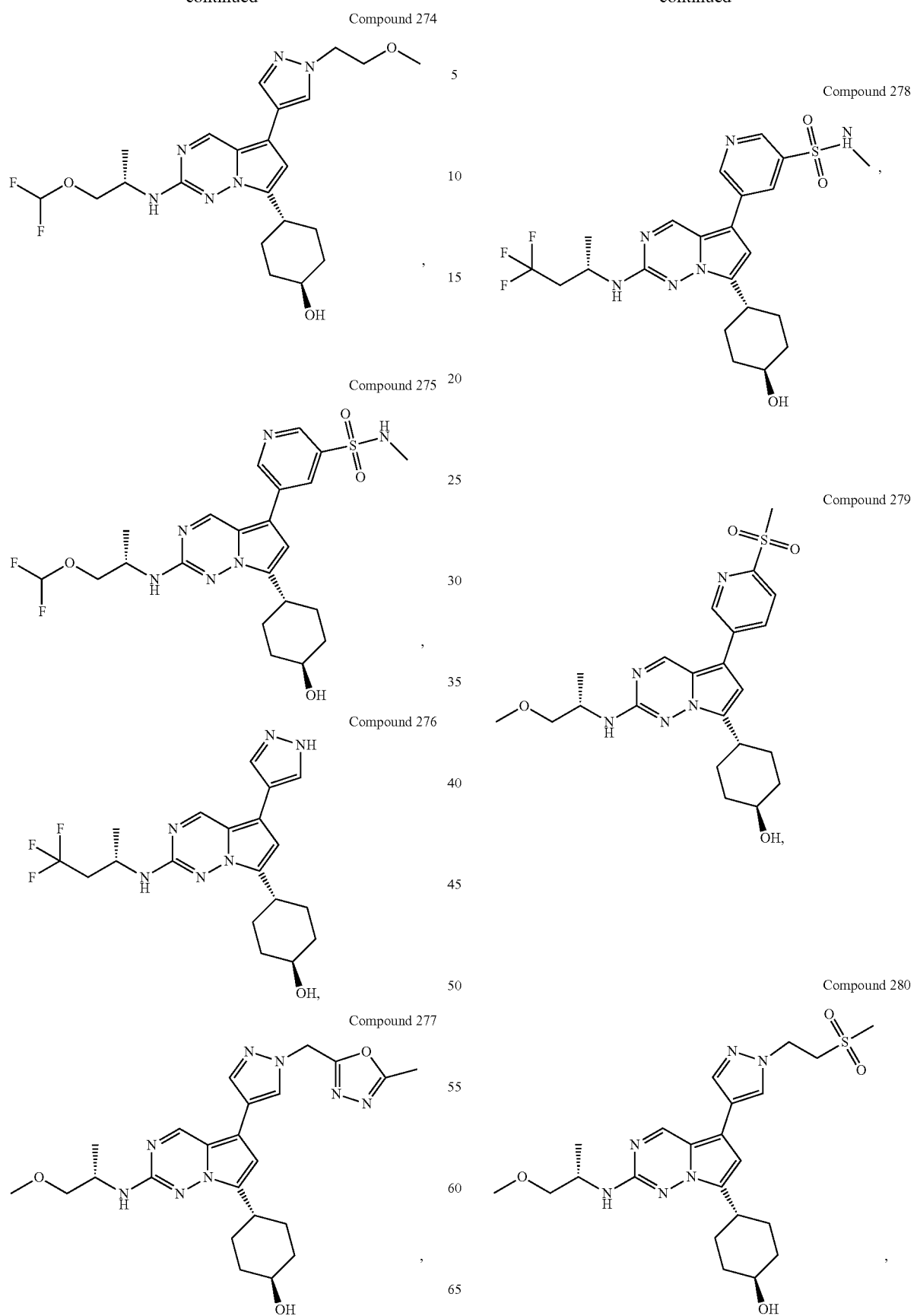

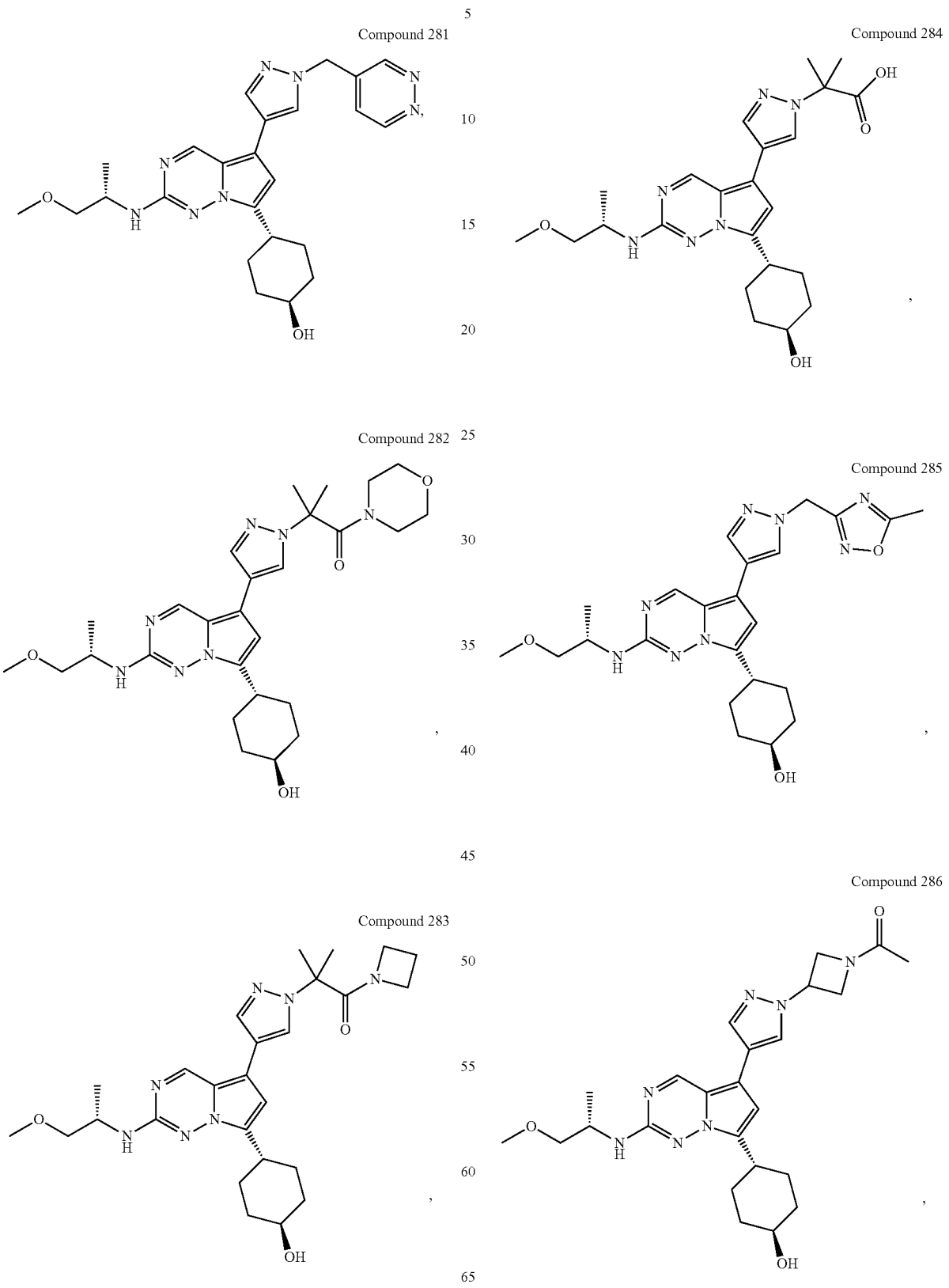

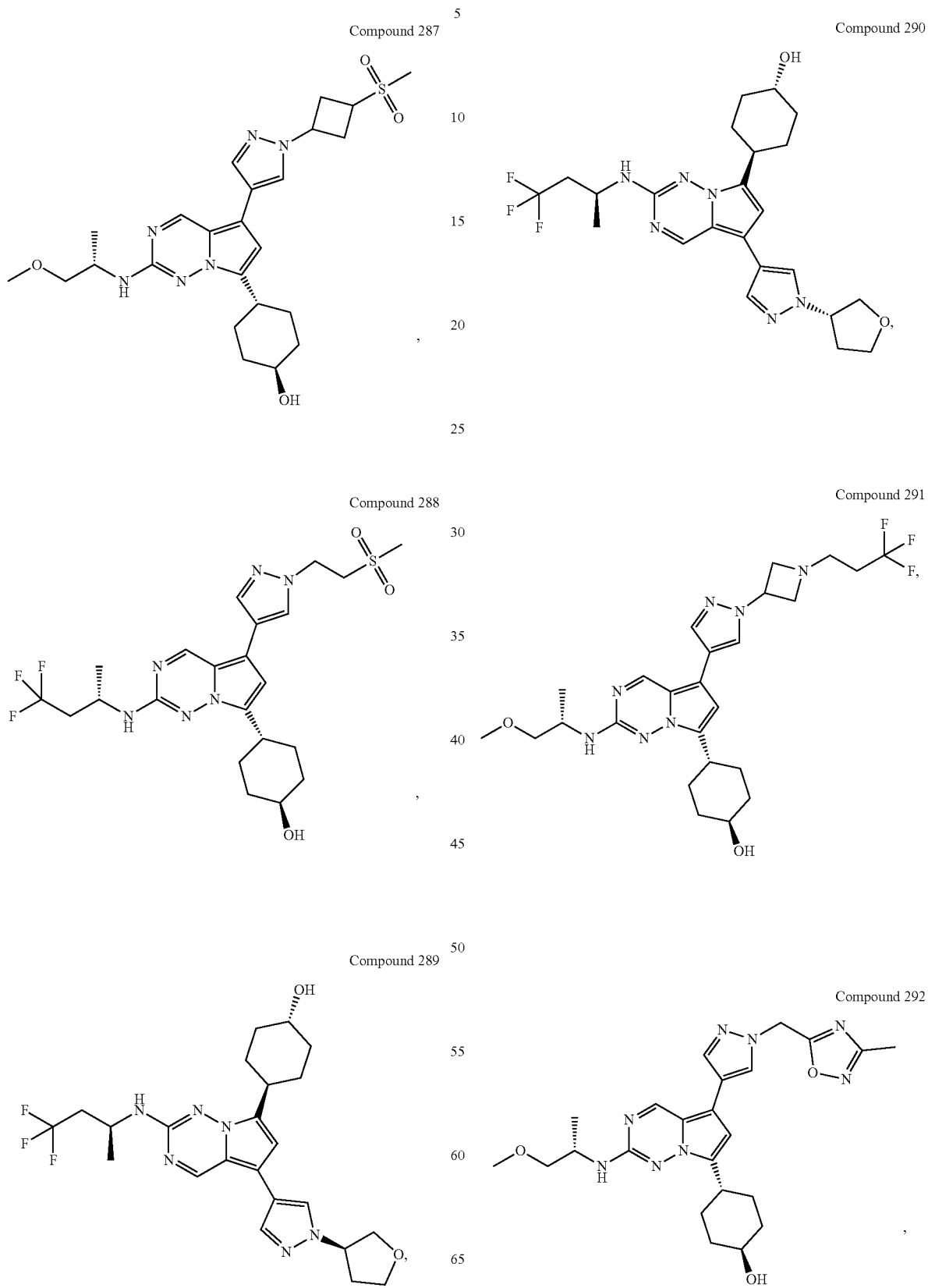

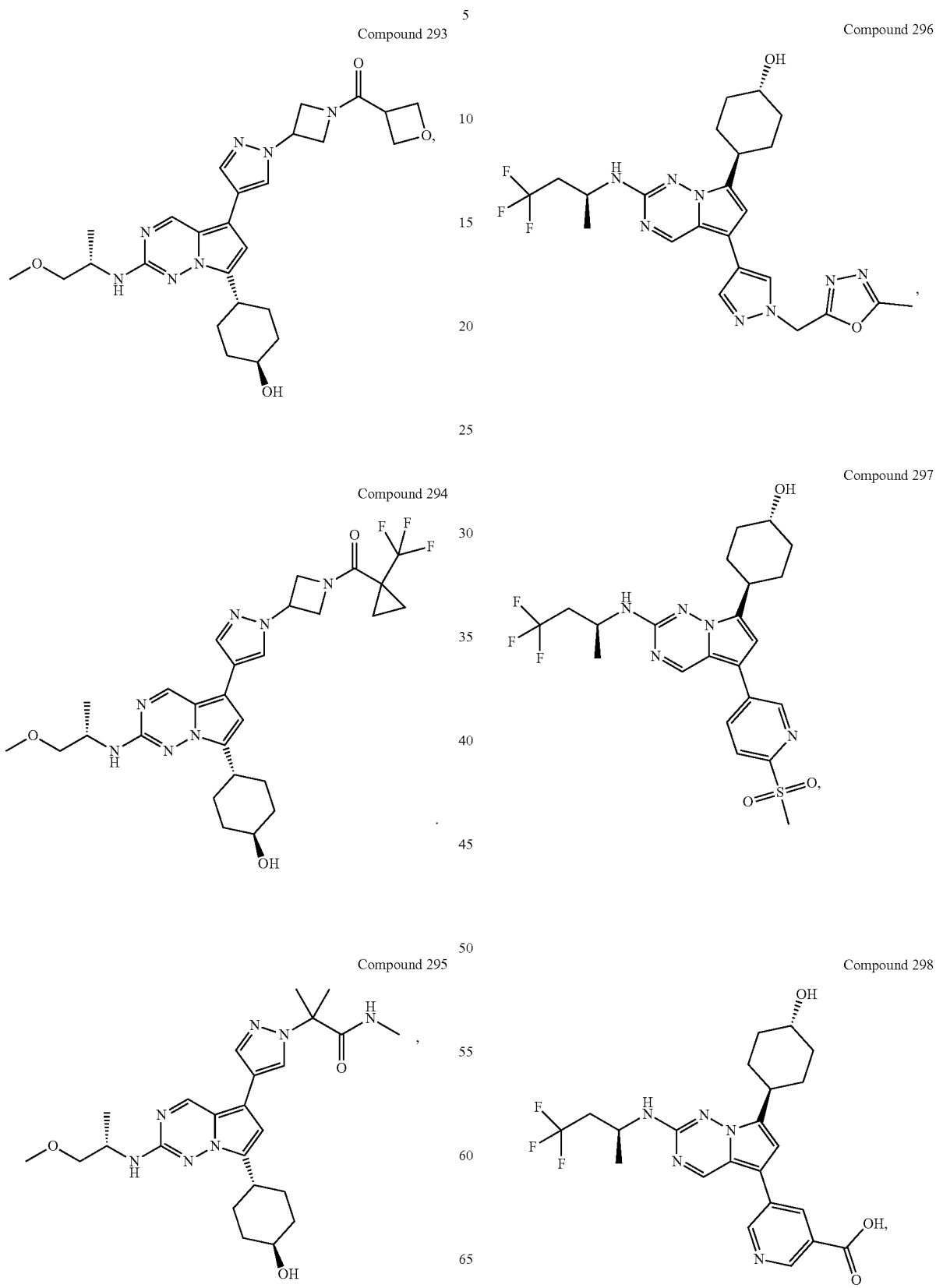

Compound 302
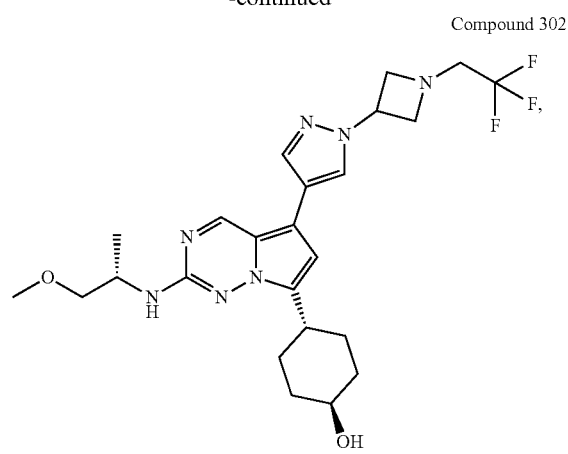
Compound 303
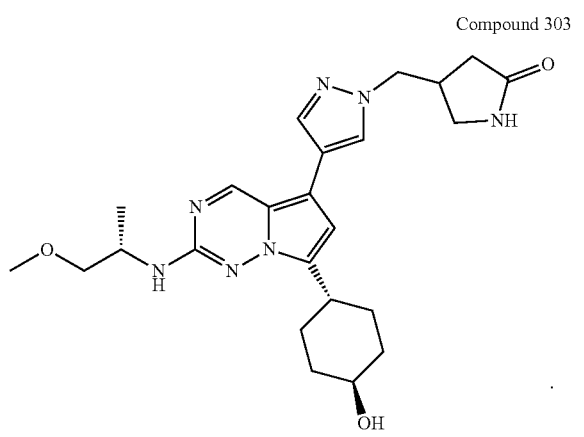
Compound 304
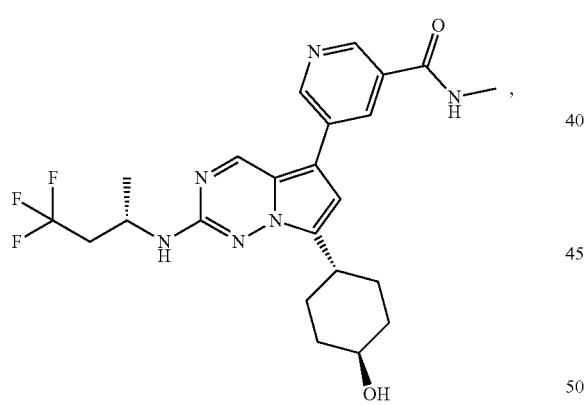
Compound 305
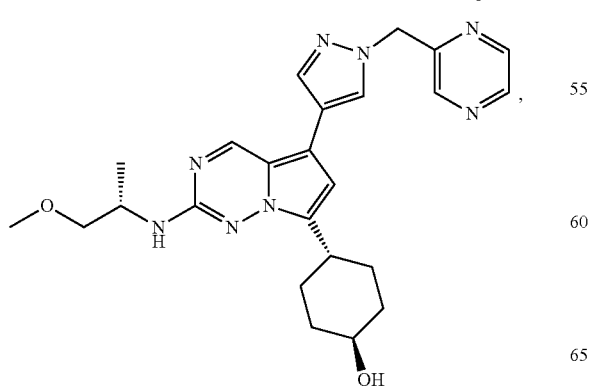
Compound 306
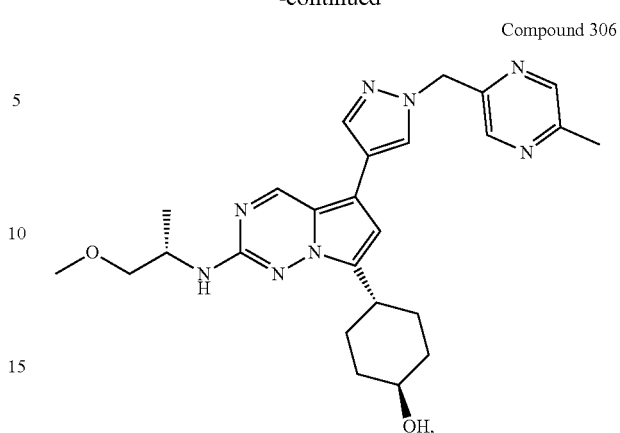
Compound 308
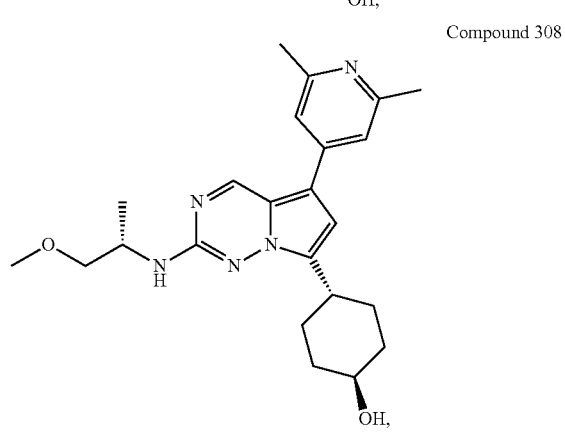
Compound 309
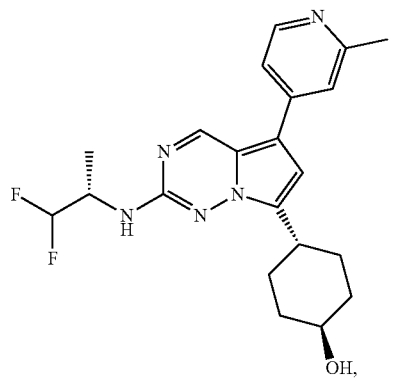
Compound 310
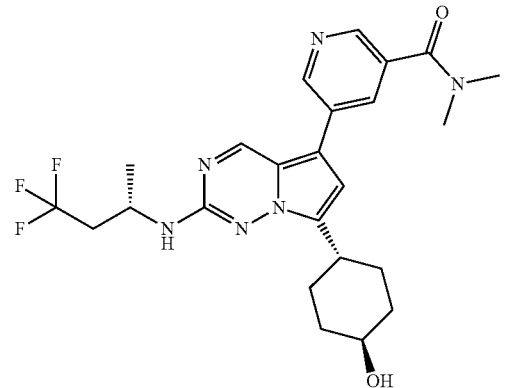

Compound 311
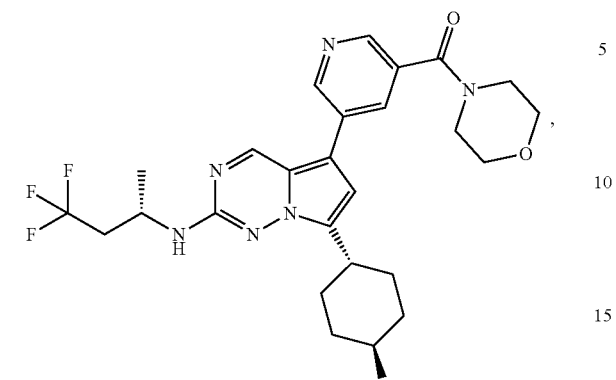
Compound 312
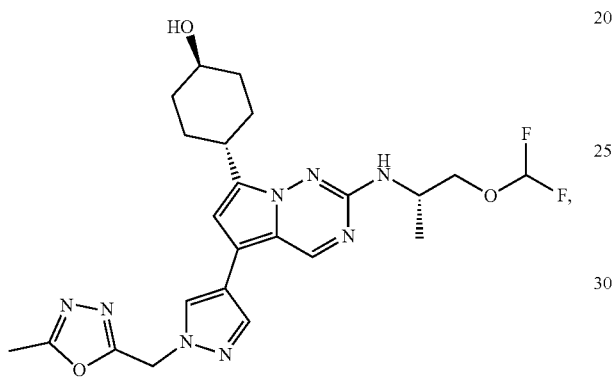
Compound 313
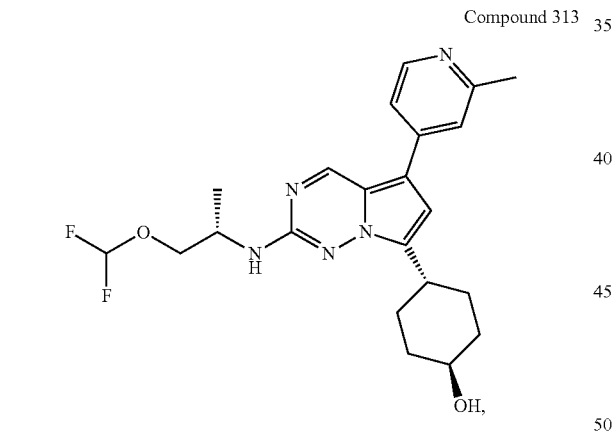
Compound 314
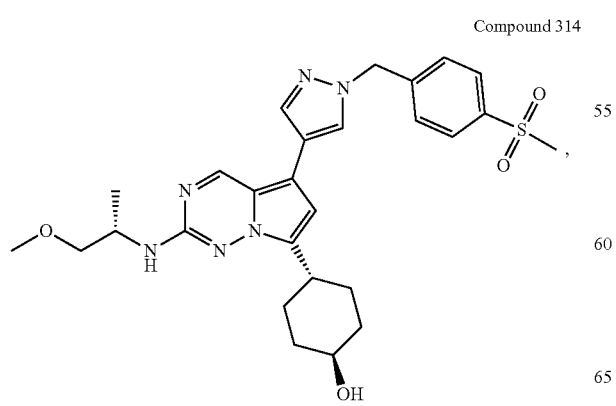
Compound 315
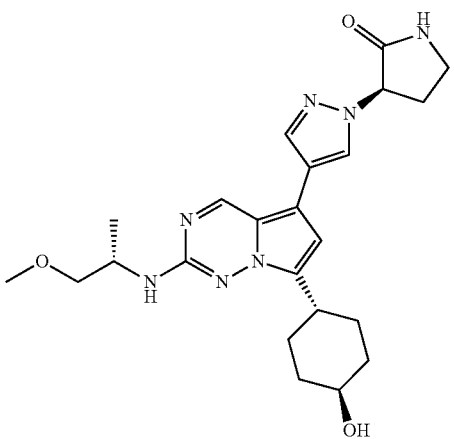
Compound 317
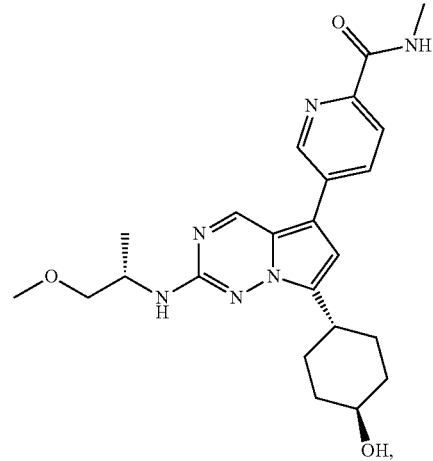
Compound 318
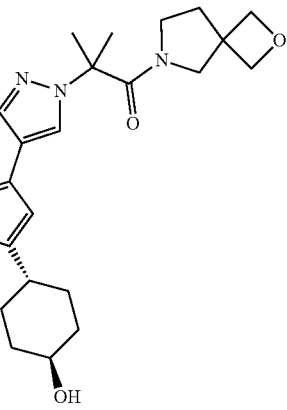

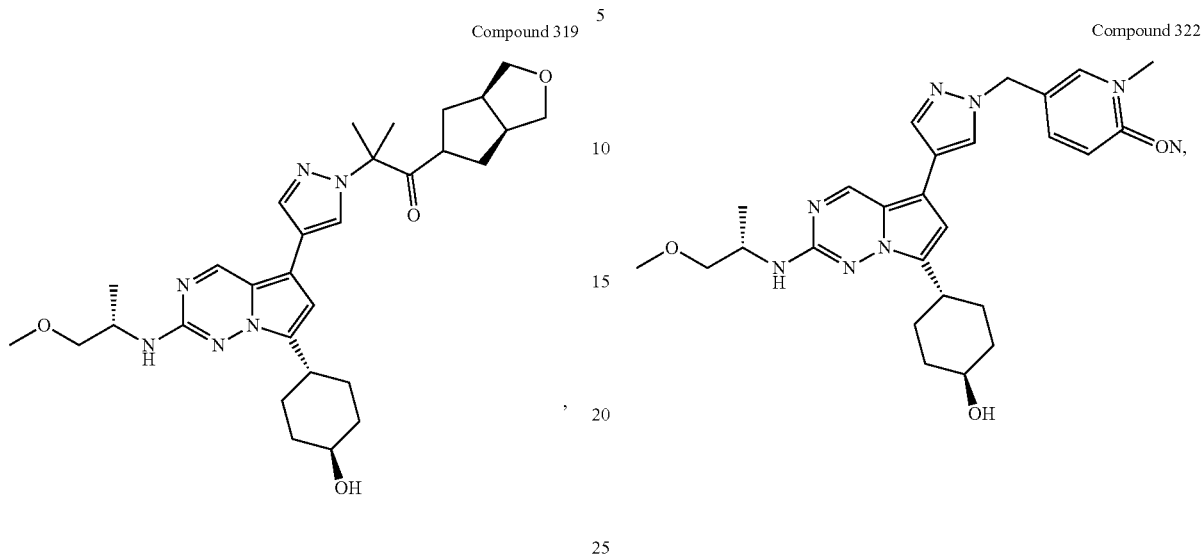
Compound 319
Compound 322
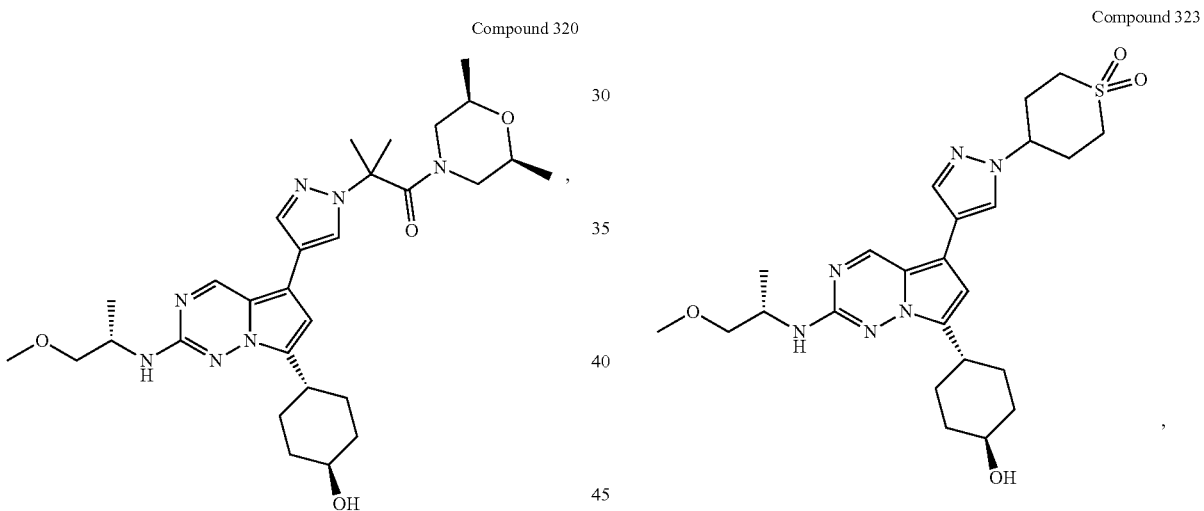
Compound 320
Compound 323
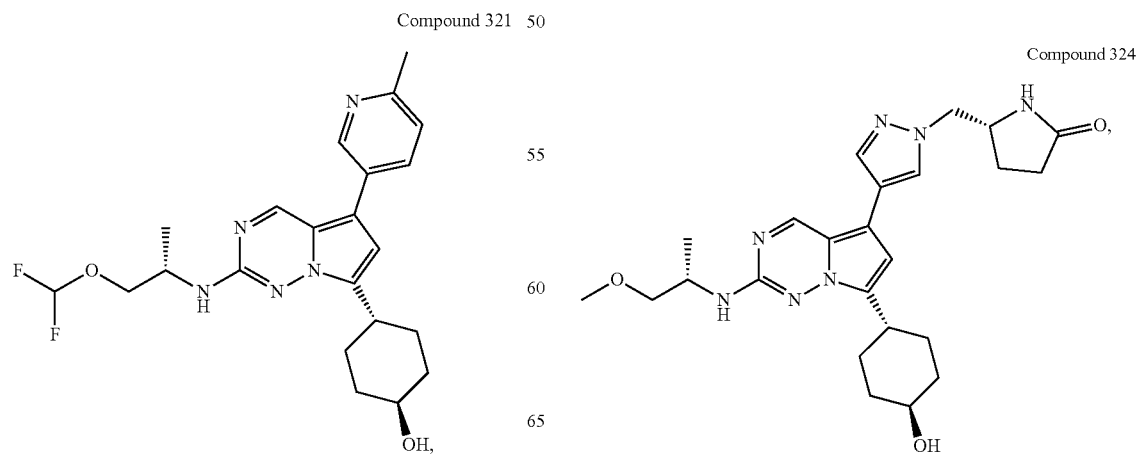
Compound 321
Compound 324

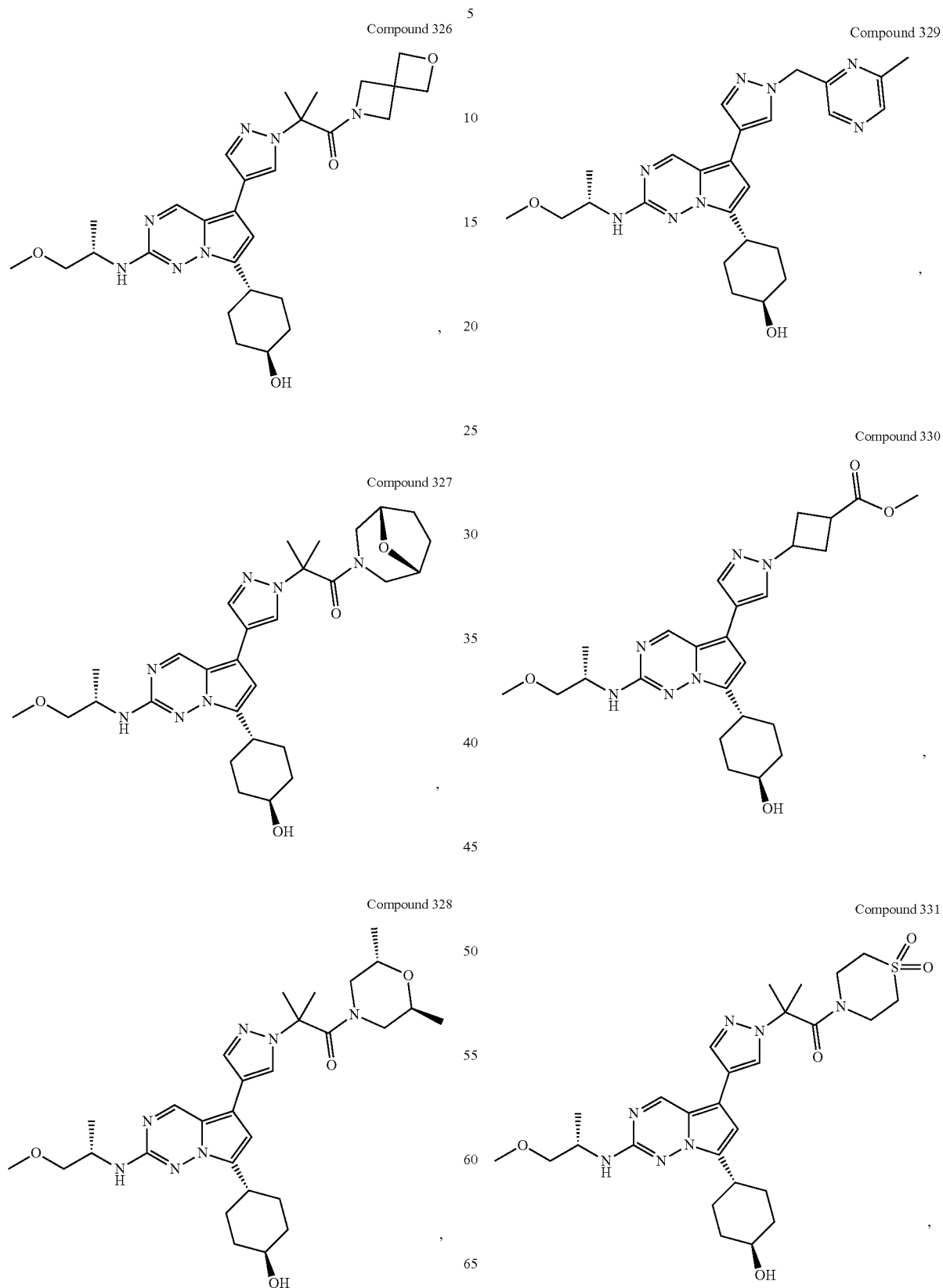

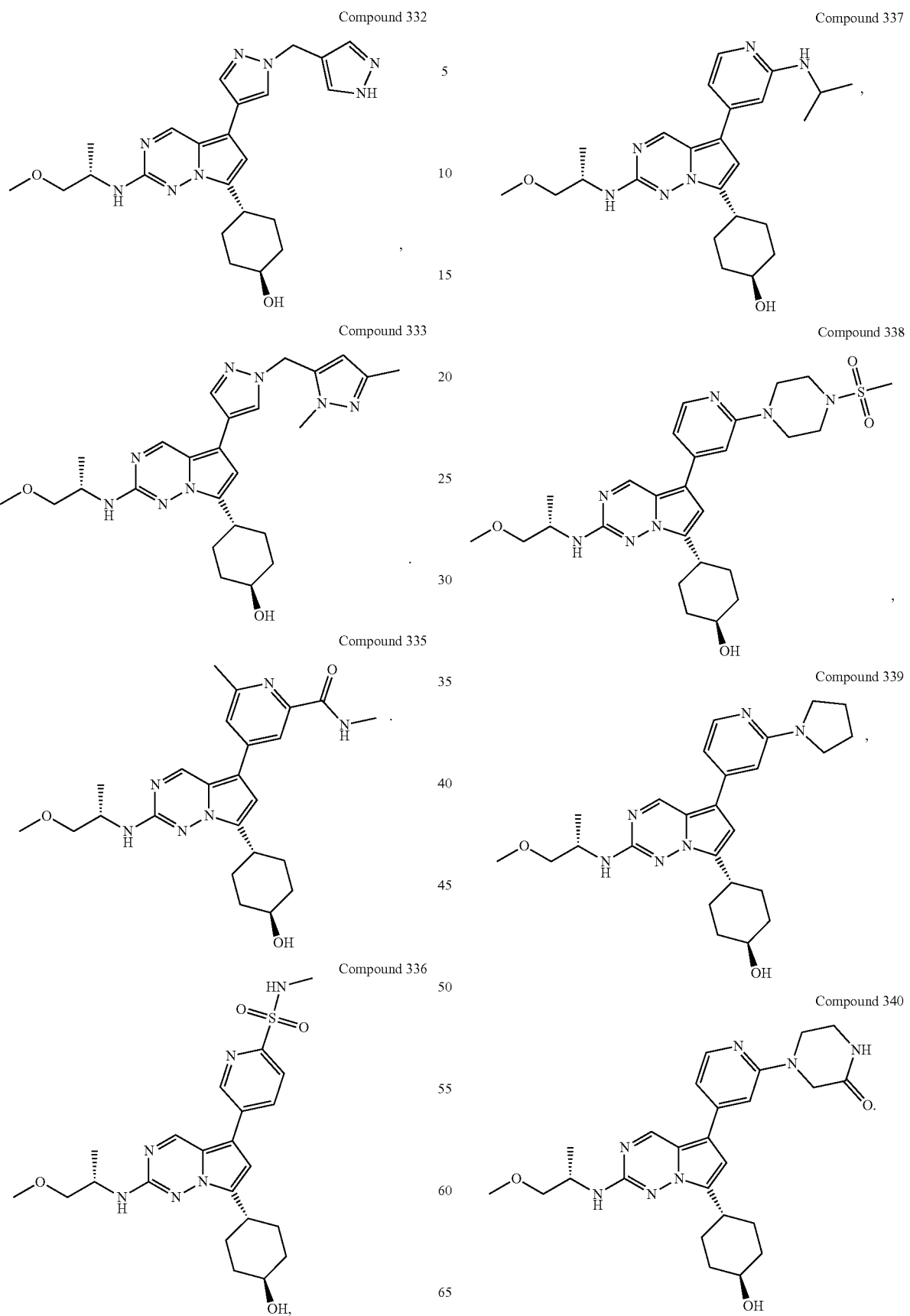

Compound 341
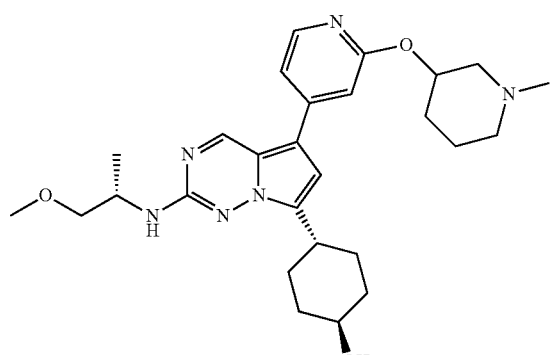
Compound 342
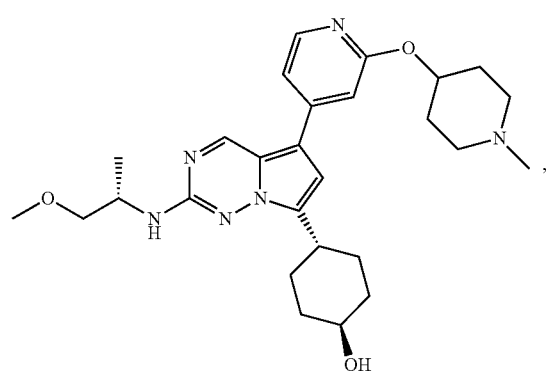
Compound 343
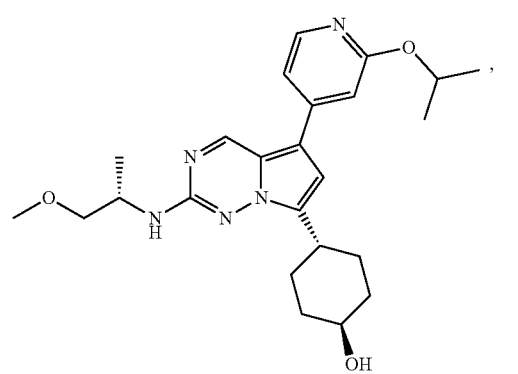
Compound 344
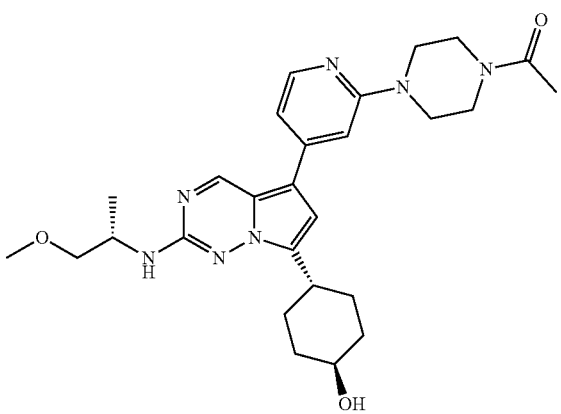
Compound 345
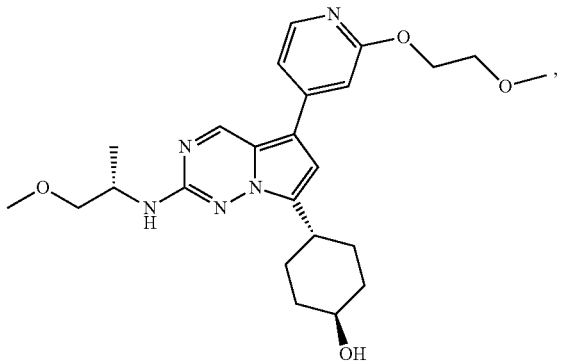
Compound 346
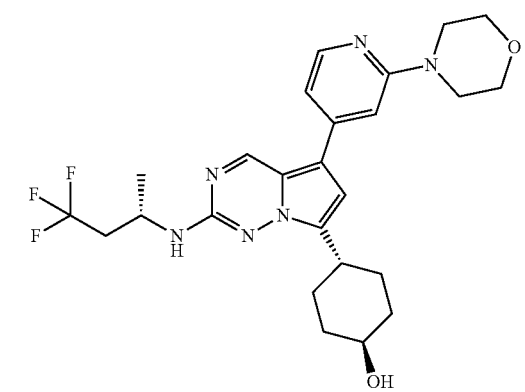
Compound 348
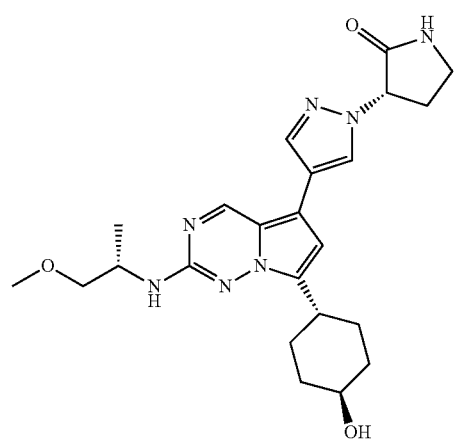
Compound 350
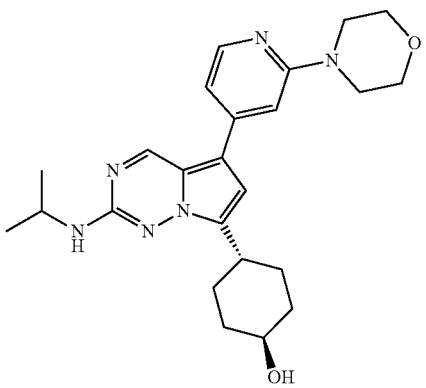

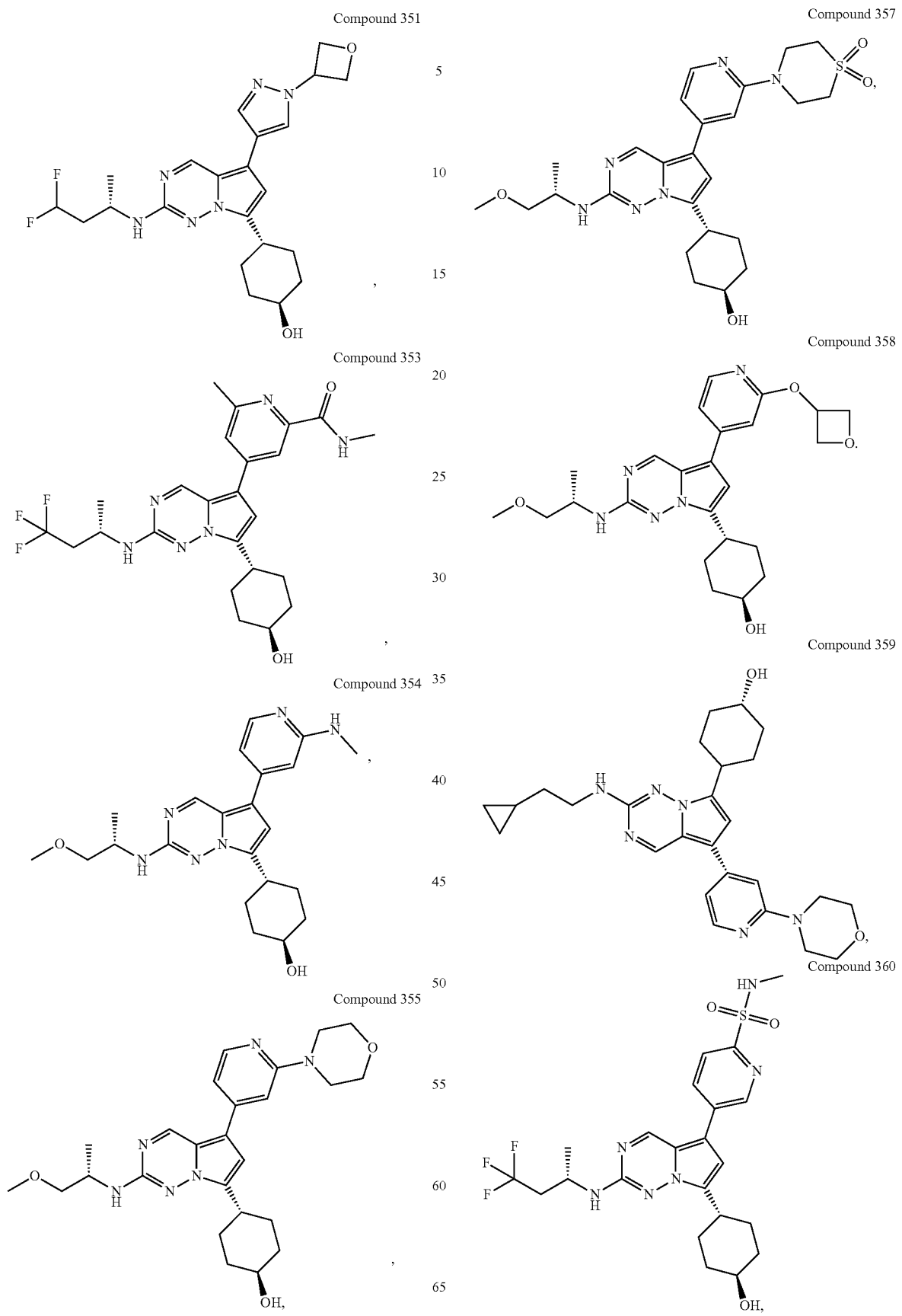

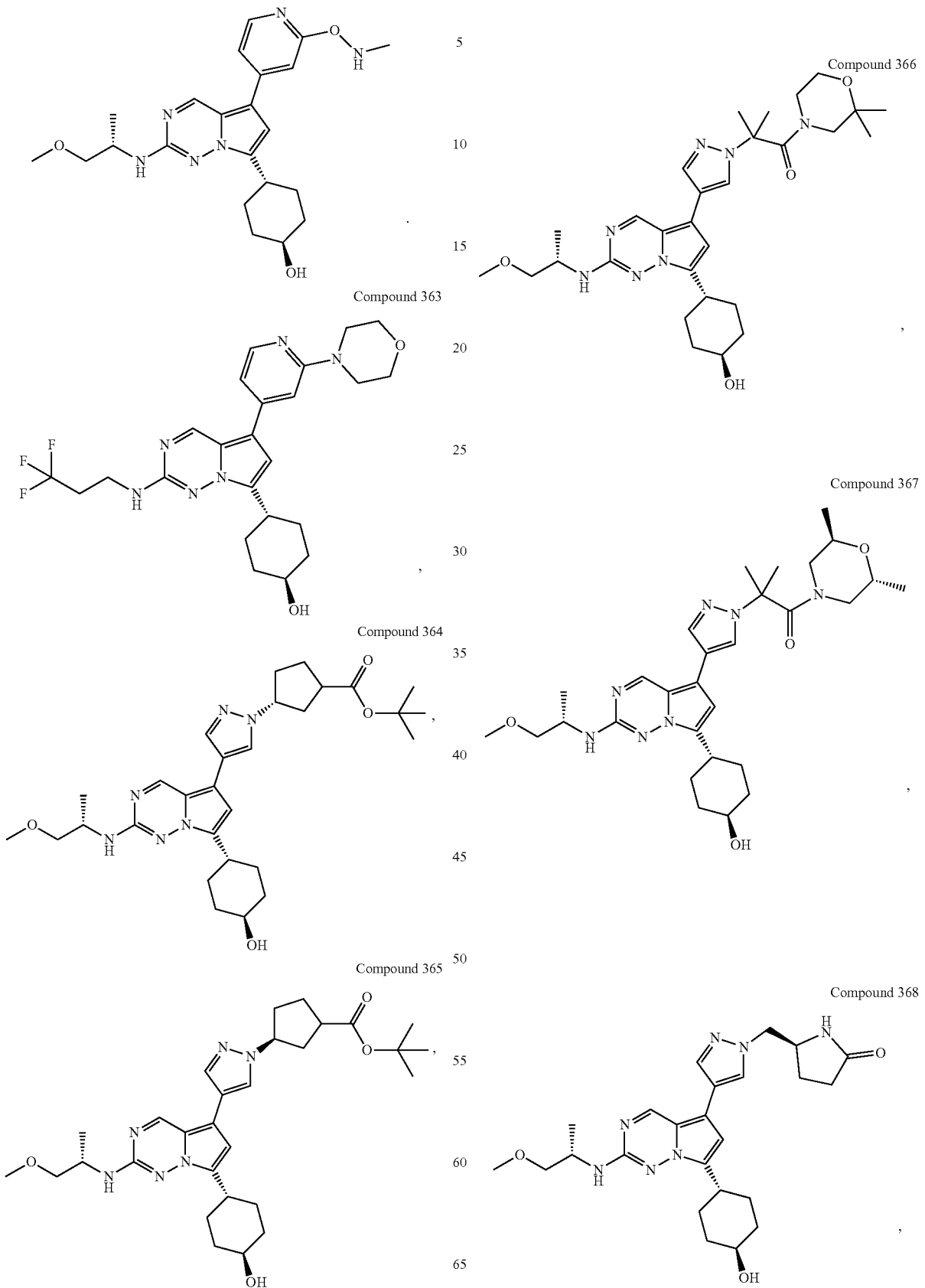

Compound 369
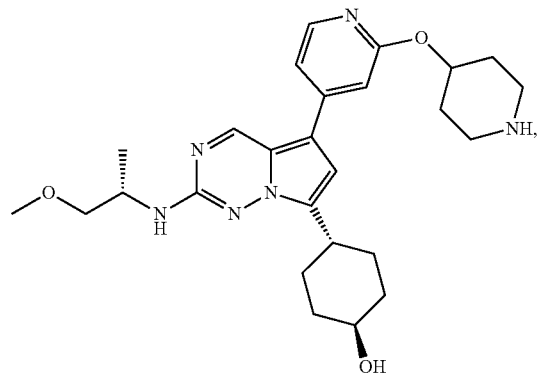
Compound 379
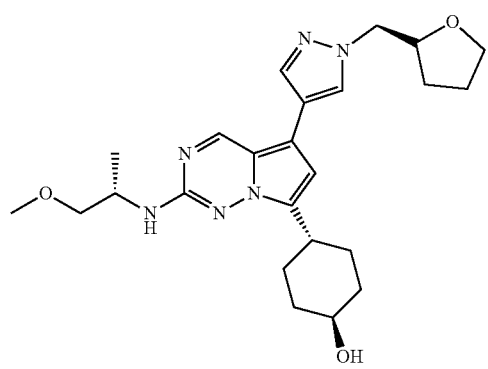
Compound 380
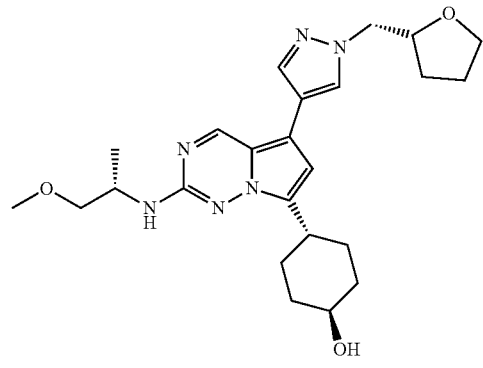
Compound 381
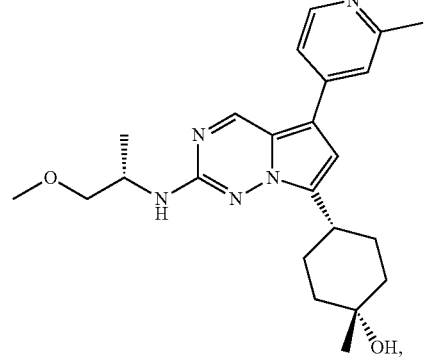
Compound 382
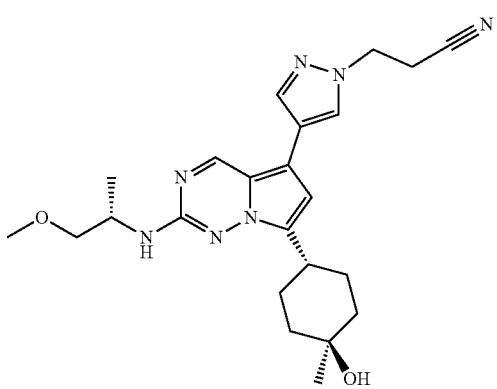
Compound 384
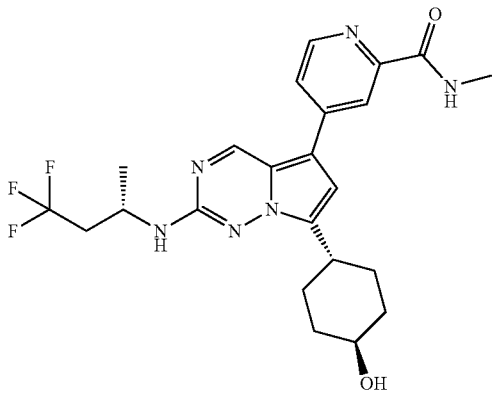
Compound 385
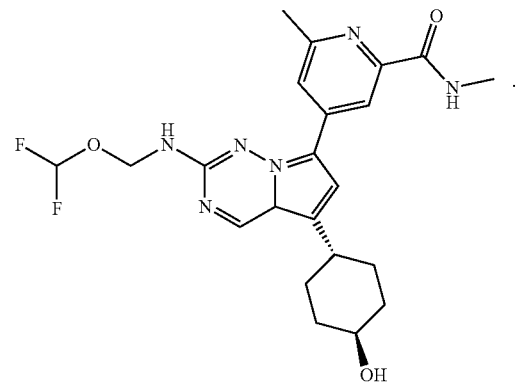
Compound 386
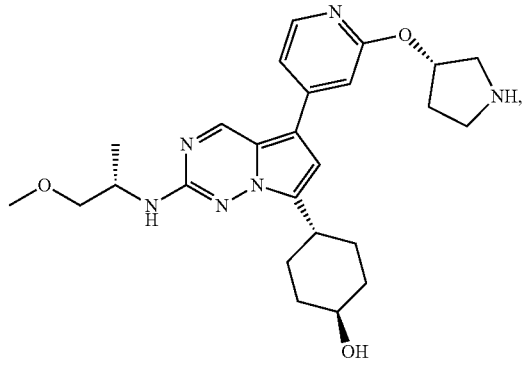

Compound 389
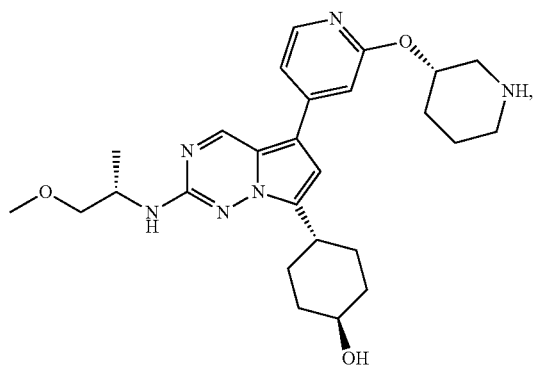
Compound 390
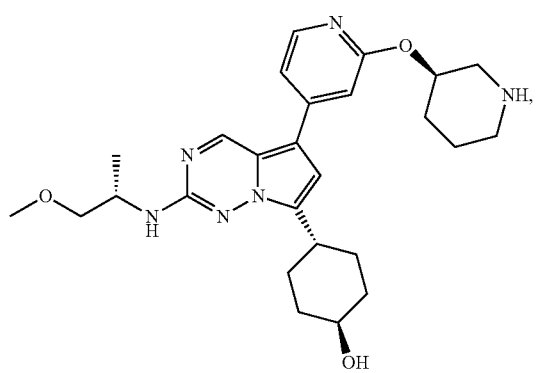
Compound 391
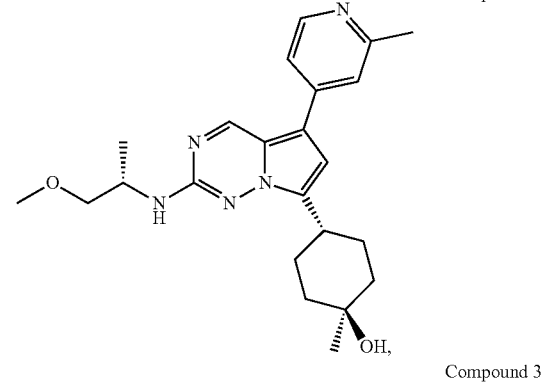
Compound 392
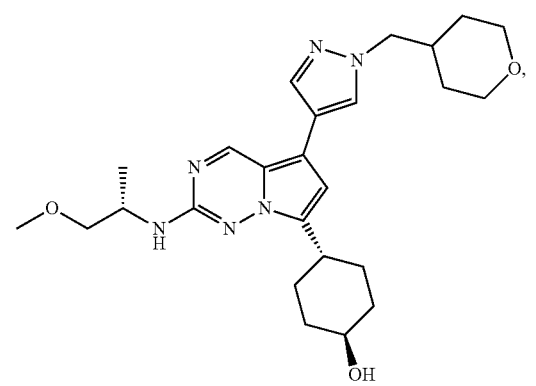
Compound 393
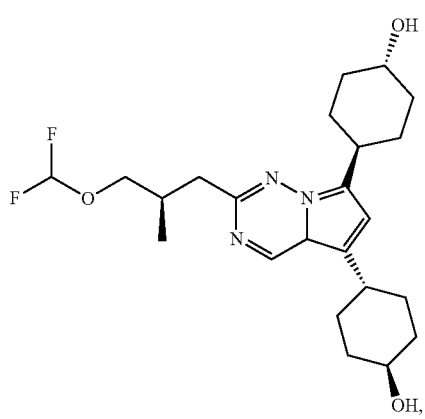
Compound 394
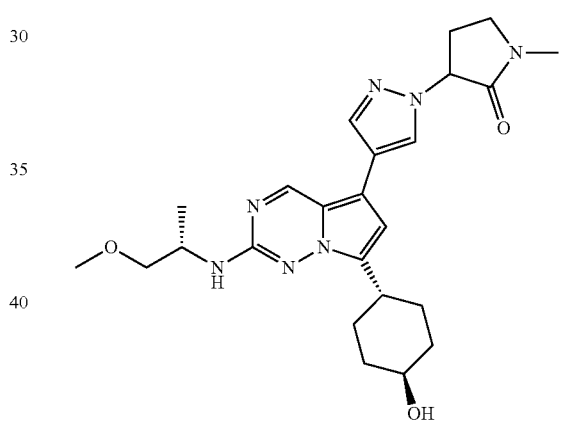
Compound 395
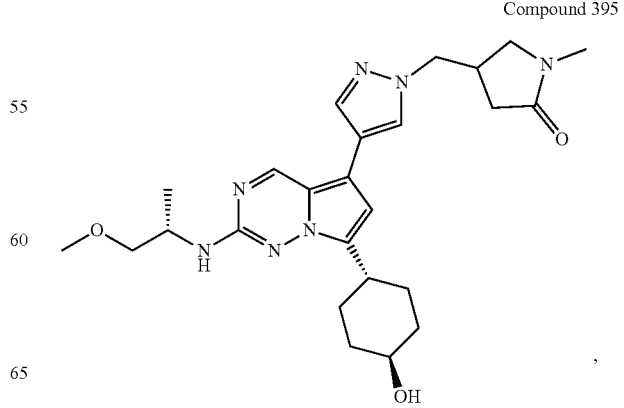

Compound 396
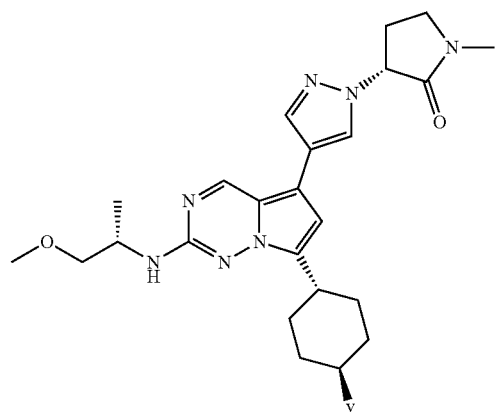
Compound 397
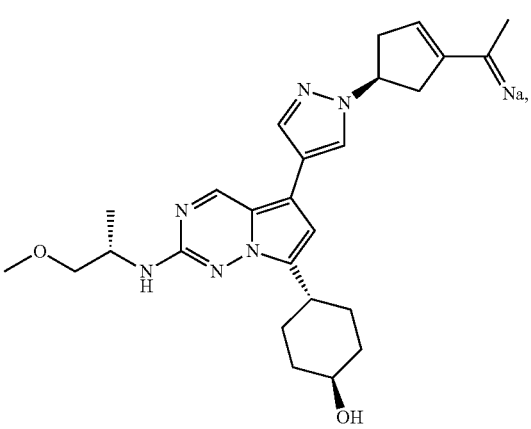
Compound 398
Compound 400
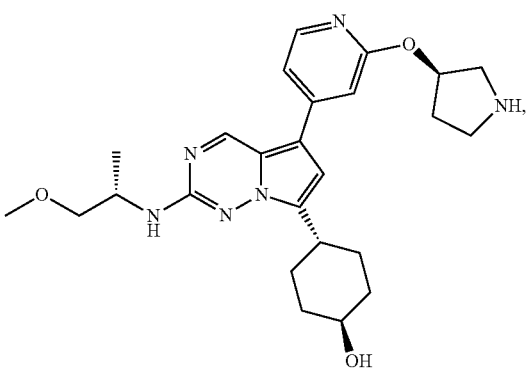
Compound 401
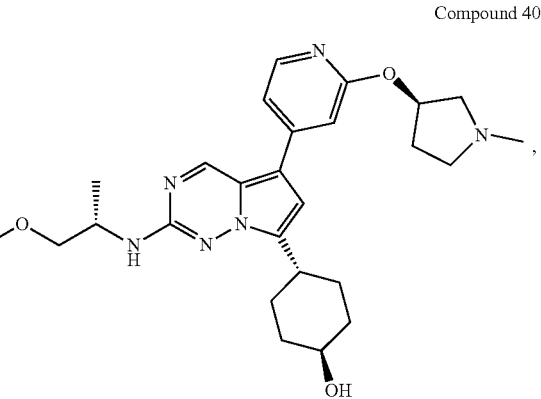
Compound 402
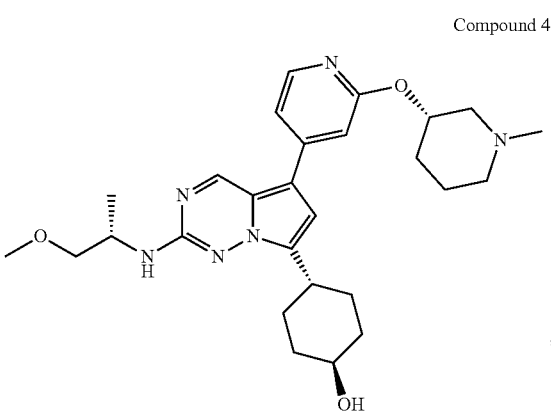
Compound 403
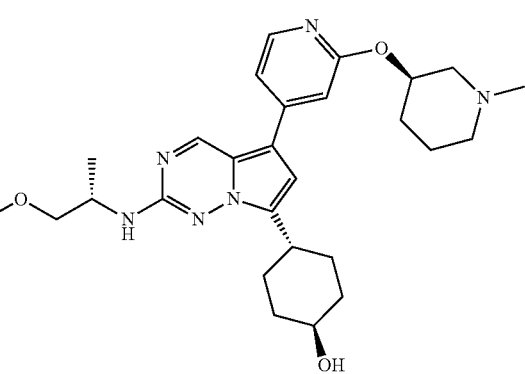
Compound 404

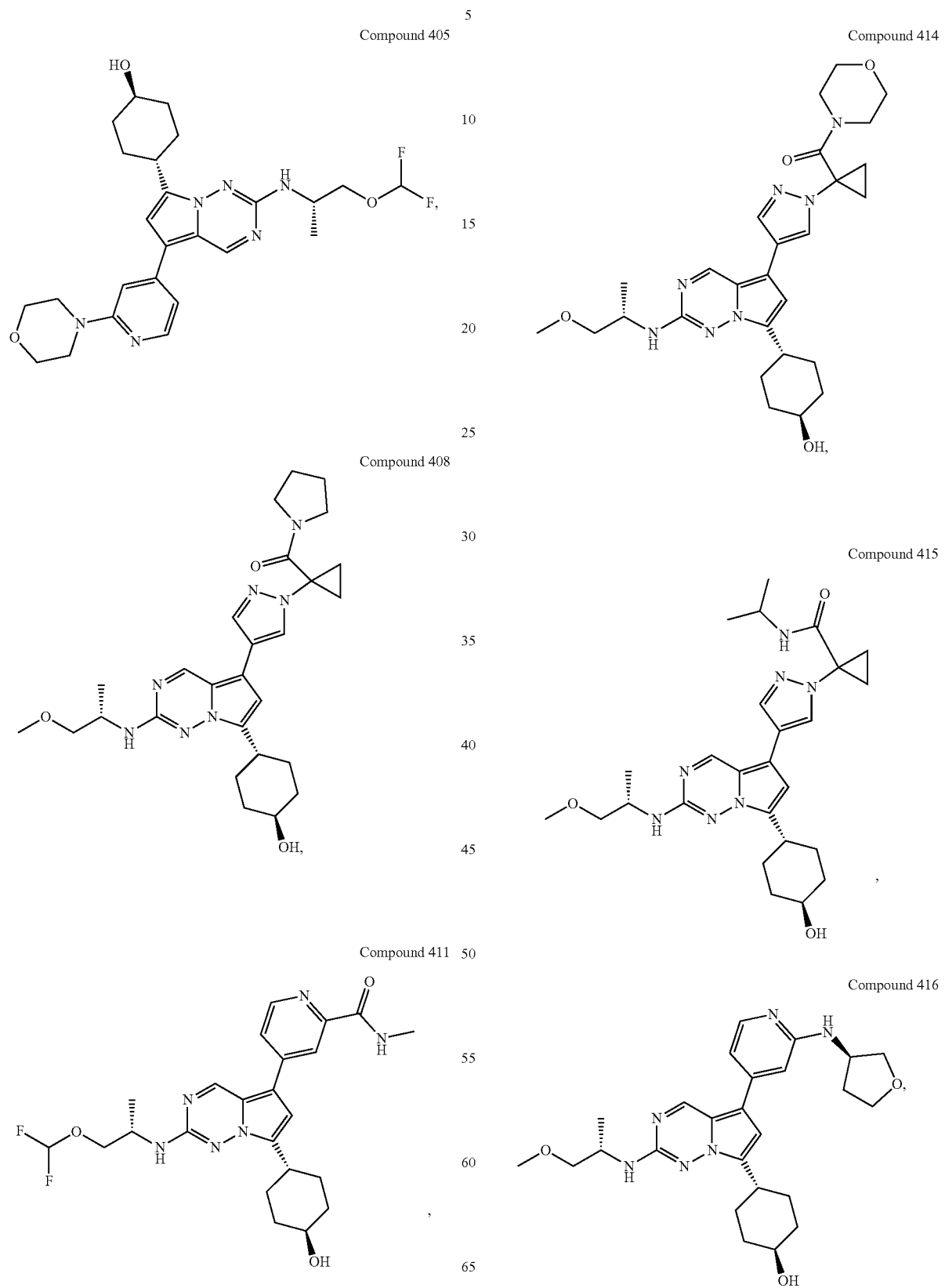

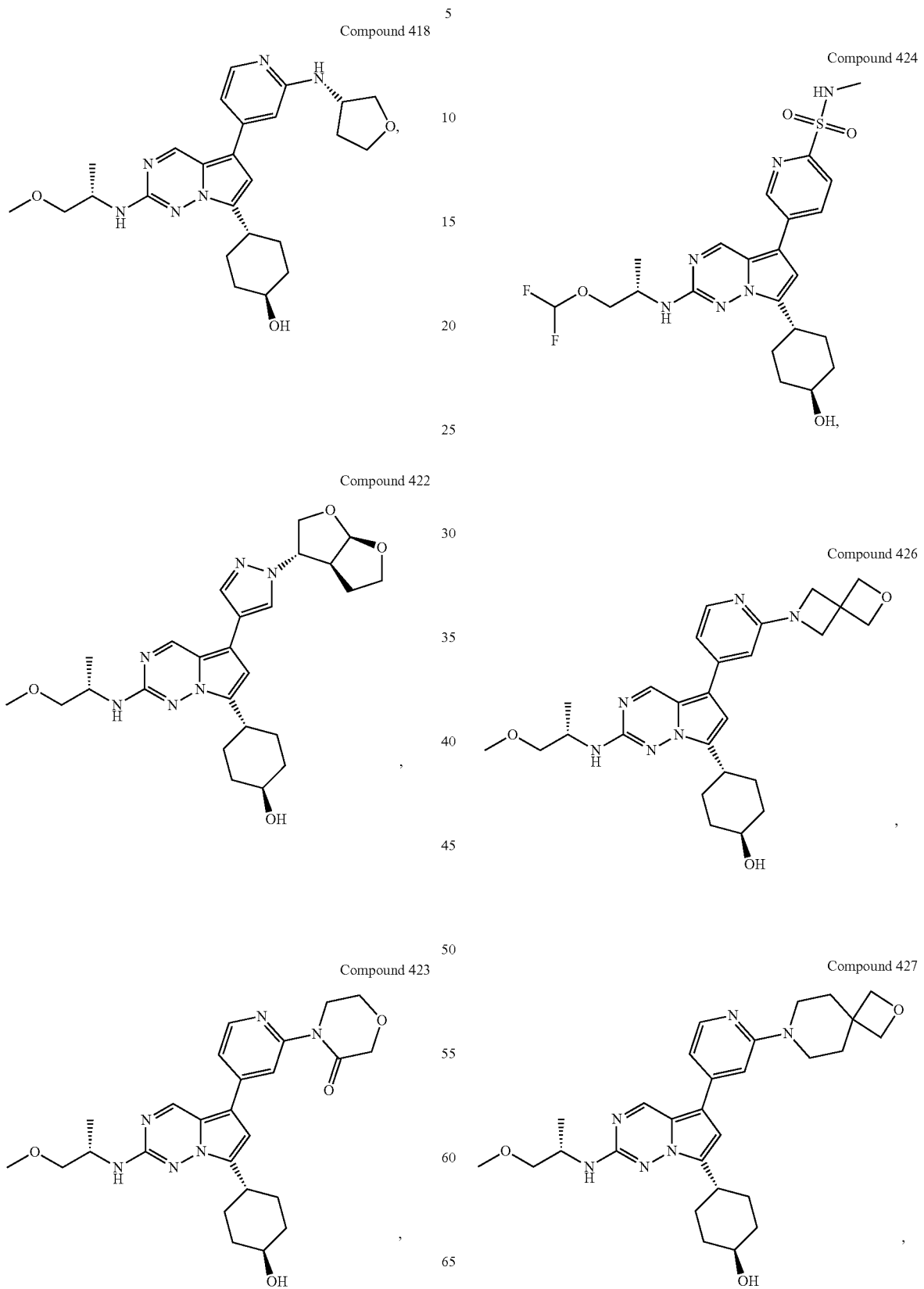

Compound 430
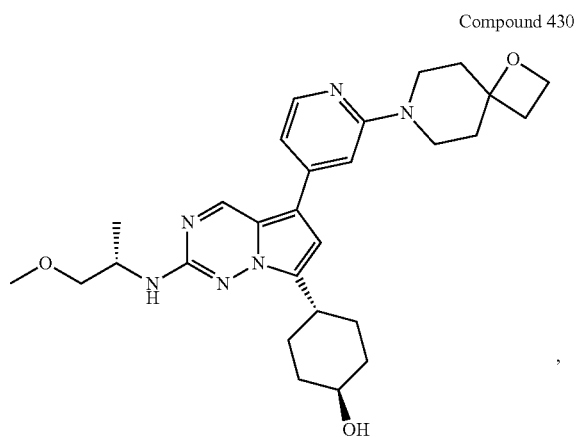
Compound 431
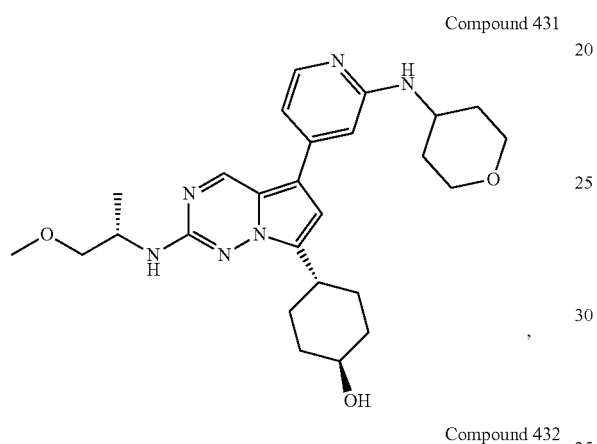
Compound 432
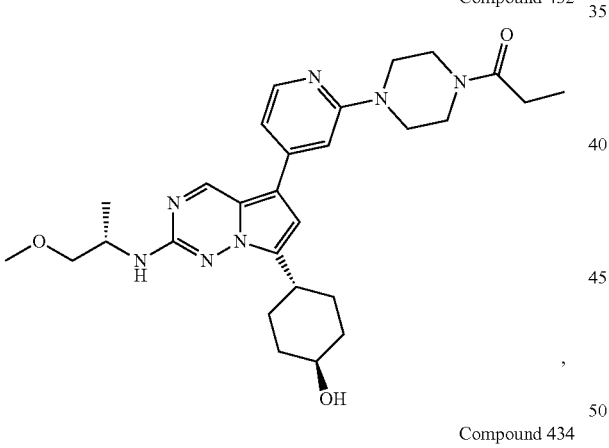
Compound 434
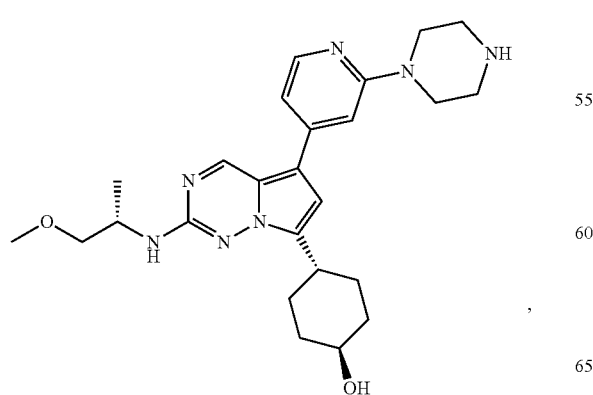
Compound 436
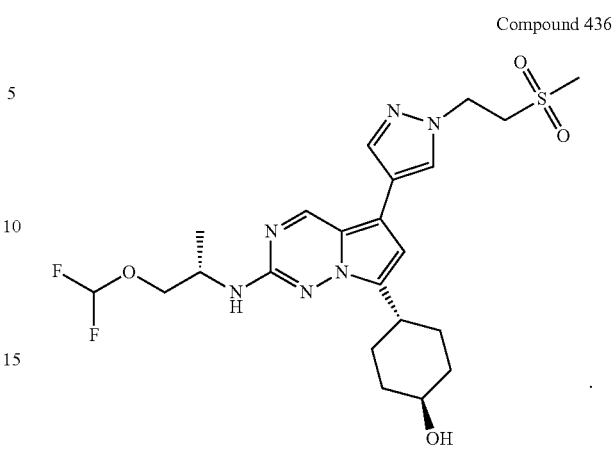
Compound 437
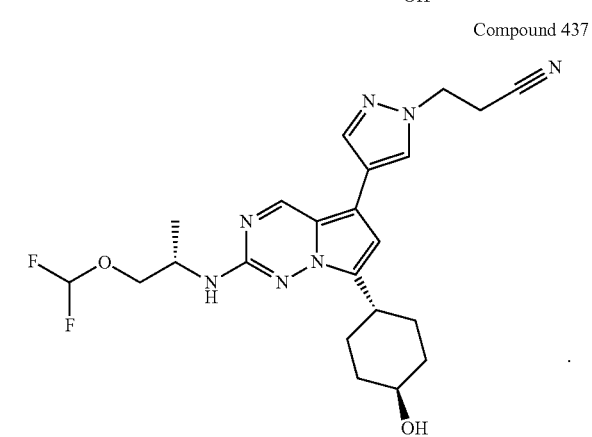
Compound 418
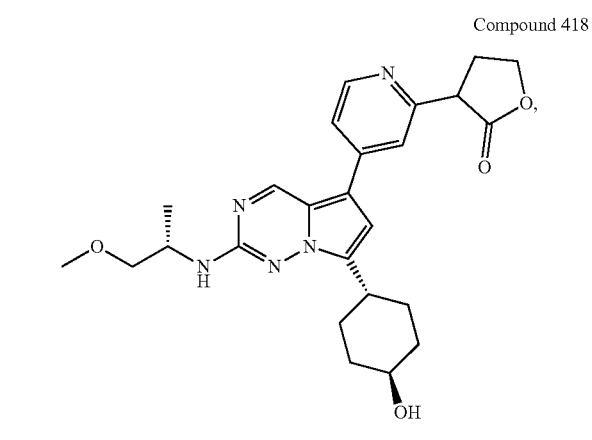
Compound 439
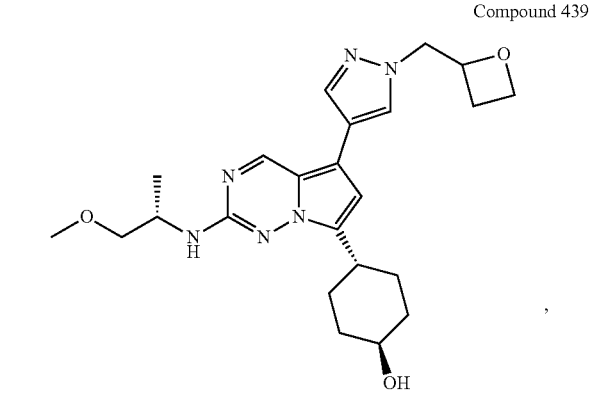

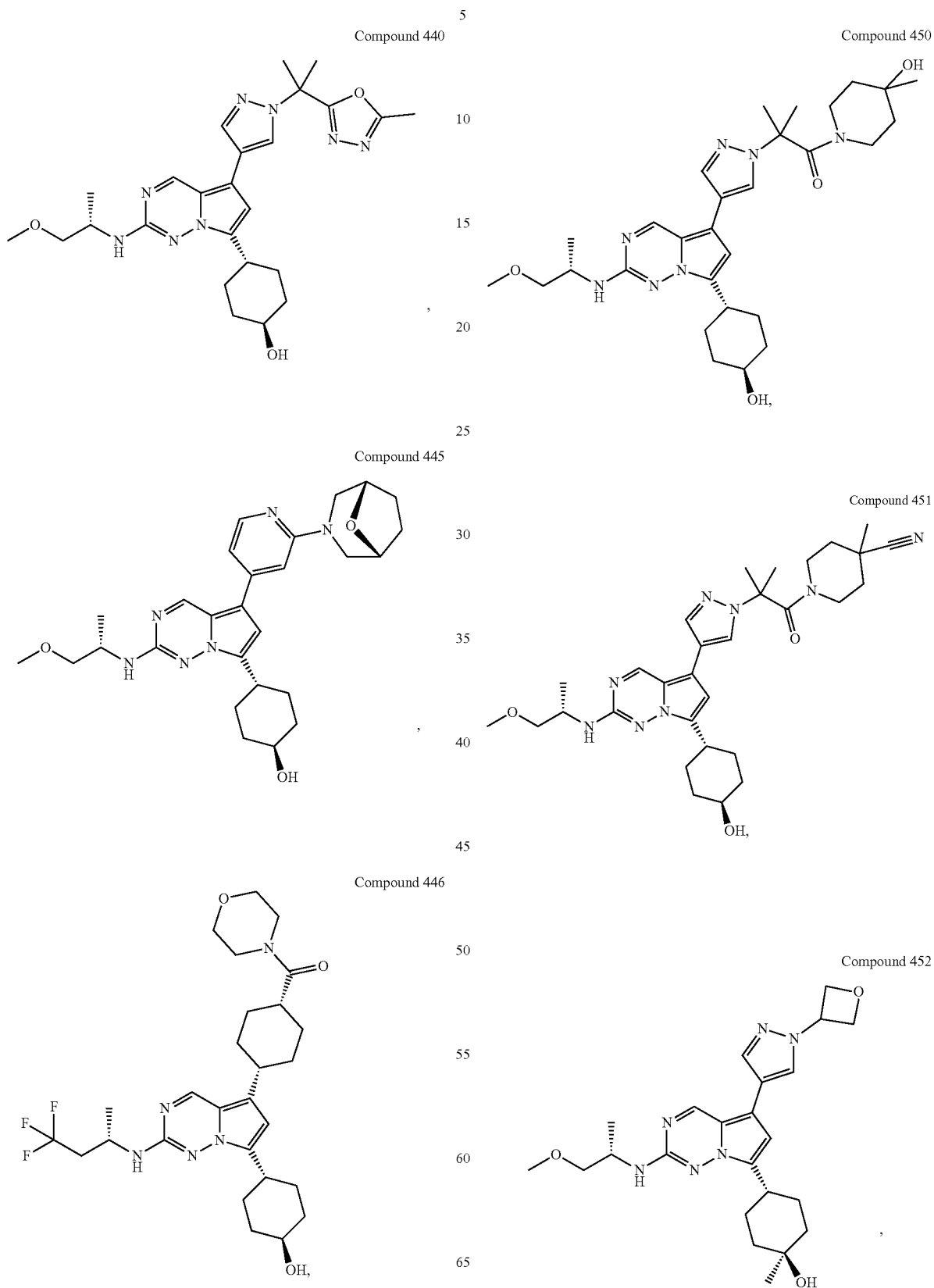

Compound 453
Compound 461
Compound 456
Compound 462
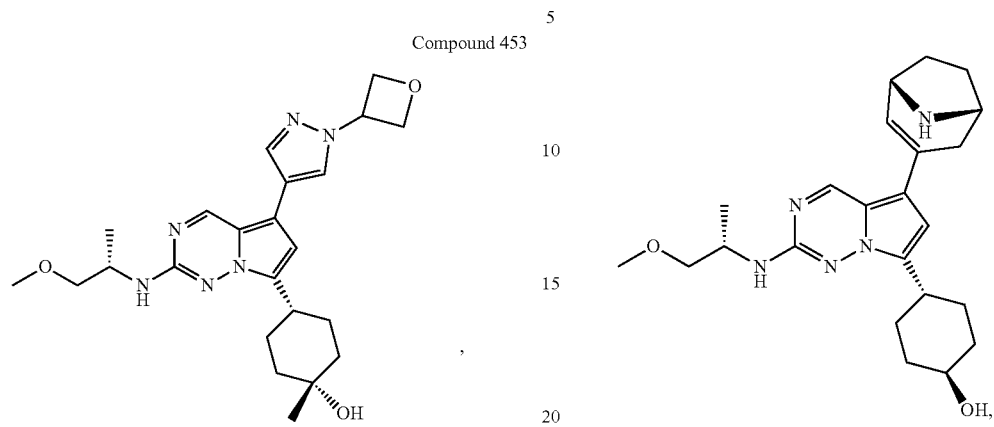
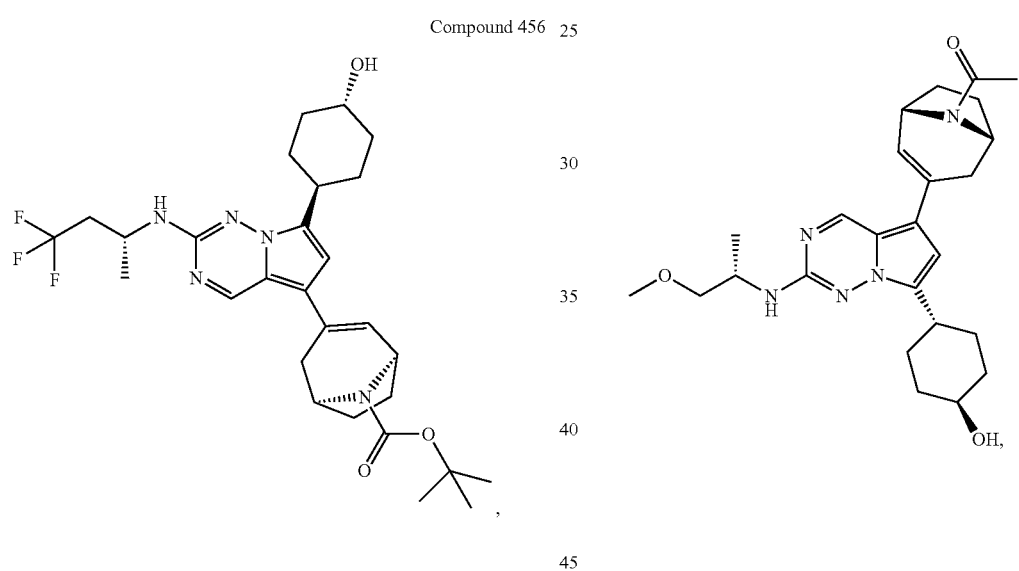
Compound 459
Compound 463
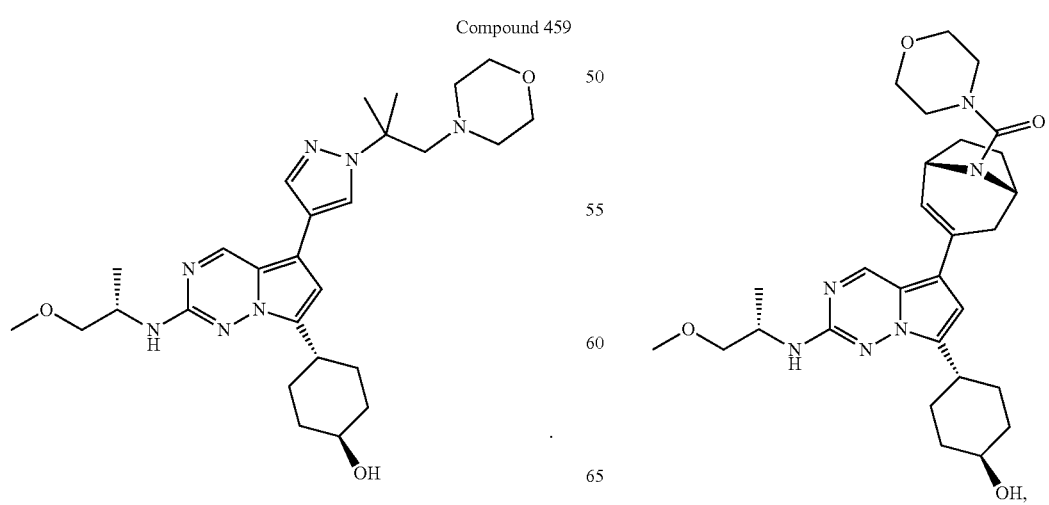

Compound 464
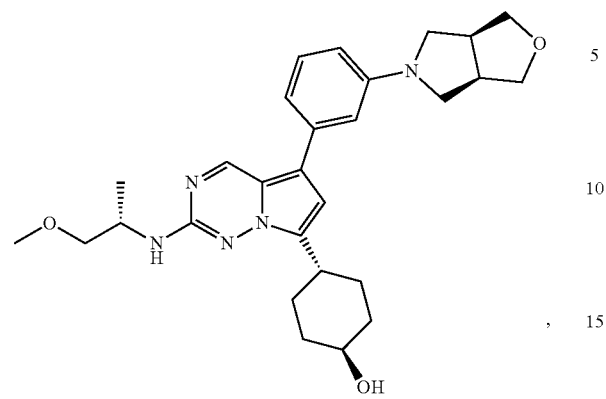
Compound 465
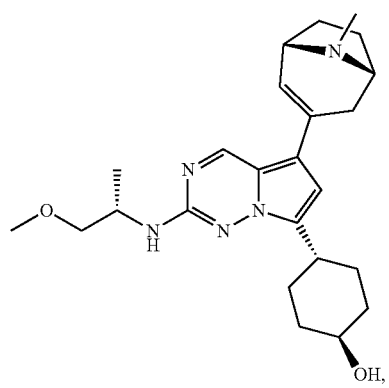
Compound 466
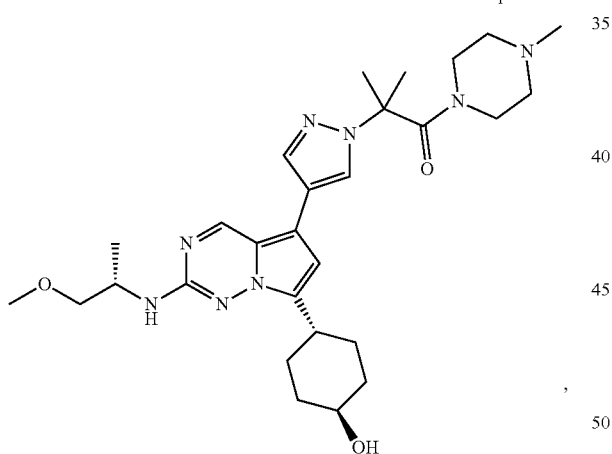
Compound 467
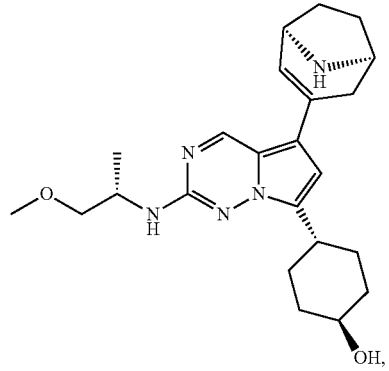
Compound 468
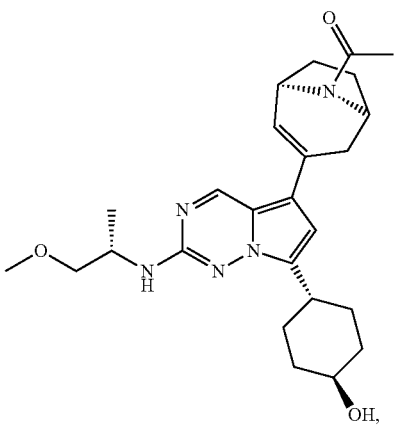
Compound 469
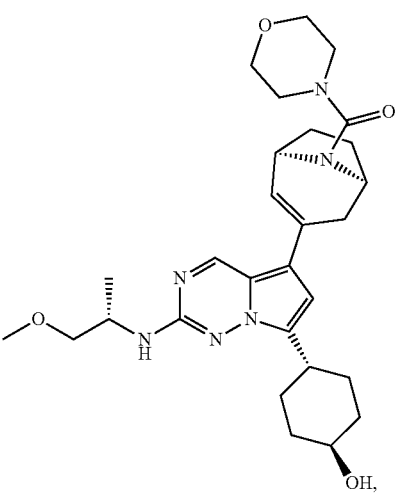
Compound 470
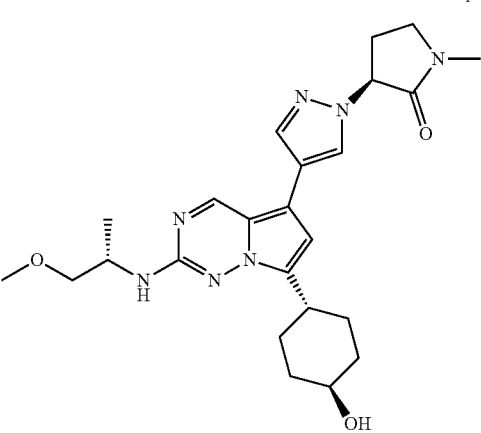

Compound 471
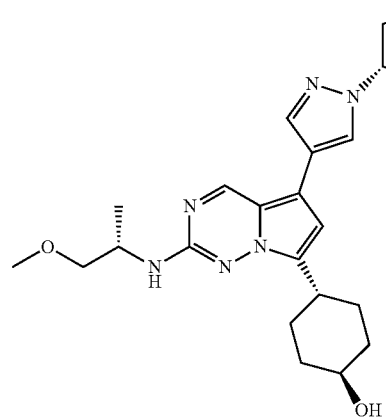
Compound 472
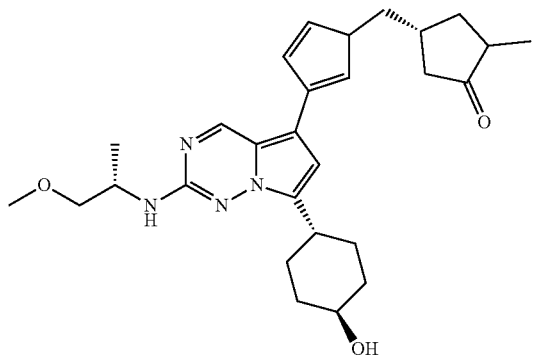
Compound 473
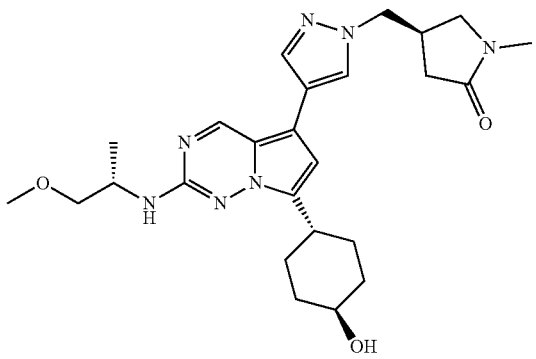
Compound 474
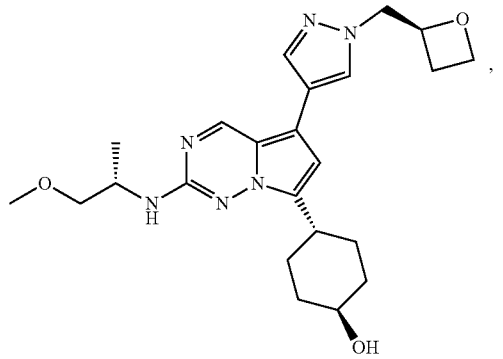
Compound 475
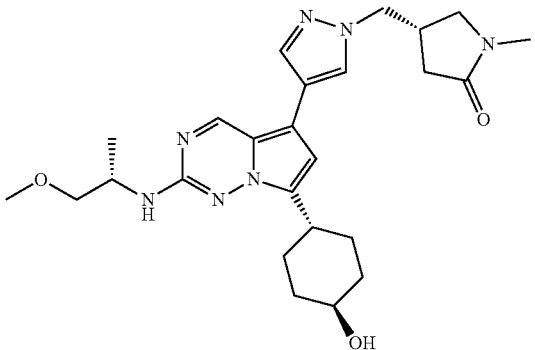
,
Compound 476
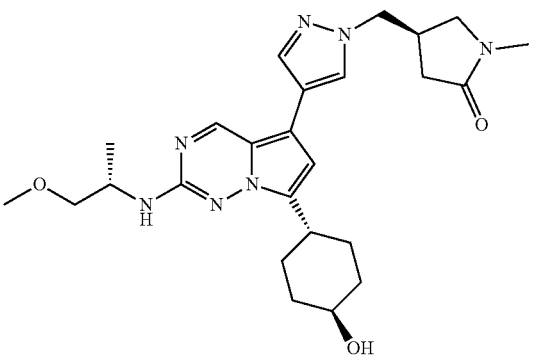
,
Compound 478
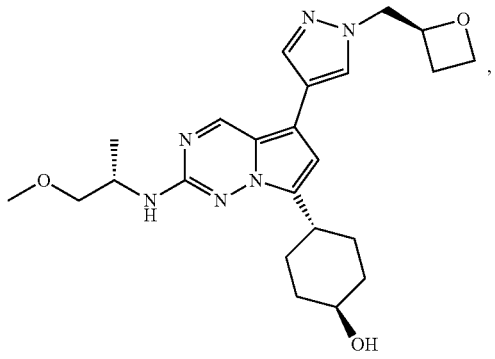
,
Compound 479
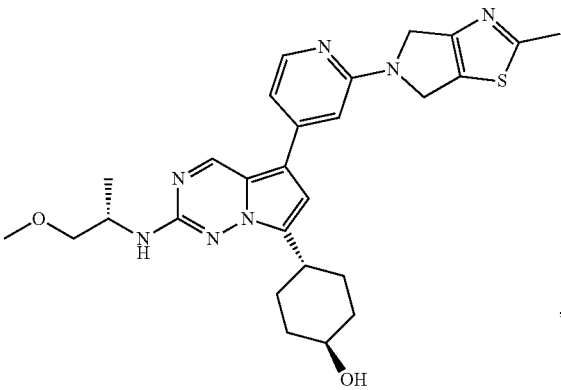
,

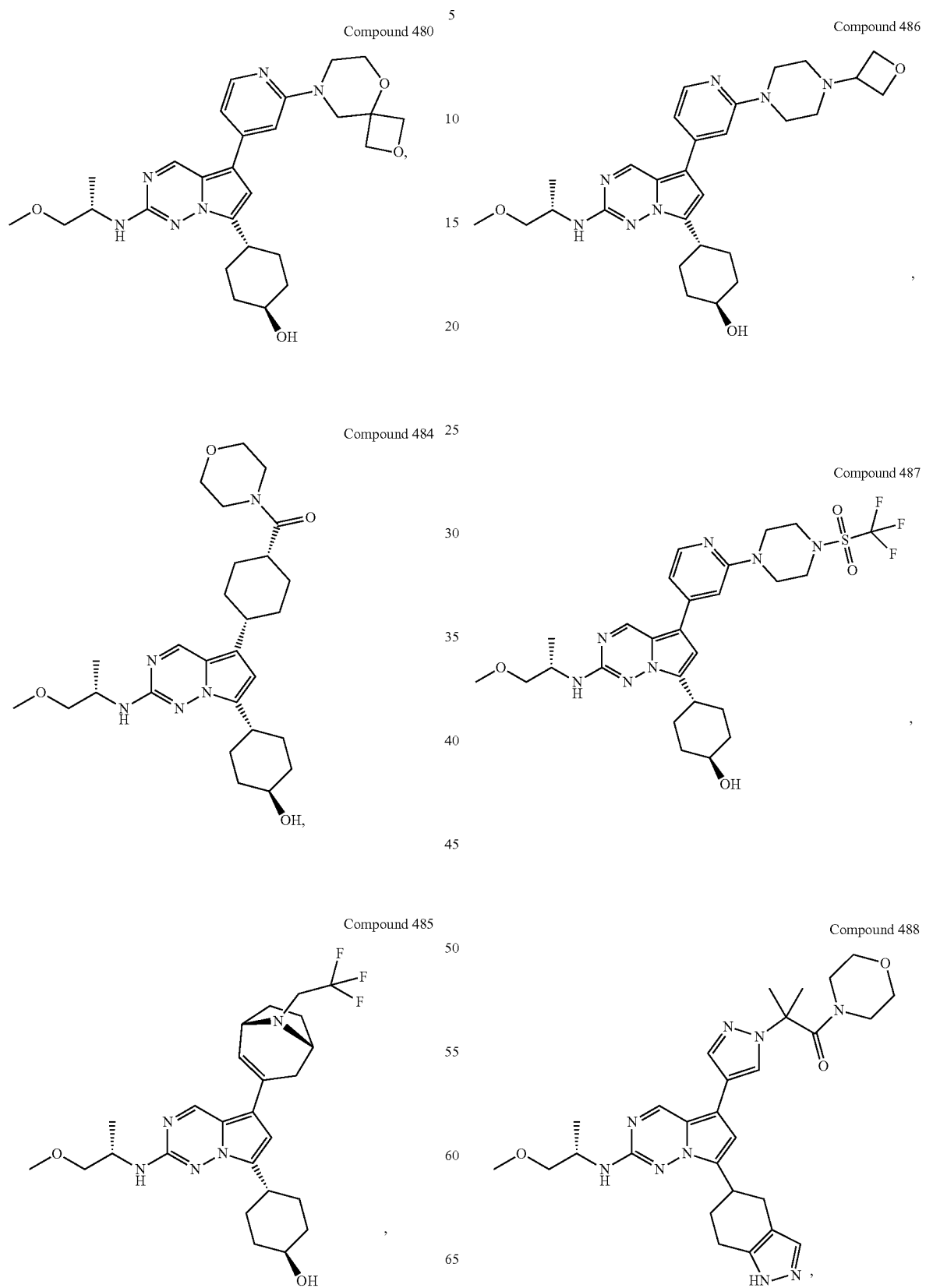

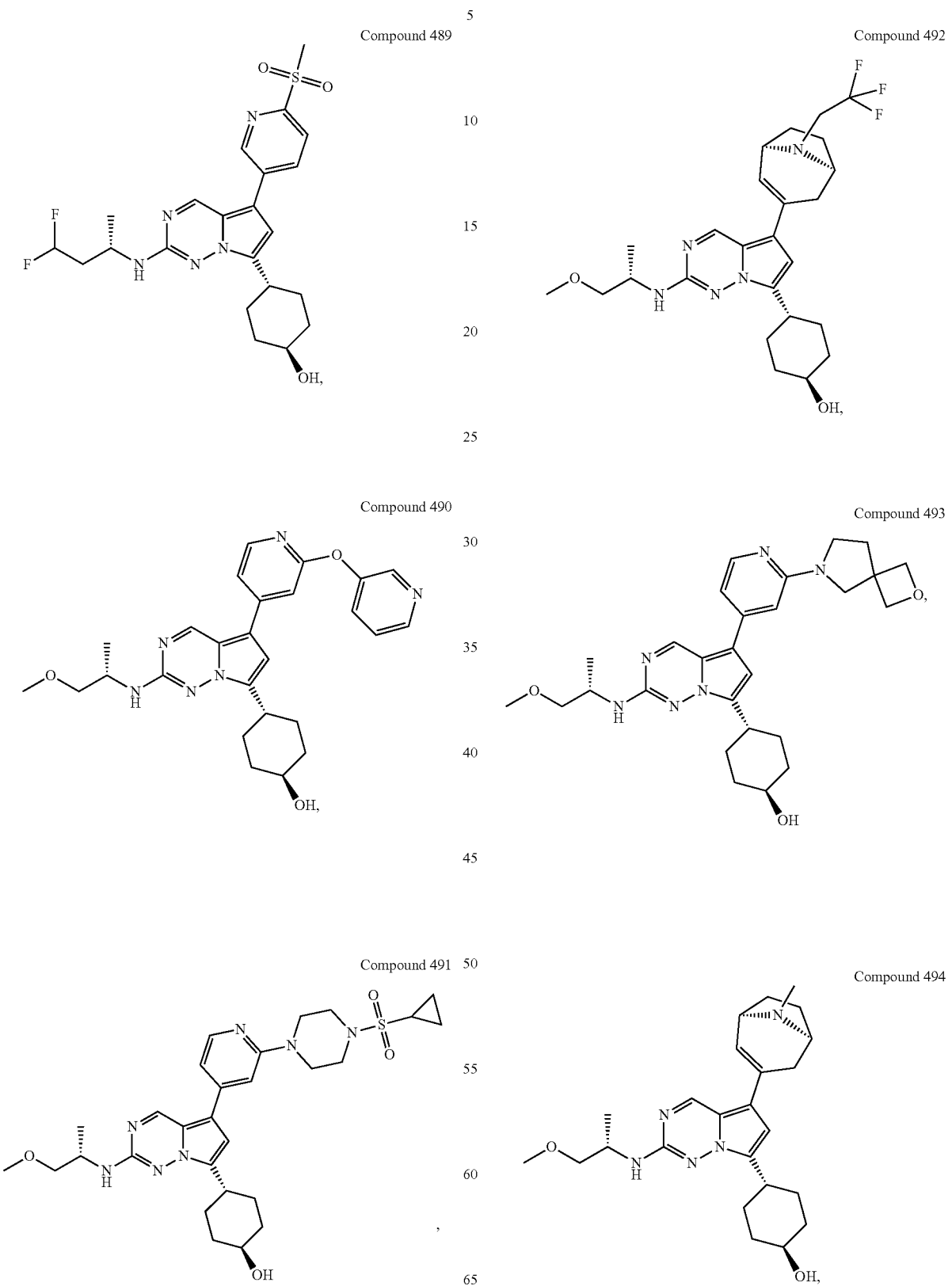

-continued
Compound 495
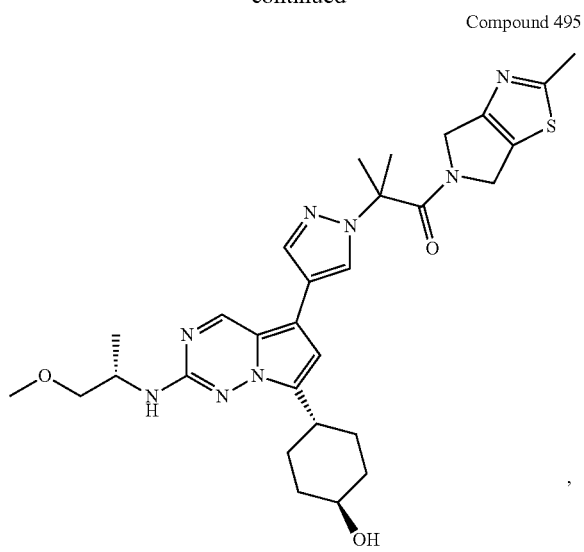
Compound 496
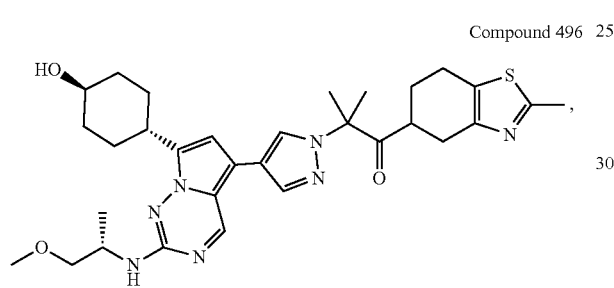
Compound 498
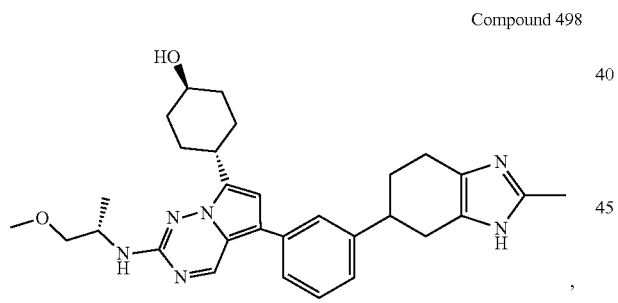
Compound 499
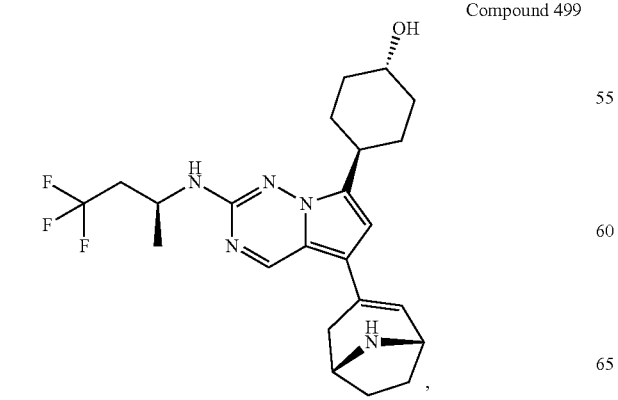
-continued
Compound 500
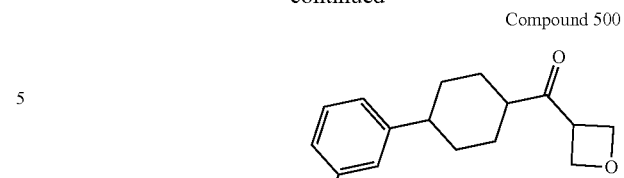
Compound 504
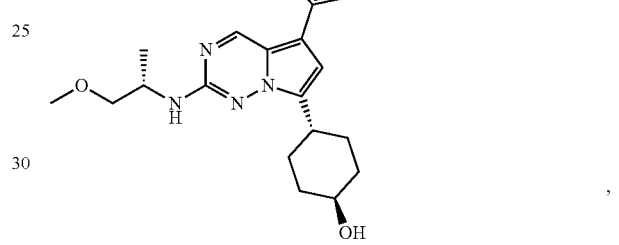
Compound 505
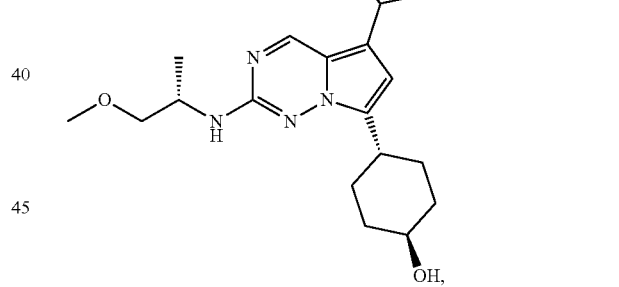
Compound 507
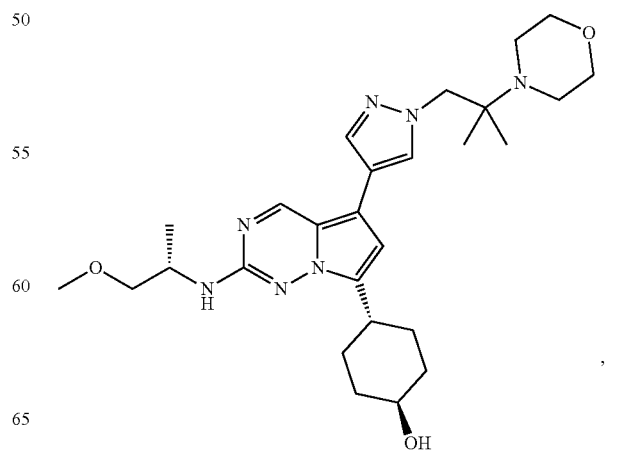

Compound 509
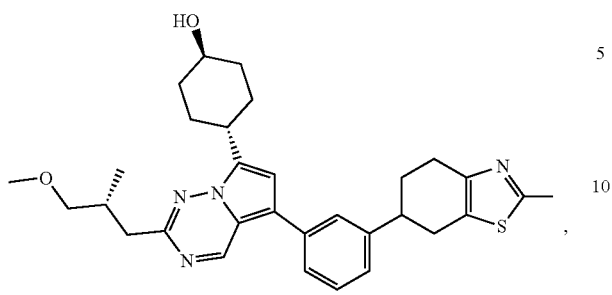
Compound 510
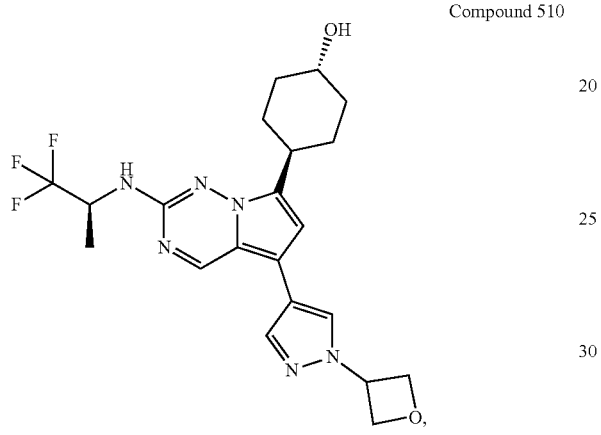
Compound 511
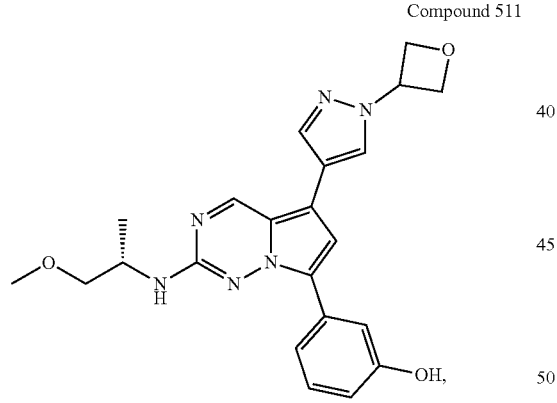
Compound 512
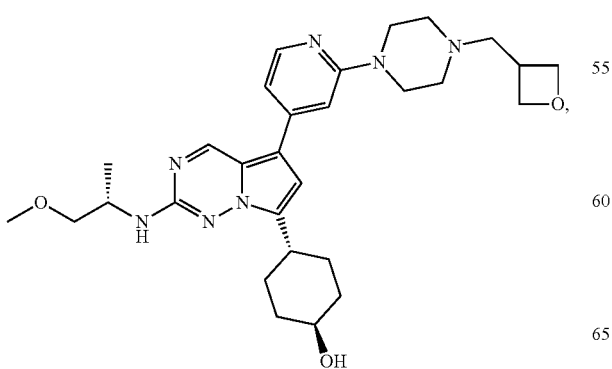
Compound 513
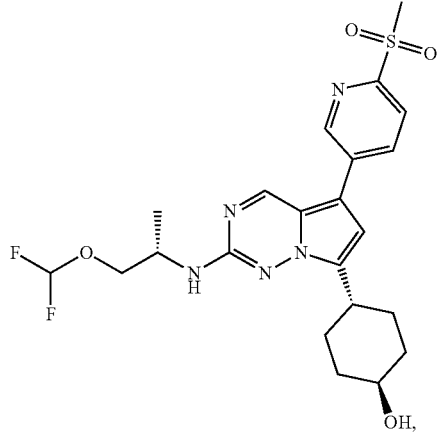
Compound 514
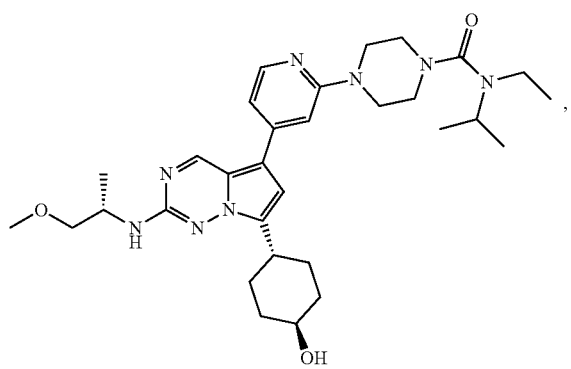
Compound 516
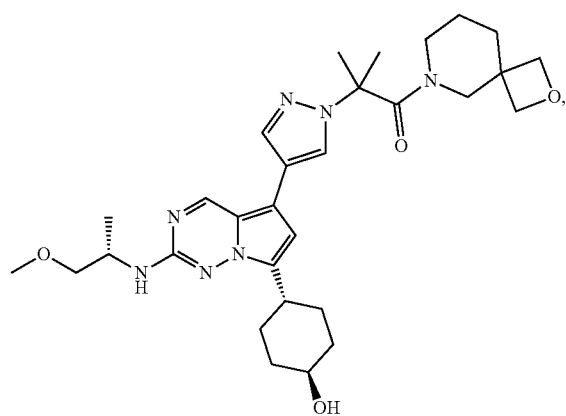

Compound 517
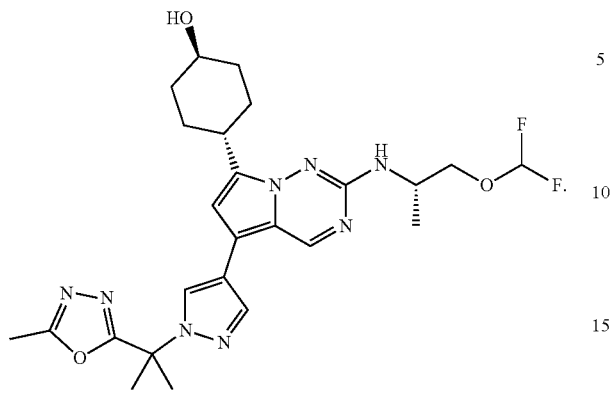
Compound 518
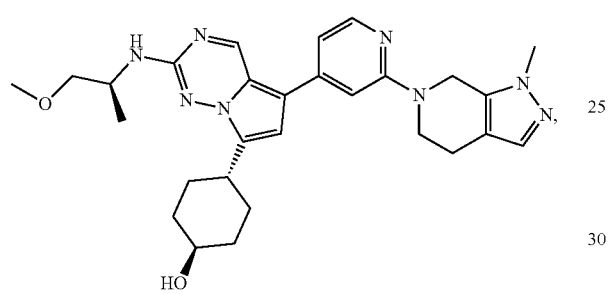
Compound 527
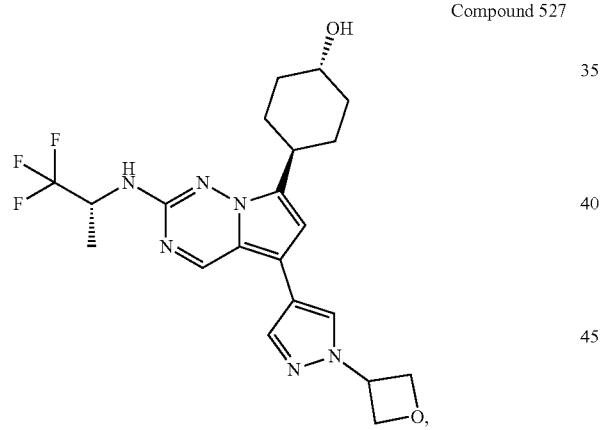
Compound 532
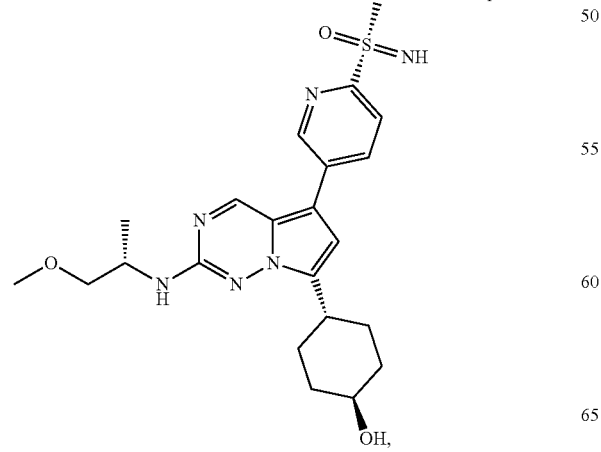
Compound 533
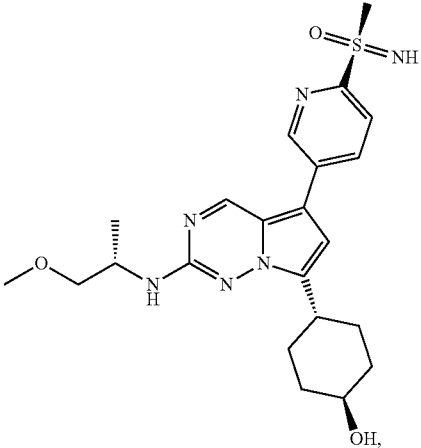
Compound 534
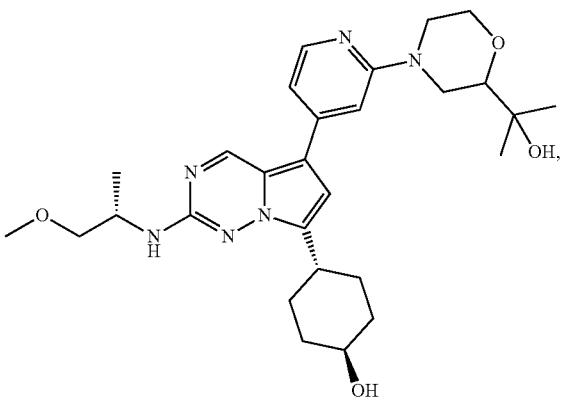
Compound 537
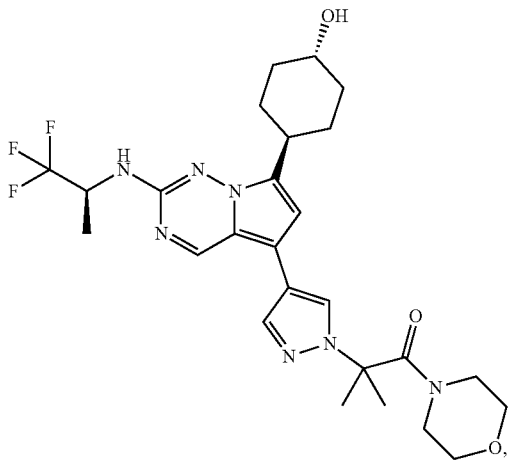

Compound 540
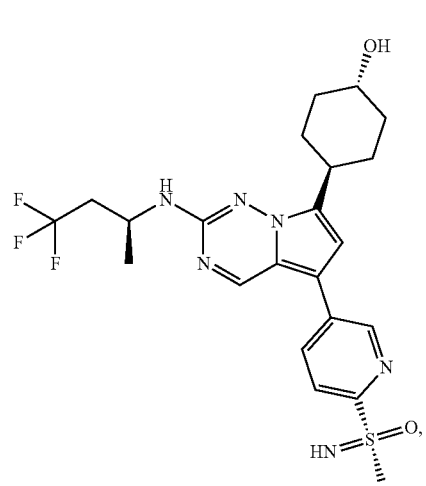
Compound 547
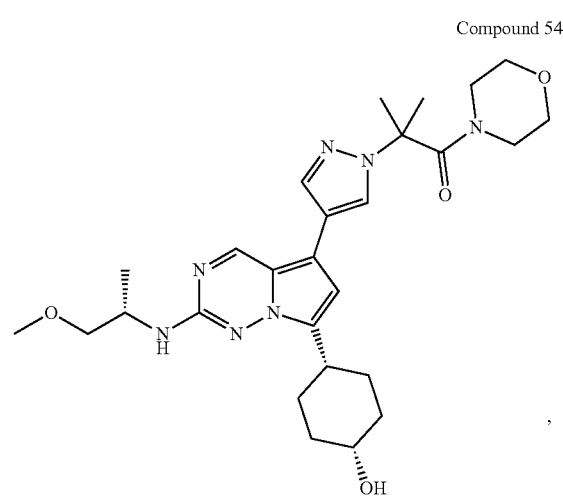
Compound 541
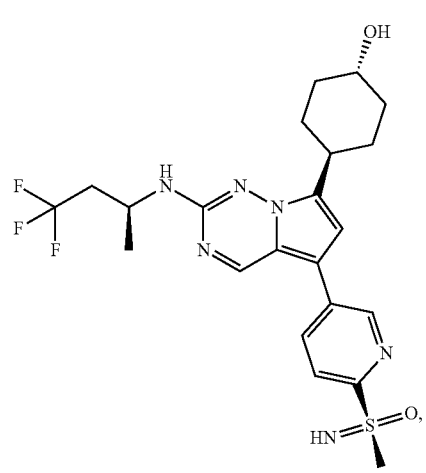
Compound 548
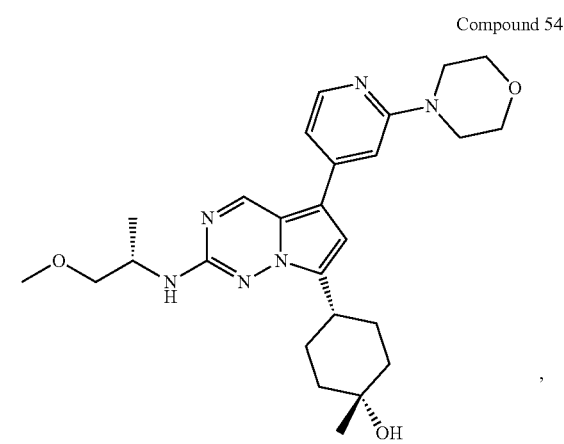
Compound 546
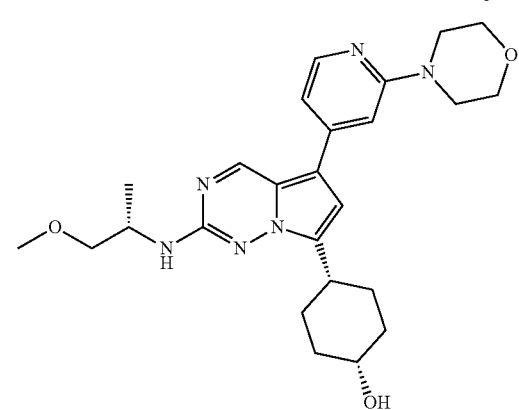
Compound 549
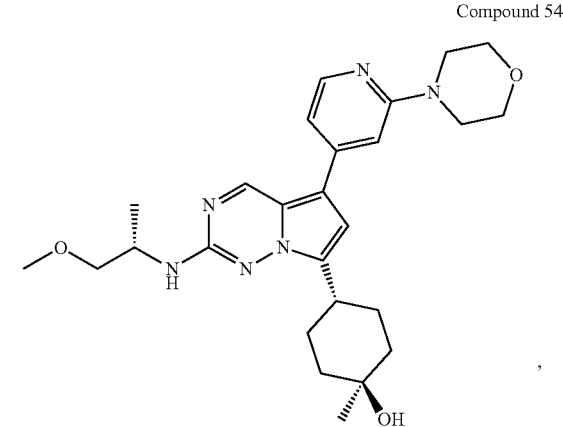

-continued
Compound 554
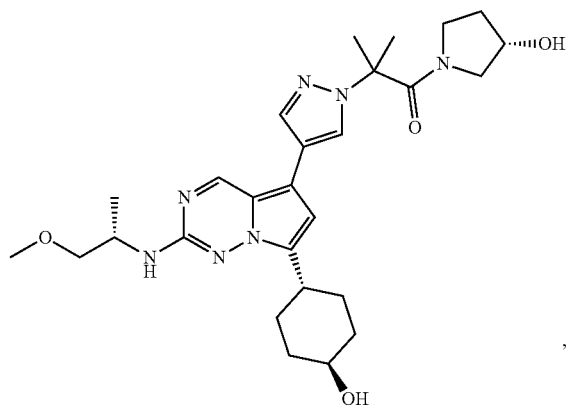
Compound 555
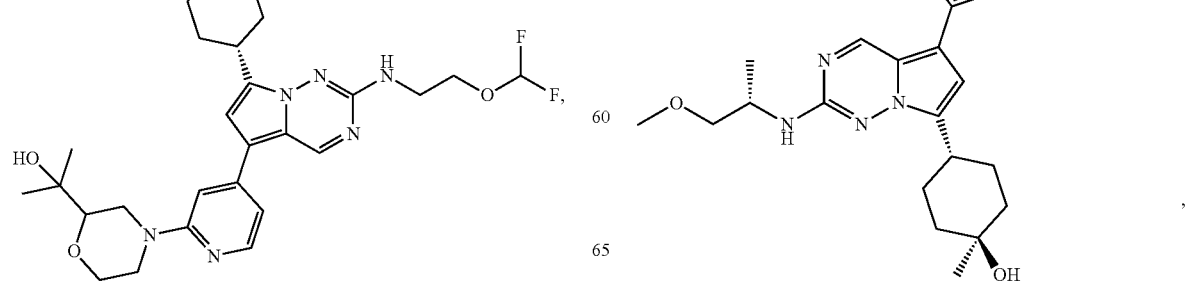
Compound 556
Compound 557
-continued
Compound 558
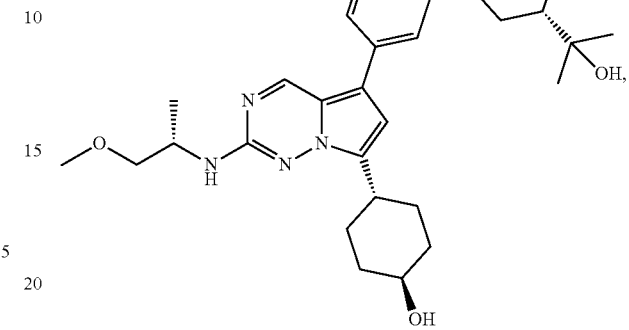
Compound 559
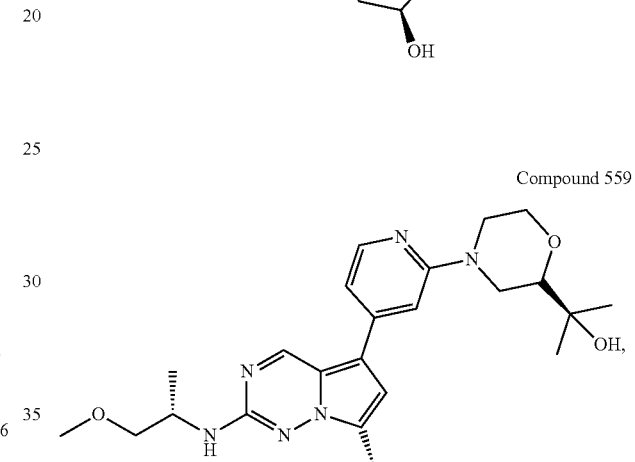
Compound 560
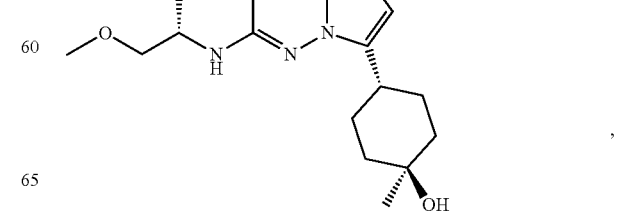

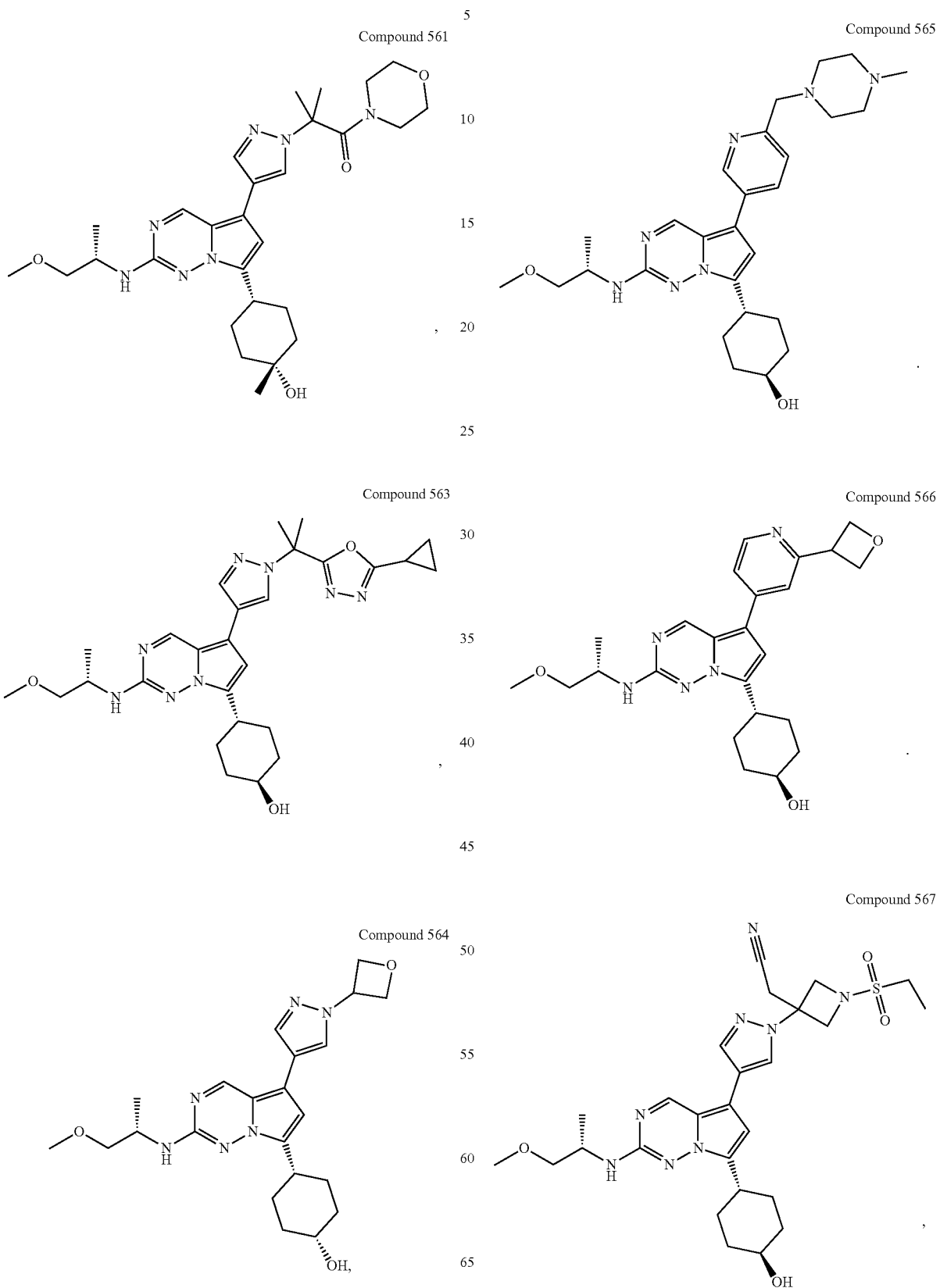

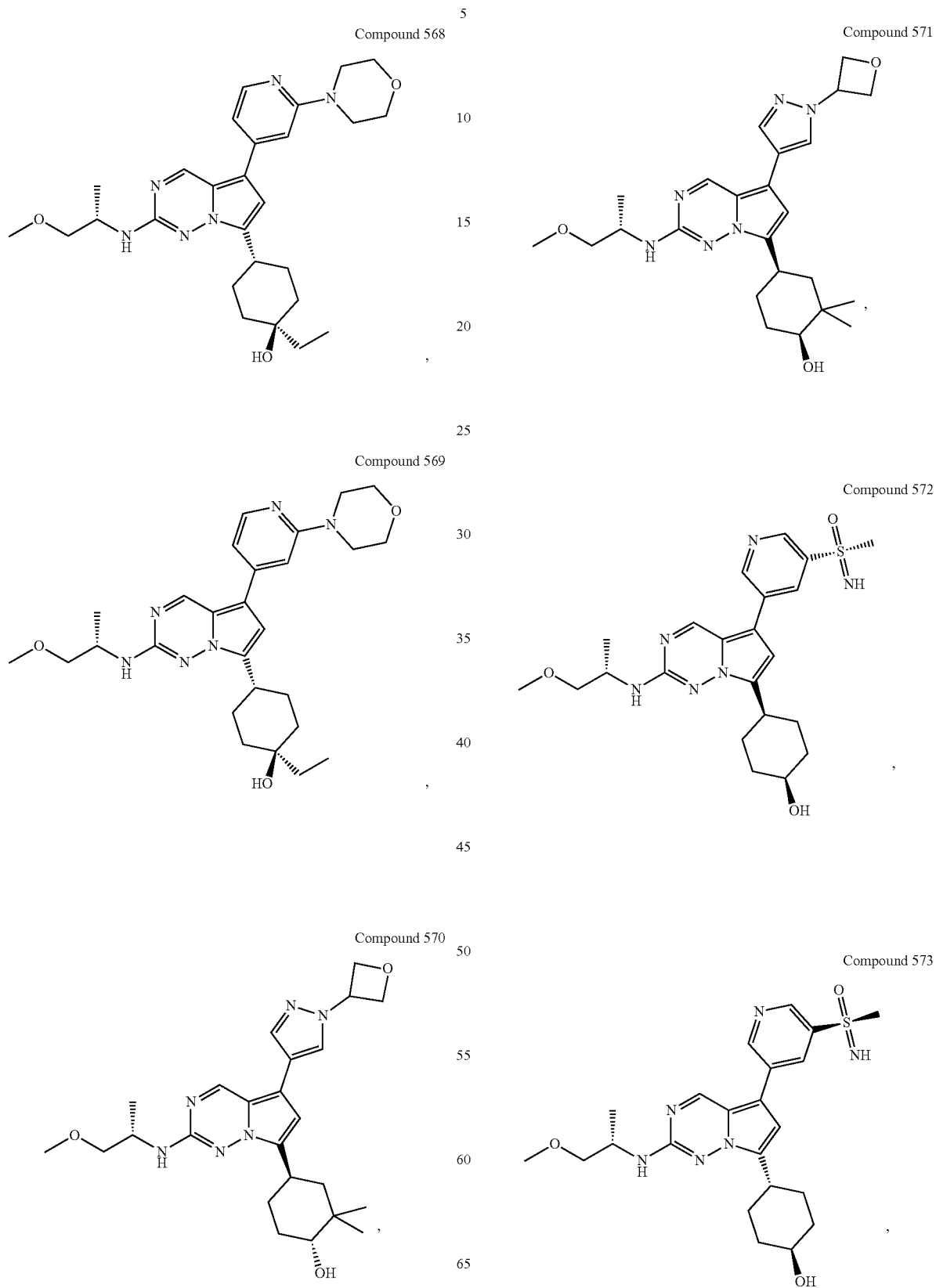

Compound 574
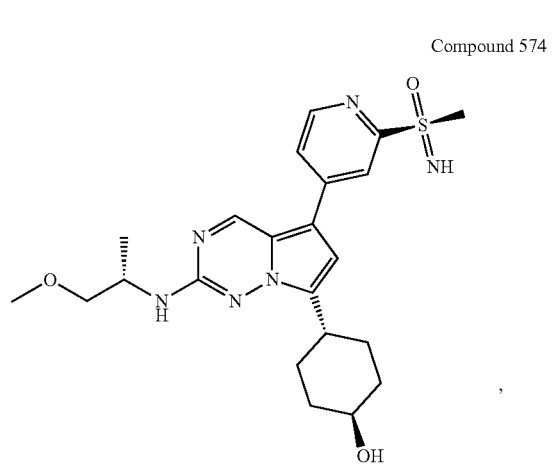
Compound 575
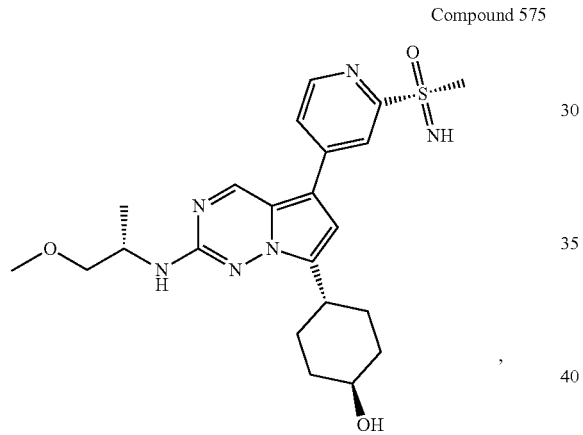
Compound 576
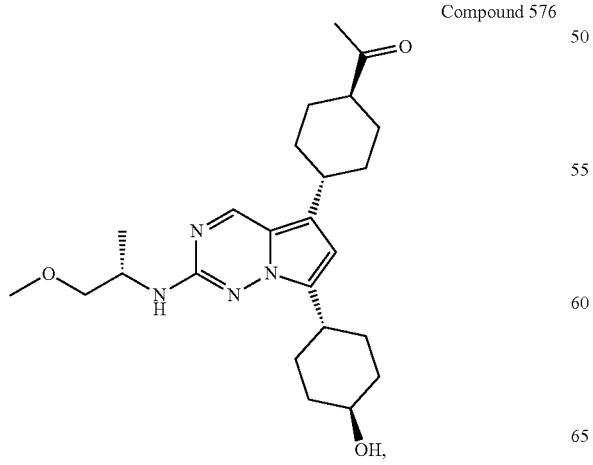
Compound 577
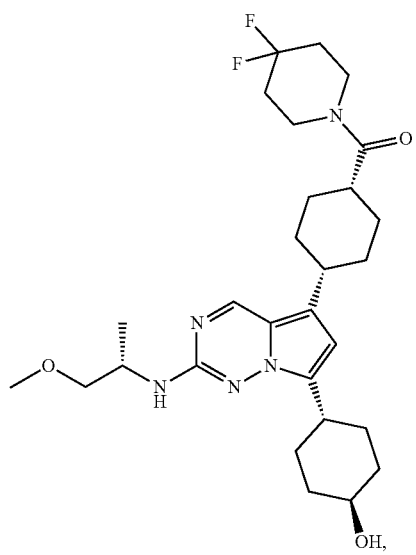
Compound 578
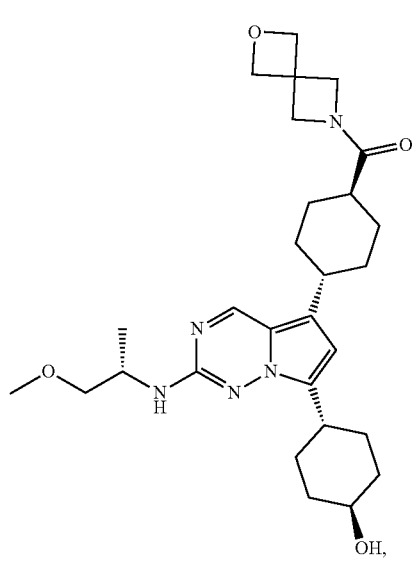
Compound 579
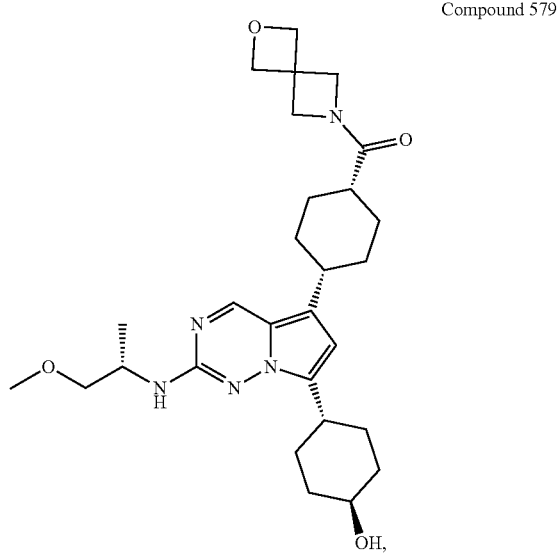

Compound 580
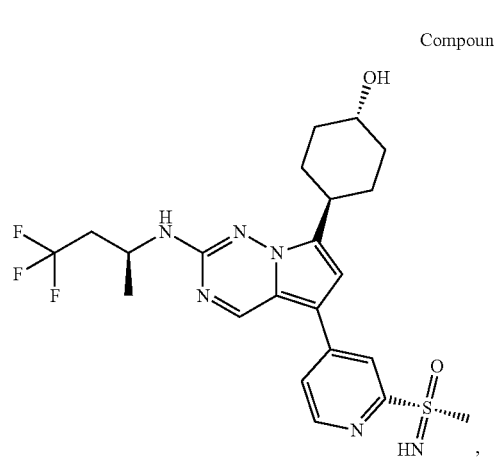
Compound 583
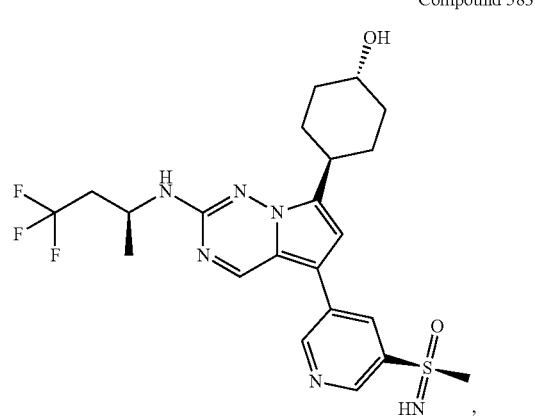
Compound 581
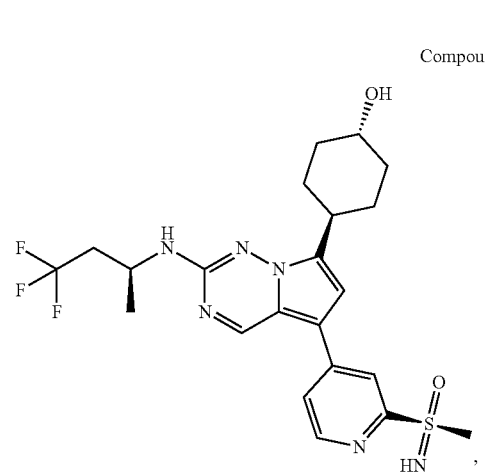
Compound 584
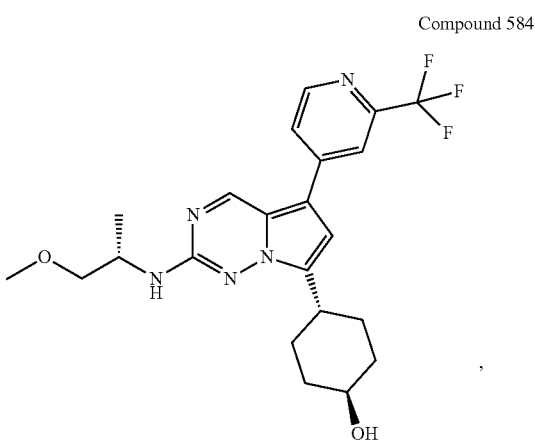
Compound 582
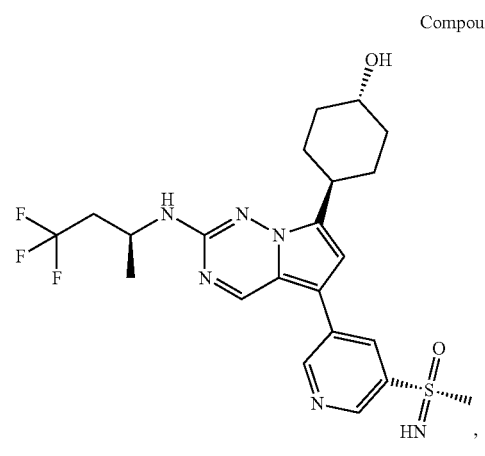
Compound 585
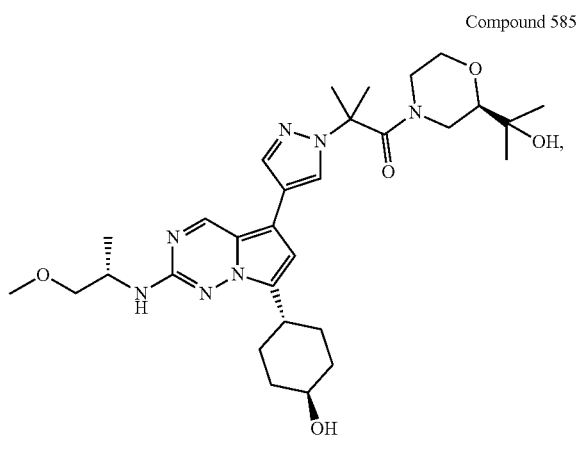

Compound 586
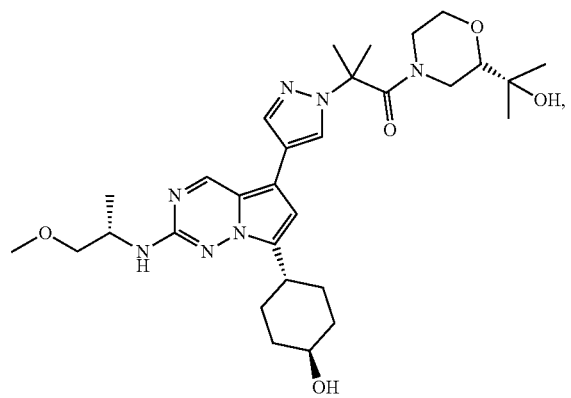
Compound 587
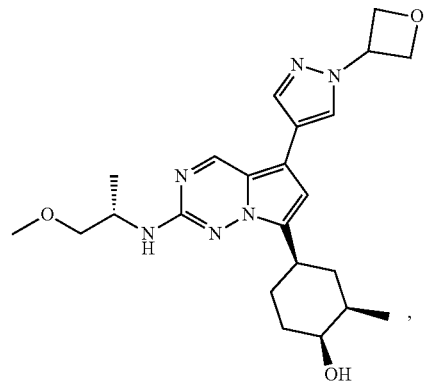
Compound 588
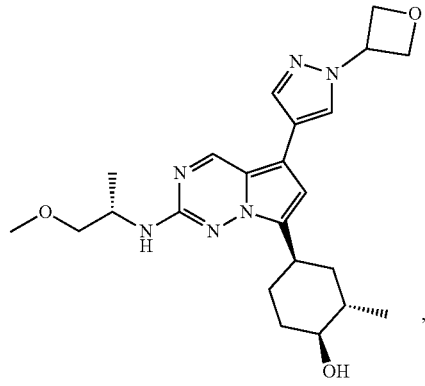
Compound 589
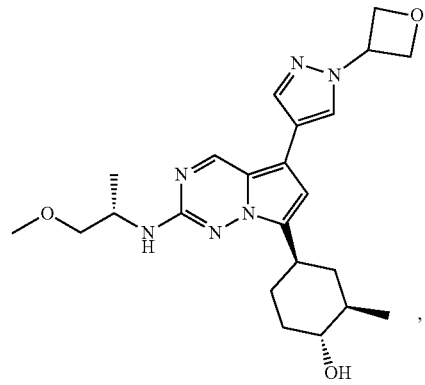
Compound 591
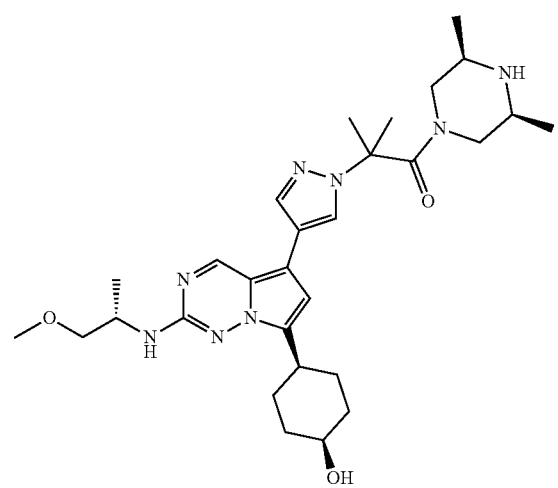
Compound 593
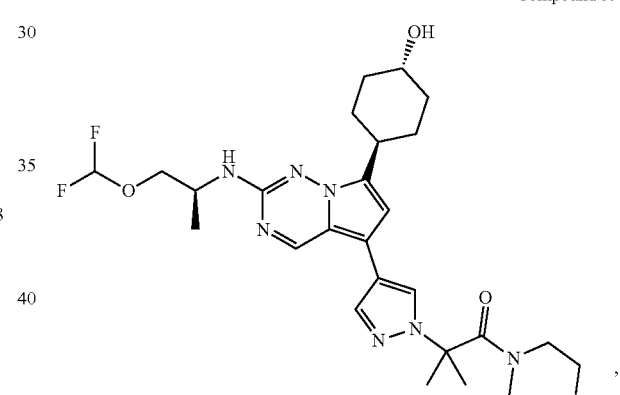
Compound 594
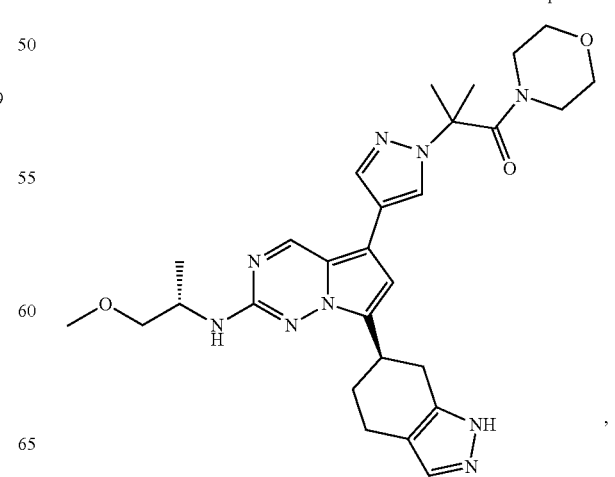

Compound 596
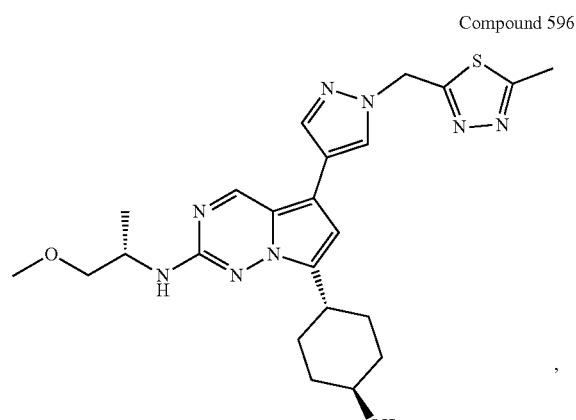
Compound 597
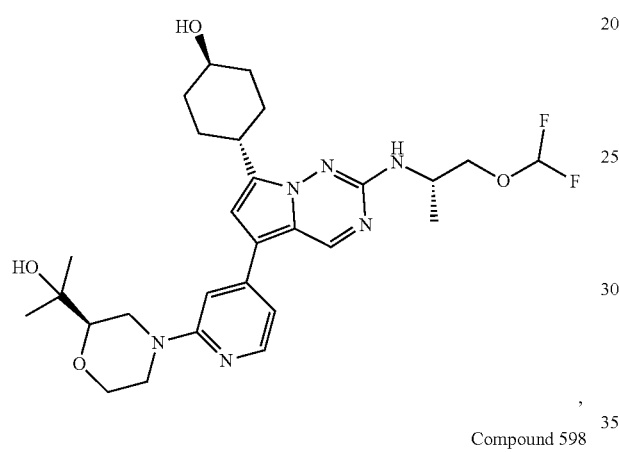
Compound 598
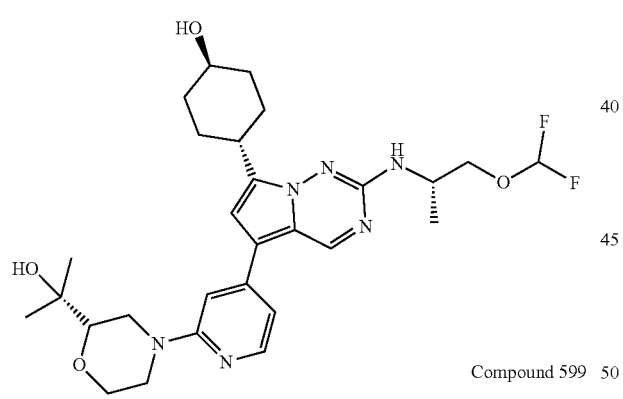
Compound 599
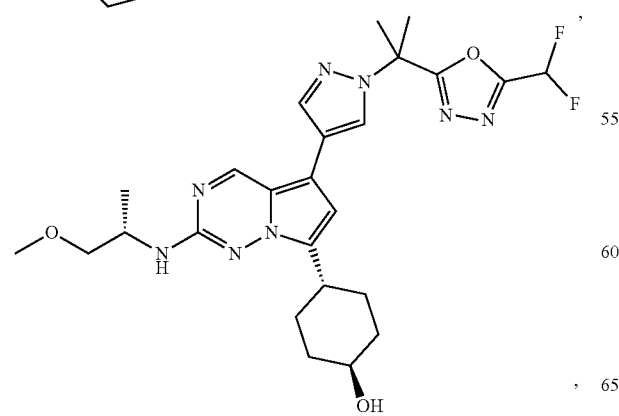
Compound 600
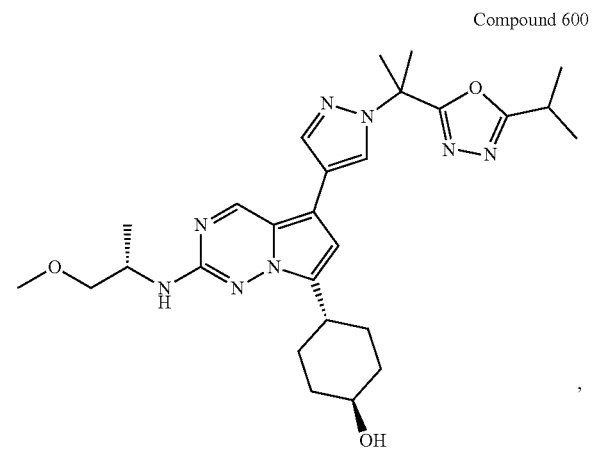
Compound 601
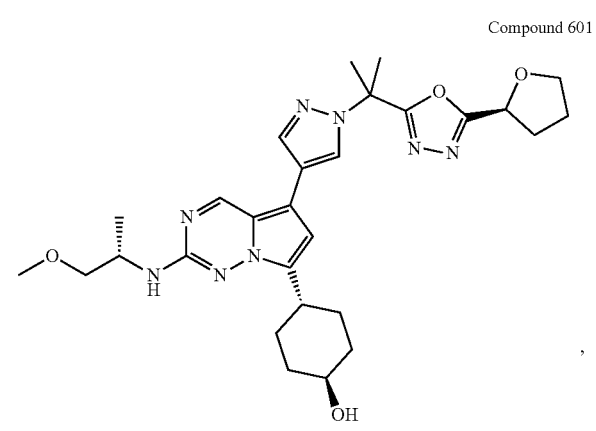
Compound 602
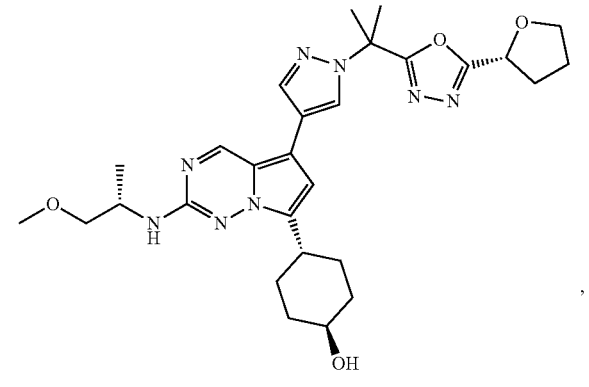
Compound 603
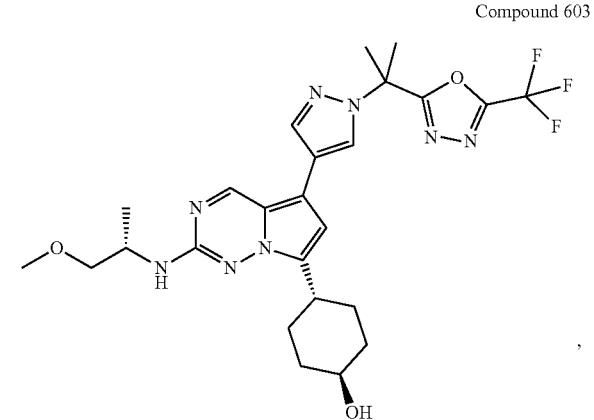

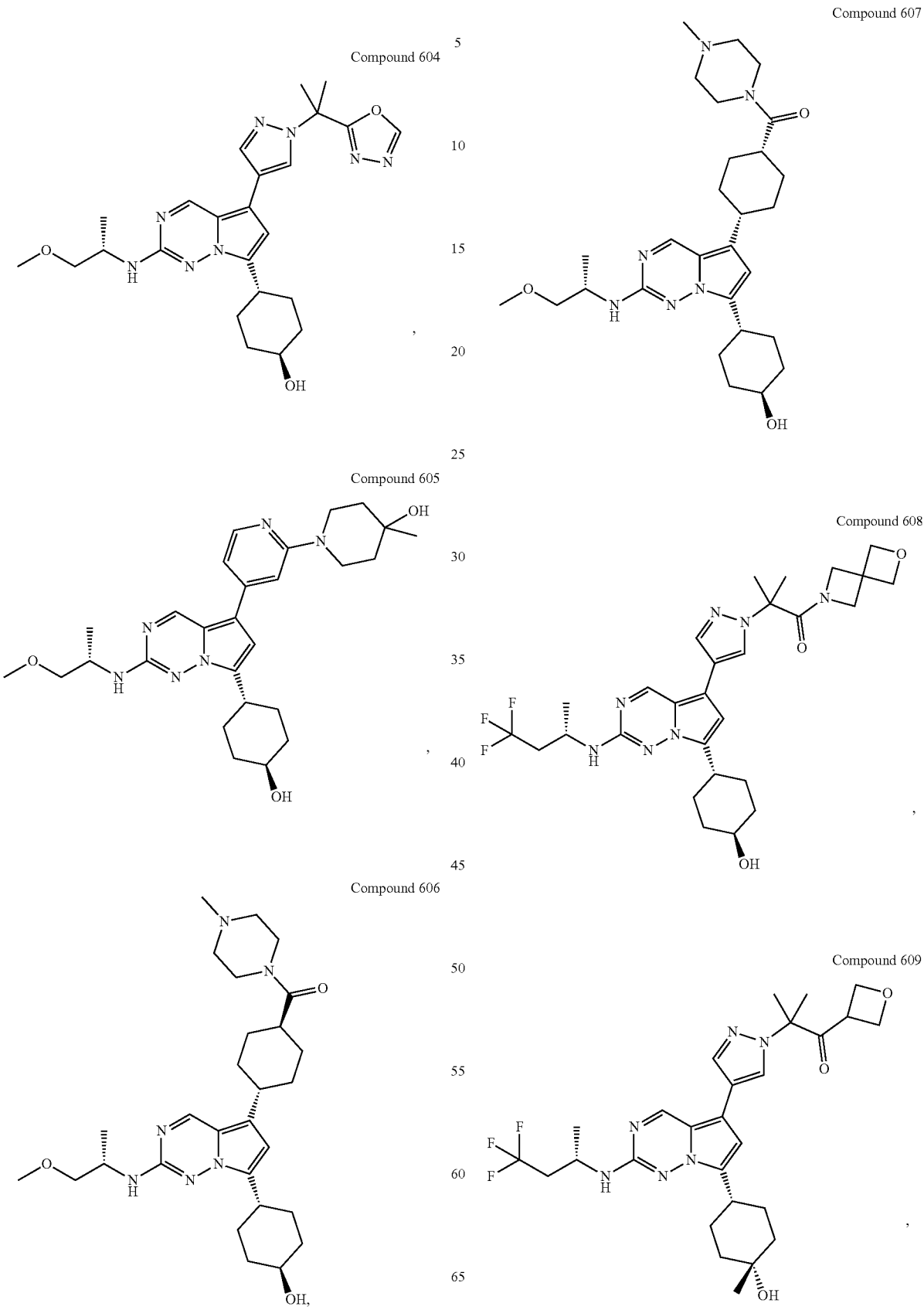

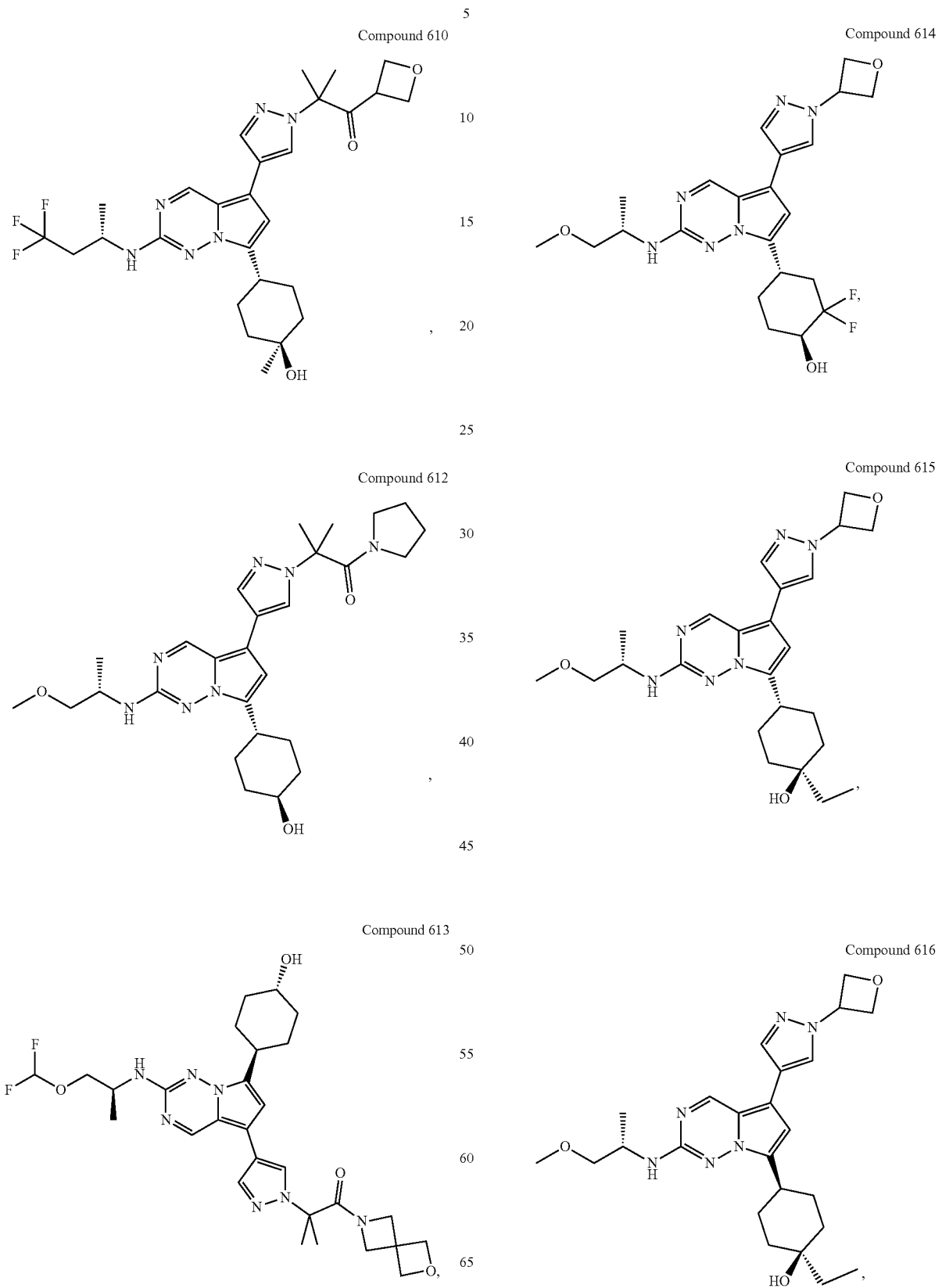

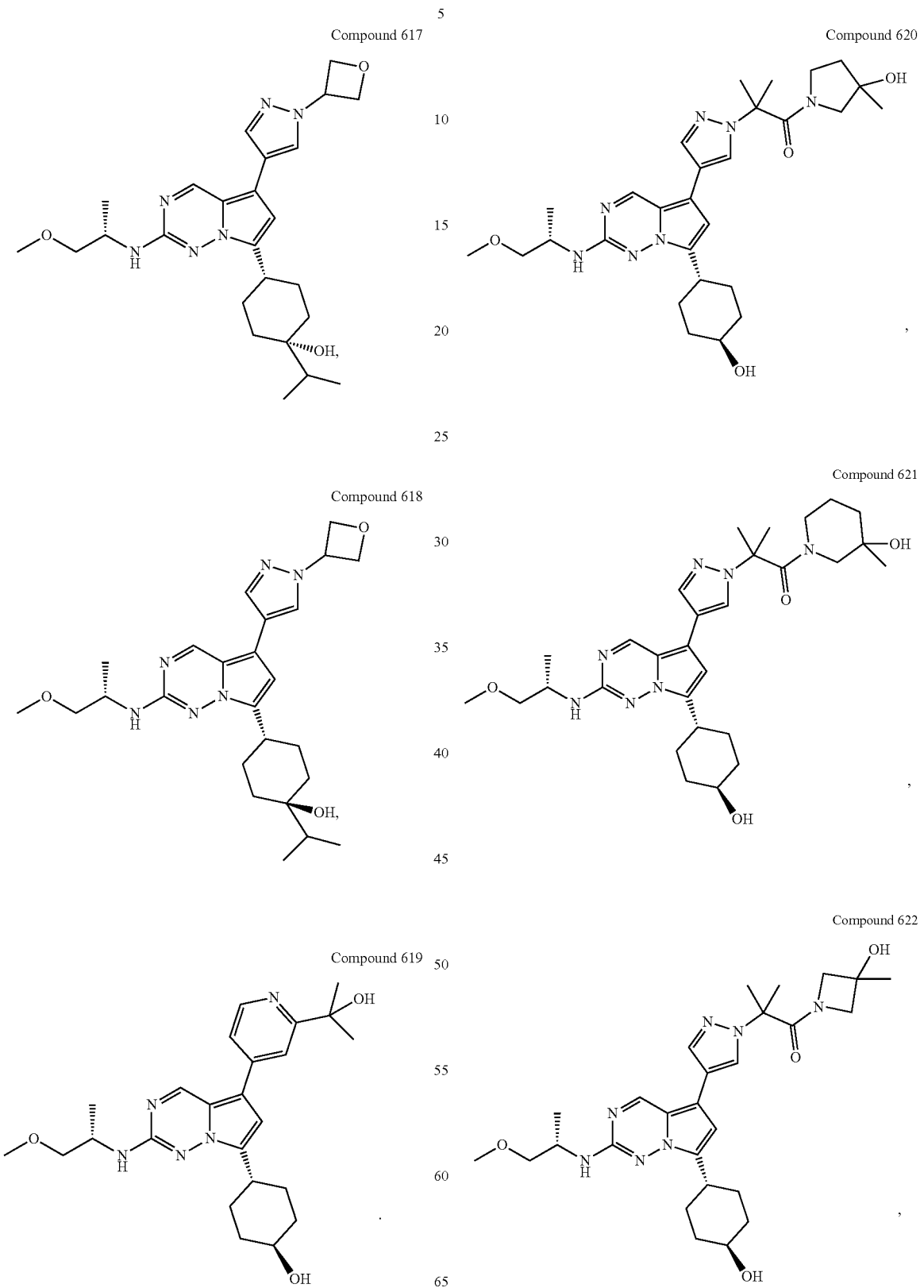

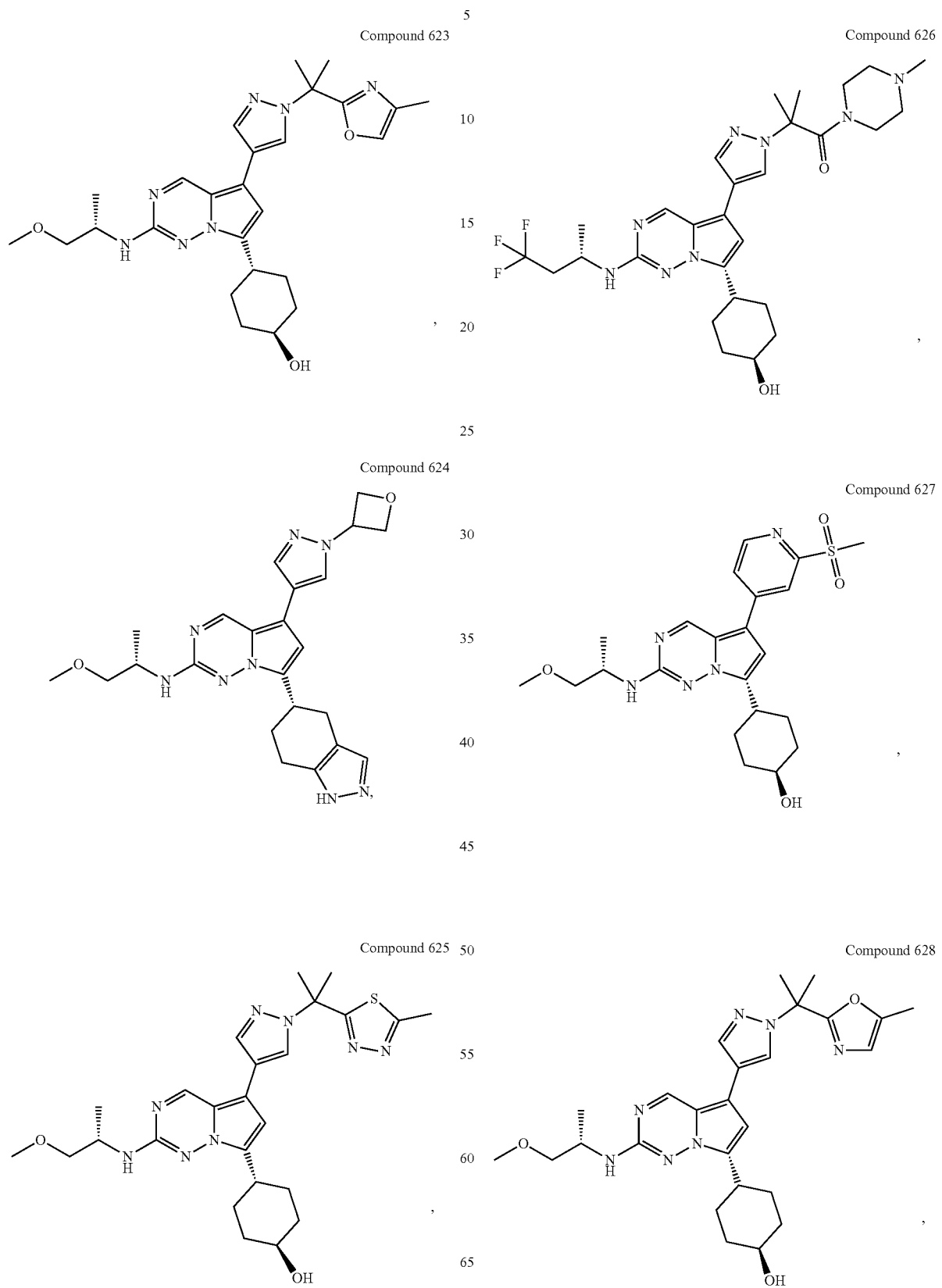

Compound 629

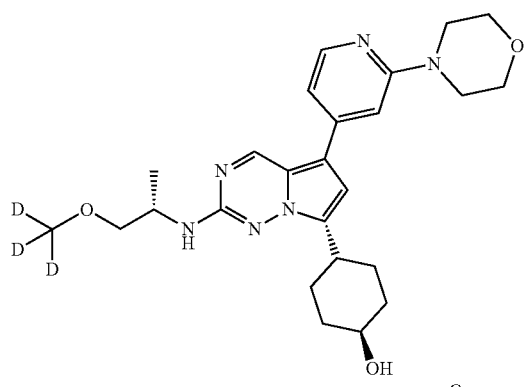

Compound 630

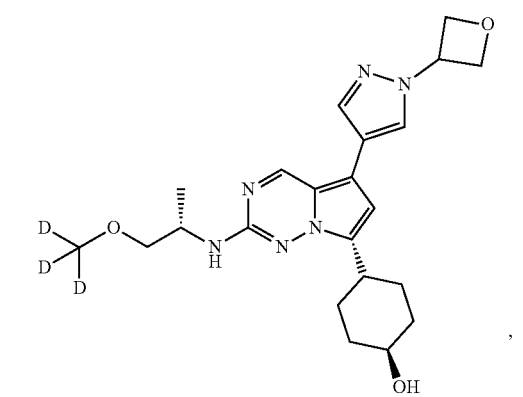

Compound 631

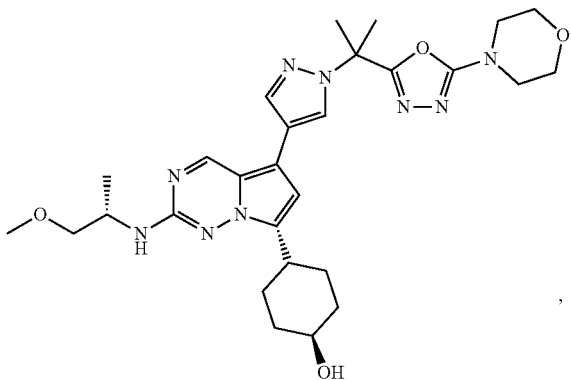

Compound 632

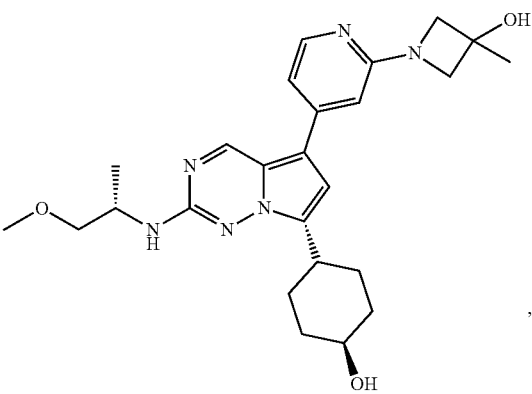

or

Compound 633

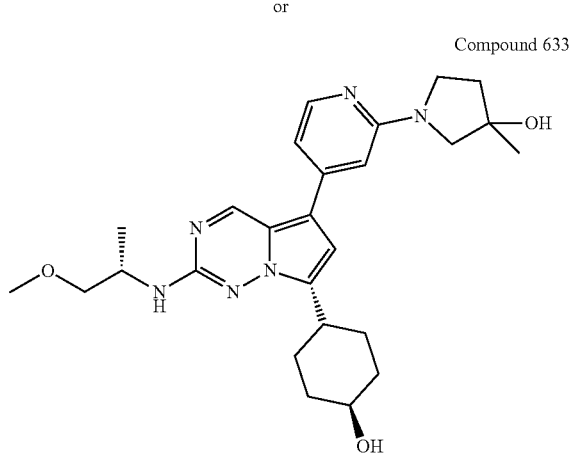

or a pharmaceutically acceptable salt of any of foregoing compounds.

26. The compound of claim 1 or the pharmaceutically acceptable salt thereof, wherein the compound demonstrates a $K_i$ against MERTK at least two times lower than its $K_i$ against FLT3.

27. A pharmaceutical composition comprising the compound of claim 1 or the pharmaceutically acceptable salt thereof and a pharmaceutically acceptable carrier.

28. A pharmaceutical composition comprising the compound of claim 25 or the pharmaceutically acceptable salt thereof and a pharmaceutically acceptable carrier.

* * * * *